US012297426B2

(12) United States Patent
Ben-David et al.

(10) Patent No.: US 12,297,426 B2
(45) Date of Patent: May 13, 2025

(54) DNA DAMAGE RESPONSE SIGNATURE GUIDED RATIONAL DESIGN OF CRISPR-BASED SYSTEMS AND THERAPIES

(71) Applicants: THE BROAD INSTITUTE, INC., Cambridge, MA (US); DANA-FARBER CANCER INSTITUTE, INC., Boston, MA (US)

(72) Inventors: Uri Ben-David, Cambridge, MA (US); Todd Golub, Cambridge, MA (US); Rameen Beroukhim, Boston, MA (US); Oana Enache, Cambridge, MA (US); Veronica Rendo, Boston, MA (US)

(73) Assignees: THE BROAD INSTITUTE, INC., Cambridge, MA (US); DANA-FARBER CANCER INSTITUTE, INC., Boston, MA (US)

( * ) Notice: Subject to any disclaimer, the term of this patent is extended or adjusted under 35 U.S.C. 154(b) by 1052 days.

(21) Appl. No.: 17/148,477

(22) Filed: Jan. 13, 2021

(65) Prior Publication Data

US 2021/0147828 A1 May 20, 2021

Related U.S. Application Data

(63) Continuation of application No. 17/061,574, filed on Oct. 1, 2020, now abandoned.

(60) Provisional application No. 62/909,131, filed on Oct. 1, 2019.

(51) Int. Cl.

| | |
|---|---|
| ***C12N 15/10*** | (2006.01) |
| ***A61K 35/13*** | (2015.01) |
| ***C12N 9/22*** | (2006.01) |
| ***C12N 15/11*** | (2006.01) |
| ***C12Q 1/6883*** | (2018.01) |

(52) U.S. Cl.

CPC .......... *C12N 15/1024* (2013.01); *A61K 35/13* (2013.01); *C12N 9/22* (2013.01); *C12N 15/11* (2013.01); *C12Q 1/6883* (2013.01); *C12N 2310/20* (2017.05); *C12N 2800/80* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 4,751,180 | A | 6/1988 | Cousens et al. |
| 4,797,368 | A | 1/1989 | Carter et al. |
| 4,873,316 | A | 10/1989 | Meade et al. |
| 4,935,233 | A | 6/1990 | Bell et al. |
| 5,173,414 | A | 12/1992 | Lebkowski et al. |
| 5,543,158 | A | 8/1996 | Gref et al. |
| 5,563,055 | A | 10/1996 | Townsend et al. |
| 5,686,281 | A | 11/1997 | Roberts |
| 5,789,156 | A | 8/1998 | Bujard et al. |
| 5,814,618 | A | 9/1998 | Bujard et al. |
| 5,843,728 | A | 12/1998 | Seed et al. |
| 5,851,828 | A | 12/1998 | Seed et al. |
| 5,855,913 | A | 1/1999 | Hanes et al. |
| 5,858,358 | A | 1/1999 | June et al. |
| 5,869,326 | A | 2/1999 | Hofmann |
| 5,883,223 | A | 3/1999 | Gray |
| 5,906,936 | A | 5/1999 | Eshhar et al. |
| 5,912,170 | A | 6/1999 | Seed et al. |
| 5,912,172 | A | 6/1999 | Eshhar et al. |
| 5,965,443 | A | 10/1999 | Reznikoff et al. |
| 5,985,309 | A | 11/1999 | Edwards et al. |
| 6,004,811 | A | 12/1999 | Seed et al. |
| 6,007,845 | A | 12/1999 | Domb et al. |
| 6,040,177 | A | 3/2000 | Riddell et al. |
| 6,284,240 | B1 | 9/2001 | Seed et al. |
| 6,352,694 | B1 | 3/2002 | June et al. |
| 6,392,013 | B1 | 5/2002 | Seed et al. |
| 6,410,014 | B1 | 6/2002 | Seed et al. |
| 6,437,109 | B1 | 8/2002 | Reznikoff et al. |

(Continued)

FOREIGN PATENT DOCUMENTS

| | | |
|---|---|---|
| EP | 0 264 166 A1 | 4/1988 |
| EP | 2 047 910 B1 | 4/2009 |

(Continued)

OTHER PUBLICATIONS

Haapaniemi E, Botla S, Persson J, Schmierer B, Taipale J. CRISPR-Cas9 genome editing induces a p53-mediated DNA damage response. Nat Med. Jul. 2018;24(7):927-930. doi: 10.1038/s41591-018-0049-z. Epub Jun. 11, 2018. (Year: 2018).*

(Continued)

*Primary Examiner* — Allison M Fox

*Assistant Examiner* — Qinhua Gu

(74) *Attorney, Agent, or Firm* — Foley & Lardner LLP; Sunit Talapatra

(57) ABSTRACT

Described herein are embodiments of methods to rationally design CRISPR-Cas system-based therapeutics and therapies based on expression of a DNA-damage response signature in a cell. In some embodiments, the methods include screening a set of CRISPR-Cas systems by expressing each CRISPR-Cas system in a test cell population and modifying one or more target sequences in the test cell population; screening in the test cell population for each CRISPR-Cas system and expression of a DNA-damage response signature; and selecting one or more CRISPR-Cas systems that do not result in expression of a DNA-damage response signature.

22 Claims, 39 Drawing Sheets

Specification includes a Sequence Listing.

(56) References Cited

U.S. PATENT DOCUMENTS 6,489,458 B2 12/2002 Hackett et al.
6,534,055 B1 3/2003 June et al.
6,740,525 B2 5/2004 Roelvink et al.
6,750,059 B1 6/2004 Blakesley et al.
6,753,162 B1 6/2004 Seed et al.
6,797,514 B2 9/2004 Berenson et al.
6,867,041 B2 3/2005 Berenson et al.
6,887,466 B2 5/2005 June et al.
6,905,680 B2 6/2005 June et al.
6,905,681 B1 6/2005 June et al.
6,905,874 B2 6/2005 Berenson et al.
6,911,199 B2 6/2005 Vigne et al.
7,041,481 B2 5/2006 Anderson et al.
7,144,575 B2 12/2006 June et al.
7,148,203 B2 12/2006 Hackett et al.
7,160,682 B2 1/2007 Hackett et al.
7,175,843 B2 2/2007 June et al.
7,232,566 B2 6/2007 June et al.
7,256,036 B2 8/2007 Legrand et al.
7,259,015 B2 8/2007 Kingsman et al.
7,303,910 B2 12/2007 Bebbington et al.
7,344,872 B2 3/2008 Gao et al.
7,351,585 B2 4/2008 Mitrophanous et al.
7,446,190 B2 11/2008 Sadelain et al.
7,572,631 B2 8/2009 Berenson et al.
7,708,949 B2 5/2010 Stone et al.
7,741,465 B1 6/2010 Eshhar et al.
7,776,321 B2 8/2010 Cascalho et al.
RE41,780 E 9/2010 Anderson et al.
7,985,739 B2 7/2011 Kay et al.
8,034,334 B2 10/2011 Dudley et al.
8,071,082 B2 12/2011 Zugates et al.
8,088,379 B2 1/2012 Robbins et al.
8,211,422 B2 7/2012 Eshhar et al.
8,227,432 B2 7/2012 Hackett et al.
8,372,951 B2 2/2013 Chang et al.
8,399,645 B2 3/2013 Campana et al.
8,404,658 B2 3/2013 Hajjar et al.
8,454,972 B2 6/2013 Nabel et al.
8,637,307 B2 1/2014 June et al.
8,697,854 B2 4/2014 Schendel et al.
8,709,843 B2 4/2014 Shakuda
8,906,682 B2 12/2014 June et al.
8,911,993 B2 12/2014 June et al.
8,916,381 B1 12/2014 June et al.
8,975,071 B1 3/2015 June et al.
9,101,584 B2 8/2015 June et al.
9,102,760 B2 8/2015 June et al.
9,102,761 B2 8/2015 June et al.
9,233,125 B2 1/2016 Davila et al.
9,410,129 B2 8/2016 Ranki et al.
2002/0150626 A1 10/2002 Kohane et al.
2004/0013648 A1 1/2004 Kingsman et al.
2004/0171156 A1 9/2004 Hartley et al.
2004/0224402 A1 11/2004 Bonyhadi et al.
2005/0019923 A1 1/2005 Uchegbu et al.
2005/0172476 A1 8/2005 Stone et al.
2006/0281180 A1 12/2006 Radcliffe et al.
2007/0025970 A1 2/2007 Kingsman et al.
2007/0054961 A1 3/2007 Maden et al.
2007/0195127 A1 8/2007 Ahn et al.
2008/0003142 A1 1/2008 Link et al.
2008/0014589 A1 1/2008 Link et al.
2008/0267903 A1 10/2008 Uchegbu et al.
2009/0007284 A1 1/2009 Radcliffe et al.
2009/0017543 A1 1/2009 Wilkes et al.
2009/0111106 A1 4/2009 Mitrophanous et al.
2009/0215879 A1 8/2009 Diprimio et al.
2010/0002241 A1 1/2010 Hirose
2010/0104509 A1 4/2010 King et al.
2010/0129793 A1 5/2010 Mirkin et al.
2010/0137163 A1 6/2010 Link et al.
2010/0172803 A1 7/2010 Stone et al.
2010/0317109 A1 12/2010 Maden et al.
2011/0027239 A1 2/2011 Paek
2011/0117189 A1 5/2011 Mazzone et al.
2011/0212179 A1 9/2011 Liu
2011/0293571 A1 12/2011 Widdowson et al.
2011/0293703 A1 12/2011 Mahon et al.
2012/0003201 A1 1/2012 Nicholas et al.
2012/0164118 A1 6/2012 Trobridge et al.
2012/0219947 A1 8/2012 Yurkovetsky et al.
2012/0244133 A1 9/2012 Rosenberg et al.
2012/0251618 A1 10/2012 Schrum et al.
2012/0295960 A1 11/2012 Palfi et al.
2013/0071414 A1 3/2013 Dotti et al.
2013/0185823 A1 7/2013 Kuang et al.
2013/0244279 A1 9/2013 De Fougerolles et al.
2013/0245107 A1 9/2013 De Fougerolles et al.
2013/0252281 A1 9/2013 De Fougerolles et al.
2013/0302401 A1 11/2013 Ma et al.
2014/0301951 A1 10/2014 Liu et al.
2015/0105538 A1 4/2015 Chromy et al.
2015/0232881 A1 8/2015 Glucksmann et al.
2015/0250725 A1 9/2015 Bader et al.
2015/0291966 A1 10/2015 Zhang et al.
2015/0368342 A1 12/2015 Wu et al.
2015/0368360 A1 12/2015 Liang et al.
2016/0006069 A1 1/2016 Gerhardt et al.
2016/0027264 A1 1/2016 Choi et al.
2016/0046724 A1 2/2016 Brogdon et al.
2016/0129109 A1 5/2016 Davila et al.
2016/0129120 A1 5/2016 Xu et al.
2016/0166613 A1 6/2016 Spencer et al.
2016/0174546 A1 6/2016 Berg et al.
2016/0175359 A1 6/2016 Spencer et al.
2016/0208323 A1 7/2016 Bernstein et al.
2016/0244761 A1 8/2016 Payne et al.
2016/0257951 A1 9/2016 Koizumi et al.
2016/0354487 A1 12/2016 Zhang et al.
2016/0367686 A1 12/2016 Anderson et al.
2017/0028377 A1 2/2017 Bernstein et al.
2017/0079916 A1 3/2017 Khan et al.
2017/0166903 A1 6/2017 Zhang et al.
2017/0283504 A1 10/2017 Wiltzius et al.
2018/0085444 A1 3/2018 Morgan et al.
2019/0203212 A1 7/2019 Zhang et al.
2020/0248229 A1 8/2020 Zhang et al.
2021/0147828 A1 5/2021 Ben-David et al.

FOREIGN PATENT DOCUMENTS

EP 1 664 316 B1 8/2012
WO WO-92/15322 A1 9/1992
WO WO-93/01294 A1 1/1993
WO WO-93/24641 A2 12/1993
WO WO-94/26877 A1 11/1994
WO WO-97/49450 A1 12/1997
WO WO-98/52609 A1 11/1998
WO WO-03/020763 A2 3/2003
WO WO-03/057171 A2 7/2003
WO WO-2004/002627 A2 1/2004
WO WO-2004/015075 A2 2/2004
WO WO-2004/033685 A1 4/2004
WO WO-2004/044004 A2 5/2004
WO WO-2004/074322 A1 9/2004
WO WO-2005/113595 A2 12/2005
WO WO-2005/114215 A2 12/2005
WO WO-2006/000830 A2 1/2006
WO WO-2006/125962 A2 11/2006
WO WO-2007/089541 A2 8/2007
WO WO-2008/038002 A2 4/2008
WO WO-2008/039818 A2 4/2008
WO WO-2008/042156 A1 4/2008
WO WO-2008/042973 A2 4/2008
WO WO-2011/008730 A2 1/2011
WO WO-2011/028929 A2 3/2011
WO WO-2011/141027 A1 11/2011
WO WO-2011/146862 A1 11/2011
WO WO-2012/058460 A2 5/2012
WO WO-2012/079000 A1 6/2012
WO WO-2012/135025 A2 10/2012
WO WO-2013/039889 A1 3/2013
WO WO-2013/040371 A2 3/2013

(56) References Cited

FOREIGN PATENT DOCUMENTS

| | | | |
|---|---|---|---|
| WO | WO-2013/044225 | A1 | 3/2013 |
| WO | WO-2013/093648 | A2 | 6/2013 |
| WO | WO-2013/154760 | A1 | 10/2013 |
| WO | WO-2013/166321 | A1 | 11/2013 |
| WO | WO-2013/176915 | A1 | 11/2013 |
| WO | WO-2014/011987 | A1 | 1/2014 |
| WO | WO-2014/018423 | A1 | 1/2014 |
| WO | WO-2014/018423 | A2 | 1/2014 |
| WO | WO-2014/018863 | A1 | 1/2014 |
| WO | WO-2014/047556 | A1 | 3/2014 |
| WO | WO-2014/047561 | A1 | 3/2014 |
| WO | WO-2014/059173 | A2 | 4/2014 |
| WO | WO-2014/083173 | A1 | 6/2014 |
| WO | WO-2014/093622 | A2 | 6/2014 |
| WO | WO-2014/118272 | A1 | 8/2014 |
| WO | WO-2014/133567 | A1 | 9/2014 |
| WO | WO-2014/133568 | A1 | 9/2014 |
| WO | WO-2014/134165 | A1 | 9/2014 |
| WO | WO-2014/143158 | A1 | 9/2014 |
| WO | WO-2014/172606 | A1 | 10/2014 |
| WO | WO-2014/184744 | A1 | 11/2014 |
| WO | WO-2014/186366 | A1 | 11/2014 |
| WO | WO-2014/191128 | A1 | 12/2014 |
| WO | WO-2014/210353 | A2 | 12/2014 |
| WO | WO-2015/050998 | A2 | 4/2015 |
| WO | WO-2015/057834 | A1 | 4/2015 |
| WO | WO-2015/057852 | A1 | 4/2015 |
| WO | WO-2015/070083 | A1 | 5/2015 |
| WO | WO-2015/089351 | A1 | 6/2015 |
| WO | WO-2015/089419 | A1 | 6/2015 |
| WO | WO-2015/089427 | A1 | 6/2015 |
| WO | WO-2015/120096 | A2 | 8/2015 |
| WO | WO-2015/142675 | A1 | 9/2015 |
| WO | WO-2015/158671 | A1 | 10/2015 |
| WO | WO-2015/187528 | A1 | 12/2015 |
| WO | WO-2016/000304 | A1 | 1/2016 |
| WO | WO-2016/011210 | A2 | 1/2016 |
| WO | WO-2016/014789 | A2 | 1/2016 |
| WO | WO-2016/040476 | A1 | 3/2016 |
| WO | WO-2016/070061 | A1 | 5/2016 |
| WO | WO-2016/094867 | A1 | 6/2016 |
| WO | WO-2016/094874 | A1 | 6/2016 |
| WO | WO-2016/106236 | A1 | 6/2016 |
| WO | WO-2016/106244 | A1 | 6/2016 |
| WO | WO-2016/161516 | A1 | 10/2016 |
| WO | WO-2016/168584 | A1 | 10/2016 |
| WO | WO-2016/186745 | A1 | 11/2016 |
| WO | WO-2016/191756 | A1 | 12/2016 |
| WO | WO-2016/196388 | A1 | 12/2016 |
| WO | WO-2016/205613 | A1 | 12/2016 |
| WO | WO-2017/004916 | A1 | 1/2017 |
| WO | WO-2017/011804 | A1 | 1/2017 |
| WO | WO-2017/070395 | A1 | 4/2017 |
| WO | WO-2017/070632 | A2 | 4/2017 |
| WO | WO-2017/156336 | A1 | 9/2017 |
| WO | WO-2017/160689 | A1 | 9/2017 |
| WO | WO-2017/164936 | A1 | 9/2017 |
| WO | WO-2017/211900 | A1 | 12/2017 |
| WO | WO-2018/009399 | | 1/2018 |
| WO | WO-2018/028647 | A1 | 2/2018 |
| WO | WO-2018/197495 | | 11/2018 |
| WO | WO-2018/197520 | | 11/2018 |
| WO | WO-2019/034784 | | 2/2019 |
| WO | WO-2019/060450 | A1 | 3/2019 |
| WO | WO-2019/067011 | | 4/2019 |
| WO | WO-2019/071048 | A1 | 4/2019 |
| WO | WO-2019/076651 | | 4/2019 |
| WO | WO-2019/084058 | A2 | 5/2019 |
| WO | WO-2019/084063 | A1 | 5/2019 |
| WO | WO-2019/089761 | | 5/2019 |
| WO | WO-2019/094791 | A2 | 5/2019 |
| WO | WO-2019/126709 | A1 | 6/2019 |
| WO | WO-2019/126716 | A1 | 6/2019 |
| WO | WO-2019/126762 | A2 | 6/2019 |
| WO | WO-2019/126774 | A1 | 6/2019 |

OTHER PUBLICATIONS

Ihry RJ, et al. p53 inhibits CRISPR-Cas9 engineering in human pluripotent stem cells. Nat Med. Jul. 11, 2018 (Year: 2018).*

Savić N, Schwank G. Advances in therapeutic CRISPR/Cas9 genome editing. Transl Res. Feb. 2016;168:15-21. doi: 10.1016/j.trsl.2015.09.008. Epub Sep. 26, 2015. PMID: 26470680. (Year: 2015).*

Tycko J, Myer VE, Hsu PD. Methods for Optimizing CRISPR-Cas9 Genome Editing Specificity. Mol Cell. Aug. 4, 2016;63(3):355-70. doi: 10.1016/j.molcel.2016.07.004. PMID: 27494557; PMCID: PMC4976696. (Year: 2016).*

Shin J, Jiang F, Liu JJ, Bray NL, Rauch BJ, Baik SH, Nogales E, Bondy-Denomy J, Corn JE, Doudna JA. Disabling Cas9 by an anti-CRISPR DNA mimic. Sci Adv. Jul. 12, 2017;3(7):e1701620. doi: 10.1126/sciadv.1701620. PMID: 28706995; PMCID: PMC5507636. (Year: 2017).*

Abudayyeh et al., "A cytosine deaminase for programmable single-base RNA editing," Science, Jul. 26, 2019, vol. 365, No. 6451 (pp. 382-386).

Agathanggelou et al., "Expression of immune regulatory molecules in Epstein-Barr virus-associated nasopharyngeal carcinomas with prominent lymphoid stroma. Evidence for a functional interaction between epithelial tumor cells and infiltrating lymphoid cells," American Journal of Pathology, Oct. 1995, vol. 147, No. 4 (pp. 1152-1160).

Ahmad et al., "In silico modelling of drug-polymer interactions for pharmaceutical formulations," Journal of the Royal Society Interface, 2010, vol. 7 (pp. S423-S433).

Alba et al., "Gutless adenovirus: last-generation adenovirus for gene therapy," Gene therapy, 2005, vol. 12 (pp. S18-S27).

Alhasan et al., "Exosome Encased Spherical Nucleic Acid Gold Nanoparticle Conjugates as Potent MicroRNA Regulation Agents," Jan. 15, 2014, vol. 10, No. 1 (pp. 186-192).

Allerson et al., "Fully 2'-Modified Oligonucleotide Duplexes with Improved in Vitro Potency and Stability Compared to Unmodified Small Interfering RNA," American Chemical Society, Journal of Medicinal Chemistry, Feb. 2005, vol. 48 (pp. 901-904).

Altman et al., "Phenotypic Analysis of Antigen-specific T Lymphocytes," Science, Oct. 4, 1996, vol. 274, No. 5284 (pp. 94-96).

Altschul et al., "Basic Local Alignment Search Tool", Journal of Molecular Biology, 1990, pp. 403-410, vol. 215, 1990 Academic Press Limited.

Alvarez-Erviti et al., "Delivery of siRNA to the mouse brain by systemic injection of targeted exosomes," Nature Biotechnology, 2011, vol. 29, No. 4 (pp. 341-345).

Amalfitano et al., "Production and characterization of improved adenovirus vectors with the E1, E2b, and E3 genes deleted," Journal of Virology, Feb. 1998, vol. 72, No. 2 (pp. 926-933).

Amann et al., "Tightly regulated tac promoter vectors useful for the expression of unfused and fused proteins in *Escherichia coli*," Gene, Jun. 15, 1988, vol. 69 (pp. 301-315).

Anders et al., "Structural plasticity of PAM recognition by engineered variants of the RNA-guided endonuclease Cas9," Molecular Cell, Mar. 17, 2016, vol. 61, No. 6 (pp. 895-902).

Andersen et al., "Parallel detection of antigen-specific T cell responses by combinatorial encoding of MHC multimers," Nature Protocols, vol. 7, No. 5, 2012 (pp. 891-902).

Anzalone et al., "Genome editing with CRISPR-Cas nucleases, base editors, transposases and prime editors," Nature Biotechnology, Jul. 2020, vol. 38, No. 7 (pp. 824-844).

Ausubel, "A botanical macroscope" Proceedings of the National Academy of Sciences, Aug. 4, 2009, vol. 106, No. 31 (pp. 12569-12570).

Azzouz et al., "Multicistronic Lentiviral Vector-Mediated Striatal Gene Transfer of Aromatic I-Amino Acid Decarboxylase, Tyrosine Hydroxylase, and GTP Cyclohydrolase I Induces Sustained Transgene Expression, Dopamine Production, and Functional Improvement in a Rat Model of Parkinson's Disease," Journal of Neuroscience, Dec. 1, 2002, vol. 22, No. 23 (pp. L10302-L10312).

Baba et al., "Highly Enhanced Expression of CD70 on Human T-Lymphotropic Virus Type 1-Carrying T-Cell Lines and Adult T-Cell Leukemia Cells," Journal of Virology, Apr. 2008, vol. 82, No. 8 (pp. 3843-3852).

(56) References Cited

OTHER PUBLICATIONS

Balaggan et al., "Ocular gene delivery using lentiviral vectors," Gene Therapy, Feb. 2012, vol. 19, No. 2 (pp. 145-153.
Balaggan et al., "Stable and efficient intraocular gene transfer using pseudotyped EIAV lentiviral vectors," The Journal of Gene Medicine, Mar. 2006, vol. 8, No. 3 (pp. 275-285).
Balague et al., "Sustained high-level expression of full-length human factor VIII and restoration of clotting activity in hemophilic mice using a minimal adenovirus vector," Blood, The Journal of the American Society of Hematology, Feb. 1, 2000, vol. 95, No. 3 (pp. 820-828).
Baldari et al., "A novel leader peptide which allows efficient secretion of a fragment of human interleukin 1 beta in *Saccharomyces cerevisiae*", EMBO Journal, Jan. 1, 1987, vol. 6, No. 1 (pp. 229-234).
Bamford et al., "The COSMIC (Catalogue of Somatic Mutations in Cancer) database and website", British Journal of Cancer, vol. 91, 2004, pp. 355-358.
Banerji et al., "A lymphocyte-specific cellular enhancer is located downstream of the joining region in immunoglobulin heavy chain genes," Cell, Jul. 1983, vol. 33, No. 3 (pp. 729-740).
Bartlett et al., "Impact of tumor-specific targeting on the biodistribution and efficacy of siRNA nanoparticles measured by multimodality in vivo imaging," Proceedings of the National Academy of Sciences, USA, Sep. 25, 2007, vol. 104, No. 39 (pp. 15549-15554).
Bates et al., "Carbon nanotubes as vectors for gene therapy: past achievements, present challenges and future goals," Advanced Drug Delivery Reviews, Dec. 2013, vol. 65, No. 15 (pp. 2023-2033).
Bawage et al., "Synthetic mRNA expressed Cas13a mitigates RNA virus infections," bioRxiv, posted Jul. 23, 2018 (pp. 1-9).
Behlke et al., "Chemical Modification of siRNAs for In Vivo Use", Oligonucleotides, 2008 vol. 18 (pp. 305-320).
Ben-David et al., "Genetic and transcriptional evolution alters cancer cell line drug response," Nature, Aug. 2018, vol. 560, No. 7718 (pp. 325-330).
Ben-David et al., "Genomic evolution of cancer models: perils and opportunities," Nature Reviews, Cancer, Feb. 2019, vol. 19, No. 2 (pp. 97-109).
Ben-David et al., "The landscape of chromosomal aberrations in breast cancer mouse models reveals driver-specific routes to tumorigenesis," Nature Communications, Jul. 4, 2016, vol. 7, No. 12160 (pp. 1-13).
Bender et al., "Receptor-Targeted Nipah Virus Glycoproteins Improve Cell-Type Selective Gene Delivery and Reveal a Preference for Membrane-Proximal Cell Attachment," PLOS Pathogens, Jun. 9, 2016, vol. 12 (pp. 1-28).
Bennetzen et al., "The primary structure of the *Saccharomyces cerevisiae* gene for alcohol dehydrogenase," Journal of Biological Chemistry, Mar. 25, 1982, vol. 257, No. 6 (pp. 3018-3025).
Berdeja et al., "Durable Clinical Responses in Heavily Pretreated Patients with Relapsed/Refractory Multiple Myeloma: Updated Results from a Multicenter Study of bb2121 Anti-Bcma CAR T Cell Therapy," Blood, 2017, vol. 130 (740 pages—Abstract).
Besser et al., "Clinical responses in a phase II study using adoptive transfer of short-term cultured tumor infiltration lymphocytes in metastatic melanoma patients," Clinical Cancer Research, May 1, 2010, vol. 16, No. 9 (pp. 2646-2655).
Betchen et al., "Future and current surgical therapies in Parkinson's disease," Current Opinion in Neurology, 2003, vol. 16 (pp. 487-493).
Birrell et al., "A genome-wide screen in Saccharomyces cerevisiae for genes affecting UV radiation sensitivity," Proceedings of the National Academy of Sciences, USA, Oct. 23, 2001, vol. 98, No. 22 (pp. 12608-12613).
Blundell, et al., "Knowledge-Based Protein Modelling and Design," Eur. J. Biochem., (1988), 172:513-520.
Boni et al., "Adoptive transfer of allogeneic tumor-specific T cells mediates effective regression of large tumors across major histocompatibility barriers," Blood, Dec. 1, 2008, vol. 112, No. 12 (pp. 4746-4754).
Boshart et al., "A Very Strong Enhancer Is Located Upstream of an Immediate Early Gene of Human Cytomegalovirus", Cell, Jun. 1985 vol. 41 (pp. 521-530).
Bramsen et al., "Development of Therapeutic-Grade Small Interfering RNAs by Chemical Engineering," Frontiers in Genetics, Aug. 20, 2012, vol. 3, Article 154 (pp. 1-22).
Buchholz et al., "Surface-engineered viral vectors for selective and cell type-specific gene delivery," Trends in Biotechnology, 2015, vol. 33 (pp. 777-790).
Buchschacher et al., "Human Immunodeficiency Virus Vectors for Inducible Expression of Foreign Genes," Journal of Virology, May 1992, vol. 66, No. 5 (pp. 2731-2739).
Buckholz et al., "Yeast systems for the commercial production of heterologous proteins," Biotechnology, 1991, vol. 9, No. 11 (pp. 1067-1072).
Budde et al., "Combining a CD20 Chimeric Antigen Receptor and an Inducible Caspase 9 Suicide Switch to Improve the Efficacy and Safety of T Cell Adoptive Immunotherapy for Lymphoma," PLoS ONE, 2013, vol. 8, No. 12, e82742 (10 pages).
Buenrostro et al. "Transposition of native chromatin for fast and sensitive epigenomic profiling of open chromatin, DNA-binding proteins and nucleosome position," Nature Methods, Dec. 2013, vol. 10, No. 12 (pp. 1213-1218).
Buenrostro et al., "Single-cell chromatin accessibility reveals principles of regulatory variation," Nature, Jul. 23, 2015, vol. 523, No. 7561 (pp. 486-490).
Buning et al., "Engineering the AAV capsid to optimize vector-host-interactions," Current Opinion in Pharmacology, Oct. 2015, vol. 24 (pp. 94-104).
Bunz et al., "Requirement for p53 and p21 to sustain G2 arrest after DNA damage," Science, Nov. 20, 1998, vol. 282 (pp. 1497-1501).
Byrne et al., "Multiplex gene regulation: a two-tiered approach to transgene regulation in transgenic mice," Proceedings of the National Academy of Sciences, USA, Jul. 1989, vol. 86 (pp. 5473-5477).
Caliando et al., "Targeted DNA degradation using a CRISPR device stably carried in the host genome," Nature Communications, May 19, 2015, vol. 6, No. 6989 (pp. 1-10).
Cameron et al., "Mapping the genomic landscape of CRISPR-Cas9 cleavage," Nature Methods, Advanced Online Publication, May 1, 2017, vol. 14 (pp. 1-10).
Campbell et al., "Codon Usage in Higher Plants, Green Algae, and Cyanobacteria," Plant Physiology, Jan. 1990, vol. 92, No. 1 (pp. 1-11).
Camper et al., "Postnatal repression of the alpha-fetoprotein gene is enhancer independent," Genes & Development, 1989, vol. 3 (pp. 537-546).
Canela et al., "DNA breaks and end resection measured genome-wide by end sequencing," Molecular Cell, 2016, vol. 63 (pp. 898-911).
Cao et al., "Comprehensive single cell transcriptional profiling of a multicellular organism by combinatorial indexing," bioRxiv preprint first posted online Feb. 2, 2017 (35 pages).
Cao et al., "Comprehensive single-cell transcriptional profiling of a multicellular organism," Science, Aug. 18, 2017, vol. 357, No. 6352 (pp. 661-667).
Capone et al., "Expression in different populations of cells of the root meristem is controlled by different domains of the rolB promoter," Plant Molecular Biology, Jul. 1994, vol. 25 (pp. 681-691).
Carr et al., "Genome Engineering," Nature Biotechnology, Dec. 2009, vol. 27, No. 12 (pp. 1151-1162).
Casas et al., "Transgenic sorghum plants via microprojectile bombardment," Proceedings of the National Academy of Sciences, Dec. 1, 1993, vol. 90, No. 23 (pp. 11212-11216).
CBOL Plant Working Group, "A Dna barcode for land plants," Proceedings of the National Academy of Sciences, Aug. 4, 2009, vol. 106, No. 31 (pp. 12794-12797).
Cekaite et al., "Gene expression analysis in blood cells in response to unmodified and 2'-modified siRNAs reveals TLR-dependent and independent effects," Journal of Molecular Biology, 2007, vol. 365 (pp. 90-108).

(56) References Cited

OTHER PUBLICATIONS

Chahlavi et al., "Glioblastomas Induce T-Lymphocyte Death by Two Distinct Pathways Involving Gangliosides and CD70," Cancer Research, Jun. 15, 2005, vol. 65, No. 12 (pp. 5428-5438).
Chamoun-Emaneulli et al., "In vitro incorporation of a cell-binding protein to a lentiviral vector using an engineered split intein enables targeted delivery of genetic cargo," Biotechnology and Bioengineering, 2015, vol. 112 (pp. 2611-2617).
Chen et al., "Predicting Peptide-Mediated Interactions on a Genome-Wide Scale," PLOS Computational Biology, May 4, 2015, vol. 11, No. 5, e1004248 (pp. 1-13).
Chen et al., "Enhanced proofreading governs CRISPR-Cas9 targeting accuracy," Nature, Sep. 20, 2017, vol. 550 (pp. 407-410).
Chin et al., "Optimized Mitochondrial Targeting of Proteins Encoded by Modified mRNAs Rescues Cells Harboring Mutations in mtATP6," Cell Reports, Mar. 13, 2018, vol. 22, No. 11 (pp. 2818-2826).
Cho et al., "A degron created by SMN2 exon 7 skipping is a principal contributor to spinal muscular atrophy severity," Genes and Development, 2010, vol. 24 (pp. 438-442).
Choi et al., "Mechanism for the endocytosis of spherical nucleic acid nanoparticle conjugates," Proceedings of the National Academy of Sciences, USA, May 7, 2013 Vol. 110, No. 19 (pp. 7625-7630).
Choi et al., "Targeted genomic rearrangements using CRISPR/Cas technology," Nature Communications, Apr. 2014, vol. 5, No. 3728 (pp. 1-6).
Chu et al., "Efficient Generation of Rosa26 Knock-in Mice using Crispr/Cas9 in C57bl/6 Zygotes," BMC Biotechnology, Jan. 16, 2016, vol. 16, No. 4 (15 pages).
Chung et al., "Tunable and reversible drug control of protein production via a self-excising degron," Nature Chemical Biology 2015, vol. 11, No. 9 (pp. 713-720).
Cibulskis et al. "Sensitive Detection of Somatic Point Mutations in Impure and Heterogeneous Cancer Samples," Nature Biotechnology, 2013, vol. 31, No. 3 (pp. 213-219).
Cideciyan et al., "Vision 1 year after gene therapy for Leber's congenital amaurosis," New England Journal of Medicine, 2009, vol. 361, No. 7 (pp. 725-727).
Claeboe et al., "3'-Modified oligonucleotides by reverse DNA synthesis," Nucleic Acids Research, Oct. 1, 2003, vol. 31, No. 19 (pp. 5685-5691).
Cockrell et al., "Gene delivery by lentivirus vectors," Molecular biotechnology, 2007, vol. 36 (pp. 184-204).
Cong et al., "CRISPR-Assisted Mammalian Genome Engineering," published as "Multiplex Genome Engineering Using CRISPR-Cas Systems," Science, Oct. 5, 2012, vol. 339 (pp. 819-823) [Manuscript including Supplementary Materials—36 pages].
Cooney et al., "Hybrid nonviral/viral vector systems for improved piggyBac DNA transposon in vivo delivery," Molecular Therapy, 2015, vol. 23, No. 4 (pp. 667-674).
Cooper et al., "T-cell clones can be rendered specific for CD19: Toward the selective augmentation of the graft-versus-lineage leukemia effect," Blood, Feb. 15, 2003, vol. 101, No. 4 (pp. 1637-1644).
Cox et al., "RNA editing with CRISPR-Cas13," Science, Nov. 24, 2017, vol. 358, No. 6366 (pp. 1019-1027).
Crane et al., "Rescue administration of a helper-dependent adenovirus vector with long-term efficacy in dogs with glycogen storage disease type la," Gene therapy, 2012, vol. 19, No. 4 (pp. 443-452).
Crosetto et al., "Nucleotide-resolution DNA double-strand break mapping by next-generation sequencing," Nature methods, Apr. 2013, vol. 10, No. 4 (pp. 361-365).
Croyle et al., "PEGylated helper-dependent adenoviral vectors: highly efficient vectors with an enhanced safety profile," Gene Therapy, 2005, vol. 12 (pp. 579-587).
Cusanovich et al., "Multiplex single-cell profiling of chromatin accessibility by combinatorial cellular indexing" Science, May 22, 2015, vol. 348, No. 6237 (pp. 910-914).
Cutler et al., "Polyvalent nucleic acid nanostructures," Journal of the American Chemical Society, Jun. 22, 2011, vol. 133, No. 24 (pp. 9254-9257).
Cutler et al., "Spherical Nucleic Acids," Journal of the American Chemical Society 2012, vol. 134, No. 3 (pp. 1376-1391).
D'Astolfo et al., "Efficient Intracellular Delivery of Native Proteins," Cell, Apr. 23, 2015 vol. 161 (pp. 674-690).
Dahlman et al., "In vivo endothelial siRNA delivery using polymeric nanoparticles with low molecular weight," Nature Nanotechnology, 2014, vol. 9 (pp. 648-655).
Dar et al.—Abstract 1540: Allogeneic chimeric antigen receptor T cells targeting B cell maturation antigen American Association of Cancer Research, Poster Presentations—Proffered Abstracts, Jul. 1, 2018 (3 pages).
Davey et al., "Direct DNA transfer to plant cells," Plant Molecular Biology, Sep. 1989, vol. 13, No. 3 (pp. 273-285).
Davis et al., "Evidence of RNAi in humans from systemically administered siRNA via targeted nanoparticles," Nature, Apr. 15, 2010, vol. 464, No. 7291 (pp. 1067-1070).
De Veylder et al., "Herbicide Safener-Inducible Gene Expression in *Arabidopsis thaliana,*" Plant Cell Physiology, 1997, vol. 38, No. 5 (pp. 568-577).
Dellinger et al., "Streamlined process for the chemical synthesis of RNA using 2'-O-thionocarbamate-protected nucleoside phosphoramidites in the solid phase," Journal of the American Chemical Society, Aug. 3, 2011, vol. 133, No. 30 (pp. 11540-11556).
Dempster et al., "Extracting Biological Insights from the Project Achilles Genome-Scale CRISPR Screens in Cancer Cell Lines," bioRxiv, posted Jul. 31, 2019 (pp. 1-35).
Deng et al., "CASFISH: CRISPR/Cas9-mediated in situ labeling of genomic loci in fixed cells," Proceedings of the National Academy of Sciences, USA, Sep. 22, 2015, vol. 112, No. 38 (pp. 11870-11875).
Depristo et al., "A framework for variation discovery and genotyping using next-generation DNA sequencing data" Nature Genetics, May 2011, vol. 43, No. 5 (pp. 491-498).
Deshpande et al., "Current trends in the use of liposomes for tumor targeting," Nanomedicine, Sep. 2013, vol. 8, No. 9 (32 pages).
Devereux, J., et al., A comprehensive set of sequence analysis programs for the VAX, Nucleic Acids Research, 1984, vol. 12, Issue 1, pp. 387-395.
Dey et al., "Toward a 'Structural BLAST' Using structural relationships to infer function," Protein Science, 2013, vol. 22 (pp. 359-366).
Di Stasi et al., "Inducible apoptosis as a safety switch for adoptive cell therapy," Clinical Trial, New England Journal of Medicine, Nov. 3, 2011, vol. 365, No. 18 (pp. 1673-1683).
Digiusto et al., "RNA-Based Gene Therapy for HIV with Lentiviral Vector-Modified CD34(+) Cells in Patients Undergoing Transplantation for AIDS-Related Lymphoma," Science Translational Medicine, Jun. 16, 2010, vol. 2, No. 36 (pp. 1-18).
Doench et al., "Optimized sgRNA design to maximize activity and minimize off-target effects of CRISPR-Cas9," Nature Biotechnology, Feb. 2016, vol. 34, No. 2 (pp. 184-191).
Doench et al., "Rational design of highly active sgRNAs for CRISPR-Cas9-mediated gene inactivation," Nature Biotechnology, 2014, vol. 32 (pp. 1262-1267) [including Supplementary Material, 17 pages].
Doman et al., "Evaluation and minimization of Cas9-independent off-target DNA editing by cytosine base editors," Nat Biotechnology, May 2020 ;38(5):620-628.
Doyle et al., "Evidence of evolutionary constraints that influences the sequence composition and diversity of mitochondrial matrix targeting signals," PLoS ONE, Jun. 2013, vol. 8, No. 6, e67938 (pp. 1-8).
Du et al., "Label-free dendrimer-like silica nanohybrids for traceable and controlled gene delivery," Biomaterials, Jul. 2014, vol. 35, No. 21 (pp. 5580-5590).
Dudley et al., "Adoptive Cell Transfer Therapy Following Non-Myeloablative but Lymphodepleting Chemotherapy for the Treatment of Patients with Refractory Metastatic Melanoma," Journal of Clinical Oncology, Apr. 1, 2005, vol. 23, No. 10 (pp. 2346-2357).

(56) References Cited

OTHER PUBLICATIONS

Dudley et al., "Cancer regression and autoimmunity in patients after clonal repopulation with antitumor lymphocytes," Science, 2002, vol. 298, No. 5594 (pp. 850-854).
Durfee et al., "Mesoporous Silica Nanoparticle-Supported Lipid Bilayers (Protocells) for Active Targeting and Delivery to Individual Leukemia Cells," ACS Nano, Sep. 27, 2016, vol. 10, No. 9 (pp. 8325-8345).
Edd et al., "Controlled encapsulation of single-cells into monodisperse picolitre drops," Lab Chip, 2008, vol. 8, No. 8 (pp. 1262-1264).
Edlund et al., "Cell-Specific Expression of the Rat Insulin Gene: Evidence for Role of Two Distinct 5' Flanking Elements," Science, Nov. 22, 1985, vol. 230, No. 4728 (pp. 912-916).
Ehrhardt et al., "Somatic integration from an adenoviral hybrid vector into a hot spot in mouse liver results in persistent transgene expression levels in vivo," Molecular Therapy, Jan. 2007, vol. 15, No. 1 (pp. 146-156).
El-Andaloussi et al., "Exosome-mediated delivery of siRNA in vitro and in vivo," Nature Protocols, Dec. 2012, vol. 7, No. 12 (pp. 2112-2126).
Elkon et al., "Dissection of a DNA-damage-induced transcriptional network using a combination of microarrays, RNA interference and computational promoter analysis," Genome Biology, 2005, vol. 6, No. R43 (pp. 1-8).
Enache et al., "Cas9 activates the p53 pathway and selects for p53-inactivating mutations," Nature Genetics, Jul. 2020, vol. 52, No. 7 (pp. 662-668).
Enache et al., "The GCTx format and cmap {Py, R, M, J} packages: resources for optimized storage and integrated traversal of annotated dense matrices," Bioinformatics, Apr. 2019, vol. 35, No. 8 (pp. 1427-1429).
Enkirch et al., "Targeted lentiviral vectors pseudotyped with the Tupaia paramyxovirus glycoproteins," Gene therapy, 2013, vol. 20, pp. 16-23 [Dissertation attached—pp. 1-125].
Eyquem et al., "Targeting a CAR to the TRAC Locus with CRISPR/Cas9 Enhances Tumour Rejection," Nature, Mar. 2, 2017, vol. 543, No. 7643 (pp. 113-117).
Finn et al., "A Single Administration of CRISPR/Cas9 Lipid Nanoparticles Achieves Robust and Persistent In Vivo Genome Editing," Cell Reports, Cell Press, 2018, vol. 22 (pp. 2227-2235).
Flotte et al., "A phase I study of an adeno-associated virus-cftr gene vector in adult cf patients with mild lung disease. Johns Hopkins Children's Center, Baltimore, Maryland," Human Gene Therapy, 1996, vol. 7 (pp. 1145-1159).
Fortman et al., "A Regulated, Ubiquitin-Independent Degron in I-kappaB-alpha," Journal of Molecular Biology, Aug. 28, 2015, vol. 427, No. 17 (pp. 2748-2756).
Friedman et al., "Effective Targeting of Multiple BCMA-Expressing Hematological Malignancies by Anti-BCMA CAR T Cells," Human Gene Therapy, Mar. 8, 2018, vol. 29, No. 5 (pp. 585-601).
Friedrich et al., "DARPin-targeting of measles virus: unique bispecificity, effective oncolysis, and enhanced safety," Molecular Therapy, Apr. 2013, vol. 21, No. 4 (pp. 849-859).
Frock et al., "Genome-wide Detection of DNA Double-Stranded Breaks Induced by Engineered Nucleases," Nature Biotechnology, Dec. 15, 2014, vol. 33, No. 2 (pp. 179-186).
Fu et al., "Gene expression regulation mediated through reversible m6A RNA methylation," Nature Reviews Genetics, Mar. 25, 2014, vol. 15, No. 5 (pp. 293-306).
Fu et al., "Linear transgene constructs lacking vector backbone sequences generate low-copy-number transgenic plants with simple integration patterns," Transgenic Research, Feb. 2000, vol. 9, No. 1 (pp. 11-19).
Fukuda et al., "Supplementary Information to Construction of a guide-RNA for site-directed RNA mutagenesis utilising intracellular A-to-I RNA editing", Scientific Reports, Feb. 2, 2017, vol. 7, No. 41478 (pp. 1-49).
Fukui, K., "DNA mismatch repair in eukaryotes and bacteria," Journal of Nucleic Acids, 2010, vol. 2010, No. 260512 (pp. 1-16).
Funes et al., "The typically mitochondrial DNA-encoded ATP6 subunit of the F1F0-ATPase is encoded by a nuclear gene in Chlamydomonas reinhardtii," Journal of Biological Chemistry, Feb. 22, 2002, vol. 277, No. 8 (pp. 6051-6058).
Funke et al., "Targeted Cell Entry of Lentiviral Vectors," Molecular Therapy, Aug. 2008, vol. 16, No. 8 (pp. 1427-1436).
Galanis et al., "Duplication of leader sequence for protein targeting to mitochondria leads to increased import efficiency," FEBS letters, May 1991, vol. 282, No. 2 (pp. 425-430).
Gao et al., "Antibody-Targeted Immunoliposomes for Cancer Treatment," Mini-Reviews in Medicinal Chemistry, Dec. 2013, vol. 13, No. 14 (pp. 2026-2035).
Gao et al., "Engineered Cpf1 Enzymes with Altered PAM Specificities," BioRxiv Preprint, doi:https://doi.org/10.1101/091611, posted Dec. 4, 2016 (pp. 1-17).
Gao et al., "Engineered Cpf1 Enzymes with Altered PAM Specificities," Nature Biotechnology, Aug. 2017, vol. 35, No. 8 (pp. 789-792).
Garrett et al., "Exploring uptake mechanisms of oral nanomedicines using multimodal nonlinear optical microscopy," Journal of Biophotonics, 2012, vol. 5, Nos. 5-6 (pp. 458-468).
Garrett et al., "Label-free imaging of polymeric nanomedicines using coherent anti-stokes Raman scattering microscopy," Journal of Raman Spectroscopy, 2012, vol. 43, No. 5 (pp. 681-688).
Gatz et al., "Regulation of a modified CaMV 35S promoter by the Tn10-encoded Tet repressor in transgenic tobacco," Molecular and General Genetics MGG, 1991, vol. 227 (pp. 229-237).
Gaudelli et al., "Programmable base editing of A-T to G-C in genomic DNA without DNA cleavage," Nature, Nov. 23, 2017, vol. 551, No. 7681 (pp. 464-471).
Geisbert et al., "Postexposure protection of non-human primates against a lethal Ebola virus challenge with RNA interference: a proof-of-concept study," The Lancet, May 2010, vol. 375, No. 9729 (pp. 1896-1905).
Genbank identifier NM_006139 *Homos Sapiens* CD28 molecule (CD28), transcript variant1, mRNA (6 pages).
Georgiadis et al., "Long Terminal Repeat CRISPR-CAR-Coupled 'Universal' T Cells Mediate Potent Anti-leukemic Effects," Molecular Therapy, May 2, 2018 vol. 26, No. 5 (pp. 1215-1227).
Giacomelli et al., "Mutational processes shape the landscape of TP53 mutations in human cancer," Nature Genetics, Oct. 2018, vol. 50, No. 10 (pp. 1381-1387).
Giaever et al., "Functional profiling of the *Saccharomyces cerevisiae* genome," Nature, Jul. 25, 2002, vol. 418 (pp. 387-391).
Gierahn et al., "Seq-Well: Portable, Low-Cost RNA Sequencing of Single Cells at High Throughput," Nature Methods, Apr. 2017, vol. 14, No. 4 (8 pages).
Girard-Gagnepain et al., "Baboon envelope pseudotyped LVs outperform VSV-G-LVs for gene transfer into early-cytokine-stimulated and resting HSCs," Blood, Aug. 21, 2014, vol. 124, No. 8 (pp. 1221-1231).
Gorleku et al., "Endoplasmic reticulum localization of DHHC palmitoyltransferases mediated by lysine-based sorting signals," Journal of Biological Chemistry, November Nov. 11, 2011, vol. 286, No. 45 (pp. 39573-39584).
Greco et al., "Improving the safety of cell therapy with the TK-suicide gene," Frontiers in Pharmacology, May 5, 2015, vol. 6, No. 95 (13 pages).
Greer, J., "Model Structure for the Inflammatory Protein C5a," Science, (1985), 228: 1055-1060.
Grimm et al., "In vitro and in vivo gene therapy vector evolution via multispecies interbreeding and retargeting of adeno-associated viruses," Journal of Virology, 2008, vol. 82, No. 12 (pp. 5887-5911).
Gruber et al., "The Vienna RNA Websuite," Nucleic Acids Research, Apr. 19, 2008, vol. 36 (pp. W70-W74).
Grunebaum et al., "Recent advances in understanding and managing adenosine deaminase and purine nucleoside phosphorylase deficiencies," Current Opinion in Allergy and Clinical Immunology, Dec. 2013, vol. 13, No. 6 (pp. 630-638).
Guo et al., "Droplet microfluidics for high-throughput biological assays" Lab Chip, 2012, vol. 12 (pp. 2146-2155).

(56) References Cited

OTHER PUBLICATIONS

Habib et al., "Div-Seq: Single-nucleus RNA-Seq reveals dynamics of rare adult newborn neurons," Science, Aug. 26, 2016, vol. 353, No. 6302 (pp. 925-928).
Habib et al., "Massively parallel single-nucleus RNA-seq with DroNc-seq," Nature Methods, Oct. 2017, vol. 14, No. 10 (pp. 955-958).
Hanawa et al., "Comparison of various envelope proteins for their ability to pseudotype lentiviral vectors and transduce primitive hematopoietic cells from human blood," Molecular Therapy, Mar. 2002, vol. 5, No. 3 (pp. 242-251).
Hao et al., "Nucleic Acid-Gold Nanoparticle Conjugates as Mimics of microRNA," Small, Nov. 18, 2011, vol. 7, No. 22 (pp. 3158-3162).
Harris et al., "RNA Editing Enzyme APOBEC1 and Some of Its HOMOLOGS Can Act as DNA Mutators," Molecular Cell, Nov. 2002, vol. 10 (pp. 1247-1253).
Hashimshony, et al., "CEL-Seq: Single-Cell RNA-Seq by Multiplexed Linear Amplification," Cell Reports, 2012, vol. 2, No. 3 (pp. 666-673).
He et al., "Conjugation and Evaluation of Triazole-Linked Single Guide RNA for CRISPR-Cas9 Gene Editing," Chembiochem, Oct. 4, 2016, vol. 17, No. 19 (pp. 1809-1812).
Hendel et al., "Chemically modified guide RNAs enhance CRISPR-Cas genome editing in human primary cells," Nature Biotechnology, Sep. 2015, vol. 33, No. 9 (pp. 985-989).
Hermonat & Muzyczka, "Use of adeno-associated virus as a mammalian DNA cloning vector" Transduction of neomycin resistance into mammalian tissue culture cells, Proceedings of the National Academy of Sciences USA, 1984, vol. 81 (pp. 6466-6470).
Hicke et al., "Escort aptamers: a delivery service for diagnosis and therapy," The Journal of Clinical Investigation, Oct. 2000, vol. 106, No. 8 (pp. 923-928).
Higgins et al., "CLUSTAL: a package for performing multiple sequence alignment on a microcomputer," Gene, Dec. 15, 1998, vol. 73, No. 1 (pp. 237-244).
Hinrichs et al., "Exploiting the curative potential of adoptive T-cell therapy for cancer," Immunological Reviews, Jan. 2014, vol. 257, No. 1 (pp. 56-71).
Hirano et al., "Structural basis for the altered PAM specificities of engineered CRISPR-Cas9," Molecular cell, Mar. 17, 2016, vol. 61, No. 6 (pp. 886-894).
Hirel et al., "Forcing expression of a soybean root glutamine synthetase gene in tobacco leaves induces a native gene encoding cytosolic enzyme," Plant Molecular Biology, 1992, vol. 20 (pp. 207-218).
Horwell et al., "The 'peptoid' approach to the design of non-peptide, small molecule agonists and antagonists of neuropeptides," Trends in Biotechnology, Apr. 1995, vol. 13, No. 4 (pp. 132-134).
Houot et al., "T-cell-based immunotherapy: adoptive cell transfer and checkpoint inhibition," Cancer Immunology Research, 2015, vol. 3, No. 10 (pp. 1115-1122).
Hsu et al., "DNA targeting specificity of RNA-guided Cas9 nucleases," Nature Biotechnology, Sep. 2013, vol. 31, No. 9 (pp. 827-832).
Huang et al., "Circularly Permuted and PAM-Modified Cas9 variants broaden the targeting scope of base editors," Nature Biotechnology, Jun. 2019, vol. 37, No. 6 (pp. 626-631).
Huang et al., "Precision Genome Editing Using Cytosine and Adenine Base Editors," Nature Protocols, Feb. 2021, vol. 16, No. 2 (pp. 1089-1128).
Huang et al., "The DAVID Gene Functional Classification Tool: a novel biological module-centric algorithm to functionally analyze large gene lists," Genome Biology, 2007 Vol. 8, No. RI83 (pp. 1-16).
Hughes et al., "Transfer of a TCR gene derived from a patient with a marked antitumor response conveys highly active T-cell effector functions," Human Gene Therapy, Apr. 2005, vol. 16, No. 4 (pp. 457-472).
Hunter et al., "High Levels of Soluble Immunoregulatory Receptors in Patients with Waldenstro¨M's Macroglobulinemia," Blood, Nov. 16, 2004, vol. 104, No. 11 (2 pages).
Iacovoni et al., "High-resolution profiling of gammaH2AX around DNA double strand breaks in the mammalian genome," The EMBO Journal, 2010, vol. 29, No. 8 (pp. 1446-1457).
Irving et al., "Engineering Chimeric Antigen Receptor T-Cells for Racing in Solid Tumors: Don't Forget the Fuel," Frontiers in Immunology, Apr. 3, 2017, vol. 8, Article 267 (19 pages).
Isaac et al., "Nucleosome breathing and remodeling constrain CRISPR-Cas9 function," eLife 2016, vol. 5, e13450 (pp. 1-14).
Islam et al., "Characterization of the single-cell transcriptional landscape by highly multiplex RNA-seq," Genome Research, 2011, vol. 21, No. 7 (pp. 1160-1167).
Islam et al., "Quantitative single-cell RNA-seq with unique molecular identifiers," Nature Methods, Feb. 2014, vol. 11, No. 2 (pp. 163-166).
Jayaraman et al., "Maximizing the potency of siRNA lipid nanoparticles for hepatic gene silencing in vivo," Angewandte Chemie, 2012, vol. 124 (pp. 8657-8661).
Jensen et al., "Design and Implementation of Adoptive Therapy with Chimeric Antigen Receptor-Modified T Cells," Immunological Reviews, Jan. 2014, vol. 257, No. 1 (32 pages).
Jensen et al., "Spherical nucleic acid nanoparticle conjugates as an RNAi-based therapy for glioblastoma," Science Translational Medicine, Oct. 30, 2013, vol. 5, No. 209 (pp. 1-22).
Jiang et al., "Chemical Modification of Adenine Base Editor mRNA and Guide RNA expand its application scope," Nature Communications, Apr. 24, 2020, vol. 11, Article 1979 (pp. 1-8).
Jin et al.,"CD70, a novel target of CAR T-cell therapy for gliomas," Neuro-Oncology Jan. 10, 2018, vol. 20, No. 1 (pp. 55-65).
Jinek et al., "RNA-programmed genome editing in human cells," eLife Research Article, Genetics and Genomics, Jan. 29, 2013, vol. 2, Reviewing editor: Detlef Weigel, Max Planck Institute for Developmental Biology, Germany (pp. 1-9).
Jinek, M., et al., Figures and figure supplements for: "RNA-programmed genome editing in human cells," eLIFE, vol. 2, Jan. 29, 2013, 5 pages.
Johann et al., "GLVR1, a receptor for gibbon ape leukemia virus, is homologous to a phosphate permease of Neurospora crassa and is expressed at high levels in the brain and thymus.," Journal of Virology, 1992, vol. 66, No. 3 (pp. 1635-1640).
Johnson et al., "Adjusting batch effects in microarray expression data using empirical Bayes methods," Biostatistics, Jan. 2007, vol. 8 (pp. 118-127).
Johnson et al., "Gene therapy with human and mouse T-cell receptors mediates cancer regression and targets normal tissues expressing cognate antigen," Blood, Jul. 2009, vol. 114, No. 3 (pp. 535-546).
Jonkers et al., "Cocal virus, a new agent in Trinidad related to vesicular stomatitis virus, type Indiana," American Journal of Veterinary Research, Jan. 1964, vol. 25 (pp. 236-242).
Judge et al., "Confirming the RNAi-mediated mechanism of action of siRNA-based cancer therapeutics in mice," The Journal of Clinical Investigation, Feb. 23, 2009, vol. 119, No. 3 (pp. 661-673).
Judge et al., "Design of noninflammatory synthetic siRNA mediating potent gene silencing in vivo," Molecular Therapy, 2006, vol. 13 (pp. 494-505).
Junker et al., "CD70: a new tumor specific biomarker for renal cell carcinoma," The Journal of Urology, Jun. 2005, vol. 173, No. 6 (pp. 2150-2153).
Kalisky et al., "Genomic Analysis at the Single-Cell Level," Annual Review of Genetics, 2011, vol. 45 (pp. 431-445).
Kalisky et al., "Single-cell genomics," Nature Methods, Apr. 2011, vol. 8, No. 4 (pp. 311-314).
Kalos et al., "T Cells with Chimeric Antigen Receptors Have Potent Antitumor Effects and Can Establish Memory in Patients with Advanced Leukemia," Science Translational Medicine, Aug. 10, 2011, vol. 3, No. 95 (12 pages).
Kamta et al. "Advancing Cancer Therapy with Present and Emerging Immuno-Oncology Approaches," Frontiers in Oncology, Apr. 18, 2017, vol. 7, No. 64 (15 pages).
Karczewski et al., "Variation across 141,456 human exomes and genomes reveals the spectrum of loss-of-function intolerance across human protein-coding genes," bioRxiv, Aug. 13, 2019 (pp. 1-44).

(56) References Cited

OTHER PUBLICATIONS

Kasaraneni et al., "A simple strategy for retargeting lentiviral vectors to desired cell types via a disulfide-bond-forming protein-peptide pair," Scientific Reports, Jul. 20, 2018, vol. 8 (pp. 1-9).
Kaufman et al., "Translational efficiency of polycistronic mRNAs and their utilization to express heterologous genes in mammalian cells," EMBO Journal, 1987, vol. 6, No. 1 (pp. 187-195).
Kawamata et al., "Temporal and spatial pattern of expression of the pea phenylalanine ammonia-lyase genel promoter in transgenic tobacco," Plant and cell physiology, 1997, vol. 38, No. 7 (pp. 792-803).
Kay et al., "Evidence for gene transfer and expression of factor IX in haemophilia B patients treated with an AAV vector," Nature Genetics, Mar. 2000, vol. 24 (pp. 257-261).
Keefe et al., "Aptamers as therapeutics," Nature Reviews, Jul. 2010, vol. 9 (pp. 537-550).
Kelley et al., "Versatility of chemically synthesized guide RNAs for CRISPR-Cas9 genome editing," Journal of Biotechnology, Sep. 2016, vol. 233, 10 (pp. 74-83).
Kessel et al., "Murine developmental control genes," Science, Jul. 1990, vol. 249 (pp. 374-379).
Kim et al. "Increasing the genome-targeting scope and precision of base editing with engineered Cas9-cytidine deaminase fusions," Nature Biotechnology, Feb. 13, 2017, vol. 35 (pp. 371-376).
Kim et al., "Digenome-seq: genome-wide profiling of CRISPR-Cas9 off-target effects in human cells," Nature Methods, Mar. 2015, vol. 12, No. 3 (pp. 237-243).
Kim et al., "Structural and Kinetic Characterization of *Escherichia coli* TadA, the Wobble-Specific tRNA Deaminase," Biochemistry, 2006, 45 (pp. 6407-6416).
Kim et al., "Highly efficient RNA-guided genome editing in human cells via delivery of purified Cas9 ribonucleoproteins," Genome Research, Jun. 2014, vol. 24, No. 6 (pp. 1012-1019).
Klein et al., "Droplet Barcoding for Single-Cell Transcriptomics Applied to Embryonic Stem Cells," Cell, 2015, vol. 161, No. 5 (pp. 1187-1201).
Klein et al., "High-velocity microprojectiles for delivering nucleic acids into living cells," Nature, May 1987, vol. 327 (pp. 70-73).
Kleinstiver et al., "Broadening *Staphylococcus aureus* Cas9 targeting range by modifying PAM recognition," Nature Biotechnology, Dec. 2015, vol. 33, No. 12 (pp. 1293-1298).
Kleinstiver et al., "Engineered CRISPR-Cas9 nucleases with altered PAM specificities," Nature, Jul. 23, 2015, vol. 523, No. 7561 (pp. 481-485).
Kleinstiver et al., "High-fidelity CRISPR-Cas9 variants with undetectable genome-wide off-targets," Nature, Jan. 28, 2016, vol. 529, No. 7587 (pp. 490-495).
Koch, "Combining morphology and DNA barcoding resolves the taxonomy of Western Malagasy Liotrigona Moure, 1961," African Invertebrates, Dec. 2010, vol. 51, No. 2 (pp. 413-421).
Kochenderfer et al., "Construction and Pre-clinical Evaluation of Anti-CD19 Chimeric Antigen Receptor," Journal of Immunotherapy, Sep. 2009, vol. 32, No. 7 (pp. 689-702).
Kogure et al., "Development of a non-viral multifunctional envelope-type nano device by a novel lipid film hydration method," Journal of Controlled Release, Aug. 11, 2004, vol. 98, No. 2 (pp. 317-323).
Komor et al., "Programmable editing of a target base in genomic DNA without double-stranded DNA cleavage," Nature, 2016, vol. 533 (pp. 420-424).
Konermann et al., "Genome-scale transcriptional activation by an engineered CRISPR-Cas9 complex," Nature, 2015, vol. 517 (pp. 583-588) [Including Supplemental information, 12 pages].
Koonin et al., "Origins and evolution of CRISPR-Cas systems," Philosophical Transactions of the Royal Society B. May 13, 2019, vol. 374, No. 1772 (16 pages).
Kooreman et al., "Autologous iPSC-Based Vaccines Elicit Anti-tumor Responses In Vivo," Cell Stem Cell, Apr. 5, 2018, vol. 22, No. 4 (pp. 501-513).
Kormann et al., "Expression of therapeutic proteins after delivery of chemically modified mRNA in mice," Nature Biotechnology, Feb. 2011, vol. 29, No. 2 (pp. 154-157).
Kotin, Robert M., "Prospects for the Use of Adeno-Associated Virus as a Vector for Human Gene Therapy," Human Gene Therapy, 1994, vol. 5 (pp. 793-801).
Kress et al., "DNA barcodes: Genes, genomics, and bioinformatics," Proceedings of the National Academy of Sciences, Feb. 26, 2008, vol. 105, No. 8 (pp. 2761-2762).
Kress et al., "Use of DNA barcodes to identify flowering plants" Proceedings of the National Academy of Sciences, USA, vol. 102, No. 23 (pp. 8369-8374).
Kubo et al., "A new hybrid system capable of efficient lentiviral vector production and stable gene transfer mediated by a single helper-dependent adenoviral vector," Journal of Virology, Mar. 2003, vol. 77, No. 5 (pp. 2964-2971).
Kudla et al., "High Guanine and Cytosine Content Increases mRNA Levels in Mammalian Cells," PLOS Biology, Jun. 2006, vol. 4, No. 6, e180 (pp. 1-10).
Kung et al., "Identification of TRIML2, a novel p53 target, that enhances p53 SUMOylation and regulates the transactivation of proapoptotic genes," Molecular Cancer Research, Feb. 2015, vol. 13, No. 2 (pp. 250-262).
Kurjan et al., "Structure of a yeast pheromone gene (MF alpha): a putative alpha-factor precursor contains four tandem copies of mature alpha-factor," Cell, 1982, vol. 30 (pp. 933-943).
Kuster et al., "The promoter of the Vicia faba L. VfENOD-GRP3 gene encoding a glycine-rich early nodulin mediates a predominant gene expression in the interzone II-III region of transgenic Vicia hirsuta root nodules," Plant Molecular Biology, 1995, vol. 29 (pp. 759-772).
Kuttan et al., "Mechanistic insights into editing-site specificity of ADARs," Proceedings of the National Academy of Sciences, USA, Nov. 27, 2012, vol. 109, No. 48 (pp. E3295-E3304).
Lagauzere, S., "Viromer RED, a powerful tool for transfection of keratinocytes," Aug. 2017 (7 pages of data).
Lahaye et al., "DNA barcoding the floras of biodiversity hotspots," Proceedings of the National Academy of Sciences, USA, Feb. 26, 2008, vol. 105, No. 8 (pp. 2923-2928).
Lai et al., "Adenovirus and adeno-associated virus vectors," DNA and Cell Biology, 2002, vol. 21 (pp. 895-913).
Lalatsa et al., "Amphiphilic poly(L-amino acids)—new materials for drug delivery," Journal of Control Release, Jul. 20, 2012, vol. 161, No. 2 (pp. 523-236).
Lalatsa et al., "Delivery of peptides to the blood and brain after oral uptake of quaternary ammonium palmitoyl glycol chitosan nanoparticles," Molecular Pharmaceutics, Jun. 4, 2012, vol. 9, No. 6 (pp. 1764-1774).
Lawrence et al., "Supercharging proteins can impart unusual resilience," Journal of the American Chemical Society, Aug. 22, 2007, vol. 129, No. 33 (pp. 10046-10298).
Le Mercier et al., "Beyond CTLA-4 and PD-1, the generation Z of negative checkpoint regulators," Frontiers in Immunology, Aug. 21, 2015, vol. 6, Article 418 (15 pages).
Lee et al., "Nanoparticle delivery of CRISPR into the brain rescues a mouse model of fragile X syndrome from exaggerated repetitive behaviours," Nature Biomedical Engineering, Jul. 2018, vol. 2, No. 7 (pp. 497-507).
Lee et al., "Synthetically modified guide RNA and donor DNA are a versatile platform for CRISPR-Cas9 engineering," Elife, May 2, 2017, vol. 6 e25312 (17 pages).
Legut et al., "CRISPR-mediated TCR replacement generates superior anticancer transgenic T cells," Blood, 2018, vol. 131, No. 3 (pp. 311-322).
Lek et al., "Analysis of protein-coding genetic variation in 60,706 humans," Nature, Aug. 18, 2016, vol. 536 (pp. 285-291).
Lensing et al., "DSBCapture: in situ capture and sequencing of DNA breaks," Nature methods, Oct. 2016, vol. 13, No. 10 (pp. 855-857).
Levy et al., "Cytosine and adenine base editing of the brain, liver, retina, heart and skeletal muscle of mice via adeno-associated viruses," Nature Biomedical Engineering, Jan. 2020, vol. 4, No. 1 (pp. 97-110).

(56) References Cited

OTHER PUBLICATIONS

Levy-Nissenbaum et al., Nanotechnology and aptamers: applications in drug delivery, Trends in Biotechnology, Aug. 2008, vol. 26, No. 8 (pp. 442-449).
Li et al., "Adoptive cell therapy with CD4+ T helper 1 cells and CD8+ cytotoxic T cells enhances complete rejection of an established tumour, leading to generation of endogenous memory responses to non-targeted tumour epitopes," Clinical Translational Immunology, Oct. 20, 2017, vol. 6, No. 10 e160 (10 pages).
Li et al., "Engineering CRISPR-Cpf1 crRNAs and mRNAs to maximize genome editing efficiency," Nature Biomedical Engineering, May 2017, vol. 1, No. 5 (21 pages).
Li et al., "Fast and accurate short read alignment with Burrows-Wheeler transform," Bioinformatics, 2009, vol. 25, No. 14 (pp. 1754-1760).
Liang et al., "Genome editing of bread wheat using biolistic delivery of CRISPR/Cas9 in vitro transcripts or ribonucleoproteins," Nature Protocols, Mar. 2018, vol. 13, No. 3 (pp. 413-430).
Liberzon et al, "The molecular signatures database (MSigDB) hallmark gene set collection," Cell Systems, Dec. 2015, vol. 1, No. 6 (pp. 417-425).
Lino et al., "Delivering CRISPR: a review of the challenges and approaches," Drug Delivery, 2018, vol. 25, No. 1 (pp. 1234-1257).
Liu et al., "Endoplasmic reticulum and Golgi localization sequences for mammalian target of rapamycin," Molecular Biology of the Cell, Mar. 2007, vol. 18, No. 3 (pp. 1073-1082).
Liu et al., "Recombinant human foamy virus, a novel vector for neurological disorders gene therapy, drives production of GAD in cultured astrocytes," Molecular Therapy, Oct. 2007, vol. 15, No. 10 (pp. 1834-1841).
Livingston et al., "Protein sequence alignments: a strategy for the hierarchical analysis of residue conservation," Bioinformatics, Dec. 1993, vol. 9, No. 6 (pp. 745-756).
Lorenzer et al., "Going beyond the liver: Progress and challenges of targeted delivery of siRNA therapeutics," Journal of Controlled Release, 2015, vol. 203 (pp. 1-15).
Lu et al., "Demethylation of the Same Promoter Sequence Increases CD70 Expression in Lupus T Cells and T Cells Treated with Lupus-Inducing Drugs," The Journal of Immunology, May 15, 2005, vol. 174, No. 10 (pp. 6212-6219).
Luckow et al. "High Level Expression of Nonfused Foreign Genes with Autographa californica Nuclear Polyhedrosis Virus Expression Vectors," Virology, May 1989, vol. 170 (pp. 31-39).
Luo et al., "Enhancement of transfection by physical concentration of DNA at the cell surface," Nature Biotechnology, Aug. 2000, vol. 18 (pp. 893-895).
Luo et al., "Multifunctional enveloped mesoporous silica nanoparticles for subcellular co-delivery of drug and therapeutic peptide," Scientific Reports, 2014, vol. 4, No. 6064 (pp. 1-10).
Lux et al., "Green fluorescent protein-tagged adeno-associated virus particles allow the study of cytosolic and nuclear trafficking," Journal of Virology, Sep. 2005, vol. 79, No. 18 (pp. 11776-11787).
Macosko et al., "Highly Parallel Genome-wide Expression Profiling of Individual Cells Using Nanoliter Droplets," Cell, May 21, 2015, vol. 161 (pp. 1202-1214).
Maher et al., "Human T-lymphocyte cytotoxicity and proliferation directed by a single chimeric TCRzeta /CD28 receptor," Nature Biotechnology, Jan. 2002, vol. 20, No. 1 (pp. 70-75).
Maji et al., "A high-throughput platform to identify small-molecule inhibitors of CRISPR-Cas9," Cell, May 2, 2019, vol. 177, (pp. 1067-1079).
Maji et al., "Multidimensional chemical control of CRISPR-Cas9," Nature Chemical Biology, Jan. 2017, vol. 13, No. 1 (pp. 9-12).
Makarova et al., "An updated evolutionary classification of CRISPR-Cas systems," Nature Reviews—Microbiology, Sep. 28, 2015, vol. 13 (pp. 722-736).
Makarova et al., "Evolutionary classification of CRISPR-Cas systems: a burst of class 2 and derived variant," Nature Reviews, Microbiology, 2020, vol. 18, Issue 2 (pp. 67-83).
Mali et al., "RNA-Guided Human Genome Engineering Via Cas9" Science, dated Feb. 15, 2013, vol. 339 [Includes Supplemental Information—41 pages] (pp. 823-826).
Manjappa et al., "Antibody Derivatization and Conjugation Strategies: Application in Preparation of Stealth Immunoliposome to Target Chemotherapeutics to Tumor," Journal of Controlled Release, Feb. 28, 2011, vol. 150, No. 1 (pp. 2-22).
Manoharan, M., "RNA interference and chemically modified small interfering RNAs," Current Opinion in Chemical Biology, Dec. 2004, vol. 8, No. 6 (pp. 570-579).
Maratea et al., "Deletion and fusion analysis of the phage omega-X174 lysis gene E," Gene, 1985, vol. 40, No. 1 (pp. 39-46).
Martin-Orozco et al., "T helper 17 cells promote cytotoxic T cell activation in tumor immunity," Immunity, Nov. 20, 2009, vol. 31, No. 5 (pp. 787-798).
Matouschek et al., "Active unfolding of precursor proteins during mitochondrial protein import," The EMBO Journal, Nov. 1997, vol. 16, No. 22 (pp. 6727-6736).
Matsuda et al., "Controlled expression of transgenes introduced by in vivo electroporation," Proceedings of the National Academy of Sciences, Jan. 16, 2007, vol. 104, No. 3 (pp. 1027-1032).
Matthews et al., "Structures of human ADAR2 bound to dsRNA reveal base-flipping mechanism and basis for site selectivity," Nature Structural & Molecular Biology, May 2016, Epub Apr. 11, 2016, vol. 23, No. 5 (pp. 426-433).
Matthews, Q., "Capsid-Incorporation of Antigens into Adenovirus Capsid Proteins for a Vaccine Approach," Molecular Pharmaceutics Journal, Feb. 2011, vol. 8, No. 1 (pp. 1-14).
Maus et al., "Adoptive immunotherapy for cancer or viruses," Annual Review of Immunology, 2014, vol. 32 (pp. 189-225).
Mazza et al., "Nanofiber-Based Delivery of Therapeutic Peptides to the Brain," ACS Nano, Jan. 4, 2013, vol. 7, No. 2 (pp. 1016-1026).
McFarland et al., "Improved estimation of cancer dependencies from large-scale RNAi screens using model-based normalization and data integration," Nature Communications, 2018, vol. 9, No. 4610 (pp. 1-13).
McKenna et al., "The Genome Analysis Toolkit: A MapReduce framework for analyzing next-generation DNA sequencing data," Genome Research, 2010, vol. 20 (pp. 1297-1303).
McLaren et al., "Deriving the consequences of genomic variants with the Ensembl API and SNP Effect Predictor," Bioinformatics, 2010, vol. 26, No. 16 (pp. 2069-2070).
Mettananda et al., "Editing an alpha-globin enhancer in primary human hematopoietic stem cells as a treatment for beta-thalassemia," Nature Communications, Sep. 4, 2017, vol. 8, No. 1 (11 pages).
Meyers et al., "Computational correction of copy number effect improves specificity of CRISPR-Cas9 essentiality screens in cancer cells," Nature Genetics, Dec. 2017, vol. 49, No. 12 (pp. 1779-1784).
Miller et al., "Construction and Properties of Retrovirus Packaging Cells Based on Gibbon Ape Leukemia Virus," Journal of Virology, May 1991, vol. 65, No. 5 (pp. 2220-2224).
Miller et al., "Continuous evolution of SpCas9 variants compatible with non-G PAMs," Nature Biotechnology, Apr. 2020, vol. 38, No. 4 (pp. 471-481).
Miyamoto et al., "Rapid and orthogonal logic gating with a gibberellin-induced dimerization system," Nature Chemical Biology, 2012, vol. 8, No. 5 (pp. 465-470).
Miyazaki et al., "Destabilizing Domains Derived from the Human Estrogen Receptor," Journal of the American Chemical Society, Mar. 7, 2012, vol. 134 (pp. 3942-3945).
Mok et al., "A bacterial cytidine deaminase toxin enables CRISPR-free mitochondrial base editing," Nature, Jul. 2020, vol. 583, No. 7817 (pp. 631-637).
Molavi et al., "Anti-CD30 Antibody Conjugated Liposomal Doxorubicin with Significantly Improved Therapeutic Efficacy against Anaplastic Large Cell Lymphoma," Biomaterials, Nov. 2013, vol. 34, No. 34 (18 pages).
Morgan et al., "Cancer Regression in Patients After Transfer of Genetically Engineered Lymphocytes," Science, Oct. 6, 2006, vol. 314, No. 5796 (pp. 126-129).

(56) References Cited

OTHER PUBLICATIONS

Morissey et al., "Potent and persistent in vivo anti-HBV activity of chemically modified siRNAs," Nature Biotechnology, Aug. 2005, vol. 23, No. 8 (pp. 1-6).
Morizono et al., "A versatile targeting system with lentiviral vectors bearing the biotin-adaptor peptide," The Journal of Gene Medicine, Aug. 2009, vol. 11, No. 8 (pp. 655-663).
Morizono et al., "Antibody-directed targeting of retroviral vectors via cell surface antigens," Journal of Virology, 2021, vol. 75, No. 17 (pp. 8016-8020).
Morizono et al., "Lentiviral vector retargeting to P-glycoprotein on metastatic melanoma through intravenous injection," Nature Medicine, Mar. 2005, vol. 11, No. 3 (pp. 346-352).
Morizono et al., "Redirecting lentiviral vectors by insertion of integrin-targeting peptides into envelope proteins," The Journal of Gene Medicine, May 11, 2009, vol. 11, No. 7 (pp. 549-558).
Morizono et al., "Redirecting lentiviral vectors pseudotyped with Sindbis virus-derived envelope proteins to DC-SIGN by modification of N-linked glycans of envelope proteins," Journal of virology, 2010, vol. 84, No. 14 (pp. 6923-6934).
Morizono et al., "Transient low pH treatment enhances infection of lentiviral vector pseudotypes with a targeting Sindbis envelope," Virology, 2006, vol. 355 (pp. 71-81).
Morocz et al., "Brain edema development after MRI-guided focused ultrasound treatment," Journal of Magnetic Resonance Imaging, Jan.-Feb. 1998, vol. 8, No. 1 (pp. 136-142).
Morral et al., "Administration of helper-dependent adenoviral vectors and sequential delivery of different vector serotype for long-term liver-directed gene transfer in baboons," Proceedings of the National Academy of Sciences, USA, 1999, vol. 96 (pp. 12816-12821).
Morral et al., "High Doses of a Helper-Dependent Adenoviral Vector Yield Supraphysiological Levels of alpha1-Antitrypsin with Negligible Toxicity," Human Gene Therapy, Dec. 10, 1998, vol. 9 (pp. 2709-2716).
Morton et al., "Selection on the codon bias of chloroplast and cyanelle genes in different plant and algal lineages," Journal of Molecular Evolution, Apr. 1998, vol. 46, No. 4 (pp. 449-459).
Mouhieddine et al., "Immunotherapy in Multiple Myeloma: The Era of CAR T Cell Therapy," Hematologist, Apr. 2018, vol. 15, No. 3 (8 pages).
Moussatov et al., "A Possible Approach To The Treatment of Polycystic Ovarian Syndrome Using Focused Ultrasound," Ultrasonics, 1998, vol. 36, No. 8 (pp. 893-900).
Mout et al., "Cytosolic and Nuclear Delivery of CRISPR/Cas9-ribonucleoprotein for Gene Editing Using Arginine Functionalized Gold Nanoparticles," Bio-protocol, Oct. 20, 2017, vol. 7, No. 20 e2586 (pp. 1-5).
Munch et al., "Displaying high-affinity ligands on adeno-associated viral vectors enables tumor cell-specific and safe gene transfer," Molecular Therapy, Jan. 2013, vol. 21, No. 1 (pp. 109-118).
Muranski et al., "Tumor-specific Th17-polarized cells eradicate large established melanoma," Blood, Jul. 15, 2008, vol. 112, No. 2 (pp. 362-373).
Murphy et al., "Genetic construction, expression, and melanoma-selective cytotoxicity of diphtheria toxin-related alpha-melanocyte-stimulating hormone fusion protein," Proceedings of the National Academy of Sciences, USA, Nov. 1986, vol. 83 (pp. 8258-8262).
Murray et al., "Codon usage in plant genes," Nucleic Acids Research, 1989, vol. 17 (pp. 477-498).
Muzyczka, Nicholas, "Adeno-associated Virus (AAV) Vectors: Will They Work?," Journal of Clinical Investigation, Oct. 1994, vol. 94 (p. 1351).
Nair et al., "Multivalent N-acetylgalactosamine-conjugated siRNA localizes in hepatocytes and elicits robust RNAi-mediated gene silencing," Journal of the American Chemical Society, Dec. 1, 2014, vol. 136 (pp. 16958-16961).
Nakamura et al., "A multifunctional envelope-type nanodevice for use in nanomedicine: concept and applications," Accounts of Chemical Research, Feb. 10, 2012, vol. 45 (pp. 1113-1121).
Nakamura et al., "Codon usage tabulated from the international DNA sequence databases: status for the year 2000," Nucleic Acids Research, 2000, vol. 28, No. 1 (p. 292).
Nance et al., "Perspective on Adeno-Associated Virus Capsid Modification for Duchenne Muscular Dystrophy Gene Therapy," Human Gene Therapy, 2015, vol. 26, No. 12 (pp. 786-800).
Negi et al., "LocSigDB: a database of protein localization signals," Database, Feb. 27, 2015, vol. 2015 (pp. 1-17).
Nicholson et al., "Construction and characterisation of a functional CD19 specific single chain Fv fragment for immunotherapy of B lineage leukaemia and lymphoma," Molecular Immunology, Nov.-Dec. 1997, vol. 34, Nos. 16-17 (pp. 1157-1165).
Nihongaki et al., "Photoactivatable CRISPR-Cas9 for optogenetic genome editing," Nature Biotechnology, Jul. 2015, vol. 33, No. 7 (pp. 755-760).
O'Hare et al., "Transformation of mouse fibroblasts to methotrexate resistance by a recombinant plasmid expressing a prokaryotic dihydrofolate reductase," Proceedings of the National Academy of Sciences, USA, Mar. 1981, vol. 78, No. 3 (pp. 1527-1531).
Oca-Cossio et al., "Limitations of Allotopic Expression of Mitochondrial Genes in Mammalian Cells," Genetics, Oct. 1, 2003, vol. 165, No. 2 (pp. 707-720).
Ogunniyi et al., "Profiling Human Antibody Responses by Integrated Single-Cell Analysis," Vaccine, May 19, 2014, vol. 32, No. 24 (pp. 2866-2873).
Ono et al., "Transient Assay System for the Analysis of PR-1a Gene Promoter in Tobacco BY-2 Cells," Bioscience, Biotechnology, and Biochemistry, 2004, vol. 68, No. 4 (pp. 803-807).
Ortega-Escalante et al., "CRISPR/Cas9 mutagenesis in Volvox carteri," The Plant Journal, Feb. 2019, vol. 97, No. 4 (pp. 661-672).
Osborn et al., "Base editor correction of COL7A1 in recessive dystrophic epidermolysis bullosa patient-derived fibroblasts and iPSCs," Journal of Investigative Dermatology, Feb. 2020 vol. 140, No. 2 (pp. 338-347).
Ostergaard et al., "Efficient Synthesis and Biological Evaluation of 5'-GalNAc Conjugated Antisense Oligonucleotides," Bioconjugate Chemistry, 2015 Vol. 26, No. 8 (pp. 1451-1455).
Padalia et al., Abstract 2551: Allogeneic CRISPR engineered anti CD70 CAR T cells demonstrate potent preclinical activity against both solid and hematological cancer cells, American Association of Cancer Research, Poster Presentations—Proffered Abstracts, Jul. 1, 2018 (3 pages).
Paige et al., "RNA mimics of green fluorescent protein," Science, Jul. 29, 2011, vol. 333, No. 6042 (pp. 642-646).
Paix et al., "High Efficiency, Homology-Directed Genome Editing in Caenorhabditis elegans Using CRISPR-Cas9 Ribonucleoprotein Complexes," Genetics, Sep. 2015, vol. 201 (pp. 47-54).
Pardridge, W., "Preparation of Trojan Horse Liposomes (THLs) for Gene Transfer across the Blood-Brain Barrier," Cold Spring Harbor Protocols, 2010 http://cshprotocols.cshlp.org/ at UCLA Library on Aug. 31, 2013; Adapted from Gene Transfer: Delivery and Expression of DNA and RNA (ed. Friedmann and Rossi) CSHL Press, Cold Spring Harbor, NY, USA, 2007 (pp. 1-8).
Park et al., "CD70 as a target for chimeric antigen receptor T cells in head and neck squamous cell carcinoma," Oral Oncology Mar. 2018, vol. 78 (pp. 145-150).
Parker et al., "Scheme for ranking potential HLA-A2 binding peptides based on independent binding of individual peptide side-chains," The Journal of Immunology, Jan. 1, 1994, vol. 152, No. 1 (pp. 163-175).
Pattanayak et al., "High-throughput profiling of off-target DNA cleavage reveals RNA-programmed Cas9 nuclease specificity," Nature Biotechnology, 2013, vol. 31 (pp. 839-843) [Including Supplementary Materials].
Peters et al., "Recruitment of CRISPR-Cas systems by Tn7-like transposons," Proceedings of the National Academy of Sciences, U.S.A, Online Aug. 15, 2017, vol. 29, No. 114 (pp. E7358-E7366).
Picelli et al. "Full-length RNA-seq from single cells using Smart-seq2," Nature Protocols, Jan. 2014, vol. 9, No. 1 (pp. 171-181).
Pinkert et al., "An albumin enhancer located 10 kb upstream functions along with its promoter to direct efficient, liver-specific expression in transgenic mice," Genes Development, May 1987, vol. 1 (pp. 268-276).

(56) References Cited

OTHER PUBLICATIONS

Piras et al., "Lentiviral vectors escape innate sensing but trigger p53 in human hematopoietic stem and progenitor cells," EMBO Molecular Medicine, Sep. 2017, vol. 9, No. 9 (pp. 1198-1211).
Platt et al., "CRISPR-Cas9 Knockin Mice for Genome Editing and Cancer Modeling," Cell, 2014, vol. 159 (pp. 440-455).
Poirot et al., "Multiplex genome edited T-cell manufacturing platform for 'off-the-shelf' adoptive T-cell immunotherapies," Cancer Research, Sep. 15, 2015, vol. 75, No. 18 (pp. 3853-3864).
Qasim et al., "Molecular remission of infant B-ALL after infusion of universal TALEN gene-edited CAR T cells," Cancer, Science Translational Medicine, Jan. 25, 2017, vol. 9 (pp. 1-8).
Qu et al., "Carbohydrate-based micelle clusters which enhance hydrophobic drug bioavailability by up to 1 order of magnitude," Biomacromolecules, Nov. 7, 2006, vol. 7, No. 12 (pp. 3452-3459).
Queen et al., "Immunoglobulin gene transcription is activated by downstream sequence elements," Cell, Jul. 1983, vol. 33, No. 3 (pp. 741-748).
Rahdar et al., "Synthetic CRISPR RNA-Cas9-guided genome editing in human cells," Proceedings of the American Academy of Sciences, U.S.A. Nov. 16, 2015 (pp. E7110-E7117).
Rajasagi et al., "Systematic Identification of Personal Tumor-specific Neoantigens in Chronic Lymphocytic Leukemia," Blood, 2014, vol. 124, No. 3 (pp. 453-462).
Ramirez et al., "Engineering split intein DnaE from Nostoc punctiforme for rapid protein purification," Protein Engineering, Design & Selection, Mar. 2013, vol. 26, No. 3 (pp. 215-233).
Ramos et al., "An inducible caspase 9 suicide gene to improve the safety of mesenchymal stromal cell therapies," Stem Cells, Jun. 2010, vol. 28, No. 6 (pp. 1107-1115).
Ramskold et al., "Full-length mRNA-Seq from single-cell levels of RNA and individual circulating tumor cells," Nature Biotechnology, Aug. 2012, vol. 30, No. 8 (777-782).
Ran et al., "In vivo genome editing using *Staphylococcus aureus* Cas9," Nature, 2015, vol. 520 (pp. 186-191). [Includes Supplemental information, 12 pages].
Rauch et al., "Inhibition of CRISPR-Cas9 with Bacteriophage Proteins," Cell, 2017, vol. 168, No. 2 (pp. 150-158).
Rees et al., "Analysis and Minimization of Cellular RNA Editing by DNA Adenine Base Editors," Science Advances, May 8, 2019, vol. 5 (pp. 1-10).
Ren et al., "Multiplex Genome Editing to Generate Universal CAR T Cells Resistant to PD1 Inhibition," Clinical Cancer Research, May 1, 2017, vol. 23, No. 9 (pp. 2255-2266).
Restifo et al., "Adoptive Immunotherapy for Cancer: Harnessing the T Cell Response," Nature Reviews Immunology, Mar. 22, 2012, vol. 12, No. 4 (pp. 269-281).
Richter et al., "Phage-assisted evolution of an adenine base editor with enhanced Cas domain Compatibility and Activity," Nature Biotechnology, Jul. 2020, vol. 38, No. 7 (pp. 883-891).
Rosenberg et al., "Adoptive cell transfer as personalized immunotherapy for human cancer," Cancer Immunology and Immunotherapy, Apr. 2015, vol. 348, Issue 6230 (pp. 62-69).
Rosenberg et al., "Scaling single cell transcriptomics through split pool barcoding," bioRxiv preprint first posted online Feb. 2, 2017 (13 pages).
Rosenberg et al., "Single-cell profiling of the developing mouse brain and spinal cord with split-pool barcoding," Science, Single Cell Genomics, 2018, vol. 360 (pp. 176-182).
Rosewell et al., "Helper-dependent adenoviral vectors," Genetic Syndrome & Gene Therapy, 2011, Suppl. 5 (pp. 1-34).
Ryan et al., "Improving CRISPR-Cas specificity with chemical modifications in single-guide RNAs," Nucleic Acids Research, Jan. 25, 2018, vol. 46, No. 2 (pp. 792-803).
Rybniker et al., "Incorporation of Antigens into Viral Capsids Augments Immunogenicity of Adena-Associated Virus Vector-Based Vaccines," Journal of Virology, Dec. 2012, vol. 86, No. 24 (pp. 13800-13804).
Sadelain et al., "Eliminating Cells Gone Astray," New England Journal of Medicine, Nov. 3, 2011, vol. 365, No. 18 (pp. 1735-1737).
Samulski et al., "Helper-Free Stocks of Recombinant Adeno-Associated Viruses: Normal Integration Does Not Require Viral Gene Expression," Journal of Virology, 1989, vol. 63, No. 9 (pp. 3822-3828).
Sapranauskas, R., et. al., "The *Streptococcus thermophilus* CRISPR/Cas System Provides Immunity in *Escherichia coli*," Nucleic Acids Research, Aug. 3, 2011, vol. 39, No. 21 (pp. 9275-9282).
Scaringe et al., "Advanced 5'-silyl-2'-orthoester approach to RNA oligonucleotide synthesis," Methods in Enzymology, 2000, vol. 317 (pp. 3-18).
Scaringe et al., "Novel RNA Synthesis Method Using 5'-O-Silyl-2'-O-orthoester Protecting Groups," Journal of the American Chemical Society, 1998, vol. 120, No. 45 (pp. 11820-11821).
Schifflers et al., "Cancer siRNA therapy by tumor selective delivery with ligand-targeted sterically stabilized nanoparticle," Nucleic Acids Research, 2004, vol. 32, No. 19 (pp. 1-10).
Schiroli et al., "Precise Gene Editing Preserves Hematopoietic Stem Cell Function following Transient p53-Mediated DNA Damage Response," Cell Stem Cell, Apr. 4, 2019, vol. 24 (pp. 551-565).
Scholthof et al., "Plant virus gene vectors for transient expression of foreign proteins in plants," Annual Review of Phytopathology, 1996, vol. 34 (pp. 299-323).
Schroeder et al., "Lipid-based nanotherapeutics for siRNA delivery," Journal of Internal Medicine, Jan. 2010, vol. 267, No. 1 (pp. 9-21).
Schultz et al., "Expression and secretion in yeast of a 400-kDa envelope glycoprotein derived from Epstein-Barr virus," Gene, Mar. 2, 1987, vol. 54 (pp. 113-123).
Seberg et al., "How many loci does it take to DNA barcode a crocus?" PLoS One, Feb. 2009, vol. 4, No. 2 e4598 (pp. 1-6).
Seed, B., "An LFA-3 cDNA encodes a phospholipid-linked membrane protein homologous to its receptor CD2," Nature, Oct. 1987, vol. 329 (pp. 840-842).
Semple et al., "Rational design of cationic lipids for siRNA delivery," Nature Biotechnology, Feb. 2010, vol. 28, No. 2 (pp. 172-178).
Sharma et al., "Antisense oligonucleotides: modifications and clinical trials," Medical Chemistry Journal, 2014, vol. 5 (pp. 1454-1471).
Shcneider et al., "Optimal guideRNAs for re-directing deaminase activity of hADAR1 and hADAR2 in trans," Nucleic Acids Research, Jun. 1, 2014, vol. 42, No. 10 (pp. 1-9).
Shimatani et al., "Targeted base editing in rice and tomato using a CRISPR-Cas9 cytidine deaminase fusion," Nature Biotechnology, Mar. 2017, vol. 35, No. 5 (pp. 441-443).
Shmakov et al., "Discovery and Functional Characterization of Diverse Class 2 CRISPR-Cas Systems," Molecular Cell, Nov. 1, 2015, vol. 60, No. 3 (pp. 385-397).
Sholl et al., "Institutional implementation of clinical tumor profiling on an unselected cancer population," JCI Insight, Nov. 17, 2016, vol. 1, No. 19 (pp. 1-19).
Shukla et al., "Exploring chemical modifications for siRNA therapeutics: a structural and functional outlook," ChemMedChem, Mar. 1, 2010, vol. 5, No. 3 (pp. 328-349).
Sierig et al., "Cytotoxic effects of streptolysin O and streptolysin S enhance the virulence of poorly encapsulated group A streptococci," Infection and Immunity, Jan. 2003, vol. 71 (pp. 446-455).
Siew et al., "Enhanced oral absorption of hydrophobic and hydrophilic drugs using quaternary ammonium palmitoyl glycol chitosan nanoparticles," Molecular Pharmaceutics, Jan. 1, 2012, vol. 9, No. 1 (pp. 14-28).
Simon et al., "Peptoids: a modular approach to drug discovery," Proceedings of the National Academy of Sciences, USA, Oct. 1992, vol. 89 (pp. 9367-9371).
Simonelli et al., "Gene Therapy for Leber's Congenital Amaurosis is Safe and Effective Through 1.5 Years After Vector Administration," Molecular Therapy, 2010, vol. 18, No. 3 (pp. 643-650).
Sinha et al., "Integrated computational and experimental identification ofp53, KRAS and VHL mutant selection associated with CRISPR-Cas9 editing," bioRxiv, this version posted Nov. 2, 2019 (pp. 1-26).

(56) References Cited

OTHER PUBLICATIONS

Slaymaker et al., "Rationally engineered Cas9 nucleases with improved specificity," Science, Jan. 1, 2016, vol. 351, No. 6268 (pp. 84-88).
Sletten et al., "Bioorthogonal Chemistry: Fishing for selectivity in a sea of functionality," Angewandte Chemie International Edition, 2009, vol. 48, (pp. 6974-6998).
Smith et al., "Single-step purification of polypeptides expressed in *Escherichia coli* as fusions with glutathione S-transferase," Gene, Mar. 16, 1988, vol. 67 (pp. 31-40).
Smith et al., "Production of Human Beta Interferon in Insect Cells Infected with a Baculovirus Expression Vector," Molecular and Cellular Biology, vol. 3, No. 12, Dec. 1983 (pp. 2156-2165).
Sofou et al., "Antibody-Targeted Liposomes in Cancer Therapy and Imaging," Expert Opinion on Drug Delivery, Feb. 2008, vol. 5, No. 2 (pp. 189-204).
Soininen et al., "Analysing diet of small herbivores: the efficiency of DNA barcoding coupled with high-throughput pyrosequencing for deciphering the composition of complex plant mixtures," Frontiers in Zoology, Aug. 2009, vol. 6, No. 16 (pp. 1-9).
Sommerfelt et al., "Receptor Interference Groups of 20 Retroviruses Plating on Human Cells," Virology, 1990, vol. 176 (pp. 58-69).
Sonoke et al.,"Galactose-modified cationic liposomes as a liver-targeting delivery system for small interfering RNA," Biological and Pharmaceutical Bulletin, 2011, vol. 34, No. 8 (pp. 1338-2342).
Spuch et al., "Liposomes for Targeted Delivery of Active Agents against Neurodegenerative Diseases (Alzheimer's Disease and Parkinson's Disease)," Journal of Drug Delivery, 2011, vol. 2011, No. 469679 (pp. 1-12).
Stanwix, Ed. "Interview: An Interview with Chad Mirkin: Nanomedicine Expert," Nanomedicine, 2012, vol. 7, No. 5 (pp. 635-638).
Sternberg et al., "Conformational control of DNA target cleavage by CRISPR-Cas9," Nature, Oct. 28, 2015, vol. 527, No. 7576 (pp. 110-113).
Subramanian et al., "A Next Generation Connectivity Map: LI000 Platform and the First 1,000,000 Profiles," Cell, 2017, vol. 171 (pp. 1437-1452).
Subramanian et al., "Gene set enrichment analysis: a knowledge-based approach for interpreting genome-wide expression profiles," Proceedings of the National Academy of Sciences, Oct. 25, 2005, vol. 102 (pp. 15545-15550).
Sun et al., "Morphology-conductivity relationship in crystalline and amorphous sequence-defined peptoid block copolymer electrolytes," Journal of the American Chemical Society, Oct. 22, 2014, vol. 136, No. 42 (pp. 14990-14997).
Sun et al., "Self-Assembled DNA Nanoclews for the Efficient Delivery of CRISPR-Cas9 for Genome Editing," Angewandte Chemie, Intl., Oct. 5, 2015, vol. 54, No. 41 (pp. 12029-12033).
Surace et al., "Lipoplexes Targeting the CD44 Hyaluronic Acid Receptor for Efficient Transfection of Breast Cancer Cells," Molecular Pharmaceutics, Jul.-Aug. 2009, vol. 6, No. 4 (pp. 1062-1073).
Svitashev et al., "Genome editing in maize directed by CRISPR-Cas9 ribonucleoprotein complexes," Nature Communications, Nov. 16, 2016, vol. 7, No. 13274 (pp. 1-7).
Swiech et al., "In vivo interrogation of gene function in the mammalian brain using CRISPR-Cas9," Nature Biotechnology, 2014, vol. 33 (pp. 102-106) [Including Supplemental information, 4 pages].
Szilard et al., "Systematic identification of fragile sites via genome-wide location analysis of gamma-H2AX," Nature Structural & Molecular Biology, 2010, vol. 17 (pp. 299-305).
Tabernero et al., "First-in-humans trial of an RNA interference therapeutic targeting VEGF and KSP in cancer patients with liver involvement," Cancer Discovery, Apr. 2013, vol. 3, No. 4 (pp. 406-417).
Takebe et al., "SR-alpha Promoter: an Efficient and Versatile Mammalian cDNA Expression System Composed of the Simian Virus 40 Early Promoter and the R-U5 Segment of Human T-Cell Leukemia Virus Type 1 Long Terminal Repeat," Molecular and Cellular Biology, 1988, vol. 8, No. 1 (pp. 466-472).
Takeda et al., "Synthetic and nature-derived lipid nanoparticles for neural regeneration," Neural Regeneration Research, May 2015, vol. 10, No. 5 (pp. 689-690).
Tang et al., "mRNA-Seq whole-transcriptome analysis of a single cell," Nature Methods, May 2009, vol. 6, No. 5 (pp. 377-382).
Tang et al., "RNA-Seq analysis to capture the transcriptome landscape of a single cell," Nature Protocols, Mar. 2010, vol. 5, No. 3 (pp. 516-535).
Tatusova et al., "Blast 2 sequences, a new tool for comparing protein and nucleotide sequences," FEMS Microbiology Letters, 1999 Vol. 174 (pp. 247-250).
Tatusova et al., Erratum to: "BLAST 2 Sequences, a new tool for comparing protein and nucleotide sequences," FEMS Microbiology Letters, 1999, vol. 177 (pp. 187-188).
Taylor et al., "The classification of amino acid conservation," Journal of Theoretical Biology, 1986, vol. 119, No. 2 (pp. 205-218).
Teng et al., "Labeling Proteins Inside Living Cells Using External Fluorophores for Fluorescence Microscopy," Elife, Dec. 9, 2016 (pp. 1-13).
Teramato et al., "Crisis of adenoviruses in human gene therapy," The Lancet, May 27, 2000, vol. 355 (pp. 1911-1912).
The R Project for Statical Computing, "R Development Core Team. R: A language and environment for statistical computing," Vienna, Austria: R Foundation for Statistical Computing, 2010; https://www.r-project.org/ (pp. 1-4).
Thrasher et al., "X-SCID transgene leukaemogenicity," Nature, 2006, vol. 443 (pp. E5-E7).
Thuronyi et al., "Continuous evolution of base editors with expanded target compatibility and improved activity," Nature Biotechnology, Sep. 2019, vol. 379, No. 9 (pp. 1070-1079).
Torchilin, V., "Antibody-Modified Liposomes for Cancer Chemotherapy," Expert Opinion on Drug Delivery, Sep. 2008, vol. 5, No. 9 (pp. 1003-10025).
Torelli et al., "Paracrine rescue of MYR1-deficient Toxoplasma gondii mutants reveals limitations of pooled in vivo CRISPR screens," Microbiology and Infectious Disease, Procured from the internet via eLife Oct. 15, 2024 (24 pages).
Tran-Huu-Hue et al., "Practical Systems for the Generation of High Power Continuous Wave-Non Focused Ultrasound in the MHz Range," Acustica, acta acustica, 1997, vol. 83 (pp. 1103-1106).
Tratschin et al., "A Human Parvovirus, Adeno-Associated Virus, as a Eurcaryotic Vector: Transient Expression and Encapsidation of the Procaryotic Gene for Chloramphenicol Acetyltransferase", Molecular and Cellular Biology, vol. 4, No. 10, Oct. 1984 (pp. 2072-2081).
Tratschin et al., "Adeno-Associated Virus Vector for High-Frequency Integration, Expression, and Rescue of Genes in Mammalian Cells," Molecular and Cellular Biology, Nov. 1985, vol. 5, No. 11, (pp. 3251-3260).
Travassos Da Rosa et al., "Carajas and Maraba Viruses, Two New Vesiculoviruses Isolated from Phlebotomine Sand Flies in Brazil," The American Journal of Tropical Medicine and Hygiene, 1984, vol. 33 (pp. 999-1006).
Trobridge, G., "Foamy virus vectors for gene transfer," Expert Opinion on Biological Therapy, Nov. 2009, vol. 9, No. 11 (pp. 1427-1436).
Tsai et al., "CIRCLE-seq: a highly sensitive in vitro screen for genome-wide CRISPR-Cas9 nuclease off-targets," Nature Methods, Jun. 2017, vol. 14 (pp. 607-614).
Tsai et al., "Dimeric CRISPR RNA-guided FokI nucleases for highly specific genome editing," Nature Biotechnology, 2014, vol. 32, No. 6 (pp. 569-576).
Tsai et al., "GUIDE-seq enables genome-wide profiling of off-target cleavage by CRISPR-Cas nucleases," Nature Biotechnology, Feb. 2015, vol. 33, No. 2 (pp. 187-197).
Tsherniak et al., "Defining a Cancer Dependency Map," Cell, Jul. 27, 2017, vol. 170, No. 3 (pp. 564-576).
Tuerk et al., "Systematic evolution of ligands by exponential enrichment: RNA ligands to bacteriophage T4 DNA polymerase," Science, Aug. 3, 1990, vol. 249, No. 4968 (pp. 505-510).
Uchegbu et al., "Quaternary ammonium palmitoyl glycol chitosan—a new polysoap for drug delivery," International Journal of Pharmaceutics, Aug. 14, 2001, vol. 224, Nos. 1-2 (pp. 185-199).

(56) References Cited

OTHER PUBLICATIONS

Uchegbu, I.F., "Pharmaceutical nanotechnology: polymeric vesicles for drug and gene delivery," Expert Opinion on Drug Delivery, Sep. 2006, vol. 3, No. 5 (pp. 629-640).
Uno et al., "High-Density Lipoprotein Facilitates In Vivo Delivery of alpha-Tocopherol-Conjugated Short-Interfering RNA to the Brain," Human Gene Therapy, Jun. 2011, vol. 22 (pp. 711-719).
Vitak et al., "Sequencing thousands of single-cell genomes with combinatorial indexing," Nature Methods, Mar. 2017, vol. 14, No. 3 (pp. 302-308).
Von Essen, "Constitutive and ligand-induced TCR degradation," Journal of Immunology, vol. 173, No. 1 (pp. 384-393).
Wagner et al., "Revealing the vectors of cellular identity with single-cell genomics," Nature Biotechnology, Nov. 8, 2016, vol. 34, No. 11 (pp. 1145-1160).
Wahlgren et al., "Plasma exosomes can deliver exogenous short interfering RNA to monocytes and lymphocytes," Nucleic Acids Research, 2012, vol. 40, No. 17 (pp. 1-12).
Walev et al., "Delivery of proteins into living cells by reversible membrane permeabilization with streptolysin-O," Proceedings of the National Academy of Sciences, USA, Mar. 13, 2001, vol. 98, No. 6 (pp. 3185-3190).
Waltner et al., "Influence of the Mature Portion of a Precursor Protein on the Mitochondrial Signal Sequence," The Journal of Biological Chemistry, Aug. 1996, vol. 271, No. 35 (pp. 21226-21230).
Wang et al., "A Combinatorial Library of Unsaturated Lipidoids for Efficient Intracellular Gene Delivery," ACS Synthetic Biology, May 25, 2012, vol. 1, No. 9 (pp. 403-407).
Wang et al., "A Phenotypic Screen for Functional Mutants of Human Adenosine Deaminase Acting on RNA 1," ACS Chemical Biology, Nov. 20, 2015, vol. 10, No. 11 (pp. 2512-2519).
Wang et al., "DNA damage-induced nuclear factor-kappa B activation and its roles in cancer progression," Journal of Cancer Metastasis Treatment, 2017, vol. 3 (pp. 45-59).
Wang et al., "Efficient delivery of genome-editing proteins using bioreducible lipid nanoparticles," Proceedings of the National Academy of Sciences, USA, Mar. 15, 2016, vol. 113, No. 11 (pp. 2868-2873).
Wang et al., "Hyaluronic acid modification of RNase A and its intracellular delivery using lipid-like nanoparticles," Journal of Controlled Release, Oct. 10, 2017, vol. 263 (pp. 39-45).
Wang et al., "Integrating Protein Engineering and Bioorthogonal Click Conjugation for Extracellular Vesicle Modulation and Intracellular Delivery," PLoS ONE, Nov. 3, 2015, vol. 10, No. 11 (pp. 1-12).
Wang et al., "Probing RNA recognition by human ADAR2 using a high-throughput mutagenesis method," Nucleic Acids Research, 2016, vol. 44, No. 20 (pp. 9872-9880).
Wang et al., "RNA-guided endonuclease provides a therapeutic strategy to cure latent herpesviridae infection," Proceedings of the National Academy of Sciences, USA, Sep. 9, 2014, vol. 111, No. 36 (pp. 13157-13162).
Wang et al., "One-Step Generation Of Mice Carrying Mutations In Multiple Genes By CRISPR/Cas-Mediated Genome Engineering," Cell, May 9, 2013, vol. 153 (pp. 910-918).
Warrington et al., "Adena-associated virus type 2 VP2 capsid protein is nonessential and can tolerate large peptide insertions at its N terminus," The Journal of Virology, Jun. 2004, vol. 78 (pp. 6595-6609).
Watson et al., "SHP-1: the next checkpoint target for cancer immunotherapy?" Biochemical Society Transactions, Apr. 15, 2016, vol. 44, No. 2 (pp. 356-362).
Watts et al., "Chemically modified siRNA: tools and applications," Drug Discovery Today, Oct. 2008, vol. 13, Nos. 19-20 (pp. 842-855).
Weintraub et al., "Biomedicine: The new gold standard," Nature, 2013, vol. 495 (pp. S14-S16).
West et al., "Gene Expression in Adeno-Associated Virus Vectors: The Effects of Chimeric mRNA Structure, Helper Virus, and Adenovirus VA, RNA," Virology, 1987, vol. 160 (pp. 38-47).
Wilcox et al., "Effect of protein structure on mitochondrial import," Proceedings of the National Academy of Sciences, USA, 2005, vol. 102 (pp. 15435-15440).
Wilson et al., "Formation of Infectious Hybrid Virions with Gibbon Ape Leukemia Virus and Human T-Cell Leukemia Virus Retroviral Envelope Glycoproteins and the gag and pol Proteins of Moloney Murine Leukemia Virus," Journal of Virology, vol. 63, No. 5, May 1989 (pp. 2374-2378).
Wilson et al., "Programmable m6A modification of cellular RNAs with a Cas13-directed methyltransferase," Nature Biotechnology, Dec. 2020, vol. 38, No. 12 (pp. 1431-1440).
Winoto et al., "A novel, inducible and T cell-specific enhancer located at the 3' end of the T cell receptor alpha locus," The EMBO Journal, 1989, vol. 8, No. 3 (pp. 729-733).
Winzeler et al., "Functional characterization of the *S. cerevisiae* genome by gene deletion and parallel analysis," Science, Aug. 6, 1999, vol. 285, No. 5429 (pp. 901-906).
Wolf et al., "tadA, an essential tRNA-specific adenosine deaminase from *Escherichia coli,*" The EMBO Journal, 2002 vol. 21, No. 14 (pp. 3841-3851).
Wong et al., "Lentivirus-mediated gene transfer to the central nervous system: therapeutic and research applications," Human Gene Therapy, Jan./Feb. 2006, vol. 17 (pp. 1-9).
Wong et al., "Substrate recognition by ADAR1 and ADAR2," RNA, 2001, vol. 7 (pp. 846-858).
Woo et al, "DNA-free genome editing in plants with preassembled CRISPR-Cas9 ribonucleoproteins," Nature Biotechnology, Oct. 19, 2015, vol. 3, No. 11 (pp. 1162-1164).
Wu et al., "Correction of a genetic disease by CRISPR-Cas9-mediated gene editing in mouse spermatogonial stem cells," Cell Research, Jan. 2015, vol. 25, No. 1 (pp. 67-79).
Wu et al., "Highly efficient therapeutic gene editing of human hematopoietic stem cells," Nature Medicine, May 2019, vol. 25, No. 5 (pp. 776-783).
Wu et al., "Remote control of therapeutic T cells through a small molecule-gated chimeric receptor," Science, Oct. 16, 2015, vol. 350, No. 6258 (pp. 1-21).
Xu et al., "Design of 240,000 orthogonal 25mer DNA barcode probes," Proceedings of the National Academy of Sciences, USA, Feb. 17, 2009, vol. 106, No. 7 (pp. 2289-2294).
Yamamoto et al., "Light-responsive elements of the tobacco PSI-D gene are located both upstream and within the transcribed region," The Plant Journal, 1997, vol. 12, No. 2 (pp. 255-265).
Yan et al., "BLISS: quantitative and versatile genome-wide profiling of DNA breaks in situ," BioRxiv, Dec. 4, 2016 (pp. 1-23).
Yang et al., "A dual AAV system enables the Cas9-mediated correction of a metabolic liver disease in newborn mice," Nature Biotechnology, Mar. 2016, vol. 34, No. 3 (pp. 334-338).
Ye et al., "An engineered exosome for delivering sgRNA: Cas9 ribonucleoprotein complex and genome editing in recipient cells," Biomaterials Science, 2020, vol. 8 (pp. 2966-2976).
Ye et al., "Seamless modification of wild-type induced pluripotent stem cells to the natural CCR5delta32 mutation confers resistance to HIV infection," Proceedings of the National Academy of Sciences, USA, Jul. 1, 2014, vol. 111, No. 26 (pp. 9591-9596).
Yeh et al., "In vivo postnatal base editing rescues hearing in a mouse model of recessive deafness," Science Translational Medicine, Jun. 3, 2020, vol. 12, No. 546 (pp. 1-24).
Yin et al., "Structure-guided chemical modification of guide RNA enables potent non-viral in vivo genome editing," Nature Biotechnology, Dec. 2017, vol. 35 (pp. 1-22).
Yin et al., "Therapeutic genome editing by combined viral and non-viral delivery of CRISPR system components in vivo," Nature Biotechnology, 2016, vol. 34, No. 3 (pp. 328-333).
Young et al., "Hollow spherical nucleic acids for intracellular gene regulation based upon biocompatible silica shells," Nano Letters, Jul. 11, 2012, vol. 12, No. 7 (pp. 3867-3871).
Yu et al., "Small molecules enhance CRISPR genome editing in pluripotent stem cells," Cell Stem Cell, Feb. 5, 2015, vol. 16, No. 2 (pp. 142-147).
Zacharakis et al., "Immune recognition of somatic mutations leading to complete durable regression in metastatic breast cancer," Nature Medicine, Jun. 2018, vol. 24, No. 6 (pp. 724-730).

(56) References Cited

OTHER PUBLICATIONS

Zacharias et al., "p53 inhibits adeno-associated viral vector integration," Human Gene Therapy, Nov. 2011, vol. 22 (pp. 1445-1451).
Zetsche et al., "A split-Cas9 architecture for inducible genome editing and transcription modulation," Nature Biotechnology, Feb. 2015, vol. 33, No. 2 (pp. 139-142).
Zetsche et al., "Cpf1 is a single RNA-guided endonuclease of a class 2 CRISPR-Cas system," Cell, Oct. 22, 2015, vol. 163 (pp. 759-771).
Zhang et al., "Anti-CRISPRs: The natural inhibitors for CRISPR-Cas systems," Animal Models and Experimental Medicine, Jun. 2019, vol. 2, No. 2 (pp. 69-75).
Zhang et al., "Antibody-linked spherical nucleic acids for cellular targeting," Journal of the American Chemistry Society, Oct. 10, 2012, vol. 134, No. 40 (pp. 16488-16491).
Zhang et al., "Hybrid adeno-associated viral vectors utilizing transposase-mediated somatic integration for stable transgene expression in human cells," PloS one, Oct. 2013, vol. 8, No. 10, e76771 (pp. 1-17).
Zhang et al., "Strategy for increasing drug solubility and efficacy through covalent attachment to polyvalent DNA-nanoparticle conjugates," ACS Nano, Sep. 27, 2011, vol. 5, No. 9 (pp. 6962-6970).
Zhang et al., "Structure-based prediction of protein-protein interactions on a genome-wide scale," Nature, Oct. 25, 2012, vol. 490, No. 7421 (pp. 556-560).
Zheng et al. "Haplotyping germline and cancer genomes with high-throughput linked-read sequencing," Nature Biotechnology, Feb. 1, 2016, vol. 34, No. 3 (pp. 303-311) [with Supplemental Material].
Zheng et al., "DNA editing in DNA/RNA hybrids by adenosine deaminases that act on RNA," Nucleic Acids Research, Jan. 28, 2017, vol. 45, No. 6 (pp. 3369-3377).
Zheng et al., "Massively parallel digital transcriptional profiling of single cells," Nature Communications, Jan. 16, 2017, vol. 8, No. 14049 (12 pages).
Zheng et al., "Topical delivery of siRNA-based spherical nucleic acid nanoparticle conjugates for gene regulation," Proceedings of the National Academy of Sciences, USA, Jul. 24, 2012, vol. 109, No. 30 (pp. 11975-11980).
Zhong et al., "Cpf1 proteins excise CRISPR RNAs from mRNA transcripts in mammalian cells," Nature Chemical Biology, Aug. 2017, vol. 13, No. 8 (pp. 839-841).
Zhou et al., "Aptamer-targeted cell-specific RNA interference," Silence, Feb. 1, 2010, vol. 1, No. 4 (10 pages).
Zhou et al., "Long-term outcome after haploidentical stem cell transplant and infusion of T cells expressing the inducible caspase 9 safety transgene," Blood, Jun. 19, 2014, vol. 123, No. 25 (pp. 3895-3905).
Zhu et al. "Reverse transcriptase template switching: a SMART approach for full-length cDNA library construction" Biotechniques, 2001, vol. 30, No. 4 (pp. 892-897).
Zilionis et al., "Single-cell barcoding and sequencing using droplet microfluidics," Nature Protocols, 2017, vol. 12, No. 1 (pp. 44-73).
Zimmermann et al., "RNAi-mediated gene silencing in non-human primates," Nature, May 4, 2006, vol. 441 (pp. 111-114).
Zong et al., "Precise base editing in rice, wheat and maize with a Cas9-cytidine deaminase fusion," Nature Biotechnology, May 2017, vol. 35, No. 5 (pp. 438-441).
Zou et al., Intrathecal Lentiviral-Mediated RNA Interference Targeting PKC-gamma Attenuates Chronic Constriction Injury-Induced Neuropathic Pain in Rats, Human Gene Therapy, Nov. 19, 2010, vol. 22, No. 4 (pp. 465-475).
Zuckerman et al., "Somatic CRISPR/Cas9-mediated tumour suppressor disruption enables versatile brain tumour modelling," Nature Communications, Jun. 11, 2015, vol. 6, No. 7391 (pp. 1-9).
Zuker et al., "Optimal computer folding of large RNA sequences using thermodynamics and auxiliary information," Nucleic Acids Research, Jan. 10, 1981, vol. 9, No. 1 (pp. 133-148).
Zuris et al., "Cationic lipid-mediated delivery proteins enables efficient protein-based genome editing in vitro and in vivo," Nature Biotechnology, Jan. 2015, vol. 33, No. 1 (pp. 73-80).
Zuris et al., Supplementary Information—"Cationic lipid-mediated delivery proteins enables efficient protein-based genome editing in vitro and in vivo" Nature Biotechnology, Jan. 2015, vol. 33, No. 1 (pp. 1-49).

* cited by examiner

SEQUENCE LISTING

```
<160> NUMBER OF SEQ ID NOS: 304

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Phe Trp Tyr His Lys Met Ile Leu Val Ala Gly Cys
1               5                   10


<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Phe Trp Tyr His
1


<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Trp Tyr His Lys Arg Glu Asp Cys Ser Thr Asn Gln
```

-continued 1 5 10

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

His Lys Arg Glu Asp
1 5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Val Cys Ala Gly Ser Pro Thr Asn Asp
1 5

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Gly Gly Gly Ser
1

<210> SEQ ID NO 7
<211> LENGTH: 12
<212> TYPE: PRT
<213> ORGANISM: Artificial Sequence
<220> FEATURE:
<223> OTHER INFORMATION: Synthetic

<400> SEQUENCE: 7

Gly Gly Gly Ser Gly Gly Gly Ser Gly Gly Gly Ser
1 5 10

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Ala Gly Ala Ala Ala Leu Ala
1 5

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Gly Gly Gly Gly Ser Gly Gly Gly Gly Ser Gly Gly Gly Gly Ser
1 5 10 15

<210> SEQ ID NO 10
<211> LENGTH: 30
<212> TYPE: PRT
<213> ORGANISM: Artificial Sequence
<220> FEATURE:
<223> OTHER INFORMATION: Synthetic

<400> SEQUENCE: 10

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 11
<211> LENGTH: 45
<212> TYPE: PRT
<213> ORGANISM: Artificial Sequence
<220> FEATURE:
<223> OTHER INFORMATION: Synthetic

<400> SEQUENCE: 11

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45
```

<210> SEQ ID NO 12
<211> LENGTH: 60
<212> TYPE: PRT
<213> ORGANISM: Artificial Sequence
<220> FEATURE:
<223> OTHER INFORMATION: Synthetic

<400> SEQUENCE: 12

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser
    50                  55                  60
```

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

```
Gly Gly Gly Gly Ser
1               5
```

<210> SEQ ID NO 14
<211> LENGTH: 10
<212> TYPE: PRT
<213> ORGANISM: Artificial Sequence
<220> FEATURE:
<223> OTHER INFORMATION: Synthetic

<400> SEQUENCE: 14

```
Gly Gly Gly Gly Ser Gly Gly Gly Gly Ser
1               5                   10
```

<210> SEQ ID NO 15
<211> LENGTH: 20
<212> TYPE: PRT
<213> ORGANISM: Artificial Sequence
<220> FEATURE:
<223> OTHER INFORMATION: Synthetic

<400> SEQUENCE: 15

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 16
<211> LENGTH: 25
<212> TYPE: PRT
<213> ORGANISM: Artificial Sequence
<220> FEATURE:
<223> OTHER INFORMATION: Synthetic

<400> SEQUENCE: 16

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 17
<211> LENGTH: 35
<212> TYPE: PRT
<213> ORGANISM: Artificial Sequence
<220> FEATURE:
<223> OTHER INFORMATION: Synthetic

<400> SEQUENCE: 17

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35
```

<210> SEQ ID NO 18
<211> LENGTH: 40
<212> TYPE: PRT
<213> ORGANISM: Artificial Sequence
<220> FEATURE:
<223> OTHER INFORMATION: Synthetic

<400> SEQUENCE: 18

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40
```

<210> SEQ ID NO 19
<211> LENGTH: 50
<212> TYPE: PRT

<213> ORGANISM: Artificial Sequence
<220> FEATURE:
<223> OTHER INFORMATION: Synthetic

<400> SEQUENCE: 19

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 20
<211> LENGTH: 55
<212> TYPE: PRT
<213> ORGANISM: Artificial Sequence
<220> FEATURE:
<223> OTHER INFORMATION: Synthetic

<400> SEQUENCE: 20

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser
    50                  55

<210> SEQ ID NO 21
<211> LENGTH: 229
<212> TYPE: PRT
<213> ORGANISM: Rattus sp.

<400> SEQUENCE: 21

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
    50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
        115                 120                 125

Gln Gly Leu Arg Asp Leu Ile Ser Ser Gly Val Thr Ile Gln Ile Met
    130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg 165 170 175

Leu Tyr Val Leu Glu Leu Tyr Cys Ile Ile Leu Gly Leu Pro Pro Cys
180 185 190

Leu Asn Ile Leu Arg Arg Lys Gln Pro Gln Leu Thr Phe Phe Thr Ile
195 200 205

Ala Leu Gln Ser Cys His Tyr Gln Arg Leu Pro Pro His Ile Leu Trp
210 215 220

Ala Thr Gly Leu Lys
225

<210> SEQ ID NO 22
<211> LENGTH: 236
<212> TYPE: PRT
<213> ORGANISM: Homo Sapien

<400> SEQUENCE: 22

Met Thr Ser Glu Lys Gly Pro Ser Thr Gly Asp Pro Thr Leu Arg Arg
1 5 10 15

Arg Ile Glu Pro Trp Glu Phe Asp Val Phe Tyr Asp Pro Arg Glu Leu
20 25 30

Arg Lys Glu Ala Cys Leu Leu Tyr Glu Ile Lys Trp Gly Met Ser Arg
35 40 45

Lys Ile Trp Arg Ser Ser Gly Lys Asn Thr Thr Asn His Val Glu Val
50 55 60

Asn Phe Ile Lys Lys Phe Thr Ser Glu Arg Asp Phe His Pro Ser Met
65 70 75 80

Ser Cys Ser Ile Thr Trp Phe Leu Ser Trp Ser Pro Cys Trp Glu Cys
85 90 95

Ser Gln Ala Ile Arg Glu Phe Leu Ser Arg His Pro Gly Val Thr Leu
100 105 110

Val Ile Tyr Val Ala Arg Leu Phe Trp His Met Asp Gln Gln Asn Arg
115 120 125

Gln Gly Leu Arg Asp Leu Val Asn Ser Gly Val Thr Ile Gln Ile Met
130 135 140

Arg Ala Ser Glu Tyr Tyr His Cys Trp Arg Asn Phe Val Asn Tyr Pro
145 150 155 160

Pro Gly Asp Glu Ala His Trp Pro Gln Tyr Pro Pro Leu Trp Met Met
165 170 175

Leu Tyr Ala Leu Glu Leu His Cys Ile Ile Leu Ser Leu Pro Pro Cys
180 185 190

Leu Lys Ile Ser Arg Arg Trp Gln Asn His Leu Thr Phe Phe Arg Leu
195 200 205

His Leu Gln Asn Cys His Tyr Gln Thr Ile Pro Pro His Ile Leu Leu
210 215 220

Ala Thr Gly Leu Ile His Pro Ser Val Ala Trp Arg
225 230 235

<210> SEQ ID NO 23
<211> LENGTH: 325
<212> TYPE: PRT
<213> ORGANISM: Homo Sapien

<400> SEQUENCE: 23

Met Glu Leu Lys Tyr His Pro Glu Met Arg Phe Phe His Trp Phe Ser
1 5 10 15

Lys Trp Arg Lys Leu His Arg Asp Gln Glu Tyr Glu Val Thr Trp Tyr

```
            20                  25                  30

Ile Ser Trp Ser Pro Cys Thr Lys Cys Thr Arg Asp Met Ala Thr Phe
        35                  40                  45

Leu Ala Glu Asp Pro Lys Val Thr Leu Thr Ile Phe Val Ala Arg Leu
    50                  55                  60

Tyr Tyr Phe Trp Asp Pro Asp Tyr Gln Glu Ala Leu Arg Ser Leu Cys
65                  70                  75                  80

Gln Lys Arg Asp Gly Pro Arg Ala Thr Met Lys Ile Met Asn Tyr Asp
                85                  90                  95

Glu Phe Gln His Cys Trp Ser Lys Phe Val Tyr Ser Gln Arg Glu Leu
            100                 105                 110

Phe Glu Pro Trp Asn Asn Leu Pro Lys Tyr Tyr Ile Leu Leu His Ile
        115                 120                 125

Met Leu Gly Glu Ile Leu Arg His Ser Met Asp Pro Pro Thr Phe Thr
    130                 135                 140

Phe Asn Phe Asn Asn Glu Pro Trp Val Arg Gly Arg His Glu Thr Tyr
145                 150                 155                 160

Leu Cys Tyr Glu Val Glu Arg Met His Asn Asp Thr Trp Val Leu Leu
                165                 170                 175

Asn Gln Arg Arg Gly Phe Leu Cys Asn Gln Ala Pro His Lys His Gly
            180                 185                 190

Phe Leu Glu Gly Arg His Ala Glu Leu Cys Phe Leu Asp Val Ile Pro
        195                 200                 205

Phe Trp Lys Leu Asp Leu Asp Gln Asp Tyr Arg Val Thr Cys Phe Thr
    210                 215                 220

Ser Trp Ser Pro Cys Phe Ser Cys Ala Gln Glu Met Ala Lys Phe Ile
225                 230                 235                 240

Ser Lys Asn Lys His Val Ser Leu Cys Ile Phe Thr Ala Arg Ile Tyr
                245                 250                 255

Asp Asp Gln Gly Arg Cys Gln Glu Gly Leu Arg Thr Leu Ala Glu Ala
            260                 265                 270

Gly Ala Lys Ile Ser Ile Met Thr Tyr Ser Glu Phe Lys His Cys Trp
        275                 280                 285

Asp Thr Phe Val Asp His Gln Gly Cys Pro Phe Gln Pro Trp Asp Gly
    290                 295                 300

Leu Asp Glu His Ser Gln Asp Leu Ser Gly Arg Leu Arg Ala Ile Leu
305                 310                 315                 320

Gln Asn Gln Glu Asn
                325


<210> SEQ ID NO 24
<211> LENGTH: 208
<212> TYPE: PRT
<213> ORGANISM: Petromyzon marinus

<400> SEQUENCE: 24

Met Thr Asp Ala Glu Tyr Val Arg Ile His Glu Lys Leu Asp Ile Tyr
1               5                   10                  15

Thr Phe Lys Lys Gln Phe Phe Asn Asn Lys Lys Ser Val Ser His Arg
            20                  25                  30

Cys Tyr Val Leu Phe Glu Leu Lys Arg Arg Gly Glu Arg Arg Ala Cys
        35                  40                  45

Phe Trp Gly Tyr Ala Val Asn Lys Pro Gln Ser Gly Thr Glu Arg Gly
    50                  55                  60
```

```
Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
                85                  90                  95

Cys Ala Asp Cys Ala Glu Lys Ile Leu Glu Trp Tyr Asn Gln Glu Leu
            100                 105                 110

Arg Gly Asn Gly His Thr Leu Lys Ile Trp Ala Cys Lys Leu Tyr Tyr
        115                 120                 125

Glu Lys Asn Ala Arg Asn Gln Ile Gly Leu Trp Asn Leu Arg Asp Asn
    130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Arg Ser Glu Leu Ser
            180                 185                 190

Ile Met Ile Gln Val Lys Ile Leu His Thr Thr Lys Ser Pro Ala Val
        195                 200                 205


<210> SEQ ID NO 25
<211> LENGTH: 200
<212> TYPE: PRT
<213> ORGANISM: Homo Sapien

<400> SEQUENCE: 25

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Tyr Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu Leu Asp
        195                 200


<210> SEQ ID NO 26
<211> LENGTH: 181
<212> TYPE: PRT
<213> ORGANISM: Homo Sapien
```

<400> SEQUENCE: 26

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu
            180

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Gly Gly Ser Gly Gly Ser Gly Gly Ser
1               5

<210> SEQ ID NO 28
<211> LENGTH: 32
<212> TYPE: PRT
<213> ORGANISM: Artificial Sequence
<220> FEATURE:
<223> OTHER INFORMATION: Synthetic

<400> SEQUENCE: 28

Leu Glu Pro Gly Glu Lys Pro Tyr Lys Cys Pro Glu Cys Gly Lys Ser
1               5                   10                  15

Phe Ser Gln Ser Gly Ala Leu Thr Arg His Gln Arg Thr His Thr Arg
            20                  25                  30

<210> SEQ ID NO 29
<211> LENGTH: 20
<212> TYPE: PRT
<213> ORGANISM: Artificial Sequence
<220> FEATURE:
<223> OTHER INFORMATION: Synthetic

<400> SEQUENCE: 29

Pro Lys Lys Lys Arg Lys Val Glu Ala Ser Ser Pro Lys Lys Arg Lys 1 5 10 15

Val Glu Ala Ser
20

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Gly Gly Thr Gly Gly Thr Ala Gly Thr
1 5

<210> SEQ ID NO 31
<211> LENGTH: 27
<212> TYPE: PRT
<213> ORGANISM: Artificial Sequence
<220> FEATURE:
<223> OTHER INFORMATION: Synthetic

<400> SEQUENCE: 31

Gly Gly Thr Gly Gly Thr Ala Gly Thr Gly Gly Ala Gly Gly Gly Ala
1 5 10 15

Gly Cys Gly Gly Cys Gly Gly Thr Thr Cys Ala
20 25

<210> SEQ ID NO 32
<211> LENGTH: 72
<212> TYPE: PRT
<213> ORGANISM: Artificial Sequence
<220> FEATURE:
<223> OTHER INFORMATION: Synthetic

<400> SEQUENCE: 32

Gly Gly Thr Gly Gly Ala Gly Gly Ala Gly Gly Cys Thr Cys Thr Gly
1 5 10 15

Gly Thr Gly Gly Ala Gly Gly Cys Gly Gly Thr Ala Gly Cys Gly Gly
20 25 30

Ala Gly Gly Cys Gly Gly Ala Gly Gly Gly Thr Cys Gly Gly Gly Thr
35 40 45

Gly Gly Thr Ala Gly Thr Gly Gly Ala Gly Gly Gly Ala Gly Cys Gly
50 55 60

Gly Cys Gly Gly Thr Thr Cys Ala
65 70

<210> SEQ ID NO 33
<211> LENGTH: 48
<212> TYPE: PRT
<213> ORGANISM: Artificial Sequence
<220> FEATURE:
<223> OTHER INFORMATION: Synthetic

<400> SEQUENCE: 33

Thr Cys Gly Gly Gly Ala Thr Cys Thr Gly Ala Gly Ala Cys Gly Cys
1 5 10 15

Cys Thr Gly Gly Gly Ala Cys Cys Thr Cys Gly Gly Ala Ala Thr Cys
20 25 30

Gly Gly Cys Thr Ala Cys Gly Cys Cys Cys Gly Ala Ala Ala Gly Thr
35 40 45

<210> SEQ ID NO 34
<211> LENGTH: 192
<212> TYPE: PRT
<213> ORGANISM: Artificial Sequence
<220> FEATURE:
<223> OTHER INFORMATION: Synthetic

<400> SEQUENCE: 34

```
Gly Thr Gly Gly Ala Thr Ala Ala Cys Ala Ala Ala Thr Thr Thr Ala
1               5                   10                  15

Ala Cys Ala Ala Ala Gly Ala Ala Ala Thr Gly Thr Gly Gly Gly Cys
            20                  25                  30

Gly Gly Cys Gly Thr Gly Gly Gly Ala Ala Gly Ala Ala Ala Thr Thr
        35                  40                  45

Cys Gly Thr Ala Ala Cys Cys Thr Gly Cys Cys Gly Ala Ala Cys Cys
    50                  55                  60

Thr Gly Ala Ala Cys Gly Gly Cys Thr Gly Gly Cys Ala Gly Ala Thr
65                  70                  75                  80

Gly Ala Cys Cys Gly Cys Gly Thr Thr Thr Ala Thr Thr Gly Cys Gly
                85                  90                  95

Ala Gly Cys Cys Thr Gly Gly Thr Gly Gly Ala Thr Gly Ala Thr Cys
            100                 105                 110

Cys Gly Ala Gly Cys Cys Ala Gly Ala Gly Cys Gly Cys Gly Ala Ala
        115                 120                 125

Cys Cys Thr Gly Cys Thr Gly Gly Cys Gly Gly Ala Ala Gly Cys Gly
    130                 135                 140

Ala Ala Ala Ala Ala Ala Cys Thr Gly Ala Ala Cys Gly Ala Thr Gly
145                 150                 155                 160

Cys Gly Cys Ala Gly Gly Cys Gly Cys Cys Gly Ala Ala Ala Ala Cys
                165                 170                 175

Cys Gly Gly Cys Gly Gly Thr Gly Gly Thr Thr Cys Thr Gly Gly Thr
            180                 185                 190
```

<210> SEQ ID NO 35
<211> LENGTH: 108
<212> TYPE: PRT
<213> ORGANISM: Artificial Sequence
<220> FEATURE:
<223> OTHER INFORMATION: Synthetic

<400> SEQUENCE: 35

```
Gly Gly Thr Gly Gly Thr Thr Cys Thr Gly Cys Cys Gly Gly Thr Gly
1               5                   10                  15

Gly Cys Thr Cys Cys Gly Gly Thr Thr Cys Thr Gly Gly Cys Thr Cys
            20                  25                  30

Cys Ala Gly Cys Gly Gly Thr Gly Gly Cys Ala Gly Cys Thr Cys Thr
        35                  40                  45

Gly Gly Thr Gly Cys Gly Thr Cys Cys Gly Gly Cys Ala Cys Gly Gly
    50                  55                  60

Gly Thr Ala Cys Thr Gly Cys Gly Gly Gly Thr Gly Gly Cys Ala Cys
65                  70                  75                  80

Thr Gly Gly Cys Ala Gly Cys Gly Gly Thr Thr Cys Cys Gly Gly Thr
                85                  90                  95

Ala Cys Thr Gly Gly Cys Thr Cys Thr Gly Gly Cys
            100                 105
```

<210> SEQ ID NO 36
<211> LENGTH: 12

```
<212> TYPE: DNA
<213> ORGANISM: Artificial Sequence
<220> FEATURE:
<223> OTHER INFORMATION: Synthetic

<400> SEQUENCE: 36

acttgtttaa gt                                                        12


<210> SEQ ID NO 37
<211> LENGTH: 12
<212> TYPE: DNA
<213> ORGANISM: Artificial Sequence
<220> FEATURE:
<223> OTHER INFORMATION: stemloop 2
<220> FEATURE:
<221> NAME/KEY: misc_feature
<222> LOCATION: (1)..(4)
<223> OTHER INFORMATION: n represents any set of nucleotides that are
      complementary to and together with base pair to nucleotides 9-12,
      where n is a, c, g, t, or u
<220> FEATURE:
<221> NAME/KEY: misc_feature
<222> LOCATION: (9)..(12)
<223> OTHER INFORMATION: n represents any set of nucleotides that are
      complementary to and together with base pair to nucleotides 1-4,
      where n is a, c, g, t or u

<400> SEQUENCE: 37

nnnngtttnn nn                                                        12


<210> SEQ ID NO 38
<211> LENGTH: 16
<212> TYPE: DNA
<213> ORGANISM: Artificial Sequence
<220> FEATURE:
<223> OTHER INFORMATION: Synthetic

<400> SEQUENCE: 38

ggcaccgagt cggtgc                                                    16


<210> SEQ ID NO 39
<211> LENGTH: 17
<212> TYPE: DNA
<213> ORGANISM: Artificial Sequence
<220> FEATURE:
<223> OTHER INFORMATION: stemloop 3
<220> FEATURE:
<221> NAME/KEY: misc_feature
<222> LOCATION: (1)..(7)
<223> OTHER INFORMATION: n represents any set of nucleotides that are
      complementary to and together will base pair to nucleotides 11-17,
      where n is a, c, g, t or u
<220> FEATURE:
<221> NAME/KEY: misc_feature
<222> LOCATION: (11)..(17)
<223> OTHER INFORMATION: n represents any set of nucleotides that are
      complementary to and together will base pair to nucleotides 1-7,
      where n is a, c, g, t or u

<400> SEQUENCE: 39

nnnnnnnagt nnnnnnn                                                   17


<210> SEQ ID NO 40
<211> LENGTH: 30
<212> TYPE: RNA
<213> ORGANISM: Artificial Sequence
<220> FEATURE:
<223> OTHER INFORMATION: DR:tracrRNA duplex
<220> FEATURE:
<221> NAME/KEY: misc_feature
<222> LOCATION: (8)..(8)
```

<223> OTHER INFORMATION: n represents part of the bulge of the duplex,
      where n is a, c, g, t or u
<220> FEATURE:
<221> NAME/KEY: misc_feature
<222> LOCATION: (9)..(12)
<223> OTHER INFORMATION: n represents any set of nucleotides that are
      complementary to and together will base pair to nucleotides 17-20,
      where n is a, c, g, t or u
<220> FEATURE:
<221> NAME/KEY: misc_feature
<222> LOCATION: (13)..(16)
<223> OTHER INFORMATION: n represents a linker of any length and any
      base composition so long as it does not alter the overall
      structure of the duplex
<220> FEATURE:
<221> NAME/KEY: misc_feature
<222> LOCATION: (17)..(20)
<223> OTHER INFORMATION: n represents any set of nucleotides that are
      complementary to and together will base pair to nucleotides 9-12,
      where n is a, c, g, t or u
<220> FEATURE:
<221> NAME/KEY: misc_feature
<222> LOCATION: (21)..(23)
<223> OTHER INFORMATION: part of the bulge in the duplex

<400> SEQUENCE: 40
gyyyyagnnn nnnnnnnnnn aanuurrrru 30

<210> SEQ ID NO 41
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: n is a, c, g, or t

<400> SEQUENCE: 41
nnnnnnnnnn nn 12

<210> SEQ ID NO 42
<211> LENGTH: 37
<212> TYPE: DNA
<213> ORGANISM: Artificial Sequence
<220> FEATURE:
<223> OTHER INFORMATION: Synthetic

<400> SEQUENCE: 42
gcctgtccgc ggaagcagtg gtatcaacgc agagtac 37

<210> SEQ ID NO 43
<211> LENGTH: 107
<212> TYPE: PRT
<213> ORGANISM: Artificial Sequence
<220> FEATURE:
<223> OTHER INFORMATION: Synthetic

<400> SEQUENCE: 43

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65 70 75 80

Met Thr Pro Arg Arg Pro Gly Pro Thr Arg Lys His Tyr Gln Pro Tyr
85 90 95

Ala Pro Pro Arg Asp Phe Ala Ala Tyr Arg Ser
100 105

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

Ile Glu Val Met Tyr Pro Pro Pro Tyr
1 5

<210> SEQ ID NO 45
<211> LENGTH: 9
<212> TYPE: PRT
<213> ORGANISM: Artificial Sequence
<220> FEATURE:
<223> OTHER INFORMATION: Synthetic

<400> SEQUENCE: 45

Ile Glu Val Met Tyr Pro Pro Pro Tyr
1 5

<210> SEQ ID NO 46
<211> LENGTH: 107
<212> TYPE: PRT
<213> ORGANISM: Artificial Sequence
<220> FEATURE:
<223> OTHER INFORMATION: Synthetic

<400> SEQUENCE: 46

Ile Glu Val Met Tyr Pro Pro Pro Tyr Leu Asp Asn Glu Lys Ser Asn
1 5 10 15

Gly Thr Ile Ile His Val Lys Gly Lys His Leu Cys Pro Ser Pro Leu
20 25 30

Phe Pro Gly Pro Ser Lys Pro Phe Trp Val Leu Val Val Val Gly Gly
35 40 45

Val Leu Ala Cys Tyr Ser Leu Leu Val Thr Val Ala Phe Ile Ile Phe
50 55 60

Trp Val Arg Ser Lys Arg Ser Arg Leu Leu His Ser Asp Tyr Met Asn
65 70 75 80

Met Thr Pro Arg Arg Pro Gly Pro Thr Arg Lys His Tyr Gln Pro Tyr
85 90 95

Ala Pro Pro Arg Asp Phe Ala Ala Tyr Arg Ser
100 105

<210> SEQ ID NO 47
<211> LENGTH: 20
<212> TYPE: DNA
<213> ORGANISM: Homo Sapien

<400> SEQUENCE: 47
gagtccgagc agaagaagaa 20

<210> SEQ ID NO 48
<211> LENGTH: 20

<212> TYPE: DNA
<213> ORGANISM: Artificial Sequence
<220> FEATURE:
<223> OTHER INFORMATION: Synthetic

<400> SEQUENCE: 48
gagtcctagc aggagaagaa 20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
gagtctaagc agaagaagaa 20

<210> SEQ ID NO 50
<211> LENGTH: 15
<212> TYPE: PRT
<213> ORGANISM: Artificial Sequence
<220> FEATURE:
<223> OTHER INFORMATION: Synthetic

<400> SEQUENCE: 50

Gly Gly Gly Gly Gly Gly Gly Gly Gly Gly Gly Gly Gly Gly Gly
1 5 10 15

<210> SEQ ID NO 51
<211> LENGTH: 17
<212> TYPE: DNA
<213> ORGANISM: Artificial Sequence
<220> FEATURE:
<223> OTHER INFORMATION: Synthetic

<400> SEQUENCE: 51
tatatacaca cacacac 17

<210> SEQ ID NO 52
<211> LENGTH: 12
<212> TYPE: DNA
<213> ORGANISM: Artificial Sequence
<220> FEATURE:
<223> OTHER INFORMATION: Synthetic

<400> SEQUENCE: 52
cttttttttt tt 12

<210> SEQ ID NO 53
<211> LENGTH: 12
<212> TYPE: DNA
<213> ORGANISM: Artificial Sequence
<220> FEATURE:
<223> OTHER INFORMATION: Synthetic

<400> SEQUENCE: 53
caaaaaaaaa aa 12

<210> SEQ ID NO 54
<211> LENGTH: 10
<212> TYPE: DNA
<213> ORGANISM: Artificial Sequence
<220> FEATURE:
<223> OTHER INFORMATION: Synthetic

<400> SEQUENCE: 54
tttgttgttg 10

<210> SEQ ID NO 55
<211> LENGTH: 12
<212> TYPE: DNA
<213> ORGANISM: Artificial Sequence
<220> FEATURE:
<223> OTHER INFORMATION: Synthetic

<400> SEQUENCE: 55
tttttttttt tg 12

<210> SEQ ID NO 56
<211> LENGTH: 15
<212> TYPE: DNA
<213> ORGANISM: Artificial Sequence
<220> FEATURE:
<223> OTHER INFORMATION: Synthetic

<400> SEQUENCE: 56
tacaaaaaaa aaaaa 15

<210> SEQ ID NO 57
<211> LENGTH: 15
<212> TYPE: DNA
<213> ORGANISM: Artificial Sequence
<220> FEATURE:
<223> OTHER INFORMATION: Synthetic

<400> SEQUENCE: 57
tacaaaaaaa aaaaa 15

<210> SEQ ID NO 58
<211> LENGTH: 10
<212> TYPE: DNA
<213> ORGANISM: Artificial Sequence
<220> FEATURE:
<223> OTHER INFORMATION: Synthetic

<400> SEQUENCE: 58
tggcggcggc 10

<210> SEQ ID NO 59
<211> LENGTH: 13
<212> TYPE: DNA
<213> ORGANISM: Artificial Sequence
<220> FEATURE:
<223> OTHER INFORMATION: Synthetic

<400> SEQUENCE: 59
acagcaacac cag 13

<210> SEQ ID NO 60
<211> LENGTH: 18
<212> TYPE: DNA
<213> ORGANISM: Artificial Sequence
<220> FEATURE:
<223> OTHER INFORMATION: Synthetic

<400> SEQUENCE: 60
taaaaaaaaa aaaaaaaa 18

<210> SEQ ID NO 61
<211> LENGTH: 10
<212> TYPE: DNA

<213> ORGANISM: Artificial Sequence
<220> FEATURE:
<223> OTHER INFORMATION: Synthetic

<400> SEQUENCE: 61
atttttttt 10

<210> SEQ ID NO 62
<211> LENGTH: 18
<212> TYPE: DNA
<213> ORGANISM: Artificial Sequence
<220> FEATURE:
<223> OTHER INFORMATION: Synthetic

<400> SEQUENCE: 62
taaaaaaaaa aaaaaaaa 18

<210> SEQ ID NO 63
<211> LENGTH: 13
<212> TYPE: DNA
<213> ORGANISM: Artificial Sequence
<220> FEATURE:
<223> OTHER INFORMATION: Synthetic

<400> SEQUENCE: 63
acagcaacac cag 13

<210> SEQ ID NO 64
<211> LENGTH: 10
<212> TYPE: DNA
<213> ORGANISM: Artificial Sequence
<220> FEATURE:
<223> OTHER INFORMATION: Synthetic

<400> SEQUENCE: 64
ggaaagggac 10

<210> SEQ ID NO 65
<211> LENGTH: 19
<212> TYPE: DNA
<213> ORGANISM: Artificial Sequence
<220> FEATURE:
<223> OTHER INFORMATION: Synthetic

<400> SEQUENCE: 65
acttctctgg attgggagc 19

<210> SEQ ID NO 66
<211> LENGTH: 10
<212> TYPE: DNA
<213> ORGANISM: Artificial Sequence
<220> FEATURE:
<223> OTHER INFORMATION: Synthetic

<400> SEQUENCE: 66
tgaggatgag 10

<210> SEQ ID NO 67
<211> LENGTH: 11
<212> TYPE: DNA
<213> ORGANISM: Artificial Sequence
<220> FEATURE:
<223> OTHER INFORMATION: Synthetic

<400> SEQUENCE: 67
caaaaaaaaa a 11

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
cagtgtgtgt tcagagcagt 20

<210> SEQ ID NO 69
<211> LENGTH: 18
<212> TYPE: DNA
<213> ORGANISM: Artificial Sequence
<220> FEATURE:
<223> OTHER INFORMATION: Synthetic

<400> SEQUENCE: 69
cgtaaggcac aggaggca 18

<210> SEQ ID NO 70
<211> LENGTH: 18
<212> TYPE: DNA
<213> ORGANISM: Artificial Sequence
<220> FEATURE:
<223> OTHER INFORMATION: Synthetic

<400> SEQUENCE: 70
cgtaaggcac aggaggca 18

<210> SEQ ID NO 71
<211> LENGTH: 10
<212> TYPE: DNA
<213> ORGANISM: Artificial Sequence
<220> FEATURE:
<223> OTHER INFORMATION: Synthetic

<400> SEQUENCE: 71
ggaaagggac 10

<210> SEQ ID NO 72
<211> LENGTH: 19
<212> TYPE: DNA
<213> ORGANISM: Artificial Sequence
<220> FEATURE:
<223> OTHER INFORMATION: Synthetic

<400> SEQUENCE: 72
acttctctgg attgggagc 19

<210> SEQ ID NO 73
<211> LENGTH: 10
<212> TYPE: DNA
<213> ORGANISM: Artificial Sequence
<220> FEATURE:
<223> OTHER INFORMATION: Synthetic

<400> SEQUENCE: 73
tgaggatgag 10

<210> SEQ ID NO 74
<211> LENGTH: 11
<212> TYPE: DNA
<213> ORGANISM: Artificial Sequence
<220> FEATURE:

<223> OTHER INFORMATION: Synthetic

<400> SEQUENCE: 74
atgtggtgac c 11

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
cagtgtgtgt tcagagcagt 20

<210> SEQ ID NO 76
<211> LENGTH: 13
<212> TYPE: DNA
<213> ORGANISM: Artificial Sequence
<220> FEATURE:
<223> OTHER INFORMATION: Synthetic

<400> SEQUENCE: 76
acagcaacac cag 13

<210> SEQ ID NO 77
<211> LENGTH: 13
<212> TYPE: DNA
<213> ORGANISM: Artificial Sequence
<220> FEATURE:
<223> OTHER INFORMATION: Synthetic

<400> SEQUENCE: 77 ctttttttt ttt 13

<210> SEQ ID NO 78
<211> LENGTH: 12
<212> TYPE: DNA
<213> ORGANISM: Artificial Sequence
<220> FEATURE:
<223> OTHER INFORMATION: Synthetic

<400> SEQUENCE: 78
gccccccagc cc 12

<210> SEQ ID NO 79
<211> LENGTH: 12
<212> TYPE: DNA
<213> ORGANISM: Artificial Sequence
<220> FEATURE:
<223> OTHER INFORMATION: Synthetic

<400> SEQUENCE: 79 ctttttttt tt 12

<210> SEQ ID NO 80
<211> LENGTH: 12
<212> TYPE: DNA
<213> ORGANISM: Artificial Sequence
<220> FEATURE:
<223> OTHER INFORMATION: Synthetic

<400> SEQUENCE: 80
gccccccagc cc 12

<210> SEQ ID NO 81
<211> LENGTH: 13
<212> TYPE: DNA
<213> ORGANISM: Artificial Sequence
<220> FEATURE:
<223> OTHER INFORMATION: Synthetic

<400> SEQUENCE: 81
aacacacaca cac 13

<210> SEQ ID NO 82
<211> LENGTH: 13
<212> TYPE: DNA
<213> ORGANISM: Artificial Sequence
<220> FEATURE:
<223> OTHER INFORMATION: Synthetic

<400> SEQUENCE: 82
aacacacaca cac 13

<210> SEQ ID NO 83
<211> LENGTH: 18
<212> TYPE: DNA
<213> ORGANISM: Artificial Sequence
<220> FEATURE:
<223> OTHER INFORMATION: Synthetic

<400> SEQUENCE: 83
agatcttgga cagatgtt 18

<210> SEQ ID NO 84
<211> LENGTH: 22
<212> TYPE: DNA
<213> ORGANISM: Artificial Sequence
<220> FEATURE:
<223> OTHER INFORMATION: Synthetic

<400> SEQUENCE: 84
tggcggcggc ggcggcggcg gc 22

<210> SEQ ID NO 85
<211> LENGTH: 18
<212> TYPE: DNA
<213> ORGANISM: Artificial Sequence
<220> FEATURE:
<223> OTHER INFORMATION: Synthetic

<400> SEQUENCE: 85
caaaaaaaaa aaaaaaaa 18

<210> SEQ ID NO 86
<211> LENGTH: 18
<212> TYPE: DNA
<213> ORGANISM: Artificial Sequence
<220> FEATURE:
<223> OTHER INFORMATION: Synthetic

<400> SEQUENCE: 86
agatcttgga cagatgtt 18

<210> SEQ ID NO 87
<211> LENGTH: 10
<212> TYPE: DNA
<213> ORGANISM: Artificial Sequence
<220> FEATURE:
<223> OTHER INFORMATION: Synthetic

<400> SEQUENCE: 87
caaaaaaaaa 10

<210> SEQ ID NO 88
<211> LENGTH: 22
<212> TYPE: DNA
<213> ORGANISM: Artificial Sequence
<220> FEATURE:
<223> OTHER INFORMATION: Synthetic

<400> SEQUENCE: 88
tggcggcggc ggcggcggcg gc 22

<210> SEQ ID NO 89
<211> LENGTH: 18
<212> TYPE: DNA
<213> ORGANISM: Artificial Sequence
<220> FEATURE:
<223> OTHER INFORMATION: Synthetic

<400> SEQUENCE: 89
caaaaaaaaa aaaaaaaa 18

<210> SEQ ID NO 90
<211> LENGTH: 18
<212> TYPE: DNA
<213> ORGANISM: Artificial Sequence
<220> FEATURE:
<223> OTHER INFORMATION: Synthetic

<400> SEQUENCE: 90
taaaaaaaaa aaaaaaaa 18

<210> SEQ ID NO 91
<211> LENGTH: 11
<212> TYPE: DNA
<213> ORGANISM: Artificial Sequence
<220> FEATURE:
<223> OTHER INFORMATION: Synthetic

<400> SEQUENCE: 91
caaaaaaaaa a 11

<210> SEQ ID NO 92
<211> LENGTH: 25
<212> TYPE: DNA
<213> ORGANISM: Artificial Sequence
<220> FEATURE:
<223> OTHER INFORMATION: Synthetic

<400> SEQUENCE: 92
atcgggcccc caaagtccgg ctgac 25

<210> SEQ ID NO 93
<211> LENGTH: 11
<212> TYPE: DNA
<213> ORGANISM: Artificial Sequence
<220> FEATURE:
<223> OTHER INFORMATION: Synthetic

<400> SEQUENCE: 93
gccccccccc c 11

<210> SEQ ID NO 94
<211> LENGTH: 11

<212> TYPE: DNA
<213> ORGANISM: Artificial Sequence
<220> FEATURE:
<223> OTHER INFORMATION: Synthetic

<400> SEQUENCE: 94
ccacggggtc a 11

<210> SEQ ID NO 95
<211> LENGTH: 13
<212> TYPE: DNA
<213> ORGANISM: Artificial Sequence
<220> FEATURE:
<223> OTHER INFORMATION: Synthetic

<400> SEQUENCE: 95
ctccttcctt cct 13

<210> SEQ ID NO 96
<211> LENGTH: 18
<212> TYPE: DNA
<213> ORGANISM: Artificial Sequence
<220> FEATURE:
<223> OTHER INFORMATION: Synthetic

<400> SEQUENCE: 96
caaaaaaaaa aaaaaaaa 18

<210> SEQ ID NO 97
<211> LENGTH: 25
<212> TYPE: DNA
<213> ORGANISM: Artificial Sequence
<220> FEATURE:
<223> OTHER INFORMATION: Synthetic

<400> SEQUENCE: 97
atcgggcccc caaagtccgg ctgac 25

<210> SEQ ID NO 98
<211> LENGTH: 10
<212> TYPE: DNA
<213> ORGANISM: Artificial Sequence
<220> FEATURE:
<223> OTHER INFORMATION: Synthetic

<400> SEQUENCE: 98
caaaaaaaaa 10

<210> SEQ ID NO 99
<211> LENGTH: 11
<212> TYPE: DNA
<213> ORGANISM: Artificial Sequence
<220> FEATURE:
<223> OTHER INFORMATION: Synthetic

<400> SEQUENCE: 99
caaaaaaaaa a 11

<210> SEQ ID NO 100
<211> LENGTH: 11
<212> TYPE: DNA
<213> ORGANISM: Artificial Sequence
<220> FEATURE:
<223> OTHER INFORMATION: Synthetic

<400> SEQUENCE: 100
ccacggggtc a 11

<210> SEQ ID NO 101
<211> LENGTH: 10
<212> TYPE: DNA
<213> ORGANISM: Artificial Sequence
<220> FEATURE:
<223> OTHER INFORMATION: Synthetic

<400> SEQUENCE: 101
gattatatat 10

<210> SEQ ID NO 102
<211> LENGTH: 18
<212> TYPE: DNA
<213> ORGANISM: Artificial Sequence
<220> FEATURE:
<223> OTHER INFORMATION: Synthetic

<400> SEQUENCE: 102
taaaaaaaaa aaaaaaaa 18

<210> SEQ ID NO 103
<211> LENGTH: 18
<212> TYPE: DNA
<213> ORGANISM: Artificial Sequence
<220> FEATURE:
<223> OTHER INFORMATION: Synthetic

<400> SEQUENCE: 103
taaaaaaaaa aaaaaaaa 18

<210> SEQ ID NO 104
<211> LENGTH: 12
<212> TYPE: DNA
<213> ORGANISM: Artificial Sequence
<220> FEATURE:
<223> OTHER INFORMATION: Synthetic

<400> SEQUENCE: 104
cttttttttt tt 12

<210> SEQ ID NO 105
<211> LENGTH: 11
<212> TYPE: DNA
<213> ORGANISM: Artificial Sequence
<220> FEATURE:
<223> OTHER INFORMATION: Synthetic

<400> SEQUENCE: 105
gccccccccc c 11

<210> SEQ ID NO 106
<211> LENGTH: 18
<212> TYPE: DNA
<213> ORGANISM: Artificial Sequence
<220> FEATURE:
<223> OTHER INFORMATION: Synthetic

<400> SEQUENCE: 106
taaaaaaaaa aaaaaaaa 18

<210> SEQ ID NO 107
<211> LENGTH: 11
<212> TYPE: DNA
<213> ORGANISM: Artificial Sequence
<220> FEATURE:
<223> OTHER INFORMATION: Synthetic

<400> SEQUENCE: 107 gcccccccccc c 11

<210> SEQ ID NO 108
<211> LENGTH: 12
<212> TYPE: DNA
<213> ORGANISM: Artificial Sequence
<220> FEATURE:
<223> OTHER INFORMATION: Synthetic

<400> SEQUENCE: 108
gtcactgtgt ga 12

<210> SEQ ID NO 109
<211> LENGTH: 11
<212> TYPE: DNA
<213> ORGANISM: Artificial Sequence
<220> FEATURE:
<223> OTHER INFORMATION: Synthetic

<400> SEQUENCE: 109 gcccccccccc c 11

<210> SEQ ID NO 110
<211> LENGTH: 11
<212> TYPE: DNA
<213> ORGANISM: Artificial Sequence
<220> FEATURE:
<223> OTHER INFORMATION: Synthetic

<400> SEQUENCE: 110
attttttttt t 11

<210> SEQ ID NO 111
<211> LENGTH: 12
<212> TYPE: DNA
<213> ORGANISM: Artificial Sequence
<220> FEATURE:
<223> OTHER INFORMATION: Synthetic

<400> SEQUENCE: 111
gtcactgtgt ga 12

<210> SEQ ID NO 112
<211> LENGTH: 13
<212> TYPE: DNA
<213> ORGANISM: Artificial Sequence
<220> FEATURE:
<223> OTHER INFORMATION: Synthetic

<400> SEQUENCE: 112
cttttttttt ttt 13

<210> SEQ ID NO 113
<211> LENGTH: 23
<212> TYPE: DNA
<213> ORGANISM: Artificial Sequence
<220> FEATURE:
<223> OTHER INFORMATION: Synthetic

<400> SEQUENCE: 113
ctcttggaca gctgagggaa tgg 23

<210> SEQ ID NO 114
<211> LENGTH: 10
<212> TYPE: DNA
<213> ORGANISM: Artificial Sequence
<220> FEATURE:
<223> OTHER INFORMATION: Synthetic

<400> SEQUENCE: 114
caaaaaaaaa 10

<210> SEQ ID NO 115
<211> LENGTH: 12
<212> TYPE: DNA
<213> ORGANISM: Artificial Sequence
<220> FEATURE:
<223> OTHER INFORMATION: Synthetic

<400> SEQUENCE: 115
cttttttttt tt 12

<210> SEQ ID NO 116
<211> LENGTH: 18
<212> TYPE: DNA
<213> ORGANISM: Artificial Sequence
<220> FEATURE:
<223> OTHER INFORMATION: Synthetic

<400> SEQUENCE: 116
caaaaaaaaa aaaaaaaa 18

<210> SEQ ID NO 117
<211> LENGTH: 23
<212> TYPE: DNA
<213> ORGANISM: Artificial Sequence
<220> FEATURE:
<223> OTHER INFORMATION: Synthetic

<400> SEQUENCE: 117
ctcttggaca gctgagggaa tgg 23

<210> SEQ ID NO 118
<211> LENGTH: 11
<212> TYPE: DNA
<213> ORGANISM: Artificial Sequence
<220> FEATURE:
<223> OTHER INFORMATION: Synthetic

<400> SEQUENCE: 118
caaaaaaaaa a 11

<210> SEQ ID NO 119
<211> LENGTH: 10
<212> TYPE: DNA
<213> ORGANISM: Artificial Sequence
<220> FEATURE:
<223> OTHER INFORMATION: Synthetic

<400> SEQUENCE: 119
tttgttgttg 10

<210> SEQ ID NO 120
<211> LENGTH: 12
<212> TYPE: DNA
<213> ORGANISM: Artificial Sequence
<220> FEATURE:
<223> OTHER INFORMATION: Synthetic

<400> SEQUENCE: 120
cttttttttt tt 12

<210> SEQ ID NO 121
<211> LENGTH: 10
<212> TYPE: DNA
<213> ORGANISM: Artificial Sequence
<220> FEATURE:
<223> OTHER INFORMATION: Synthetic

<400> SEQUENCE: 121
tttttttttg 10

<210> SEQ ID NO 122
<211> LENGTH: 11
<212> TYPE: DNA
<213> ORGANISM: Artificial Sequence
<220> FEATURE:
<223> OTHER INFORMATION: Synthetic

<400> SEQUENCE: 122
caaaaaaaaa a 11

<210> SEQ ID NO 123
<211> LENGTH: 10
<212> TYPE: DNA
<213> ORGANISM: Artificial Sequence
<220> FEATURE:
<223> OTHER INFORMATION: Synthetic

<400> SEQUENCE: 123
gattatatat 10

<210> SEQ ID NO 124
<211> LENGTH: 10
<212> TYPE: DNA
<213> ORGANISM: Artificial Sequence
<220> FEATURE:
<223> OTHER INFORMATION: Synthetic

<400> SEQUENCE: 124
attttttttt 10

<210> SEQ ID NO 125
<211> LENGTH: 10
<212> TYPE: DNA
<213> ORGANISM: Artificial Sequence
<220> FEATURE:
<223> OTHER INFORMATION: Synthetic

<400> SEQUENCE: 125
gattatatat 10

<210> SEQ ID NO 126
<211> LENGTH: 18
<212> TYPE: DNA
<213> ORGANISM: Artificial Sequence
<220> FEATURE:
<223> OTHER INFORMATION: Synthetic

<400> SEQUENCE: 126
caaaaaaaaa aaaaaaaa 18

<210> SEQ ID NO 127

<211> LENGTH: 18
<212> TYPE: DNA
<213> ORGANISM: Artificial Sequence
<220> FEATURE:
<223> OTHER INFORMATION: Synthetic

<400> SEQUENCE: 127
taaaaaaaaa aaaaaaaa 18

<210> SEQ ID NO 128
<211> LENGTH: 18
<212> TYPE: DNA
<213> ORGANISM: Artificial Sequence
<220> FEATURE:
<223> OTHER INFORMATION: Synthetic

<400> SEQUENCE: 128
caaaaaaaaa aaaaaaaa 18

<210> SEQ ID NO 129
<211> LENGTH: 10
<212> TYPE: DNA
<213> ORGANISM: Artificial Sequence
<220> FEATURE:
<223> OTHER INFORMATION: Synthetic

<400> SEQUENCE: 129
cttttttttt 10

<210> SEQ ID NO 130
<211> LENGTH: 18
<212> TYPE: DNA
<213> ORGANISM: Artificial Sequence
<220> FEATURE:
<223> OTHER INFORMATION: Synthetic

<400> SEQUENCE: 130
caaaaaaaaa aaaaaaaa 18

<210> SEQ ID NO 131
<211> LENGTH: 19
<212> TYPE: DNA
<213> ORGANISM: Artificial Sequence
<220> FEATURE:
<223> OTHER INFORMATION: Synthetic

<400> SEQUENCE: 131
tggcggcggc ggcggcggc 19

<210> SEQ ID NO 132
<211> LENGTH: 10
<212> TYPE: DNA
<213> ORGANISM: Artificial Sequence
<220> FEATURE:
<223> OTHER INFORMATION: Synthetic

<400> SEQUENCE: 132
cttttttttt 10

<210> SEQ ID NO 133
<211> LENGTH: 18
<212> TYPE: DNA
<213> ORGANISM: Artificial Sequence
<220> FEATURE:
<223> OTHER INFORMATION: Synthetic

<400> SEQUENCE: 133
caaaaaaaaa aaaaaaaa 18

<210> SEQ ID NO 134
<211> LENGTH: 19
<212> TYPE: DNA
<213> ORGANISM: Artificial Sequence
<220> FEATURE:
<223> OTHER INFORMATION: Synthetic

<400> SEQUENCE: 134
tggcggcggc ggcggcggc 19

<210> SEQ ID NO 135
<211> LENGTH: 10
<212> TYPE: DNA
<213> ORGANISM: Artificial Sequence
<220> FEATURE:
<223> OTHER INFORMATION: Synthetic

<400> SEQUENCE: 135
cttttttttt 10

<210> SEQ ID NO 136
<211> LENGTH: 15
<212> TYPE: DNA
<213> ORGANISM: Artificial Sequence
<220> FEATURE:
<223> OTHER INFORMATION: Synthetic

<400> SEQUENCE: 136
gcgcgcgcgc acaca 15

<210> SEQ ID NO 137
<211> LENGTH: 19
<212> TYPE: DNA
<213> ORGANISM: Artificial Sequence
<220> FEATURE:
<223> OTHER INFORMATION: Synthetic

<400> SEQUENCE: 137
tggcggcggc ggcggcggc 19

<210> SEQ ID NO 138
<211> LENGTH: 10
<212> TYPE: DNA
<213> ORGANISM: Artificial Sequence
<220> FEATURE:
<223> OTHER INFORMATION: Synthetic

<400> SEQUENCE: 138
cttttttttt 10

<210> SEQ ID NO 139
<211> LENGTH: 15
<212> TYPE: DNA
<213> ORGANISM: Artificial Sequence
<220> FEATURE:
<223> OTHER INFORMATION: Synthetic

<400> SEQUENCE: 139
gcgcgcgcgc acaca 15

<210> SEQ ID NO 140
<211> LENGTH: 19
<212> TYPE: DNA

<213> ORGANISM: Artificial Sequence
<220> FEATURE:
<223> OTHER INFORMATION: Synthetic

<400> SEQUENCE: 140
tggcggcggc ggcggcggc 19

<210> SEQ ID NO 141
<211> LENGTH: 11
<212> TYPE: DNA
<213> ORGANISM: Artificial Sequence
<220> FEATURE:
<223> OTHER INFORMATION: Synthetic

<400> SEQUENCE: 141
cggacgggac g 11

<210> SEQ ID NO 142
<211> LENGTH: 10
<212> TYPE: DNA
<213> ORGANISM: Artificial Sequence
<220> FEATURE:
<223> OTHER INFORMATION: Synthetic

<400> SEQUENCE: 142
tttttttttg 10

<210> SEQ ID NO 143
<211> LENGTH: 11
<212> TYPE: DNA
<213> ORGANISM: Artificial Sequence
<220> FEATURE:
<223> OTHER INFORMATION: Synthetic

<400> SEQUENCE: 143
cggacgggac g 11

<210> SEQ ID NO 144
<211> LENGTH: 11
<212> TYPE: DNA
<213> ORGANISM: Artificial Sequence
<220> FEATURE:
<223> OTHER INFORMATION: Synthetic

<400> SEQUENCE: 144
caaaaaaaaa a 11

<210> SEQ ID NO 145
<211> LENGTH: 22
<212> TYPE: DNA
<213> ORGANISM: Artificial Sequence
<220> FEATURE:
<223> OTHER INFORMATION: Synthetic

<400> SEQUENCE: 145
tggcggcggc ggcggcggcg gc 22

<210> SEQ ID NO 146
<211> LENGTH: 10
<212> TYPE: DNA
<213> ORGANISM: Artificial Sequence
<220> FEATURE:
<223> OTHER INFORMATION: Synthetic

<400> SEQUENCE: 146
gattatatat 10

```
<210> SEQ ID NO 147
<211> LENGTH: 10
<212> TYPE: DNA
<213> ORGANISM: Artificial Sequence
<220> FEATURE:
<223> OTHER INFORMATION: Synthetic

<400> SEQUENCE: 147

attttttttt                                                            10

<210> SEQ ID NO 148
<211> LENGTH: 26
<212> TYPE: DNA
<213> ORGANISM: Artificial Sequence
<220> FEATURE:
<223> OTHER INFORMATION: Synthetic

<400> SEQUENCE: 148

ggacagatac atgatgtaat gtatat                                          26

<210> SEQ ID NO 149
<211> LENGTH: 26
<212> TYPE: DNA
<213> ORGANISM: Artificial Sequence
<220> FEATURE:
<223> OTHER INFORMATION: Synthetic

<400> SEQUENCE: 149

ggacagatac atgatgtaat gtatat                                          26

<210> SEQ ID NO 150
<211> LENGTH: 11
<212> TYPE: DNA
<213> ORGANISM: Artificial Sequence
<220> FEATURE:
<223> OTHER INFORMATION: Synthetic

<400> SEQUENCE: 150

aacacacaca c                                                          11

<210> SEQ ID NO 151
<211> LENGTH: 10
<212> TYPE: DNA
<213> ORGANISM: Artificial Sequence
<220> FEATURE:
<223> OTHER INFORMATION: Synthetic

<400> SEQUENCE: 151

gattatatat                                                            10

<210> SEQ ID NO 152
<211> LENGTH: 10
<212> TYPE: DNA
<213> ORGANISM: Artificial Sequence
<220> FEATURE:
<223> OTHER INFORMATION: Synthetic

<400> SEQUENCE: 152

atttttttt                                                             10

<210> SEQ ID NO 153
<211> LENGTH: 22
<212> TYPE: DNA
<213> ORGANISM: Artificial Sequence
<220> FEATURE:
```

<223> OTHER INFORMATION: Synthetic

<400> SEQUENCE: 153
tggcggcggc ggcggcggcg gc 22

<210> SEQ ID NO 154
<211> LENGTH: 15
<212> TYPE: DNA
<213> ORGANISM: Artificial Sequence
<220> FEATURE:
<223> OTHER INFORMATION: Synthetic

<400> SEQUENCE: 154
gcgcgcgcgc acaca 15

<210> SEQ ID NO 155
<211> LENGTH: 11
<212> TYPE: DNA
<213> ORGANISM: Artificial Sequence
<220> FEATURE:
<223> OTHER INFORMATION: Synthetic

<400> SEQUENCE: 155
ttcttttcac a 11

<210> SEQ ID NO 156
<211> LENGTH: 11
<212> TYPE: DNA
<213> ORGANISM: Artificial Sequence
<220> FEATURE:
<223> OTHER INFORMATION: Synthetic

<400> SEQUENCE: 156
ttcttttcac a 11

<210> SEQ ID NO 157
<211> LENGTH: 13
<212> TYPE: DNA
<213> ORGANISM: Artificial Sequence
<220> FEATURE:
<223> OTHER INFORMATION: Synthetic

<400> SEQUENCE: 157
cagggagccg cag 13

<210> SEQ ID NO 158
<211> LENGTH: 18
<212> TYPE: DNA
<213> ORGANISM: Artificial Sequence
<220> FEATURE:
<223> OTHER INFORMATION: Synthetic

<400> SEQUENCE: 158
taaaaaaaaa aaaaaaaa 18

<210> SEQ ID NO 159
<211> LENGTH: 13
<212> TYPE: DNA
<213> ORGANISM: Artificial Sequence
<220> FEATURE:
<223> OTHER INFORMATION: Synthetic

<400> SEQUENCE: 159
acagcaacac cag 13

<210> SEQ ID NO 160
<211> LENGTH: 10
<212> TYPE: DNA
<213> ORGANISM: Artificial Sequence
<220> FEATURE:
<223> OTHER INFORMATION: Synthetic

<400> SEQUENCE: 160
tttgttgttg 10

<210> SEQ ID NO 161
<211> LENGTH: 10
<212> TYPE: DNA
<213> ORGANISM: Artificial Sequence
<220> FEATURE:
<223> OTHER INFORMATION: Synthetic

<400> SEQUENCE: 161
attttttttt 10

<210> SEQ ID NO 162
<211> LENGTH: 18
<212> TYPE: DNA
<213> ORGANISM: Artificial Sequence
<220> FEATURE:
<223> OTHER INFORMATION: Synthetic

<400> SEQUENCE: 162
taaaaaaaaa aaaaaaaa 18

<210> SEQ ID NO 163
<211> LENGTH: 10
<212> TYPE: DNA
<213> ORGANISM: Artificial Sequence
<220> FEATURE:
<223> OTHER INFORMATION: Synthetic

<400> SEQUENCE: 163
gattatatat 10

<210> SEQ ID NO 164
<211> LENGTH: 11
<212> TYPE: DNA
<213> ORGANISM: Artificial Sequence
<220> FEATURE:
<223> OTHER INFORMATION: Synthetic

<400> SEQUENCE: 164
taagggacca g 11

<210> SEQ ID NO 165
<211> LENGTH: 19
<212> TYPE: DNA
<213> ORGANISM: Artificial Sequence
<220> FEATURE:
<223> OTHER INFORMATION: Synthetic

<400> SEQUENCE: 165
acacactctc tctctctct 19

<210> SEQ ID NO 166
<211> LENGTH: 11
<212> TYPE: DNA
<213> ORGANISM: Artificial Sequence
<220> FEATURE:
<223> OTHER INFORMATION: Synthetic

<400> SEQUENCE: 166
taagggacca g 11

<210> SEQ ID NO 167
<211> LENGTH: 10
<212> TYPE: DNA
<213> ORGANISM: Artificial Sequence
<220> FEATURE:
<223> OTHER INFORMATION: Synthetic

<400> SEQUENCE: 167
gattatatat 10

<210> SEQ ID NO 168
<211> LENGTH: 11
<212> TYPE: DNA
<213> ORGANISM: Artificial Sequence
<220> FEATURE:
<223> OTHER INFORMATION: Synthetic

<400> SEQUENCE: 168
gccccccccc c 11

<210> SEQ ID NO 169
<211> LENGTH: 25
<212> TYPE: DNA
<213> ORGANISM: Artificial Sequence
<220> FEATURE:
<223> OTHER INFORMATION: Synthetic

<400> SEQUENCE: 169
aaaataaata aataaataaa taaat 25

<210> SEQ ID NO 170
<211> LENGTH: 25
<212> TYPE: DNA
<213> ORGANISM: Artificial Sequence
<220> FEATURE:
<223> OTHER INFORMATION: Synthetic

<400> SEQUENCE: 170
aaaataaata aataaataaa taaat 25

<210> SEQ ID NO 171
<211> LENGTH: 10
<212> TYPE: DNA
<213> ORGANISM: Artificial Sequence
<220> FEATURE:
<223> OTHER INFORMATION: Synthetic

<400> SEQUENCE: 171
tttgttgttg 10

<210> SEQ ID NO 172
<211> LENGTH: 18
<212> TYPE: DNA
<213> ORGANISM: Artificial Sequence
<220> FEATURE:
<223> OTHER INFORMATION: Synthetic

<400> SEQUENCE: 172
taaaaaaaaa aaaaaaaa 18

<210> SEQ ID NO 173
<211> LENGTH: 14

<212> TYPE: DNA
<213> ORGANISM: Artificial Sequence
<220> FEATURE:
<223> OTHER INFORMATION: Synthetic

<400> SEQUENCE: 173
cttttttttt tttt 14

<210> SEQ ID NO 174
<211> LENGTH: 18
<212> TYPE: DNA
<213> ORGANISM: Artificial Sequence
<220> FEATURE:
<223> OTHER INFORMATION: Synthetic

<400> SEQUENCE: 174
taaaaaaaaa aaaaaaaa 18

<210> SEQ ID NO 175
<211> LENGTH: 17
<212> TYPE: DNA
<213> ORGANISM: Artificial Sequence
<220> FEATURE:
<223> OTHER INFORMATION: Synthetic

<400> SEQUENCE: 175
tacacataca cacacac 17

<210> SEQ ID NO 176
<211> LENGTH: 13
<212> TYPE: DNA
<213> ORGANISM: Artificial Sequence
<220> FEATURE:
<223> OTHER INFORMATION: Synthetic

<400> SEQUENCE: 176
tggcggcggc ggc 13

<210> SEQ ID NO 177
<211> LENGTH: 12
<212> TYPE: DNA
<213> ORGANISM: Artificial Sequence
<220> FEATURE:
<223> OTHER INFORMATION: Synthetic

<400> SEQUENCE: 177
aataaaatga tg 12

<210> SEQ ID NO 178
<211> LENGTH: 17
<212> TYPE: DNA
<213> ORGANISM: Artificial Sequence
<220> FEATURE:
<223> OTHER INFORMATION: Synthetic

<400> SEQUENCE: 178
caaaaaaaaa aaaaaaa 17

<210> SEQ ID NO 179
<211> LENGTH: 22
<212> TYPE: DNA
<213> ORGANISM: Artificial Sequence
<220> FEATURE:
<223> OTHER INFORMATION: Synthetic

<400> SEQUENCE: 179
aggcgccccc gcagccgcag gc 22

<210> SEQ ID NO 180
<211> LENGTH: 15
<212> TYPE: DNA
<213> ORGANISM: Artificial Sequence
<220> FEATURE:
<223> OTHER INFORMATION: Synthetic

<400> SEQUENCE: 180
caaaaaaaaa aaaaa 15

<210> SEQ ID NO 181
<211> LENGTH: 33
<212> TYPE: DNA
<213> ORGANISM: Artificial Sequence
<220> FEATURE:
<223> OTHER INFORMATION: Synthetic

<400> SEQUENCE: 181
gccgccaccg ccgccgctgc cgccgcggaa ccc 33

<210> SEQ ID NO 182
<211> LENGTH: 13
<212> TYPE: DNA
<213> ORGANISM: Artificial Sequence
<220> FEATURE:
<223> OTHER INFORMATION: Synthetic

<400> SEQUENCE: 182
cttttttttt ttt 13

<210> SEQ ID NO 183
<211> LENGTH: 33
<212> TYPE: DNA
<213> ORGANISM: Artificial Sequence
<220> FEATURE:
<223> OTHER INFORMATION: Synthetic

<400> SEQUENCE: 183
gccgccaccg ccgccgctgc cgccgcggaa ccc 33

<210> SEQ ID NO 184
<211> LENGTH: 22
<212> TYPE: DNA
<213> ORGANISM: Artificial Sequence
<220> FEATURE:
<223> OTHER INFORMATION: Synthetic

<400> SEQUENCE: 184
aggcgccccc gcagccgcag gc 22

<210> SEQ ID NO 185
<211> LENGTH: 15
<212> TYPE: DNA
<213> ORGANISM: Artificial Sequence
<220> FEATURE:
<223> OTHER INFORMATION: Synthetic

<400> SEQUENCE: 185
atgtgtgtgt gtgtg 15

<210> SEQ ID NO 186
<211> LENGTH: 15
<212> TYPE: DNA
<213> ORGANISM: Artificial Sequence
<220> FEATURE:
<223> OTHER INFORMATION: Synthetic

<400> SEQUENCE: 186
caaaaaaaaa aaaaa 15

<210> SEQ ID NO 187
<211> LENGTH: 13
<212> TYPE: DNA
<213> ORGANISM: Artificial Sequence
<220> FEATURE:
<223> OTHER INFORMATION: Synthetic

<400> SEQUENCE: 187
cttttttttt ttt 13

<210> SEQ ID NO 188
<211> LENGTH: 10
<212> TYPE: DNA
<213> ORGANISM: Artificial Sequence
<220> FEATURE:
<223> OTHER INFORMATION: Synthetic

<400> SEQUENCE: 188
attttttttt 10

<210> SEQ ID NO 189
<211> LENGTH: 10
<212> TYPE: DNA
<213> ORGANISM: Artificial Sequence
<220> FEATURE:
<223> OTHER INFORMATION: Synthetic

<400> SEQUENCE: 189
cggcggtggt 10

<210> SEQ ID NO 190
<211> LENGTH: 10
<212> TYPE: DNA
<213> ORGANISM: Artificial Sequence
<220> FEATURE:
<223> OTHER INFORMATION: Synthetic

<400> SEQUENCE: 190
cgcgggggcg 10

<210> SEQ ID NO 191
<211> LENGTH: 13
<212> TYPE: DNA
<213> ORGANISM: Artificial Sequence
<220> FEATURE:
<223> OTHER INFORMATION: Synthetic

<400> SEQUENCE: 191
cttttttttt ttt 13

<210> SEQ ID NO 192
<211> LENGTH: 10
<212> TYPE: DNA
<213> ORGANISM: Artificial Sequence
<220> FEATURE:
<223> OTHER INFORMATION: Synthetic

<400> SEQUENCE: 192
cggcggtggt 10

<210> SEQ ID NO 193
<211> LENGTH: 10
<212> TYPE: DNA
<213> ORGANISM: Artificial Sequence
<220> FEATURE:
<223> OTHER INFORMATION: Synthetic

<400> SEQUENCE: 193
cgcgggggcg 10

<210> SEQ ID NO 194
<211> LENGTH: 10
<212> TYPE: DNA
<213> ORGANISM: Artificial Sequence
<220> FEATURE:
<223> OTHER INFORMATION: Synthetic

<400> SEQUENCE: 194
attttttttt 10

<210> SEQ ID NO 195
<211> LENGTH: 11
<212> TYPE: DNA
<213> ORGANISM: Artificial Sequence
<220> FEATURE:
<223> OTHER INFORMATION: Synthetic

<400> SEQUENCE: 195
attttttttt t 11

<210> SEQ ID NO 196
<211> LENGTH: 11
<212> TYPE: DNA
<213> ORGANISM: Artificial Sequence
<220> FEATURE:
<223> OTHER INFORMATION: Synthetic

<400> SEQUENCE: 196
gacaaacatt c 11

<210> SEQ ID NO 197
<211> LENGTH: 11
<212> TYPE: DNA
<213> ORGANISM: Artificial Sequence
<220> FEATURE:
<223> OTHER INFORMATION: Synthetic

<400> SEQUENCE: 197
gacaaacatt c 11

<210> SEQ ID NO 198
<211> LENGTH: 11
<212> TYPE: DNA
<213> ORGANISM: Artificial Sequence
<220> FEATURE:
<223> OTHER INFORMATION: Synthetic

<400> SEQUENCE: 198
attttttttt t 11

<210> SEQ ID NO 199
<211> LENGTH: 11
<212> TYPE: DNA
<213> ORGANISM: Artificial Sequence
<220> FEATURE:
<223> OTHER INFORMATION: Synthetic

```
<400> SEQUENCE: 199

gccccccccc c                                                        11

<210> SEQ ID NO 200
<211> LENGTH: 13
<212> TYPE: DNA
<213> ORGANISM: Artificial Sequence
<220> FEATURE:
<223> OTHER INFORMATION: Synthetic

<400> SEQUENCE: 200

tacacacaca cac                                                      13

<210> SEQ ID NO 201
<211> LENGTH: 12
<212> TYPE: DNA
<213> ORGANISM: Artificial Sequence
<220> FEATURE:
<223> OTHER INFORMATION: Synthetic

<400> SEQUENCE: 201

gctcagcagg ca                                                       12

<210> SEQ ID NO 202
<211> LENGTH: 16
<212> TYPE: DNA
<213> ORGANISM: Artificial Sequence
<220> FEATURE:
<223> OTHER INFORMATION: Synthetic

<400> SEQUENCE: 202

agctgccgcc gctgcc                                                   16

<210> SEQ ID NO 203
<211> LENGTH: 13
<212> TYPE: DNA
<213> ORGANISM: Artificial Sequence
<220> FEATURE:
<223> OTHER INFORMATION: Synthetic

<400> SEQUENCE: 203

tacacacaca cac                                                      13

<210> SEQ ID NO 204
<211> LENGTH: 10
<212> TYPE: DNA
<213> ORGANISM: Artificial Sequence
<220> FEATURE:
<223> OTHER INFORMATION: Synthetic

<400> SEQUENCE: 204

caaaaaaaaa                                                          10

<210> SEQ ID NO 205
<211> LENGTH: 13
<212> TYPE: DNA
<213> ORGANISM: Artificial Sequence
<220> FEATURE:
<223> OTHER INFORMATION: Synthetic

<400> SEQUENCE: 205

aaaaaaaaaa aag                                                      13

<210> SEQ ID NO 206
```

<211> LENGTH: 11
<212> TYPE: DNA
<213> ORGANISM: Artificial Sequence
<220> FEATURE:
<223> OTHER INFORMATION: Synthetic

<400> SEQUENCE: 206 atttttttt t 11

<210> SEQ ID NO 207
<211> LENGTH: 13
<212> TYPE: DNA
<213> ORGANISM: Artificial Sequence
<220> FEATURE:
<223> OTHER INFORMATION: Synthetic

<400> SEQUENCE: 207
tccaaagact cag 13

<210> SEQ ID NO 208
<211> LENGTH: 42
<212> TYPE: DNA
<213> ORGANISM: Artificial Sequence
<220> FEATURE:
<223> OTHER INFORMATION: Synthetic

<400> SEQUENCE: 208
tctccagatt caaatcaaag cataaataac acaggggcca tg 42

<210> SEQ ID NO 209
<211> LENGTH: 11
<212> TYPE: DNA
<213> ORGANISM: Artificial Sequence
<220> FEATURE:
<223> OTHER INFORMATION: Synthetic

<400> SEQUENCE: 209
gactcaccaa t 11

<210> SEQ ID NO 210
<211> LENGTH: 12
<212> TYPE: DNA
<213> ORGANISM: Artificial Sequence
<220> FEATURE:
<223> OTHER INFORMATION: Synthetic

<400> SEQUENCE: 210
cttttttttt tt 12

<210> SEQ ID NO 211
<211> LENGTH: 11
<212> TYPE: DNA
<213> ORGANISM: Artificial Sequence
<220> FEATURE:
<223> OTHER INFORMATION: Synthetic

<400> SEQUENCE: 211
gactcaccaa t 11

<210> SEQ ID NO 212
<211> LENGTH: 11
<212> TYPE: DNA
<213> ORGANISM: Artificial Sequence
<220> FEATURE:
<223> OTHER INFORMATION: Synthetic

<400> SEQUENCE: 212
gccccccccc c 11

<210> SEQ ID NO 213
<211> LENGTH: 18
<212> TYPE: DNA
<213> ORGANISM: Artificial Sequence
<220> FEATURE:
<223> OTHER INFORMATION: Synthetic

<400> SEQUENCE: 213
caaaaaaaaa aaaaaaaa 18

<210> SEQ ID NO 214
<211> LENGTH: 13
<212> TYPE: DNA
<213> ORGANISM: Artificial Sequence
<220> FEATURE:
<223> OTHER INFORMATION: Synthetic

<400> SEQUENCE: 214
cggcggcggc ggg 13

<210> SEQ ID NO 215
<211> LENGTH: 12
<212> TYPE: DNA
<213> ORGANISM: Artificial Sequence
<220> FEATURE:
<223> OTHER INFORMATION: Synthetic

<400> SEQUENCE: 215
aagccacagc tt 12

<210> SEQ ID NO 216
<211> LENGTH: 12
<212> TYPE: DNA
<213> ORGANISM: Artificial Sequence
<220> FEATURE:
<223> OTHER INFORMATION: Synthetic

<400> SEQUENCE: 216
cttttttttt tt 12

<210> SEQ ID NO 217
<211> LENGTH: 15
<212> TYPE: DNA
<213> ORGANISM: Artificial Sequence
<220> FEATURE:
<223> OTHER INFORMATION: Synthetic

<400> SEQUENCE: 217
gcgcgcgcgc acaca 15

<210> SEQ ID NO 218
<211> LENGTH: 11
<212> TYPE: DNA
<213> ORGANISM: Artificial Sequence
<220> FEATURE:
<223> OTHER INFORMATION: Synthetic

<400> SEQUENCE: 218
ggagagagag a 11

<210> SEQ ID NO 219
<211> LENGTH: 13
<212> TYPE: DNA

<213> ORGANISM: Artificial Sequence
<220> FEATURE:
<223> OTHER INFORMATION: Synthetic

<400> SEQUENCE: 219
ttagtgatga ggc 13

<210> SEQ ID NO 220
<211> LENGTH: 12
<212> TYPE: DNA
<213> ORGANISM: Artificial Sequence
<220> FEATURE:
<223> OTHER INFORMATION: Synthetic

<400> SEQUENCE: 220
caaaaaaaaa aa 12

<210> SEQ ID NO 221
<211> LENGTH: 13
<212> TYPE: DNA
<213> ORGANISM: Artificial Sequence
<220> FEATURE:
<223> OTHER INFORMATION: Synthetic

<400> SEQUENCE: 221
tggcggcggc ggc 13

<210> SEQ ID NO 222
<211> LENGTH: 12
<212> TYPE: DNA
<213> ORGANISM: Artificial Sequence
<220> FEATURE:
<223> OTHER INFORMATION: Synthetic

<400> SEQUENCE: 222
aagccacagc tt 12

<210> SEQ ID NO 223
<211> LENGTH: 11
<212> TYPE: DNA
<213> ORGANISM: Artificial Sequence
<220> FEATURE:
<223> OTHER INFORMATION: Synthetic

<400> SEQUENCE: 223
ggagagagag a 11

<210> SEQ ID NO 224
<211> LENGTH: 10
<212> TYPE: DNA
<213> ORGANISM: Artificial Sequence
<220> FEATURE:
<223> OTHER INFORMATION: Synthetic

<400> SEQUENCE: 224
tttgttgttg 10

<210> SEQ ID NO 225
<211> LENGTH: 13
<212> TYPE: DNA
<213> ORGANISM: Artificial Sequence
<220> FEATURE:
<223> OTHER INFORMATION: Synthetic

<400> SEQUENCE: 225
ttagtgatga ggc 13

<210> SEQ ID NO 226
<211> LENGTH: 12
<212> TYPE: DNA
<213> ORGANISM: Artificial Sequence
<220> FEATURE:
<223> OTHER INFORMATION: Synthetic

<400> SEQUENCE: 226
caaaaaaaaa aa 12

<210> SEQ ID NO 227
<211> LENGTH: 13
<212> TYPE: DNA
<213> ORGANISM: Artificial Sequence
<220> FEATURE:
<223> OTHER INFORMATION: Synthetic

<400> SEQUENCE: 227
tggcggcggc ggc 13

<210> SEQ ID NO 228
<211> LENGTH: 13
<212> TYPE: DNA
<213> ORGANISM: Artificial Sequence
<220> FEATURE:
<223> OTHER INFORMATION: Synthetic

<400> SEQUENCE: 228
tacacacaca cac 13

<210> SEQ ID NO 229
<211> LENGTH: 12
<212> TYPE: DNA
<213> ORGANISM: Artificial Sequence
<220> FEATURE:
<223> OTHER INFORMATION: Synthetic

<400> SEQUENCE: 229
caaaaaaaaa aa 12

<210> SEQ ID NO 230
<211> LENGTH: 10
<212> TYPE: DNA
<213> ORGANISM: Artificial Sequence
<220> FEATURE:
<223> OTHER INFORMATION: Synthetic

<400> SEQUENCE: 230
cccgcccgcg 10

<210> SEQ ID NO 231
<211> LENGTH: 19
<212> TYPE: DNA
<213> ORGANISM: Artificial Sequence
<220> FEATURE:
<223> OTHER INFORMATION: Synthetic

<400> SEQUENCE: 231
taaaaaaaaa aaaaaaaaa 19

<210> SEQ ID NO 232
<211> LENGTH: 11
<212> TYPE: DNA
<213> ORGANISM: Artificial Sequence
<220> FEATURE:

<223> OTHER INFORMATION: Synthetic

<400> SEQUENCE: 232
agggcaatgg g 11

<210> SEQ ID NO 233
<211> LENGTH: 13
<212> TYPE: DNA
<213> ORGANISM: Artificial Sequence
<220> FEATURE:
<223> OTHER INFORMATION: Synthetic

<400> SEQUENCE: 233
cctttttttt ttt 13

<210> SEQ ID NO 234
<211> LENGTH: 14
<212> TYPE: DNA
<213> ORGANISM: Artificial Sequence
<220> FEATURE:
<223> OTHER INFORMATION: Synthetic

<400> SEQUENCE: 234
caaaaaaaaa aaaa 14

<210> SEQ ID NO 235
<211> LENGTH: 11
<212> TYPE: DNA
<213> ORGANISM: Artificial Sequence
<220> FEATURE:
<223> OTHER INFORMATION: Synthetic

<400> SEQUENCE: 235
attttttttt t 11

<210> SEQ ID NO 236
<211> LENGTH: 14
<212> TYPE: DNA
<213> ORGANISM: Artificial Sequence
<220> FEATURE:
<223> OTHER INFORMATION: Synthetic

<400> SEQUENCE: 236
cttttttttt tttt 14

<210> SEQ ID NO 237
<211> LENGTH: 10
<212> TYPE: DNA
<213> ORGANISM: Artificial Sequence
<220> FEATURE:
<223> OTHER INFORMATION: Synthetic

<400> SEQUENCE: 237
caaaaaaaaa 10

<210> SEQ ID NO 238
<211> LENGTH: 11
<212> TYPE: DNA
<213> ORGANISM: Artificial Sequence
<220> FEATURE:
<223> OTHER INFORMATION: Synthetic

<400> SEQUENCE: 238 ctttttttctt t 11

<210> SEQ ID NO 239
<211> LENGTH: 10
<212> TYPE: DNA
<213> ORGANISM: Artificial Sequence
<220> FEATURE:
<223> OTHER INFORMATION: Synthetic

<400> SEQUENCE: 239
caaaaaaaaa 10

<210> SEQ ID NO 240
<211> LENGTH: 10
<212> TYPE: DNA
<213> ORGANISM: Artificial Sequence
<220> FEATURE:
<223> OTHER INFORMATION: Synthetic

<400> SEQUENCE: 240
ctgctttttt 10

<210> SEQ ID NO 241
<211> LENGTH: 10
<212> TYPE: DNA
<213> ORGANISM: Artificial Sequence
<220> FEATURE:
<223> OTHER INFORMATION: Synthetic

<400> SEQUENCE: 241
tgcccccgcc 10

<210> SEQ ID NO 242
<211> LENGTH: 11
<212> TYPE: DNA
<213> ORGANISM: Artificial Sequence
<220> FEATURE:
<223> OTHER INFORMATION: Synthetic

<400> SEQUENCE: 242
agggcaatgg g 11

<210> SEQ ID NO 243
<211> LENGTH: 14
<212> TYPE: DNA
<213> ORGANISM: Artificial Sequence
<220> FEATURE:
<223> OTHER INFORMATION: Synthetic

<400> SEQUENCE: 243
caaaaaaaaa aaaa 14

<210> SEQ ID NO 244
<211> LENGTH: 11
<212> TYPE: DNA
<213> ORGANISM: Artificial Sequence
<220> FEATURE:
<223> OTHER INFORMATION: Synthetic

<400> SEQUENCE: 244
caaaaaaaaa a 11

<210> SEQ ID NO 245
<211> LENGTH: 11
<212> TYPE: DNA
<213> ORGANISM: Artificial Sequence
<220> FEATURE:
<223> OTHER INFORMATION: Synthetic

<400> SEQUENCE: 245 atttttttt t 11

<210> SEQ ID NO 246
<211> LENGTH: 11
<212> TYPE: DNA
<213> ORGANISM: Artificial Sequence
<220> FEATURE:
<223> OTHER INFORMATION: Synthetic

<400> SEQUENCE: 246
cttttttctt t 11

<210> SEQ ID NO 247
<211> LENGTH: 17
<212> TYPE: DNA
<213> ORGANISM: Artificial Sequence
<220> FEATURE:
<223> OTHER INFORMATION: Synthetic

<400> SEQUENCE: 247 atttttttt ttttttt 17

<210> SEQ ID NO 248
<211> LENGTH: 10
<212> TYPE: DNA
<213> ORGANISM: Artificial Sequence
<220> FEATURE:
<223> OTHER INFORMATION: Synthetic

<400> SEQUENCE: 248
cttttttttt 10

<210> SEQ ID NO 249
<211> LENGTH: 10
<212> TYPE: DNA
<213> ORGANISM: Artificial Sequence
<220> FEATURE:
<223> OTHER INFORMATION: Synthetic

<400> SEQUENCE: 249
attttttttt 10

<210> SEQ ID NO 250
<211> LENGTH: 10
<212> TYPE: DNA
<213> ORGANISM: Artificial Sequence
<220> FEATURE:
<223> OTHER INFORMATION: Synthetic

<400> SEQUENCE: 250
ccggcggcgg 10

<210> SEQ ID NO 251
<211> LENGTH: 13
<212> TYPE: DNA
<213> ORGANISM: Artificial Sequence
<220> FEATURE:
<223> OTHER INFORMATION: Synthetic

<400> SEQUENCE: 251
cttttttttt ttt 13

<210> SEQ ID NO 252
<211> LENGTH: 18

<212> TYPE: DNA
<213> ORGANISM: Artificial Sequence
<220> FEATURE:
<223> OTHER INFORMATION: Synthetic

<400> SEQUENCE: 252
caaaaaaaaa aaaaaaaa 18

<210> SEQ ID NO 253
<211> LENGTH: 15
<212> TYPE: DNA
<213> ORGANISM: Artificial Sequence
<220> FEATURE:
<223> OTHER INFORMATION: Synthetic

<400> SEQUENCE: 253
atgtgtgtgt gtgtg 15

<210> SEQ ID NO 254
<211> LENGTH: 10
<212> TYPE: DNA
<213> ORGANISM: Artificial Sequence
<220> FEATURE:
<223> OTHER INFORMATION: Synthetic

<400> SEQUENCE: 254
attttttttt 10

<210> SEQ ID NO 255
<211> LENGTH: 10
<212> TYPE: DNA
<213> ORGANISM: Artificial Sequence
<220> FEATURE:
<223> OTHER INFORMATION: Synthetic

<400> SEQUENCE: 255
ccggcggcgg 10

<210> SEQ ID NO 256
<211> LENGTH: 11
<212> TYPE: DNA
<213> ORGANISM: Artificial Sequence
<220> FEATURE:
<223> OTHER INFORMATION: Synthetic

<400> SEQUENCE: 256
cttttttttt t 11

<210> SEQ ID NO 257
<211> LENGTH: 11
<212> TYPE: DNA
<213> ORGANISM: Artificial Sequence
<220> FEATURE:
<223> OTHER INFORMATION: Synthetic

<400> SEQUENCE: 257
actctctctc t 11

<210> SEQ ID NO 258
<211> LENGTH: 10
<212> TYPE: DNA
<213> ORGANISM: Artificial Sequence
<220> FEATURE:
<223> OTHER INFORMATION: Synthetic

<400> SEQUENCE: 258
gggcggcggc 10

<210> SEQ ID NO 259
<211> LENGTH: 11
<212> TYPE: DNA
<213> ORGANISM: Artificial Sequence
<220> FEATURE:
<223> OTHER INFORMATION: Synthetic

<400> SEQUENCE: 259
attttttttt t 11

<210> SEQ ID NO 260
<211> LENGTH: 11
<212> TYPE: DNA
<213> ORGANISM: Artificial Sequence
<220> FEATURE:
<223> OTHER INFORMATION: Synthetic

<400> SEQUENCE: 260
gccccccccc c 11

<210> SEQ ID NO 261
<211> LENGTH: 10
<212> TYPE: DNA
<213> ORGANISM: Artificial Sequence
<220> FEATURE:
<223> OTHER INFORMATION: Synthetic

<400> SEQUENCE: 261
attttttttt 10

<210> SEQ ID NO 262
<211> LENGTH: 28
<212> TYPE: DNA
<213> ORGANISM: Artificial Sequence
<220> FEATURE:
<223> OTHER INFORMATION: Synthetic

<400> SEQUENCE: 262
aggggacaga tgtggtccct cagcctgg 28

<210> SEQ ID NO 263
<211> LENGTH: 18
<212> TYPE: DNA
<213> ORGANISM: Artificial Sequence
<220> FEATURE:
<223> OTHER INFORMATION: Synthetic

<400> SEQUENCE: 263
caaaaaaaaa aaaaaaaa 18

<210> SEQ ID NO 264
<211> LENGTH: 13
<212> TYPE: DNA
<213> ORGANISM: Artificial Sequence
<220> FEATURE:
<223> OTHER INFORMATION: Synthetic

<400> SEQUENCE: 264
acagcaacac cag 13

<210> SEQ ID NO 265
<211> LENGTH: 26
<212> TYPE: DNA
<213> ORGANISM: Artificial Sequence
<220> FEATURE:
<223> OTHER INFORMATION: Synthetic

<400> SEQUENCE: 265
gtccaggcac atgtgtgatc agtgat 26

<210> SEQ ID NO 266
<211> LENGTH: 11
<212> TYPE: DNA
<213> ORGANISM: Artificial Sequence
<220> FEATURE:
<223> OTHER INFORMATION: Synthetic

<400> SEQUENCE: 266
atgtgtgtgt g 11

<210> SEQ ID NO 267
<211> LENGTH: 13
<212> TYPE: DNA
<213> ORGANISM: Artificial Sequence
<220> FEATURE:
<223> OTHER INFORMATION: Synthetic

<400> SEQUENCE: 267
tacaaaaaaa aaa 13

<210> SEQ ID NO 268
<211> LENGTH: 10
<212> TYPE: DNA
<213> ORGANISM: Artificial Sequence
<220> FEATURE:
<223> OTHER INFORMATION: Synthetic

<400> SEQUENCE: 268
gattatatat 10

<210> SEQ ID NO 269
<211> LENGTH: 10
<212> TYPE: DNA
<213> ORGANISM: Artificial Sequence
<220> FEATURE:
<223> OTHER INFORMATION: Synthetic

<400> SEQUENCE: 269
ggaagaggaa 10

<210> SEQ ID NO 270
<211> LENGTH: 11
<212> TYPE: DNA
<213> ORGANISM: Artificial Sequence
<220> FEATURE:
<223> OTHER INFORMATION: Synthetic

<400> SEQUENCE: 270
gcacacacac a 11

<210> SEQ ID NO 271
<211> LENGTH: 11
<212> TYPE: DNA
<213> ORGANISM: Artificial Sequence
<220> FEATURE:
<223> OTHER INFORMATION: Synthetic

<400> SEQUENCE: 271
tttttttttt g 11

<210> SEQ ID NO 272
<211> LENGTH: 15
<212> TYPE: DNA
<213> ORGANISM: Artificial Sequence
<220> FEATURE:
<223> OTHER INFORMATION: Synthetic

<400> SEQUENCE: 272
caaaaaaaaa aaaaa 15

<210> SEQ ID NO 273
<211> LENGTH: 12
<212> TYPE: DNA
<213> ORGANISM: Artificial Sequence
<220> FEATURE:
<223> OTHER INFORMATION: Synthetic

<400> SEQUENCE: 273
attttttttt tt 12

<210> SEQ ID NO 274
<211> LENGTH: 10
<212> TYPE: DNA
<213> ORGANISM: Artificial Sequence
<220> FEATURE:
<223> OTHER INFORMATION: Synthetic

<400> SEQUENCE: 274
cttttttttt 10

<210> SEQ ID NO 275
<211> LENGTH: 10
<212> TYPE: DNA
<213> ORGANISM: Artificial Sequence
<220> FEATURE:
<223> OTHER INFORMATION: Synthetic

<400> SEQUENCE: 275
gtaattccat 10

<210> SEQ ID NO 276
<211> LENGTH: 14
<212> TYPE: DNA
<213> ORGANISM: Artificial Sequence
<220> FEATURE:
<223> OTHER INFORMATION: Synthetic

<400> SEQUENCE: 276
attttttttt tttt 14

<210> SEQ ID NO 277
<211> LENGTH: 11
<212> TYPE: DNA
<213> ORGANISM: Artificial Sequence
<220> FEATURE:
<223> OTHER INFORMATION: Synthetic

<400> SEQUENCE: 277
ctgctttttt t 11

<210> SEQ ID NO 278
<211> LENGTH: 16
<212> TYPE: DNA
<213> ORGANISM: Artificial Sequence
<220> FEATURE:
<223> OTHER INFORMATION: Synthetic

<400> SEQUENCE: 278
acacacacac acacac 16

<210> SEQ ID NO 279
<211> LENGTH: 12
<212> TYPE: DNA
<213> ORGANISM: Artificial Sequence
<220> FEATURE:
<223> OTHER INFORMATION: Synthetic

<400> SEQUENCE: 279
attttttttt tt 12

<210> SEQ ID NO 280
<211> LENGTH: 12
<212> TYPE: DNA
<213> ORGANISM: Artificial Sequence
<220> FEATURE:
<223> OTHER INFORMATION: Synthetic

<400> SEQUENCE: 280
caaaaaaaaa aa 12

<210> SEQ ID NO 281
<211> LENGTH: 10
<212> TYPE: DNA
<213> ORGANISM: Artificial Sequence
<220> FEATURE:
<223> OTHER INFORMATION: Synthetic

<400> SEQUENCE: 281
ggaagaggaa 10

<210> SEQ ID NO 282
<211> LENGTH: 14
<212> TYPE: DNA
<213> ORGANISM: Artificial Sequence
<220> FEATURE:
<223> OTHER INFORMATION: Synthetic

<400> SEQUENCE: 282
tacaaaaaaa aaaa 14

<210> SEQ ID NO 283
<211> LENGTH: 13
<212> TYPE: DNA
<213> ORGANISM: Artificial Sequence
<220> FEATURE:
<223> OTHER INFORMATION: Synthetic

<400> SEQUENCE: 283
cctttttttt ttt 13

<210> SEQ ID NO 284
<211> LENGTH: 12
<212> TYPE: DNA
<213> ORGANISM: Artificial Sequence
<220> FEATURE:
<223> OTHER INFORMATION: Synthetic

<400> SEQUENCE: 284
tttttttttt tg 12

<210> SEQ ID NO 285

<211> LENGTH: 15
<212> TYPE: DNA
<213> ORGANISM: Artificial Sequence
<220> FEATURE:
<223> OTHER INFORMATION: Synthetic

<400> SEQUENCE: 285
caaaaaaaaa aaaaa 15

<210> SEQ ID NO 286
<211> LENGTH: 13
<212> TYPE: DNA
<213> ORGANISM: Artificial Sequence
<220> FEATURE:
<223> OTHER INFORMATION: Synthetic

<400> SEQUENCE: 286
attttttttt ttt 13

<210> SEQ ID NO 287
<211> LENGTH: 10
<212> TYPE: DNA
<213> ORGANISM: Artificial Sequence
<220> FEATURE:
<223> OTHER INFORMATION: Synthetic

<400> SEQUENCE: 287
cttttttttt 10

<210> SEQ ID NO 288
<211> LENGTH: 11
<212> TYPE: DNA
<213> ORGANISM: Artificial Sequence
<220> FEATURE:
<223> OTHER INFORMATION: Synthetic

<400> SEQUENCE: 288
caaaaaaaaa a 11

<210> SEQ ID NO 289
<211> LENGTH: 13
<212> TYPE: DNA
<213> ORGANISM: Artificial Sequence
<220> FEATURE:
<223> OTHER INFORMATION: Synthetic

<400> SEQUENCE: 289
caaaaaaaaa aaa 13

<210> SEQ ID NO 290
<211> LENGTH: 10
<212> TYPE: DNA
<213> ORGANISM: Artificial Sequence
<220> FEATURE:
<223> OTHER INFORMATION: Synthetic

<400> SEQUENCE: 290
gtaattccat 10

<210> SEQ ID NO 291
<211> LENGTH: 12
<212> TYPE: DNA
<213> ORGANISM: Artificial Sequence
<220> FEATURE:
<223> OTHER INFORMATION: Synthetic

<400> SEQUENCE: 291
gattatatat at 12

<210> SEQ ID NO 292
<211> LENGTH: 13
<212> TYPE: DNA
<213> ORGANISM: Artificial Sequence
<220> FEATURE:
<223> OTHER INFORMATION: Synthetic

<400> SEQUENCE: 292
attttttttt ttt 13

<210> SEQ ID NO 293
<211> LENGTH: 11
<212> TYPE: DNA
<213> ORGANISM: Artificial Sequence
<220> FEATURE:
<223> OTHER INFORMATION: Synthetic

<400> SEQUENCE: 293
ctgctttttt t 11

<210> SEQ ID NO 294
<211> LENGTH: 12
<212> TYPE: DNA
<213> ORGANISM: Artificial Sequence
<220> FEATURE:
<223> OTHER INFORMATION: Synthetic

<400> SEQUENCE: 294
attttttttt tt 12

<210> SEQ ID NO 295
<211> LENGTH: 12
<212> TYPE: DNA
<213> ORGANISM: Artificial Sequence
<220> FEATURE:
<223> OTHER INFORMATION: Synthetic

<400> SEQUENCE: 295
caaaaaaaaa aa 12

<210> SEQ ID NO 296
<211> LENGTH: 16
<212> TYPE: DNA
<213> ORGANISM: Artificial Sequence
<220> FEATURE:
<223> OTHER INFORMATION: Synthetic

<400> SEQUENCE: 296
acacacacac acacac 16

<210> SEQ ID NO 297
<211> LENGTH: 11
<212> TYPE: DNA
<213> ORGANISM: Artificial Sequence
<220> FEATURE:
<223> OTHER INFORMATION: Synthetic

<400> SEQUENCE: 297
gccccccccc c 11

<210> SEQ ID NO 298
<211> LENGTH: 11
<212> TYPE: DNA

```
<213> ORGANISM: Artificial Sequence
<220> FEATURE:
<223> OTHER INFORMATION: Synthetic

<400> SEQUENCE: 298

attttttttt t                                                      11

<210> SEQ ID NO 299
<211> LENGTH: 11
<212> TYPE: DNA
<213> ORGANISM: Artificial Sequence
<220> FEATURE:
<223> OTHER INFORMATION: Synthetic

<400> SEQUENCE: 299

attttttttt t                                                      11

<210> SEQ ID NO 300
<211> LENGTH: 26
<212> TYPE: DNA
<213> ORGANISM: Artificial Sequence
<220> FEATURE:
<223> OTHER INFORMATION: Synthetic

<400> SEQUENCE: 300

gtccaggcac atgtgtgatc agtgat                                      26

<210> SEQ ID NO 301
<211> LENGTH: 13
<212> TYPE: DNA
<213> ORGANISM: Artificial Sequence
<220> FEATURE:
<223> OTHER INFORMATION: Synthetic

<400> SEQUENCE: 301

acagcaacac cag                                                    13

<210> SEQ ID NO 302
<211> LENGTH: 11
<212> TYPE: DNA
<213> ORGANISM: Artificial Sequence
<220> FEATURE:
<223> OTHER INFORMATION: Synthetic

<400> SEQUENCE: 302

gccccccccc c                                                      11

<210> SEQ ID NO 303
<211> LENGTH: 13
<212> TYPE: DNA
<213> ORGANISM: Artificial Sequence
<220> FEATURE:
<223> OTHER INFORMATION: Synthetic

<400> SEQUENCE: 303

taaaaaaaaa aaa                                                    13

<210> SEQ ID NO 304
<211> LENGTH: 13
<212> TYPE: DNA
<213> ORGANISM: Artificial Sequence
<220> FEATURE:
<223> OTHER INFORMATION: Synthetic
```

-continued

<400> SEQUENCE: 304
taaaaaaaaa aaa 13

DNA DAMAGE RESPONSE SIGNATURE GUIDED RATIONAL DESIGN OF CRISPR-BASED SYSTEMS AND THERAPIES

CROSS-REFERENCE TO RELATED APPLICATIONS

This application is a continuation of U.S. patent application Ser. No. 17/061,574, filed on Oct. 1, 2020, entitled "DNA Damage Response Signature Guided Rational Design of CRISPR-Based Systems and Therapies," which claims the benefit of and priority to prior U.S. Provisional Patent Application No. 62/909,131, filed on Oct. 1, 2019, entitled "DNA Damage Response Signature Guided Rational Design of CRISPR-Based Systems and Therapies," the contents of which are incorporated by reference herein in their entireties.

STATEMENT REGARDING FEDERALLY SPONSORED RESEARCH

This invention was made with government support under Grant No. CA18828, CA215489, and CA219943 granted by National Institutes of Health. The government has certain rights in the invention.

SEQUENCE LISTING

This application contains a sequence listing filed in electronic form as an ASCII.txt file entitled BROD-4820US_ST25.txt, created on Sep. 25, 2020 and having a size of 77,000 bytes (on disk). The content of the sequence listing is incorporated herein in its entirety.

TECHNICAL FIELD

The subject matter disclosed herein is generally directed to gene modification using CRISPR-Cas systems, and more particularly, to the rational design and development of CRISPR-Cas systems and CRISPR-Cas system-based therapies and therapeutics.

BACKGROUND

Neutral genetic manipulations can lead to genetic and transcriptional diversification of cell lines. For example, it is well established that over time reporter cell lines carrying a neutral genetic manipulation (e.g. a cell line engineered to express a neutral reporter protein such as GFP) can become genetically distinct (beyond the expression of the GFP) from the parental cell line (see e.g. Ben-David et al. 2018. Nature. 560:325-330 (2018)). CRISPR-Cas systems are becoming a mainstay and the choice mechanism to introduce modifications into polynucleotides, particularly for the development of therapeutics. "Neutral" introduction of a CRISPR-Cas system component (e.g. a Cas or guide polynucleotide) into a cell or cell line is a common approach used when performing genetic modifications using CRISPR-Cas systems. For example, the RNA-guided DNA endonuclease enzyme Cas9 (CRISPR-associated protein 9), which is commonly introduced into cell lines to facilitate CRISPR-Cas9 genome editing (Cong et al. 2013. Science 339: 819-823; Mali et al. 2013. Science 339: 823-826; and Jinek et al. 2013. Elife. 2: e00471). CRISPR-Cas9 editing is often performed in two steps: first, a stable Cas9-expressing cell line is generated; then, single guide RNA (sgRNA) is introduced. Both of these steps involve several events that could potentially lead to genomic evolution, including the transduction, passaging and antibiotic selection of cells (Ben-David, U., et al. 2019. Nat Rev Cancer 19:97-109). Off-target effects and genotoxicity have been associated with prolonged elevated Cas9 activity (Maji et al. 2019. Cell 177: 1067-1079 e19). As such there exists a need for methods and techniques to identify any changes introduced by introduction of one or more components of a CRISPR-Cas system and/or rationally develop or design CRISPR-Cas systems and/or CRISPR-Cas based therapies that have limited and/or benign genetic and/or transcriptional changes resulting from including one or more components of a CRISPR-Cas system.

Citation or identification of any document in this application is not an admission that such a document is available as prior art to the present invention.

SUMMARY

In certain example embodiments, described herein are methods for developing or designing a CRISPR-Cas based therapy or therapeutic comprising: modifying one or more target sequence in an initial cell or cell population using CRISPR-Cas complex comprising a Cas protein and guide molecule; clonally expanding the modified cell or cell population; detecting, in cells from the expanded cell population, expression of a DNA-damage response protein signature; and selecting clones from the expanded cell population that do not express the DNA-damage response signature.

In certain example embodiments, the DNA-damage response signature indicates Cas-induced activation of a p53 pathway.

In certain example embodiments, the DNA-damage response signature indicates detection of one or more p53 inactivating mutations.

In certain example embodiments, the DNA-damage response signature is a Cas-induced DNA-damage response signature.

In certain example embodiments, selected clones are used in an adoptive cell therapy.

In certain example embodiments, the initial cell or cell population is isolated from a subject to be treated with the adoptive cell therapy.

In certain example embodiments, the Cas protein is optimized for one or more parameters selected from the group consisting of; protein size, ability of protein to access regions of high chromatin accessibility, degree of uniform enzyme activity across genomic targets, epigenetic tolerance, mismatch/budge tolerance, effector protein specificity, effector protein stability or half-life, effector protein immunogenicity or toxicity.

In certain example embodiments, wherein the guide molecule is or comprises a tru guide, an escorted guide, or a protected guide.

In certain example embodiments, the target sequences are further selected based on optimization of one or more parameters consisting of; PAM type (natural or modified), PAM nucleotide content, PAM length, target sequence length, PAM restrictiveness, target cleavage efficiency, and target sequence position within a gene, a locus or other genomic region.

In certain example embodiments, modifying the one or more target genes is done in the presence of one or more anti-CRISPR molecules or CRISPR inhibitors.

In certain example embodiments, described herein are methods for developing or designing a CRISPR-Cas based therapeutic comprising: screening a set of CRISPR-Cas systems by expressing each CRISPR-Cas system in a test cell population and modifying one or more target sequence in the test cell populations; screening in the test cell population for each CRISPR-Cas system, expression of a DNA-damage response signature; selecting one or more CRISPR-Cas systems that do not result in expression of a DNA-damage response signature.

In certain example embodiments, the DNA-damage response signature indicates Cas-induced activation of a p53 pathway.

In certain example embodiments, the DNA-damage response signature indicates detection of one or more p53 inactivating mutations.

In certain example embodiments, the DNA-damage response signature is a Cas-induced DNA-damage response signature.

In certain example embodiments, each CRISPR-Cas system in the set of CRISPR-Cas systems varies in;

a. dosage;
b. Cas protein;
c. guide molecule design; or
d. a combination thereof In certain example embodiments, the Cas protein varies in optimization of one or more parameters selected from the group consisting of; protein size, ability of protein to access regions of high chromatin accessibility, degree of uniform enzyme activity across genomic targets, epigenetic tolerance, mismatch/budge tolerance, effector protein specificity, effector protein stability or half-life, effector protein immunogenicity or toxicity.

In certain example embodiments, the guide molecule is or comprises a tru guide, an escorted guide, or a protected guide.

In certain example embodiments, the Cas protein is optimized for one or more parameters consisting of; PAM type (natural or modified), PAM nucleotide content, PAM length, target sequence length, PAM restrictiveness, target cleavage efficiency, and target sequence position within a gene, a locus or other genomic region.

In certain example embodiments, the Cas protein and/or the guide molecule are constitutively expressed.

In certain example embodiments, the Cas protein and/or the guide molecule are inducibly expressed.

In certain example embodiments, the Cas protein and guide molecule are delivered on the same or different vectors.

In certain example embodiments, the Cas protein and guide molecule are delivered as a ribonucleoprotein complex (RNP).

In certain example embodiments, the test population is previously modified to express the Cas protein or guide molecule.

In certain example embodiments, the CRISPR-Cas systems are delivered to the test cell populations by liposomes, lipid particles, nanoparticles, biolistics, or viral-based expression/delivery systems.

In certain example embodiments, screening the CRISPR-Cas systems is done in the presence of one or more anti-CRISPR molecules or CRISPR inhibitors.

In certain example embodiments, the test cell population is obtained from a subject to be treated with the CRISPR-Cas therapeutic.

In certain example embodiments, described herein are rationally designed CRISPR-based therapeutics and/or therapies. In some example embodiments, the rationally designed CRISPR-based therapeutics and/or therapies are CRISPR-Cas system(s) that do not induce a DNA-damage response signature when introduced to a cell. In some example embodiments, the rationally designed CRISPR-based therapeutics and/or therapies are CRISPR-Cas modified cells that do not express a DNA-damage response signature.

In certain example embodiments, described herein are formulations that can include one or more of the rationally designed CRISPR-based therapeutics and/or therapies.

In certain example embodiments, described herein are kits that can include one or more of the rationally designed CRISPR-based therapeutics and/or therapies and/or one or more reagents used in performing the method of rationally designing and/or developing a CRISPR-based therapeutic described herein.

In certain example embodiments, described herein methods of using the CRISPR based therapeutics and/or therapies described herein to treat or prevent a disease in a subject.

These and other embodiments, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

(FIG. 1A) The number of differentially-expressed genes (fold change>=2) across 165 Cas9 vs. WT transcriptional signatures. Dashed vertical lines highlight the median (87 genes) and the 90% percentile (389 genes). (FIG. 1B) The number of MSigDB Hallmark biological pathways that are significantly enriched (GSEA enrichment score with multiple hypotheses correction; FDR q<0.05) following the introduction of Cas9 (red) or empty/control vectors (gray) , p=0.001, two-sided KS test. Data points represent cell line pairs. (FIG. 1C) The degree and significance of modulation of the 50 MSigDB Hallmark biological pathways, following the introduction of empty vectors, reporter vectors or Cas9 into TP53-WT cell lines, and the introduction of Cas9 into TP53-mutant cell lines. Black, significantly enriched (GSEA enrichment score with multiple hypotheses correction; FDR q<0.05) pathways. Light Grey, the p53 pathway. Each plot represents the results of one Aggregate expression signature (see Online Methods). (FIG. 1D) Protein levels of Cas9, p53, p21 and a housekeeping protein in 8 TP53-WT lines and 4 TP53-mutant lines before and after Cas9 introduction. Representative results of 3 independent experiments are shown. (FIG. 1E) Left: WB quantification. Each bar represents a WB shown in (FIG. 1**D). *, p=0.027 and p=0.024 for p53 and p21, respectively; one-tailed Wilcoxon rank test. Right: The fraction of lines that activated p53 or p21 in response to Cas9 introduction. *, p=0.01, one-tailed Fisher's exact test. (FIG. 1F) Left: confirmation of p53 pathway activation in MCF7 and SNU466 by RT-qPCR analysis of 7 p53 transcriptional targets. **, p<0.0001, one-tailed t-test. Right: the average activation of p53 transcriptional targets. , p<0.01, two-sided one-sample t-test.

(FIG. 2A) Fluorescent microscopy images of γH2AX foci (green) and DAPI (blue) in WT and Cas9 MCF7 and SNU466 cells. Cells with >5 foci have been marked in white. Scale bar represents 10 μM. Representative images of three independent experiments are shown. (FIG. 2B) Quantification of γH2AX foci from three independent repeats; n=841 and n=1,056 for WT and Cas9 MCF7 cells, respectively; n=752 and n=810 for WT and Cas9 SNU466 cells, respectively. $p<0.0001$ and $p=0.0041$, for MCF7 and SNU466, respectively; one-tailed t-test. Data values represent the means, with error bars corresponding to S.D.

(FIG. 3A) The number of non-silent mutations that differ between the 41 profiled Cas9 lines and their matched WT lines (that is, mutations detected in either the parental or the Cas9 line, but not in both). Emerging mutations are shown in black, disappearing mutations in gray. *, $p=0.01$, one-tailed paired t-test. (FIG. 3B) Cancer genes ranked by their tendency to acquire non-silent mutations in the Cas9 lines. TP53 is highlighted in light grey and is among the top 4% of genes (out of 128 genes with a non-silent mutation present). (FIG. 3C) Changes in the allelic fraction (AF) of 5 non-silent TP53 mutations in four independent cell line pairs. Two of the mutations could not be detected in the parental WT line at all, while the other three were detected at lower AF. (FIG. 3D) Changes in the AF of 10 pre-existing subclonal inactivating TP53 mutations across 8 cell line pairs. *, $p=0.005$, one-tailed paired t-test. (FIG. 3E) Cancer genes ranked by the significance (based on two-tailed one-sample Wilcoxon rank test) of nonsilent subclonal mutation expansion following Cas9 introduction. TP53 is highlighted in light grey and ranks $1^{st}$ in this analysis (out of 276 genes).

(FIG. 4A) Representative flow cytometry scatter plots, gated by GFP expression. The proportion of HCT116 TP53-null/GFP+ was quantified at day 0, day 14 and day 21 post-infection with backbone-matched empty vector or Cas9 vector, or without infection at all. Representative results of three independent experiments are shown. (FIG. 4B) Quantification of the flow cytometry experiments shown in (FIG. 4A). n=3 cell culture replicates per condition. At day 14 and day 21, the proportion of TP53-null cells in the population is significantly higher in cells infected with Cas9 compared to the empty vector and no-infection controls. $p=0.003$ and $p=0.001$ for the comparisons of NIC vs. Cas9 and EV vs. Cas9 at day 14, respectively; $p=0.001$ and $p=6.4e-5$ for the comparisons of NIC vs. Cas9 and EV vs. Cas9 at day 21, respectively; two-tailed t-test. Data values represent the means of 3 cell culture replicates for each condition at each time point, with error bars corresponding to S.D. (FIG. 4C) Comparison of the cell competition experiments in ARID1A-null and FBXW7-null HCT116 cells. For ARID1A, $p=0.65$ and $p=0.34$ and $p=0.1$ for the comparisons of day 7, day 14 and day 21, respectively; for FBXW7, $p=0.94$, $p=0.79$ and $p=0.71$ for the comparisons of day 7, day 14 and day 21, respectively; two-tailed t-test. Data values represent the means of 3 replicates for each condition at each time point, with error bars corresponding to S.D. NIC, no-infection control; EV, empty vector.

(FIG. 5A) Comparison of Cas9 activity between 216 TP53-WT and 482 TP53-null cell lines, using an EGFP-based Cas9 activity assay[20]. The higher the fraction of GFP-negative cells, the higher the level of Cas9 activity. Bar, median; box, $25^{th}$ and $75^{th}$ percentile; whiskers, 1.5× inter-quartile range of the lower and upper quartiles; circles, individual cell lines. *, $p=2.7e-5$, one-tailed t-test. (FIG. 5B) Comparison of the concordance between CRISPR and RNAi gene perturbation screens in 86 TP53-WT and 207 TP53-mutant cell lines. Shown is the absolute distance from the CRISPR/RNAi linear regression line: the higher the distance the less concordant the CRISPR and RNAi screens are. *, $p=0.022$, one-tailed Wilcoxon rank test. Data points represent cell lines. (FIG. 5C) Gene sets that are significantly enriched (DAVID functional annotation analysis with multiple hypotheses correction; $p<0.01$, $q<0.25$) in the list of genes that are selectively essential in 86 TP53-WT cell lines in the CRISPR, but not in the RNAi genetic screen. Gene sets are colored by their functional category. (FIG. 5D) Comparison of the concordance between CRISPR and RNAi gene perturbation screens in 20 TP53-WT cell lines that exhibited p53 pathway activation in L1000 Cas9 vs. WT signatures and those that did not. Shown is the distance from the CRISPR/RNAi regression line: negative values represent a stronger proliferation effect of p53 inhibition in CRISPR vs. RNAi screen. *, $p=0.02$, one-tailed Wilcoxon rank sum test. Data points represent cell lines. (FIG. 5E) Dose response curves of the response of parental and Cas9-expressing MCF7 cells to the MDM2 inhibitor nutlin-3. *, $p=0.029$, $p=0.01$, $p=0.0004$, and $p=0.0099$ for 5 μM, 10 μM, 15 μM and 20 μM, respectively, two-way ANOVA. Data values represent the means of 3 cell culture replicates for each condition at each time point, with error bars corresponding to S.D.

(FIG. 6A) Unsupervised hierarchical clustering of 165 WT/Cas9 cell line pairs, based on their median L1000 transcriptional profiles (landmark space, n=978 genes). Cell line pairs are colored in red and black, alternately, to highlight that all Cas9 lines cluster together with their parental WT lines. (FIG. 6B) Transcriptional activity scores (TAS)6 comparison of technical replicates of 165 parental lines, 165 technical replicates of Cas9 lines, 165 Cas9 lines vs. parental lines, or 22 control vector lines vs. parental cell lines. *, $p<2e-16$, $p<2e-16$ and $p=2.5e-7$, two-tailed paired t-test. Data points represent cell line pairs. (FIG. 6C) Lack of correlation between Cas9 activity levels (measured by GFP levels; see Example 8) and the strength of the transcriptional response (measured by TAS). $p=0.68$, two-tailed test for association using Spearman's rho. 158 lines are colored by their TP53 mutation status; 7 lines excluded due to lack of Cas9 activity data. (FIG. 6D) The proportion of lines (n=165) with an activated p53 pathway activity following Cas9 introduction, in TP53-WT vs. TP53-mutant cell lines. *, $p=0.0007$, two-tailed Fisher's exact Test. (FIG. 6E) The proportion of TP53-WT lines (n=61) with an activated p53 pathway activity following Cas9 or empty/reporter vector introduction. *, $p=0.006$, two-tailed Fisher's exact Test. (FIG. 6F) The degree and significance of enrichment of the 50 MSigDB Hallmark biological pathways, following the introduction of empty vectors, reporter vectors and Cas9 into TP53-WT cell lines, and the introduction of Cas9 into TP53-mutant cell lines. Black, significantly enriched (GSEA enrichment score with multiple hypotheses correction; q<0.05) pathways. Orange, the p53 pathway. Each plot represents the results of one Meta expression signature (see Online Methods). (FIG. 6G) Comparison of Cas9 activity levels and TAS, as in (FIG. 6D), but only 40 available TP53-WT lines are presented. Cell lines are colored by whether their gene expression profiles were enriched for the p53 Hallmark gene set (and in which direction). p=0.30, two-tailed test for association using Spearman's rho.

(FIG. 7A) Left: confirmation of p53 pathway activation in BT159 cell lines by RT-qPCR analysis of 7 transcriptional targets of p53. *, p=0.017, , p=0.0065, , p<0.0001, one-tailed t-test. Data values represent the means of 3 replicates, with error bars corresponding to S.D. Right: the average activation of p53 transcriptional targets. p=0.08, two-tailed one-sample t-test. Data values represent the means of the 7 targets, with error bars corresponding to S.D. (FIG. 7**B) Left: RT-qPCR analysis of 7 transcriptional targets of p53 in A549 (TP53-WT) before and after its transduction with Cas9 or with three control vectors: luciferase, GFP or DNA barcode. *, p=0.048, one-tailed t-test. Data values represent the means of the 3 control vectors and of 3 biological replicates of Cas9, with error bars corresponding to S.D. Right: the average activation of p53 transcriptional targets. *, p<0.05, two-tailed one-sample t-test. Data values represent the means of the 7 targets, with error bars corresponding to S.D. (FIG. 7C) Protein levels of Cas9, p53, p21 and a housekeeping protein in HCT116 cells transfected with GFP, Cas9 or a backbone-matched empty vector (EV). Results represent a single experiment. (FIG. 7D) Protein levels of Cas9, p53, p21 and a housekeeping protein in isogenic TP53-WT (P) and TP53-null HCT116 cells before and after transduction of Cas9 (C) or of a backbone-matched control vector (EV). Results represent a single experiment. (FIG. 7E) Left: RT-qPCR analysis of 7 transcriptional targets of p53 shows p53 pathway activation specifically in the Cas9-expressing TP53-WT HCT116 cells. Data values represent the means of 2 replicates, with error bars corresponding to S.D. Right: the average activation of p53 transcriptional targets. *, p=0.028, *, p=0.0004, **, p<0.0001, two-tailed one-sample t-test. Data values represent the means of the 7 targets, with error bars corresponding to S.D.

(FIG. 8A) The proportion of cell lines (n=165) with a positively enriched DNA damage transcriptional signature, following Cas9 introduction. *, p=0.33; two-tailed Fisher's exact Test. (FIG. 8B) Fluorescent microscopy images of γH2AX foci (green) and DAPI (blue) in parental TP53-WT HCT116 cells and following Cas9 transduction. Cells with >5 foci have been marked in white. Scale bar represents 10 μM. (FIG. 8C) Quantification of γH2AX foci from three independent repeats; n=1,765 and n=2,523, for WT and Cas9 HCT116 cells, respectively. **, p=0.0095; one-tailed t-test. Data show means, with error bars corresponding to S.D.

(FIG. 9A) Unsupervised hierarchical clustering of 42 WT/Cas9 cell line pairs across 40 independent cell lines, based on their genetic profiles. Cell line pairs are colored in grey and black, alternately, to highlight that all Cas9 lines cluster together with their parental WT lines. (FIG. 9B) The count of overall mutations detected across the 42 WT/Cas9 cell line pairs. (FIG. 9C) The number of recurrent COSMIC mutations that differ between the Cas9 lines and their matched WT lines (that is, detected either in the parental or in the Cas9 line, but not in both). Emerging mutations are shown in black, disappearing mutations in gray, for the 25 cell lines with any COSMIC mutations present. *, p=0.027, one-tailed paired t-test. (FIG. 9D) Sequencing coverage of the TP53 exons in the three cell line pairs in which emergence or expansion of TP53 mutations were detected. (FIG. 9E) Cancer genes ranked by their tendency to acquire mutations in the Cas9 lines. Emerging mutations are shown in black, disappearing mutations in gray. TP53 is highlighted in light gray. (FIG. 9F) The number of non-silent mutations that differ between WT lines and their reported or barcoded derivatives. No mutation in TP53 was observed in 9 independent experiments across three TP53-WT cell lines. (FIG. 9G) Cancer genes ranked by the proportion of silent mutations out of all emerging (silent and non-silent) mutations. TP53 is highlighted in light gray and is among the top ~1% of genes (out of 128 genes with a non-silent mutation present).

Figure 1A:
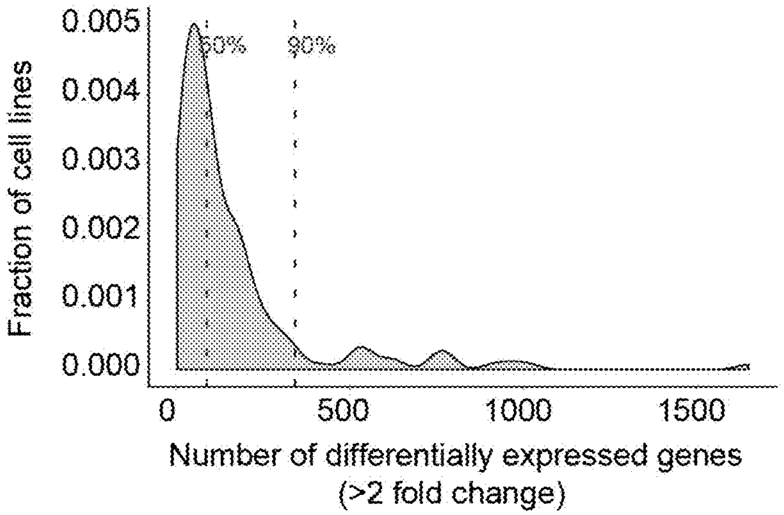
FIGS. 1A-1F—Cas9 introduction activates the p53 pathway.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader embodiments discussed herein. One embodiment described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods for rationally designing and developing CRISPR-Cas based systems and/or therapies based on the expression of a DNA-damage signature response signature in a cell in that has been modified by a CRISPR-Cas system and/or expresses or has expressed a CRISPR-Cas system or component thereof. In some embodiments, the CRISPR-based therapy or therapeutic is a cell that is modified via a CRISPR-Cas system but does not express a DNA-damage response signature. In some embodiments, the CRISPR-based therapy or therapeutic is a CRISPR-Cas system or component thereof that does not induce a DNA-damage response signature in cell in which it is introduced.

Embodiments disclosed herein thus provide rationally designed and/or developed CRISPR-Cas based therapeutics and formulations thereof.

Embodiments disclosed herein provide kits containing one or more CRISPR-Cas based therapeutics and/or formulations thereof and/or one or more reagents or compositions needed to perform a method of rationally designing a CRISPR-Cas therapeutic or therapy based on expression of a DNA-damage response signature.

Embodiments disclosed herein provide administering a rationally designed and/or developed CRISPR-Cas based therapy or therapeutic described herein to a subject in need thereof. The rationally designed and/or developed CRISPR-Cas therapies and/or therapeutics can be used to treat or prevent a disease or symptom thereof in a subject.

Methods of Rational Design of CRISPR-Based Systems and Therapies Using a DNA-Damage Signature Response Signature In some embodiments, the present invention relates to methods for developing or designing CRISPR-Cas systems. In an embodiment, the present invention relates to methods for developing or designing CRISPR-Cas system based therapy or therapeutics. The present invention in particular relates to methods for improving CRISPR-Cas systems, such as CRISPR-Cas system based therapy or therapeutics. Key characteristics of successful CRISPR-Cas systems, such as CRISPR-Cas system based therapy or therapeutics involve high specificity, high efficacy, and high safety. High specificity and high safety can be achieved among others by reduction of off-target effects.

Accordingly, in some embodiments, the present invention relates to methods of increasing the specificity, efficacy, or a combination thereof of CRISPR-Cas systems, such as CRISPR-Cas therapies and/or therapeutics. In certain example embodiments, the present invention relates to rationally developing or designing a CRISPR-Cas based therapy or therapeutic that includes detecting expression of a DNA-damage response signature and optimizing the CRISPR-Cas based therapy to reduce, minimize, or eliminate CRISPR-Cas system induction of a DNA-damage response signature. In certain example embodiments, the present invention relates to rationally developing or designing a CRISPR-Cas based therapy or therapeutic that includes detecting expression of a DNA-damage response signature in cells induced by a CRISPR-Cas system and selecting cells without expression of DNA-damage response signature.

Described herein are embodiments of rationally developing or designing a CRISPR-Cas based therapy or therapeutic that can include detecting expression of a DNA-damage response signature in a cell or cell population that have one or more modified target genes, where the modification was introduced using a CRISPR-complex that can include Cas protein and guide molecule. In embodiments, cells without expression of the DNA-damage response signature can be selected. In some embodiments, the cells without expression of the DNA-damage response signature can be suitable as a CRISPR-based therapy or therapeutic. The method can include modifying one or more target genes in an initial cell or cell population using a CRISPR-Cas complex that can include a Cas protein and a guide molecule. The method can include clonally expanding the modified cell or cell population. The method can include detecting, in cells from the expanded cells population, expression of a DNA-damage response signature. The method can include selecting clones from the expanded cell populations that do not express the DNA-damage response signature.

In some embodiments, the DNA-damage response signature indicates Cas-induced activation of a p53 pathway. In some embodiments, the DNA-damage response signature indicates detection of one or more p53 inactivating mutations. In some embodiments, the DNA-damage response signature can be a Cas-induced DNA-damage response signature. As used herein, "Cas-induced DNA-damage response signature" refers to a gene or other signature response in a cell that results from only the introduction, expression, and/or activity of a Cas protein in a cell. One of ordinary skill in the art will appreciate and be able to determine without undue experimentation the appropriate controls, techniques, and methodology to determine a Cas-induced DNA-damage signature, in view of at least the description and Examples herein. In some embodiments, Cas-induced DNA-damage response signature indicates Cas-induced activation of a p53 pathway. In some embodiments, the Cas-induced DNA damage response signature indicates detection of one or more p53 inactivating mutations.

The selected clones can be used as a treatment or in a therapy. The selected clones can be included in a formulation, such as a pharmaceutical formulation. In some embodiments, the selected clones can be used in an adoptive cell therapy. The initial cell or cell population can be any cell. The initial cell or cell population can be obtained from any biological sample from a subject. In some embodiments, the initial population of cells can include a single cell type and/or subtype, a combination of cell types/subtypes, a cell-based therapeutic, an explant, and/or an organoid. In some embodiments, the initial cell or cell population is isolated from a subject in need of a CRISPR-based therapy or therapeutic. In some embodiments, the initial cell or cell population is isolated from a subject to be treated with the adoptive cell therapy.

The Cas protein can be optimized for one or more parameters. In some embodiments, the Cas protein is optimized for one or more parameters selected from the group of protein size, ability of protein to access regions of high chromatin accessibility, degree of uniform enzyme activity across genomic targets, epigenetic tolerance, mismatch/budge tolerance, effector protein specificity, effector protein stability or half-life, effector protein immunogenicity, toxicity, and combinations thereof.

The guide molecule can be any suitable guide molecule. In some embodiments, the guide molecule can be or include a tru guide, an escorted guide, or a protected guide. Guide molecules are described in greater detail elsewhere herein.

In some embodiments, the target sequences are further selected based on optimization of one or more parameters selected from the group of; PAM type (natural or modified), PAM nucleotide content, PAM length, target sequence length, PAM restrictiveness, target cleavage efficiency, and target sequence position within a gene, a locus or other genomic region. Target sequences are described in greater detail elsewhere herein.

In some embodiments, the modifying the one or more target genes is done in the presence of one or more anti-CRISPR molecules or CRISPR inhibitors. Anti-CRISPR molecules and CRISPR inhibitors are described in greater detail elsewhere herein.

The DNA-damage response signature can also be used to rationally develop or design CRISPR-Cas systems. Also described herein are methods of rationally developing or designing a CRISPR-based system therapeutic that can include screening CRISPR-Cas systems and selecting one or more CRISPR-Cas systems that do not result in expression of a DNA-damage response signature in a cell in which the CRISPR-Cas system(s) is/are expressed.

In some embodiments, the method can include screening a set of CRISPR-Cas systems by expressing each CRISPR-Cas system in a test cell population and modifying one or more target sequences in the test cell population, screening in the test cell population for each CRISPR-Cas system, expression of a DNA-damage response signature, and selecting one or more CRISPR-Cas systems that do not result in expression of a DNA-damage response signature.

In some embodiments, the DNA-damage response signature indicates Cas-induced activation of a p53 pathway. In some embodiments, the DNA-damage response signature indicates detection of one or more p53 inactivating mutations. In some embodiments, the DNA-damage response signature can be a Cas-induced DNA-damage response signature. In some embodiments, Cas-induced DNA-damage response signature indicates Cas-induced activation of a p53 pathway. In some embodiments, the Cas-induced DNA damage response signature indicates detection of one or more p53 inactivating mutations.

Each CRISPR-Cas system in the set of CRISPR-Cas systems can vary in at least one parameter from at least one other CRISPR-Cas system in the set. In some embodiments, each CRISPR-Cas system in the set of CRISPR-Cas systems can vary in a) dosage; b) Cas protein; c) guide molecule design; or a combination thereof.

The Cas protein can be optimized for one or more parameters. In some embodiments, the Cas protein is optimized for one or more parameters selected from the group of protein size, ability of protein to access regions of high chromatin accessibility, degree of uniform enzyme activity across genomic targets, epigenetic tolerance, mismatch/budge tolerance, effector protein specificity, effector protein stability or half-life, effector protein immunogenicity, toxicity, and combinations thereof.

The guide molecule can be any suitable guide molecule. In some embodiments, the guide molecule can be or include a tru guide, an escorted guide, or a protected guide. Guide molecules are described in greater detail elsewhere herein.

In some embodiments, the target sequences are further selected based on optimization of one or more parameters selected from the group of; PAM type (natural or modified), PAM nucleotide content, PAM length, target sequence length, PAM restrictiveness, target cleavage efficiency, and target sequence position within a gene, a locus or other genomic region. Target sequences are described in greater detail elsewhere herein.

In some embodiments, the Cas protein and/or the guide molecule are constitutively expressed. In some embodiments, Cas protein and/or the guide molecule are inducibly expressed. The Cas protein and guide molecule can be delivered on the same or different vectors. In some embodiments, the Cas protein and guide molecule are delivered as a ribonucleoprotein complex (RNP).

In some embodiment, the test cell population is previously modified to express the Cas protein or the guide molecule.

The CRISPR-Cas systems can be delivered to the test cell population by any suitable method. Suitable delivery methods are described elsewhere herein. In some embodiments, the CRISPR-Cas systems are delivered to the test cell populations by liposomes, lipid particles, nanoparticles, biolistics, or viral-based expression/delivery systems.

In some embodiments, the method can further involve selection of the CRISPR-Cas system mode of delivery. In certain embodiments, gRNA (and tracr, if and where needed, optionally provided as a sgRNA) and/or CRISPR effector protein are or are to be delivered. In certain embodiments, gRNA (and tracr, if and where needed, optionally provided as a sgRNA) and/or CRISPR effector mRNA are or are to be delivered. In certain embodiments, gRNA (and tracr, if and where needed, optionally provided as a sgRNA) and/or CRISPR effector provided in a DNA-based expression system are or are to be delivered. In certain embodiments, delivery of the individual CRISPR-Cas system components comprises a combination of the above modes of delivery. In certain embodiments, delivery comprises delivering gRNA and/or CRISPR effector protein, delivering gRNA and/or CRISPR effector mRNA, or delivering gRNA and/or CRISPR effector as a DNA based expression system.

In some embodiments, the modifying the one or more target genes is done in the presence of one or more anti-CRISPR molecules or CRISPR inhibitors. Anti-CRISPR molecules and CRISPR inhibitors are described in greater detail elsewhere herein.

The test cell population can be from any suitable source. In some embodiments, test cell population is obtained from a subject to be treated with a CRISPR-Cas therapeutic. In some embodiments the CRISPR-Cas therapeutic is a CRISPR-Cas system from the set of CRISPR-Cas systems.

Modified cells expressing a DNA-damage response signature can be less desirable to use as a therapy or therapeutic because they may have “off-target” events that can affect the performance of the CRISPR-based therapy or therapeutic. Thus, the methods described herein can have at least the advantage of allowing for identification and selection against CRISPR-Cas systems that induce expression of a DNA-damage response signature and/or against modified cells that have expression of a DNA-damage response signature for use as a therapy. In this way CRISPR-Cas systems and CRISPR-Cas based therapies and therapeutics can be rationally designed based upon the expression (or not) of a DNA damage response signature. Further advantages are discussed elsewhere herein and will be apparent to those of ordinary skill in the art in view of the description herein.

Some embodiments relate to systems, compositions, methods for increasing the specificity and/or reducing off-target events of nucleic acid targeting systems (e.g. CRISPR-Cas systems), particularly for CRISPR-Cas based therapies. In a further embodiment, the invention relates to methods for increasing safety of CRISPR-Cas systems, such as CRISPR-Cas system-based therapy or therapeutics. In a further embodiment, the present invention relates to methods for increasing specificity, efficacy, and/or safety, preferably all, of CRISPR-Cas systems, such as CRISPR-Cas system-based therapy or therapeutics.

Embodiments of methods of the present invention involve optimization of selected parameters or variables associated with the CRISPR-Cas system and/or its functionality, as described herein further elsewhere. Optimization of the CRISPR-Cas system in the methods as described herein may depend on the target(s), such as the therapeutic target or therapeutic targets, the mode or type of CRISPR-Cas system modulation, such as CRISPR-Cas system based therapeutic target(s) modulation, modification, or manipulation, as well as the delivery of the CRISPR-Cas system components. One or more targets may be selected, depending on the genotypic and/or phenotypic outcome. For instance, one or more therapeutic targets may be selected, depending on (genetic) disease etiology or the desired therapeutic outcome. The (therapeutic) target(s) may be a single gene, locus, or other genomic site, or may be multiple genes, loci or other genomic sites. As is known in the art, a single gene, locus, or other genomic site may be targeted more than once, such as by use of multiple gRNAs.

DNA-Damage Response Signature and Detection Thereof

As discussed elsewhere herein the method can include screening cells or cell populations (including clonal cells and clonal cell populations (also referred to herein as “clones”) for expression of a DNA-damage response signature. The DNA-damage response signature can be a protein and/or gene expression signature, wherein detection of said signature in a sample, such as in a cell or cell population that has been genetically modified using a CRISPR-Cas system or that expresses one or more CRISPR-Cas components, can indicate that the cell or cell population contains an off-target genetic and/or transcriptional change, which can be undesirable in a cell or cell population to be used as a therapeutic or therapy. Thus, the activity and/or expression of a DNA-damage response signature in a cell or cell population can indicate that the cell contains one or more off target genetic and/or transcriptional changes from the parental cell or cell population that may make it unsuitable for use in a CRISPR-based therapeutic or treatment.

In some embodiments, the DNA-damage response signature indicates Cas-induced activation of a p53 pathway. In some embodiments, the DNA-damage response signature indicates detection of one or more p53 inactivating mutations. In some embodiments, the DNA-damage response signature can be a Cas-induced DNA-damage response signature. In some embodiments, Cas-induced DNA-damage response signature indicates Cas-induced activation of a p53 pathway. In some embodiments, the Cas-induced DNA damage response signature indicates detection of one or more p53 inactivating mutations. p53 inactivation mutations are described elsewhere herein.

In some embodiments, the DNA-damage response signature can be composed of one or more biomarkers. In some embodiments, the biomarkers include one or more p53 inactivation mutation. In some embodiments, the biomarkers include p21, p53, CCNG1, PUMA, BAX, TIGAR, GADD45, MDM2, and combinations thereof. In some embodiments, the biomarkers include one or any combination of mutations, genes, and/or signatures shown or described in in any one of Tables 13, 14, 15, and 16 and FIGS. 3A-3B, 6G, 7A-7B, 7E, and/or 9E, and/or Supplementary Data 1 and 3 of Enache, O. M., Rendo, V., Abdusamad, M. et al. Cas9 activates the p53 pathway and selects for p53-inactivating mutations. Nat Genet 52, 662-668 (2020). https://doi.org/10.1038/s41588-020-0623-4, which is incorporated by reference herein as if expressed in its entirety and also Appendix A to U.S. Provisional Ser. No. 62/909,131).

A suitable method and/or technique, such as those described below, can be utilized to determine the DNA-damage response signature described herein. In some embodiments, the technique may be an RNA-seq method or technique. In some embodiments, the technique or method may be able to measure the expression at the single-cell level. In some embodiments, the technique may be a single-cell RNA-seq method or technique.

In some embodiments, differences between the parental cell or cell line and a cell or cell population that has been modified using a CRISPR-Cas system and/or has expressed one or more components of a CRISPR-Cas system can include comparing a gene and/or protein expression distribution of the modified cell or cell population (or cells that express or have expressed one or more components of a CRISPR-Cas system) with a gene and/or protein expression distribution of the parental cell as determined by a suitable gene and/or protein expression analysis method. Suitable gene and protein analysis techniques are generally known in the art and can include, but are not limited to PCR-based methods, single-cell RNA-seq, gene and protein sequencing methods, mass-spec analysis methods, immunodetection methods (e.g. Western analysis and the like), etc.

In certain example embodiments, assessing the presence or absence of a DNA-damage response signature in a cell or cell population can include analysis of expression matrices from the expression data however derived (e.g. sc-RNA seq), performing dimensionality reduction, graph-based clustering and deriving list of cluster-specific genes in order to identify expression or no expression of a DNA-damage response signature. These marker genes and/or proteins can then be used throughout to relate one cell state to another. For example, these marker genes can be used to relate cells that have been modified using a CRISPR-Cas system or cells that express or have expressed one or more components of a CRISPR-Cas system to the wild-type (or parental cell or cell population). The same analysis may then be applied to the source material for the sample or a control. From both sets of expression (e.g. sc-RNAseq) analysis an initial distribution of gene expression data is obtained. In certain embodiments, the distribution may be a count-based metric for the number of transcripts of each gene present in a cell. Further the clustering and gene expression matrix analysis allow for the identification of key genes in the DNA-damage response signature, such as differences in the expression of key transcription factors. In certain example embodiments, this may be done conducting differential expression analysis. For example, in the Working Examples below, differential gene expression analysis identified that p53, p21, and other genes as identified in Tables 13, 14, 15, and 16 and FIGS. 3A-3B, 6G, 7A-7B, 7E, 9E, and/or Supplementary Data 1 and 3 of Enache, O. M., Rendo, V., Abdusamad, M. et al. Cas9 activates the p53 pathway and selects for p53-inactivating mutations. Nat Genet 52, 662-668 (2020). https://doi.org/10.1038/s41588-020-0623-4, which is incorporated by reference herein as if expressed in its entirety and also Appendix A to U.S. Provisional Ser. No. 62/909,131) in Cas modified cells as compared to the parental cell lines. The methods disclosed herein can both identify CRISPR-Cas based therapeutics that can have reduced off target effects and identify specific CRISPR-Cas systems that are less prone to inducing expression of a DNA-damage response signature.

In some embodiments, identification of a DNA-damage response signature can include detecting a shift, such as a statistically significant shift, in the cell-state as indicated by a modulated (e.g. an increased distance) in the gene expression space between the CRISPR-Cas modified cell-state or the CRISPR-Cas component expression cell-state and the wild-type or parental cell state. In certain embodiments, the distance is measured by a Euclidean distance, Pearson coefficient, Spearman coefficient, or combination thereof.

In certain embodiments, the gene expression space comprises 10 or more genes, 20 or more genes, 30 or more genes, 40 or more genes, 50 or more genes, 100 or more genes, 500 or more genes, or 1000 or more genes. In certain embodiments, the expression space defines one or more cell pathways. In certain embodiments, the expression space is transcriptome of the cell modified using a CRISPR-Cas system or a cell that has or does expressed one or more CRISPR-Cas system components.

In certain embodiments, the shift in cell states that increases the distance in gene expression space between the parental (or wild-type) cell-state and the CRISPR-Cas modified or CRISPR-Cas system expression cell-state is a statistically significant shift in the gene expression distribution of the parental (or wild-type) cell state to and the CRISPR-Cas modified or CRISPR-Cas system expression cell-state. The statistically significant shift may be at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%. The statistical shift may include the overall transcriptional identity or the transcriptional identity of one or more genes, gene expression cassettes, or gene expression signatures of the DAA cell state compared to the homeostatic and/or activated cell state (i.e., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% of the genes, gene expression cassettes, or gene expression signatures are statistically shifted in a gene expression distribution). A shift of 0% means that there is no difference to the parental (or wild-type) and the CRISPR-Cas modified or CRISPR-Cas system expression cell-state. A gene distribution may be the average or range of expression of particular genes, gene expression cassettes, or gene expression signatures in the parental (or wild-type) and the CRISPR-Cas modified or CRISPR-Cas system expression cell-state (e.g., a cell or a plurality of a cells from a subject may be modified using a CRISPR-Cas system or to express one or more components of a CRISPR-Cas system can be sequenced and a distribution can determined for the expression of genes, gene expression cassettes, or gene expression signatures). In certain embodiments, the distribution is a count-based metric for the number of transcripts of each gene present in a cell. A statistical difference between the distributions indicates a shift. The one or more genes, gene expression cassettes, or gene expression signatures may be selected to compare transcriptional identity based on the one or more genes, gene expression cassettes, or gene expression signatures having the most variance as determined by methods of dimension reduction (e.g., tSNE analysis). In certain embodiments, comparing a gene expression distribution comprises comparing the initial cells with the lowest statistically significant shift as compared to the homeostatic and/or activated cell state (e.g., determining shifts when comparing only the DAA cells with a shift of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10% to the homeostatic cell state). In certain example embodiments, statistical shifts may be determined by defining a parental cell (or wild-type), a CRISPR-Cas modified, and/or CRISPR-Cas system expression cell-state score.

Gene Expression Space and Expression Signatures

As used herein a "signature" may encompass any gene or genes, protein or proteins, or epigenetic element(s) whose expression profile or whose occurrence is associated with a specific cell type, subtype, or cell state of a specific cell type or subtype within a population of cells. For ease of discussion, when discussing gene expression, any of gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub)populations. Increased or decreased expression or activity or prevalence of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the DNA-damage response signature can be used to detect cells that have been modified using a CRISPR-Cas system or cells that have or do express one or more components of a CRISPR-Cas system that have off-target changes, which may be undesirable and/or deleterious as compared to the parental or wild-type line. In one embodiment, the novel signatures are used to detect multiple cell states or hierarchies that occur in subpopulations of cancer or pre-cancerous cells that are linked to particular pathological condition (e.g. cancer grade), or linked to a particular outcome or progression of the disease (e.g. metastasis), or linked to a particular response to treatment of the disease.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell, cell (sub)population, or cell state if it is upregulated or only present, detected or detectable in that particular cell, cell (sub)population, or cell state or alternatively is downregulated or only absent, or undetectable in that particular cell, cell (sub)population, or cell state. In this context, a signature consists of one or more differentially expressed genes/proteins or differential epigenetic elements when comparing different cell, cell (sub) population, or cell state, including comparing different CRISPR-Cas modified or CRISPR-Cas component(s CRISPR-Cas modified or CRISPR-Cas component(s) expressing cells or (sub)populations thereof cells with wild-type (or parental) cells or (sub)populations thereof. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least to, at least three, at least four, at least five, at least six, or all genes/proteins and/or epigenetic elements of the signature.

In further embodiments, the invention relates to gene signatures, protein signature, and/or other genetic or epigenetic signature of particular astrocyte subpopulations, as defined herein elsewhere.

scRNA-seq may be obtained from cells using standard techniques known in the art. Some exemplary scRNA-seq techniques are discussed elsewhere herein. As discussed elsewhere herein, a collection of mRNA levels for a single cell can be called an expression profile (or expression signature) and is often represented mathematically by a vector in gene expression space. See e.g. Wagner et al., 2016. Nat. Biotechnol; 34(111): 1145-1160. This is a vector space that has a dimension corresponding to each gene, with the value of the ith coordinate of an expression profile vector representing the number of copies of mRNA for the ith gene. Note that real cells only occupy an integer lattice in gene expression space (because the number of copies of mRNA is an integer), but it is assumed herein that cells can move continuously through a real-valued G dimensional vector space.

As an individual cell changes the genes it expresses over time, it moves in gene expression space and describes a trajectory. As a population of cells develops and grows, a distribution on gene expression space evolves over time. When a single cell from such a population is measured with single cell RNA sequencing, a noisy estimate of the number of molecules of mRNA for each gene is obtained. The measured expression profile of this single cell is represented as a sample from a probability distribution on gene expression space. This sampling captures both (a) the randomness in the single cell RNA sequencing measurement process (due to sub-sampling reads, technical issues, etc.) and (b) the random selection of a cell from a population. This probability distribution is treated as nonparametric in the sense that it is not specified by any finite list of parameters. In certain embodiments, methods such as optimal transport may be used to infer the ancestors and descendants of subpopulations evolving according to an unknown developmental, disease, and/or other physiological process and/or corresponding to a specific cell state at the beginning, end, or any point during the developmental process. Optimal transport analysis is described in detail in International Patent Publication No. WO 2019/060450, specifically pages 248 to 270, which are incorporated herein by reference.

Nucleic Acid Barcode, Barcode, and Unique Molecular Identifier (UMI)

The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment. Although it is not necessary to understand the mechanism of an invention, it is believed that the barcode sequence provides a high-quality individual read of a barcode associated with a single cell, a viral vector, labeling ligand (e.g., an aptamer), protein, shRNA, sgRNA or cDNA such that multiple species can be sequenced together.

Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

In preferred embodiments, sequencing is performed using unique molecular identifiers (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. The UMI may also be used to determine the number of transcripts that gave rise to an amplified product, or in the case of target barcodes as described herein, the number of binding events. In preferred embodiments, the amplification is by PCR or multiple displacement amplification (MDA).

In certain embodiments, an UMI with a random sequence of between 4 and 20 base pairs is added to a template, which is amplified and sequenced. In preferred embodiments, the UMI is added to the 5' end of the template. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No:11, 163-166). Not being bound by a theory, the UMI's are designed such that assignment to the original can take place despite up to 4-7 errors during amplification or sequencing. Not being bound by a theory, an UMI may be used to discriminate between true barcode sequences.

Unique molecular identifiers can be used, for example, to normalize samples for variable amplification efficiency. For example, in various embodiments, featuring a solid or semisolid support (for example a hydrogel bead), to which nucleic acid barcodes (for example a plurality of barcodes sharing the same sequence) are attached, each of the barcodes may be further coupled to a unique molecular identifier, such that every barcode on the particular solid or semisolid support receives a distinct unique molecule identifier. A unique molecular identifier can then be, for example, transferred to a target molecule with the associated barcode, such that the target molecule receives not only a nucleic acid barcode, but also an identifier unique among the identifiers originating from that solid or semisolid support.

A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. Target molecule and/or target nucleic acids can be labeled with multiple nucleic acid barcodes in combinatorial fashion, such as a nucleic acid barcode concatemer. Typically, a nucleic acid barcode is used to identify a target molecule and/or target nucleic acid as being from a particular discrete volume, having a particular physical property (for example, affinity, length, sequence, etc.), or having been subject to certain treatment conditions. Target molecule and/or target nucleic acid can be associated with multiple nucleic acid barcodes to provide information about all of these features (and more). Each member of a given population of UMIs, on the other hand, is typically associated with (for example, covalently bound to or a component of the same molecule as) individual members of a particular set of identical, specific (for example, discreet volume-, physical property-, or treatment condition-specific) nucleic acid barcodes. Thus, for example, each member of a set of origin-specific nucleic acid barcodes, or other nucleic acid identifier or connector oligonucleotide, having identical or matched barcode sequences, may be associated with (for example, covalently bound to or a component of the same molecule as) a distinct or different UMI.

As disclosed herein, unique nucleic acid identifiers are used to label the target molecules and/or target nucleic acids, for example origin-specific barcodes and the like. The nucleic acid identifiers, nucleic acid barcodes, can include a short sequence of nucleotides that can be used as an identifier for an associated molecule, location, or condition. In certain embodiments, the nucleic acid identifier further includes one or more unique molecular identifiers and/or barcode receiving adapters. A nucleic acid identifier can have a length of about, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt). In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 bp or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety.

One or more nucleic acid identifiers (for example a nucleic acid barcode) can be attached, or "tagged," to a target molecule. This attachment can be direct (for example, covalent or noncovalent binding of the nucleic acid identifier to the target molecule) or indirect (for example, via an additional molecule). Such indirect attachments may, for example, include a barcode bound to a specific-binding agent that recognizes a target molecule. In certain embodiments, a barcode is attached to protein G and the target molecule is an antibody or antibody fragment. Attachment of a barcode to target molecules (for example, proteins and other biomolecules) can be performed using standard methods well known in the art. For example, barcodes can be linked via cysteine residues (for example, C-terminal cysteine residues). In other examples, barcodes can be chemically introduced into polypeptides (for example, antibodies) via a variety of functional groups on the polypeptide using appropriate group-specific reagents (see for example www.drmr.com/abcon). In certain embodiments, barcode tagging can occur via a barcode receiving adapter associate with (for example, attached to) a target molecule, as described herein.

Target molecules can be optionally labeled with multiple barcodes in combinatorial fashion (for example, using multiple barcodes bound to one or more specific binding agents that specifically recognizing the target molecule), thus greatly expanding the number of unique identifiers possible within a particular barcode pool. In certain embodiments, barcodes are added to a growing barcode concatemer attached to a target molecule, for example, one at a time. In other embodiments, multiple barcodes are assembled prior to attachment to a target molecule. Compositions and methods for concatemerization of multiple barcodes are described, for example, in International Patent Publication No. WO 2014/047561, which is incorporated herein by reference in its entirety.

In some embodiments, a nucleic acid identifier (for example, a nucleic acid barcode) may be attached to sequences that allow for amplification and sequencing (for example, SB S3 and P5 elements for Illumina sequencing). In certain embodiments, a nucleic acid barcode can further include a hybridization site for a primer (for example, a single-stranded DNA primer) attached to the end of the barcode. For example, an origin-specific barcode may be a nucleic acid including a barcode and a hybridization site for a specific primer. In particular embodiments, a set of origin-specific barcodes includes a unique primer specific barcode made, for example, using a randomized oligo type NNNNNNNNNNNN (SEQ ID NO. 41).

A nucleic acid identifier can further include a unique molecular identifier and/or additional barcodes specific to, for example, a common support to which one or more of the nucleic acid identifiers are attached. Thus, a pool of target molecules can be added, for example, to a discrete volume containing multiple solid or semisolid supports (for example, beads) representing distinct treatment conditions (and/or, for example, one or more additional solid or semisolid support can be added to the discreet volume sequentially after introduction of the target molecule pool), such that the precise combination of conditions to which a given target molecule was exposed can be subsequently determined by sequencing the unique molecular identifiers associated with it.

Labeled target molecules and/or target nucleic acids associated origin-specific nucleic acid barcodes (optionally in combination with other nucleic acid barcodes as described herein) can be amplified by methods known in the art, such as polymerase chain reaction (PCR). For example, the nucleic acid barcode can contain universal primer recognition sequences that can be bound by a PCR primer for PCR amplification and subsequent high-throughput sequencing. In certain embodiments, the nucleic acid barcode includes or is linked to sequencing adapters (for example, universal primer recognition sequences) such that the barcode and sequencing adapter elements are both coupled to the target molecule. In particular examples, the sequence of the origin specific barcode is amplified, for example using PCR. In some embodiments, an origin-specific barcode further comprises a sequencing adaptor. In some embodiments, an origin-specific barcode further comprises universal priming sites. A nucleic acid barcode (or a concatemer thereof), a target nucleic acid molecule (for example, a DNA or RNA molecule), a nucleic acid encoding a target peptide or polypeptide, and/or a nucleic acid encoding a specific binding agent may be optionally sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others. In some embodiments, the sequence of labeled target molecules is determined by non-sequencing based methods. For example, variable length probes or primers can be used to distinguish barcodes (for example, origin-specific barcodes) labeling distinct target molecules by, for example, the length of the barcodes, the length of target nucleic acids, or the length of nucleic acids encoding target polypeptides. In other instances, barcodes can include sequences identifying, for example, the type of molecule for a particular target molecule (for example, polypeptide, nucleic acid, small molecule, or lipid). For example, in a pool of labeled target molecules containing multiple types of target molecules, polypeptide target molecules can receive one identifying sequence, while target nucleic acid molecules can receive a different identifying sequence. Such identifying sequences can be used to selectively amplify barcodes labeling particular types of target molecules, for example, by using PCR primers specific to identifying sequences specific to particular types of target molecules. For example, barcodes labeling polypeptide target molecules can be selectively amplified from a pool, thereby retrieving only the barcodes from the polypeptide subset of the target molecule pool.

A nucleic acid barcode can be sequenced, for example, after cleavage, to determine the presence, quantity, or other feature of the target molecule. In certain embodiments, a nucleic acid barcode can be further attached to a further nucleic acid barcode. For example, a nucleic acid barcode can be cleaved from a specific-binding agent after the specific-binding agent binds to a target molecule or a tag (for example, an encoded polypeptide identifier element cleaved from a target molecule), and then the nucleic acid barcode can be ligated to an origin-specific barcode. The resultant nucleic acid barcode concatemer can be pooled with other such concatemers and sequenced. The sequencing reads can be used to identify which target molecules were originally present in which discrete volumes.

Barcodes Reversibly Coupled to Solid Substrate

In some embodiments, the origin-specific barcodes are reversibly coupled to a solid or semisolid substrate. In some embodiments, the origin-specific barcodes further comprise a nucleic acid capture sequence that specifically binds to the target nucleic acids and/or a specific binding agent that specifically binds to the target molecules. In specific embodiments, the origin-specific barcodes include two or more populations of origin-specific barcodes, wherein a first population comprises the nucleic acid capture sequence and a second population comprises the specific binding agent that specifically binds to the target molecules. In some examples, the first population of origin-specific barcodes further comprises a target nucleic acid barcode, wherein the target nucleic acid barcode identifies the population as one that labels nucleic acids. In some examples, the second population of origin-specific barcodes further comprises a target molecule barcode, wherein the target molecule barcode identifies the population as one that labels target molecules.

Barcode with Cleavage Sites

A nucleic acid barcode may be cleavable from a specific binding agent, for example, after the specific binding agent has bound to a target molecule. In some embodiments, the origin-specific barcode further comprises one or more cleavage sites. In some examples, at least one cleavage site is oriented such that cleavage at that site releases the origin-specific barcode from a substrate, such as a bead, for example a hydrogel bead, to which it is coupled. In some examples, at least one cleavage site is oriented such that the cleavage at the site releases the origin-specific barcode from the target molecule specific binding agent. In some examples, a cleavage site is an enzymatic cleavage site, such an endonuclease site present in a specific nucleic acid sequence. In other embodiments, a cleavage site is a peptide cleavage site, such that a particular enzyme can cleave the amino acid sequence. In still other embodiments, a cleavage site is a site of chemical cleavage.

Barcode Adapters

In some embodiments, the target molecule is attached to an origin-specific barcode receiving adapter, such as a nucleic acid. In some examples, the origin-specific barcode receiving adapter comprises an overhang and the origin-specific barcode comprises a sequence capable of hybridizing to the overhang. A barcode receiving adapter is a molecule configured to accept or receive a nucleic acid barcode, such as an origin-specific nucleic acid barcode. For example, a barcode receiving adapter can include a single-stranded nucleic acid sequence (for example, an overhang) capable of hybridizing to a given barcode (for example, an origin-specific barcode), for example, via a sequence complementary to a portion or the entirety of the nucleic acid barcode. In certain embodiments, this portion of the barcode is a standard sequence held constant between individual barcodes. The hybridization couples the barcode receiving adapter to the barcode. In some embodiments, the barcode receiving adapter may be associated with (for example, attached to) a target molecule. As such, the barcode receiving adapter may serve as the means through which an origin-specific barcode is attached to a target molecule. A barcode receiving adapter can be attached to a target molecule according to methods known in the art. For example, a barcode receiving adapter can be attached to a polypeptide target molecule at a cysteine residue (for example, a C-terminal cysteine residue). A barcode receiving adapter can be used to identify a particular condition related to one or more target molecules, such as a cell of origin or a discreet volume of origin. For example, a target molecule can be a cell surface protein expressed by a cell, which receives a cell-specific barcode receiving adapter. The barcode receiving adapter can be conjugated to one or more barcodes as the cell is exposed to one or more conditions, such that the original cell of origin for the target molecule, as well as each condition to which the cell was exposed, can be subsequently determined by identifying the sequence of the barcode receiving adapter/barcode concatemer.

Barcode with Capture Moiety

In some embodiments, an origin-specific barcode further includes a capture moiety, covalently or non-covalently linked. Thus, in some embodiments the origin-specific barcode, and anything bound or attached thereto, that include a capture moiety are captured with a specific binding agent that specifically binds the capture moiety. In some embodiments, the capture moiety is adsorbed or otherwise captured on a surface. In specific embodiments, a targeting probe is labeled with biotin, for instance by incorporation of biotin-16-UTP during in vitro transcription, allowing later capture by streptavidin. Other means for labeling, capturing, and detecting an origin-specific barcode include: incorporation of aminoallyl-labeled nucleotides, incorporation of sulfhydryl-labeled nucleotides, incorporation of allyl- or azide-containing nucleotides, and many other methods described in Bioconjugate Techniques ($2^{nd}$ Ed), Greg T. Hermanson, Elsevier (2008), which is specifically incorporated herein by reference. In some embodiments, the targeting probes are covalently coupled to a solid support or other capture device prior to contacting the sample, using methods such as incorporation of aminoallyl-labeled nucleotides followed by 1-Ethyl-3-(3-dimethylaminopropyl)carbodiimide (EDC) coupling to a carboxy-activated solid support, or other methods described in Bioconjugate Techniques. In some embodiments, the specific binding agent has been immobilized for example on a solid support, thereby isolating the origin-specific barcode.

Other Barcoding Embodiments

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a crocus?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

A desirable locus for DNA barcoding can be standardized so that large databases of sequences for that locus can be developed. Most of the taxa of interest have loci that are sequencable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105 (8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8):2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31):12569 (2009).

Software for DNA barcoding requires integration of a field information management system (HMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94).

Unique Molecular Identifiers are short (usually 4-10 bp) random barcodes added to transcripts during reverse-transcription. They enable sequencing reads to be assigned to individual transcript molecules and thus the removal of amplification noise and biases from RNA-seq data. Since the number of unique barcodes (4N, N—length of UMI) is much smaller than the total number of molecules per cell (~106), each barcode will typically be assigned to multiple transcripts. Hence, to identify unique molecules both barcode and mapping location (transcript) must be used. UMI-sequencing typically consists of paired-end reads where one read from each pair captures the cell and UMI barcodes while the other read consists of exonic sequence from the transcript. UMI-sequencing typically consists of paired-end reads where one read from each pair captures the cell and UMI barcodes while the other read consists of exonic sequence from the transcript.

In some embodiments, the nucleic acids of the library are flanked by switching mechanism at 5' end of RNA templates (SMART). SMART is a technology that allows the efficient incorporation of known sequences at both ends of cDNA during first strand synthesis, without adaptor ligation. The presence of these known sequences is crucial for a number of downstream applications including amplification, RACE, and library construction. While a wide variety of technologies can be employed to take advantage of these known sequences, the simplicity and efficiency of the single-step SMART process permits unparalleled sensitivity and ensures that full-length cDNA is generated and amplified. (see, e.g., Zhu et al., 2001, Biotechniques. 30 (4): 892-7.

After processing the reads from a UMI experiment, the following conventions are often used: 1. The UMI is added to the read name of the other paired read. 2. Reads are sorted into separate files by cell barcode ° For extremely large, shallow datasets, a cell barcode may be added to the read name as well to reduce the number of files. A cell barcode indicates the cell from which mRNA is captured (e.g., Drop-Seq or Seq-Well).

Sequencing Methods

In one approach, the present invention relates to a PCR-amplification based approach to derive genetic information from single-cell RNA-seq libraries.

The method generally involves two PCR steps and size selection. Initially, a library is constructed wherein each sequence comprises a SMART sequence at the 5' end and the 3' end, a genetic region of interest at the 5' end and a UMI and Cell BC at the 3' end, e.g., 5' SMART-genetic region of interest-UMI-Cell BC-SMART 3'.

A first PCR product is generated by amplifying sequences with a biotinylated 5' primer comprising a binding site for a second PCR product and a sequence complementary to a specific gene of interest and a 3' SMART primer complementary to the SMART sequence at the 3' end of the nucleic acid to generate a first PCR product. The binding site for the second PCR product may be a partial Illumina sequencing primer binding site or an oligomer for sequencing kit, such as a NEBNext® oligos for Illumina® sequencing (see, e.g., https://www.neb.com/applications/library-preparation-for-next-generation-sequencing/illumina-library-preparation/products).

The 5' primer comprising the binding site for the second PCR product to amplify the first PCR product may further comprise a sequence to bind a flow cell, a sequence allowing multiple sequencing libraries to be sequenced simultaneously and/or a sequence providing an additional primer binding site. The sequence to bind a flow cell may be a P7 sequence and the flow cell may be an Illumina® flowcell.

In another embodiment, the SMART primer complementary to the SMART sequence at the 3' end of the nucleic acid to amplify the first PCR product may further comprise a sequence to allow fragments to bind a flowcell. The sequence to allow fragments to bind a flowcell may be a P5 sequence.

Regardless of the library construction method, submitted libraries may consist of a sequence of interest flanked on either side by adapter constructs. On each end, these adapter constructs may have flow cell binding sites, P5 and P7, which allow the library fragment to attach to the flow cell surface. The P5 and P7 regions of single-stranded library fragments anneal to their complementary oligos on the flowcell surface. The flow cell oligos act as primers and a strand complementary to the library fragment is synthesized. The original strand is washed away, leaving behind fragment copies that are covalently bonded to the flowcell surface in a mixture of orientations. 1,000 copies of each fragment are generated by bridge amplification, creating clusters. For simplification, the diagram shows only one copy (out of 1,000) in each cluster, and only two clusters (out of 30-50 million). The P5 region is cleaved, resulting in clusters containing only fragments which are attached by the P7 region. This ensures that all copies are sequenced in the same direction. The sequencing primer anneals to the P5 end of the fragment, and begins the sequencing by synthesis process. Index reads are only performed when a sample is barcoded. When Read 1 is finished, everything from Read 1 is removed and an index primer is added, which anneals at the P7 end of the fragment and sequences the barcode. Everything is stripped from the template, which forms clusters by bridge amplification as in Read 1. This leaves behind fragment copies that are covalently bonded to the flowcell surface in a mixture of orientations. This time, P7 is cut instead of P5, resulting in clusters containing only fragments which are attached by the P5 region. This ensures that all copies are sequences in the same direction (opposite Read 1). The sequencing primer anneals to the P7 region and sequences the other end of the template.

In another embodiment, the sequence allowing multiple sequencing libraries to be sequenced simultaneously may be an INDEX sequence. The INDEX allows multiple sequencing libraries to be sequenced simultaneously (and demultiplexed using Illumina's bcl2fastq command). See, e.g., https://support.illumina.com/downloads/illumina-customer-sequence-letter.html for exemplary INDEX sequences.

In another embodiment, the 5' primer comprising the binding site for the second PCR product to amplify the first PCR product may further comprise a NEXTERA sequence. See, e.g., https://support.illumina.com/downloads/illumina-customer-sequence-letter.html and U.S. Pat. Nos. 5,965,443, and 6,437,109 and European Patent No. 0927258, for exemplary NEXTERA sequences.

In another embodiment, the sequence providing an additional primer binding site may be a custom read1 primer binding site (CR1P) for sequencing. CR1P is a Custom Read1 Primer binding site that is used for Drop-Seq and Seq-Well library sequencing. CR1P may comprise the sequence: GCCTGTCCGCGGAAGCAGTGGTATCAACGCAGAGTAC (SEQ ID NO: 42) (see e.g., Gierahn et al., Nature Methods 14, 395-398 (2017).

Biotin-NEXT-GENE-for: Biotinylation enables purification of the desired product following the first PCR reaction. NEXT creates a binding site for the second PCR product as well as a partial primer binding site for standard Illumina sequencing kits. NEXT may be any sequence that allows targeted enrichment and then select addition of sequencing handles. GENE is a sequence complementary to the WTA, designed to amplify a specific region of interest (usually an exon).

SMART-rev: The SMART sequence is used in Drop-seq and Seq-Well to generate WTA libraries. Because the polyT-unique molecular identifier-unique cellular barcode (polyT-UMI-CB) sequence is followed by the SMART sequence, and the template switching oligo (TSO) also contains the SMART sequence, WTA libraries have the SMART sequence as a PCR binding site on both the 5' and the 3' end.

P7-INDEX-NEXTERA: The P7 sequence allows fragments to bind the Illumina flowcell. The INDEX allows multiple sequencing libraries to be sequenced simultaneously (and demultiplexed using Illumina's bcl2fastq command). The NEXTERA sequence provides a primer binding site for Illumina's standard Read2 sequencing primer mix.

SMART-CR1P-P5: The SMART sequence is the same as in SMART-rev. CR1P is a Custom Read1 Primer binding site that is used for Drop-Seq and Seq-Well library sequencing. The P5 sequence allows fragments to bind the Illumina flowcell. Note that the primer design can be easily modified for compatibility with additional single-cell RNA-seq technologies (SMART) or sequencing technologies (NEXTERA, CR1P).

The method also provides for biotin enrichment of the first PCR product. Biotinylation of the primer to amplify the gene, region or mutation of interest from the library allows for the purification of the PCR product of interest. Because the libraries are flanked with SMART sequences on both ends, the vast majority of the first PCR product would be amplification of the entire library. Without the biotinylated primer, enrichment of the gene, region or mutation of interest would be insufficient to efficiently and confidently call genetic mutations. Biotin enrichment may be accomplished by streptavidin binding of the biotinylated first PCR product. The streptavidin bead kilobaseBINDER kit (Thermo Fisher Cat #60101) allows for isolation of large biotinylated DNA fragments.

Gene specific primers may be mixed for simultaneous detection of multiple mutations. Libraries may also be mixed for simultaneous detection of mutations in multiple samples. However, mixed primers sometimes may not detect multiple mutations in the same gene as only the shortest fragment will be detected.

The present method may be adapted to identify any gene, region or mutation of interest and to identify cells containing specific genes, regions or mutations, deletions, insertions, indels, or translocations of interest.

Sequencing and Library Construction

In some embodiments, RNA-seq can be used. As used herein, RNA-seq methods refer to high-throughput single-cell RNA-sequencing protocols. RNA-seq includes, but is not limited to, Drop-seq, Seq-Well, InDrop and 1Cell Bio. RNA-seq methods also include, but are not limited to, smart-seq2, TruSeq, CEL-Seq, STRT, ChIRP-Seq, GRO-Seq, CLIP-Seq, Quartz-Seq, or any other similar method known in the art (see, e.g., "Sequencing Methods Review" Illumina® Technology, https://www.illumina.com/content/dam/illumina-marketing/documents/products/research_reviews/sequencing-methods-review.pdf. See e.g., Wagner et al., 2016. Nat Biotechnol. 34(111): 1145-1160.

In some embodiments, sequence adapters can be used. As used herein, sequence adapters or sequencing adapters or adapters include primers that may include additional sequences involved in for example, but not limited to, flowcell binding, cluster generation, library generation, sequencing primers, sequences for Seq-Well, and/or custom read sequencing primers. Universal primer recognition sequences The present invention may encompass incorporation of SMART sequences into the library. Switching mechanism at 5' end of RNA template (SMART) is a technology that allows the efficient incorporation of known sequences at both ends of cDNA during first strand synthesis, without adaptor ligation. The presence of these known sequences is crucial for a number of downstream applications including amplification, RACE, and library construction. While a wide variety of technologies can be employed to take advantage of these known sequences, the simplicity and efficiency of the single-step SMART process permits unparalleled sensitivity and ensures that full-length cDNA is generated and amplified. (see, e.g., Zhu et al., 2001, Biotechniques. 30 (4): 892-7.

A pooled set of nucleic acids that are tagged refer to a plurality of nucleic acid molecules that results from incorporating an identifiable sequence tag into a pool of sample-tagged nucleic acids, by any of various methods. In some embodiments, the tag serves instead as a minimal sequence adapter for adding nucleic acids onto sample-tagged nucleic acids, rendering the pool compatible with a particular DNA sequencing platform or amplification strategy.

In some embodiments, a 3' barcoded single cell RNA library can be generated. The 3' barcoded single cell RNA library includes a plurality of nucleic acids, each nucleic acid including a gene of interest, a unique molecular identifier (UMI) and a cell barcode (cell BC). The cell barcode is located on the 3' end of the transcript. As the single cell RNA library comprises a cell barcode on the 3' end of the transcripts, at least a subset of the library from the 3' barcoded single cell RNA library contains a transcript of interest at least 1 kb away from the 3' end of the transcript. The 5' side of transcripts are typically underrepresented in standard 3' barcoded libraries.

In a preferred embodiment, each nucleic acid sequence is flanked by switching mechanism at 5' end of RNA template (SMART) sequences at the 5' end and 3' end, that is, in this embodiment, an exemplary nucleic acid in the library would be 5' SMART-genetic region of interest-UMI-Cell BC-SMART 3'.

Multiple technologies have been described that massively parallelize the generation of single cell RNA seq libraries that can be used in the present disclosure. As used herein, RNA-seq methods refer to high-throughput single-cell RNA-sequencing protocols. RNA-seq includes, but is not limited to, Drop-seq, Seq-Well, InDrop and 1Cell Bio. RNA-seq methods also include, but are not limited to, smart-seq2, TruSeq, CEL-Seq, STRT, ChIRP-Seq, GRO-Seq, CLIP-Seq, Quartz-Seq, or any other similar method known in the art (see, e.g., "Sequencing Methods Review" Illumina® Technology, Sequencing Methods Review available at illumina.com.

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In some embodiments, Drop-sequence methods or Drop-seq are contemplated for the present invention and can be used. Cells come in different types, sub-types and activity states, which are classify based on their shape, location, function, or molecular profiles, such as the set of RNAs that they express. RNA profiling is in principle particularly informative, as cells express thousands of different RNAs. Approaches that measure for example the level of every type of RNA have until recently been applied to "homogenized" samples—in which the contents of all the cells are mixed together. Methods to profile the RNA content of tens and hundreds of thousands of individual human cells have been recently developed, including from brain tissues, quickly and inexpensively. To do so, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. See, e.g., methods of Macosko et al., 2015, Cell 161, 1202-1214 and Klein et al., 2015, Cell 161, 1187-1201 are contemplated for the present invention.

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, “Highly Parallel Genome-wide Expression Profiling of Individual Cells Using Nanoliter Droplets” Cell 161, 1202-1214; International patent application number PCT/US2015/049178, published as WO2016/040476 on Mar. 17, 2016; Klein et al., 2015, “Droplet Barcoding for Single-Cell Transcriptomics Applied to Embryonic Stem Cells” Cell 161, 1187-1201; International patent application number PCT/US2016/027734, published as WO2016168584A1 on Oct. 20, 2016; Zheng, et al., 2016, “Haplotyping germline and cancer genomes with high-throughput linked-read sequencing” Nature Biotechnology 34, 303-311; Zheng, et al., 2017, “Massively parallel digital transcriptional profiling of single cells” Nat. Commun. 8, 14049 doi: 10.1038/ncomms14049; International patent publication number WO2014210353A2; Zilionis, et al., 2017, “Single-cell barcoding and sequencing using droplet microfluidics” Nat Protoc. January; 12(1):44-73; Cao et al., 2017, “Comprehensive single cell transcriptional profiling of a multicellular organism by combinatorial indexing” bioRxiv preprint first posted online Feb. 2, 2017, doi: dx.doi.org/10.1101/104844; Rosenberg et al., 2017, “Scaling single cell transcriptomics through split pool barcoding” bioRxiv preprint first posted online Feb. 2, 2017, doi: dx.doi.org/10.1101/105163; Vitak, et al., “Sequencing thousands of single-cell genomes with combinatorial indexing” Nature Methods, 14(3):302-308, 2017; Cao, et al., Comprehensive single-cell transcriptional profiling of a multicellular organism. Science, 357(6352):661-667, 2017; and Gierahn et al., “Seq-Well: portable, low-cost RNA sequencing of single cells at high throughput” Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, “In vivo interrogation of gene function in the mammalian brain using CRISPR-Cas9” Nature Biotechnology Vol. 33, pp. 102-106; Habib et al., 2016, “Div-Seq: Single-nucleus RNA-Seq reveals dynamics of rare adult newborn neurons” Science, Vol. 353, Issue 6302, pp. 925-928; Habib et al., 2017, “Massively parallel single-nucleus RNA-seq with DroNc-seq” Nat Methods. 2017 October; 14(10):955-958; and International patent application number PCT/US2016/059239, published as WO2017164936 on Sep. 28, 2017, which are herein incorporated by reference in their entirety.

Microfluidics involves micro-scale devices that handle small volumes of fluids. Because microfluidics may accurately and reproducibly control and dispense small fluid volumes, in particular volumes less than 1 μl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets or microwells. The ability to conduct reactions in microdroplets depends on being able to merge different sample fluids and different microdroplets. See, e.g., US Patent Publication No. 20120219947. See also international patent application serial no. PCT/US2014/058637 for disclosure regarding a microfluidic laboratory on a chip.

Droplet/microwell microfluidics offers significant advantages for performing high-throughput screens and sensitive assays. Droplets allow sample volumes to be significantly reduced, leading to concomitant reductions in cost. Manipulation and measurement at kilohertz speeds enable up to 108 discrete biological entities (including, but not limited to, individual cells or organelles) to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

Drop-Sequence methods and apparatus provides a high-throughput single-cell RNA-Seq and/or targeted nucleic acid profiling (for example, sequencing, quantitative reverse transcription polymerase chain reaction, and the like) where the RNAs from different cells are tagged individually, allowing a single library to be created while retaining the cell identity of each read. A combination of molecular barcoding and emulsion-based microfluidics to isolate, lyse, barcode, and prepare nucleic acids from individual cells in high-throughput is used. Microfluidic devices (for example, fabricated in polydimethylsiloxane), sub-nanoliter reverse emulsion droplets. These droplets are used to co-encapsulate nucleic acids with a barcoded capture bead. Each bead, for example, is uniquely barcoded so that each drop and its contents are distinguishable. The nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells.

InDrop™, also known as in-drop seq, involves a high-throughput droplet-microfluidic approach for barcoding the RNA from thousands of individual cells for subsequent analysis by next-generation sequencing (see, e.g., Klein et al., Cell 161(5), pp 1187-1201, 21 May 2015). Specifically, in in-drop seq, one may use a high diversity library of barcoded primers to uniquely tag all DNA that originated from the same single cell. Alternatively, one may perform all steps in drop.

Well-based biological analysis or Seq-Well is also contemplated for the present invention. The well-based biological analysis platform, also referred to as Seq-well, facilitates the creation of barcoded single-cell sequencing libraries from thousands of single cells using a device that contains 100,000 40-micron wells. Importantly, single beads can be loaded into each microwell with a low frequency of duplicates due to size exclusion (average bead diameter 35 μm). By using a microwell array, loading efficiency is greatly increased compared to drop-seq, which requires poison loading of beads to avoid duplication at the expense of increased cell input requirements. Seq-well, however, is capable of capturing nearly 100% of cells applied to the surface of the device.

Seq-well is a methodology which allows attachment of a porous membrane to a container in conditions which are benign to living cells. Combined with arrays of picoliter-scale volume containers made, for example, in PDMS, the platform provides the creation of hundreds of thousands of isolated dialysis chambers which can be used for many different applications. The platform also provides single cell lysis procedures for single cell RNA-seq, whole genome amplification or proteome capture; highly multiplexed single cell nucleic acid preparation (~100× increase over current approaches); highly parallel growth of clonal bacterial populations thus providing synthetic biology applications as well as basic recombinant protein expression; selection of bacterial that have increased secretion of a recombinant product possible product could also be small molecule metabolite which could have considerable utility in chemical industry and biofuels; retention of cells during multiple microengraving events; long term capture of secreted products from single cells; and screening of cellular events. Principles of the present methodology allow for addition and subtraction of materials from the containers, which has not previously been available on the present scale in other modalities.

Seq-Well also enables stable attachment (through multiple established chemistries) of porous membranes to PDMS nanowell devices in conditions that do not affect cells. Based on requirements for downstream assays, amines are functionalized to the PDMS device and oxidized to the membrane with plasma. With regard to general cell culture uses, the PDMS is amine functionalized by air plasma treatment followed by submersion in an aqueous solution of poly (lysine) followed by baking at 80° C. For processes that require robust denaturing conditions, the amine must be covalently linked to the surface. This is accomplished by treating the PDMS with air plasma, followed by submersion in an ethanol solution of amine-silane, followed by baking at 80° C., followed by submersion in 0.2% phenylene diisothiocyanate (PDITC) DMF/pyridine solution, followed by baking, followed by submersion in chitosan or poly (lysine) solution. For functionalization of the membrane for protein capture, membrane can be amine-silanized using vapor deposition and then treated in solution with NHS-biotin or NHS-maleimide to turn the amine groups into the crosslinking species.

After functionalization, the device is loaded with cells (bacterial, mammalian or yeast) in compatible buffers. The cell-laden device is then brought in contact with the functionalized membrane using a clamping device. A plain glass slide is placed on top of the membrane in the clamp to provide force for bringing the two surfaces together. After an hour incubation, as one hour is a preferred time span, the clamp is opened and the glass slide is removed. The device can then be submerged in any aqueous buffer for days without the membrane detaching, enabling repetitive measurements of the cells without any cell loss. The covalently-linked membrane is stable in many harsh buffers including guanidine hydrochloride which can be used to robustly lyse cells. If the pore size of the membrane is small, the products from the lysed cells will be retained in each well. The lysing buffer can be washed out and replaced with a different buffer which allows binding of biomolecules to probes preloaded in the wells. The membrane can then be removed, enabling addition of enzymes to reverse transcribe or amplify nucleic acids captured in the wells after lysis. Importantly, the chemistry enables removal of one membrane and replacement with a membrane with a different pore size to enable integration of multiple activities on the same array.

As discussed, while the platform has been optimized for the generation of individually barcoded single-cell sequencing libraries following confinement of cells and mRNA capture beads (Macosko, et al. Cell. 2015 May 21; 161(5): 1202-1214), it is capable of multiple levels of data acquisition. The platform is compatible with other assays and measurements performed with the same array. For example, profiling of human antibody responses by integrated single-cell analysis is discussed with regard to measuring levels of cell surface proteins (Ogunniyi, A. O., B. A. Thomas, T. J. Politano, N. Varadarajan, E. Landais, P. Poignard, B. D. Walker, D. S. Kwon, and J. C. Love, "Profiling Human Antibody Responses by Integrated Single-Cell Analysis" Vaccine, 32(24), 2866-2873.) The authors demonstrate a complete characterization of the antigen-specific B cells induced during infections or following vaccination, which enables and informs one of skill in the art how interventions shape protective humoral responses. Specifically, this disclosure combines single-cell profiling with on-chip image cytometry, microengraving, and single-cell RT-PCR.

The invention provides a method for creating a single-cell sequencing library comprising: merging one uniquely barcoded mRNA capture microbead with a single-cell in an emulsion droplet having a diameter of 75-125 μm; lysing the cell to make its RNA accessible for capturing by hybridization onto RNA capture microbead; performing a reverse transcription either inside or outside the emulsion droplet to convert the cell's mRNA to a first strand cDNA that is covalently linked to the mRNA capture microbead; pooling the cDNA-attached microbeads from all cells; and preparing and sequencing a single composite RNA-Seq library.

The invention provides a method for preparing uniquely barcoded mRNA capture microbeads, which has a unique barcode and diameter suitable for microfluidic devices comprising: 1) performing reverse phosphoramidite synthesis on the surface of the bead in a pool-and-split fashion, such that in each cycle of synthesis the beads are split into four reactions with one of the four canonical nucleotides (T, C, G, or A) or unique oligonucleotides of length two or more bases; 2) repeating this process a large number of times, at least two, and optimally more than twelve, such that, in the latter, there are more than 16 million unique barcodes on the surface of each bead in the pool. (See http://www.ncbi.nlm.nih.gov/pmc/articles/PMC206447)

In another embodiment, the invention encompasses making beads specific to the panel of desired mutations or mutations plus mRNA and a capture of both. In one embodiment, one or more mutation hot spots may be near the 3' end.

Generally, the invention provides a method for preparing a large number of beads, particles, microbeads, nanoparticles, or the like with unique nucleic acid barcodes comprising performing polynucleotide synthesis on the surface of the beads in a pool-and-split fashion such that in each cycle of synthesis the beads are split into subsets that are subjected to different chemical reactions; and then repeating this split-pool process in two or more cycles, to produce a combinatorially large number of distinct nucleic acid barcodes. Invention further provides performing a polynucleotide synthesis wherein the synthesis may be any type of synthesis known to one of skill in the art for "building" polynucleotide sequences in a step-wise fashion. Examples include, but are not limited to, reverse direction synthesis with phosphoramidite chemistry or forward direction synthesis with phosphoramidite chemistry. Previous and well-known methods synthesize the oligonucleotides separately then "glue" the entire desired sequence onto the bead enzymatically. Applicants present a complexed bead and a novel process for producing these beads where nucleotides are chemically built onto the bead material in a high-throughput manner. Moreover, Applicants generally describe delivering a "packet" of beads which allows one to deliver millions of sequences into separate compartments and then screen all at once.

The invention further provides an apparatus for creating a single-cell sequencing library via a microfluidic system, comprising: an oil-surfactant inlet comprising a filter and a carrier fluid channel, wherein said carrier fluid channel further comprises a resistor; an inlet for an analyte comprising a filter and a carrier fluid channel, wherein said carrier fluid channel further comprises a resistor; an inlet for mRNA capture microbeads and lysis reagent comprising a filter and a carrier fluid channel, wherein said carrier fluid channel further comprises a resistor; said carrier fluid channels have a carrier fluid flowing therein at an adjustable or predetermined flow rate; wherein each said carrier fluid channels merge at a junction; and said junction being connected to a mixer, which contains an outlet for drops.

A mixture comprising a plurality of microbeads adorned with combinations of the following elements: bead-specific oligonucleotide barcodes created by the discussed methods; additional oligonucleotide barcode sequences which vary among the oligonucleotides on an individual bead and can therefore be used to differentiate or help identify those individual oligonucleotide molecules; additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), or random sequences (for priming throughout the transcriptome or genome). In an embodiment, the individual oligonucleotide molecules on the surface of any individual microbead contain all three of these elements, and the third element includes both oligo-dT and a primer sequence.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'-disulfonic acid; acridine and derivatives: acridine, acridine isothiocyanate; 5-(2'-aminoethyl)aminonaphthalene-1-sulfonic acid (EDANS); 4-amino-N-[3-vinyl sulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methyl coumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

The invention discussed herein enables high throughput and high-resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets are carried in a flowing oil phase and stabilized by a surfactant. In one embodiment single cells or single organelles or single molecules (proteins, RNA, DNA) are encapsulated into uniform droplets from an aqueous solution/dispersion. In a related embodiment, multiple cells or multiple molecules may take the place of single cells or single molecules. The aqueous droplets of volume ranging from 1 pL to 10 nL work as individual reactors. Disclosed embodiments provide $10^4$ to $10^5$ single cells in droplets which can be processed and analyzed in a single run.

To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination.

Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another embodiment, the expansion and/or contraction of the liquid reservoir may be combined with other flow-controlling devices and methods, e.g., as discussed herein. Non-limiting examples of devices able to cause the expansion and/or contraction of a liquid reservoir include pistons.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module discussed herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element may include, but is not limited to, hybridomas, B-cells, primary cells, cultured cell lines, cancer cells, stem cells, cells obtained from tissue, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as discussed in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A bead-based library element may contain one or more beads, of a given type and may also contain other reagents, such as antibodies, enzymes or other proteins. In the case where all library elements contain different types of beads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids.

Often it is desirable to have exactly one cell per droplet with only a few droplets containing more than one cell when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, small molecules, DNA, primers, antibodies. Smaller droplets may be in the order of femtoliter (fL) volume drops, which are especially contemplated with the droplet dispensors. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the emulsion libraries of the present invention may be contained within an immiscible oil which may comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays discussed herein. Fluids (e.g., aqueous fluids, immiscible oils, etc.) and other surfactants that may be utilized in the droplet libraries of the present invention are discussed in greater detail herein.

The present invention provides an emulsion library which may comprise a plurality of aqueous droplets within an immiscible oil (e.g., fluorocarbon oil) which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library.

For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In one example, the cells may comprise cancer cells of a tissue biopsy, and each cell type is encapsulated to be screened for genomic data or against different drug therapies. Another example is that $10^{11}$ or $10^{15}$ different type of bacteria; each having a different plasmid spliced therein, are encapsulated. One example is a bacterial library where each library element grows into a clonal population that secretes a variant on an enzyme.

In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 μm droplets were made at 10 kHz per second. Formation of these libraries rely on limiting dilutions.

Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Raindance Technologies Inc. The content of each of which is incorporated by reference herein in its entirety.

In certain embodiments, the carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioninformatically record information can be found at US Provisional Patent Application entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at US Provisional Patent Application entitled "Systems and Methods for Droplet Tagging" filed Sep. 21, 2012.

Applications of the disclosed device may include use for the dynamic generation of molecular barcodes (e.g., DNA oligonucleotides, fluorophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner. Disclosed embodiments provide a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Hence, the invention proves advantageous over prior art systems by being able to dynamically track individual cells and droplet treatments/combinations during life cycle experiments. Additional advantages of the disclosed invention provide an ability to create a library of emulsion droplets on demand with the further capability of manipulating the droplets through the disclosed process(es). Disclosed embodiments may, thereby, provide dynamic tracking of the droplets and create a history of droplet deployment and application in a single cell based environment.

Droplet generation and deployment is produced via a dynamic indexing strategy and in a controlled fashion in accordance with disclosed embodiments of the present invention. Disclosed embodiments of the microfluidic device discussed herein provides the capability of microdroplets that be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays.

The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment the adapters are compatible with the methods described herein.

In certain embodiments, tagmentation is used to introduce adaptor sequences to genomic DNA in regions of accessible chromatin (e.g., between individual nucleosomes) (see, e.g., US20160208323A1; US20160060691A1; WO2017156336A1; and Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. *Science.* 2015 May 22; 348(6237):910-4. doi: 10.1126/science.aab1601. Epub 2015 May 7). In certain embodiments, tagmentation is applied to bulk samples or to single cells in discrete volumes.

The 3' barcoded libraries can be used in the methods as described herein to provide enriched libraries containing transcripts of interest that are not as abundant or accessible in the original single cell RNAseq libraries. Other Seq-Well embodiments that may be used with the current invention are described in PCT Application entitled "Functionalized Solid Support" filed on Oct. 23, 2018, PCT/US2018/057173.

Methods of Distinguishing Cells by Genotype

In an embodiment, the present invention relates to a method of distinguishing cells by genotype by enriching libraries for transcripts of interest which may comprise a PCR-based method, for example: constructing a library comprising a plurality of nucleic acids wherein each nucleic acid may comprise a gene, a unique molecular identifier (UMI) and a cell barcode (cell BC) flanked by switching mechanism at 5' end of RNA template (SMART) sequences at the 5' and 3' end, amplifying each nucleic acid in the library to create a first PCR product using a tagged 5' primer which may comprise a binding site for a second PCR product and a sequence complementary to a specific gene of interest and a 3' SMART primer complementary to the SMART sequence at the 3' end of the nucleic acid thereby generating a first PCR product, selective enrichment of the first PCR product by binding to the tag introduced by the 5' primer or a targeted 3' capture with a bifunctional bead or targeted capture bead, amplifying the tag-enriched first PCR product with a 5' primer which may comprise the binding site for the second PCR product and a 3' SMART primer complementary to the SMART sequence at the 3' end of the nucleic acid thereby generating the second PCR product, size-selecting a final product comprising the specific gene of interest and determining the genotype of the cell by identifying the UMI and cell BC. Specific sequences can be used to uniquely enable Next Generation Sequencing (NGS) or third-generation sequencing can also be performed by using specific sequences to uniquely enable NGS or third-generation sequencing. Advantageously, the methods allow for determination of expressed DNA sequences, such as mutations, translocations, insertions/deletions (indels), etc. Methods for distinguishing cells by genotype by enriching sequencing libraries for transcripts are known in the art and include, for example, methods disclosed in WO 2019/08406 and W/2019/4055 which are incorporated by reference.

RNA-Seq

As described above, in some embodiments, gene expression can be determined using an RNA-seq-based method. In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-6'73, 2012).

In certain embodiments, the invention involves plate based single cell RNA sequencing (see, e.g., Picelli, S. et al., 2014, "Full-length RNA-seq from single cells using Smart-seq2" Nature protocols 9, 171-181, doi: 10.1038/nprot.2014.006).

In certain embodiments, the invention involves high-throughput single-cell RNA-seq. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

In certain embodiments, the invention involves the Assay for Transposase Accessible Chromatin using sequencing (ATAC-seq) as described. (see, e.g., Buenrostro, et al., Transposition of native chromatin for fast and sensitive epigenomic profiling of open chromatin, DNA-binding proteins and nucleosome position. Nature methods 2013; 10 (12): 1213-1218; Buenrostro et al., Single-cell chromatin accessibility reveals principles of regulatory variation. Nature 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237): 910-4. doi: 10.1126/science.aab1601. Epub 2015 May 7; US20160208323A1; US20160060691A1; and WO2017156336A1).

Polymorphic Gene Typing and Somatic Change Detection Using Sequencing Data

In some embodiments, the DNA-damage response signature can be determined using a method of polymorphic gene typing and somatic change detection that uses sequencing data. In some embodiments such a method can include generating an alignment of reads from a sequencing data set to a gene reference set comprising allele variants of the polymorphic gene, determining a first posterior probability or a posterior probability derived score for each allele variant in the alignment, identifying the allele variant with a maximum first posterior probability or posterior probability derived score as a first allele variant, identifying one or more overlapping reads that aligned with the first allele variant and one or more other allele variants, determining a second posterior probability or posterior probability derived score for the one or more other allele variants using a weighting factor, and identifying a second allele variant by selecting the allele variant with a maximum second posterior probability or posterior probability derived score, the first and second allele variant defining the gene type for the polymorphic gene. In some embodiments, the such a method can include comprises determining a polymorphic gene type based on a first sequencing data set from a normal tissue sample as described above, extracting from a second sequencing data set obtained from a diseased tissue sample reads mapping to the polymorphic gene, aligning the extracted reads with sequences representing the determined polymorphic gene type to generate a sequence alignment, and detecting mutations in the diseased tissue sample based at least in part on the sequence alignment.

Some embodiments herein can provide computer-implemented techniques for gene typing a polymorphic gene using sequencing data. In certain example embodiments the sequencing data is whole exome sequencing data (WES), RNA-Seq data, whole genome data, targeted exome sequencing data, or any form of sequencing data that covers the polymorphic loci at either the exome, genome, or RNA levels. For ease of reference, the example embodiments will be described below with reference to WES data, but other sequencing data as described above may be used interchangeably.

In some embodiments, process starts by extracting reads from a set of whole exome sequencing (WES) data that map to the polymorphic gene of interest ("target polymorphic gene"). More than one polymorphic gene may be analyzed at the same time. For example, multiple genes at the same locus, such as p53, p21, or any of those set forth in Tables 13, 14, 15, and 16 and FIGS. 3A-3B, 6G, 7A-7B, 7E, and/or 9E, and/or Supplementary Data 1 and 3 of Enache, O. M., Rendo, V., Abdusamad, M. et al. Cas9 activates the p53 pathway and selects for p53-inactivating mutations. Nat Genet 52, 662-668 (2020). https://doi.org/10.1038/s41588-020-0623-4, which is incorporated by reference herein as if expressed in its entirety and also Appendix A to U.S. Provisional Ser. No. 62/909,131). The extracted reads are then aligned to a gene reference sequence set comprising known allele variants of the target polymorphic gene. The generated sequence alignment and other information, such as an insert size distribution for the aligned reads, alignment quality scores and population frequencies, are used to calculate a first posterior probability or posterior probability derived score for each allele variant. The allele variant that maximizes the first posterior probability or posterior probability derived score is selected as the first allele variant of target polymorphic gene type. A second posterior probability or posterior probability derived score is calculated for each allele by applying a heuristic weighting strategy to the score contribution of each of its aligned reads from the first stage, taking into consideration whether a read under consideration also mapped the first inferred allele variant. The allele variant that maximizes the second posterior probability or posterior probability derived score is selected as the second allele variant. The first and second allele variants define the polymorphic gene type.

In another embodiment, embodiments herein provide computer-implemented techniques for detecting mutations in polymorphic genes by comparing WES data obtained from normal and diseased tissue. A WES data set is obtained from normal germline cells (e.g. a wild-type or parental cell) of the subject or cell line to be tested and/or modified using a CRISPR-Cas system or modified to express one or more components of a CRISPR-Cas system and a polymorphic gene type is determined according the polymorphic gene typing method described above (POLYSOLVER). A second WES data set is obtained from cells that have been modified using a CRISPR-Cas system and/or modified to express one or more components from a CRISPR-Cas system, from the subject or cell line to be tested. Reads from the modified cells WES data set mapping to the target polymorphic gene are then extracted. The extracted reads are then aligned to sequences representing the determined polymorphic gene type. The resulting alignment is then used to detect mutations in the sequences obtained from the CRISPR-Cas modified cells or CRISPR-Cas system component expressing cells.

p53 Inactivating Mutations

In some embodiments, the DNA-damage response signature can include one or more p53 inactivating mutations. The p53 inactivating mutations can be any one or more of those provided in Supplementary Data 3 of Enache, O. M., Rendo, V., Abdusamad, M. et al. Cas9 activates the p53 pathway and selects for p53-inactivating mutations. Nat Genet 52, 662-668 (2020). https://doi.org/10.1038/s41588-020-0623-4, which is incorporated by reference herein as if expressed in its entirety.

CRISPR-Cas Systems and Complexes

In general, a CRISPR-Cas or CRISPR system as used herein and in other documents, such as International Patent Publication No. WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

CRISPR-Cas systems can generally fall into two classes based on their architectures of their effector molecules, which are each further subdivided by type and subtype. The two classes are Class 1 and Class 2. Class 1 CRISPR-Cas systems have effector modules composed of multiple Cas proteins, some of which form crRNA-binding complexes, while Class 2 CRISPR-Cas systems include a single, multi-domain crRNA-binding protein.

In some embodiments, the CRISPR-Cas system that can be used to modify a polynucleotide of the present invention described herein can be a Class 1 CRISPR-Cas system. In some embodiments, the CRISPR-Cas system that can be used to modify a polynucleotide of the present invention described herein can be a Class 2 CRISPR-Cas system.

Class 1 CRISPR-Cas Systems

In some embodiments, the CRISPR-Cas system that can be used to modify a polynucleotide of the present invention described herein can be a Class 1 CRISPR-Cas system. Class 1 CRISPR-Cas systems are divided into types I, II, and IV. Makarova et al. 2020. Nat. Rev. 18: 67-83., particularly as described in FIG. 1. Type I CRISPR-Cas systems are divided into 9 subtypes (I-A, I-B, I-C, I-D, I-E, I-F1, I-F2, I-F3, and IG). Makarova et al., 2020. Class 1, Type I CRISPR-Cas systems can contain a Cas3 protein that can have helicase activity. Type III CRISPR-Cas systems are divided into 6 subtypes (III-A, III-B, III-E, and III-F). Type III CRISPR-Cas systems can contain a Cas10 that can include an RNA recognition motif called Palm and a cyclase domain that can cleave polynucleotides. Makarova et al., 2020. Type IV CRISPR-Cas systems are divided into 3 subtypes. (IV-A, IV-B, and IV-C). Makarova et al., 2020. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas.1709035114; see also, Makarova et al. 2018. The CRISPR Journal, v. 1, n5, FIG. 5.

The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g., Cas1, Cas2, RNA nuclease), and/or one or more accessory proteins (e.g., Cas 4, DNA nuclease), CRISPR associated Rossman fold (CARF) domain containing proteins, and/or RNA transcriptase.

The backbone of the Class 1 CRISPR-Cas system effector complexes can be formed by RNA recognition motif domain-containing protein(s) of the repeat-associated mysterious proteins (RAMPs) family subunits (e.g., Cas 5, Cas6, and/or Cas7). RAMP proteins are characterized by having one or more RNA recognition motif domains. In some embodiments, multiple copies of RAMPs can be present. In some embodiments, the Class I CRISPR-Cas system can include 1, 2, 3, 4, 5, 6, 7, 8, 9, 10, 11, 12 or more Cas5, Cas6, and/or Cas 7 proteins. In some embodiments, the Cas6 protein is an RNAse, which can be responsible for pre-crRNA processing. When present in a Class 1 CRISPR-Cas system, Cas6 can be optionally physically associated with the effector complex.

Class 1 CRISPR-Cas system effector complexes can, in some embodiments, also include a large subunit. The large subunit can be composed of or include a Cas8 and/or Cas10 protein. See, e.g., FIGS. 1 and 2. Koonin E V, Makarova K S. 2019. Phil. Trans. R. Soc. B 374: 20180087, DOI: 10.1098/rstb.2018.0087 and Makarova et al. 2020.

Class 1 CRISPR-Cas system effector complexes can, in some embodiments, include a small subunit (for example, Cash 1). See, e.g., FIGS. 1 and 2. Koonin E V, Makarova K S. 2019 Origins and Evolution of CRISPR-Cas systems. Phil. Trans. R. Soc. B 374: 20180087, DOI: 10.1098/rstb.2018.0087.

In some embodiments, the Class 1 CRISPR-Cas system can be a Type I CRISPR-Cas system. In some embodiments, the Type I CRISPR-Cas system can be a subtype I-A CRISPR-Cas system. In some embodiments, the Type I CRISPR-Cas system can be a subtype I-B CRISPR-Cas system. In some embodiments, the Type I CRISPR-Cas system can be a subtype I-C CRISPR-Cas system. In some embodiments, the Type I CRISPR-Cas system can be a subtype I-D CRISPR-Cas system. In some embodiments, the Type I CRISPR-Cas system can be a subtype I-E CRISPR-Cas system. In some embodiments, the Type I CRISPR-Cas system can be a subtype I-F1 CRISPR-Cas system. In some embodiments, the Type I CRISPR-Cas system can be a subtype I-F2 CRISPR-Cas system. In some embodiments, the Type I CRISPR-Cas system can be a subtype I-F3 CRISPR-Cas system. In some embodiments, the Type I CRISPR-Cas system can be a subtype I-G CRISPR-Cas system. In some embodiments, the Type I CRISPR-Cas system can be a CRISPR Cas variant, such as a Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems as previously described.

In some embodiments, the Class 1 CRISPR-Cas system can be a Type III CRISPR-Cas system. In some embodiments, the Type III CRISPR-Cas system can be a subtype III-A CRISPR-Cas system. In some embodiments, the Type III CRISPR-Cas system can be a subtype III-B CRISPR-Cas system. In some embodiments, the Type III CRISPR-Cas system can be a subtype III-C CRISPR-Cas system. In some embodiments, the Type III CRISPR-Cas system can be a subtype III-D CRISPR-Cas system. In some embodiments, the Type III CRISPR-Cas system can be a subtype III-E CRISPR-Cas system. In some embodiments, the Type III CRISPR-Cas system can be a subtype III-F CRISPR-Cas system.

In some embodiments, the Class 1 CRISPR-Cas system can be a Type IV CRISPR-Cas-system. In some embodiments, the Type IV CRISPR-Cas system can be a subtype IV-A CRISPR-Cas system. In some embodiments, the Type IV CRISPR-Cas system can be a subtype IV-B CRISPR-Cas system. In some embodiments, the Type IV CRISPR-Cas system can be a subtype IV-C CRISPR-Cas system.

The effector complex of a Class 1 CRISPR-Cas system can, in some embodiments, include a Cas3 protein that is optionally fused to a Cas2 protein, a Cas4, a Cas5, a Cash, a Cas7, a Cas8, a Cas10, a Cas11, or a combination thereof. In some embodiments, the effector complex of a Class 1 CRISPR-Cas system can have multiple copies, such as 1, 2, 3, 4, 5, 6, 7, 8, 9, 10, 11, 12, 13, or 14, of any one or more Cas proteins.

Class 2 CRISPR-Cas Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1(V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), CasY(Cas12d), CasX (Cas12e), Cas14, and/or CasΦ.

In some embodiments the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d.

CRISPR-Cas system activity, such as CRISPR-Cas system design may involve target disruption, such as target mutation, such as leading to gene knockout. CRISPR-Cas system activity, such as CRISPR-Cas system design may involve replacement of particular target sites, such as leading to target correction. CRISPR-Cas system design may involve removal of particular target sites, such as leading to target deletion. CRISPR-Cas system activity can involve modulation of target site functionality, such as target site activity or accessibility, leading for instance to (transcriptional and/or epigenetic) gene or genomic region activation or gene or genomic region silencing. The skilled person will understand that modulation of target site functionality may involve CRISPR effector mutation (such as for instance generation of a catalytically inactive CRISPR effector) and/or functionalization (such as for instance fusion of the CRISPR effector with a heterologous functional domain, such as a transcriptional activator or repressor), as described herein elsewhere.

In some embodiments, the CRISPR-Cas system may comprise a Cas and a non-Cas protein. In some embodiments, the Cas protein is a Cas9 protein. Example Cas9 proteins are described elsewhere herein. In certain example embodiments, the non-Cas protein is a transposase. In certain example embodiments, the transposase is a single stranded DNA transposase. In certain example embodiments, the single stranded DNA transposase is TnpA. In certain example embodiments, the CRISPR-CAs csystem can include a Cas9 associated transposase. In certain example embodiments, the transposase is a TnpA, or a functional fragment thereof. The Cas9 associated transposase systems may comprise a local architecture of Cas9-TnpA, Cas1-Cas2-CRISPR array. The Cas9 may or may not have a tracrRNA associated with it. The Cas9-associated systems may be coded on the same strand or b part of a larger operon. In certain embodiments, the Cas9 may confer target specificity, allowing the TnpA to move a polynucleotide cargo from other target sites in a sequence specific matter. In certain example embodiments, the Cas9-associated transposase are derived from *Flavobacterium granuli* strain DSM-19729, *Salinivirga cyanobacteriivorans* strain L21-Spi-D4, *Flavobacterium aciduliphilum* strain DSM 25663, *Flavobacterium glacii* strain DSM 19728, *Niabella soli* DSM 19437, *Salnivirga cyanobactriivorans* strain L21-Spi-D4, *Alkaliflexus imshenetskii* DSM 150055 strain Z-7010, or *Alkalitala saponilacus*.

Cas Effector Molecules

The CRISPR-Cas system described herein can include one or more Cas effector proteins. In some embodiments, the Cas protein is Class I CRISPR-Cas system Cas polypeptide. In some embodiments, the Cas protein is a Class II CRISPR-Cas system Cas polypeptide. In some embodiments, the Cas polypeptide is a Type I Cas polypeptide. In some embodiments, the Cas polypeptide is a Type II Cas polypeptide. In some embodiments, the Cas polypeptide is a Type III Cas polypeptide. In some embodiments, the Cas polypeptide is a Type IV Cas polypeptide. In some embodiments, the Cas polypeptide is a Type V Cas polypeptide. In some embodiments, the Cas polypeptides is a Type VI Cas polypeptide. In some embodiments, the Cas polypeptide is a Type VII Cas polypeptide. Non-limiting examples of Cas proteins include Cas1, Cas1B, Cas2, Cas3, Cas4, Cas5, Cash, Cas7, Cas8, Cas9 (also known as Csn1 and Csx12), Cas10, Cas 12, Cas 12a, Cas 13a, Cas 13b, Cas 13c, Cas 13d, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In some embodiments, the Cas13 is a Cas13-ADAR.

The Cas9 gene is found in several diverse bacterial genomes, typically in the same locus with cas1, cas2, and cas4 genes and a CRISPR cassette. Furthermore, the Cas9 protein contains a readily identifiable C-terminal region that is homologous to the transposon ORF-B and includes an active RuvC-like nuclease, an arginine-rich region.

In particular embodiments, Cas9 is from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium*, or *Corynebacte*.

In particular embodiments, the Cas9 is from an organism from a genus comprising *Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium* or *Acidaminococcus*.

In further particular embodiments, the Cas9 protein is from an organism selected from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii*. In particular embodiments, the effector protein is a Cas9 effector protein from an organism from *Streptococcus pyogenes, Staphylococcus aureus*, or *Streptococcus thermophilus* Cas9.

In an embodiment, the Cas9 is derived from a bacterial species selected from *Streptococcus pyogenes, Staphylococcus aureus*, or *Streptococcus thermophilus* Cas9.

In certain embodiments, the Cas9 is derived from a bacterial species selected from *Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens* and *Porphyromonas macacae*. In certain embodiments, the Cas9p is derived from a bacterial species selected from *Acidaminococcus* sp. BV3L6 or *Lachnospiraceae bacterium* MA2020. In certain embodiments, the effector protein is derived from a subspecies of *Francisella tularensis* 1, including but not limited to *Francisella tularensis* subsp. *Novicida*.

In certain example embodiments, the Cas protein (e.g. Cas9) is an ortholog or homolog of a Cas protein described elsewhere herein. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of Homologous proteins may but need not be structurally related, or are only partially structurally related. An "orthologue" of a protein as used herein is a protein of a different species which performs the same or a similar function as the protein it is an orthologue of Orthologous proteins may but need not be structurally related, or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22(4):359-66. doi: 10.1002/pro.2225.). See also Shmakov et al. (2015) for application in the field of CRISPR-Cas loci. Homologous proteins may but need not be structurally related, or are only partially structurally related.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 *Nuc. Acids Research* 12 p387). Examples of other software than may perform sequence comparisons include, but are not limited to, the BLAST package (see Ausubel et al., 1999 *Short Protocols in Molecular Biology*, $4^{th}$ Ed.—Chapter 18), FASTA (Altschul et al., 1990 *J Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60). However, for some applications, it is preferred to use the GCG Bestfit program. A new tool, called BLAST 2 Sequences is also available for comparing protein and nucleotide sequences (see *FEMS Microbiol Lett.* 1999 174 (2): 247-50; *FEMS Microbiol Lett.* 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS' (Hitachi Software), based on an algorithm, analogous to CLUSTAL (Higgins D G & Sharp P M (1988), *Gene* 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" *Comput. Appl. Biosci.* 9: 745-756) (Taylor W. R. (1986) "The classification of amino acid conservation" *J. Theor. Biol.* 119; 205-218). Conservative substitutions may be made, for example according to Table 1 which describes a generally accepted Venn diagram grouping of amino acids.

TABLE 1

Amino Acid Grouping

| | Set | Sub-set | |
|---|---|---|---|
| Hydrophobic | F W Y H K M I L V A G C (SEQ ID NO: 1) | Aromatic | F W Y H (SEQ ID NO: 2) |
| | | Aliphatic | I L V |
| Polar | W Y H K R E D C S T N Q (SEQ ID NO: 3) | Charged | H K R E D (SEQ ID NO: 4) |
| | | Positively charged | H K R |
| | | Negatively charged | E D |
| Small | V C A G S P T N D (SEQ ID NO: 5) | Tiny | A G S |

In embodiments, the Cas9 is an ortholog or homologue of Cas9 and can have a sequence homology or identity of at least 80%, more preferably at least 85%, even more preferably at least 90%, such as for instance at least 95% with Cas9. In further embodiments, the homologue or orthologue of Cas9 as referred to herein has a sequence identity of at least 80%, more preferably at least 85%, even more preferably at least 90%, such as for instance at least 95% with the wild type Cas9. Where the Cas9 has one or more mutations (mutated), the homologue or orthologue of said Cas9 as referred to herein has a sequence identity of at least 80%, more preferably at least 85%, even more preferably at least 90%, such as for instance at least 95% with the mutated Cas9.

In an embodiment, the Cas9 protein may be an ortholog of an organism of a genus which includes, but is not limited to *Streptococcus* sp. or *Staphylococcus* sp.; in particular embodiments, Cas9 protein may be an ortholog of an organism of a species which includes, but is not limited to *Streptococcus pyogenes, Staphylococcus aureus*, or *Streptococcus thermophilus* Cas9.In particular embodiments, the homologue or orthologue of Cas9p as referred to herein has a sequence homology or identity of at least 80%, more preferably at least 85%, even more preferably at least 90%, such as for instance at least 95% with one or more of the Cas9 sequences disclosed herein. In further embodiments, the homologue or orthologue of Cas9 as referred to herein has a sequence identity of at least 80%, more preferably at least 85%, even more preferably at least 90%, such as for instance at least 95% with the wild type SpCas9, SaCas9 or StCas9.

In particular embodiments, the Cas9 has a sequence homology or identity of at least 60%, more particularly at least 70%, such as at least 80%, more preferably at least 85%, even more preferably at least 90%, such as for instance at least 95% with SpCas9, SaCas9 or StCas9. In further embodiments, the Cas9 protein as referred to herein has a sequence identity of at least 60%, such as at least 70%, more particularly at least 80%, more preferably at least 85%, even more preferably at least 90%, such as for instance at least 95% with the wild type SpCas9, SaCas9 or StCas9. The skilled person will understand that this includes truncated forms of the Cas9 protein whereby the sequence identity is determined over the length of the truncated form.

Cas12 (or Cpf1) is a Class II, Type V CRISPR-Cas system. The reference or wild-type Cas12 can be a Cas12 from *Prevotella* or *Francisella*. Generally, Cas 12 is a smaller endonuclease than Cas9 and contains about 1300 amino acids, depending on variant.

The Cpf1 locus contains a mixed alpha-beta domain, a RuvC-1 followed by a helical region, a RuvC-II and a zinc finger-like domain. Zetsche et al. (2015) Cell 163(3):759-771. The Cpf1 protein has a RuvC-like nuclease domain that is similar to the RuvC domain of Cas9. Further, Cpf1 lacks an HNH domain, and the N-terminal does not have the alpha-helical recognition lobe of Cas9. Makarova et al. Nature Rev. Microbiol. (2015) "An updated evolutionary classification of CRISPR-Cas systems."

The Cpf1 does not require a tracrRNA and therefore only a crRNA is required. The Cpf1-crRNA complex cleaves target DNA and RNA by identification of a PAM (5'-YTN-3'), where Y is a pyrimidine and N is any nucleobase. This is in contrast to the G-rich PAM targeted by Cas9. After identification of PAM, Cpf1 can introduce a sticky-end-like double stranded break of about 4-5 nucleotides overhang.

As previously discussed, the Cas12 protein can be similar, but not identical, in structure and/or function to a wild-type or reference Cas12 protein. Suitable reference Cas12 reference or wild-type proteins are discussed herein.

In some embodiments, the reference or wild-type Cas12 is that as discussed in Zetsche et al. (2015), which reported characterization of Cpf1, a class 2 CRISPR nuclease from *Francisella* novicidin U112 having features distinct from Cas9. Cpf1 is a single RNA-guided endonuclease lacking tracrRNA, utilizes a T-rich protospacer-adjacent motif, and cleaves DNA via a staggered DNA double-stranded break.

In some embodiments, the reference or wild-type Cas12 is that as discussed Shmakov et al. (2015), which reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

In some embodiments, the Cas protein is a Cas12 is that as discussed Gao et al, "Engineered Cpf1 Enzymes with Altered PAM Specificities," bioRxiv 091611; doi: http://dx.doi.org/10.1101/091611 (Dec. 4, 2016).

Activatable Functional Domains

In addition to the domains previously discussed, the Cas effectors can have other optional domains. In some embodiments the Cas effectors can have one or more activatable functional domains. The activatable functional domains can include or form functional domains that are not necessarily base-editors as discussed elsewhere herein. This can provide alternative or additional functionalities and/or control to the CRISPR-Cas systems described herein other than or in addition to base editing. In embodiments, one or both of the activatable functional domains in a matched activatable functional domain pair can have activity selected from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, optical activity (e.g. emits a wavelength of light), molecular switch activity (e.g., light inducible), and combinations thereof.

In some embodiments, one or more of the activatable functional domains comprise a transcriptional activator, repressor, a recombinase, a transposase, a histone remodeler, a demethylase, a DNA methyltransferase, a cryptochrome, a light inducible/controllable domain, a chemically inducible/controllable domain, an optically active protein domain, an epigenetic modifying domain, or a combination thereof. The functional domain can include an activator, repressor or nuclease.

Examples of activators include P65, a tetramer of the herpes simplex activation domain VP16, termed VP64, optimized use of VP64 for activation through modification of both the sgRNA design and addition of additional helper molecules, MS2, P65 and HSF1 in the system called the synergistic activation mediator (SAM) (Konermann et al, "Genome-scale transcriptional activation by an engineered CRISPR-Cas9 complex," Nature 517(7536):583-8 (2015)); and examples of repressors include the KRAB (Kruppel-associated box) domain of Kox1 or SID domain (e.g. SID4X); and an example of a nuclease or nuclease domain suitable for a functional domain comprises Fok1.

Example of optically active molecules include, dyes (e.g. fluorescent dyes, infrared, near-IR, and UV dyes) chemiluminescent molecules, and quantum dots. Examples of optically active proteins include, but are not limited to, fluorescent proteins and bioluminescent proteins (e.g. luciferase). Fluorescent proteins can be engineered to fluoresce at a variety of wavelengths to yield proteins that fluoresce in different colors or in UV. Blue and UV fluorescent proteins include, but are not limited to, BFP, tagBFP, mTagBFB2, Azurite, EBFP2, mKalamal, Sirius, Sapphire, and T-Sapphire. Cyan fluorescent proteins include, but are not limited to, ECFP, Cerulean, SCFP3A, mTurquoise, mTurquoise2, monomeric Midoriishi-Cyan, TagCFP, and mTFP1. Green fluorescent proteins include, but are not limited to, GFP, EGFP, Emerald, Superfolder GFP, Monomeric Azami Green, TagGFP2, mUKG, mWasabi, Clover, mNeonGreen. Yellow fluorescent proteins include, but are not limited to, YFP, EYFP, Citrine, Venus, SYFP2, TagYFP. Orange fluorescent proteins include, but are not limited to, Monomeric Kusabira-Orange, mKOk, mKO2, mOrange, and mOrange2. Red fluorescent proteins include, but are not limited to RFP, mRaspberry, mCherry, mStrwberry, mTangerine, tdTomato, TagRFP, TagRFP-T, mApple, mRuby, and mRuby2. Far-Red proteins include, but are not limited to mPlum, HcRed-tandem, mKate2, mNeptune, and NirFP. Near-IR proteins include, but are not limited to, IFP1.4 and iRFP. Long Stokes Shift proteins include, but are not limited to mKeimaRed, LSS-mKate1, LSS-mKate2, and mBeRFP.

Examples of photoactivatable proteins include, but are not limited to, Kaede (green), Kaede (red), KikGR1 (green), KikGR1 (red), PS-CFP2, mEos2 (green), mEos3.2 (green), mEos3.2(red), PSmOrange.

Examples of photoswitchable proteins include, but are not limited to, Dronapa.

As used in this context herein "activatable functional domain" refers to a functional domain that can interact with another activatable functional domain to induce one or both of the activatable functional domains to activate, associate, interact, and/or fuse to form a new single active functional domain to elicit an enzymatic or other biological activity to affect a target with the attributed function. A pair of activatable functional domains that matched such that their association, interaction, or fusion elicits an enzymatic or other biological activity is referred to herein as a "matched pair of activatable functional domains". In embodiments, association, interaction, and/or fusion of matched pair of activatable functional domains occurs after allosteric interaction between two or more of the same or different Cas proteins. In embodiments, the enzymatic or other biological activity is elicited at the target after association, interaction, and/or fusion of matched pair of activatable functional domains. In embodiments, the enzymatic or other biological activity is elicited at the target after allosteric interaction of two or more of the same or different Cas proteins.

In some embodiments, a Cas protein described herein can change conformation upon allosteric interaction that results in exposure of an active site in a functional domain such that it can interact with a substrate. In some embodiments, a Cas protein described herein or domain thereof can change in spatial position within the system upon allosteric interaction that results in exposure or accessibility of an active site in a functional domain such to a substrate (e.g. a target substrate). In some embodiments, a functional domain of a Cas protein can be in an inactive state prior to allosteric interaction due to the presence of a protector molecule or group. In these embodiments, an inactive functional domain of a first Cas protein can interact with a functional domain on a second Cas protein upon or after direct or indirect allosteric interaction between the two Cas proteins such that the second functional domain alters the protection group on the first functional domain and thus activates the functional domain on the first Cas protein. In some embodiments, allosteric interaction two Cas proteins can bring an inactive functional domain on one Cas protein into effective proximity of a domain (e.g. another functional domain) on another protein in the CRISPR-Cas system (e.g. another Cas protein) such that the first functional domain is activated. Such examples include fluorescent proteins that can be activated (or in activated) based on resonant energy transfer. It will be appreciated that the system can be configured in some embodiments as a "switched-off" system, meaning that the functional group can be active until allosteric interaction between two Cas proteins. One example of this may be a system where the first functional domain is optically active until allosteric interaction between the two Cas proteins. It will be appreciated that the system can be configured as a "switched-on" system, meaning that the a functional group can be inactive until allosteric interaction between two Cas proteins occurs.

One or both of the activatable functional domains in a matched activatable functional domain pair can have activity selected from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, deaminase activity, optical activity (e.g. emits a wavelength of light), molecular switch activity (e.g., light inducible), base excision repair inhibiting activity and combinations thereof.

In some embodiments, one or more of the activatable functional domains comprise a transcriptional activator, repressor, a recombinase, a transposase, a histone remodeler, a demethylase, a DNA methyltransferase, a cryptochrome, a light inducible/controllable domain, a chemically inducible/controllable domain, an optically active protein domain, a deaminase, base excision repair inhibiting domain. an epigenetic modifying domain, or a combination thereof. The functional domain can include an activator, repressor or nuclease.

In general, the positioning of the one or more activatable functional domain on the Cas enzyme is one which allows for correct spatial orientation for the activatable functional domain to affect the target with the attributed functional effect upon or after allosteric interaction with another Cas protein described herein. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the CRISPR enzyme.

A split protein approach may be used with respect to the activatable functional domain. The so-called 'split protein' approach allows for the following. The protein (e.g. complete active functional domain) is split into two pieces and each of these are fused to one half of a dimer or each to a different Cas polypeptide or different Cas domain on a single polypeptide. Upon dimerization and/or other allosteric interaction between the two Cas proteins, the two parts of the split protein (or split functional domain) are brought together and the reconstituted protein and/or functional domain becomes functional. It will be appreciated that in the context of an AAV or other viral delivery system (described in greater detail herein), one Cas protein with one part of the split protein or split functional domain can be associated with one VP domain (e.g. VP2) and the second Cas protein with another part of the split protein or split functional domain can be on another or different VP (e.g. VP2) domain. The two VP domains (e.g. VP2 domains) may be in the same or different capsid. In other words, the split parts of the split protein or split functional domain can be on the same virus particle or on different virus particles. Likewise one Cas protein can be on the same virus particle or on different virus particles. The split protein or split functional domain can be derived or generated from or be based on any other functional protein or functional domain described herein.

In some embodiments, one or more functional domains may be associated with or tethered to one or more CRISPR-Cas enzymes and/or may be associated with or tethered to nucleic acid components (e.g. modified guides) via adaptor proteins. These can be used irrespective of the fact that the CRISPR enzyme may also be tethered to a virus outer protein or capsid or envelope, such as a VP2 domain or a capsid, via modified guides with aptamer RNA sequences that recognize correspond adaptor proteins.

Attachment of a functional domain or fusion protein can be via a linker, e.g., a flexible glycine-serine (GlyGlyGlySer) (SEQ ID NO: 6) or $(GGGS)_3$ (SEQ ID NO: 7) or a rigid alpha-helical linker such as (Ala(GluAlaAlaAlaLys)Ala) (SEQ ID NO: 8). Linkers such as $(GGGGS)_3$ (SEQ ID NO: 9) are preferably used herein to separate protein or peptide domains. $(GGGGS)_3$ (SEQ ID NO: 9) is preferable because it is a relatively long linker (15 amino acids). The glycine residues are the most flexible and the serine residues enhance the chance that the linker is on the outside of the protein. $(GGGGS)_6$ (SEQ ID NO: 10) $(GGGGS)_9$ (SEQ ID NO: 11) or $(GGGGS)_{12}$ (SEQ ID NO: 12) may preferably be used as alternatives. Other preferred alternatives are $(GGGGS)_1$(SEQ ID NO: 13), $(GGGGS)_2$ (SEQ ID NO: 14), $(GGGGS)_4$ (SEQ ID NO: 15), $(GGGGS)_5$ (SEQ ID NO: 16), $(GGGGS)_7$ (SEQ ID NO: 17), $(GGGGS)_8$ (SEQ ID NO: 18), $(GGGGS)_{10}$ (SEQ ID NO: 19), or (GGGGS)ii (SEQ ID NO: 20). Alternative linkers are available, but highly flexible linkers are thought to work best to allow for maximum opportunity for the 2 parts of the Cas protein to come together and thus reconstitute Cas protein activity. One alternative is that the NLS of nucleoplasmin can be used as a linker. For example, a linker can also be used between the Cas protein and any functional domain. Again, a $(GGGGS)_3$ (SEQ ID NO: 9) linker may be used here (or the 6, 9, or 12 repeat versions therefore) or the NLS of nucleoplasmin can be used as a linker between a Cas protein and the functional domain. Other linkers are described herein and/or will be instantly appreciated by those of ordinary skill in the art in view of the disclosure herein.

ii. Base Editors

1. General Discussion

The present disclosure also provides for a base editing system. In general, such a system may comprise a deaminase (e.g., an adenosine deaminase or cytidine deaminase) fused with a Cas protein. The Cas protein may be a Cas, dead Cas protein, and/or a Cas nickase protein. In certain examples, the system comprises a mutated form of an adenosine deaminase fused with a dead CRISPR-Cas or CRISPR-Cas nickase. The mutated form of the adenosine deaminase may have both adenosine deaminase and cytidine deaminase activities.

In certain example embodiments, a Cas protein include a deaminase domain (e.g. an adenosine deaminase, cytosine deaminase and/or cytidine deaminase), as described elsewhere herein for base-editing purposes. The deaminase domain can be configured as an activatable functional domain or matched pair thereof as previously described elsewhere herein. In some embodiments the deaminase into a matched pair of activatable functional domains as a "split protein" with each portion of the deaminase being incorporated into the engineered CRISPR-Cas system described herein into activatable functional domains that are attached to, integrated in, and/or fused with one or more Cas proteins described herein. An overview of base editing systems variations thereof, and rational design choice of base editing systems are described in Anzalone et al. 2020. Nature Biotechnol. 38: 824-844, particularly at pages 829-835 and FIGS. 3-5 therein, which is incorporated herein by reference as if expressed in its entirety.

In addition to those described elsewhere herein, additional non-limiting examples of base editing systems include those described in International Patent Publication Nos. WO 2019/071048 (e.g. paragraphs [0933]-[0938]), WO 2019/084063 (e.g., paragraphs [0173]-[0186], [0323]-[0475], [0893]-[1094]), WO 2019/126716 (e.g., paragraphs [0290]-[0425], [1077]-[1084]), WO 2019/126709 (e.g., paragraphs [0294]-[0453]), WO 2019/126762 (e.g., paragraphs [0309]-[0438]), WO 2019/126774 (e.g., paragraphs [0511]-[0670]), Cox DBT, et al., RNA editing with CRISPR-Cas13, Science. 2017 Nov. 24; 358(6366):1019-1027; Abudayyeh 00, et al., A cytosine deaminase for programmable single-base RNA editing, Science 26 Jul. 2019: Vol. 365, Issue 6451, pp. 382-386; Gaudelli N M et al., Programmable base editing of A•T to G•C in genomic DNA without DNA cleavage, Nature volume 551, pages 464-471 (23 Nov. 2017); Komor A C, et al., Programmable editing of a target base in genomic DNA without double-stranded DNA cleavage. Nature. 2016 May 19; 533(7603):420-4; Jordan L. Doman et al., Evaluation and minimization of Cas9-independent off-target DNA editing by cytosine base editors, Nat Biotechnol (2020). doi.org/10.1038/s41587-020-0414-6; and Richter M F et al., Phage-assisted evolution of an adenine base editor with improved Cas domain compatibility and activity, Nat Biotechnol (2020). doi.org/10.1038/s41587-020-0453-z; Mok et al. Nature. 2020. 583, 631-637 (which describes CRISPR-Cas and TALEN systems including a Cas or a TALEN coupled to a bacterial cytidine deaminase capable of acting on double stranded DNA (DddA) and split variations thereof), Wilson et al. 2020. Nature Biotech. https://doi.org/10.1038/s41587-020-0572-6 (which describes an RNA editor which includes a dCas13 coupled to a methyltransferase which modifies adenine to $m^6A$), Rees et al., Analysis and Minimization of Cellular RNA Editing by DNA Adenine Base Editors. Science. Adv. 5. Eaax5717 (2019); Huang et al. Circularly Permuted and PAM-Modified Cas9 variants broaden the targeting scope of base editors. Nat. Biotechnol. 37, 626-631 (2019); Thuronyi et al. Continuous evolution of base editors with expanded target compatibility and improved activity. Nat. Commu. 10:2905 (2019); Osborn et al. J. Invest. Derm. 140:338-347. (2020; Levy et al., Biomed. Eng. 1:97-110 (2020); Miller et al. Continuous evolution of SpCas9 variants compatible with non-G PAMs. Nat. Biotechnol. 38:4710481 (2020); Jiang et al., Chemical Modification of Adenine Base Editor mRNA and Guide RNA expand its application scope. Nat. Commun. 11:1979 (2020), Phage-assisted evolution of an adenine base editor with enhanced Cas domain Compatibility and Activity. Nat. Biotechnol. 38:883-891 (2020); Yeh et al., In vivo postnatal base editing rescues hearing in a mouse model of recessive deafness. Scei. Trans. Med. 12: eaay9101(2020); Huang et al. Precision Genome Editing Using Cytosine and Adenine Base Editors. Nature Protocols accepted in principle (2020) which are incorporated by reference herein in their entireties.

2. Cytosine Deaminase

In some embodiments, the deaminase is a cytosine deaminase. Programmable deamination of cytosine has been reported and may be used for correction of A→G and T→C point mutations. For example, Komor et al., Nature (2016) 533:420-424 reports targeted deamination of cytosine by APOBEC1 cytidine deaminase in a non-targeted DNA stranded displaced by the binding of a Cas-guide RNA complex to a targeted DNA strand, which results in conversion of cytosine to uracil. See also Kim et al., Nature Biotechnology (2017) 35:371-376; Shimatani et al., Nature Biotechnology (2017) doi:10.1038/nbt.3833; Zong et al., Nature Biotechnology (2017) doi:10.1038/nbt.3811; Yang Nature Communication (2016) doi:10.1038/ncomms13330.

3. Adenosine Deaminase

The term "adenosine deaminase" or "adenosine deaminase protein" as used herein refers to a protein, a polypeptide, or one or more functional domain(s) of a protein or a polypeptide that is capable of catalyzing a hydrolytic deamination reaction that converts an adenine (or an adenine moiety of a molecule) to a hypoxanthine (or a hypoxanthine moiety of a molecule), as shown below. In some embodiments, the adenine-containing molecule is an adenosine (A), and the hypoxanthine-containing molecule is an inosine (I). The adenine-containing molecule can be deoxyribonucleic acid (DNA) or ribonucleic acid (RNA).

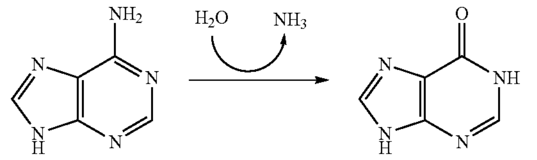

Adenine Hypoxanthine

In one embodiment, the present disclosure provides an engineered adenosine deaminase. The engineered adenosine deaminase may comprise one or more mutations herein. In some embodiments, the engineered adenosine deaminase has cytidine deaminase activity. In certain examples, the engineered adenosine deaminase has both cytidine deaminase activity and adenosine deaminase.

According to the present disclosure, adenosine deaminases that can be used in connection with the present disclosure include, but are not limited to, members of the enzyme family known as adenosine deaminases that act on RNA (ADARs), members of the enzyme family known as adenosine deaminases that act on tRNA (ADATs), and other adenosine deaminase domain-containing (ADAD) family members. According to the present disclosure, the adenosine deaminase is capable of targeting adenine in a RNA/DNA and RNA duplexes. Indeed, Zheng et al. (Nucleic Acids Res. 2017, 45(6): 3369-3377) demonstrate that ADARs can carry out adenosine to inosine editing reactions on RNA/DNA and RNA/RNA duplexes. In particular embodiments, the adenosine deaminase has been modified to increase its ability to edit DNA in a RNA/DNA heteroduplex of in an RNA duplex as detailed elsewhere herein.

In some embodiments, the adenosine deaminase is derived from one or more metazoa species, including but not limited to, mammals, birds, frogs, squids, fish, flies and worms. In some embodiments, the adenosine deaminase is a human, squid or *Drosophila* adenosine deaminase.

In some embodiments, the adenosine deaminase is a human ADAR, including hADAR1, hADAR2, hADAR3. In some embodiments, the adenosine deaminase is a *Caenorhabditis elegans* ADAR protein, including ADR-1 and ADR-2. In some embodiments, the adenosine deaminase is a *Drosophila* ADAR protein, including dAdar. In some embodiments, the adenosine deaminase is a squid *Loligo pealeii* ADAR protein, including sqADAR2a and sqADAR2b. In some embodiments, the adenosine deaminase is a human ADAT protein. In some embodiments, the adenosine deaminase is a *Drosophila* ADAT protein. In some embodiments, the adenosine deaminase is a human ADAD protein, including TENR (hADAD1) and TENRL (hADAD2).

In some embodiments, the adenosine deaminase is a TadA protein such as *E. coli* TadA. See Kim et al., Biochemistry 45:6407-6416 (2006); Wolf et al., EMBO J. 21:3841-3851 (2002). In some embodiments, the adenosine deaminase is mouse ADA. See Grunebaum et al., Curr. Opin. Allergy Clin. Immunol. 13:630-638 (2013). In some embodiments, the adenosine deaminase is human ADAT2. See Fukui et al., J. Nucleic Acids 2010:260512 (2010).). In some embodiments, the deaminase (e.g., adenosine or cytidine deaminase) is one or more of those described in Cox et al., Science. 2017, November 24; 358(6366): 1019-1027; Komore et al., Nature. 2016 May 19; 533(7603):420-4; and Gaudelli et al., Nature. 2017 Nov. 23; 551(7681):464-471.

In some embodiments, the adenosine deaminase protein recognizes and converts one or more target adenosine residue(s) in a double-stranded nucleic acid substrate into inosine residues (s). In some embodiments, the double-stranded nucleic acid substrate is a RNA-DNA hybrid duplex. In some embodiments, the adenosine deaminase protein recognizes a binding window on the double-stranded substrate. In some embodiments, the binding window contains at least one target adenosine residue(s). In some embodiments, the binding window is in the range of about 3 bp to about 100 bp. In some embodiments, the binding window is in the range of about 5 bp to about 50 bp. In some embodiments, the binding window is in the range of about 10 bp to about 30 bp. In some embodiments, the binding window is about 1 bp, 2 bp, 3 bp, 5 bp, 7 bp, 10 bp, 15 bp, 20 bp, 25 bp, 30 bp, 40 bp, 45 bp, 50 bp, 55 bp, 60 bp, 65 bp, 70 bp, 75 bp, 80 bp, 85 bp, 90 bp, 95 bp, or 100 bp.

In some embodiments, the adenosine deaminase protein comprises one or more deaminase domains. Not intended to be bound by a particular theory, it is contemplated that the deaminase domain functions to recognize and convert one or more target adenosine (A) residue(s) contained in a double-stranded nucleic acid substrate into inosine (I) residue(s). In some embodiments, the deaminase domain comprises an active center. In some embodiments, the active center comprises a zinc ion. In some embodiments, during the A-to-I editing process, base pairing at the target adenosine residue is disrupted, and the target adenosine residue is "flipped" out of the double helix to become accessible by the adenosine deaminase. In some embodiments, amino acid residues in or near the active center interact with one or more nucleotide(s) 5' to a target adenosine residue. In some embodiments, amino acid residues in or near the active center interact with one or more nucleotide(s) 3' to a target adenosine residue. In some embodiments, amino acid residues in or near the active center further interact with the nucleotide complementary to the target adenosine residue on the opposite strand. In some embodiments, the amino acid residues form hydrogen bonds with the 2' hydroxyl group of the nucleotides.

In some embodiments, the adenosine deaminase comprises human ADAR2 full protein (hADAR2) or the deaminase domain thereof (hADAR2-D). In some embodiments, the adenosine deaminase is an ADAR family member that is homologous to hADAR2 or hADAR2-D.

Particularly, in some embodiments, the homologous ADAR protein is human ADAR1 (hADAR1) or the deaminase domain thereof (hADAR1-D). In some embodiments, glycine 1007 of hADAR1-D corresponds to glycine 487 hADAR2-D, and glutamic Acid 1008 of hADAR1-D corresponds to glutamic acid 488 of hADAR2-D.

In some embodiments, the adenosine deaminase comprises the wild-type amino acid sequence of hADAR2-D. In some embodiments, the adenosine deaminase comprises one or more mutations in the hADAR2-D sequence, such that the editing efficiency, and/or substrate editing preference of hADAR2-D is changed according to specific needs.

The engineered adenosine deminase may be fused or otherwise attached to, coupled to, or integrated with a Cas protein, e.g., Cas (e.g. Cas9, Cas12), Cas9, Cas 12 (e.g., Cas12a, Cas12b, Cas12c, Cas12d, etc.), Cas13 (e.g., Cas13a, Cas13b (such as Cas13b-t1, Cas13b-t2, Cas13b-t3), Cas13c, Cas13d, etc.), Cas14, CasX, CasY, or an engineered form of the Cas protein (e.g., an inactive, dead form, a nickase form). In some examples, provided herein include an engineered adenosine deminase fused with a Cas protein such as Cas9 and/or Cas12.

Certain mutations of hADAR1 and hADAR2 proteins have been described in Kuttan et al., Proc Natl Acad Sci USA. (2012) 109(48):E3295-304; Want et al. ACS Chem Biol. (2015) 10(11):2512-9; and Zheng et al. Nucleic Acids Res. (2017) 45(6):3369-337, each of which is incorporated herein by reference in its entirety.

In some embodiments, the adenosine deaminase comprises a mutation at glycine336 of the hADAR2-D amino acid sequence, or a corresponding position in a homologous ADAR protein. In some embodiments, the glycine residue at position 336 is replaced by an aspartic acid residue (G336D).

In some embodiments, the adenosine deaminase comprises a mutation at Glycine487 of the hADAR2-D amino acid sequence, or a corresponding position in a homologous ADAR protein. In some embodiments, the glycine residue at position 487 is replaced by a non-polar amino acid residue with relatively small side chains. For example, in some embodiments, the glycine residue at position 487 is replaced by an alanine residue (G487A). In some embodiments, the glycine residue at position 487 is replaced by a valine residue (G487V). In some embodiments, the glycine residue at position 487 is replaced by an amino acid residue with relatively large side chains. In some embodiments, the glycine residue at position 487 is replaced by a arginine residue (G487R). In some embodiments, the glycine residue at position 487 is replaced by a lysine residue (G487K). In some embodiments, the glycine residue at position 487 is replaced by a tryptophan residue (G487W). In some embodiments, the glycine residue at position 487 is replaced by a tyrosine residue (G487Y).

In some embodiments, the adenosine deaminase comprises a mutation at glutamic acid488 of the hADAR2-D amino acid sequence, or a corresponding position in a homologous ADAR protein. In some embodiments, the glutamic acid residue at position 488 is replaced by a glutamine residue (E488Q). In some embodiments, the glutamic acid residue at position 488 is replaced by a histidine residue (E488H). In some embodiments, the glutamic acid residue at position 488 is replace by an arginine residue (E488R). In some embodiments, the glutamic acid residue at position 488 is replace by a lysine residue (E488K). In some embodiments, the glutamic acid residue at position 488 is replace by an asparagine residue (E488N). In some embodiments, the glutamic acid residue at position 488 is replace by an alanine residue (E488A). In some embodiments, the glutamic acid residue at position 488 is replace by a Methionine residue (E488M). In some embodiments, the glutamic acid residue at position 488 is replace by a serine residue (E488S). In some embodiments, the glutamic acid residue at position 488 is replace by a phenylalanine residue (E488F). In some embodiments, the glutamic acid residue at position 488 is replace by a lysine residue (E488L). In some embodiments, the glutamic acid residue at position 488 is replace by a tryptophan residue (E488W).

In some embodiments, the adenosine deaminase comprises a mutation at threonine490 of the hADAR2-D amino acid sequence, or a corresponding position in a homologous ADAR protein. In some embodiments, the threonine residue at position 490 is replaced by a cysteine residue (T490C). In some embodiments, the threonine residue at position 490 is replaced by a serine residue (T490S). In some embodiments, the threonine residue at position 490 is replaced by an alanine residue (T490A). In some embodiments, the threonine residue at position 490 is replaced by a phenylalanine residue (T490F). In some embodiments, the threonine residue at position 490 is replaced by a tyrosine residue (T490Y). In some embodiments, the threonine residue at position 490 is replaced by a serine residue (T490R). In some embodiments, the threonine residue at position 490 is replaced by an alanine residue (T490K). In some embodiments, the threonine residue at position 490 is replaced by a phenylalanine residue (T490P). In some embodiments, the threonine residue at position 490 is replaced by a tyrosine residue (T490E).

In some embodiments, the adenosine deaminase comprises a mutation at valine493 of the hADAR2-D amino acid sequence, or a corresponding position in a homologous ADAR protein. In some embodiments, the valine residue at position 493 is replaced by an alanine residue (V493A). In some embodiments, the valine residue at position 493 is replaced by a serine residue (V493S). In some embodiments, the valine residue at position 493 is replaced by a threonine residue (V493T). In some embodiments, the valine residue at position 493 is replaced by an arginine residue (V493R). In some embodiments, the valine residue at position 493 is replaced by an aspartic acid residue (V493D). In some embodiments, the valine residue at position 493 is replaced by a proline residue (V493P). In some embodiments, the valine residue at position 493 is replaced by a glycine residue (V493G).

In some embodiments, the adenosine deaminase comprises a mutation at alanine589 of the hADAR2-D amino acid sequence, or a corresponding position in a homologous ADAR protein. In some embodiments, the alanine residue at position 589 is replaced by a valine residue (A589V).

In some embodiments, the adenosine deaminase comprises a mutation at asparagine597 of the hADAR2-D amino acid sequence, or a corresponding position in a homologous ADAR protein. In some embodiments, the asparagine residue at position 597 is replaced by a lysine residue (N597K). In some embodiments, the adenosine deaminase comprises a mutation at position 597 of the amino acid sequence, which has an asparagine residue in the wild type sequence. In some embodiments, the asparagine residue at position 597 is replaced by an arginine residue (N597R). In some embodiments, the adenosine deaminase comprises a mutation at position 597 of the amino acid sequence, which has an asparagine residue in the wild type sequence. In some embodiments, the asparagine residue at position 597 is replaced by an alanine residue (N597A). In some embodiments, the adenosine deaminase comprises a mutation at position 597 of the amino acid sequence, which has an asparagine residue in the wild type sequence. In some embodiments, the asparagine residue at position 597 is replaced by a glutamic acid residue (N597E). In some embodiments, the adenosine deaminase comprises a mutation at position 597 of the amino acid sequence, which has an asparagine residue in the wild type sequence. In some embodiments, the asparagine residue at position 597 is replaced by a histidine residue (N597H). In some embodiments, the adenosine deaminase comprises a mutation at position 597 of the amino acid sequence, which has an asparagine residue in the wild type sequence. In some embodiments, the asparagine residue at position 597 is replaced by a glycine residue (N597G). In some embodiments, the adenosine deaminase comprises a mutation at position 597 of the amino acid sequence, which has an asparagine residue in the wild type sequence. In some embodiments, the asparagine residue at position 597 is replaced by a tyrosine residue (N597Y). In some embodiments, the asparagine residue at position 597 is replaced by a phenylalanine residue (N597F). In some embodiments, the adenosine deaminase comprises mutation N597I. In some embodiments, the adenosine deaminase comprises mutation N597L. In some embodiments, the adenosine deaminase comprises mutation N597V. In some embodiments, the adenosine deaminase comprises mutation N597M. In some embodiments, the adenosine deaminase comprises mutation N597C. In some embodiments, the adenosine deaminase comprises mutation N597P. In some embodiments, the adenosine deaminase comprises mutation N597T. In some embodiments, the adenosine deaminase comprises mutation N597S. In some embodiments, the adenosine deaminase comprises mutation N597W. In some embodiments, the adenosine deaminase comprises mutation N597Q. In some embodiments, the adenosine deaminase comprises mutation N597D. In certain example embodiments, the mutations at N597 described above are further made in the context of an E488Q background In some embodiments, the adenosine deaminase comprises a mutation at serine599 of the hADAR2-D amino acid sequence, or a corresponding position in a homologous ADAR protein. In some embodiments, the serine residue at position 599 is replaced by a threonine residue (S599T).

In some embodiments, the adenosine deaminase comprises a mutation at asparagine613 of the hADAR2-D amino acid sequence, or a corresponding position in a homologous ADAR protein. In some embodiments, the asparagine residue at position 613 is replaced by a lysine residue (N613K). In some embodiments, the adenosine deaminase comprises a mutation at position 613 of the amino acid sequence, which has an asparagine residue in the wild type sequence. In some embodiments, the asparagine residue at position 613 is replaced by an arginine residue (N613R). In some embodiments, the adenosine deaminase comprises a mutation at position 613 of the amino acid sequence, which has an asparagine residue in the wild type sequence. In some embodiments, the asparagine residue at position 613 is replaced by an alanine residue (N613A) In some embodiments, the adenosine deaminase comprises a mutation at position 613 of the amino acid sequence, which has an asparagine residue in the wild type sequence. In some embodiments, the asparagine residue at position 613 is replaced by a glutamic acid residue (N613E). In some embodiments, the adenosine deaminase comprises mutation N613I. In some embodiments, the adenosine deaminase comprises mutation N613L. In some embodiments, the adenosine deaminase comprises mutation N613V. In some embodiments, the adenosine deaminase comprises mutation N613F. In some embodiments, the adenosine deaminase comprises mutation N613M. In some embodiments, the adenosine deaminase comprises mutation N613C. In some embodiments, the adenosine deaminase comprises mutation N613G. In some embodiments, the adenosine deaminase comprises mutation N613P. In some embodiments, the adenosine deaminase comprises mutation N613T. In some embodiments, the adenosine deaminase comprises mutation N613S. In some embodiments, the adenosine deaminase comprises mutation N613Y. In some embodiments, the adenosine deaminase comprises mutation N613W. In some embodiments, the adenosine deaminase comprises mutation N613Q. In some embodiments, the adenosine deaminase comprises mutation N613H. In some embodiments, the adenosine deaminase comprises mutation N613D. In some embodiments, the mutations at N613 described above are further made in combination with a E488Q mutation.

In some embodiments, to improve editing efficiency, the adenosine deaminase may comprise one or more of the mutations: G336D, G487A, G487V, E488Q, E488H, E488R, E488N, E488A, E488S, E488M, T490C, T490S, V493T, V493S, V493A, V493R, V493D, V493P, V493G, N597K, N597R, N597A, N597E, N597H, N597G, N597Y, A589V, S599T, N613K, N613R, N613A, N613E, based on amino acid sequence positions of hADAR2-D, and mutations in a homologous ADAR protein corresponding to the above.

In some embodiments, to reduce editing efficiency, the adenosine deaminase may comprise one or more of the mutations: E488F, E488L, E488W, T490A, T490F, T490Y, T490R, T490K, T490P, T490E, N597F, based on amino acid sequence positions of hADAR2-D, and mutations in a homologous ADAR protein corresponding to the above. In particular embodiments, it can be of interest to use an adenosine deaminase enzyme with reduced efficacy to reduce off-target effects.

In some embodiments, to reduce off-target effects, the adenosine deaminase comprises one or more of mutations at R348, V351, T375, K376, E396, C451, R455, N473, R474, K475, R477, R481, S486, E488, T490, S495, R510, based on amino acid sequence positions of hADAR2-D, and mutations in a homologous ADAR protein corresponding to the above. In some embodiments, the adenosine deaminase comprises mutation at E488 and one or more additional positions selected from R348, V351, T375, K376, E396, C451, R455, N473, R474, K475, R477, R481, S486, T490, S495, R510. In some embodiments, the adenosine deaminase comprises mutation at T375, and optionally at one or more additional positions. In some embodiments, the adenosine deaminase comprises mutation at N473, and optionally at one or more additional positions. In some embodiments, the adenosine deaminase comprises mutation at V351, and optionally at one or more additional positions. In some embodiments, the adenosine deaminase comprises mutation at E488 and T375, and optionally at one or more additional positions. In some embodiments, the adenosine deaminase comprises mutation at E488 and N473, and optionally at one or more additional positions. In some embodiments, the adenosine deaminase comprises mutation E488 and V351, and optionally at one or more additional positions. In some embodiments, the adenosine deaminase comprises mutation at E488 and one or more of T375, N473, and V351.

In some embodiments, to reduce off-target effects, the adenosine deaminase comprises one or more of mutations selected from R348E, V351L, T375G, T375S, R455G, R455S, R455E, N473D, R474E, K475Q, R477E, R481E, S486T, E488Q, T490A, T490S, S495T, and R510E, based on amino acid sequence positions of hADAR2-D, and mutations in a homologous ADAR protein corresponding to the above. In some embodiments, the adenosine deaminase comprises mutation E488Q and one or more additional mutations selected from R348E, V351L, T375G, T375S, R455G, R455S, R455E, N473D, R474E, K475Q, R477E, R481E, S486T, T490A, T490S, S495T, and R510E. In some embodiments, the adenosine deaminase comprises mutation T375G or T375S, and optionally one or more additional mutations. In some embodiments, the adenosine deaminase comprises mutation N473D, and optionally one or more additional mutations. In some embodiments, the adenosine deaminase comprises mutation V351L, and optionally one or more additional mutations. In some embodiments, the adenosine deaminase comprises mutation E488Q, and T375G or T375G, and optionally one or more additional mutations. In some embodiments, the adenosine deaminase comprises mutation E488Q and N473D, and optionally one or more additional mutations. In some embodiments, the adenosine deaminase comprises mutation E488Q and V351L, and optionally one or more additional mutations. In some embodiments, the adenosine deaminase comprises mutation E488Q and one or more of T375G/S, N473D and V351L.

In certain examples, the adenosine deaminase protein or catalytic domain thereof has been modified to comprise a mutation at E488, preferably E488Q, of the hADAR2-D amino acid sequence, or a corresponding position in a homologous ADAR protein and/or wherein the adenosine deaminase protein or catalytic domain thereof has been modified to comprise a mutation at T375, preferably T375G of the hADAR2-D amino acid sequence, or a corresponding position in a homologous ADAR protein. In certain examples, the adenosine deaminase protein or catalytic domain thereof has been modified to comprise a mutation at E1008, preferably E1008Q, of the hADAR1d amino acid sequence, or a corresponding position in a homologous ADAR protein.

Crystal structures of the human ADAR2 deaminase domain bound to duplex RNA reveal a protein loop that binds the RNA on the 5' side of the modification site. This 5' binding loop is one contributor to substrate specificity differences between ADAR family members. See Wang et al., Nucleic Acids Res., 44(20):9872-9880 (2016), the content of which is incorporated herein by reference in its entirety. In addition, an ADAR2-specific RNA-binding loop was identified near the enzyme active site. See Mathews et al., Nat. Struct. Mol. Biol., 23(5):426-33 (2016), the content of which is incorporated herein by reference in its entirety. In some embodiments, the adenosine deaminase comprises one or more mutations in the RNA binding loop to improve editing specificity and/or efficiency.

In some embodiments, the adenosine deaminase comprises a mutation at alanine454 of the hADAR2-D amino acid sequence, or a corresponding position in a homologous ADAR protein. In some embodiments, the alanine residue at position 454 is replaced by a serine residue (A454S). In some embodiments, the alanine residue at position 454 is replaced by a cysteine residue (A454C). In some embodiments, the alanine residue at position 454 is replaced by an aspartic acid residue (A454D).

In some embodiments, the adenosine deaminase comprises a mutation at arginine455 of the hADAR2-D amino acid sequence, or a corresponding position in a homologous ADAR protein. In some embodiments, the arginine residue at position 455 is replaced by an alanine residue (R455A). In some embodiments, the arginine residue at position 455 is replaced by a valine residue (R455V). In some embodiments, the arginine residue at position 455 is replaced by a histidine residue (R455H). In some embodiments, the arginine residue at position 455 is replaced by a glycine residue (R455G). In some embodiments, the arginine residue at position 455 is replaced by a serine residue (R455S). In some embodiments, the arginine residue at position 455 is replaced by a glutamic acid residue (R455E). In some embodiments, the adenosine deaminase comprises mutation R455C. In some embodiments, the adenosine deaminase comprises mutation R455I. In some embodiments, the adenosine deaminase comprises mutation R455K. In some embodiments, the adenosine deaminase comprises mutation R455L. In some embodiments, the adenosine deaminase comprises mutation R455M. In some embodiments, the adenosine deaminase comprises mutation R455N. In some embodiments, the adenosine deaminase comprises mutation R455Q. In some embodiments, the adenosine deaminase comprises mutation R455F. In some embodiments, the adenosine deaminase comprises mutation R455W. In some embodiments, the adenosine deaminase comprises mutation R455P. In some embodiments, the adenosine deaminase comprises mutation R455Y. In some embodiments, the adenosine deaminase comprises mutation R455E. In some embodiments, the adenosine deaminase comprises mutation R455D. In some embodiments, the mutations at R455 described above are further made in combination with a E488Q mutation.

In some embodiments, the adenosine deaminase comprises a mutation at isoleucine456 of the hADAR2-D amino acid sequence, or a corresponding position in a homologous ADAR protein. In some embodiments, the isoleucine residue at position 456 is replaced by a valine residue (I456V). In some embodiments, the isoleucine residue at position 456 is replaced by a leucine residue (I456L). In some embodiments, the isoleucine residue at position 456 is replaced by an aspartic acid residue (I456D).

In some embodiments, the adenosine deaminase comprises a mutation at phenylalanine457 of the hADAR2-D amino acid sequence, or a corresponding position in a homologous ADAR protein. In some embodiments, the phenylalanine residue at position 457 is replaced by a tyrosine residue (F457Y). In some embodiments, the phenylalanine residue at position 457 is replaced by an arginine residue (F457R). In some embodiments, the phenylalanine residue at position 457 is replaced by a glutamic acid residue (F457E).

In some embodiments, the adenosine deaminase comprises a mutation at serine458 of the hADAR2-D amino acid sequence, or a corresponding position in a homologous ADAR protein. In some embodiments, the serine residue at position 458 is replaced by a valine residue (S458V). In some embodiments, the serine residue at position 458 is replaced by a phenylalanine residue (S458F). In some embodiments, the serine residue at position 458 is replaced by a proline residue (S458P). In some embodiments, the adenosine deaminase comprises mutation S458I. In some embodiments, the adenosine deaminase comprises mutation S458L. In some embodiments, the adenosine deaminase comprises mutation S458M. In some embodiments, the adenosine deaminase comprises mutation S458C. In some embodiments, the adenosine deaminase comprises mutation S458A. In some embodiments, the adenosine deaminase comprises mutation S458G. In some embodiments, the adenosine deaminase comprises mutation S458T. In some embodiments, the adenosine deaminase comprises mutation S458Y. In some embodiments, the adenosine deaminase comprises mutation S458W. In some embodiments, the adenosine deaminase comprises mutation S458Q. In some embodiments, the adenosine deaminase comprises mutation S458N. In some embodiments, the adenosine deaminase comprises mutation S458H. In some embodiments, the adenosine deaminase comprises mutation S458E. In some embodiments, the adenosine deaminase comprises mutation S458D. In some embodiments, the adenosine deaminase comprises mutation S458K. In some embodiments, the adenosine deaminase comprises mutation S458R. In some embodiments, the mutations at S458 described above are further made in combination with a E488Q mutation.

In some embodiments, the adenosine deaminase comprises a mutation at proline459 of the hADAR2-D amino acid sequence, or a corresponding position in a homologous ADAR protein. In some embodiments, the proline residue at position 459 is replaced by a cysteine residue (P459C). In some embodiments, the proline residue at position 459 is replaced by a histidine residue (P459H). In some embodiments, the proline residue at position 459 is replaced by a tryptophan residue (P459W).

In some embodiments, the adenosine deaminase comprises a mutation at histidine460 of the hADAR2-D amino acid sequence, or a corresponding position in a homologous ADAR protein. In some embodiments, the histidine residue at position 460 is replaced by an arginine residue (H460R). In some embodiments, the histidine residue at position 460 is replaced by an isoleucine residue (H460I). In some embodiments, the histidine residue at position 460 is replaced by a proline residue (H460P). In some embodiments, the adenosine deaminase comprises mutation H460L. In some embodiments, the adenosine deaminase comprises mutation H460V. In some embodiments, the adenosine deaminase comprises mutation H460F. In some embodiments, the adenosine deaminase comprises mutation H460M. In some embodiments, the adenosine deaminase comprises mutation H460C. In some embodiments, the adenosine deaminase comprises mutation H460A. In some embodiments, the adenosine deaminase comprises mutation H460G. In some embodiments, the adenosine deaminase comprises mutation H460T. In some embodiments, the adenosine deaminase comprises mutation H460S. In some embodiments, the adenosine deaminase comprises mutation H460Y. In some embodiments, the adenosine deaminase comprises mutation H460W. In some embodiments, the adenosine deaminase comprises mutation H460Q. In some embodiments, the adenosine deaminase comprises mutation H460N. In some embodiments, the adenosine deaminase comprises mutation H460E. In some embodiments, the adenosine deaminase comprises mutation H460D. In some embodiments, the adenosine deaminase comprises mutation H460K. In some embodiments, the mutations at H460 described above are further made in combination with a E488Q mutation.

In some embodiments, the adenosine deaminase comprises a mutation at proline462 of the hADAR2-D amino acid sequence, or a corresponding position in a homologous ADAR protein. In some embodiments, the proline residue at position 462 is replaced by a serine residue (P462S). In some embodiments, the proline residue at position 462 is replaced by a tryptophan residue (P462W). In some embodiments, the proline residue at position 462 is replaced by a glutamic acid residue (P462E).

In some embodiments, the adenosine deaminase comprises a mutation at aspartic acid469 of the hADAR2-D amino acid sequence, or a corresponding position in a homologous ADAR protein. In some embodiments, the aspartic acid residue at position 469 is replaced by a glutamine residue (D469Q). In some embodiments, the aspartic acid residue at position 469 is replaced by a serine residue (D469S). In some embodiments, the aspartic acid residue at position 469 is replaced by a tyrosine residue (D469Y).

In some embodiments, the adenosine deaminase comprises a mutation at arginine470 of the hADAR2-D amino acid sequence, or a corresponding position in a homologous ADAR protein. In some embodiments, the arginine residue at position 470 is replaced by an alanine residue (R470A). In some embodiments, the arginine residue at position 470 is replaced by an isoleucine residue (R470I). In some embodiments, the arginine residue at position 470 is replaced by an aspartic acid residue (R470D).

In some embodiments, the adenosine deaminase comprises a mutation at histidine471 of the hADAR2-D amino acid sequence, or a corresponding position in a homologous ADAR protein. In some embodiments, the histidine residue at position 471 is replaced by a lysine residue (H471K). In some embodiments, the histidine residue at position 471 is replaced by a threonine residue (H471T). In some embodiments, the histidine residue at position 471 is replaced by a valine residue (H471V).

In some embodiments, the adenosine deaminase comprises a mutation at proline472 of the hADAR2-D amino acid sequence, or a corresponding position in a homologous ADAR protein. In some embodiments, the proline residue at position 472 is replaced by a lysine residue (P472K). In some embodiments, the proline residue at position 472 is replaced by a threonine residue (P472T). In some embodiments, the proline residue at position 472 is replaced by an aspartic acid residue (P472D).

In some embodiments, the adenosine deaminase comprises a mutation at asparagine473 of the hADAR2-D amino acid sequence, or a corresponding position in a homologous ADAR protein. In some embodiments, the asparagine residue at position 473 is replaced by an arginine residue (N473R). In some embodiments, the asparagine residue at position 473 is replaced by a tryptophan residue (N473W). In some embodiments, the asparagine residue at position 473 is replaced by a proline residue (N473P). In some embodiments, the asparagine residue at position 473 is replaced by an aspartic acid residue (N473D).

In some embodiments, the adenosine deaminase comprises a mutation at arginine 474 of the hADAR2-D amino acid sequence, or a corresponding position in a homologous ADAR protein. In some embodiments, the arginine residue at position 474 is replaced by a lysine residue (R474K). In some embodiments, the arginine residue at position 474 is replaced by a glycine residue (R474G). In some embodiments, the arginine residue at position 474 is replaced by an aspartic acid residue (R474D). In some embodiments, the arginine residue at position 474 is replaced by a glutamic acid residue (R474E).

In some embodiments, the adenosine deaminase comprises a mutation at lysine475 of the hADAR2-D amino acid sequence, or a corresponding position in a homologous ADAR protein. In some embodiments, the lysine residue at position 475 is replaced by a glutamine residue (K475Q). In some embodiments, the lysine residue at position 475 is replaced by an asparagine residue (K475N). In some embodiments, the lysine residue at position 475 is replaced by an aspartic acid residue (K475D).

In some embodiments, the adenosine deaminase comprises a mutation at alanine476 of the hADAR2-D amino acid sequence, or a corresponding position in a homologous ADAR protein. In some embodiments, the alanine residue at position 476 is replaced by a serine residue (A476S). In some embodiments, the alanine residue at position 476 is replaced by an arginine residue (A476R). In some embodiments, the alanine residue at position 476 is replaced by a glutamic acid residue (A476E).

In some embodiments, the adenosine deaminase comprises a mutation at arginine477 of the hADAR2-D amino acid sequence, or a corresponding position in a homologous ADAR protein. In some embodiments, the arginine residue at position 477 is replaced by a lysine residue (R477K). In some embodiments, the arginine residue at position 477 is replaced by a threonine residue (R477T). In some embodiments, the arginine residue at position 477 is replaced by a phenylalanine residue (R477F). In some embodiments, the arginine residue at position 474 is replaced by a glutamic acid residue (R477E).

In some embodiments, the adenosine deaminase comprises a mutation at glycine478 of the hADAR2-D amino acid sequence, or a corresponding position in a homologous ADAR protein. In some embodiments, the glycine residue at position 478 is replaced by an alanine residue (G478A). In some embodiments, the glycine residue at position 478 is replaced by an arginine residue (G478R). In some embodiments, the glycine residue at position 478 is replaced by a tyrosine residue (G478Y). In some embodiments, the adenosine deaminase comprises mutation G478I. In some embodiments, the adenosine deaminase comprises mutation G478L. In some embodiments, the adenosine deaminase comprises mutation G478V. In some embodiments, the adenosine deaminase comprises mutation G478F. In some embodiments, the adenosine deaminase comprises mutation G478M. In some embodiments, the adenosine deaminase comprises mutation G478C. In some embodiments, the adenosine deaminase comprises mutation G478P. In some embodiments, the adenosine deaminase comprises mutation G478T. In some embodiments, the adenosine deaminase comprises mutation G478S. In some embodiments, the adenosine deaminase comprises mutation G478W. In some embodiments, the adenosine deaminase comprises mutation G478Q. In some embodiments, the adenosine deaminase comprises mutation G478N. In some embodiments, the adenosine deaminase comprises mutation G478H. In some embodiments, the adenosine deaminase comprises mutation G478E. In some embodiments, the adenosine deaminase comprises mutation G478D. In some embodiments, the adenosine deaminase comprises mutation G478K. In some embodiments, the mutations at G478 described above are further made in combination with a E488Q mutation.

In some embodiments, the adenosine deaminase comprises a mutation at glutamine479 of the hADAR2-D amino acid sequence, or a corresponding position in a homologous ADAR protein. In some embodiments, the glutamine residue at position 479 is replaced by an asparagine residue (Q479N). In some embodiments, the glutamine residue at position 479 is replaced by a serine residue (Q479S). In some embodiments, the glutamine residue at position 479 is replaced by a proline residue (Q479P).

In some embodiments, the adenosine deaminase comprises a mutation at arginine348 of the hADAR2-D amino acid sequence, or a corresponding position in a homologous ADAR protein. In some embodiments, the arginine residue at position 348 is replaced by an alanine residue (R348A). In some embodiments, the arginine residue at position 348 is replaced by a glutamic acid residue (R348E).

In some embodiments, the adenosine deaminase comprises a mutation at valine351 of the hADAR2-D amino acid sequence, or a corresponding position in a homologous ADAR protein. In some embodiments, the valine residue at position 351 is replaced by a leucine residue (V351L). In some embodiments, the adenosine deaminase comprises mutation V351Y. In some embodiments, the adenosine deaminase comprises mutation V351M. In some embodiments, the adenosine deaminase comprises mutation V351T. In some embodiments, the adenosine deaminase comprises mutation V351G. In some embodiments, the adenosine deaminase comprises mutation V351A. In some embodiments, the adenosine deaminase comprises mutation V351F. In some embodiments, the adenosine deaminase comprises mutation V351E. In some embodiments, the adenosine deaminase comprises mutation V351I. In some embodiments, the adenosine deaminase comprises mutation V351C. In some embodiments, the adenosine deaminase comprises mutation V351H. In some embodiments, the adenosine deaminase comprises mutation V351P. In some embodiments, the adenosine deaminase comprises mutation V351S. In some embodiments, the adenosine deaminase comprises mutation V351K. In some embodiments, the adenosine deaminase comprises mutation V351N. In some embodiments, the adenosine deaminase comprises mutation V351W. In some embodiments, the adenosine deaminase comprises mutation V351Q. In some embodiments, the adenosine deaminase comprises mutation V351D. In some embodiments, the adenosine deaminase comprises mutation V351R. In some embodiments, the mutations at V351 described above are further made in combination with a E488Q mutation.

In some embodiments, the adenosine deaminase comprises a mutation at threonine375 of the hADAR2-D amino acid sequence, or a corresponding position in a homologous ADAR protein. In some embodiments, the threonine residue at position 375 is replaced by a glycine residue (T375G). In some embodiments, the threonine residue at position 375 is replaced by a serine residue (T375S). In some embodiments, the adenosine deaminase comprises mutation T375H. In some embodiments, the adenosine deaminase comprises mutation T375Q. In some embodiments, the adenosine deaminase comprises mutation T375C. In some embodiments, the adenosine deaminase comprises mutation T375N. In some embodiments, the adenosine deaminase comprises mutation T375M. In some embodiments, the adenosine deaminase comprises mutation T375A. In some embodiments, the adenosine deaminase comprises mutation T375W. In some embodiments, the adenosine deaminase comprises mutation T375V. In some embodiments, the adenosine deaminase comprises mutation T375R. In some embodiments, the adenosine deaminase comprises mutation T375E. In some embodiments, the adenosine deaminase comprises mutation T375K. In some embodiments, the adenosine deaminase comprises mutation T375F. In some embodiments, the adenosine deaminase comprises mutation T375I. In some embodiments, the adenosine deaminase comprises mutation T375D. In some embodiments, the adenosine deaminase comprises mutation T375P. In some embodiments, the adenosine deaminase comprises mutation T375L. In some embodiments, the adenosine deaminase comprises mutation T375Y. In some embodiments, the mutations at T375Y described above are further made in combination with an E488Q mutation.

In some embodiments, the adenosine deaminase comprises a mutation at Arg481 of the hADAR2-D amino acid sequence, or a corresponding position in a homologous ADAR protein. In some embodiments, the arginine residue at position 481 is replaced by a glutamic acid residue (R481E).

In some embodiments, the adenosine deaminase comprises a mutation at Ser486 of the hADAR2-D amino acid sequence, or a corresponding position in a homologous ADAR protein. In some embodiments, the serine residue at position 486 is replaced by a threonine residue (S486T).

In some embodiments, the adenosine deaminase comprises a mutation at Thr490 of the hADAR2-D amino acid sequence, or a corresponding position in a homologous ADAR protein. In some embodiments, the threonine residue at position 490 is replaced by an alanine residue (T490A). In some embodiments, the threonine residue at position 490 is replaced by a serine residue (T490S).

In some embodiments, the adenosine deaminase comprises a mutation at Ser495 of the hADAR2-D amino acid sequence, or a corresponding position in a homologous ADAR protein. In some embodiments, the serine residue at position 495 is replaced by a threonine residue (S495T).

In some embodiments, the adenosine deaminase comprises a mutation at Arg510 of the hADAR2-D amino acid sequence, or a corresponding position in a homologous ADAR protein. In some embodiments, the arginine residue at position 510 is replaced by a glutamine residue (R510Q). In some embodiments, the arginine residue at position 510 is replaced by an alanine residue (R510A). In some embodiments, the arginine residue at position 510 is replaced by a glutamic acid residue (R510E).

In some embodiments, the adenosine deaminase comprises a mutation at Gly593 of the hADAR2-D amino acid sequence, or a corresponding position in a homologous ADAR protein. In some embodiments, the glycine residue at position 593 is replaced by an alanine residue (G593A). In some embodiments, the glycine residue at position 593 is replaced by a glutamic acid residue (G593E).

In some embodiments, the adenosine deaminase comprises a mutation at Lys594 of the hADAR2-D amino acid sequence, or a corresponding position in a homologous ADAR protein. In some embodiments, the lysine residue at position 594 is replaced by an alanine residue (K594A).

In some embodiments, the adenosine deaminase comprises a mutation at any one or more of positions A454, R455, 1456, F457, S458, P459, H460, P462, D469, R470, H471, P472, N473, R474, K475, A476, R477, G478, Q479, R348, R510, G593, K594 of the hADAR2-D amino acid sequence, or a corresponding position in a homologous ADAR protein.

In some embodiments, the adenosine deaminase comprises any one or more of mutations A454S, A454C, A454D, R455A, R455V, R455H, I456V, I456L, I456D, F457Y, F457R, F457E, S458V, S458F, S458P, P459C, P459H, P459W, H460R, H460I, H460P, P462S, P462W, P462E, D469Q, D469S, D469Y, R470A, R470I, R470D, H471K, H471T, H471V, P472K, P472T, P472D, N473R, N473W, N473P, R474K, R474G, R474D, K475Q, K475N, K475D, A476S, A476R, A476E, R477K, R477T, R477F, G478A, G478R, G478Y, Q479N, Q479S, Q479P, R348A, R510Q, R510A, G593A, G593E, K594A of the hADAR2-D amino acid sequence, or a corresponding position in a homologous ADAR protein.

In some embodiments, the adenosine deaminase comprises a mutation at any one or more of positions T375, V351, G478, S458, H460 of the hADAR2-D amino acid sequence, or a corresponding position in a homologous ADAR protein, optionally in combination a mutation at E488. In some embodiments, the adenosine deaminase comprises one or more of mutations selected from T375G, T375C, T375H, T375Q, V351M, V351T, V351Y, G478R, S458F, H460I, optionally in combination with E488Q.

In some embodiments, the adenosine deaminase comprises one or more of mutations selected from T375H, T375Q, V351M, V351Y, H460P, optionally in combination with E488Q.

In some embodiments, the adenosine deaminase comprises mutations T375S and S458F, optionally in combination with E488Q.

In some embodiments, the adenosine deaminase comprises a mutation at two or more of positions T375, N473, R474, G478, S458, P459, V351, R455, R455, T490, R348, Q479 of the hADAR2-D amino acid sequence, or a corresponding position in a homologous ADAR protein, optionally in combination a mutation at E488. In some embodiments, the adenosine deaminase comprises two or more of mutations selected from T375G, T375S, N473D, R474E, G478R, S458F, P459W, V351L, R455G, R455S, T490A, R348E, Q479P, optionally in combination with E488Q.

In some embodiments, the adenosine deaminase comprises mutations T375G and V351L. In some embodiments, the adenosine deaminase comprises mutations T375G and R455G. In some embodiments, the adenosine deaminase comprises mutations T375G and R455S. In some embodiments, the adenosine deaminase comprises mutations T375G and T490A. In some embodiments, the adenosine deaminase comprises mutations T375G and R348E. In some embodiments, the adenosine deaminase comprises mutations T375S and V351L. In some embodiments, the adenosine deaminase comprises mutations T375S and R455G. In some embodiments, the adenosine deaminase comprises mutations T375S and R455S. In some embodiments, the adenosine deaminase comprises mutations T375S and T490A. In some embodiments, the adenosine deaminase comprises mutations T375S and R348E. In some embodiments, the adenosine deaminase comprises mutations N473D and V351L. In some embodiments, the adenosine deaminase comprises mutations N473D and R455G. In some embodiments, the adenosine deaminase comprises mutations N473D and R455S. In some embodiments, the adenosine deaminase comprises mutations N473D and T490A. In some embodiments, the adenosine deaminase comprises mutations N473D and R348E. In some embodiments, the adenosine deaminase comprises mutations R474E and V351L. In some embodiments, the adenosine deaminase comprises mutations R474E and R455G. In some embodiments, the adenosine deaminase comprises mutations R474E and R455S. In some embodiments, the adenosine deaminase comprises mutations R474E and T490A. In some embodiments, the adenosine deaminase comprises mutations R474E and R348E. In some embodiments, the adenosine deaminase comprises mutations S458F and T375G. In some embodiments, the adenosine deaminase comprises mutations S458F and T375S. In some embodiments, the adenosine deaminase comprises mutations S458F and N473D. In some embodiments, the adenosine deaminase comprises mutations S458F and R474E. In some embodiments, the adenosine deaminase comprises mutations S458F and G478R. In some embodiments, the adenosine deaminase comprises mutations G478R and T375G. In some embodiments, the adenosine deaminase comprises mutations G478R and T375S. In some embodiments, the adenosine deaminase comprises mutations G478R and N473D. In some embodiments, the adenosine deaminase comprises mutations G478R and R474E. In some embodiments, the adenosine deaminase comprises mutations P459W and T375G. In some embodiments, the adenosine deaminase comprises mutations P459W and T375S. In some embodiments, the adenosine deaminase comprises mutations P459W and N473D. In some embodiments, the adenosine deaminase comprises mutations P459W and R474E. In some embodiments, the adenosine deaminase comprises mutations P459W and G478R. In some embodiments, the adenosine deaminase comprises mutations P459W and S458F. In some embodiments, the adenosine deaminase comprises mutations Q479P and T375G. In some embodiments, the adenosine deaminase comprises mutations Q479P and T375S. In some embodiments, the adenosine deaminase comprises mutations Q479P and N473D. In some embodiments, the adenosine deaminase comprises mutations Q479P and R474E. In some embodiments, the adenosine deaminase comprises mutations Q479P and G478R. In some embodiments, the adenosine deaminase comprises mutations Q479P and S458F. In some embodiments, the adenosine deaminase comprises mutations Q479P and P459W. All mutations described in this paragraph may also further be made in combination with a E488Q mutations.

In some embodiments, the adenosine deaminase comprises a mutation at any one or more of positions K475, Q479, P459, G478, S458 of the hADAR2-D amino acid sequence, or a corresponding position in a homologous ADAR protein, optionally in combination a mutation at E488. In some embodiments, the adenosine deaminase comprises one or more of mutations selected from K475N, Q479N, P459W, G478R, S458P, S458F, optionally in combination with E488Q.

In some embodiments, the adenosine deaminase comprises a mutation at any one or more of positions T375, V351, R455, H460, A476 of the hADAR2-D amino acid sequence, or a corresponding position in a homologous ADAR protein, optionally in combination a mutation at E488. In some embodiments, the adenosine deaminase comprises one or more of mutations selected from T375G, T375C, T375H, T375Q, V351M, V351T, V351Y, R455H, H460P, H460I, A476E, optionally in combination with E488Q.

ADAR has been known to demonstrate a preference for neighboring nucleotides on either side of the edited A (www.nature.com/nsmb/journal/v23/n5/full/nsmb.3203.html, Matthews et al. (2017), Nature Structural Mol Biol, 23(5): 426-433, incorporated herein by reference in its entirety). Accordingly, in certain embodiments, the gRNA, target, and/or ADAR is selected optimized for motif preference.

Intentional mismatches have been demonstrated in vitro to allow for editing of non-preferred motifs (https://academic.oup.com/nar/article-lookup/doi/10.1093/nar/gku272; Schneider et al (2014), Nucleic Acid Res, 42(10):e87); Fukuda et al. (2017), Scientific Reports, 7, doi:10.1038/srep41478, incorporated herein by reference in its entirety). Accordingly, in certain embodiments, to enhance RNA editing efficiency on non-preferred 5' or 3' neighboring bases, intentional mismatches in neighboring bases are introduced.

In some embodiments, the adenosine deaminase may be a tRNA-specific adenosine deaminase or a variant thereof. In some embodiments, the adenosine deaminase may comprise one or more of the mutations: W23L, W23R, R26G, H36L, N37S, P48S, P48T, P48A, I49V, R51L, N72D, L84F, S97C, A106V, D108N, H123Y, G125A, A142N, S146C, D147Y, R152H, R152P, E155V, I156F, K157N, K161T, based on amino acid sequence positions of *E. coli* TadA, and mutations in a homologous deaminase protein corresponding to the above. In some embodiments, the adenosine deaminase may comprise one or more of the mutations: D108N based on amino acid sequence positions of *E. coli* TadA, and mutations in a homologous deaminase protein corresponding to the above. In some embodiments, the adenosine deaminase may comprise one or more of the mutations: A106V, D108N, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, based on amino acid sequence positions of *E. coli* TadA, and mutations in a homologous deaminase protein corresponding to the above. In some embodiments, the adenosine deaminase may comprise one or more of the mutations: A106V, D108N, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, A142N, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, P48S, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, P48S, A142N, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, P48S, W23R, P48A, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, P48S, W23R, P48A, A142N, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, P48S, W23R, P48A, R152P, based on amino acid sequence positions of *E. coli* TadA, and mutations in a homologous deaminase protein corresponding to the above. In some embodiments, the adenosine deaminase may comprise one or more of the mutations: A106V, D108N, D147Y, E155V, L84F, H123Y, I156F, H36L, R51L, S146C, K157N, P48S, W23R, P48A, R152P, A142N, based on amino acid sequence positions of *E. coli* TadA, and mutations in a homologous deaminase protein corresponding to the above.

A's opposite C's in the targeting window of the ADAR deaminase domain can be preferentially edited over other bases. Additionally, A's base-paired with U's within a few bases of the targeted base can have low levels of editing by CRISPR-Cas-ADAR fusions, suggesting that there is flexibility for the enzyme to edit multiple A's. These two observations suggest that multiple A's in the activity window of CRISPR-Cas-ADAR fusions could be specified for editing by mismatching all A's to be edited with C's. Accordingly, in certain embodiments, multiple A:C mismatches in the activity window are designed to create multiple A:I edits. In certain embodiments, to suppress potential off-target editing in the activity window, non-target A's are paired with A's or G's.

The terms "editing specificity" and "editing preference" are used interchangeably herein to refer to the extent of A-to-I editing at a particular adenosine site in a double-stranded substrate. In some embodiment, the substrate editing preference is determined by the 5' nearest neighbor and/or the 3' nearest neighbor of the target adenosine residue. In some embodiments, the adenosine deaminase has preference for the 5' nearest neighbor of the substrate ranked as U>A>C>G (">" indicates greater preference). In some embodiments, the adenosine deaminase has preference for the 3' nearest neighbor of the substrate ranked as G>C~A>U (">" indicates greater preference; "~" indicates similar preference). In some embodiments, the adenosine deaminase has preference for the 3' nearest neighbor of the substrate ranked as G>C>U~A (">" indicates greater preference; "~" indicates similar preference). In some embodiments, the adenosine deaminase has preference for the 3' nearest neighbor of the substrate ranked as G>C>A>U (">" indicates greater preference). In some embodiments, the adenosine deaminase has preference for the 3' nearest neighbor of the substrate ranked as C~G~A>U (">" indicates greater preference; "~" indicates similar preference). In some embodiments, the adenosine deaminase has preference for a triplet sequence containing the target adenosine residue ranked as TAG>AAG>CAC>AAT>GAA>GAC (">" indicates greater preference), the center A being the target adenosine residue.

In some embodiments, the substrate editing preference of an adenosine deaminase is affected by the presence or absence of a nucleic acid binding domain in the adenosine deaminase protein. In some embodiments, to modify substrate editing preference, the deaminase domain is connected with a double-strand RNA binding domain (dsRBD) or a double-strand RNA binding motif (dsRBM). In some embodiments, the dsRBD or dsRBM may be derived from an ADAR protein, such as hADAR1 or hADAR2. In some embodiments, a full-length ADAR protein that comprises at least one dsRBD and a deaminase domain is used. In some embodiments, the one or more dsRBM or dsRBD is at the N-terminus of the deaminase domain. In other embodiments, the one or more dsRBM or dsRBD is at the C-terminus of the deaminase domain.

In some embodiments, the substrate editing preference of an adenosine deaminase is affected by amino acid residues near or in the active center of the enzyme. In some embodiments, to modify substrate editing preference, the adenosine deaminase may comprise one or more of the mutations: G336D, G487R, G487K, G487W, G487Y, E488Q, E488N, T490A, V493A, V493T, V493S, N597K, N597R, A589V, S599T, N613K, N613R, based on amino acid sequence positions of hADAR2-D, and mutations in a homologous ADAR protein corresponding to the above.

Particularly, in some embodiments, to reduce editing specificity, the adenosine deaminase can comprise one or more of mutations E488Q, V493A, N597K, N613K, based on amino acid sequence positions of hADAR2-D, and mutations in a homologous ADAR protein corresponding to the above. In some embodiments, to increase editing specificity, the adenosine deaminase can comprise mutation T490A.

In some embodiments, to increase editing preference for target adenosine (A) with an immediate 5' G, such as substrates comprising the triplet sequence GAC, the center A being the target adenosine residue, the adenosine deaminase can comprise one or more of mutations G336D, E488Q, E488N, V493T, V493S, V493A, A589V, N597K, N597R, S599T, N613K, N613R, based on amino acid sequence positions of hADAR2-D, and mutations in a homologous ADAR protein corresponding to the above.

Particularly, in some embodiments, the adenosine deaminase comprises mutation E488Q or a corresponding mutation in a homologous ADAR protein for editing substrates comprising the following triplet sequences: GAC, GAA, GAU, GAG, CAU, AAU, UAC, the center A being the target adenosine residue.

In some embodiments, the adenosine deaminase comprises the wild-type amino acid sequence of hADAR1-D. In some embodiments, the adenosine deaminase comprises one or more mutations in the hADAR1-D sequence, such that the editing efficiency, and/or substrate editing preference of hADAR1-D is changed according to specific needs.

In some embodiments, the adenosine deaminase comprises a mutation at Glycine1007 of the hADAR1-D amino acid sequence, or a corresponding position in a homologous ADAR protein. In some embodiments, the glycine residue at position 1007 is replaced by a non-polar amino acid residue with relatively small side chains. For example, in some embodiments, the glycine residue at position 1007 is replaced by an alanine residue (G1007A). In some embodiments, the glycine residue at position 1007 is replaced by a valine residue (G1007V). In some embodiments, the glycine residue at position 1007 is replaced by an amino acid residue with relatively large side chains. In some embodiments, the glycine residue at position 1007 is replaced by an arginine residue (G1007R). In some embodiments, the glycine residue at position 1007 is replaced by a lysine residue (G1007K). In some embodiments, the glycine residue at position 1007 is replaced by a tryptophan residue (G1007W). In some embodiments, the glycine residue at position 1007 is replaced by a tyrosine residue (G1007Y). Additionally, in other embodiments, the glycine residue at position 1007 is replaced by a leucine residue (G1007L). In other embodiments, the glycine residue at position 1007 is replaced by a threonine residue (G1007T). In other embodiments, the glycine residue at position 1007 is replaced by a serine residue (G1007S).

In some embodiments, the adenosine deaminase comprises a mutation at glutamic acid1008 of the hADAR1-D amino acid sequence, or a corresponding position in a homologous ADAR protein. In some embodiments, the glutamic acid residue at position 1008 is replaced by a polar amino acid residue having a relatively large side chain. In some embodiments, the glutamic acid residue at position 1008 is replaced by a glutamine residue (E1008Q). In some embodiments, the glutamic acid residue at position 1008 is replaced by a histidine residue (E1008H). In some embodiments, the glutamic acid residue at position 1008 is replaced by an arginine residue (E1008R). In some embodiments, the glutamic acid residue at position 1008 is replaced by a lysine residue (E1008K). In some embodiments, the glutamic acid residue at position 1008 is replaced by a nonpolar or small polar amino acid residue. In some embodiments, the glutamic acid residue at position 1008 is replaced by a phenylalanine residue (E1008F). In some embodiments, the glutamic acid residue at position 1008 is replaced by a tryptophan residue (E1008W). In some embodiments, the glutamic acid residue at position 1008 is replaced by a glycine residue (E1008G). In some embodiments, the glutamic acid residue at position 1008 is replaced by an isoleucine residue (E10081). In some embodiments, the glutamic acid residue at position 1008 is replaced by a valine residue (E1008V). In some embodiments, the glutamic acid residue at position 1008 is replaced by a proline residue (E1008P). In some embodiments, the glutamic acid residue at position 1008 is replaced by a serine residue (E1008S). In other embodiments, the glutamic acid residue at position 1008 is replaced by an asparagine residue (E1008N). In other embodiments, the glutamic acid residue at position 1008 is replaced by an alanine residue (E1008A). In other embodiments, the glutamic acid residue at position 1008 is replaced by a Methionine residue (E1008M). In some embodiments, the glutamic acid residue at position 1008 is replaced by a leucine residue (E1008L).

In some embodiments, to improve editing efficiency, the adenosine deaminase may comprise one or more of the mutations: E1007S, E1007A, E1007V, E1008Q, E1008R, E1008H, E1008M, E1008N, E1008K, based on amino acid sequence positions of hADAR1-D, and mutations in a homologous ADAR protein corresponding to the above.

In some embodiments, to reduce editing efficiency, the adenosine deaminase may comprise one or more of the mutations: E1007R, E1007K, E1007Y, E1007L, E1007T, E1008G, E10081, E1008P, E1008V, E1008F, E1008W, E1008S, E1008N, E1008K, based on amino acid sequence positions of hADAR1-D, and mutations in a homologous ADAR protein corresponding to the above.

In some embodiments, the substrate editing preference, efficiency and/or selectivity of an adenosine deaminase is affected by amino acid residues near or in the active center of the enzyme. In some embodiments, the adenosine deaminase comprises a mutation at the glutamic acid 1008 position in hADAR1-D sequence, or a corresponding position in a homologous ADAR protein. In some embodiments, the mutation is E1008R, or a corresponding mutation in a homologous ADAR protein. In some embodiments, the E1008R mutant has an increased editing efficiency for target adenosine residue that has a mismatched G residue on the opposite strand.

In some embodiments, the adenosine deaminase protein further comprises or is connected to one or more double-stranded RNA (dsRNA) binding motifs (dsRBMs) or domains (dsRBDs) for recognizing and binding to double-stranded nucleic acid substrates. In some embodiments, the interaction between the adenosine deaminase and the double-stranded substrate is mediated by one or more additional proteins, including a CRISPR/CAS protein described elsewhere herein, including but not limited to one or more Cas (e.g. Cas9 and/or Cas12) proteins. In some embodiments, the interaction between the adenosine deaminase and the double-stranded substrate is further mediated by one or more nucleic acid component(s), including a guide RNA.

In certain example embodiments, directed evolution may be used to design modified ADAR proteins capable of catalyzing additional reactions besides deamination of an adenine to a hypoxanthine.

4. Modified Adenosine Deaminase Having C to U Deamination Activity

In certain example embodiments, directed evolution may be used to design modified ADAR proteins capable of catalyzing additional reactions besides deamination of an adenine to a hypoxanthine. For example, the modified ADAR protein may be capable of catalyzing deamination of a cytidine to a uracil. While not bound by a particular theory, mutations that improve C to U activity may alter the shape of the binding pocket to be more amenable to the smaller cytidine base.

In certain embodiments the adenosine deaminase is engineered to convert the activity to cytidine deaminase. Such engineered adenosine deaminase may also retain its adenosine deaminase activity, i.e., such mutated adenosine deaminase may have both adenosine deaminase and cytidine deaminase activities. Accordingly in some embodiments, the adenosine deaminase comprises one or more mutations in positions selected from E396, C451, V351, R455, T375, K376, S486, Q488, R510, K594, R348, G593, S397, H443, L444, Y445, F442, E438, T448, A353, V355, T339, P539, T339, P539, V525 1520, P462 and N579. In particular embodiments, the adenosine deaminase comprises one or more mutations in a position selected from V351, L444, V355, V525 and 1520. In some embodiments, the adenosine deaminase may comprise one or more of mutations at E488, V351, S486, T375, S370, P462, N597, based on amino acid sequence positions of hADAR2-D, and mutations in a homologous ADAR protein corresponding to the above.

In some embodiments, the adenosine deaminase may comprise one or more of the mutations: E488Q based on amino acid sequence positions of hADAR2-D, and mutations in a homologous ADAR protein corresponding to the above. In some embodiments, the adenosine deaminase may comprise one or more of the mutations: E488Q, V351G, based on amino acid sequence positions of hADAR2-D, and mutations in a homologous ADAR protein corresponding to the above. In some embodiments, the adenosine deaminase may comprise one or more of the mutations: E488Q, V351G, S486A, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L3321, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L3321, I398V, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L3321, I398V, K3501, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L3321, I398V, K3501, M383L, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L3321, I398V, K3501, M383L, D619G, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L3321, I398V, K3501, M383L, D619G, S582T, based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L3321, I398V, K3501, M383L, D619G, S582T, V4401 based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L3321, I398V, K3501, M383L, D619G, S582T, V4401, S495N based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L3321, I398V, K3501, M383L, D619G, S582T, V4401, S495N, K418E based on amino acid sequence positions of hADAR2-D, and mutations in a homologous ADAR protein corresponding to the above. In some embodiments, the adenosine deaminase may comprise one or more of the mutations: E488Q, V351G, S486A, T375S, S370C, P462A, N597I, L3321, I398V, K3501, M383L, D619G, S582T, V4401, S495N, K418E, S661T based on amino acid sequence positions of hADAR2-D, and mutations in a homologous ADAR protein corresponding to the above. In some examples, provided herein includes a mutated adenosine deaminase e.g., an adenosine deaminase comprising one or more mutations of E488Q, V351G, S486A, T375S, S370C, P462A, N597I, L3321, I398V, K3501, M383L, D619G, S582T, V4401, S495N, K418E, S661T, fused with a CRISPR-Cas protein (e.g. a Cas protein (e.g. Cas9 and/or Cas12), dead CRISPR-Cas protein and/or CRISPR-Cas nickase) described elsewhere herein. In a particular example, provided herein includes a mutated adenosine deaminase e.g., an adenosine deaminase comprising E488Q, V351G, S486A, T375S, S370C, P462A, N597I, L3321, I398V, K3501, M383L, D619G, S582T, V4401, S495N, K418E, and S661T, fused with a CRISPR-Cas protein (e.g. a Cas protein (e.g. Cas9 and/or Cas12), dead CRISPR-Cas protein and/or CRISPR-Cas nickase) described elsewhere herein.

In some embodiments, the modified adenosine deaminase having C-to-U deamination activity comprises a mutation at any one or more of positions V351, T375, R455, and E488 of the hADAR2-D amino acid sequence, or a corresponding position in a homologous ADAR protein. In some embodiments, the adenosine deaminase comprises mutation E488Q. In some embodiments, the adenosine deaminase comprises one or more of mutations selected from V351I, V351L, V351F, V351M, V351C, V351A, V351G, V351P, V351T, V351S, V351Y, V351W, V351Q, V351N, V351H, V351E, V351D, V351K, V351R, T375I, T375L, T375V, T375F, T375M, T375C, T375A, T375G, T375P, T375S, T375Y, T375W, T375Q, T375N, T375H, T375E, T375D, T375K, T375R, R455I, R455L, R455V, R455F, R455M, R455C, R455A, R455G, R455P, R455T, R455S, R455Y, R455W, R455Q, R455N, R455H, R455E, R455D, R455K. In some embodiments, the adenosine deaminase comprises mutation E488Q, and further comprises one or more of mutations selected from V351I, V351L, V351F, V351M, V351C, V351A, V351G, V351P, V351T, V351S, V351Y, V351W, V351Q, V351N, V351H, V351E, V351D, V351K, V351R, T375I, T375L, T375V, T375F, T375M, T375C, T375A, T375G, T375P, T375S, T375Y, T375W, T375Q, T375N, T375H, T375E, T375D, T375K, T375R, R455I, R455L, R455V, R455F, R455M, R455C, R455A, R455G, R455P, R455T, R455S, R455Y, R455W, R455Q, R455N, R455H, R455E, R455D, R455K.

In connection with the aforementioned deaminases, including modified ADAR proteins having C-to-U deamination activity, the invention described herein also relates to a method for deaminating a C in a target RNA sequence of interest, comprising delivering to a target RNA or DNA an AD-functionalized composition disclosed herein.

In certain example embodiments, the method for deaminating a C in a target RNA sequence comprising delivering to said target RNA: (a) a Cas protein described herein; (b) a guide molecule which comprises a guide sequence linked to a direct repeat sequence; and (c) a deaminase, (including but not limited to an ADAR protein (including but not limited to a modified ADAR protein having C-to-U deamination activity or catalytic domain thereof); wherein said modified ADAR protein or catalytic domain thereof is covalently or non-covalently linked to said Cas protein or said guide molecule or is adapted to link thereto after delivery; wherein guide molecule forms a complex with said Cas protein and directs said complex to bind said target RNA sequence of interest; wherein said guide sequence is capable of hybridizing with a target sequence comprising said C to form an RNA duplex; wherein, optionally, said guide sequence comprises a non-pairing A or U at a position corresponding to said C resulting in a mismatch in the RNA duplex formed; and wherein said modified ADAR protein or catalytic domain thereof deaminates said C in said RNA duplex.

In connection with the aforementioned modified ADAR protein having C-to-U deamination activity, the invention described herein further relates to an engineered, non-naturally occurring system suitable for deaminating a C in a target locus of interest, comprising: (a) a guide molecule which comprises a guide sequence linked to a direct repeat sequence, or a nucleotide sequence encoding said guide molecule; (b) a catalytically inactive CRISPR-Cas protein, or a nucleotide sequence encoding said catalytically inactive CRISPR-Cas protein; (c) a modified ADAR protein having C-to-U deamination activity or catalytic domain thereof, or a nucleotide sequence encoding said modified ADAR protein or catalytic domain thereof; wherein said modified ADAR protein or catalytic domain thereof is covalently or non-covalently linked to said CRISPR-Cas protein or said guide molecule or is adapted to link thereto after delivery; wherein said guide sequence is capable of hybridizing with a target RNA sequence comprising a C to form an RNA duplex; wherein, optionally, said guide sequence comprises a non-pairing A or U at a position corresponding to said C resulting in a mismatch in the RNA duplex formed; wherein, optionally, the system is a vector system comprising one or more vectors comprising: (a) a first regulatory element operably linked to a nucleotide sequence encoding said guide molecule which comprises said guide sequence, (b) a second regulatory element operably linked to a nucleotide sequence encoding said catalytically inactive CRISPR-Cas protein; and (c) a nucleotide sequence encoding a modified ADAR protein having C-to-U deamination activity or catalytic domain thereof which is under control of said first or second regulatory element or operably linked to a third regulatory element; wherein, if said nucleotide sequence encoding a modified ADAR protein or catalytic domain thereof is operably linked to a third regulatory element, said modified ADAR protein or catalytic domain thereof is adapted to link to said guide molecule or said CRISPR-Cas protein after expression; wherein components (a), (b) and (c) are located on the same or different vectors of the system, optionally wherein said first, second, and/or third regulatory element is an inducible promoter.

In an embodiment of the invention, the substrate of the adenosine deaminase is an RNA/DNA heteroduplex formed upon binding of the guide molecule to its DNA target which then forms the CRISPR-Cas complex with the CRISPR-Cas enzyme. The RNA/DNA or DNA/RNA heteroduplex is also referred to herein as the “RNA/DNA hybrid”, “DNA/RNA hybrid” or “double-stranded substrate”.

According to the present invention, the substrate of the adenosine deaminase is an RNA/DNAn RNA duplex formed upon binding of the guide molecule to its DNA target which then forms the CRISPR-Cas complex with the CRISPR-Cas enzyme. The substrate of the adenosine deaminase can also be an RNA/RNA duplex formed upon binding of the guide molecule to its RNA target which then forms the CRISPR-Cas complex with the CRISPR-Cas enzyme. The RNA/DNA or DNA/RNAn RNA duplex is also referred to herein as the “RNA/DNA hybrid”, “DNA/RNA hybrid” or “double-stranded substrate”. The particular features of the guide molecule and CRISPR-Cas enzyme are detailed below.

The term “editing selectivity” as used herein refers to the fraction of all sites on a double-stranded substrate that is edited by an adenosine deaminase. Without being bound by theory, it is contemplated that editing selectivity of an adenosine deaminase is affected by the double-stranded substrate’s length and secondary structures, such as the presence of mismatched bases, bulges and/or internal loops.

In some embodiments, when the substrate is a perfectly base-paired duplex longer than 50 bp, the adenosine deaminase may be able to deaminate multiple adenosine residues within the duplex (e.g., 50% of all adenosine residues). In some embodiments, when the substrate is shorter than 50 bp, the editing selectivity of an adenosine deaminase is affected by the presence of a mismatch at the target adenosine site. Particularly, in some embodiments, adenosine (A) residue having a mismatched cytidine (C) residue on the opposite strand is deaminated with high efficiency. In some embodiments, adenosine (A) residue having a mismatched guanosine (G) residue on the opposite strand is skipped without editing.

In particular embodiments, the adenosine deaminase protein or catalytic domain thereof is delivered to the cell or expressed within the cell as a separate protein, but is modified so as to be able to link to either the Cas protein described herein (e.g. Cas (e.g. Cas9-lik and/or Cas12) protein or the guide molecule. In particular embodiments, this is ensured by the use of orthogonal RNA-binding protein or adaptor protein/aptamer combinations that exist within the diversity of bacteriophage coat proteins. Examples of such coat proteins include but are not limited to: MS2, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s and PRR1. Aptamers can be naturally occurring or synthetic oligonucleotides that have been engineered through repeated rounds of in vitro selection or SELEX (systematic evolution of ligands by exponential enrichment) to bind to a specific target.

In particular embodiments, the guide molecule is provided with one or more distinct RNA loop(s) or distinct sequence(s) that can recruit an adaptor protein. A guide molecule may be extended, without colliding with the Cas protein described herein (e.g. Cas (e.g. Cas9 and/or Cas12) protein by the insertion of distinct RNA loop(s) or distinct sequence(s) that may recruit adaptor proteins that can bind to the distinct RNA loop(s) or distinct sequence(s). Examples of modified guides and their use in recruiting effector domains to the C2c1 complex are provided in Konermann (Nature 2015, 517(7536): 583-588), which can be used to similarly design and construct guides for use with a Cas protein described herein (e.g. Cas (e.g. Cas9 and/or Cas12) protein in view of the description provided herein. In particular embodiments, the aptamer is a minimal hairpin aptamer which selectively binds dimerized MS2 bacteriophage coat proteins in mammalian cells and is introduced into the guide molecule, such as in the stemloop and/or in a tetraloop. In these embodiments, the adenosine deaminase protein is fused to MS2. The adenosine deaminase protein is then co-delivered together with the C2c1 protein and corresponding guide RNA.

In some embodiments, the C2c1-ADAR, Cas-ADAR, Cas protein-ADAR base editing system described herein comprises (a) one Cas protein described herein (e.g. Cas (e.g. Cas9 and/or Cas12, and/or C2c1) which is catalytically inactive or a nickase; (b) a guide molecule which comprises a guide sequence; and (c) an adenosine deaminase protein or catalytic domain thereof; wherein the adenosine deaminase protein or catalytic domain thereof is covalently or non-covalently linked to the Cas protein described herein (e.g. Cas (e.g. Cas9 and/or Cas12, and/or C2c1) or the guide molecule or is adapted to link thereto after delivery; wherein the guide sequence is substantially complementary to the target sequence but comprises a non-pairing C corresponding to the A being targeted for deamination, resulting in a A-C mismatch in a DNA-RNA or RNA-RNA duplex formed by the guide sequence and the target sequence. For application in eukaryotic cells, the Cas protein described herein (e.g. Cas (e.g. Cas9 and/or Cas12, and/or C2c1) and/or the adenosine deaminase are preferably NLS-tagged.

In some embodiments, the components (a), (b) and (c) are delivered to the cell as a ribonucleoprotein complex. The ribonucleoprotein complex can be delivered via one or more lipid nanoparticles.

In some embodiments, the components (a), (b) and (c) are delivered to the cell as one or more RNA molecules, such as one or more guide RNAs and one or more mRNA molecules encoding the Cas, ADAR, or Cas-ADAR protein, the adenosine deaminase protein, and optionally the adaptor protein. The RNA molecules can be delivered via one or more lipid nanoparticles.

In some embodiments, the components (a), (b) and (c) are delivered to the cell as one or more DNA molecules. In some embodiments, the one or more DNA molecules are comprised within one or more vectors such as viral vectors (e.g., AAV). In some embodiments, the one or more DNA molecules comprise one or more regulatory elements operably configured to express the Cas, ADAR, or Cas-ADAR protein, the guide molecule, and the adenosine deaminase protein or catalytic domain thereof, optionally wherein the one or more regulatory elements comprise inducible promoters.

In some embodiments of the guide molecule is capable of hybridizing with a target sequence comprising the Adenine to be deaminated within a first DNA strand or an RNA strand at the target locus to form a DNA-RNA or RNA-RNA duplex which comprises a non-pairing Cytosine opposite to said Adenine. In some embodiments, upon duplex formation, the guide molecule forms a complex with one or more Cas proteins described herein and directs the complex to bind said first DNA strand or said RNA strand at the target locus of interest. Details on the embodiment of the guide of the C2c1-ADAR base editing system are provided herein below.

In some embodiments, a C2c1 guide RNA having a canonical length (e.g., about 20 nt for AacC2c1) is used to form a DNA-RNA or RNA-RNA duplex with the target DNA or RNA. In some embodiments, a C2c1 guide molecule longer than the canonical length (e.g., >20 nt for AacC2c1) is used to form a DNA-RNA or RNA-RNA duplex with the target DNA or RNA including outside of the C2c1-guide RNA-target DNA complex. In certain example embodiments, the guide sequence has a length of about 29-53 nt capable of forming a DNA-RNA or RNA-RNA duplex with said target sequence. In certain other example embodiments, the guide sequence has a length of about 40-50 nt capable of forming a DNA-RNA or RNA-RNA duplex with said target sequence. In certain example embodiments, the distance between said non-pairing C and the 5' end of said guide sequence is 20-30 nucleotides. In certain example embodiments, the distance between said non-pairing C and the 3' end of said guide sequence is 20-30 nucleotides.

In at least a first design, the Cas protein (includes any cas protein, including but not limited to C2c1 and Cas proteins)-ADAR system comprises (a) an adenosine deaminase fused or linked to a Cas protein, wherein the Cas protein is catalytically inactive or a nickase, and (b) a guide molecule comprising a guide sequence designed to introduce a A-C mismatch in a DNA-RNA or RNA-RNA duplex formed between the guide sequence and the target sequence. In some embodiments, the Cas protein and/or the adenosine deaminase are NLS-tagged, on either the N- or C-terminus or both.

In at least a second design, the Cas-ADAR system comprises (a) a Cas protein that is catalytically inactive or a nickase, (b) a guide molecule comprising a guide sequence designed to introduce a A-C mismatch in a DNA-RNA or RNA-RNA duplex formed between the guide sequence and the target sequence, and an aptamer sequence (e.g., MS2 RNA motif or PP7 RNA motif) capable of binding to an adaptor protein (e.g., MS2 coating protein or PP7 coat protein), and (c) an adenosine deaminase fused or linked to an adaptor protein, wherein the binding of the aptamer and the adaptor protein recruits the adenosine deaminase to the DNA-RNA or RNA-RNA duplex formed between the guide sequence and the target sequence for targeted deamination at the A of the A-C mismatch. In some embodiments, the adaptor protein and/or the adenosine deaminase are NLS-tagged, on either the N- or C-terminus or both. The Cas protein can also be NLS-tagged.

The use of different aptamers and corresponding adaptor proteins also allows orthogonal gene editing to be implemented. In one example in which adenosine deaminase are used in combination with cytidine deaminase for orthogonal gene editing/deamination, sgRNA targeting different loci are modified with distinct RNA loops in order to recruit MS2-adenosine deaminase and PP7-cytidine deaminase (or PP7-adenosine deaminase and MS2-cytidine deaminase), respectively, resulting in orthogonal deamination of A or C at the target loci of interested, respectively. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. For example, an sgRNA targeting locus A can be modified with MS2 loops, recruiting MS2-adenosine deaminase, while another sgRNA targeting locus B can be modified with PP7 loops, recruiting PP7-cytidine deaminase. In the same cell, orthogonal, locus-specific modifications are thus realized. This principle can be extended to incorporate other orthogonal RNA-binding proteins.

In at least a third design, the Cas-ADAR CRISPR system comprises (a) an adenosine deaminase inserted into an internal loop or unstructured region of a Cas protein, wherein the Cas protein is catalytically inactive or a nickase, and (b) a guide molecule comprising a guide sequence designed to introduce a A-C mismatch in a DNA-RNA or RNA-RNA duplex formed between the guide sequence and the target sequence.

C2c1 protein split sites that are suitable for insertion of adenosine deaminase can be identified with the help of a crystal structure. For example, with respect to AacC2c1 mutants, it should be readily apparent what the corresponding position for, for example, a sequence alignment. For other C2c1 protein one can use the crystal structure of an ortholog if a relatively high degree of homology exists between the ortholog and the intended C2c1 protein. Homologous appropriate split sites can be determined in other Cas proteins (e.g. Cas9 and/or Cas12) based on corresponding sites in the other Cas proteins compared to C2c1 protein. Methods of alignment and determining homologous sites are described elsewhere herein.

The split position may be located within a region or loop. Preferably, the split position occurs where an interruption of the amino acid sequence does not result in the partial or full destruction of a structural feature (e.g. alpha-helixes or (β-sheets). Unstructured regions (regions that did not show up in the crystal structure because these regions are not structured enough to be “frozen” in a crystal) are often preferred options. Splits in all unstructured regions that are exposed on the surface of the Cas protein (e.g. a Cas protein (e.g. Cas9 and/or Cas12 or C2c1) are envisioned in the practice of the invention. The positions within the unstructured regions or outside loops may not need to be exactly the numbers provided above, but may vary by, for example 1, 2, 3, 4, 5, 6, 7, 8, 9, or even 10 amino acids either side of the position given above, depending on the size of the loop, so long as the split position still falls within an unstructured region of outside loop.

The Cas-ADAR system described herein can be used to target a specific Adenine within a DNA sequence for deamination. For example, the guide molecule can form a complex with the Cas protein and directs the complex to bind a target sequence at the target locus of interest. Because the guide sequence is designed to have a non-pairing C, the heteroduplex formed between the guide sequence and the target sequence comprises a A-C mismatch, which directs the adenosine deaminase to contact and deaminate the A opposite to the non-pairing C, converting it to a Inosine (I). Since Inosine (I) base pairs with C and functions like G in cellular process, the targeted deamination of A described herein are useful for correction of undesirable G-A and C-T mutations, as well as for obtaining desirable A-G and T-C mutations.

5. Base Excision Repair Inhibitor

In some embodiments, the D-functionalized and/or AD-functionalized CRISPR system (i.e. a CRISPR system described herein containing an deaminase (D) or adenosine deaminase (AD)) further comprises a base excision repair (BER) inhibitor. The BER can be configured as an activatable functional domain as described elsewhere herein. In some embodiments, the BER is configured in a matched pair of activatable functional domains as a split protein between the two domains in the matched pair. Other configurations within a matched pair of activatable functional domain are also envisioned and as described elsewhere herein.

Without wishing to be bound by any particular theory, cellular DNA-repair response to the presence of I:T pairing may be responsible for a decrease in nucleobase editing efficiency in cells. Alkyladenine DNA glycosylase (also known as DNA-3-methyladenine glycosylase, 3-alkyladenine DNA glycosylase, or N-methylpurine DNA glycosylase) catalyzes removal of hypoxanthine from DNA in cells, which may initiate base excision repair, with reversion of the I:T pair to a A:T pair as outcome.

In some embodiments, the BER inhibitor is an inhibitor of alkyladenine DNA glycosylase. In some embodiments, the BER inhibitor is an inhibitor of human alkyladenine DNA glycosylase. In some embodiments, the BER inhibitor is a polypeptide inhibitor. In some embodiments, the BER inhibitor is a protein that binds hypoxanthine. In some embodiments, the BER inhibitor is a protein that binds hypoxanthine in DNA. In some embodiments, the BER inhibitor is a catalytically inactive alkyladenine DNA glycosylase protein or binding domain thereof. In some embodiments, the BER inhibitor is a catalytically inactive alkyladenine DNA glycosylase protein or binding domain thereof that does not excise hypoxanthine from the DNA. Other proteins that are capable of inhibiting (e.g., sterically blocking) an alkyladenine DNA glycosylase base-excision repair enzyme are within the scope of this disclosure. Additionally, any proteins that block or inhibit base-excision repair as also within the scope of this disclosure.

Without wishing to be bound by any particular theory, base excision repair may be inhibited by molecules that bind the edited strand, block the edited base, inhibit alkyladenine DNA glycosylase, inhibit base excision repair, protect the edited base, and/or promote fixing of the non-edited strand. It is believed that the use of the BER inhibitor described herein can increase the editing efficiency of an adenosine deaminase that is capable of catalyzing a A to I change.

Accordingly, in the first design of the AD-functionalized CRISPR system discussed above, the CRISPR-Cas protein or the adenosine deaminase can be fused to or linked to a BER inhibitor (e.g., an inhibitor of alkyladenine DNA glycosylase).

In some embodiments, the BER inhibitor can be comprised in one of the following structures (Cas protein=any suitable Cas protein (e.g. C2c1 and variants thereof and Cas proteins (e.g. Cas9 and/or Cas12 and variants thereof): [AD]-[optional linker]-[Cas protein]-[optional linker]-[BER inhibitor]; [AD]-[optional linker]-[BER inhibitor]-[optional linker]-[Cas protein]; [BER inhibitor]-[optional linker]-[AD]-[optional linker]-[Cas protein]; [BER inhibitor]-[optional linker]-[nC2c1/dC2c1]-[optional linker]-[AD]; [Cas protein]-[optional linker]-[AD]-[optional linker]-[BER inhibitor]; [Cas protein]-[optional linker]-[BER inhibitor]-[optional linker]-[AD].

In some embodiments, the BER inhibitor can be comprised in one of the following structures (nC2c1=C2c1 nickase; dC2c1=dead C2c1): [AD]-[optional linker]-[nC2c1/dC2c1]-[optional linker]-[BER inhibitor]; [AD]-[optional linker]-[BER inhibitor]-[optional linker]-[nC2c1/dC2c1]; [BER inhibitor]-[optional linker]-[AD]-[optional linker]-[nC2c1/dC2c1]; [BER inhibitor]-[optional linker]-[nC2c1/dC2c1]-[optional linker]-[AD]; [nC2c1/dC2c1]-[optional linker]-[AD]-[optional linker]-[BER inhibitor]; [nC2c1/dC2c1]-[optional linker]-[BER inhibitor]-[optional linker]-[AD].

Similarly, in the second design of the AD-functionalized CRISPR system discussed above, the CRISPR-Cas protein, the adenosine deaminase, or the adaptor protein can be fused to or linked to a BER inhibitor (e.g., an inhibitor of alkyladenine DNA glycosylase).

In some embodiments, the BER inhibitor can be comprised in one of the following structures (Cas protein=any suitable Cas protein (e.g. C2c1 and variants thereof and Cas proteins (e.g. Cas9 and/or Cas12 and variants thereof): [Cas Protein]-[optional linker]-[BER inhibitor]; [BER inhibitor]-[optional linker]-[Cas Protein]; [AD]-[optional linker]-[Adaptor]-[optional linker]-[BER inhibitor]; [AD]-[optional linker]-[BER inhibitor]-[optional linker]-[Adaptor]; [BER inhibitor]-[optional linker]-[AD]-[optional linker]-[Adaptor]; [BER inhibitor]-[optional linker]-[Adaptor]-[optional linker]-[AD]; [Adaptor]-[optional linker]-[AD]-[optional linker]-[BER inhibitor]; [Adaptor]-[optional linker]-[BER inhibitor]-[optional linker]-[AD].

In some embodiments, the BER inhibitor can be comprised in one of the following structures (nC2c1=C2c1 nickase; dC2c1=dead C2c1): [nC2c1/dC2c1]-[optional linker]-[BER inhibitor]; [BER inhibitor]-[optional linker]-[nC2c1/dC2c1]; [AD]-[optional linker]-[Adaptor]-[optional linker]-[BER inhibitor]; [AD]-[optional linker]-[BER inhibitor]-[optional linker]-[Adaptor]; [BER inhibitor]-[optional linker]-[AD]-[optional linker]-[Adaptor]; [BER inhibitor]-[optional linker]-[Adaptor]-[optional linker]-[AD]; [Adaptor]-[optional linker]-[AD]-[optional linker]-[BER inhibitor]; [Adaptor]-[optional linker]-[BER inhibitor]-[optional linker]-[AD].

In the third design of the AD-functionalized CRISPR system discussed above, the BER inhibitor can be inserted into an internal loop or unstructured region of a CRISPR-Cas protein.

6. Cytidine Deaminase

In some embodiments, the deaminase is a cytidine deaminase. In some embodiments, the cytidine deaminase is configured in a matched pair of activatable functional domains as a split protein between the two domains in the matched pair. Other configurations within a matched pair of activatable functional domain are also envisioned and as described elsewhere herein.

The term "cytidine deaminase" or "cytidine deaminase protein" or "cytidine deaminase activity" as used herein refers to a protein, a polypeptide, or one or more functional domain(s) of a protein or a polypeptide that is capable of catalyzing a hydrolytic deamination reaction that converts an cytosine (or an cytosine moiety of a molecule) to an uracil (or a uracil moiety of a molecule), as shown below. In some embodiments, the cytosine-containing molecule is a cytidine (C), and the uracil-containing molecule is an uridine (U). The cytosine-containing molecule can be deoxyribonucleic acid (DNA) or ribonucleic acid (RNA).

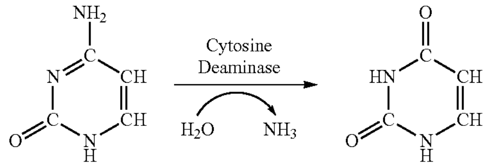

Cytosine (4-amino-2-oxopyrimidine) Uracil (2,4-dioxopyrimidine)

According to the present disclosure, cytidine deaminases that can be used in connection with the present disclosure include, but are not limited to, members of the enzyme family known as apolipoprotein B mRNA-editing complex (APOBEC) family deaminase, an activation-induced deaminase (AID), or a cytidine deaminase 1 (CDA1). In particular embodiments, the deaminase in an APOBEC1 deaminase, an APOBEC2 deaminase, an APOBEC3A deaminase, an APOBEC3B deaminase, an APOBEC3C deaminase, and APOBEC3D deaminase, an APOBEC3E deaminase, an APOBEC3F deaminase an APOBEC3G deaminase, an APOBEC3H deaminase, or an APOBEC4 deaminase.

In the methods and systems of the present invention, the cytidine deaminase or engineered adenosine deaminase with cytidine deaminase activity is capable of targeting Cytosine in a DNA single strand. In certain example embodiments the cytidine deaminase activity may edit on a single strand present outside of the binding component e.g. bound CRISPR-Cas. In other example embodiments, the cytidine deaminase may edit at a localized bubble, such as a localized bubble formed by a mismatch at the target edit site but the guide sequence. In certain example embodiments the cytodine deaminase may contain mutations that help focus the area of activity such as those disclosed in Kim et al., Nature Biotechnology (2017) 35(4):371-377 (doi:10.1038/nbt.3803.

In some embodiments, the cytidine deaminase is derived from one or more metazoa species, including but not limited to, mammals, birds, frogs, squids, fish, flies and worms. In some embodiments, the cytidine deaminase is a human, primate, cow, dog rat or mouse cytidine deaminase.

In some embodiments, the cytidine deaminase is a human APOBEC, including hAPOBEC1 or hAPOBEC3. In some embodiments, the cytidine deaminase is a human AID.

In some embodiments, the cytidine deaminase protein recognizes and converts one or more target cytosine residue (s) in a single-stranded bubble of a RNA duplex into uracil residues (s). In some embodiments, the cytidine deaminase protein recognizes a binding window on the single-stranded bubble of a RNA duplex. In some embodiments, the binding window contains at least one target cytosine residue(s). In some embodiments, the binding window is in the range of about 3 bp to about 100 bp. In some embodiments, the binding window is in the range of about 5 bp to about 50 bp. In some embodiments, the binding window is in the range of about 10 bp to about 30 bp. In some embodiments, the binding window is about 1 bp, 2 bp, 3 bp, 5 bp, 7 bp, 10 bp, 15 bp, 20 bp, 25 bp, 30 bp, 40 bp, 45 bp, 50 bp, 55 bp, 60 bp, 65 bp, 70 bp, 75 bp, 80 bp, 85 bp, 90 bp, 95 bp, or 100 bp.

In some embodiments, the cytidine deaminase protein comprises one or more deaminase domains. Not intended to be bound by theory, it is contemplated that the deaminase domain functions to recognize and convert one or more target cytosine (C) residue(s) contained in a single-stranded bubble of a RNA duplex into (an) uracil (U) residue (s). In some embodiments, the deaminase domain comprises an active center. In some embodiments, the active center comprises a zinc ion. In some embodiments, amino acid residues in or near the active center interact with one or more nucleotide(s) 5' to a target cytosine residue. In some embodiments, amino acid residues in or near the active center interact with one or more nucleotide(s) 3' to a target cytosine residue.

In some embodiments, the cytidine deaminase comprises human APOBEC1 full protein (hAPOBEC1) or the deaminase domain thereof (hAPOBEC1-D) or a C-terminally truncated version thereof (hAPOBEC-T). In some embodiments, the cytidine deaminase is an APOBEC family member that is homologous to hAPOBEC1, hAPOBEC-D or hAPOBEC-T. In some embodiments, the cytidine deaminase comprises human AID1 full protein (hAID) or the deaminase domain thereof (hAID-D) or a C-terminally truncated version thereof (hAID-T). In some embodiments, the cytidine deaminase is an AID family member that is homologous to hAID, hAID-D or hAID-T. In some embodiments, the hAID-T is a hAID which is C-terminally truncated by about 20 amino acids.

In some embodiments, the cytidine deaminase comprises the wild-type amino acid sequence of a cytosine deaminase. In some embodiments, the cytidine deaminase comprises one or more mutations in the cytosine deaminase sequence, such that the editing efficiency, and/or substrate editing preference of the cytosine deaminase is changed according to specific needs.

Certain mutations of APOBEC1 and APOBEC3 proteins have been described in Kim et al., Nature Biotechnology (2017) 35(4):371-377 (doi:10.1038/nbt.3803); and Harris et al. Mol. Cell (2002) 10:1247-1253, each of which is incorporated herein by reference in its entirety.

In some embodiments, the cytidine deaminase is an APOBEC1 deaminase comprising one or more mutations at amino acid positions corresponding to W90, R118, H121, H122, R126, or R132 in rat APOBEC1, or an APOBEC3G deaminase comprising one or more mutations at amino acid positions corresponding to W285, R313, D316, D317X, R320, or R326 in human APOBEC3 G.

In some embodiments, the cytidine deaminase comprises a mutation at tryptophane90 of the rat APOBEC1 amino acid sequence, or a corresponding position in a homologous APOBEC protein, such as tryptophane285 of APOBEC3G. In some embodiments, the tryptophane residue at position 90 is replaced by an tyrosine or phenylalanine residue (W90Y or W90F).

In some embodiments, the cytidine deaminase comprises a mutation at Arginine118 of the rat APOBEC1 amino acid sequence, or a corresponding position in a homologous APOBEC protein. In some embodiments, the arginine residue at position 118 is replaced by an alanine residue (R118A).

In some embodiments, the cytidine deaminase comprises a mutation at Histidine121 of the rat APOBEC1 amino acid sequence, or a corresponding position in a homologous APOBEC protein. In some embodiments, the histidine residue at position 121 is replaced by an arginine residue (H121R).

In some embodiments, the cytidine deaminase comprises a mutation at Histidine122 of the rat APOBEC1 amino acid sequence, or a corresponding position in a homologous APOBEC protein. In some embodiments, the histidine residue at position 122 is replaced by an arginine residue (H122R).

In some embodiments, the cytidine deaminase comprises a mutation at Arginine126 of the rat APOBEC1 amino acid sequence, or a corresponding position in a homologous APOBEC protein, such as Arginine320 of APOBEC3G. In some embodiments, the arginine residue at position 126 is replaced by an alanine residue (R126A) or by a glutamic acid (R126E).

In some embodiments, the cytidine deaminase comprises a mutation at arginine132 of the APOBEC1 amino acid sequence, or a corresponding position in a homologous APOBEC protein. In some embodiments, the arginine residue at position 132 is replaced by a glutamic acid residue (R132E).

In some embodiments, to narrow the width of the editing window, the cytidine deaminase may comprise one or more of the mutations: W90Y, W90F, R126E and R132E, based on amino acid sequence positions of rat APOBEC1, and mutations in a homologous APOBEC protein corresponding to the above.

In some embodiments, to reduce editing efficiency, the cytidine deaminase may comprise one or more of the mutations: W90A, R118A, R132E, based on amino acid sequence positions of rat APOBEC1, and mutations in a homologous APOBEC protein corresponding to the above. In particular embodiments, it can be of interest to use a cytidine deaminase enzyme with reduced efficacy to reduce off-target effects.

In some embodiments, the cytidine deaminase is wild-type rat APOBEC1 (rAPOBEC1, or a catalytic domain thereof. In some embodiments, the cytidine deaminase comprises one or more mutations in the rAPOBEC1 sequence, such that the editing efficiency, and/or substrate editing preference of rAPOBEC1 is changed according to specific needs.

```
rAPOBEC1:
                                         (SEQ ID NO: 21)
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLK
```

In some embodiments, the cytidine deaminase is wild-type human APOBEC1 (hAPOBEC1) or a catalytic domain thereof. In some embodiments, the cytidine deaminase comprises one or more mutations in the hAPOBEC1 sequence, such that the editing efficiency, and/or substrate editing preference of hAPOBEC1 is changed according to specific needs.

```
APOBEC1:
                                         (SEQ ID NO: 22)
MTSEKGPSTGDPTLRRRIEPWEFDVFYDPRELRKEACLLYEIKWGMSRKI

WRSSGKNTTNHVEVNFIKKFTSERDFHPSMSCSITWFLSWSPCWECSQAI

REFLSRHPGVTLVIYVARLFWHMDQQNRQGLRDLVNSGVTIQIMRASEYY

HCWRNFVNYPPGDEAHWPQYPPLWMMLYALELHCIILSLPPCLKISRRWQ

NHLTFFRLHLQNCHYQTIPPHILLATGLIHPSVAWR
```

In some embodiments, the cytidine deaminase is wild-type human APOBEC3G (hAPOBEC3G) or a catalytic domain thereof. In some embodiments, the cytidine deaminase comprises one or more mutations in the hAPOBEC3G sequence, such that the editing efficiency, and/or substrate editing preference of hAPOBEC3G is changed according to specific needs.

```
hAPOBEC3G:
                                         (SEQ ID NO: 23)
MELKYHPEMRFFHWFSKWRKLHRDQEYEVTWYISWSPCTKCTRDMATFLA

EDPKVTLTIFVARLYYFWDPDYQEALRSLCQKRDGPRATMKIMNYDEFQH

CWSKFVYSQRELFEPWNNLPKYYILLHIMLGEILRHSMDPPTFTFNFNNE

PWVRGRHETYLCYEVERMHNDTWVLLNQRRGFLCNQAPHKHGFLEGRHAE
```

-continued

```
LCFLDVIPFWKLDLDQDYRVTCFTSWSPCFSCAQEMAKFISKNKHVSLCI

FTARIYDDQGRCQEGLRTLAEAGAKISIMTYSEFKHCWDTFVDHQGCPFQ

PWDGLDEHSQDLSGRLRAILQNQEN
```

In some embodiments, the cytidine deaminase is wild-type *Petromyzon marinus* CDA1 (pmCDA1) or a catalytic domain thereof. In some embodiments, the cytidine deaminase comprises one or more mutations in the pmCDA1 sequence, such that the editing efficiency, and/or substrate editing preference of pmCDA1 is changed according to specific needs.

```
pmCDA1:
                                         (SEQ ID NO: 24)
MTDAEYVRIHEKLDIYTFKKQFFNNKKSVSHRCYVLFELKRRGERRACFW

GYAVNKPQSGTERGIHAEIFSIRKVEEYLRDNPGQFTINWYSSWSPCADC

AEKILEWYNQELRGNGHTLKIWACKLYYEKNARNQIGLWNLRDNGVGLNV

MVSEHYQCCRKIFIQSSHNQLNENRWLEKTLKRAEKRRSELSIMIQVKIL

HTTKSPAV
```

In some embodiments, the cytidine deaminase is wild-type human AID (hAID) or a catalytic domain thereof. In some embodiments, the cytidine deaminase comprises one or more mutations in the pmCDA1 sequence, such that the editing efficiency, and/or substrate editing preference of pmCDA1 is changed according to specific needs.

```
hAID:
                                         (SEQ ID NO: 25)
MDSLLMNRRKFLYQFKNVRWAKGRRETYLCYVVKRRDSATSFSLDFGYLR

NKNGCHVELLFLRYISDWDLDPGRCYRVTWFTSWSPCYDCARHVADFLRG

NPYLSLRIFTARLYFCEDRKAEPEGLRRLHRAGVQIAIMTFKDYFYCWNT

FVENHERTFKAWEGLHENSVRLSRQLRRILLPLYEVDDLRDAFRTLGLLD
```

In some embodiments, the cytidine deaminase is truncated version of hAID (hAID-DC) or a catalytic domain thereof. In some embodiments, the cytidine deaminase comprises one or more mutations in the hAID-DC sequence, such that the editing efficiency, and/or substrate editing preference of hAID-DC is changed according to specific needs.

```
hAID-DC:
                                         (SEQ ID NO: 26)
MDSLLMNRRKFLYQFKNVRWAKGRRETYLCYVVKRRDSATSFSLDFGYLR

NKNGCHVELLFLRYISDWDLDPGRCYRVTWFTSWSPCYDCARHVADFLRG

NPNLSLRIFTARLYFCEDRKAEPEGLRRLHRAGVQIAIMTFKDYFYCWNT

FVENHERTFKAWEGLHENSVRLSRQLRRILL
```

Additional embodiments of the cytidine deaminase are disclosed in International Patent Publication No. WO WO2017/070632, titled "Nucleobase Editor and Uses Thereof," which is incorporated herein by reference in its entirety.

In some embodiments, the cytidine deaminase has an efficient deamination window that encloses the nucleotides susceptible to deamination editing. Accordingly, in some embodiments, the "editing window width" refers to the number of nucleotide positions at a given target site for which editing efficiency of the cytidine deaminase exceeds the half-maximal value for that target site. In some embodiments, the cytidine deaminase has an editing window width in the range of about 1 to about 6 nucleotides. In some embodiments, the editing window width of the cytidine deaminase is 1, 2, 3, 4, 5, or 6 nucleotides.

Not intended to be bound by theory, it is contemplated that in some embodiments, the length of the linker sequence affects the editing window width. In some embodiments, the editing window width increases (e.g., from about 3 to about 6 nucleotides) as the linker length extends (e.g., from about 3 to about 21 amino acids). In a non-limiting example, a 16-residue linker offers an efficient deamination window of about 5 nucleotides. In some embodiments, the length of the guide RNA affects the editing window width. In some embodiments, shortening the guide RNA leads to a narrowed efficient deamination window of the cytidine deaminase.

In some embodiments, mutations to the cytidine deaminase affect the editing window width. In some embodiments, the cytidine deaminase component of the CD-functionalized CRISPR system comprises one or more mutations that reduce the catalytic efficiency of the cytidine deaminase, such that the deaminase is prevented from deamination of multiple cytidines per DNA binding event. In some embodiments, tryptophan at residue 90 (W90) of APOBEC1 or a corresponding tryptophan residue in a homologous sequence is mutated. In some embodiments, the catalytically inactive CRISPR-Cas is fused to or linked to an APOBEC1 mutant that comprises a W90Y or W90F mutation. In some embodiments, tryptophan at residue 285 (W285) of APOBEC3G, or a corresponding tryptophan residue in a homologous sequence is mutated. In some embodiments, the catalytically inactive CRISPR-Cas is fused to or linked to an APOBEC3G mutant that comprises a W285Y or W285F mutation.

In some embodiments, the cytidine deaminase component of CD-functionalized CRISPR system comprises one or more mutations that reduce tolerance for non-optimal presentation of a cytidine to the deaminase active site. In some embodiments, the cytidine deaminase comprises one or more mutations that alter substrate binding activity of the deaminase active site. In some embodiments, the cytidine deaminase comprises one or more mutations that alter the conformation of DNA to be recognized and bound by the deaminase active site. In some embodiments, the cytidine deaminase comprises one or more mutations that alter the substrate accessibility to the deaminase active site. In some embodiments, arginine at residue 126 (R126) of APOBEC1 or a corresponding arginine residue in a homologous sequence is mutated. In some embodiments, the catalytically inactive CRISPR-Cas is fused to or linked to an APOBEC1 that comprises a R126A or R126E mutation. In some embodiments, tryptophan at residue 320 (R320) of APOBEC3G, or a corresponding arginine residue in a homologous sequence is mutated. In some embodiments, the catalytically inactive CRISPR-Cas is fused to or linked to an APOBEC3G mutant that comprises a R320A or R320E mutation. In some embodiments, arginine at residue 132 (R132) of APOBEC1 or a corresponding arginine residue in a homologous sequence is mutated. In some embodiments, the catalytically inactive CRISPR-Cas is fused to or linked to an APOBEC1 mutant that comprises a R132E mutation.

In some embodiments, the APOBEC1 domain of the CD-functionalized CRISPR system comprises one, two, or three mutations selected from W90Y, W90F, R126A, R126E, and R132E. In some embodiments, the APOBEC1 domain comprises double mutations of W90Y and R126E. In some embodiments, the APOBEC1 domain comprises double mutations of W90Y and R132E. In some embodiments, the APOBEC1 domain comprises double mutations of R126E and R132E. In some embodiments, the APOBEC1 domain comprises three mutations of W90Y, R126E and R132E.

In some embodiments, one or more mutations in the cytidine deaminase as disclosed herein reduce the editing window width to about 2 nucleotides. In some embodiments, one or more mutations in the cytidine deaminase as disclosed herein reduce the editing window width to about 1 nucleotide. In some embodiments, one or more mutations in the cytidine deaminase as disclosed herein reduce the editing window width while only minimally or modestly affecting the editing efficiency of the enzyme. In some embodiments, one or more mutations in the cytidine deaminase as disclosed herein reduce the editing window width without reducing the editing efficiency of the enzyme. In some embodiments, one or more mutations in the cytidine deaminase as disclosed herein enable discrimination of neighboring cytidine nucleotides, which would be otherwise edited with similar efficiency by the cytidine deaminase.

In some embodiments, the cytidine deaminase protein further comprises or is connected to one or more double-stranded RNA (dsRNA) binding motifs (dsRBMs) or domains (dsRBDs) for recognizing and binding to double-stranded nucleic acid substrates. In some embodiments, the interaction between the cytidine deaminase and the substrate is mediated by one or more additional protein factor(s), including a CRISPR/CAS protein factor. In some embodiments, the interaction between the cytidine deaminase and the substrate is further mediated by one or more nucleic acid component(s), including a guide RNA.

According to the present invention, the substrate of the cytidine deaminase is an DNA single strand bubble of a RNA duplex comprising a Cytosine of interest, made accessible to the cytidine deaminase upon binding of the guide molecule to its DNA target which then forms the CRISPR-Cas complex with the CRISPR-Cas enzyme, whereby the cytosine deaminase is fused to or is capable of binding to one or more components of the CRISPR-Cas complex, i.e. the CRISPR-Cas enzyme and/or the guide molecule. The particular features of the guide molecule and CRISPR-Cas enzyme are detailed below.

The cytidine deaminase or catalytic domain thereof may be a human, a rat, or a lamprey cytidine deaminase protein or catalytic domain thereof.

The cytidine deaminase protein or catalytic domain thereof may be an apolipoprotein B mRNA-editing complex (APOBEC) family deaminase. The cytidine deaminase protein or catalytic domain thereof may be an activation-induced deaminase (AID). The cytidine deaminase protein or catalytic domain thereof may be a cytidine deaminase 1 (CDA1).

The cytidine deaminase protein or catalytic domain thereof may be an APOBEC1 deaminase. The APOBEC1 deaminase may comprise one or more mutations corresponding to W90A, W90Y, R118A, H121R, H122R, R126A, R126E, or R132E in rat APOBEC1, or an APOBEC3G deaminase comprising one or more mutations corresponding to W285A, W285Y, R313A, D316R, D317R, R320A, R320E, or R326E in human APOBEC3G.

The system may further comprise a uracil glycosylase inhibitor (UGI). Inn some embodiments, the cytidine deaminase protein or catalytic domain thereof is delivered together with a uracil glycosylase inhibitor (UGI). The GI may be linked (e.g., covalently linked) to the cytidine deaminase protein or catalytic domain thereof and/or a catalytically inactive CRISPR-Cas protein.

Regulation of Post-Translational Modification of Gene Products

In some cases, base editing may be used for regulating post-translational modification of a gene products. In some cases, an amino acid residue that is a post-translational modification site may be mutated by base editing to an amino residue that cannot be modified. Examples of such post-translational modifications include disulfide bond formation, glycosylation, lipidation, acetylation, phosphorylation, methylation, ubiquitination, sumoylation, or any combinations thereof.

In some embodiments, the base editors herein may regulate Stat3/IRF-5 pathway, e.g., for reduction of inflammation. For example, phosphorylation on Tyr705 of Stat3, Thr10, Ser158, Ser309, Ser317, Ser451, and/or Ser462 of IRF-5 may be involved with interleukin signaling. Base editors herein may be used to mutate one or more of these procreation sites for regulating immunity, autoimmunity, and/or inflammation.

In some embodiments, the base editors herein may regulate insulin receptor substrate (IRS) pathway. For example, phosphorylation on Ser265, Ser302, Ser325, Ser336, Ser358, Ser407, and/or Ser408 may be involved in regulating (e.g., inhibit) ISR pathway. Alternatively or additionally, Serine 307 in mouse (or Serine 312 in human) may be mutated so the phosphorylation may be regulated. For example, Serine 307 phosphorylation may lead to degradation of IRS-1 and reduce MAPK signaling. Serine 307 phosphorylation may be induced under insulin insensitivity conditions, such as insulin overstimulation and/or TNFα treatment. In some examples, 5307F mutation may be generated for stabilizing the interaction between IRS-1 and other components in the pathway. Base editors herein may be used to mutate one or more of these procreation sites for regulating IRS pathway.

Regulation of Stability of Gene Products

In some embodiments, base editing may be used for regulating the stability of gene products. For example, one or more amino acid residues that regulate protein degradation rates may be mutated by the base editors herein. In some cases, such amino acid residues may be in a degron. A degron may refer to a portion of a protein involved in regulating the degradation rate of the protein. Degrons may include short amino acid sequences, structural motifs, and exposed amino acids (e.g., lysine or arginine). Some protein may comprise multiple degrons. The degrons be ubiquitin-dependent (e.g., regulating protein degradation based on ubiquitination of the protein) or ubiquitin-independent.

In some cases, the based editing may be used to mutate one or more amino acid residues in a signal peptide for protein degradation. In some examples, the signal peptide may be a PEST sequence, which is a peptide sequence that is rich in proline (P), glutamic acid (E), serine (S), and threonine (T). For example, the stability of NANOG, which comprises a PEST sequence, may be increased, e.g., to promote embryonic stem cell pluripotency.

In some examples, the base editors may be used for mutating SMN2 (e.g., to generate S270A mutilation) to increase stability of the SMN2 protein, which is involved in spinal muscular atrophy. Other mutations in SMN2 that may be generated by based editors include those described in Cho S. et al., Genes Dev. 2010 Mar. 1; 24(5): 438-442. In certain examples, the base editors may be used for generating mutations on IκBα, as described in Fortmann K T et al., J Mol Biol. 2015 Aug. 28; 427(17): 2748-2756. Target sites in degrons may be identified by computational tools, e.g., the online tools provided on slim.ucd.ie/apc/index.php. Other targets include Cdc25A phosphatase.

9. Examples of Genes that can be Targeted by Base Editors

Any desired genes can be targeted by the base editors in the CRISPR-Cas systems described herein. In some examples, the base editors may be used for modifying PCSK9. The base editors may introduce stop codons and/or disease-associated mutations that reduce PCSK9 activity. The base editing may introduce one or more of the following mutations in PCSK9: R46L, R46A, A53V, A53A, E57K, Y142X, L253F, R237W, H391N, N425S, A443T, I474V, I474A, Q554E, Q619P, E670G, E670A, C679X, H417Q, R469W, E482G, F515L, and/or H553R.

In some examples, the base editors may be used for modifying ApoE. The base editors may target ApoE in synthetic model and/or patient-derived neurons (e.g., those derived from iPSC). The targeting may be tested by sequencing.

In some examples, the base editors may be used for modifying Stat1/3. The base editor may target Y705 and/or 5727 for reducing Stat1/3 activation. The base editing may be tested by luciferase-based promoter. Targeting Stat1/3 by base editing may block monocyte to macrophage differentiation, and inflammation in response to ox-LDL stimulation of macrophages.

In some examples, the base editors may be used for modifying TFEB (transcription factor for EB). The base editor may target one or more amino acid residues that regulate translocation of the TFEB. In some cases, the base editor may target one or more amino acid residues that regulate autophagy.

In some examples, the base editors may be used for modifying Lipin1. The base editor may target one or more serine's that can be phosphorylated by mTOR. Base editing of Lipin1 may regulate lipid accumulation. The base editors may target Lipin1 in 3T3L1 preadipocyte model. Effects of the base editing may be tested by measuring reduction of lipid accumulation (e.g., via oil red).

Base Editing Guide Molecule Design Considerations

In some embodiments, the guide sequence is an RNA sequence of between 10 to 50 nt in length, but more particularly of about 20-30 nt advantageously about 20 nt, 23-25 nt or 24 nt. In base editing embodiments, the guide sequence is selected so as to ensure that it hybridizes to the target sequence comprising the adenosine to be deaminated. This is described more in detail below. Selection can encompass further steps which increase efficacy and specificity of deamination.

In some embodiments, the guide sequence is about 20 nt to about 30 nt long and hybridizes to the target DNA strand to form an almost perfectly matched duplex, except for having a dA-C mismatch at the target adenosine site. Particularly, in some embodiments, the dA-C mismatch is located close to the center of the target sequence (and thus the center of the duplex upon hybridization of the guide sequence to the target sequence), thereby restricting the adenosine deaminase to a narrow editing window (e.g., about 4 bp wide). In some embodiments, the target sequence may comprise more than one target adenosine to be deaminated. In further embodiments the target sequence may further comprise one or more dA-C mismatch 3' to the target adenosine site. In some embodiments, to avoid off-target editing at an unintended Adenine site in the target sequence, the guide sequence can be designed to comprise a non-pairing Guanine at a position corresponding to said unintended Adenine to introduce a dA-G mismatch, which is catalytically unfavorable for certain adenosine deaminases such as ADAR1 and ADAR2. See Wong et al., RNA 7:846-858 (2001), which is incorporated herein by reference in its entirety.

In some embodiments, a CRISPR-Cas guide sequence having a canonical length (e.g., about 20 nt for AacC2c1) is used to form a heteroduplex with the target DNA. In some embodiments, a CRISPR-Cas guide molecule longer than the canonical length (e.g., >20 nt for AacC2c1) is used to form a heteroduplex with the target DNA including outside of the CRISPR-Cas-guide RNA-target DNA complex. This can be of interest where deamination of more than one adenine within a given stretch of nucleotides is of interest. In alternative embodiments, it is of interest to maintain the limitation of the canonical guide sequence length. In some embodiments, the guide sequence is designed to introduce a dA-C mismatch outside of the canonical length of CRISPR-Cas guide, which may decrease steric hindrance by CRISPR-Cas and increase the frequency of contact between the adenosine deaminase and the dA-C mismatch.

In some base editing embodiments, the position of the mismatched nucleobase (e.g., cytidine) is calculated from where the PAM would be on a DNA target. In some embodiments, the mismatched nucleobase is positioned 12-21 nt from the PAM, or 13-21 nt from the PAM, or 14-21 nt from the PAM, or 14-20 nt from the PAM, or 15-20 nt from the PAM, or 16-20 nt from the PAM, or 14-19 nt from the PAM, or 15-19 nt from the PAM, or 16-19 nt from the PAM, or 17-19 nt from the PAM, or about 20 nt from the PAM, or about 19 nt from the PAM, or about 18 nt from the PAM, or about 17 nt from the PAM, or about 16 nt from the PAM, or about 15 nt from the PAM, or about 14 nt from the PAM. In a preferred embodiment, the mismatched nucleobase is positioned 17-19 nt or 18 nt from the PAM.

Mismatch distance is the number of bases between the 3' end of the CRISPR-Cas spacer and the mismatched nucleobase (e.g., cytidine), wherein the mismatched base is included as part of the mismatch distance calculation. In some embodiment, the mismatch distance is 1-10 nt, or 1-9 nt, or 1-8 nt, or 2-8 nt, or 2-7 nt, or 2-6 nt, or 3-8 nt, or 3-7 nt, or 3-6 nt, or 3-5 nt, or about 2 nt, or about 3 nt, or about 4 nt, or about 5 nt, or about 6 nt, or about 7 nt, or about 8 nt. In a preferred embodiment, the mismatch distance is 3-5 nt or 4 nt.

In some embodiment, the editing window of a CRISPR-Cas-ADAR system described herein is 12-21 nt from the PAM, or 13-21 nt from the PAM, or 14-21 nt from the PAM, or 14-20 nt from the PAM, or 15-20 nt from the PAM, or 16-20 nt from the PAM, or 14-19 nt from the PAM, or 15-19 nt from the PAM, or 16-19 nt from the PAM, or 17-19 nt from the PAM, or about 20 nt from the PAM, or about 19 nt from the PAM, or about 18 nt from the PAM, or about 17 nt from the PAM, or about 16 nt from the PAM, or about 15 nt from the PAM, or about 14 nt from the PAM. In some embodiment, the editing window of the CRISPR-Cas-ADAR system described herein is 1-10 nt from the 3' end of the CRISPR-Cas spacer, or 1-9 nt from the 3' end of the CRISPR-Cas spacer, or 1-8 nt from the 3' end of the CRISPR-Cas spacer, or 2-8 nt from the 3' end of the C2c1 spacer, or 2-7 nt from the 3' end of the CRISPR-Cas spacer, or 2-6 nt from the 3' end of the CRISPR-Cas spacer, or 3-8 nt from the 3' end of the CRISPR-Cas spacer, or 3-7 nt from the 3' end of the CRISPR-Cas spacer, or 3-6 nt from the 3' end of the CRISPR-Cas spacer, or 3-5 nt from the 3' end of the CRISPR-Cas spacer, or about 2 nt from the 3' end of the CRISPR-Cas spacer, or about 3 nt from the 3' end of the CRISPR-Cas spacer, or about 4 nt from the 3' end of the CRISPR-Cas spacer, or about 5 nt from the 3' end of the CRISPR-Cas spacer, or about 6 nt from the 3' end of the CRISPR-Cas spacer, or about 7 nt from the 3' end of the CRISPR-Cas spacer, or about 8 nt from the 3' end of the CRISPR-Cas spacer.

Linkers

The deaminase herein may be fused to a Cas protein described herein via a linker. It will be appreciated that other methods of incorporating a deaminase into the CRISPR-Cas system or Cas protein described herein are discussed elsewhere herein. It is further envisaged that RNA adenosine methylase (N(6)-methyladenosine) can be fused to the RNA targeting effector proteins of the invention and targeted to a transcript of interest. This methylase causes reversible methylation, has regulatory roles and may affect gene expression and cell fate decisions by modulating multiple RNA-related cellular pathways (Fu et al Nat Rev Genet. 2014; 15(5):293-306).

ADAR or other RNA modification enzymes may be linked (e.g., fused) to CRISPR-Cas or a dead CRISPR-Cas protein via a linker, e.g., to the C terminus or the N-terminus of CRISPR-Cas or dead CRISPR-Cas.

The term "linker" as used in reference to a fusion protein refers to a molecule which joins the proteins to form a fusion protein. Generally, such molecules have no specific biological activity other than to join or to preserve some minimum distance or other spatial relationship between the proteins. However, in certain embodiments, the linker may be selected to influence some property of the linker and/or the fusion protein such as the folding, net charge, or hydrophobicity of the linker.

Suitable linkers for use in the methods of the present invention are well known to those of skill in the art and include, but are not limited to, straight or branched-chain carbon linkers, heterocyclic carbon linkers, or peptide linkers. However, as used herein the linker may also be a covalent bond (carbon-carbon bond or carbon-heteroatom bond). In particular embodiments, the linker is used to separate the CRISPR-Cas protein and the nucleotide deaminase by a distance sufficient to ensure that each protein retains its required functional property. Preferred peptide linker sequences adopt a flexible extended conformation and do not exhibit a propensity for developing an ordered secondary structure. In certain embodiments, the linker can be a chemical moiety which can be monomeric, dimeric, multimeric or polymeric. Preferably, the linker comprises amino acids. Typical amino acids in flexible linkers include Gly, Asn and Ser. Accordingly, in particular embodiments, the linker comprises a combination of one or more of Gly, Asn and Ser amino acids. Other near neutral amino acids, such as Thr and Ala, also may be used in the linker sequence. Exemplary linkers are disclosed in Maratea et al. (1985), Gene 40: 39-46; Murphy et al. (1986) Proc. Nat'l. Acad. Sci. USA 83: 8258-62; U.S. Pat. Nos. 4,935,233; and 4,751,180. For example, GlySer linkers GGS, GGGS or GSG can be used. GGS, GSG, GGGS (SEQ ID NO: 6) or GGGGS (SEQ ID NO: 13) linkers can be used in repeats of 3 (such as $(GGS)_3$ (SEQ ID No. 27), $(GGGGS)_3$ (SEQ ID NO: 9)) or 5, 6, 7, 9 or even 12 or more, to provide suitable lengths. In some cases, the linker may be $(GGGGS)_{3-15}$, For example, in some cases, the linker may be $(GGGGS)_{3-11}$, e.g., GGGGS (SEQ ID NO: 13), $(GGGGS)_2$ (SEQ ID NO: 14), $(GGGGS)_3$ (SEQ ID NO: 9), $(GGGGS)_4$ (SEQ ID NO: 15), $(GGGGS)_5$ (SEQ ID NO: 16), $(GGGGS)_6$ (SEQ ID NO: 10), $(GGGGS)_7$ (SEQ ID NO: 17), $(GGGGS)_8$ (SEQ ID NO: 18), $(GGGGS)_9$ (SEQ ID NO: 11), $(GGGGS)_{10}$ (SEQ ID NO: 19), or (GGGGS)ii (SEQ ID NO: 20).

In particular embodiments, linkers such as $(GGGGS)_3$ (SEQ ID NO: 9) are preferably used herein. $(GGGGS)_6$ (SEQ ID NO: 10) $(GGGGS)_9$ (SEQ ID NO: 11) or $(GGGGS)_{12}$ (SEQ ID NO: 12) may preferably be used as alternatives. Other preferred alternatives are $(GGGGS)_1$ (SEQ ID No 13), $(GGGGS)_2$ (SEQ ID No. 14), $(GGGGS)_4$ (SEQ ID NO: 15), $(GGGGS)_5$ (SEQ ID NO: 16), $(GGGGS)_7$ (SEQ ID NO: 17), $(GGGGS)_8$ (SEQ ID NO: 18), $(GGGGS)_{10}$ (SEQ ID NO: 19), or $(GGGGS)_{11}$ (SEQ ID NO: 20). In yet a further embodiment, LEP-GEKPYKCPECGKSFSQSGALTRHQRTHTR (SEQ ID No:28) is used as a linker. In yet an additional embodiment, the linker is an XTEN linker. In particular embodiments, the CRISPR-cas protein is a CRISPR-Cas protein and is linked to the deaminase protein or its catalytic domain by means of an LEPGEKPYKCPECGKSFSQSGALTRHQRTHTR (SEQ ID No. 28) linker. In further particular embodiments, the CRISPR-Cas protein is linked C-terminally to the N-terminus of a deaminase protein or its catalytic domain by means of an LEPGEKPYKCPECGKSFSQSGAL-TRHQRTHTR (SEQ ID No. 28) linker. In addition, N- and C-terminal NLSs can also function as linker (e.g., PKKKRKVEASSPKKRKVEAS (SEQ ID No. 29)). Examples of linkers are shown in the Table 2.

TABLE 2

Exemplary Linkers

| | | SEQ ID NO: |
|---|---|---|
| GGS | GGTGGTAGT | 30 |
| GGSx3 (9) | GGTGGTAGTGGAGGGAGCGGCGGTTCA | 31 |
| GGSx7 (21) | ggtggaggaggctctggtggaggcggtagcggaggcggagggtcgGGTGGTAGTGGAGGGAGCGGCGGTTCA | 32 |
| XTEN | TCGGGATCTGAGACGCCTGGGACCTCGGAATCGGCTACGCCCGAAAGT | 33 |
| Z-EGFR_Short | gtggataacaaatttaacaaagaaatgtgggcggcgtgggaagaaattcgtaacctgccgaacctgaacggctggcagatgaccgcgtttattgcgagcctggtggatgatccgagccagagcgcgaacctgctggcggaagcgaaaaaactgaacgatgcgcaggcgccgaaaaccggcggtggactggt | 34 |
| GSAT | ggtggttctgccggtggctccggttctggctccagcggtggcagctctggtgcgtccggcacgggtactgcgggtggcactggcagcggttccggtactggctctggc | |

A nucleotide deaminase or other RNA modification enzyme may be linked to CRISPR-Cas or a dead CRISPR-Cas via one or more amino acids. In some cases, the nucleotide deaminase may be linked to the CRISPR-Cas or a dead CRISPR-Cas via one or more amino acids 411-429, 114-124, 197-241, and 607-624. The amino acid position may correspond to a CRISPR-Cas ortholog disclosed herein. In certain examples, the nucleotide deaminase may be is linked to the dead CRISPR-Cas via one or more amino acids corresponding to amino 411-429, 114-124, 197-241, and 607-624 of *Prevotella buccae* CRISPR-Cas.

Modified Cas Effector Proteins

The Cas polypeptides described herein can be mutated or otherwise modified.

In particular embodiments, it is of interest to make use of an engineered Cas protein as defined herein, wherein the protein complexes with a nucleic acid molecule comprising RNA to form a CRISPR complex, wherein when in the CRISPR complex, the nucleic acid molecule targets one or more target polynucleotide loci, the protein comprises at least one modification compared to unmodified Cas protein, and wherein the CRISPR complex comprising the modified protein has altered activity as compared to the complex comprising the unmodified Cas protein.

In one embodiment, a modified Cas or Cas protein comprises at least one modification that alters editing preference as composed to wild type. In certain embodiments, the editing preference is for a specific insert or deletion within the target region. In certain example embodiments, the at least one modification increases formation of one or more specific indels. In one example embodiment, the at least on modification is in the binding region including the targeting region and/or a PAM interacting region. In another example embodiment, the at least one modification is not in the binding region including the targeting region and/or the PAM interacting region. In one example embodiment, the one or more modifications are located in or proximate to an active or inactive RuvC domain. In another example embodiment, the one or more modifications are located in or proximate to a HNH domain or Nuc lobe. In another example embodiment, the one or more modifications are in or proximate to a bridge helix. In another example embodiment, the one or more modifications are in or proximate to a recognition (REC) lobe. In another example embodiment, the at least one modification is present or proximate to a D10 active site residue. In another example embodiment, the at least one modification is present in or proximate to a linker region. The linker region may form a linker from an optional active or inactive RuCv domain to the bridge helix. In certain example embodiments, the one or more modifications are located at at residues 6-19, 51-60, 690-696, 698-700, 725-734, 764-786, 802-811, 837-871, 902-929, 976-982, 998-1007, or a combination thereof, of SpCas9 or a residue in an ortholog corresponding or functionally equivalent to a Cas9 protein described herein.

In certain example embodiments, the at least one modification increases formation of one or more specific insertions. In certain example embodiments, the at least one modification results in an insertion of an A adjacent to an A, T, G, or C in the target region. In another example embodiment, the at least one modification results in insertion of a T adjacent to an A, T, G, or C in the target region. In another example embodiment, the at least one modification results in insertion of a G adjacent to an A, T, G, or C in the target region. In another example embodiment, the at least one modification results in insertion of a C adjacent to an A, T, C, or G in the target region. The insertion may be 5' or 3' to the adjacent nucleotide. In one example embodiment, the one or more modification direct insertion of a T adjacent to an existing T. In certain example embodiments, the existing T corresponds to the $4^{th}$ position in the binding region of a guide sequence. In certain example embodiments, the one or more modifications result in an enzyme which ensures more precise one-base insertions or deletions, such as those described above. More particularly, the one or more modifications may reduce the formations of other types of indels by the enzyme. The ability to generate one-base insertions or deletions can be of interest in a number of applications, such as correction of genetic mutants in diseases caused by small deletions, more particularly where HDR is not possible. For example, correction of the F508del mutation in CFTR via delivery of three sRNA directing insertion of three T's, which is the most common genotype of cystic fibrosis, or correction of Alia Jafar's single nucleotide deletion in CDKLS in the brain. As the editing method only requires NHEJ, the editing would be possible in post-mitotic cells such as the brain. The ability to generate one base pair insertions/deletions may also be useful in genome-wide CRISPR-Cas negative selection screens. In certain example embodiments, the at least one modification, is a mutation. In certain other example embodiment, the one or more modification may be combined with one or more additional modifications or mutations described below including modifications to increase binding specificity, decrease off-target effects, modify allosteric interaction one or more other polypeptides, e.g. a Cas12 polypeptide, Cas9, and combinations thereof.

In certain example embodiments, the Cas polypeptide comprising at least one modification that alters editing preference as compared to wild type Cas polypeptide may further comprise one or more additional modifications that alters the binding property as to a nucleic acid component, nucleic acid molecule comprising RNA and/or the target polypeptide loci, altering binding kinetics as to the nucleic acid molecule or target molecule or target polynucleotide, alters binding specificity as to a polynucleotide such as a nucleic acid component and/or a target sequence, and/or alters the allosteric interaction capability described herein of the Cas polypeptide. Example of such modifications are summarized in the following paragraph.

Suitable polypeptide modifications which enhance specificity in particular by reducing off-target effects, are described for instance in PCT/US2016/038034, which is incorporated herein by reference in its entirety. In particular embodiments, a reduction of off-target cleavage is ensured by destabilizing strand separation, more particularly by introducing mutations in the Cas enzyme decreasing the positive charge in the DNA interacting regions (as described herein and further exemplified for Cas9 by Slaymaker et al. 2016 (Science, 1; 351(6268):84-8). In further embodiments, a reduction of off-target cleavage is ensured by introducing mutations into one or more Cas enzyme which affect the interaction between the target strand and the guide RNA sequence, more particularly disrupting interactions between a Cas protein and the phosphate backbone of the target DNA strand in such a way as to retain target specific activity but reduce off-target activity (as described for Cas9 by Kleinstiver et al. 2016, Nature, 28; 529(7587):490-5). In particular embodiments, the off-target activity is reduced by way of a modified Cas wherein both interaction with target strand and non-target strand are modified compared to wild-type Cas.

The methods and mutations which can be employed in various combinations to increase or decrease activity and/or specificity of on-target vs. off-target activity, or increase or decrease binding and/or specificity of on-target vs. off-target binding, can be used to compensate or enhance mutations or modifications made to promote other effects. Such mutations or modifications made to promote other effects include mutations or modification to the Cas effector protein and or mutation or modification made to a guide RNA.

With a similar strategy used to improve Cas specificity (Slaymaker et al. 2015 "Rationally engineered Cas9 nucleases with improved specificity"), specificity of Cas polypeptide can be further improved by mutating residues that stabilize the non-targeted DNA strand. This may be accomplished without a crystal structure by using linear structure alignments to predict 1) which domain of Cas polypeptide binds to which strand of DNA and 2) which residues within these domains contact DNA. It may be desirable to probe the function of all likely DNA interacting amino acids (lysine, histidine and arginine) of the Cas polypeptide (e.g. a Cas (e.g. Cas9 or Cas12 protein) described herein.

Without being bound by theory, in an embodiment, the methods and mutations described can enhance conformational rearrangement of Cas domains or proteins to positions that results in cleavage at on-target sites and avoidance of those conformational states at off-target sites. In embodiments, the confirmation rearrangement of the Cas domains or proteins occurs upon allosteric interaction of two or more Cas polypeptides.

In embodiments, a Cas cleaves target DNA in a series of coordinated steps. First, the PAM-interacting domain recognizes the PAM sequence 5' of the target DNA. After PAM binding, the first 10-12 nucleotides of the target sequence (seed sequence) are sampled for sgRNA:DNA complementarity, a process dependent on DNA duplex separation. If the seed sequence nucleotides complement the sgRNA, the remainder of DNA is unwound and the full length of sgRNA hybridizes with the target DNA strand. The nt-groove between the RuvC and HNH domains stabilizes the non-targeted DNA strand and facilitates unwinding through non-specific interactions with positive charges of the DNA phosphate backbone. RNA:cDNA and Cas:ncDNA interactions drive DNA unwinding in competition against cDNA:ncDNA rehybridization. Other Cas9 and/or Cas12 domains can affect the conformation of nuclease domains as well, for example linkers connecting HNH with RuvCII and RuvCIII, RuvC-like, RuvC (inactive or active).

The methods and mutations described herein encompass, without limitation, RuvCI, RuvCIII, RuvCIII and HNH domains and linkers. Conformational changes in Cas and/or Cas protein brought about by allosteric interaction with other Cas and/or Cas proteins, target DNA binding, including seed sequence interaction, and interactions with the target and non-target DNA strand determine whether the domains are positioned to trigger nickase, nuclease, and/or other enzymatic activity. Thus, the Cas and Cas protein mutations and methods provided herein demonstrate and enable modifications that go beyond PAM recognition and RNA-DNA base pairing. In an embodiment, the invention provides Cas proteins that comprise an improved equilibrium towards conformations associated with cleavage activity when involved in on-target interactions and/or improved equilibrium away from conformations associated with cleavage activity when involved in off-target interactions. In one embodiment, the invention provides Cas proteins with or improved proof-reading function, i.e. a Cas or Cas nickase or nuclease which adopts a conformation comprising nickase or nuclease activity at an on-target site, and which conformation has increased unfavourability at an off-target site. Sternberg et al., Nature 527(7576):110-3, doi: 10.1038/nature15544, published online 28 Oct. 2015. Epub 2015 Oct. 28, used Förster resonance energy transfer FRET) experiments to detect relative orientations of the Cas9 catalytic domains when associated with on- and off-target DNA. Similar assays can be used to detect the relative orientations of the Cas effector (e.g. Cas9 or Cas12) domains described herein.

Where the Cas polypeptide has nuclease activity, the Cas polypeptide can be modified to have diminished nuclease activity e.g., nuclease inactivation of at least 70%, at least 80%, at least 90%, at least 95%, at least 97%, or 100% as compared with the wild type enzyme; or to put in another way, a Cas enzyme having advantageously about 0% of the nuclease activity of the non-mutated or wild type Cas enzyme or reference Cas CRISPR enzyme, or no more than about 3% or about 5% or about 10% of the nuclease activity of the non-mutated or wild type Cas or Cas enzyme. This is possible by introducing mutations into the nuclease domains of the Cas-polypeptide and orthologs thereof. In certain embodiments, the Cas enzyme is engineered and can comprise one or more mutations that reduce or eliminate a nuclease activity. When the enzyme is not SpCas9 (e.g. is a Cas protein (e.g. Cas9 or Cas12)), mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9 or SpCas9: D10, E762, H840, N854, N863, or D986; as well as conservative substitution for any of the replacement amino acids is also envisaged. The point mutations to be generated to substantially reduce nuclease activity include but are not limited to D10A, E762A, H840A, N854A, N863A and/or D986A. In an embodiment, the invention provides a herein-discussed composition, wherein the Cas polypeptide comprises two or more mutations, wherein the two or more mutations are two or more of D10, E762, H840, N854, N863, or D986 according or corresponding to the SpCas9 or SpCas9 protein or any corresponding to N580 according or corresponding to the SaCas9 or SaCas9 protein ortholog are mutated, or the Cas polypeptide comprises at least one mutation wherein at least H840 is mutated. In an embodiment, the invention provides a herein-discussed composition wherein the Cas polypeptide comprises two or more mutations comprising D10A, E762A, H840A, N854A, N863A or D986A according or corresponding to SpCas9 or SpCas9protein or any corresponding ortholog, or N580A according or corresponding to SaCas9 or SaCas9 protein, or at least one mutation comprising H840A, or, optionally wherein the Cas polypeptide comprises: N580A according or corresponding to SaCas9 or SaCas protein or any corresponding ortholog; or D10A according or corresponding to SpCas9 or SpCas9 protein, or any corresponding ortholog, and N580A according to or corresponding to SaCas9 or SaCas protein. In an embodiment, the invention provides a herein-discussed composition, wherein the Cas polypeptide comprises H840A, or D10A and H840A, or D10A and N863A, according or corresponding to SpCas9 or SpCas9 protein or any corresponding ortholog.

Mutations can also be made at neighboring residues, e.g., at amino acids near those indicated above that participate in the nuclease activity. In some embodiments, the RuvC domain is inactivated, and in other embodiments, another putative nuclease domain is inactivated, wherein the effector protein complex functions as a nickase and cleaves only one DNA strand as discussed elsewhere herein. In a preferred embodiment, the other putative nuclease domain is a HincII-like endonuclease domain. In some embodiments, two Cas or Cas variants (each a different nickase) are used to increase specificity, two nickase variants are used to cleave DNA at a target (where both nickases cleave a DNA strand, while minimizing or eliminating off-target modifications where only one DNA strand is cleaved and subsequently repaired). In a preferred embodiment, a homodimer may comprise two Cas or Cas effector protein molecules comprising a different mutation in their respective RuvC domains.

In certain embodiments, the modification or mutation comprises a mutation in a RuvCI, RuvCIII, RuvCIII or HNH domain. In certain embodiments, the modification or mutation comprises an amino acid substitution at one or more of positions corresponding to positions 12, 13, 63, 415, 610, 775, 779, 780, 810, 832, 848, 855, 861, 862, 866, 961, 968, 974, 976, 982, 983, 1000, 1003, 1014, 1047, 1060, 1107, 1108, 1109, 1114, 1129, 1240, 1289, 1296, 1297, 1300, 1311, and 1325; preferably 855; 810, 1003, and 1060; or 848, 1003 with reference to amino acid position numbering of SpCas9. Corresponding locations can be identified in a Cas polypeptide as described elsewhere herein. In certain embodiments, the modification or mutation corresponding to position(s) 63, 415, 775, 779, 780, 810, 832, 848, 855, 861, 862, 866, 961, 968, 974, 976, 982, 983, 1000, 1003, 1014, 1047, 1060, 1107, 1108, 1109, 1114, 1129, 1240, 1289, 1296, 1297, 1300, 1311, or 1325; preferably 855; 810, 1003, and 1060; 848, 1003, and 1060; or 497, 661, 695, and 926 comprises an alanine substitution with corresponding reference to amino acid position numbering of SpCas9. Corresponding locations can be identified in a Cas polypeptide as described elsewhere herein. In certain embodiments, the modification comprises K855A; K810A, K1003A, and R1060A; or K848A, K1003A (with reference to SpCas9), and R1060A. in certain embodiments, in certain embodiments, the modification comprises N497A, R661A, Q695A, and Q926A, with reference to amino acid position numbering of SpCas9. Corresponding locations can be identified in a Cas polypeptide as described elsewhere herein.

Other mutations may include N692A, M694A, Q695A, H698A or combinations thereof and as otherwise described in Kleinstiver et al. "High-fidelity CRISP-Cas9 nucleases with no detectable genome-wide off-target effects" Nature 529, 590-607 (2016). Where the mutations are made in reference to a non-Cas protein, corresponding locations can be identified in a Cas polypeptide as described elsewhere herein. In addition, mutations and or modifications within a REC3 domain (with reference to SpCas9-HF1 and eSpCas9 (1.1)) may also be targeted for increased target specify and as further described in Chen et al. "Enhanced proofreading governs CRISPR-Cas9 targeting accuracy" bioRxv Jul. 6, 2017 doi: http://dx.doi.org/10.1101/160036. Other mutations may be located in an HNH nuclease domain as further described in Sternberg et al. Nature 2015 doi:10.1038/nature15544. Where the mutations are made in reference to a non-Cas protein, corresponding locations can be identified in a Cas polypeptide as described elsewhere herein.

Where the Cas protein has nuclease activity, the Cas protein may be modified to have diminished nuclease activity e.g., nuclease inactivation of at least 70%, at least 80%, at least 90%, at least 95%, at least 97%, or 100% as compared with the wild type enzyme; or to put in another way, a Cas enzyme having advantageously about 0% of the nuclease activity of the non-mutated or wild type Cas enzyme or CRISPR enzyme, or no more than about 3% or about 5% or about 10% of the nuclease activity of the non-mutated or wild type Cas enzyme. In some embodiments, a nucleic acid-targeting effector protein may be considered to substantially lack all RNA cleavage activity when the RNA cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form. This is possible by introducing mutations into the nuclease domains of the Cas and orthologs thereof.

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, *Trends Biotechnol.* (1995) 13(4), 132-134.

Homology modelling: Corresponding residues in other Cas orthologs can be identified by the methods of Zhang et al., 2012 (Nature; 490(7421): 556-60) and Chen et al., 2015 (PLoS Comput Biol; 11(5): e1004248)—a computational protein-protein interaction (PPI) method to predict interactions mediated by domain-motif interfaces. PrePPI (Predicting PPI), a structure-based PPI prediction method, combines structural evidence with non-structural evidence using a Bayesian statistical framework. The method involves taking a pair a query proteins and using structural alignment to identify structural representatives that correspond to either their experimentally determined structures or homology models. Structural alignment is further used to identify both close and remote structural neighbours by considering global and local geometric relationships. Whenever two neighbors of the structural representatives form a complex reported in the Protein Data Bank, this defines a template for modelling the interaction between the two query proteins. Models of the complex are created by superimposing the representative structures on their corresponding structural neighbour in the template. This approach is further described in Dey et al., 2013 (Prot Sci; 22: 359-66).

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR.

Accessory Molecules

Additional accessory molecules, such as additional CRISPR effectors and/or other accessory molecules can be included in the CRISPR-Cas systems described herein in addition to the Cas polypeptides described elsewhere herein. In some embodiments, the accessory molecules can be other effector and/or targeting proteins or molecules. Accessory molecules can be or be derived from a Type I, II, III, IV, V, CRISPR-Cas system.

In embodiments, an accessory molecule can be identified by their proximity to a Cas gene and/or a CRISPR array (e.g. within the region 20 kb from the start of the Cas gene and/or CRISPR array). Non-limiting examples of Cas proteins that can be included as accessory molecules include, but are not limited to, Cas 1, Cas1B, Cas2, Cas3, Cas4, Cas5, Cash, Cas7, Cas8, Cas9 (also known as Csn1 and Csx12), Cas10, Cas12 (also know as Cpf1), Cas13, Cas 14, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, C2c2, homologues thereof, orthologues thereof, or modified versions thereof. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of Orthologous proteins may, but need not be structurally related, or are only partially structurally related.

In some embodiments, one or more elements of the CRISPR-Cas system is derived from a particular organism comprising an endogenous RNA-targeting system. In particular embodiments, the Type VI RNA-targeting Cas enzyme is C2c2. In an embodiment of the invention, there is provided a effector protein which comprises an amino acid sequence having at least 80% sequence homology to the wild-type sequence of any of *Leptotrichia shahii* C2c2, *Lachnospiraceae bacterium* MA2020 C2c2, *Lachnospiraceae bacterium* NK4A179 C2c2, *Clostridium aminophilum* (DSM 10710) C2c2, *Carnobacterium gallinarum* (DSM 4847) C2c2, *Paludibacter propionicigenes* (WB4) C2c2, *Listeria weihenstephanensis* (FSL R9-0317) C2c2, *Listeriaceae bacterium* (FSL M6-0635) C2c2, *Listeria newyorkensis* (FSL M6-0635) C2c2, *Leptotrichia wadei* (F0279) C2c2, *Rhodobacter capsulatus* (SB 1003) C2c2, *Rhodobacter capsulatus* (R121) C2c2, *Rhodobacter capsulatus* (DE442) C2c2, *Leptotrichia wadei* (Lw2) C2c2, or *Listeria seeligeri* C2c2.

Adaptors

In embodiments, and as is also described elsewhere herein, the CRISPR-Cas system described herein can include on or more adaptor proteins. In embodiments, the adaptor protein can bind to RNA. The adaptor proteins can be capable of recruitment of, for example, effector proteins or fusions that can have one or more functional domains. In some embodiments, the functional domain is a transcriptional activation domain, preferably VP64. In some embodiments, the functional domain is a transcription repression domain, preferably KRAB. In some embodiments, the transcription repression domain is SID, or concatemers of SID (e.g. SID4X). In some embodiments, the functional domain is an epigenetic modifying domain, such that an epigenetic modifying enzyme is provided. In some embodiments, the functional domain is an activation domain, which may be the P65 activation domain.

The functional domain can be, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). In some embodiments, the functional domain may be selected from the group of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease.

Endogenous transcriptional repression is often mediated by chromatin modifying enzymes such as histone methyltransferases (HMTs) and deacetylases (HDACs). Repressive histone effector domains are generally known and representative examples are provided below. In the exemplary table, preference was given to proteins and functional truncations of small size to facilitate efficient viral packaging (for instance via AAV). In general, however, the domains may include HDACs, histone methyltransferases (HMTs), and histone acetyltransferase (HAT) inhibitors, as well as HDAC and HMT recruiting proteins. The functional domain may be or include, in some embodiments, HDAC Effector Domains, HDAC Recruiter Effector Domains, Histone Methyltransferase (HMT) Effector Domains, Histone Methyltransferase (HMT) Recruiter Effector Domains, or Histone Acetyltransferase Inhibitor Effector Domains. Exemplary HDAC Effector domains are shown in Tables 3-7.

TABLE 3

HDAC Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| HDAC I | HDA C8 | — | — | *X. laevis* | 325 | 1-325 | 325 | 1-272: HDAC |
| HDAC I | RPD 3 | — | — | *S. cerevisiae* | 433 | 19-340 | 322 (Vannier) | 19-331: HDAC |
| HDAC IV | Meso Lo4 | — | — | *M. loti* | 300 | 1-300 (Gregoretti) | 300 | — |
| HDAC IV | HDA C11 | — | — | *H. sapiens* | 347 | 1-347 (Gao) | 347 | 14-326: HDAC |
| HD2 | HDT 1 | — | — | *A. thaliana* | 245 | 1-211 (Wu) | 211 | — |
| SIRT I | SIRT 3 | H3K9Ac H4K16Ac H3K56Ac | — | *H. sapiens* | 399 | 143-399 (Scher) | 257 | 126-382: SIRT |
| SIRT I | HST 2 | — | — | *C. albicans* | 331 | 1-331 (Hnisz) | 331 | — |
| SIRT I | CobB | — | — | *E. coli* (K12) | 242 | 1-242 (Landry) | 242 | — |
| SIRT I | HST 2 | — | — | *S. cerevisiae* | 357 | 8-298 (Wilson) | 291 | — |
| SIRT III | SIRT 5 | H4K8Ac H4K16Ac | — | *H. sapiens* | 310 | 37-310 (Gertz) | 274 | 41-309: SIRT |
| SIRT III | Sir2 A | — | — | *P. falciparum* | 273 | 1-273 (Zhu) | 273 | 19-273: SIRT |
| SIRT IV | SIRT 6 | H3K9Ac H3K56Ac | — | *H. sapiens* | 355 | 1-289 (Tennen) | 289 | 35-274: SIRT |

Accordingly, the repressor domains of the present invention may be selected from histone methyltransferases (HMTs), histone deacetylases (HDACs), histone acetyltransferase (HAT) inhibitors, as well as HDAC and HMT recruiting proteins.

The HDAC domain may be any of those in the Table 3, namely: HDAC8, RPD3, MesoLo4, HDAC11, HDT1, SIRT3, HST2, CobB, HST2, SIRT5, Sir2A, or SIRT6.

TABLE 4

HDAC Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| Sin3a | MeC P2 | — | — | *R. norvegicus* | 492 | 207-492 (Nan) | 286 | — |
| Sin3a | MBD 2b | — | — | *H. sapiens* | 262 | 45-262 (Boeke) | 218 | — |

TABLE 4-continued

HDAC Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| Sin3a | Sin3a | — | — | *H. sapiens* | 1273 | 524-851 (Laherty) | 328 | 627-829: HDAC1 interaction |
| NcoR | NcoR | — | — | *H. sapiens* | 2440 | 420-488 (Zhang) | 69 | — |
| NuRD | SAL L1 | — | — | *M. musculus* | 1322 | 1-93 (Lauberth) | 93 | — |
| CoREST | RCO R1 | — | — | *H. sapiens* | 482 | 81-300 (Gu, Ouyang) | 220 | — |

In some embodiment, the functional domain may be a HDAC Recruiter Effector Domain. Preferred examples include those in Table 4, namely MeCP2, MBD2b, Sin3a, NcoR, SALL1, RCOR1. In some embodiments NcoR is exemplified in the present Examples and, although preferred, it is envisaged that others in the class will also be useful.

In some embodiment, the functional domain may be a Methyltransferase (HMT) Effector Domain. Preferred examples include those in the Table 5 below, namely NUE, vSET, EHMT2/G9A, SUV39H1, dim-5, KYP, SUVR4, SET4, SET1, SETD8, and TgSET8. NUE is exemplified in the present Examples and, although preferred, it is envisaged that others in the class will also be useful.

TABLE 5

Histone Methyltransferase (HMT) Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| SET | NUE | H2B, H3, H4 | — | *C. trachomatis* | 219 | 1-219 (Pennini) | 219 | — |
| SET | vSET | — | H3K27me3 | P. bursaria chlorella virus | 119 | 1-119 (Mujtaba) | 119 | 4-112: SET2 |
| SUV39 family | EHM T2/G9 A | H1.4K2, H3K9, H3K27 | H3K9me1/ 2, HlK25me1 | *M. musculus* | 1263 | 969-1263 (Tachibana) | 295 | 1025-1233: preSET, SET, postSET |
| SUV39 | SUV3 9H1 | — | H3K9me2/ 3 | *H. sapiens* | 412 | 79-412 (Snowden) | 334 | 172-412: preSET, SET, postSET |
| Suvar3-9 | dim-5 | — | H3K9me3 | *N. crassa* | 331 | 1-331 (Rathert) | 331 | 77-331: preSET, SET, postSET |
| Suvar3-9 (SUVH subfamily) | KYP | — | H3K9me1/ 2 | *A. thaliana* | 624 | 335-601 | 267 (Jackson) | — |
| Suvar3-9 (SUVR subfamily) | SUVR 4 | H3K9me1 | H3K9me2/ 3 | *A. thaliana* | 492 | 180-492 | 313 (Thorstensen) | 192-462: preSET, SET, postSET |
| Suvar4-20 | SET4 | — | H4K20me3 | *C. elegans* | 288 | 1-288 (Vielle) | 288 | — |
| SET8 | SET1 | — | H4K20me1 | *C. elegans* | 242 | 1-242 (Vielle) | 242 | — |
| SET8 | SETD 8 | — | H4K20me1 | *H. sapiens* | 393 | 185-393 | 209 (Couture) | 256-382: SET |
| SET8 | TgSE T8 | — | H4K20me1/ 2/3 | *T. gondii* | 1893 | 1590-1893 (Sautel) | 304 | 1749-1884: SET |

In some embodiment, the functional domain may be a Histone Methyltransferase (HMT) Recruiter Effector Domain. Preferred examples include those in Table 6 below, namely Hp1a, PHF19, and NIPP1.

TABLE 6

| Histone Methyltransferase (HMT) Recruiter Effector Domains | | | | | | | | |
|---|---|---|---|---|---|---|---|---|
| Subtype/ Complex | Name | Substrate (if known) | Modification (if known) | Organism | Full size (aa) | Selected truncation (aa) | Final size (aa) | Catalytic domain |
| — | Hp1a | — | H3K9me3 | *M. musculus* | 191 | 73-191 | 119 (Hathaway) | 121-179: chromoshadow |
| — | PHF19 | — | H3K27me3 | *H. sapiens* | 580 | (1-250) + GGSG linker + (500-580) | 335 (Ballaré) | 163-250: PHD2 |
| — | NIPP1 | — | H3K27me3 | *H. sapiens* | 351 | 1-329 (Jin) | 329 | 310-329: EED |

In some embodiments, the functional domain may be Histone Acetyltransferase Inhibitor Effector Domain. Preferred examples include SET/TAF-1β listed in the Table 7 below.

TABLE 7

| Histone Acetyltransferase Inhibitor Effector Domains | | | | | | | | |
|---|---|---|---|---|---|---|---|---|
| Subtype/ Complex | Name | Substrate (if known) | Modification (if known) | Organism | Full size (aa) | Selected truncation (aa) | Final size (aa) | Catalytic domain |
| — | SET/TAF-1β | — | — | *M. musculus* | 289 | 1-289 (Cervoni) | 289 | — |

It is also preferred to target endogenous (regulatory) control elements (such as enhancers and silencers) in addition to a promoter or promoter-proximal elements. Thus, the invention can also be used to target endogenous control elements (including enhancers and silencers) in addition to targeting of the promoter. These control elements can be located upstream and downstream of the transcriptional start site (TSS), starting from 200 bp from the TSS to 100 kb away. Targeting of known control elements can be used to activate or repress the gene of interest. In some cases, a single control element can influence the transcription of multiple target genes. Targeting of a single control element could therefore be used to control the transcription of multiple genes simultaneously.

Targeting of putative control elements on the other hand (e.g. by tiling the region of the putative control element as well as 200 bp up to 100 kB around the element) can be used as a means to verify such elements (by measuring the transcription of the gene of interest) or to detect novel control elements (e.g. by tiling 100 kb upstream and downstream of the TSS of the gene of interest). In addition, targeting of putative control elements can be useful in the context of understanding genetic causes of disease. Many mutations and common SNP variants associated with disease phenotypes are located outside coding regions. Targeting of such regions with either the activation or repression systems described herein can be followed by readout of transcription of either a) a set of putative targets (e.g. a set of genes located in closest proximity to the control element) or b) whole-transcriptome readout by e.g. RNAseq or microarray. This would allow for the identification of likely candidate genes involved in the disease phenotype. Such candidate genes could be useful as novel drug targets.

Histone acetyltransferase (HAT) inhibitors are mentioned herein. However, an alternative in some embodiments is for the one or more functional domains to comprise an acetyltransferase, preferably a histone acetyltransferase. These are useful in the field of epigenomics, for example in methods of interrogating the epigenome. Methods of interrogating the epigenome may include, for example, targeting epigenomic sequences. Targeting epigenomic sequences may include the guide being directed to an epigenomic target sequence. Epigenomic target sequence may include, in some embodiments, include a promoter, silencer or an enhancer sequence.

Histone modifying domains are also preferred in some embodiments. Exemplary histone modifying domains are discussed elsewhere herein. Transposase domains, HR (Homologous Recombination) machinery domains, recombinase domains, and/or integrase domains are also preferred as the present functional domains. In some embodiments, DNA integration activity includes HR machinery domains, integrase domains, recombinase domains and/or transposase domains. Histone acetyltransferases are preferred in some embodiments.

In some embodiments, the DNA cleavage activity is due to a nuclease. In some embodiments, the nuclease comprises a Fok1 nuclease. See, "Dimeric CRISPR RNA-guided Fok1 nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided Fok1 Nucleases that recognize extended sequences and can edit endogenous genes with high efficiencies in human cells.

In some preferred embodiments, the functional domain is a transcriptional activation domain, such as, without limitation, VP64, p65, MyoD1, HSF1, RTA, SET7/9 or a histone acetyltransferase. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, it is advantageous that additionally at least one NLS is provided. In some instances, it is advantageous to position the NLS at the N terminus. When more than one functional domain is included, the functional domains may be the same or different. Positioning the functional domain in the Rec1 domain, the Rec2 domain, the HNH domain, or the PI domain of the Cas protein or any ortholog corresponding to these domains is advantageous in an adaptor or accessory protein; and again, it is mentioned that the functional domain can be a DD. Positioning of the functional domains to the Rec1 domain or the Rec2 domain, of the Cas protein or any ortholog corresponding to these domains, in some instances may be preferred. Positioning of the functional domains to the Rec1 domain at position 553, Rec1 domain at 575, the Rec2 domain at any position of 175-306 or replacement thereof, the HNH domain at any position of 715-901 or replacement thereof, or the PI domain at position 1153 a reference SpCas9 protein or any ortholog corresponding to these domains or corresponding positions, in some instances may be preferred. Fok1 functional domain may be attached at the N terminus. When more than one functional domain is included, the functional domains may be the same or different.

The adaptor protein may be any number of proteins that binds to an aptamer or recognition site introduced into a modified nucleic acid component and which allows proper positioning of one or more functional domains, once the nucleic acid component has been incorporated into the CRISPR complex, to affect the target with the attributed function. As explained in detail in this application such may be coat proteins, preferably bacteriophage coat proteins. The functional domains associated with such adaptor proteins (e.g. in the form of fusion protein) may include, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). Preferred domains are Fok1, VP64, P65, HSF1, MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains. The adaptor protein may utilize known linkers to attach such functional domains. Such linkers may be used to associate the AAV (e.g., capsid or VP2) with the CRISPR enzyme or have the CRISPR enzyme comprise the AAV (or vice versa).

Attachment of a functional domain or fusion protein can be via a linker, e.g., a flexible glycine-serine (GlyGlyGly-Ser) (SEQ ID NO: 6) or $(GGGS)_3$ (SEQ ID NO: 7) or a rigid alpha-helical linker such as (Ala(GluAlaAlaAlaLys)Ala) (SEQ ID NO: 8). Linkers such as $(GGGGS)_3$ (SEQ ID NO: 9) are preferably used herein to separate protein or peptide domains. $(GGGGS)_3$ (SEQ ID NO: 9) is preferable because it is a relatively long linker (15 amino acids). The glycine residues are the most flexible and the serine residues enhance the chance that the linker is on the outside of the protein. $(GGGGS)_6$ (SEQ ID NO: 10) $(GGGGS)_9$ (SEQ ID NO: 11) or $(GGGGS)_{12}$ (SEQ ID NO: 12) may preferably be used as alternatives. Other preferred alternatives are (GGGGS)i (SEQ ID NO: 13), $(GGGGS)_2$ (SEQ ID NO: 14), $(GGGGS)_4$ (SEQ ID NO: 15), $(GGGGS)_5$ (SEQ ID NO: 16), $(GGGGS)_7$ (SEQ ID NO: 17), $(GGGGS)_8$ (SEQ ID NO: 18), $(GGGGS)_{10}$ (SEQ ID NO: 19), or (GGGGS)ii (SEQ ID NO: 20). Alternative linkers are available, but highly flexible linkers are thought to work best to allow for maximum opportunity for the 2 parts of the Cas to come together and thus reconstitute Cas activity. One alternative is that the NLS of nucleoplasmin can be used as a linker. For example, a linker can also be used between the Cas and any functional domain. Again, a $(GGGGS)_3$ (SEQ ID NO: 9) linker may be used here (or the 6, 9, or 12 repeat versions therefore) or the NLS of nucleoplasmin can be used as a linker between Cas and the functional domain.

Other Components

In some embodiments and as described in greater detail elsewhere herein, one or more of the polypeptides of the one or more of the CRISPR-Cas systems described herein can be configured for expression and/or delivery via an AAV. As such one or more of the polypeptides of a CRISPR-Cas system described herein can be provided as an AAV-CRISPR enzyme. In some embodiments, one or more of the AAV-CRISPR enzyme is part of a complexed with one or more polynucleotides (e.g. nucleic acid components described herein, repair templates, etc. described herein).

In one embodiment, the invention provides an AAV-CRISPR enzyme comprising one or more nuclear localization sequences and/or NES (nuclear export sequences). In some embodiments, said AAV-CRISPR enzyme includes a regulatory element that drives transcription of component(s) of the CRISPR system (e.g., RNA, such as guide RNA and/or HR template nucleic acid molecule) in a eukaryotic cell such that said AAV-CRISPR enzyme delivers the CRISPR system accumulates in a detectable amount in the nucleus of the eukaryotic cell and/or is exported from the nucleus. In some embodiments, the regulatory element is a polymerase II promoter. In some embodiments, the AAV-CRISPR enzyme is a type II AAV-CRISPR system enzyme. In some embodiments, the AAV-CRISPR enzyme is an AAV-Cas enzyme. In some embodiments, the AAV-Cas enzyme is derived from *S. pneumoniae, S. pyogenes, S. thermophilus, F. novicida* or *S. aureus* Cas9, Cas9 and/or Cas12 (e.g., modified to have or be associated with at least one AAV), and may include further alteration or mutation of the Cas9, Cas9, cas12, and/or Cas12, and can be a chimeric Cas9 or chimeric Cas12. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length.

With respect to the AAV-CRISPR enzyme described herein the CRISPR enzyme component can be a mutant (e.g. a Cas or Cas mutant as described elsewhere herein). In some embodiments, when the CRISPR enzyme is not SpCas9 (e.g. is Cas (e.g. Cas9 or Cas12), mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. Corresponding positions in Cas) Cas (e.g. Cas9 or Cas12) will be appreciated. In an embodiment the invention provides as to any or each or all embodiments herein-discussed wherein the AAV-CRISPR enzyme comprises at least one or more, or at least two or more mutations, wherein the at least one or more mutation or the at least two or more mutations is as to D10, E762, H840, N854, N863, or D986 according or corresponding to SpCas9 or SpCas9 protein, e.g., D10A, E762A, H840A, N854A, N863A and/or D986A as to SpCas9, or N580 according to SaCas9 or SaCas9, e.g., N580A as to SaCas9 or SaCas9, or any corresponding mutation(s) in a Cas9 or Cas9 of an ortholog to Sp or Sa, or the CRISPR enzyme comprises at least one mutation wherein at least H840 or N863A as to Sp Cas9 or N580A as to SaCas9 is mutated; e.g., wherein the CRISPR enzyme comprises H840A, or D10A and H840A, or D10A and N863A, according to SpCas9 or SpCas9 protein, or any corresponding mutation(s) in a Cas9 or Cas9 of an ortholog to Sp protein or Sa protein.

In an embodiment of the invention the AAV-CRISPR enzyme comprises one or two or more mutations in a residue selected from the group comprising, consisting essentially of, or consisting of D10, E762, H840, N854, N863, or D986. In a further embodiment the AAV-CRISPR enzyme comprises one or two or more mutations selected from the group comprising D10A, E762A, H840A, N854A, N863A or D986A. In another embodiment, the functional domain comprises, consist essentially of a transcriptional activation domain, e.g., VP64. In another embodiment, the functional domain comprises, consist essentially of a transcriptional repressor domain, e.g., KRAB domain, SID domain or a SID4X domain. In embodiments of the invention, the one or more heterologous functional domains have one or more activities selected from the group comprising, consisting essentially of, or consisting of methylase activity, demethylase activity, transcription activation activity, transcription repression activity, transcription release factor activity, histone modification activity, RNA cleavage activity and nucleic acid binding activity. In further embodiments of the invention the cell is a eukaryotic cell or a mammalian cell or a human cell. In further embodiments, the adaptor protein is selected from the group comprising, consisting essentially of, or consisting of MS2, PP7, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s, PRR1. In another embodiment, the at least one loop of the sgRNA is tetraloop and/or loop2.

Further, the AAV-CRISPR enzyme with diminished nuclease activity is most effective when the nuclease activity is inactivated (e.g., nuclease inactivation of at least 70%, at least 80%, at least 90%, at least 95%, at least 97%, or 100% as compared with the wild type enzyme; or to put in another way, a AAV-Cas enzyme or AAV-CRISPR enzyme having advantageously about 0% of the nuclease activity of the non-mutated or wild type Cas enzyme or CRISPR enzyme, or no more than about 3% or about 5% or about 10% of the nuclease activity of the non-mutated or wild type Cas enzyme or CRISPR enzyme). This is possible by introducing mutations into the RuvC and HNH nuclease domains of the SpCas9 or SpCas protein (e.g. SpCas9 or SpCas12) and orthologs thereof. For example, utilizing mutations in a residue selected from the group comprising, consisting essentially of, or consisting of D10, E762, H840, N854, N863, or D986 and more preferably introducing one or more of the mutations selected from the group comprising, consisting essentially of, or consisting of D10A, E762A, H840A, N854A, N863A or D986A. A preferable pair of mutations is D10A with H840A, more preferable is D10A with N863A of SpCas9 or SpCas9 and orthologs thereof.

Guide Sequences

As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. Each gRNA may be designed to include multiple binding recognition sites (e.g., aptamers) specific to the same or different adapter protein. Each gRNA may be designed to bind to the promoter region −1000-+1 nucleic acids upstream of the transcription start site (i.e. TSS), preferably −200 nucleic acids. This positioning improves functional domains which affect gene activation (e.g., transcription activators) or gene inhibition (e.g., transcription repressors). The modified gRNA may be one or more modified gRNAs targeted to one or more target loci (e.g., at least 1 gRNA, at least 2 gRNA, at least 5 gRNA, at least 10 gRNA, at least 20 gRNA, at least 30 g RNA, at least 50 gRNA) comprised in a composition. Said multiple gRNA sequences can be tandemly arranged and are preferably separated by a direct repeat.

In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

As used herein, the term "crRNA" or "guide RNA" or "single guide RNA" or "sgRNA" or "one or more nucleic acid components" of a Type V or Type VI CRISPR-Cas locus effector protein comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence.

In general, degree of complementarity is with reference to the optimal alignment of the sca sequence and tracr sequence, along the length of the shorter of the two sequences. Optimal alignment may be determined by any suitable alignment algorithm, and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In general, the CRISPR-Cas, CRISPR-Cas9 or CRISPR system may be as used in the foregoing documents, such as International Patent Publication No. WO 2014/093622 (PCT/US2013/074667) and refers collectively to transcripts and other elements involved in the expression of or directing the activity of CRISPR-associated ("Cas") genes, including sequences encoding a Cas gene, in particular a Cas9 gene in the case of CRISPR-Cas9, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and trans-activating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. The section of the guide sequence through which complementarity to the target sequence is important for cleavage activity is referred to herein as the seed sequence. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes or particles present within the cell. In some embodiments, especially for non-nuclear uses, NLSs are not preferred. In some embodiments, a CRISPR system comprises one or more nuclear exports signals (NESs). In some embodiments, a CRISPR system comprises one or more NLSs and one or more NESs. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments of CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an embodiment of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it may be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example *S. pyogenes* Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

Guide Modifications

In certain embodiments, guides of the invention comprise non-naturally occurring nucleic acids and/or non-naturally occurring nucleotides and/or nucleotide analogs, and/or chemically modifications. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, boranophosphate linkage, a locked nucleic acid (LNA) nucleotides comprising a methylene bridge between the 2' and 4' carbons of the ribose ring, peptide nucleic acids (PNA), or bridged nucleic acids (BNA). Other examples of modified nucleotides include 2'-O-methyl analogs, 2'-deoxy analogs, 2-thiouridine analogs, N6-methyladenosine analogs, or 2'-fluoro analogs. Further examples of modified nucleotides include linkage of chemical moieties at the 2' position, including but not limited to peptides, nuclear localization sequence (NLS), peptide nucleic acid (PNA), polyethylene glycol (PEG), triethylene glycol, or tetraethyleneglycol (TEG). Further examples of modified bases include, but are not limited to, 2-aminopurine, 5-bromo-uridine, pseudouridine (Ψ), $N^1$-methylpseudouridine ($me^1Ψ$), 5-methoxyuridine (5moU), inosine, 7-methylguanosine. Examples of guide RNA chemical modifications include, without limitation, incorporation of 2'-O-methyl (M), 2'-O-methyl-3'-phosphorothioate (MS), phosphorothioate (PS), S-constrained ethyl (cEt), 2'-O-methyl-3'-thioPACE (MSP), or 2'-O-methyl-3'-phosphonoacetate (MP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015; Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., Med Chem Comm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066; Ryan et al., Nucleic Acids Res. (2018) 46(2): 792-803). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target DNA and one or more deoxyribonucleotides and/or nucleotide analogs in a region that binds to Cas9, Cpf1, or C2c1. In an embodiment of the invention, deoxyribonucleotides and/or nucleotide analogs are incorporated in engineered guide structures, such as, without limitation, 5' and/or 3' end, stem-loop regions, and the seed region. In certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl-3'-phosphorothioate (MS), S-constrained ethyl(cEt), 2'-O-methyl-3'-thioPACE (MSP), or 2'-O-methyl-3'-phosphonoacetate (MP). Such modification can enhance genome editing efficiency (see Hendel et al., Nat. Biotechnol. (2015) 33(9): 985-989; Ryan et al., Nucleic Acids Res. (2018) 46(2): 792-803). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), Rhodamine, peptides, nuclear localization sequence (NLS), peptide nucleic acid (PNA), polyethylene glycol (PEG), triethylene glycol, or tetraethyleneglycol (TEG). In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554). In some embodiments, 3 nucleotides at each of the 3' and 5' ends are chemically modified. In a specific embodiment, the modifications comprise 2'-O-methyl or phosphorothioate analogs. In a specific embodiment, 12 nucleotides in the tetraloop and 16 nucleotides in the stem-loop region are replaced with 2'-O-methyl analogs. Such chemical modifications improve in vivo editing and stability (see Finn et al., Cell Reports (2018), 22: 2227-2235). In some embodiments, more than 60 or 70 nucleotides of the guide are chemically modified. In some embodiments, this modification comprises replacement of nucleotides with 2'-O-methyl or 2'-fluoro nucleotide analogs or phosphorothioate (PS) modification of phosphodiester bonds. In some embodiments, the chemical modification comprises 2'-O-methyl or 2'-fluoro modification of guide nucleotides extending outside of the nuclease protein when the CRISPR complex is formed or PS modification of 20 to 30 or more nucleotides of the 3'-terminus of the guide. In a particular embodiment, the chemical modification further comprises 2'-O-methyl analogs at the 5' end of the guide or 2'-fluoro analogs in the seed and tail regions. Such chemical modifications improve stability to nuclease degradation and maintain or enhance genome-editing activity or efficiency, but modification of all nucleotides may abolish the function of the guide (see Yin et al., Nat. Biotech. (2018), 35(12): 1179-1187). Such chemical modifications may be guided by knowledge of the structure of the CRISPR complex, including knowledge of the limited number of nuclease and RNA 2'-OH interactions (see Yin et al., Nat. Biotech. (2018), 35(12): 1179-1187). In some embodiments, one or more guide RNA nucleotides may be replaced with DNA nucleotides. In some embodiments, up to 2, 4, 6, 8, 10, or 12 RNA nucleotides of the 5'-end tail/seed guide region are replaced with DNA nucleotides. In certain embodiments, the majority of guide RNA nucleotides at the 3' end are replaced with DNA nucleotides. In particular embodiments, 16 guide RNA nucleotides at the 3' end are replaced with DNA nucleotides. In particular embodiments, 8 guide RNA nucleotides of the 5'-end tail/seed region and 16 RNA nucleotides at the 3' end are replaced with DNA nucleotides. In particular embodiments, guide RNA nucleotides that extend outside of the nuclease protein when the CRISPR complex is formed are replaced with DNA nucleotides. Such replacement of multiple RNA nucleotides with DNA nucleotides leads to decreased off-target activity but similar on-target activity compared to an unmodified guide; however, replacement of all RNA nucleotides at the 3' end may abolish the function of the guide (see Yin et al., Nat. Chem. Biol. (2018) 14, 311-316). Such modifications may be guided by knowledge of the structure of the CRISPR complex, including knowledge of the limited number of nuclease and RNA 2'-OH interactions (see Yin et al., Nat. Chem. Biol. (2018) 14, 311-316).

In one embodiment of the invention, the guide comprises a modified crRNA for Cpf1, having a 5'-handle and a guide segment further comprising a seed region and a 3'-terminus. In some embodiments, the modified guide can be used with a Cpf1 of any one of *Acidaminococcus* sp. BV3L6 Cpf1 (AsCpf1); *Francisella tularensis* subsp. *Novicida* U112 Cpf1 (FnCpf1); *L. bacterium* MC2017 Cpf1 (Lb3Cpf1); *Butyrivibrio proteoclasticus* Cpf1 (BpCpf1); *Parcubacteria bacterium* GWC2011_GWC2_44_17 Cpf1 (PbCpf1); *Peregrinibacteria bacterium* GW2011_GWA_33_10 Cpf1 (PeCpf1); *Leptospira inadai* Cpf1 (LiCpf1); *Smithella* sp. SC_K08D17 Cpf1 (SsCpf1); *L. bacterium* MA2020 Cpf1 (Lb2Cpf1); *Porphyromonas crevioricanis* Cpf1 (PcCpf1); *Porphyromonas macacae* Cpf1 (PmCpf1); *Candidatus Methanoplasma termitum* Cpf1 (CMtCpf1); *Eubacterium eligens* Cpf1 (EeCpf1); *Moraxella bovoculi* 237 Cpf1

(MbCpf1); *Prevotella disiens* Cpf1 (PdCpf1); or *L. bacterium* ND2006 Cpf1 (LbCpf1).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), $N^1$-methylpseudouridine ($me^1Ψ$), 5-methoxyuridine(5moU), inosine, 7-methylguanosine, 2'-O-methyl-3'-phosphorothioate (MS), S-constrained ethyl(cEt), phosphorothioate (PS), 2'-O-methyl-3'-thioPACE (MSP), or 2'-O-methyl-3'-phosphonoacetate (MP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In some embodiments, all nucleotides are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 or 10 nucleotides in the 3'-terminus are chemically modified. Such chemical modifications at the 3'-terminus of the Cpf1 CrRNA improve gene cutting efficiency (see Li, et al., Nature Biomedical Engineering, 2017, 1:0066). In a specific embodiment, 5 nucleotides in the 3'-terminus are replaced with 2'-fluoro analogues. In a specific embodiment, 10 nucleotides in the 3'-terminus are replaced with 2'-fluoro analogues. In a specific embodiment, 5 nucleotides in the 3'-terminus are replaced with 2'-O-methyl (M) analogs. In some embodiments, 3 nucleotides at each of the 3' and 5' ends are chemically modified. In a specific embodiment, the modifications comprise 2'-O-methyl or phosphorothioate analogs. In a specific embodiment, 12 nucleotides in the tetraloop and 16 nucleotides in the stem-loop region are replaced with 2'-O-methyl analogs. Such chemical modifications improve in vivo editing and stability (see Finn et al., Cell Reports (2018), 22: 2227-2235).

In some embodiments, the loop of the 5'-handle of the guide is modified. In some embodiments, the loop of the 5'-handle of the guide is modified to have a deletion, an insertion, a split, or chemical modifications. In certain embodiments, the loop comprises 3, 4, or 5 nucleotides. In certain embodiments, the loop comprises the sequence of UCUU, UUUU, UAUU, or UGUU. In some embodiments, the guide molecule forms a stemloop with a separate non-covalently linked sequence, which can be DNA or RNA.

Synthetically Linked Guide

In one embodiment, the guide comprises a tracr sequence and a tracr mate sequence that are chemically linked or conjugated via a non-phosphodiester bond. In one embodiment, the guide comprises a tracr sequence and a tracr mate sequence that are chemically linked or conjugated via a non-nucleotide loop. In some embodiments, the tracr and tracr mate sequences are joined via a non-phosphodiester covalent linker. Examples of the covalent linker include but are not limited to a chemical moiety selected from the group consisting of carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, the tracr and tracr mate sequences are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, the tracr or tracr mate sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sufonyl, ally, propargyl, diene, alkyne, and azide. Once the tracr and the tracr mate sequences are functionalized, a covalent chemical bond or linkage can be formed between the two oligonucleotides. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, the tracr and tracr mate sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In some embodiments, the tracr and tracr mate sequences can be covalently linked using various bioconjugation reactions, loops, bridges, and non-nucleotide links via modifications of sugar, internucleotide phosphodiester bonds, purine and pyrimidine residues. Sletten et al., Angew. Chem. Int. Ed. (2009) 48:6974-6998; Manoharan, M. Curr. Opin. Chem. Biol. (2004) 8: 570-9; Behlke et al., Oligonucleotides (2008) 18: 305-19; Watts, et al., Drug. Discov. Today (2008) 13: 842-55; Shukla, et al., ChemMedChem (2010) 5: 328-49.

In some embodiments, the tracr and tracr mate sequences can be covalently linked using click chemistry. In some embodiments, the tracr and tracr mate sequences can be covalently linked using a triazole linker. In some embodiments, the tracr and tracr mate sequences can be covalently linked using Huisgen 1,3-dipolar cycloaddition reaction involving an alkyne and azide to yield a highly stable triazole linker (He et al., ChemBioChem (2015) 17: 1809-1812; International Patent Publication No. WO 2016/186745). In some embodiments, the tracr and tracr mate sequences are covalently linked by ligating a 5'-hexyne tracrRNA and a 3'-azide crRNA. In some embodiments, either or both of the 5'-hexyne tracrRNA and a 3'-azide crRNA can be protected with 2'-acetoxyethl orthoester (2'-ACE) group, which can be subsequently removed using Dharmacon protocol (Scaringe et al., J. Am. Chem. Soc. (1998) 120: 11820-11821; Scaringe, Methods Enzymol. (2000) 317: 3-18).

In some embodiments, the tracr and tracr mate sequences can be covalently linked via a linker (e.g., a non-nucleotide loop) that comprises a moiety such as spacers, attachments, bioconjugates, chromophores, reporter groups, dye labeled RNAs, and non-naturally occurring nucleotide analogues. More specifically, suitable spacers for purposes of this invention include, but are not limited to, polyethers (e.g., polyethylene glycols, polyalcohols, polypropylene glycol or mixtures of ethylene and propylene glycols), polyamines group (e.g., spennine, spermidine and polymeric derivatives thereof), polyesters (e.g., poly(ethyl acrylate)), polyphosphodiesters, alkylenes, and combinations thereof. Suitable attachments include any moiety that can be added to the linker to add additional properties to the linker, such as but not limited to, fluorescent labels. Suitable bioconjugates include, but are not limited to, peptides, glycosides, lipids, cholesterol, phospholipids, diacyl glycerols and dialkyl glycerols, fatty acids, hydrocarbons, enzyme substrates, steroids, biotin, digoxigenin, carbohydrates, polysaccharides. Suitable chromophores, reporter groups, and dye-labeled RNAs include, but are not limited to, fluorescent dyes such as fluorescein and rhodamine, chemiluminescent, electrochemiluminescent, and bioluminescent marker compounds. The design of example linkers conjugating two RNA components are also described in WO 2004/015075.

The linker (e.g., a non-nucleotide loop) can be of any length. In some embodiments, the linker has a length equivalent to about 0-16 nucleotides. In some embodiments, the linker has a length equivalent to about 0-8 nucleotides. In some embodiments, the linker has a length equivalent to about 0-4 nucleotides. In some embodiments, the linker has a length equivalent to about 2 nucleotides. Example linker design is also described in WO2011/008730.

A typical Type II Cas9 sgRNA comprises (in 5' to 3' direction): a guide sequence, a poly U tract, a first complimentary stretch (the "repeat"), a loop (tetraloop), a second complimentary stretch (the "anti-repeat" being complimentary to the repeat), a stem, and further stem loops and stems and a poly A (often poly U in RNA) tail (terminator). In preferred embodiments, certain embodiments of guide architecture are retained, certain embodiment of guide architecture cam be modified, for example by addition, subtraction, or substitution of features, whereas certain other embodiments of guide architecture are maintained. Preferred locations for engineered sgRNA modifications, including but not limited to insertions, deletions, and substitutions include guide termini and regions of the sgRNA that are exposed when complexed with CRISPR protein and/or target, for example the tetraloop and/or loop2.

In certain embodiments, guides of the invention comprise specific binding sites (e.g. aptamers) for adapter proteins, which may comprise one or more functional domains (e.g. via fusion protein). When such a guides forms a CRISPR complex (i.e. CRISPR enzyme binding to guide and target) the adapter proteins bind and, the functional domain associated with the adapter protein is positioned in a spatial orientation which is advantageous for the attributed function to be effective. For example, if the functional domain is a transcription activator (e.g. VP64 or p65), the transcription activator is placed in a spatial orientation which allows it to affect the transcription of the target. Likewise, a transcription repressor will be advantageously positioned to affect the transcription of the target and a nuclease (e.g. Fok1) will be advantageously positioned to cleave or partially cleave the target.

The skilled person will understand that modifications to the guide which allow for binding of the adapter+functional domain but not proper positioning of the adapter+functional domain (e.g. due to steric hindrance within the three-dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and most preferably at both the tetra loop and stem loop 2.

The repeat:anti repeat duplex will be apparent from the secondary structure of the sgRNA. It may be typically a first complimentary stretch after (in 5' to 3' direction) the poly U tract and before the tetraloop; and a second complimentary stretch after (in 5' to 3' direction) the tetraloop and before the poly A tract. The first complimentary stretch (the "repeat") is complimentary to the second complimentary stretch (the "anti-repeat"). As such, they Watson-Crick base pair to form a duplex of dsRNA when folded back on one another. As such, the anti-repeat sequence is the complimentary sequence of the repeat and in terms to A-U or C-G base pairing, but also in terms of the fact that the anti-repeat is in the reverse orientation due to the tetraloop.

In an embodiment of the invention, modification of guide architecture comprises replacing bases in stemloop 2. For example, in some embodiments, "actt" ("acuu" in RNA) and "aagt" ("aagu" in RNA) bases in stemloop2 are replaced with "cgcc" and "gcgg". In some embodiments, "actt" and "aagt" bases in stemloop2 are replaced with complimentary GC-rich regions of 4 nucleotides. In some embodiments, the complimentary GC-rich regions of 4 nucleotides are "cgcc" and "gcgg" (both in 5' to 3' direction). In some embodiments, the complimentary GC-rich regions of 4 nucleotides are "gcgg" and "cgcc" (both in 5' to 3' direction). Other combination of C and G in the complimentary GC-rich regions of 4 nucleotides will be apparent including CCCC and GGGG.

In one embodiment, the stemloop 2, e.g., "ACTTgtttAAGT" (SEQ ID NO: 36) can be replaced by any "XXXXgtttYYYY" (SEQ ID NO. 37), e.g., where XXXX and YYYY represent any complementary sets of nucleotides that together will base pair to each other to create a stem.

In one embodiment, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-12 and Y2-12 (wherein X and Y represent any complementary set of nucleotides) may be contemplated. In one embodiment, the stem made of the X and Y nucleotides, together with the "gttt," will form a complete hairpin in the overall secondary structure; and, this may be advantageous and the amount of base pairs can be any amount that forms a complete hairpin. In one embodiment, any complementary X:Y base-pairing sequence (e.g., as to length) is tolerated, so long as the secondary structure of the entire sgRNA is preserved. In one embodiment, the stem can be a form of X:Y base-pairing that does not disrupt the secondary structure of the whole sgRNA in that it has a DR:tracr duplex, and 3 stemloops. In one embodiment, the "gttt" tetraloop that connects ACTT and AAGT (or any alternative stem made of X:Y base pairs) can be any sequence of the same length (e.g., 4 base pair) or longer that does not interrupt the overall secondary structure of the sgRNA. In one embodiment, the stemloop can be something that further lengthens stemloop2, e.g. can be MS2 aptamer. In one embodiment, the stemloop3 "GGCACCGagtCGGTGC" (SEQ ID NO: 38) can likewise take on a "XXXXXXXagtYYYYYYY" (SEQ ID NO: 39) form, e.g., wherein X7 and Y7 represent any complementary sets of nucleotides that together will base pair to each other to create a stem. In one embodiment, the stem comprises about 7 bp comprising complementary X and Y sequences, although stems of more or fewer base pairs are also contemplated. In one embodiment, the stem made of the X and Y nucleotides, together with the "agt", will form a complete hairpin in the overall secondary structure. In one embodiment, any complementary X:Y base pairing sequence is tolerated, so long as the secondary structure of the entire sgRNA is preserved. In one embodiment, the stem can be a form of X:Y basepairing that doesn't disrupt the secondary structure of the whole sgRNA in that it has a DR:tracr duplex, and 3 stemloops. In one embodiment, the "agt" sequence of the stemloop 3 can be extended or be replaced by an aptamer, e.g., a MS2 aptamer or sequence that otherwise generally preserves the architecture of stemloop3. In one embodiment for alternative Stemloops 2 and/or 3, each X and Y pair can refer to any base pair. In one embodiment, non-Watson Crick base pairing is contemplated, where such pairing otherwise generally preserves the architecture of the stemloop at that position.

In one embodiment, the DR:tracrRNA duplex can be replaced with the form: gYYYYag(N)NNNNxxxxNNNN(AAN)uuRRRRu (SEQ ID NO: 40) (using standard IUPAC nomenclature for nucleotides), wherein (N) and (AAN) represent part of the bulge in the duplex, and "xxxx" represents a linker sequence. NNNN on the direct repeat can be anything so long as it base-pairs with the corresponding NNNN portion of the tracrRNA. In one embodiment, the DR:tracrRNA duplex can be connected by a linker of any length (xxxx . . . ), any base composition, as long as it doesn't alter the overall structure.

In one embodiment, the sgRNA structural requirement is to have a duplex and 3 stemloops. In most embodiments, the actual sequence requirement for many of the particular base requirements are lax, in that the architecture of the DR:tracrRNA duplex should be preserved, but the sequence that creates the architecture, i.e., the stems, loops, bulges, etc., may be altered.

Aptamers

One guide with a first aptamer/RNA-binding protein pair can be linked or fused to an activator, whilst a second guide with a second aptamer/RNA-binding protein pair can be linked or fused to a repressor. The guides are for different targets (loci), so this allows one gene to be activated and one repressed. For example, the following schematic shows such an approach:

Guide 1—MS2 aptamer - - - MS2 RNA-binding protein - - - VP64 activator; and

Guide 2—PP7 aptamer - - - PP7 RNA-binding protein - - - SID4x repressor.

The present invention also relates to orthogonal PP7/MS2 gene targeting. In this example, sgRNA targeting different loci are modified with distinct RNA loops in order to recruit MS2-VP64 or PP7-SID4X, which activate and repress their target loci, respectively. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. For example, an sgRNA targeting locus A can be modified with MS2 loops, recruiting MS2-VP64 activators, while another sgRNA targeting locus B can be modified with PP7 loops, recruiting PP7-SID4X repressor domains. In the same cell, dCas9 can thus mediate orthogonal, locus-specific modifications. This principle can be extended to incorporate other orthogonal RNA-binding proteins such as Q-beta.

An alternative option for orthogonal repression includes incorporating non-coding RNA loops with transactive repressive function into the guide (either at similar positions to the MS2/PP7 loops integrated into the guide or at the 3' terminus of the guide). For instance, guides were designed with non-coding (but known to be repressive) RNA loops (e.g. using the Alu repressor (in RNA) that interferes with RNA polymerase II in mammalian cells). The Alu RNA sequence was located: in place of the MS2 RNA sequences as used herein (e.g. at tetraloop and/or stem loop 2); and/or at 3' terminus of the guide. This gives possible combinations of MS2, PP7 or Alu at the tetraloop and/or stemloop 2 positions, as well as, optionally, addition of Alu at the 3' end of the guide (with or without a linker).

The use of two different aptamers (distinct RNA) allows an activator-adaptor protein fusion and a repressor-adaptor protein fusion to be used, with different guides, to activate expression of one gene, whilst repressing another. They, along with their different guides can be administered together, or substantially together, in a multiplexed approach. A large number of such modified guides can be used all at the same time, for example 10 or 20 or 30 and so forth, whilst only one (or at least a minimal number) of Cas9s to be delivered, as a comparatively small number of Cas9s can be used with a large number modified guides. The adaptor protein may be associated (preferably linked or fused to) one or more activators or one or more repressors. For example, the adaptor protein may be associated with a first activator and a second activator. The first and second activators may be the same, but they are preferably different activators. For example, one might be VP64, whilst the other might be p65, although these are just examples and other transcriptional activators are envisaged. Three or more or even four or more activators (or repressors) may be used, but package size may limit the number being higher than 5 different functional domains. Linkers are preferably used, over a direct fusion to the adaptor protein, where two or more functional domains are associated with the adaptor protein. Suitable linkers might include the GlySer linker.

It is also envisaged that the enzyme-guide complex as a whole may be associated with two or more functional domains. For example, there may be two or more functional domains associated with the enzyme, or there may be two or more functional domains associated with the guide (via one or more adaptor proteins), or there may be one or more functional domains associated with the enzyme and one or more functional domains associated with the guide (via one or more adaptor proteins).

The fusion between the adaptor protein and the activator or repressor may include a linker. For example, GlySer linkers GGGS (SEQ ID NO: 6) can be used. They can be used in repeats of 3 ($(GGGGS)_3$ (SEQ ID NO: 9)) or 6, 9 or even 12 or more, to provide suitable lengths, as required. Linkers can be used between the RNA-binding protein and the functional domain (activator or repressor), or between the CRISPR Enzyme (Cas9) and the functional domain (activator or repressor). The linkers the user to engineer appropriate amounts of "mechanical flexibility".

Dead Guides

In one embodiment, the invention provides guide sequences which are modified in a manner which allows for formation of the CRISPR complex and successful binding to the target, while at the same time, not allowing for successful nuclease activity (i.e. without nuclease activity/without indel activity). For matters of explanation such modified guide sequences are referred to as "dead guides" or "dead guide sequences". These dead guides or dead guide sequences can be thought of as catalytically inactive or conformationally inactive with regard to nuclease activity. Nuclease activity may be measured using surveyor analysis or deep sequencing as commonly used in the art, preferably surveyor analysis. Similarly, dead guide sequences may not sufficiently engage in productive base pairing with respect to the ability to promote catalytic activity or to distinguish on-target and off-target binding activity. Briefly, the surveyor assay involves purifying and amplifying a CRISPR target site for a gene and forming heteroduplexes with primers amplifying the CRISPR target site. After re-anneal, the products are treated with SURVEYOR nuclease and SURVEYOR enhancer S (Transgenomics) following the manufacturer's recommended protocols, analyzed on gels, and quantified based upon relative band intensities.

Hence, in a related embodiment, the invention provides a non-naturally occurring or engineered composition Cas9 CRISPR-Cas system comprising a functional Cas9 as described herein, and guide RNA (gRNA) wherein the gRNA comprises a dead guide sequence whereby the gRNA is capable of hybridizing to a target sequence such that the Cas9 CRISPR-Cas system is directed to a genomic locus of interest in a cell without detectable indel activity resultant from nuclease activity of a non-mutant Cas9 enzyme of the system as detected by a SURVEYOR assay. For shorthand purposes, a gRNA comprising a dead guide sequence whereby the gRNA is capable of hybridizing to a target sequence such that the Cas9 CRISPR-Cas system is directed to a genomic locus of interest in a cell without detectable indel activity resultant from nuclease activity of a non-mutant Cas9 enzyme of the system as detected by a SURVEYOR assay is herein termed a "dead gRNA". It is to be understood that any of the gRNAs according to the invention as described herein elsewhere may be used as dead gRNAs/gRNAs comprising a dead guide sequence as described herein below. Any of the methods, products, compositions and uses as described herein elsewhere is equally applicable with the dead gRNAs/gRNAs comprising a dead guide sequence as further detailed below. By means of further guidance, the following particular embodiments and embodiments are provided.

The ability of a dead guide sequence to direct sequence-specific binding of a CRISPR complex to a target sequence may be assessed by any suitable assay. For example, the components of a CRISPR system sufficient to form a CRISPR complex, including the dead guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the dead guide sequence to be tested and a control guide sequence different from the test dead guide sequence, and comparing binding or rate of cleavage at the target sequence between the test and control guide sequence reactions. Other assays are possible, and will occur to those skilled in the art. A dead guide sequence may be selected to target any target sequence. In some embodiments, the target sequence is a sequence within a genome of a cell.

As explained further herein, several structural parameters allow for a proper framework to arrive at such dead guides. Dead guide sequences are shorter than respective guide sequences which result in active Cas9-specific indel formation. Dead guides are 5%, 10%, 20%, 30%, 40%, 50%, shorter than respective guides directed to the same Cas9 leading to active Cas9-specific indel formation.

As explained below and known in the art, one embodiment of gRNA—Cas9 specificity is the direct repeat sequence, which is to be appropriately linked to such guides. In particular, this implies that the direct repeat sequences are designed dependent on the origin of the Cas9. Thus, structural data available for validated dead guide sequences may be used for designing Cas9 specific equivalents. Structural similarity between, e.g., the orthologous nuclease domains RuvC of two or more Cas9 effector proteins may be used to transfer design equivalent dead guides. Thus, the dead guide herein may be appropriately modified in length and sequence to reflect such Cas9 specific equivalents, allowing for formation of the CRISPR complex and successful binding to the target, while at the same time, not allowing for successful nuclease activity.

The use of dead guides in the context herein as well as the state of the art provides a surprising and unexpected platform for network biology and/or systems biology in both in vitro, ex vivo, and in vivo applications, allowing for multiplex gene targeting, and in particular bidirectional multiplex gene targeting. Prior to the use of dead guides, addressing multiple targets, for example for activation, repression and/or silencing of gene activity, has been challenging and in some cases not possible. With the use of dead guides, multiple targets, and thus multiple activities, may be addressed, for example, in the same cell, in the same animal, or in the same patient. Such multiplexing may occur at the same time or staggered for a desired timeframe.

For example, the dead guides now allow for the first time to use gRNA as a means for gene targeting, without the consequence of nuclease activity, while at the same time providing directed means for activation or repression. Guide RNA comprising a dead guide may be modified to further include elements in a manner which allow for activation or repression of gene activity, in particular protein adaptors (e.g. aptamers) as described herein elsewhere allowing for functional placement of gene effectors (e.g. activators or repressors of gene activity). One example is the incorporation of aptamers, as explained herein and in the state of the art. By engineering the gRNA comprising a dead guide to incorporate protein-interacting aptamers (Konermann et al., "Genome-scale transcription activation by an engineered CRISPR-Cas9 complex," doi:10.1038/nature14136, incorporated herein by reference), one may assemble a synthetic transcription activation complex consisting of multiple distinct effector domains. Such may be modeled after natural transcription activation processes. For example, an aptamer, which selectively binds an effector (e.g. an activator or repressor; dimerized MS2 bacteriophage coat proteins as fusion proteins with an activator or repressor), or a protein which itself binds an effector (e.g. activator or repressor) may be appended to a dead gRNA tetraloop and/or a stem-loop 2. In the case of MS2, the fusion protein MS2-VP64 binds to the tetraloop and/or stem-loop 2 and in turn mediates transcriptional up-regulation, for example for Neurog2. Other transcriptional activators are, for example, VP64. P65, HSF1, and MyoD 1. By mere example of this concept, replacement of the MS2 stem-loops with PP7-interacting stem-loops may be used to recruit repressive elements.

Thus, one embodiment is a gRNA of the invention which comprises a dead guide, wherein the gRNA further comprises modifications which provide for gene activation or repression, as described herein. The dead gRNA may comprise one or more aptamers. The aptamers may be specific to gene effectors, gene activators or gene repressors. Alternatively, the aptamers may be specific to a protein which in turn is specific to and recruits/binds a specific gene effector, gene activator or gene repressor. If there are multiple sites for activator or repressor recruitment, it is preferred that the sites are specific to either activators or repressors. If there are multiple sites for activator or repressor binding, the sites may be specific to the same activators or same repressors. The sites may also be specific to different activators or different repressors. The gene effectors, gene activators, gene repressors may be present in the form of fusion proteins.

In an embodiment, the dead gRNA as described herein or the Cas9 CRISPR-Cas complex as described herein includes a non-naturally occurring or engineered composition comprising two or more adaptor proteins, wherein each protein is associated with one or more functional domains and wherein the adaptor protein binds to the distinct RNA sequence(s) inserted into the at least one loop of the dead gRNA.

Hence, an embodiment provides a non-naturally occurring or engineered composition comprising a guide RNA (gRNA) comprising a dead guide sequence capable of hybridizing to a target sequence in a genomic locus of interest in a cell, wherein the dead guide sequence is as defined herein, a Cas9 comprising at least one or more nuclear localization sequences, wherein the Cas9 optionally comprises at least one mutation wherein at least one loop of the dead gRNA is modified by the insertion of distinct RNA sequence(s) that bind to one or more adaptor proteins, and wherein the adaptor protein is associated with one or more functional domains; or, wherein the dead gRNA is modified to have at least one non-coding functional loop, and wherein the composition comprises two or more adaptor proteins, wherein the each protein is associated with one or more functional domains.

In certain embodiments, the adaptor protein is a fusion protein comprising the functional domain, the fusion protein optionally comprising a linker between the adaptor protein and the functional domain, the linker optionally including a GlySer linker.

In certain embodiments, the at least one loop of the dead gRNA is not modified by the insertion of distinct RNA sequence(s) that bind to the two or more adaptor proteins.

In certain embodiments, the one or more functional domains associated with the adaptor protein is a transcriptional activation domain.

In certain embodiments, the one or more functional domains associated with the adaptor protein is a transcriptional activation domain comprising VP64, p65, MyoD1, HSF1, RTA or SETT/9.

In certain embodiments, the one or more functional domains associated with the adaptor protein is a transcriptional repressor domain.

In certain embodiments, the transcriptional repressor domain is a KRAB domain.

In certain embodiments, the transcriptional repressor domain is a NuE domain, NcoR domain, SID domain or a SID4X domain.

In certain embodiments, at least one of the one or more functional domains associated with the adaptor protein have one or more activities comprising methylase activity, demethylase activity, transcription activation activity, transcription repression activity, transcription release factor activity, histone modification activity, DNA integration activity RNA cleavage activity, DNA cleavage activity or nucleic acid binding activity.

In certain embodiments, the DNA cleavage activity is due to a Fok1 nuclease.

In certain embodiments, the dead gRNA is modified so that, after dead gRNA binds the adaptor protein and further binds to the Cas9 and target, the functional domain is in a spatial orientation allowing for the functional domain to function in its attributed function.

In certain embodiments, the at least one loop of the dead gRNA is tetra loop and/or loop2. In certain embodiments, the tetra loop and loop 2 of the dead gRNA are modified by the insertion of the distinct RNA sequence(s).

In certain embodiments, the insertion of distinct RNA sequence(s) that bind to one or more adaptor proteins is an aptamer sequence. In certain embodiments, the aptamer sequence is two or more aptamer sequences specific to the same adaptor protein. In certain embodiments, the aptamer sequence is two or more aptamer sequences specific to different adaptor protein.

In certain embodiments, the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s, PRR1.

In certain embodiments, the cell is a eukaryotic cell. In certain embodiments, the eukaryotic cell is a mammalian cell, optionally a mouse cell. In certain embodiments, the mammalian cell is a human cell.

In certain embodiments, a first adaptor protein is associated with a p65 domain and a second adaptor protein is associated with a HSF1 domain.

In certain embodiments, the composition comprises a Cas9 CRISPR-Cas complex having at least three functional domains, at least one of which is associated with the Cas9 and at least two of which are associated with dead gRNA.

In certain embodiments, the composition further comprises a second gRNA, wherein the second gRNA is a live gRNA capable of hybridizing to a second target sequence such that a second Cas9 CRISPR-Cas system is directed to a second genomic locus of interest in a cell with detectable indel activity at the second genomic locus resultant from nuclease activity of the Cas9 enzyme of the system.

In certain embodiments, the composition further comprises a plurality of dead gRNAs and/or a plurality of live gRNAs.

One embodiment of the invention is to take advantage of the modularity and customizability of the gRNA scaffold to establish a series of gRNA scaffolds with different binding sites (in particular aptamers) for recruiting distinct types of effectors in an orthogonal manner. Again, for matters of example and illustration of the broader concept, replacement of the MS2 stem-loops with PP7-interacting stem-loops may be used to bind/recruit repressive elements, enabling multiplexed bidirectional transcriptional control. Thus, in general, gRNA comprising a dead guide may be employed to provide for multiplex transcriptional control and preferred bidirectional transcriptional control. This transcriptional control is most preferred of genes. For example, one or more gRNA comprising dead guide(s) may be employed in targeting the activation of one or more target genes. At the same time, one or more gRNA comprising dead guide(s) may be employed in targeting the repression of one or more target genes. Such a sequence may be applied in a variety of different combinations, for example the target genes are first repressed and then at an appropriate period other targets are activated, or select genes are repressed at the same time as select genes are activated, followed by further activation and/or repression. As a result, multiple components of one or more biological systems may advantageously be addressed together.

In an embodiment, the invention provides nucleic acid molecule(s) encoding dead gRNA or the Cas9 CRISPR-Cas complex or the composition as described herein.

In an embodiment, the invention provides a vector system comprising: a nucleic acid molecule encoding dead guide RNA as defined herein. In certain embodiments, the vector system further comprises a nucleic acid molecule(s) encoding Cas9. In certain embodiments, the vector system further comprises a nucleic acid molecule(s) encoding (live) gRNA. In certain embodiments, the nucleic acid molecule or the vector further comprises regulatory element(s) operable in a eukaryotic cell operably linked to the nucleic acid molecule encoding the guide sequence (gRNA) and/or the nucleic acid molecule encoding Cas9 and/or the optional nuclear localization sequence(s).

In another embodiment, structural analysis may also be used to study interactions between the dead guide and the active Cas9 nuclease that enable DNA binding, but no DNA cutting. In this way amino acids important for nuclease activity of Cas9 are determined. Modification of such amino acids allows for improved Cas9 enzymes used for gene editing.

A further embodiment is combining the use of dead guides as explained herein with other applications of CRISPR, as explained herein as well as known in the art. For example, gRNA comprising dead guide(s) for targeted multiplex gene activation or repression or targeted multiplex bidirectional gene activation/repression may be combined with gRNA comprising guides which maintain nuclease activity, as explained herein. Such gRNA comprising guides which maintain nuclease activity may or may not further include modifications which allow for repression of gene activity (e.g. aptamers). Such gRNA comprising guides which maintain nuclease activity may or may not further include modifications which allow for activation of gene activity (e.g. aptamers). In such a manner, a further means for multiplex gene control is introduced (e.g. multiplex gene targeted activation without nuclease activity/without indel activity may be provided at the same time or in combination with gene targeted repression with nuclease activity).

For example, 1) using one or more gRNA (e.g. 1-50, 1-40, 1-30, 1-20, preferably 1-10, more preferably 1-5) comprising dead guide(s) targeted to one or more genes and further modified with appropriate aptamers for the recruitment of gene activators; 2) may be combined with one or more gRNA (e.g. 1-50, 1-40, 1-30, 1-20, preferably 1-10, more preferably 1-5) comprising dead guide(s) targeted to one or more genes and further modified with appropriate aptamers for the recruitment of gene repressors. 1) and/or 2) may then be combined with 3) one or more gRNA (e.g. 1-50, 1-40, 1-30, 1-20, preferably 1-10, more preferably 1-5) targeted to one or more genes. This combination can then be carried out in turn with 1)+2)+3) with 4) one or more gRNA (e.g. 1-50, 1-40, 1-30, 1-20, preferably 1-10, more preferably 1-5) targeted to one or more genes and further modified with appropriate aptamers for the recruitment of gene activators. This combination can then be carried in turn with 1)+2)+3)+4) with 5) one or more gRNA (e.g. 1-50, 1-40, 1-30, 1-20, preferably 1-10, more preferably 1-5) targeted to one or more genes and further modified with appropriate aptamers for the recruitment of gene repressors. As a result various uses and combinations are included in the invention. For example, combination 1)+2); combination 1)+3); combination 2)+3); combination 1)+2)+3); combination 1)+2)+3)+4); combination 1)+3)+4); combination 2)+3)+4); combination 1)+2)+4); combination 1)+2)+3)+4)+5); combination 1)+3)+4)+5); combination 2)+3)+4)+5); combination 1)+2)+4)+5); combination 1)+2)+3)+5); combination 1)+3)+5); combination 2)+3)+5); combination 1)+2)+5).

In an embodiment, the invention provides an algorithm for designing, evaluating, or selecting a dead guide RNA targeting sequence (dead guide sequence) for guiding a Cas9 CRISPR-Cas system to a target gene locus. In particular, it has been determined that dead guide RNA specificity relates to and can be optimized by varying i) GC content and ii) targeting sequence length. In an embodiment, the invention provides an algorithm for designing or evaluating a dead guide RNA targeting sequence that minimizes off-target binding or interaction of the dead guide RNA. In an embodiment of the invention, the algorithm for selecting a dead guide RNA targeting sequence for directing a CRISPR system to a gene locus in an organism comprises a) locating one or more CRISPR motifs in the gene locus, analyzing the 20 nt sequence downstream of each CRISPR motif by i) determining the GC content of the sequence; and ii) determining whether there are off-target matches of the 15 downstream nucleotides nearest to the CRISPR motif in the genome of the organism, and c) selecting the 15 nucleotide sequence for use in a dead guide RNA if the GC content of the sequence is 70% or less and no off-target matches are identified. In an embodiment, the sequence is selected for a targeting sequence if the GC content is 60% or less. In certain embodiments, the sequence is selected for a targeting sequence if the GC content is 55% or less, 50% or less, 45% or less, 40% or less, 35% or less or 30% or less. In an embodiment, two or more sequences of the gene locus are analyzed and the sequence having the lowest GC content, or the next lowest GC content, or the next lowest GC content is selected. In an embodiment, the sequence is selected for a targeting sequence if no off-target matches are identified in the genome of the organism. In an embodiment, the targeting sequence is selected if no off-target matches are identified in regulatory sequences of the genome.

In an embodiment, the invention provides a method of selecting a dead guide RNA targeting sequence for directing a functionalized CRISPR system to a gene locus in an organism, which comprises: a) locating one or more CRISPR motifs in the gene locus; b) analyzing the 20 nt sequence downstream of each CRISPR motif by: i) determining the GC content of the sequence; and ii) determining whether there are off-target matches of the first 15 nt of the sequence in the genome of the organism; c) selecting the sequence for use in a guide RNA if the GC content of the sequence is 70% or less and no off-target matches are identified. In an embodiment, the sequence is selected if the GC content is 50% or less. In an embodiment, the sequence is selected if the GC content is 40% or less. In an embodiment, the sequence is selected if the GC content is 30% or less. In an embodiment, two or more sequences are analyzed and the sequence having the lowest GC content is selected. In an embodiment, off-target matches are determined in regulatory sequences of the organism. In an embodiment, the gene locus is a regulatory region. An embodiment provides a dead guide RNA comprising the targeting sequence selected according to the aforementioned methods.

In an embodiment, the invention provides a dead guide RNA for targeting a functionalized CRISPR system to a gene locus in an organism. In an embodiment of the invention, the dead guide RNA comprises a targeting sequence wherein the CG content of the target sequence is 70% or less, and the first 15 nt of the targeting sequence does not match an off-target sequence downstream from a CRISPR motif in the regulatory sequence of another gene locus in the organism. In certain embodiments, the GC content of the targeting sequence 60% or less, 55% or less, 50% or less, 45% or less, 40% or less, 35% or less or 30% or less. In certain embodiments, the GC content of the targeting sequence is from 70% to 60% or from 60% to 50% or from 50% to 40% or from 40% to 30%. In an embodiment, the targeting sequence has the lowest CG content among potential targeting sequences of the locus.

In an embodiment of the invention, the first 15 nt of the dead guide match the target sequence. In another embodiment, first 14 nt of the dead guide match the target sequence. In another embodiment, the first 13 nt of the dead guide match the target sequence. In another embodiment first 12 nt of the dead guide match the target sequence. In another embodiment, first 11 nt of the dead guide match the target sequence. In another embodiment, the first 10 nt of the dead guide match the target sequence. In an embodiment of the invention the first 15 nt of the dead guide does not match an off-target sequence downstream from a CRISPR motif in the regulatory region of another gene locus. In other embodiments, the first 14 nt, or the first 13 nt of the dead guide, or the first 12 nt of the guide, or the first 11 nt of the dead guide, or the first 10 nt of the dead guide, does not match an off-target sequence downstream from a CRISPR motif in the regulatory region of another gene locus. In other embodiments, the first 15 nt, or 14 nt, or 13 nt, or 12 nt, or 11 nt of the dead guide do not match an off-target sequence downstream from a CRISPR motif in the genome.

In certain embodiments, the dead guide RNA includes additional nucleotides at the 3'-end that do not match the target sequence. Thus, a dead guide RNA that includes the first 15 nt, or 14 nt, or 13 nt, or 12 nt, or 11 nt downstream of a CRISPR motif can be extended in length at the 3' end to 12 nt, 13 nt, 14 nt, 15 nt, 16 nt, 17 nt, 18 nt, 19 nt, 20 nt, or longer.

The invention provides a method for directing a Cas9 CRISPR-Cas system, including but not limited to a dead Cas9 (dCas9) or functionalized Cas9 system (which may comprise a functionalized Cas9 or functionalized guide) to a gene locus. In an embodiment, the invention provides a method for selecting a dead guide RNA targeting sequence and directing a functionalized CRISPR system to a gene locus in an organism. In an embodiment, the invention provides a method for selecting a dead guide RNA targeting sequence and effecting gene regulation of a target gene locus by a functionalized Cas9 CRISPR-Cas system. In certain embodiments, the method is used to effect target gene regulation while minimizing off-target effects. In an embodiment, the invention provides a method for selecting two or more dead guide RNA targeting sequences and effecting gene regulation of two or more target gene loci by a functionalized Cas9 CRISPR-Cas system. In certain embodiments, the method is used to effect regulation of two or more target gene loci while minimizing off-target effects.

In an embodiment, the invention provides a method of selecting a dead guide RNA targeting sequence for directing a functionalized Cas9 to a gene locus in an organism, which comprises: a) locating one or more CRISPR motifs in the gene locus; b) analyzing the sequence downstream of each CRISPR motif by: i) selecting 10 to 15 nt adjacent to the CRISPR motif, ii) determining the GC content of the sequence; and c) selecting the 10 to 15 nt sequence as a targeting sequence for use in a guide RNA if the GC content of the sequence is 40% or more. In an embodiment, the sequence is selected if the GC content is 50% or more. In an embodiment, the sequence is selected if the GC content is 60% or more. In an embodiment, the sequence is selected if the GC content is 70% or more. In an embodiment, two or more sequences are analyzed and the sequence having the highest GC content is selected. In an embodiment, the method further comprises adding nucleotides to the 3' end of the selected sequence which do not match the sequence downstream of the CRISPR motif. An embodiment provides a dead guide RNA comprising the targeting sequence selected according to the aforementioned methods.

In an embodiment, the invention provides a dead guide RNA for directing a functionalized CRISPR system to a gene locus in an organism wherein the targeting sequence of the dead guide RNA consists of 10 to 15 nucleotides adjacent to the CRISPR motif of the gene locus, wherein the CG content of the target sequence is 50% or more. In certain embodiments, the dead guide RNA further comprises nucleotides added to the 3' end of the targeting sequence which do not match the sequence downstream of the CRISPR motif of the gene locus.

In an embodiment, the invention provides for a single effector to be directed to one or more, or two or more gene loci. In certain embodiments, the effector is associated with a Cas9, and one or more, or two or more selected dead guide RNAs are used to direct the Cas9-associated effector to one or more, or two or more selected target gene loci. In certain embodiments, the effector is associated with one or more, or two or more selected dead guide RNAs, each selected dead guide RNA, when complexed with a Cas9 enzyme, causing its associated effector to localize to the dead guide RNA target. One non-limiting example of such CRISPR systems modulates activity of one or more, or two or more gene loci subject to regulation by the same transcription factor.

In an embodiment, the invention provides for two or more effectors to be directed to one or more gene loci. In certain embodiments, two or more dead guide RNAs are employed, each of the two or more effectors being associated with a selected dead guide RNA, with each of the two or more effectors being localized to the selected target of its dead guide RNA. One non-limiting example of such CRISPR systems modulates activity of one or more, or two or more gene loci subject to regulation by different transcription factors. Thus, in one non-limiting embodiment, two or more transcription factors are localized to different regulatory sequences of a single gene. In another non-limiting embodiment, two or more transcription factors are localized to different regulatory sequences of different genes. In certain embodiments, one transcription factor is an activator. In certain embodiments, one transcription factor is an inhibitor. In certain embodiments, one transcription factor is an activator and another transcription factor is an inhibitor. In certain embodiments, gene loci expressing different components of the same regulatory pathway are regulated. In certain embodiments, gene loci expressing components of different regulatory pathways are regulated.

In an embodiment, the invention also provides a method and algorithm for designing and selecting dead guide RNAs that are specific for target DNA cleavage or target binding and gene regulation mediated by an active Cas9 CRISPR-Cas system. In certain embodiments, the Cas9 CRISPR-Cas system provides orthogonal gene control using an active Cas9 which cleaves target DNA at one gene locus while at the same time binds to and promotes regulation of another gene locus.

In an embodiment, the invention provides an method of selecting a dead guide RNA targeting sequence for directing a functionalized Cas9 to a gene locus in an organism, without cleavage, which comprises a) locating one or more CRISPR motifs in the gene locus; b) analyzing the sequence downstream of each CRISPR motif by i) selecting 10 to 15 nt adjacent to the CRISPR motif, ii) determining the GC content of the sequence, and c) selecting the 10 to 15 nt sequence as a targeting sequence for use in a dead guide RNA if the GC content of the sequence is 30% more, 40% or more. In certain embodiments, the GC content of the targeting sequence is 35% or more, 40% or more, 45% or more, 50% or more, 55% or more, 60% or more, 65% or more, or 70% or more. In certain embodiments, the GC content of the targeting sequence is from 30% to 40% or from 40% to 50% or from 50% to 60% or from 60% to 70%. In an embodiment of the invention, two or more sequences in a gene locus are analyzed and the sequence having the highest GC content is selected.

In an embodiment of the invention, the portion of the targeting sequence in which GC content is evaluated is 10 to 15 contiguous nucleotides of the 15 target nucleotides nearest to the PAM. In an embodiment of the invention, the portion of the guide in which GC content is considered is the 10 to 11 nucleotides or 11 to 12 nucleotides or 12 to 13 nucleotides or 13, or 14, or 15 contiguous nucleotides of the 15 nucleotides nearest to the PAM.

In an embodiment, the invention further provides an algorithm for identifying dead guide RNAs which promote CRISPR system gene locus cleavage while avoiding functional activation or inhibition. It is observed that increased GC content in dead guide RNAs of 16 to 20 nucleotides coincides with increased DNA cleavage and reduced functional activation.

In some embodiments, the efficiency of functionalized Cas9 can be increased by addition of nucleotides to the 3' end of a guide RNA which do not match a target sequence downstream of the CRISPR motif. For example, of dead guide RNA 11 to 15 nt in length, shorter guides may be less likely to promote target cleavage, but are also less efficient at promoting CRISPR system binding and functional control. In certain embodiments, addition of nucleotides that don't match the target sequence to the 3' end of the dead guide RNA increase activation efficiency while not increasing undesired target cleavage. In an embodiment, the invention also provides a method and algorithm for identifying improved dead guide RNAs that effectively promote CRISPR system function in DNA binding and gene regulation while not promoting DNA cleavage. Thus, in certain embodiments, the invention provides a dead guide RNA that includes the first 15 nt, or 14 nt, or 13 nt, or 12 nt, or 11 nt downstream of a CRISPR motif and is extended in length at the 3' end by nucleotides that mismatch the target to 12 nt, 13 nt, 14 nt, 15 nt, 16 nt, 17 nt, 18 nt, 19 nt, 20 nt, or longer.

In an embodiment, the invention provides a method for effecting selective orthogonal gene control. As will be appreciated from the disclosure herein, dead guide selection according to the invention, taking into account guide length and GC content, provides effective and selective transcription control by a functional Cas9 CRISPR-Cas system, for example to regulate transcription of a gene locus by activation or inhibition and minimize off-target effects. Accordingly, by providing effective regulation of individual target loci, the invention also provides effective orthogonal regulation of two or more target loci.

In certain embodiments, orthogonal gene control is by activation or inhibition of two or more target loci. In certain embodiments, orthogonal gene control is by activation or inhibition of one or more target locus and cleavage of one or more target locus.

In one embodiment, the invention provides a cell comprising a non-naturally occurring Cas9 CRISPR-Cas system comprising one or more dead guide RNAs disclosed or made according to a method or algorithm described herein wherein the expression of one or more gene products has been altered. In an embodiment of the invention, the expression in the cell of two or more gene products has been altered. The invention also provides a cell line from such a cell.

In one embodiment, the invention provides a multicellular organism comprising one or more cells comprising a non-naturally occurring Cas9 CRISPR-Cas system comprising one or more dead guide RNAs disclosed or made according to a method or algorithm described herein. In one embodiment, the invention provides a product from a cell, cell line, or multicellular organism comprising a non-naturally occurring Cas9 CRISPR-Cas system comprising one or more dead guide RNAs disclosed or made according to a method or algorithm described herein.

A further embodiment of this invention is the use of gRNA comprising dead guide(s) as described herein, optionally in combination with gRNA comprising guide(s) as described herein or in the state of the art, in combination with systems e.g. cells, transgenic animals, transgenic mice, inducible transgenic animals, inducible transgenic mice) which are engineered for either overexpression of Cas9 or preferably knock in Cas9. As a result a single system (e.g. transgenic animal, cell) can serve as a basis for multiplex gene modifications in systems/network biology. On account of the dead guides, this is now possible in both in vitro, ex vivo, and in vivo.

For example, once the Cas9 is provided for, one or more dead gRNAs may be provided to direct multiplex gene regulation, and preferably multiplex bidirectional gene regulation. The one or more dead gRNAs may be provided in a spatially and temporally appropriate manner if necessary or desired (for example tissue specific induction of Cas9 expression). On account that the transgenic/inducible Cas9 is provided for (e.g. expressed) in the cell, tissue, animal of interest, both gRNAs comprising dead guides or gRNAs comprising guides are equally effective. In the same manner, a further embodiment of this invention is the use of gRNA comprising dead guide(s) as described herein, optionally in combination with gRNA comprising guide(s) as described herein or in the state of the art, in combination with systems (e.g. cells, transgenic animals, transgenic mice, inducible transgenic animals, inducible transgenic mice) which are engineered for knockout Cas9 CRISPR-Cas.

As a result, the combination of dead guides as described herein with CRISPR applications described herein and CRISPR applications known in the art results in a highly efficient and accurate means for multiplex screening of systems (e.g. network biology). Such screening allows, for example, identification of specific combinations of gene activities for identifying genes responsible for diseases (e.g. on/off combinations), in particular gene related diseases. A preferred application of such screening is cancer. In the same manner, screening for treatment for such diseases is included in the invention. Cells or animals may be exposed to aberrant conditions resulting in disease or disease like effects. Candidate compositions may be provided and screened for an effect in the desired multiplex environment. For example a patient's cancer cells may be screened for which gene combinations will cause them to die, and then use this information to establish appropriate therapies.

In one embodiment, the invention provides a kit comprising one or more of the components described herein. The kit may include dead guides as described herein with or without guides as described herein.

The structural information provided herein allows for interrogation of dead gRNA interaction with the target DNA and the Cas9 permitting engineering or alteration of dead gRNA structure to optimize functionality of the entire Cas9 CRISPR-Cas system. For example, loops of the dead gRNA may be extended, without colliding with the Cas9 protein by the insertion of adaptor proteins that can bind to RNA. These adaptor proteins can further recruit effector proteins or fusions which comprise one or more functional domains.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (e.g. SID4X). In some embodiments, the functional domain is an epigenetic modifying domain, such that an epigenetic modifying enzyme is provided. In some embodiments, the functional domain is an activation domain, which may be the P65 activation domain.

An embodiment of the invention is that the above elements are comprised in a single composition or comprised in individual compositions. These compositions may advantageously be applied to a host to elicit a functional effect on the genomic level.

In general, the dead gRNA are modified in a manner that provides specific binding sites (e.g. aptamers) for adapter proteins comprising one or more functional domains (e.g. via fusion protein) to bind to. The modified dead gRNA are modified such that once the dead gRNA forms a CRISPR complex (i.e. Cas9 binding to dead gRNA and target) the adapter proteins bind and, the functional domain on the adapter protein is positioned in a spatial orientation which is advantageous for the attributed function to be effective. For example, if the functional domain is a transcription activator (e.g. VP64 or p65), the transcription activator is placed in a spatial orientation which allows it to affect the transcription of the target. Likewise, a transcription repressor will be advantageously positioned to affect the transcription of the target and a nuclease (e.g. Fok1) will be advantageously positioned to cleave or partially cleave the target.

The skilled person will understand that modifications to the dead gRNA which allow for binding of the adapter+functional domain but not proper positioning of the adapter+functional domain (e.g. due to steric hindrance within the three-dimensional structure of the CRISPR complex) are modifications which are not intended. The one or more modified dead gRNA may be modified at the tetra loop, the stem loop 1, stem loop 2, or stem loop 3, as described herein, preferably at either the tetra loop or stem loop 2, and most preferably at both the tetra loop and stem loop 2.

As explained herein the functional domains may be, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). In some cases it is advantageous that additionally at least one NLS is provided. In some instances, it is advantageous to position the NLS at the N terminus. When more than one functional domain is included, the functional domains may be the same or different.

The dead gRNA may be designed to include multiple binding recognition sites (e.g. aptamers) specific to the same or different adapter protein. The dead gRNA may be designed to bind to the promoter region −1000-+1 nucleic acids upstream of the transcription start site (i.e. TSS), preferably −200 nucleic acids. This positioning improves functional domains which affect gene activation (e.g. transcription activators) or gene inhibition (e.g. transcription repressors). The modified dead gRNA may be one or more modified dead gRNAs targeted to one or more target loci (e.g. at least 1 gRNA, at least 2 gRNA, at least 5 gRNA, at least 10 gRNA, at least 20 gRNA, at least 30 gRNA, at least 50 gRNA) comprised in a composition.

The adaptor protein may be any number of proteins that binds to an aptamer or recognition site introduced into the modified dead gRNA and which allows proper positioning of one or more functional domains, once the dead gRNA has been incorporated into the CRISPR complex, to affect the target with the attributed function. As explained in detail in this application such may be coat proteins, preferably bacteriophage coat proteins. The functional domains associated with such adaptor proteins (e.g. in the form of fusion protein) may include, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). Preferred domains are Fok1, VP64, P65, HSF1, MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains.

Thus, the modified dead gRNA, the (inactivated) Cas9 (with or without functional domains), and the binding protein with one or more functional domains, may each individually be comprised in a composition and administered to a host individually or collectively. Alternatively, these components may be provided in a single composition for administration to a host. Administration to a host may be performed via viral vectors known to the skilled person or described herein for delivery to a host (e.g. lentiviral vector, adenoviral vector, AAV vector). As explained herein, use of different selection markers (e.g. for lentiviral gRNA selection) and concentration of gRNA (e.g. dependent on whether multiple gRNAs are used) may be advantageous for eliciting an improved effect.

On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g. gene activation of lincRNA and identification of function; gain-of-function modeling; loss-of-function modeling; the use the compositions of the invention to establish cell lines and transgenic animals for optimization and screening purposes).

The current invention comprehends the use of the compositions of the current invention to establish and utilize conditional or inducible CRISPR transgenic cell/animals, which are not believed prior to the present invention or application. For example, the target cell comprises Cas9 conditionally or inducibly (e.g. in the form of Cre dependent constructs) and/or the adapter protein conditionally or inducibly and, on expression of a vector introduced into the target cell, the vector expresses that which induces or gives rise to the condition of Cas9 expression and/or adaptor expression in the target cell. By applying the teaching and compositions of the current invention with the known method of creating a CRISPR complex, inducible genomic events affected by functional domains are also an embodiment of the current invention. One example of this is the creation of a CRISPR knock-in/conditional transgenic animal (e.g. mouse comprising e.g. a Lox-Stop-polyA-Lox(LSL) cassette) and subsequent delivery of one or more compositions providing one or more modified dead gRNA (e.g. −200 nucleotides to TSS of a target gene of interest for gene activation purposes) as described herein (e.g. modified dead gRNA with one or more aptamers recognized by coat proteins, e.g. MS2), one or more adapter proteins as described herein (MS2 binding protein linked to one or more VP64) and means for inducing the conditional animal (e.g. Cre recombinase for rendering Cas9 expression inducible). Alternatively, the adaptor protein may be provided as a conditional or inducible element with a conditional or inducible Cas9 to provide an effective model for screening purposes, which advantageously only requires minimal design and administration of specific dead gRNAs for a broad number of applications.

In another embodiment the dead guides are further modified to improve specificity. Protected dead guides may be synthesized, whereby secondary structure is introduced into the 3' end of the dead guide to improve its specificity. A protected guide RNA (pgRNA) comprises a guide sequence capable of hybridizing to a target sequence in a genomic locus of interest in a cell and a protector strand, wherein the protector strand is optionally complementary to the guide sequence and wherein the guide sequence may in part be hybridizable to the protector strand. The pgRNA optionally includes an extension sequence. The thermodynamics of the pgRNA-target DNA hybridization is determined by the number of bases complementary between the guide RNA and target DNA. By employing ‘thermodynamic protection’, specificity of dead gRNA can be improved by adding a protector sequence. For example, one method adds a complementary protector strand of varying lengths to the 3' end of the guide sequence within the dead gRNA. As a result, the protector strand is bound to at least a portion of the dead gRNA and provides for a protected gRNA (pgRNA). In turn, the dead gRNA references herein may be easily protected using the described embodiments, resulting in pgRNA. The protector strand can be either a separate RNA transcript or strand or a chimeric version joined to the 3' end of the dead gRNA guide sequence.

The inventors have shown that CRISPR enzymes as defined herein can employ more than one RNA guide without losing activity. This enables the use of the CRISPR enzymes, systems or complexes as defined herein for targeting multiple DNA targets, genes or gene loci, with a single enzyme, system or complex as defined herein. The guide RNAs may be tandemly arranged, optionally separated by a nucleotide sequence such as a direct repeat as defined herein. The position of the different guide RNAs is the tandem does not influence the activity. It is noted that the terms “CRISPR-Cas system”, “CRISP-Cas complex” “CRISPR complex” and “CRISPR system” are used interchangeably. Also, the terms “CRISPR enzyme”, “Cas enzyme”, or “CRISPR-Cas enzyme”, can be used interchangeably. In preferred embodiments, said CRISPR enzyme, CRISP-Cas enzyme or Cas enzyme is Cas9, or any one of the modified or mutated variants thereof described herein elsewhere.

In one embodiment, the invention provides a non-naturally occurring or engineered CRISPR enzyme, preferably a class 2 CRISPR enzyme, preferably a Type V or VI CRISPR enzyme as described herein, such as without limitation Cas9 as described herein elsewhere, used for tandem or multiplex targeting. It is to be understood that any of the CRISPR (or CRISPR-Cas or Cas) enzymes, complexes, or systems according to the invention as described herein elsewhere may be used in such an approach. Any of the methods, products, compositions and uses as described herein elsewhere are equally applicable with the multiplex or tandem targeting approach further detailed below. By means of further guidance, the following particular embodiments and embodiments are provided.

In one embodiment, the invention provides for the use of a Cas9 enzyme, complex or system as defined herein for targeting multiple gene loci. In one embodiment, this can be established by using multiple (tandem or multiplex) guide RNA (gRNA) sequences.

In one embodiment, the invention provides methods for using one or more elements of a Cas9 enzyme, complex or system as defined herein for tandem or multiplex targeting, wherein said CRISP system comprises multiple guide RNA sequences. Preferably, said gRNA sequences are separated by a nucleotide sequence, such as a direct repeat as defined herein elsewhere.

The Cas9 enzyme, system or complex as defined herein provides an effective means for modifying multiple target polynucleotides. The Cas9 enzyme, system or complex as defined herein has a wide variety of utility including modifying (e.g., deleting, inserting, translocating, inactivating, activating) one or more target polynucleotides in a multiplicity of cell types. As such the Cas9 enzyme, system or complex as defined herein of the invention has a broad spectrum of applications in, e.g., gene therapy, drug screening, disease diagnosis, and prognosis, including targeting multiple gene loci within a single CRISPR system.

In one embodiment, the invention provides a Cas9 enzyme, system or complex as defined herein, i.e. a Cas9 CRISPR-Cas complex having a Cas9 protein having at least one destabilization domain associated therewith, and multiple guide RNAs that target multiple nucleic acid molecules such as DNA molecules, whereby each of said multiple guide RNAs specifically targets its corresponding nucleic acid molecule, e.g., DNA molecule. Each nucleic acid molecule target, e.g., DNA molecule can encode a gene product or encompass a gene locus. Using multiple guide RNAs hence enables the targeting of multiple gene loci or multiple genes. In some embodiments the Cas9 enzyme may cleave the DNA molecule encoding the gene product. In some embodiments expression of the gene product is altered. The Cas9 protein and the guide RNAs do not naturally occur together. The invention comprehends the guide RNAs comprising tandemly arranged guide sequences. The invention further comprehends coding sequences for the Cas9 protein being codon optimized for expression in a eukaryotic cell. In a preferred embodiment the eukaryotic cell is a mammalian cell, a plant cell or a yeast cell and in a more preferred embodiment the mammalian cell is a human cell. Expression of the gene product may be decreased. The Cas9 enzyme may form part of a CRISPR system or complex, which further comprises tandemly arranged guide RNAs (gRNAs) comprising a series of 2, 3, 4, 5, 6, 7, 8, 9, 10, 15, 25, 25, 30, or more than 30 guide sequences, each capable of specifically hybridizing to a target sequence in a genomic locus of interest in a cell. In some embodiments, the functional Cas9 CRISPR system or complex binds to the multiple target sequences. In some embodiments, the functional CRISPR system or complex may edit the multiple target sequences, e.g., the target sequences may comprise a genomic locus, and in some embodiments, there may be an alteration of gene expression. In some embodiments, the functional CRISPR system or complex may comprise further functional domains. In some embodiments, the invention provides a method for altering or modifying expression of multiple gene products. The method may comprise introducing into a cell containing said target nucleic acids, e.g., DNA molecules, or containing and expressing target nucleic acid, e.g., DNA molecules; for instance, the target nucleic acids may encode gene products or provide for expression of gene products (e.g., regulatory sequences).

In preferred embodiments the CRISPR enzyme used for multiplex targeting is Cas9, or the CRISPR system or complex comprises Cas9. In some embodiments, the CRISPR enzyme used for multiplex targeting is AsCas9, or the CRISPR system or complex used for multiplex targeting comprises an AsCas9. In some embodiments, the CRISPR enzyme is an LbCas9, or the CRISPR system or complex comprises LbCas9. In some embodiments, the Cas9 enzyme used for multiplex targeting cleaves both strands of DNA to produce a double strand break (DSB). In some embodiments, the CRISPR enzyme used for multiplex targeting is a nickase. In some embodiments, the Cas9 enzyme used for multiplex targeting is a dual nickase. In some embodiments, the Cas9 enzyme used for multiplex targeting is a Cas9 enzyme such as a DD Cas9 enzyme as defined herein elsewhere.

In some general embodiments, the Cas9 enzyme used for multiplex targeting is associated with one or more functional domains. In some more specific embodiments, the CRISPR enzyme used for multiplex targeting is a deadCas9 as defined herein elsewhere.

In an embodiment, the present invention provides a means for delivering the Cas9 enzyme, system or complex for use in multiple targeting as defined herein or the polynucleotides defined herein. Non-limiting examples of such delivery means are e.g. particle(s) delivering component(s) of the complex, vector(s) comprising the polynucleotide(s) discussed herein (e.g., encoding the CRISPR enzyme, providing the nucleotides encoding the CRISPR complex). In some embodiments, the vector may be a plasmid or a viral vector such as AAV, or lentivirus. Transient transfection with plasmids, e.g., into HEK cells may be advantageous, especially given the size limitations of AAV and that while Cas9 fits into AAV, one may reach an upper limit with additional guide RNAs.

Also provided is a model that constitutively expresses the Cas9 enzyme, complex or system as used herein for use in multiplex targeting. The organism may be transgenic and may have been transfected with the present vectors or may be the offspring of an organism so transfected. In a further embodiment, the present invention provides compositions comprising the CRISPR enzyme, system and complex as defined herein or the polynucleotides or vectors described herein. Also provides are Cas9 CRISPR systems or complexes comprising multiple guide RNAs, preferably in a tandemly arranged format. Said different guide RNAs may be separated by nucleotide sequences such as direct repeats.

Also provided is a method of treating a subject, e.g., a subject in need thereof, comprising inducing gene editing by transforming the subject with the polynucleotide encoding the Cas9 CRISPR system or complex or any of polynucleotides or vectors described herein and administering them to the subject. A suitable repair template may also be provided, for example delivered by a vector comprising said repair template. Also provided is a method of treating a subject, e.g., a subject in need thereof, comprising inducing transcriptional activation or repression of multiple target gene loci by transforming the subject with the polynucleotides or vectors described herein, wherein said polynucleotide or vector encodes or comprises the Cas9 enzyme, complex or system comprising multiple guide RNAs, preferably tandemly arranged. Where any treatment is occurring ex vivo, for example in a cell culture, then it will be appreciated that the term 'subject' may be replaced by the phrase "cell or cell culture."

Compositions comprising Cas9 enzyme, complex or system comprising multiple guide RNAs, preferably tandemly arranged, or the polynucleotide or vector encoding or comprising said Cas9 enzyme, complex or system comprising multiple guide RNAs, preferably tandemly arranged, for use in the methods of treatment as defined herein elsewhere are also provided. A kit of parts may be provided including such compositions. Use of said composition in the manufacture of a medicament for such methods of treatment are also provided. Use of a Cas9 CRISPR system in screening is also provided by the present invention, e.g., gain of function screens. Cells which are artificially forced to overexpress a gene are be able to down regulate the gene over time (re-establishing equilibrium) e.g. by negative feedback loops. By the time the screen starts the unregulated gene might be reduced again. Using an inducible Cas9 activator allows one to induce transcription right before the screen and therefore minimizes the chance of false negative hits. Accordingly, by use of the instant invention in screening, e.g., gain of function screens, the chance of false negative results may be minimized.

In one embodiment, the invention provides an engineered, non-naturally occurring CRISPR system comprising a Cas9 protein and multiple guide RNAs that each specifically target a DNA molecule encoding a gene product in a cell, whereby the multiple guide RNAs each target their specific DNA molecule encoding the gene product and the Cas9 protein cleaves the target DNA molecule encoding the gene product, whereby expression of the gene product is altered; and, wherein the CRISPR protein and the guide RNAs do not naturally occur together. The invention comprehends the multiple guide RNAs comprising multiple guide sequences, preferably separated by a nucleotide sequence such as a direct repeat and optionally fused to a tracr sequence. In an embodiment of the invention the CRISPR protein is a type V or VI CRISPR-Cas protein and in a more preferred embodiment the CRISPR protein is a Cas9 protein. The invention further comprehends a Cas9 protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another embodiment, the invention provides an engineered, non-naturally occurring vector system comprising one or more vectors comprising a first regulatory element operably linked to the multiple Cas9 CRISPR system guide RNAs that each specifically target a DNA molecule encoding a gene product and a second regulatory element operably linked coding for a CRISPR protein. Both regulatory elements may be located on the same vector or on different vectors of the system. The multiple guide RNAs target the multiple DNA molecules encoding the multiple gene products in a cell and the CRISPR protein may cleave the multiple DNA molecules encoding the gene products (it may cleave one or both strands or have substantially no nuclease activity), whereby expression of the multiple gene products is altered; and, wherein the CRISPR protein and the multiple guide RNAs do not naturally occur together. In a preferred embodiment the CRISPR protein is Cas9 protein, optionally codon optimized for expression in a eukaryotic cell. In a preferred embodiment the eukaryotic cell is a mammalian cell, a plant cell or a yeast cell and in a more preferred embodiment the mammalian cell is a human cell. In a further embodiment of the invention, the expression of each of the multiple gene products is altered, preferably decreased.

In one embodiment, the invention provides a vector system comprising one or more vectors. In some embodiments, the system comprises: (a) a first regulatory element operably linked to a direct repeat sequence and one or more insertion sites for inserting one or more guide sequences up- or downstream (whichever applicable) of the direct repeat sequence, wherein when expressed, the one or more guide sequence(s) direct(s) sequence-specific binding of the CRISPR complex to the one or more target sequence(s) in a eukaryotic cell, wherein the CRISPR complex comprises a Cas9 enzyme complexed with the one or more guide sequence(s) that is hybridized to the one or more target sequence(s); and (b) a second regulatory element operably linked to an enzyme-coding sequence encoding said Cas9 enzyme, preferably comprising at least one nuclear localization sequence and/or at least one NES; wherein components (a) and (b) are located on the same or different vectors of the system. Where applicable, a tracr sequence may also be provided. In some embodiments, component (a) further comprises two or more guide sequences operably linked to the first regulatory element, wherein when expressed, each of the two or more guide sequences direct sequence specific binding of a Cas9 CRISPR complex to a different target sequence in a eukaryotic cell. In some embodiments, the CRISPR complex comprises one or more nuclear localization sequences and/or one or more NES of sufficient strength to drive accumulation of said Cas9 CRISPR complex in a detectable amount in or out of the nucleus of a eukaryotic cell. In some embodiments, the first regulatory element is a polymerase III promoter. In some embodiments, the second regulatory element is a polymerase II promoter. In some embodiments, each of the guide sequences is at least 16, 17, 18, 19, 20, 25 nucleotides, or between 16-30, or between 16-25, or between 16-20 nucleotides in length.

Recombinant expression vectors can comprise the polynucleotides encoding the Cas9 enzyme, system or complex for use in multiple targeting as defined herein in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

In some embodiments, a host cell is transiently or non-transiently transfected with one or more vectors comprising the polynucleotides encoding the Cas9 enzyme, system or complex for use in multiple targeting as defined herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art and exemplified herein elsewhere. Cell lines are available from a variety of sources known to those with skill in the art (see, e.g., the American Type Culture Collection (ATCC) (Manassas, Va.)). In some embodiments, a cell transfected with one or more vectors comprising the polynucleotides encoding the Cas9 enzyme, system or complex for use in multiple targeting as defined herein is used to establish a new cell line comprising one or more vector-derived sequences. In some embodiments, a cell transiently transfected with the components of a Cas9 CRISPR system or complex for use in multiple targeting as described herein (such as by transient transfection of one or more vectors, or transfection with RNA), and modified through the activity of a Cas9 CRISPR system or complex, is used to establish a new cell line comprising cells containing the modification but lacking any other exogenous sequence. In some embodiments, cells transiently or non-transiently transfected with one or more vectors comprising the polynucleotides encoding the Cas9 enzyme, system or complex for use in multiple targeting as defined herein, or cell lines derived from such cells are used in assessing one or more test compounds.

The term "regulatory element" is as defined herein elsewhere.

Advantageous vectors include lentiviruses and adeno-associated viruses, and types of such vectors can also be selected for targeting particular types of cells.

In one embodiment, the invention provides a eukaryotic host cell comprising (a) a first regulatory element operably linked to a direct repeat sequence and one or more insertion sites for inserting one or more guide RNA sequences up- or downstream (whichever applicable) of the direct repeat sequence, wherein when expressed, the guide sequence(s) direct(s) sequence-specific binding of the Cas9 CRISPR complex to the respective target sequence(s) in a eukaryotic cell, wherein the Cas9 CRISPR complex comprises a Cas9 enzyme complexed with the one or more guide sequence(s) that is hybridized to the respective target sequence(s); and/or (b) a second regulatory element operably linked to an enzyme-coding sequence encoding said Cas9 enzyme comprising preferably at least one nuclear localization sequence and/or NES. In some embodiments, the host cell comprises components (a) and (b). Where applicable, a tracr sequence may also be provided. In some embodiments, component (a), component (b), or components (a) and (b) are stably integrated into a genome of the host eukaryotic cell. In some embodiments, component (a) further comprises two or more guide sequences operably linked to the first regulatory element, and optionally separated by a direct repeat, wherein when expressed, each of the two or more guide sequences direct sequence specific binding of a Cas9 CRISPR complex to a different target sequence in a eukaryotic cell. In some embodiments, the Cas9 enzyme comprises one or more nuclear localization sequences and/or nuclear export sequences or NES of sufficient strength to drive accumulation of said CRISPR enzyme in a detectable amount in and/or out of the nucleus of a eukaryotic cell.

In some embodiments, the Cas9 enzyme is a type V or VI CRISPR system enzyme. In some embodiments, the Cas9 enzyme is a Cas9 enzyme. In some embodiments, the Cas9 enzyme is derived from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens*, or *Porphyromonas macacae* Cas9, and may include further alterations or mutations of the Cas9 as defined herein elsewhere, and can be a chimeric Cas9. In some embodiments, the Cas9 enzyme is codon-optimized for expression in a eukaryotic cell. In some embodiments, the CRISPR enzyme directs cleavage of one or two strands at the location of the target sequence. In some embodiments, the first regulatory element is a polymerase III promoter. In some embodiments, the second regulatory element is a polymerase II promoter. In some embodiments, the one or more guide sequence(s) is (are each) at least 16, 17, 18, 19, 20, 25 nucleotides, or between 16-30, or between 16-25, or between 16-20 nucleotides in length. When multiple guide RNAs are used, they are preferably separated by a direct repeat sequence. In an embodiment, the invention provides a non-human eukaryotic organism; preferably a multicellular eukaryotic organism, comprising a eukaryotic host cell according to any of the described embodiments. In other embodiments, the invention provides a eukaryotic organism; preferably a multicellular eukaryotic organism, comprising a eukaryotic host cell according to any of the described embodiments. The organism in some embodiments of these embodiments may be an animal; for example a mammal. Also, the organism may be an arthropod such as an insect. The organism also may be a plant. Further, the organism may be a fungus.

In one embodiment, the invention provides a kit comprising one or more of the components described herein. In some embodiments, the kit comprises a vector system and instructions for using the kit. In some embodiments, the vector system comprises (a) a first regulatory element operably linked to a direct repeat sequence and one or more insertion sites for inserting one or more guide sequences up- or downstream (whichever applicable) of the direct repeat sequence, wherein when expressed, the guide sequence directs sequence-specific binding of a Cas9 CRISPR complex to a target sequence in a eukaryotic cell, wherein the Cas9 CRISPR complex comprises a Cas9 enzyme complexed with the guide sequence that is hybridized to the target sequence; and/or (b) a second regulatory element operably linked to an enzyme-coding sequence encoding said Cas9 enzyme comprising a nuclear localization sequence. Where applicable, a tracr sequence may also be provided. In some embodiments, the kit comprises components (a) and (b) located on the same or different vectors of the system. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the Cas9 enzyme comprises one or more nuclear localization sequences of sufficient strength to drive accumulation of said CRISPR enzyme in a detectable amount in the nucleus of a eukaryotic cell. In some embodiments, the CRISPR enzyme is a type V or VI CRISPR system enzyme. In some embodiments, the CRISPR enzyme is a Cas9 enzyme. In some embodiments, the Cas9 enzyme is derived from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens*, or *Porphyromonas macacae* Cas9 (e.g., modified to have or be associated with at least one DD), and may include further alteration or mutation of the Cas9, and can be a chimeric Cas9. In some embodiments, the DD-CRISPR enzyme is codon-optimized for expression in a eukaryotic cell. In some embodiments, the DD-CRISPR enzyme directs cleavage of one or two strands at the location of the target sequence. In some embodiments, the DD-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 16, 17, 18, 19, 20, 25 nucleotides, or between 16-30, or between 16-25, or between 16-20 nucleotides in length.

In one embodiment, the invention provides a method of modifying multiple target polynucleotides in a host cell such as a eukaryotic cell. In some embodiments, the method comprises allowing a Cas9CRISPR complex to bind to multiple target polynucleotides, e.g., to effect cleavage of said multiple target polynucleotides, thereby modifying multiple target polynucleotides, wherein the Cas9CRISPR complex comprises a Cas9 enzyme complexed with multiple guide sequences each of the being hybridized to a specific target sequence within said target polynucleotide, wherein said multiple guide sequences are linked to a direct repeat sequence. Where applicable, a tracr sequence may also be provided (e.g. to provide a single guide RNA, sgRNA). In some embodiments, said cleavage comprises cleaving one or two strands at the location of each of the target sequence by said Cas9 enzyme. In some embodiments, said cleavage results in decreased transcription of the multiple target genes. In some embodiments, the method further comprises repairing one or more of said cleaved target polynucleotide by homologous recombination with an exogenous template polynucleotide, wherein said repair results in a mutation comprising an insertion, deletion, or substitution of one or more nucleotides of one or more of said target polynucleotides. In some embodiments, said mutation results in one or more amino acid changes in a protein expressed from a gene comprising one or more of the target sequence(s). In some embodiments, the method further comprises delivering one or more vectors to said eukaryotic cell, wherein the one or more vectors drive expression of one or more of: the Cas9 enzyme and the multiple guide RNA sequence linked to a direct repeat sequence. Where applicable, a tracr sequence may also be provided. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one embodiment, the invention provides a method of modifying expression of multiple polynucleotides in a eukaryotic cell. In some embodiments, the method comprises allowing a Cas9 CRISPR complex to bind to multiple polynucleotides such that said binding results in increased or decreased expression of said polynucleotides; wherein the Cas9 CRISPR complex comprises a Cas9 enzyme complexed with multiple guide sequences each specifically hybridized to its own target sequence within said polynucleotide, wherein said guide sequences are linked to a direct repeat sequence. Where applicable, a tracr sequence may also be provided. In some embodiments, the method further comprises delivering one or more vectors to said eukaryotic cells, wherein the one or more vectors drive expression of one or more of: the Cas9 enzyme and the multiple guide sequences linked to the direct repeat sequences. Where applicable, a tracr sequence may also be provided.

In one embodiment, the invention provides a recombinant polynucleotide comprising multiple guide RNA sequences up- or downstream (whichever applicable) of a direct repeat sequence, wherein each of the guide sequences when expressed directs sequence-specific binding of a Cas9CRISPR complex to its corresponding target sequence present in a eukaryotic cell. In some embodiments, the target sequence is a viral sequence present in a eukaryotic cell. Where applicable, a tracr sequence may also be provided. In some embodiments, the target sequence is a proto-oncogene or an oncogene.

Embodiments of the invention encompass a non-naturally occurring or engineered composition that may comprise a guide RNA (gRNA) comprising a guide sequence capable of hybridizing to a target sequence in a genomic locus of interest in a cell and a Cas9 enzyme as defined herein that may comprise at least one or more nuclear localization sequences.

An embodiment of the invention encompasses methods of modifying a genomic locus of interest to change gene expression in a cell by introducing into the cell any of the compositions described herein.

An embodiment of the invention is that the above elements are comprised in a single composition or comprised in individual compositions. These compositions may advantageously be applied to a host to elicit a functional effect on the genomic level.

As used herein, the term "guide RNA" or "gRNA" has the leaning as used herein elsewhere and comprises any polynucleotide sequence having sufficient complementarity with a target nucleic acid sequence to hybridize with the target nucleic acid sequence and direct sequence-specific binding of a nucleic acid-targeting complex to the target nucleic acid sequence. Each gRNA may be designed to include multiple binding recognition sites (e.g., aptamers) specific to the same or different adapter protein. Each gRNA may be designed to bind to the promoter region −1000-+1 nucleic acids upstream of the transcription start site (i.e. TSS), preferably −200 nucleic acids. This positioning improves functional domains which affect gene activation (e.g., transcription activators) or gene inhibition (e.g., transcription repressors). The modified gRNA may be one or more modified gRNAs targeted to one or more target loci (e.g., at least 1 gRNA, at least 2 gRNA, at least 5 gRNA, at least 10 gRNA, at least 20 gRNA, at least 30 g RNA, at least 50 gRNA) comprised in a composition. Said multiple gRNA sequences can be tandemly arranged and are preferably separated by a direct repeat.

Thus, gRNA, the CRISPR enzyme as defined herein may each individually be comprised in a composition and administered to a host individually or collectively. Alternatively, these components may be provided in a single composition for administration to a host. Administration to a host may be performed via viral vectors known to the skilled person or described herein for delivery to a host (e.g., lentiviral vector, adenoviral vector, AAV vector). As explained herein, use of different selection markers (e.g., for lentiviral sgRNA selection) and concentration of gRNA (e.g., dependent on whether multiple gRNAs are used) may be advantageous for eliciting an improved effect. On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes).

The current invention comprehends the use of the compositions of the current invention to establish and utilize conditional or inducible CRISPR transgenic cell/animals; see, e.g., Platt et al., Cell (2014), 159(2): 440-455, or PCT patent publications cited herein, such as WO 2014/093622 (PCT/US2013/074667). For example, cells or animals such as non-human animals, e.g., vertebrates or mammals, such as rodents, e.g., mice, rats, or other laboratory or field animals, e.g., cats, dogs, sheep, etc., may be 'knock-in' whereby the animal conditionally or inducibly expresses Cas9 akin to Platt et al. The target cell or animal thus comprises the CRISPR enzyme (e.g., Cas9) conditionally or inducibly (e.g., in the form of Cre dependent constructs), on expression of a vector introduced into the target cell, the vector expresses that which induces or gives rise to the condition of the CRISPR enzyme (e.g., Cas9) expression in the target cell. By applying the teaching and compositions as defined herein with the known method of creating a CRISPR complex, inducible genomic events are also an embodiment of the current invention. Examples of such inducible events have been described herein elsewhere.

In some embodiments, phenotypic alteration is preferably the result of genome modification when a genetic disease is targeted, especially in methods of therapy and preferably where a repair template is provided to correct or alter the phenotype.

In some embodiments diseases that may be targeted include those concerned with disease-causing splice defects.

In some embodiments, cellular targets include Hemopoietic Stem/Progenitor Cells (CD34+); Human T cells; and Eye (retinal cells)—for example photoreceptor precursor cells.

In some embodiments Gene targets include: Human Beta Globin—HBB (for treating Sickle Cell Anemia, including by stimulating gene-conversion (using closely related HBD gene as an endogenous template)); CD3 (T-Cells); and CEP920—retina (eye).

In some embodiments disease targets also include: cancer; Sickle Cell Anemia (based on a point mutation); HBV, HIV; Beta-Thalassemia; and ophthalmic or ocular disease—for example Leber Congenital Amaurosis (LCA)-causing Splice Defect.

In some embodiments delivery methods include: Cationic Lipid Mediated "direct" delivery of Enzyme-Guide complex (RiboNucleoProtein) and electroporation of plasmid DNA.

Methods, products and uses described herein may be used for non-therapeutic purposes. Furthermore, any of the methods described herein may be applied in vitro and ex vivo.

In an embodiment, provided is a non-naturally occurring or engineered composition comprising:

I. two or more CRISPR-Cas system polynucleotide sequences comprising a. a first guide sequence capable of hybridizing to a first target sequence in a polynucleotide locus, b. a second guide sequence capable of hybridizing to a second target sequence in a polynucleotide locus, c. a direct repeat sequence, and II. a Cas9 enzyme or a second polynucleotide sequence encoding it, wherein when transcribed, the first and the second guide sequences direct sequence-specific binding of a first and a second Cas9 CRISPR complex to the first and second target sequences respectively, wherein the first CRISPR complex comprises the Cas9 enzyme complexed with the first guide sequence that is hybridizable to the first target sequence, wherein the second CRISPR complex comprises the Cas9 enzyme complexed with the second guide sequence that is hybridizable to the second target sequence, and wherein the first guide sequence directs cleavage of one strand of the DNA duplex near the first target sequence and the second guide sequence directs cleavage of the other strand near the second target sequence inducing a double strand break, thereby modifying the organism or the non-human or non-animal organism. Similarly, compositions comprising more than two guide RNAs can be envisaged e.g. each specific for one target, and arranged tandemly in the composition or CRISPR system or complex as described herein.

In another embodiment, the Cas9 is delivered into the cell as a protein. In another and particularly preferred embodiment, the Cas9 is delivered into the cell as a protein or as a nucleotide sequence encoding it. Delivery to the cell as a protein may include delivery of a Ribonucleoprotein (RNP) complex, where the protein is complexed with the multiple guides.

In an embodiment, host cells and cell lines modified by or comprising the compositions, systems or modified enzymes of present invention are provided, including stem cells, and progeny thereof.

In an embodiment, methods of cellular therapy are provided, where, for example, a single cell or a population of cells is sampled or cultured, wherein that cell or cells is or has been modified ex vivo as described herein, and is then re-introduced (sampled cells) or introduced (cultured cells) into the organism. Stem cells, whether embryonic or induce pluripotent or totipotent stem cells, are also particularly preferred in this regard. But, of course, in vivo embodiments are also envisaged.

Inventive methods can further comprise delivery of templates, such as repair templates, which may be dsODN or ssODN, see below. Delivery of templates may be via the cotemporaneous or separate from delivery of any or all the CRISPR enzyme or guide RNAs and via the same delivery mechanism or different. In some embodiments, it is preferred that the template is delivered together with the guide RNAs and, preferably, also the CRISPR enzyme. An example may be an AAV vector where the CRISPR enzyme is AsCas9 or LbCas9.

Inventive methods can further comprise: (a) delivering to the cell a double-stranded oligodeoxynucleotide (dsODN) comprising overhangs complimentary to the overhangs created by said double strand break, wherein said dsODN is integrated into the locus of interest; or -(b) delivering to the cell a single-stranded oligodeoxynucleotide (ssODN), wherein said ssODN acts as a template for homology directed repair of said double strand break. Inventive methods can be for the prevention or treatment of disease in an individual, optionally wherein said disease is caused by a defect in said locus of interest. Inventive methods can be conducted in vivo in the individual or ex vivo on a cell taken from the individual, optionally wherein said cell is returned to the individual.

The invention also comprehends products obtained from using CRISPR enzyme or Cas enzyme or Cas9 enzyme or CRISPR-CRISPR enzyme or CRISPR-Cas system or CRISPR-Cas9 system for use in tandem or multiple targeting as defined herein.

Escorted Guides for the Cas9 CRISPR-Cas System According to the Invention

In one embodiment the invention provides escorted Cas9 CRISPR-Cas systems or complexes, especially such a system involving an escorted Cas9 CRISPR-Cas system guide. By "escorted" is meant that the Cas9 CRISPR-Cas system or complex or guide is delivered to a selected time or place within a cell, so that activity of the Cas9 CRISPR-Cas system or complex or guide is spatially or temporally controlled. For example, the activity and destination of the Cas9 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted Cas9 CRISPR-Cas systems or complexes have a gRNA with a functional structure designed to improve gRNA structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. “RNA mimics of green fluorescent protein.” Science 333.6042 (2011): 642-646). It has also been suggested that aptamers may be used as components of targeted siRNA therapeutic delivery systems, for example targeting cell surface proteins (Zhou, Jiehua, and John J. Rossi. “Aptamer-targeted cell-specific RNA interference.” Silence 1.1 (2010): 4).

Accordingly, provided herein is a gRNA modified, e.g., by one or more aptamer(s) designed to improve gRNA delivery, including delivery across the cellular membrane, to intracellular compartments, or into the nucleus. Such a structure can include, either in addition to the one or more aptamer(s) or without such one or more aptamer(s), moiety(ies) so as to render the guide deliverable, inducible or responsive to a selected effector. The invention accordingly comprehends an gRNA that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

An embodiment of the invention provides non-naturally occurring or engineered composition comprising an escorted guide RNA (egRNA) comprising:

- an RNA guide sequence capable of hybridizing to a target sequence in a genomic locus of interest in a cell; and,
- an escort RNA aptamer sequence, wherein the escort aptamer has binding affinity for an aptamer ligand on or in the cell, or the escort aptamer is responsive to a localized aptamer effector on or in the cell, wherein the presence of the aptamer ligand or effector on or in the cell is spatially or temporally restricted.

The escort aptamer may for example change conformation in response to an interaction with the aptamer ligand or effector in the cell.

The escort aptamer may have specific binding affinity for the aptamer ligand.

The aptamer ligand may be localized in a location or compartment of the cell, for example on or in a membrane of the cell. Binding of the escort aptamer to the aptamer ligand may accordingly direct the egRNA to a location of interest in the cell, such as the interior of the cell by way of binding to an aptamer ligand that is a cell surface ligand. In this way, a variety of spatially restricted locations within the cell may be targeted, such as the cell nucleus or mitochondria.

Once intended alterations have been introduced, such as by editing intended copies of a gene in the genome of a cell, continued CRISPR/Cas9 expression in that cell is no longer necessary. Indeed, sustained expression would be undesirable in certain casein case of off-target effects at unintended genomic sites, etc. Thus time-limited expression would be useful. Inducible expression offers one approach, but in addition Applicants have engineered a Self-Inactivating Cas9 CRISPR-Cas system that relies on the use of a non-coding guide target sequence within the CRISPR vector itself. Thus, after expression begins, the CRISPR system will lead to its own destruction, but before destruction is complete it will have time to edit the genomic copies of the target gene (which, with a normal point mutation in a diploid cell, requires at most two edits). Simply, the self-inactivating Cas9 CRISPR-Cas system includes additional RNA (i.e., guide RNA) that targets the coding sequence for the CRISPR enzyme itself or that targets one or more non-coding guide target sequences complementary to unique sequences present in one or more of the following: (a) within the promoter driving expression of the non-coding RNA elements, (b) within the promoter driving expression of the Cas9 gene, (c) within 100 bp of the ATG translational start codon in the Cas9 coding sequence, (d) within the inverted terminal repeat (iTR) of a viral delivery vector, e.g., in an AAV genome.

The egRNA may include an RNA aptamer linking sequence, operably linking the escort RNA sequence to the RNA guide sequence.

In embodiments, the egRNA may include one or more photolabile bonds or non-naturally occurring residues.

In one embodiment, the escort RNA aptamer sequence may be complementary to a target miRNA, which may or may not be present within a cell, so that only when the target miRNA is present is there binding of the escort RNA aptamer sequence to the target miRNA which results in cleavage of the egRNA by an RNA-induced silencing complex (RISC) within the cell.

In embodiments, the escort RNA aptamer sequence may for example be from 10 to 200 nucleotides in length, and the egRNA may include more than one escort RNA aptamer sequence.

It is to be understood that any of the RNA guide sequences as described herein elsewhere can be used in the egRNA described herein. In certain embodiments of the invention, the guide RNA or mature crRNA comprises, consists essentially of, or consists of a direct repeat sequence and a guide sequence or spacer sequence. In certain embodiments, the guide RNA or mature crRNA comprises, consists essentially of, or consists of a direct repeat sequence linked to a guide sequence or spacer sequence. In certain embodiments the guide RNA or mature crRNA comprises 19 nts of partial direct repeat followed by 23-25 nt of guide sequence or spacer sequence. In certain embodiments, the effector protein is a FnCas9 effector protein and requires at least 16 nt of guide sequence to achieve detectable DNA cleavage and a minimum of 17 nt of guide sequence to achieve efficient DNA cleavage in vitro. In certain embodiments, the direct repeat sequence is located upstream (i.e., 5') from the guide sequence or spacer sequence. In a preferred embodiment the seed sequence (i.e. the sequence essential critical for recognition and/or hybridization to the sequence at the target locus) of the FnCas9 guide RNA is approximately within the first 5 nt on the 5' end of the guide sequence or spacer sequence.

The egRNA may be included in a non-naturally occurring or engineered Cas9 CRISPR-Cas complex composition, together with a Cas9 which may include at least one mutation, for example a mutation so that the Cas9 has no more than 5% of the nuclease activity of a Cas9 not having the at least one mutation, for example having a diminished nuclease activity of at least 97%, or 100% as compared with the Cas9 not having the at least one mutation. The Cas9 may also include one or more nuclear localization sequences. Mutated Cas9 enzymes having modulated activity such as diminished nuclease activity are described herein elsewhere.

The engineered Cas9 CRISPR-Cas composition may be provided in a cell, such as a eukaryotic cell, a mammalian cell, or a human cell.

In embodiments, the compositions described herein comprise a Cas9 CRISPR-Cas complex having at least three functional domains, at least one of which is associated with Cas9 and at least two of which are associated with egRNA.

The compositions described herein may be used to introduce a genomic locus event in a host cell, such as an eukaryotic cell, in particular a mammalian cell, or a non-human eukaryote, in particular a non-human mammal such as a mouse, in vivo. The genomic locus event may comprise affecting gene activation, gene inhibition, or cleavage in a locus. The compositions described herein may also be used to modify a genomic locus of interest to change gene expression in a cell. Methods of introducing a genomic locus event in a host cell using the Cas9 enzyme provided herein are described herein in detail elsewhere. Delivery of the composition may for example be by way of delivery of a nucleic acid molecule(s) coding for the composition, which nucleic acid molecule(s) is operatively linked to regulatory sequence(s), and expression of the nucleic acid molecule(s) in vivo, for example by way of a lentivirus, an adenovirus, or an AAV.

The present invention provides compositions and methods by which gRNA-mediated gene editing activity can be adapted. The invention provides gRNA secondary structures that improve cutting efficiency by increasing gRNA and/or increasing the amount of RNA delivered into the cell. The gRNA may include light labile or inducible nucleotides.

To increase the effectiveness of gRNA, for example gRNA delivered with viral or non-viral technologies, Applicants added secondary structures into the gRNA that enhance its stability and improve gene editing. Separately, to overcome the lack of effective delivery, Applicants modified gRNAs with cell penetrating RNA aptamers; the aptamers bind to cell surface receptors and promote the entry of gRNAs into cells. Notably, the cell-penetrating aptamers can be designed to target specific cell receptors, in order to mediate cell-specific delivery. Applicants also have created guides that are inducible.

Light responsiveness of an inducible system may be achieved via the activation and binding of cryptochrome-2 and CIB 1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Crytochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 $mW/cm^2$. In a preferred embodiment, a stimulation paradigm of as low as 0.25 sec every 15 sec should result in maximal activation.

Cells involved in the practice of the present invention may be a prokaryotic cell or a eukaryotic cell, advantageously an animal cell a plant cell or a yeast cell, more advantageously a mammalian cell.

The chemical or energy sensitive guide may undergo a conformational change upon induction by the binding of a chemical source or by the energy allowing it act as a guide and have the Cas9 CRISPR-Cas system or complex function. The invention can involve applying the chemical source or energy so as to have the guide function and the Cas9 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., http://stke.sciencemag.org/cgi/content/abstract/sigtrans; 4/164/r52), 2. FKBP-FRB based system inducible by rapamycin (or related chemicals based on rapamycin) (see, e.g., http://www.nature.com/nmeth/journal/v2/n6/full/nmeth763.html), 3. GID1-GAI based system inducible by Gibberellin (GA) (see, e.g., http://www.nature.com/nchembio/journal/v8/n5/full/nchembio.922.html).

Another system contemplated by the present invention is a chemical inducible system based on change in sub-cellular localization. Applicants also developed a system in which the polypeptide include a DNA binding domain comprising at least five or more Transcription activator-like effector (TALE) monomers and at least one or more half-monomers specifically ordered to target the genomic locus of interest linked to at least one or more effector domains are further linker to a chemical or energy sensitive protein. This protein will lead to a change in the sub-cellular localization of the entire polypeptide (i.e. transportation of the entire polypeptide from cytoplasm into the nucleus of the cells) upon the binding of a chemical or energy transfer to the chemical or energy sensitive protein. This transportation of the entire polypeptide from one sub-cellular compartments or organelles, in which its activity is sequestered due to lack of substrate for the effector domain, into another one in which the substrate is present would allow the entire polypeptide to come in contact with its desired substrate (i.e. genomic DNA in the mammalian nucleus) and result in activation or repression of target gene expression.

This type of system could also be used to induce the cleavage of a genomic locus of interest in a cell when the effector domain is a nuclease.

A chemical inducible system can be an estrogen receptor (ER) based system inducible by 4-hydroxytamoxifen (4OHT) (see, e.g., http://www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., http://www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas9 CRISPR-Cas complex or system, and the binding will induce the change of sub-cellular localization of the polypeptide, leading to the entire polypeptide entering the nucleus of cells. Once inside the nucleus, the guide protein and the other components of the Cas9 CRISPR-Cas complex will be active and modulating target gene expression in cells.

This type of system could also be used to induce the cleavage of a genomic locus of interest in a cell; and, in this regard, it is noted that the Cas9 enzyme is a nuclease. The light could be generated with a laser or other forms of energy sources. The heat could be generated by raise of temperature results from an energy source, or from nano-particles that release heat after absorbing energy from an energy source delivered in the form of radio-wave.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm$^2$ to about 100 W/cm$^2$. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm$^2$ (FDA recommendation), although energy densities of up to 750 mW/cm$^2$ have been used. In physiotherapy, ultrasound is typically used as an energy source in a range up to about 3 to 4 W/cm$^2$ (WHO recommendation). In other therapeutic applications, higher intensities of ultrasound may be employed, for example, HIFU at 100 W/cm up to 1 kW/cm$^2$ (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 $Wcm^{-2}$. Even more preferably, the exposure to an ultrasound energy source is at a power density of from about 1 to about 15 $Wcm^{-2}$.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 $Wcm^{-2}$ to about 10 $Wcm^{-2}$ with a frequency ranging from about 0.015 to about 10 MHz (see International Patent Publication No. WO 98/52609). However, alternatives are also possible, for example, exposure to an ultrasound energy source at an acoustic power density of above 100 $Wcm^{-2}$, but for reduced periods of time, for example, 1000 $Wcm^{-2}$ for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 $Wcm^{-2}$ or 1.25 $Wcm^{-2}$ as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

The rapid transcriptional response and endogenous targeting of the instant invention make for an ideal system for the study of transcriptional dynamics. For example, the instant invention may be used to study the dynamics of variant production upon induced expression of a target gene. On the other end of the transcription cycle, mRNA degradation studies are often performed in response to a strong extracellular stimulus, causing expression level changes in a plethora of genes. The instant invention may be utilized to reversibly induce transcription of an endogenous target, after which point stimulation may be stopped and the degradation kinetics of the unique target may be tracked.

The temporal precision of the instant invention may provide the power to time genetic regulation in concert with experimental interventions. For example, targets with suspected involvement in long-term potentiation (LTP) may be modulated in organotypic or dissociated neuronal cultures, but only during stimulus to induce LTP, so as to avoid interfering with the normal development of the cells. Similarly, in cellular models exhibiting disease phenotypes, targets suspected to be involved in the effectiveness of a particular therapy may be modulated only during treatment. Conversely, genetic targets may be modulated only during a pathological stimulus. Any number of experiments in which timing of genetic cues to external experimental stimuli is of relevance may potentially benefit from the utility of the instant invention.

The in vivo context offers equally rich opportunities for the instant invention to control gene expression. Photoinducibility provides the potential for spatial precision. Taking advantage of the development of optrode technology, a stimulating fiber optic lead may be placed in a precise brain region. Stimulation region size may then be tuned by light intensity. This may be done in conjunction with the delivery of the Cas9 CRISPR-Cas system or complex of the invention, or, in the case of transgenic Cas9 animals, guide RNA of the invention may be delivered and the optrode technology can allow for the modulation of gene expression in precise brain regions. A transparent Cas9 expressing organism, can have guide RNA of the invention administered to it and then there can be extremely precise laser induced local gene expression changes.

A culture medium for culturing host cells includes a medium commonly used for tissue culture, such as M199-earle base, Eagle MEM (E-MEM), Dulbecco MEM (DMEM), SC-UCM102, UP-SFM (GIBCO BRL), EX-CELL302 (Nichirei), EX-CELL293-S(Nichirei), TFBM-01 (Nichirei), ASF104, among others. Suitable culture media for specific cell types may be found at the American Type Culture Collection (ATCC) or the European Collection of Cell Cultures (ECACC). Culture media may be supplemented with amino acids such as L-glutamine, salts, anti-fungal or anti-bacterial agents such as Fungizone®, penicillin-streptomycin, animal serum, and the like. The cell culture medium may optionally be serum-free.

The invention may also offer valuable temporal precision in vivo. The invention may be used to alter gene expression during a particular stage of development. The invention may be used to time a genetic cue to a particular experimental window. For example, genes implicated in learning may be overexpressed or repressed only during the learning stimulus in a precise region of the intact rodent or primate brain. Further, the invention may be used to induce gene expression changes only during particular stages of disease development. For example, an oncogene may be overexpressed only once a tumor reaches a particular size or metastatic stage. Conversely, proteins suspected in the development of Alzheimer's may be knocked down only at defined time points in the animal's life and within a particular brain region. Although these examples do not exhaustively list the potential applications of the invention, they highlight some of the areas in which the invention may be a powerful technology.

Protected Guides: Enzymes According to the Invention can be Used in Combination with Protected Guide RNAs In one embodiment, an object of the current invention is to further enhance the specificity of Cas9 given individual guide RNAs through thermodynamic tuning of the binding specificity of the guide RNA to target DNA. This is a general approach of introducing mismatches, elongation or truncation of the guide sequence to increase/decrease the number of complimentary bases vs. mismatched bases shared between a genomic target and its potential off-target loci, in order to give thermodynamic advantage to targeted genomic loci over genomic off-targets.

In one embodiment, the invention provides for the guide sequence being modified by secondary structure to increase the specificity of the Cas9 CRISPR-Cas system and whereby the secondary structure can protect against exonuclease activity and allow for 3' additions to the guide sequence.

In one embodiment, the invention provides for hybridizing a "protector RNA" to a guide sequence, wherein the "protector RNA" is an RNA strand complementary to the 5' end of the guide RNA (gRNA), to thereby generate a partially double-stranded gRNA. In an embodiment of the invention, protecting the mismatched bases with a perfectly complementary protector sequence decreases the likelihood of target DNA binding to the mismatched base pairs at the 3' end. In embodiments of the invention, additional sequences comprising an extended length may also be present.

Guide RNA (gRNA) extensions matching the genomic target provide gRNA protection and enhance specificity. Extension of the gRNA with matching sequence distal to the end of the spacer seed for individual genomic targets is envisaged to provide enhanced specificity. Matching gRNA extensions that enhance specificity have been observed in cells without truncation. Prediction of gRNA structure accompanying these stable length extensions has shown that stable forms arise from protective states, where the extension forms a closed loop with the gRNA seed due to complimentary sequences in the spacer extension and the spacer seed. These results demonstrate that the protected guide concept also includes sequences matching the genomic target sequence distal of the 20mer spacer-binding region. Thermodynamic prediction can be used to predict completely matching or partially matching guide extensions that result in protected gRNA states. This extends the concept of protected gRNAs to interaction between X and Z, where X will generally be of length 17-20 nt and Z is of length 1-30 nt. Thermodynamic prediction can be used to determine the optimal extension state for Z, potentially introducing small numbers of mismatches in Z to promote the formation of protected conformations between X and Z. Throughout the present application, the terms "X" and seed length (SL) are used interchangeably with the term exposed length (EpL) which denotes the number of nucleotides available for target DNA to bind; the terms "Y" and protector length (PL) are used interchangeably to represent the length of the protector; and the terms "Z", "E", "E'" and "EL" are used interchangeably to correspond to the term extended length (ExL) which represents the number of nucleotides by which the target sequence is extended.

An extension sequence which corresponds to the extended length (ExL) may optionally be attached directly to the guide sequence at the 3' end of the protected guide sequence. The extension sequence may be 2 to 12 nucleotides in length. Preferably ExL may be denoted as 0, 2, 4, 6, 8, 10 or 12 nucleotides in length. In a preferred embodiment the ExL is denoted as 0 or 4 nucleotides in length. In a more preferred embodiment the ExL is 4 nucleotides in length. The extension sequence may or may not be complementary to the target sequence.

An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence. It will be understood that the above-described relationship of seed, protector, and extension applies where the distal end (i.e., the targeting end) of the guide is the 5' end, e.g. a guide that functions is a Cas9 system. In an embodiment wherein the distal end of the guide is the 3' end, the relationship will be the reverse. In such an embodiment, the invention provides for hybridizing a "protector RNA" to a guide sequence, wherein the "protector RNA" is an RNA strand complementary to the 3' end of the guide RNA (gRNA), to thereby generate a partially double-stranded gRNA.

Addition of gRNA mismatches to the distal end of the gRNA can demonstrate enhanced specificity. The introduction of unprotected distal mismatches in Y or extension of the gRNA with distal mismatches (Z) can demonstrate enhanced specificity. This concept as mentioned is tied to X, Y, and Z components used in protected gRNAs. The unprotected mismatch concept may be further generalized to the concepts of X, Y, and Z described for protected guide RNAs.

Cas9. In one embodiment, the invention provides for enhanced Cas9 specificity wherein the double stranded 3' end of the protected guide RNA (pgRNA) allows for two possible outcomes: (1) the guide RNA-protector RNA to guide RNA-target DNA strand exchange will occur and the guide will fully bind the target, or (2) the guide RNA will fail to fully bind the target and because Cas9 target cleavage is a multiple step kinetic reaction that requires guide RNA: target DNA binding to activate Cas9-catalyzed DSBs, wherein Cas9 cleavage does not occur if the guide RNA does not properly bind. According to particular embodiments, the protected guide RNA improves specificity of target binding as compared to a naturally occurring CRISPR-Cas system. According to particular embodiments the protected modified guide RNA improves stability as compared to a naturally occurring CRISPR-Cas. According to particular embodiments the protector sequence has a length between 3 and 120 nucleotides and comprises 3 or more contiguous nucleotides complementary to another sequence of guide or protector. According to particular embodiments, the protector sequence forms a hairpin. According to particular embodiments the guide RNA further comprises a protected sequence and an exposed sequence. According to particular embodiments the exposed sequence is 1 to 19 nucleotides. More particularly, the exposed sequence is at least 75%, at least 90% or about 100% complementary to the target sequence. According to particular embodiments the guide sequence is at least 90% or about 100% complementary to the protector strand. According to particular embodiments the guide sequence is at least 75%, at least 90% or about 100% complementary to the target sequence. According to particular embodiments, the guide RNA further comprises an extension sequence. More particularly, when the distal end of the guide is the 3' end, the extension sequence is operably linked to the 3' end of the protected guide sequence, and optionally directly linked to the 3' end of the protected guide sequence. According to particular embodiments the extension sequence is 1-12 nucleotides. According to particular embodiments the extension sequence is operably linked to the guide sequence at the 3' end of the protected guide sequence and the 5' end of the protector strand and optionally directly linked to the 3' end of the protected guide sequence and the 5' end of the protector strand, wherein the extension sequence is a linking sequence between the protected sequence and the protector strand. According to particular embodiments the extension sequence is 100% not complementary to the protector strand, optionally at least 95%, at least 90%, at least 80%, at least 70%, at least 60%, or at least 50% not complementary to the protector strand. According to particular embodiments the guide sequence further comprises mismatches appended to the end of the guide sequence, wherein the mismatches thermodynamically optimize specificity.

According to the invention, in certain embodiments, guide modifications that impede strand invasion will be desirable. For example, to minimize off-target activity, in certain embodiments, it will be desirable to design or modify a guide to impede strand invasion at off-target sites. In certain such embodiments, it may be acceptable or useful to design or modify a guide at the expense of on-target binding efficiency. In certain embodiments, guide-target mismatches at the target site may be tolerated that substantially reduce off-target activity.

In certain embodiments of the invention, it is desirable to adjust the binding characteristics of the protected guide to minimize off-target CRISPR activity. Accordingly, thermodynamic prediction algorithms are used to predict strengths of binding on target and off target. Alternatively or in addition, selection methods are used to reduce or minimize off-target effects, by absolute measures or relative to on-target effects.

Design options include, without limitation, i) adjusting the length of protector strand that binds to the protected strand, ii) adjusting the length of the portion of the protected strand that is exposed, iii) extending the protected strand with a stem-loop located external (distal) to the protected strand (i.e. designed so that the stem loop is external to the protected strand at the distal end), iv) extending the protected strand by addition of a protector strand to form a stem-loop with all or part of the protected strand, v) adjusting binding of the protector strand to the protected strand by designing in one or more base mismatches and/or one or more non-canonical base pairings, vi) adjusting the location of the stem formed by hybridization of the protector strand to the protected strand, and vii) addition of a non-structured protector to the end of the protected strand.

In one embodiment, the invention provides an engineered, non-naturally occurring CRISPR-Cas system comprising a Cas9 protein and a protected guide RNA that targets a DNA molecule encoding a gene product in a cell, whereby the protected guide RNA targets the DNA molecule encoding the gene product and the Cas9 protein cleaves the DNA molecule encoding the gene product, whereby expression of the gene product is altered; and, wherein the Cas9 protein and the protected guide RNA do not naturally occur together. The invention comprehends the protected guide RNA comprising a guide sequence fused to a direct repeat sequence. The invention further comprehends the CRISPR protein being codon optimized for expression in a eukaryotic cell. In a preferred embodiment the eukaryotic cell is a mammalian cell, a plant cell or a yeast cell and in a more preferred embodiment the mammalian cell is a human cell. In a further embodiment of the invention, the expression of the gene product is decreased. In some embodiments the CRISPR protein is Cas9. In some embodiments the CRISPR protein is Cas12a. In some embodiments, the Cas12a protein is *Acidaminococcus* sp. BV3L6, *Lachnospiraceae bacterium* or *Francisella Novicida* Cas12a, and may include mutated Cas12a derived from these organisms. The protein may be a further Cas9 or Cas12a homolog or ortholog. In some embodiments, the nucleotide sequence encoding the Csa9 or Cas12a protein is codon-optimized for expression in a eukaryotic cell. In some embodiments, the Cas9 or Cas12a protein directs cleavage of one or two strands at the location of the target sequence. In some embodiments, the first regulatory element is a polymerase III promoter. In some embodiments, the second regulatory element is a polymerase II promoter. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

Advantageous vectors include lentiviruses and adeno-associated viruses, and types of such vectors can also be selected for targeting particular types of cells.

In one embodiment, the invention provides a eukaryotic host cell comprising (a) a first regulatory element operably linked to a direct repeat sequence and one or more insertion sites for inserting one or more guide sequences downstream of the direct repeat sequence, wherein when expressed, the guide sequence directs sequence-specific binding of a CRISPR complex to a target sequence in a eukaryotic cell, wherein the CRISPR complex comprises a CRISPR enzyme complexed with the guide RNA comprising the guide sequence that is hybridized to the target sequence and/or (b) a second regulatory element operably linked to an enzyme-coding sequence encoding said Cas9 enzyme comprising a nuclear localization sequence. In some embodiments, the host cell comprises components (a) and (b). In some embodiments, component (a), component (b), or components (a) and (b) are stably integrated into a genome of the host eukaryotic cell. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the Cas9 enzyme directs cleavage of one or two strands at the location of the target sequence. In some embodiments, the Cas9 enzyme lacks DNA strand cleavage activity. In some embodiments, the first regulatory element is a polymerase III promoter. In some embodiments, the second regulatory element is a polymerase II promoter.

In an embodiment, the invention provides a non-human eukaryotic organism; preferably a multicellular eukaryotic organism, comprising a eukaryotic host cell according to any of the described embodiments. In other embodiments, the invention provides a eukaryotic organism; preferably a multicellular eukaryotic organism, comprising a eukaryotic host cell according to any of the described embodiments. The organism in some embodiments of these embodiments may be an animal; for example a mammal. Also, the organism may be an arthropod such as an insect. The organism also may be a plant or a yeast. Further, the organism may be a fungus.

In one embodiment, the invention provides a kit comprising one or more of the components described herein above. In some embodiments, the kit comprises a vector system and instructions for using the kit. In some embodiments, the vector system comprises (a) a first regulatory element operably linked to a direct repeat sequence and one or more insertion sites for inserting one or more guide sequences downstream of the direct repeat sequence, wherein when expressed, the guide sequence directs sequence-specific binding of a Cas9 CRISPR complex to a target sequence in a eukaryotic cell, wherein the CRISPR complex comprises a Cas9 enzyme complexed with the protected guide RNA comprising the guide sequence that is hybridized to the target sequence and/or (b) a second regulatory element operably linked to an enzyme-coding sequence encoding said Cas9 enzyme comprising a nuclear localization sequence. In some embodiments, the kit comprises components (a) and (b) located on the same or different vectors of the system. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the Cas9 enzyme comprises one or more nuclear localization sequences of sufficient strength to drive accumulation of said Cas9 enzyme in a detectable amount in the nucleus of a eukaryotic cell. In some embodiments, the Cas9 enzyme is *Acidaminococcus* sp. BV3L6, *Lachnospiraceae bacterium* MA2020 or *Francisella tularensis* 1 Novicida Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter.

In one embodiment, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a Cas9 enzyme complexed with protected guide RNA comprising a guide sequence hybridized to a target sequence within said target polynucleotide. In some embodiments, said cleavage comprises cleaving one or two strands at the location of the target sequence by said Cas9 enzyme. In some embodiments, said cleavage results in decreased transcription of a target gene. In some embodiments, the method further comprises repairing said cleaved target polynucleotide by non-homologous end joining (NHEJ)-based gene insertion mechanisms, more particularly with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the Cas9 enzyme, the protected guide RNA comprising the guide sequence linked to direct repeat sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one embodiment, the invention provides a method of modifying expression of a polynucleotide in a eukaryotic cell. In some embodiments, the method comprises allowing a Cas9 CRISPR complex to bind to the polynucleotide such that said binding results in increased or decreased expression of said polynucleotide; wherein the CRISPR complex comprises a Cas9 enzyme complexed with a protected guide RNA comprising a guide sequence hybridized to a target sequence within said polynucleotide. In some embodiments, the method further comprises delivering one or more vectors to said eukaryotic cells, wherein the one or more vectors drive expression of one or more of: the Cas9 enzyme and the protected guide RNA.

In one embodiment, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a Cas9 enzyme and a protected guide RNA comprising a guide sequence linked to a direct repeat sequence; and (b) allowing a CRISPR complex to bind to a target polynucleotide to effect cleavage of the target polynucleotide within said disease gene, wherein the CRISPR complex comprises the Cas9 enzyme complexed with the guide RNA comprising the sequence that is hybridized to the target sequence within the target polynucleotide, thereby generating a model eukaryotic cell comprising a mutated disease gene. In some embodiments, said cleavage comprises cleaving one or two strands at the location of the target sequence by said Cas9 enzyme. In some embodiments, said cleavage results in decreased transcription of a target gene. In some embodiments, the method further comprises repairing said cleaved target polynucleotide by non-homologous end joining (NHEJ)-based gene insertion mechanisms with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one embodiment, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one embodiment, the invention provides a recombinant polynucleotide comprising a protected guide sequence downstream of a direct repeat sequence, wherein the protected guide sequence when expressed directs sequence-specific binding of a CRISPR complex to a corresponding target sequence present in a eukaryotic cell. In some embodiments, the target sequence is a viral sequence present in a eukaryotic cell. In some embodiments, the target sequence is a proto-oncogene or an oncogene.

In one embodiment the invention provides for a method of selecting one or more cell(s) by introducing one or more mutations in a gene in the one or more cell (s), the method comprising: introducing one or more vectors into the cell (s), wherein the one or more vectors drive expression of one or more of: a Cas9 enzyme, a protected guide RNA comprising a guide sequence, and an editing template; wherein the editing template comprises the one or more mutations that abolish Cas9 enzyme cleavage; allowing non-homologous end joining (NHEJ)-based gene insertion mechanisms of the editing template with the target polynucleotide in the cell(s) to be selected; allowing a CRISPR complex to bind to a target polynucleotide to effect cleavage of the target polynucleotide within said gene, wherein the CRISPR complex comprises the Cas9 enzyme complexed with the protected guide RNA comprising a guide sequence that is hybridized to the target sequence within the target polynucleotide, wherein binding of the CRISPR complex to the target polynucleotide induces cell death, thereby allowing one or more cell(s) in which one or more mutations have been introduced to be selected. In a preferred embodiment of the invention the cell to be selected may be a eukaryotic cell. Embodiments of the invention allow for selection of specific cells without requiring a selection marker or a two-step process that may include a counter-selection system.

With respect to mutations of the Cas9 enzyme, when the enzyme is not FnCas9, mutations may be as described herein elsewhere; conservative substitution for any of the replacement amino acids is also envisaged. In an embodiment the invention provides as to any or each or all embodiments herein-discussed wherein the CRISPR enzyme comprises at least one or more, or at least two or more mutations, wherein the at least one or more mutation or the at least two or more mutations are selected from those described herein elsewhere.

In a further embodiment, the invention involves a computer-assisted method for identifying or designing potential compounds to fit within or bind to CRISPR-Cas9 system or a functional portion thereof or vice versa (a computer-assisted method for identifying or designing potential CRISPR-Cas9 systems or a functional portion thereof for binding to desired compounds) or a computer-assisted method for identifying or designing potential CRISPR-Cas9 systems (e.g., with regard to predicting areas of the CRISPR-Cas9 system to be able to be manipulated—for instance, based on crystal structure data or based on data of Cas9 orthologs, or with respect to where a functional group such as an activator or repressor can be attached to the CRISPR-Cas9 system, or as to Cas9 truncations or as to designing nickases), said method comprising:

using a computer system, e.g., a programmed computer comprising a processor, a data storage system, an input device, and an output device, the steps of:

(a) inputting into the programmed computer through said input device data comprising the three-dimensional co-ordinates of a subset of the atoms from or pertaining to the CRISPR-Cas9 crystal structure, e.g., in the CRISPR-Cas9 system binding domain or alternatively or additionally in domains that vary based on variance among Cas9 orthologs or as to Cas9s or as to nickases or as to functional groups, optionally with structural information from CRISPR-Cas9 system complex(es), thereby generating a data set;

(b) comparing, using said processor, said data set to a computer database of structures stored in said computer data storage system, e.g., structures of compounds that bind or putatively bind or that are desired to bind to a CRISPR-Cas9 system or as to Cas9 orthologs (e.g., as Cas9s or as to domains or regions that vary amongst Cas9 orthologs) or as to the CRISPR-Cas9 crystal structure or as to nickases or as to functional groups;

(c) selecting from said database, using computer methods, structure(s)—e.g., CRISPR-Cas9 structures that may bind to desired structures, desired structures that may bind to certain CRISPR-Cas9 structures, portions of the CRISPR-Cas9 system that may be manipulated, e.g., based on data from other portions of the CRISPR-Cas9 crystal structure and/or from Cas9 orthologs, truncated Cas9s, novel nickases or particular functional groups, or positions for attaching functional groups or functional-group-CRISPR-Cas9 systems;

(d) constructing, using computer methods, a model of the selected structure(s); and (e) outputting to said output device the selected structure(s);

and optionally synthesizing one or more of the selected structure(s);

and further optionally testing said synthesized selected structure(s) as or in a CRISPR-Cas9 system;

or, said method comprising: providing the co-ordinates of at least two atoms of the CRISPR-Cas9 crystal structure, e.g., at least two atoms of the herein Crystal Structure Table of the CRISPR-Cas9 crystal structure or co-ordinates of at least a sub-domain of the CRISPR-Cas9 crystal structure ("selected co-ordinates"), providing the structure of a candidate comprising a binding molecule or of portions of the CRISPR-Cas9 system that may be manipulated, e.g., based on data from other portions of the CRISPR-Cas9 crystal structure and/or from Cas9 orthologs, or the structure of functional groups, and fitting the structure of the candidate to the selected co-ordinates, to thereby obtain product data comprising CRISPR-Cas9 structures that may bind to desired structures, desired structures that may bind to certain CRISPR-Cas9 structures, portions of the CRISPR-Cas9 system that may be manipulated, truncated Cas9s, novel nickases, or particular functional groups, or positions for attaching functional groups or functional-group-CRISPR-Cas9 systems, with output thereof; and optionally synthesizing compound(s) from said product data and further optionally comprising testing said synthesized compound(s) as or in a CRISPR-Cas9 system.

The testing can comprise analyzing the CRISPR-Cas9 system resulting from said synthesized selected structure(s), e.g., with respect to binding, or performing a desired function.

The output in the foregoing methods can comprise data transmission, e.g., transmission of information via telecommunication, telephone, video conference, mass communication, e.g., presentation such as a computer presentation (e.g. POWERPOINT), internet, email, documentary communication such as a computer program (e.g. WORD) document and the like. Accordingly, the invention also comprehends computer readable media containing: atomic co-ordinate data according to the herein-referenced Crystal Structure, said data defining the three dimensional structure of CRISPR-Cas9 or at least one sub-domain thereof, or structure factor data for CRISPR-Cas9, said structure factor data being derivable from the atomic co-ordinate data of herein-referenced Crystal Structure. The computer readable media can also contain any data of the foregoing methods. The invention further comprehends methods a computer system for generating or performing rational design as in the foregoing methods containing either: atomic co-ordinate data according to herein-referenced Crystal Structure, said data defining the three dimensional structure of CRISPR-Cas9 or at least one sub-domain thereof, or structure factor data for CRISPR-Cas9, said structure factor data being derivable from the atomic co-ordinate data of herein-referenced Crystal Structure. The invention further comprehends a method of doing business comprising providing to a user the computer system or the media or the three dimensional structure of CRISPR-Cas9 or at least one sub-domain thereof, or structure factor data for CRISPR-Cas9, said structure set forth in and said structure factor data being derivable from the atomic co-ordinate data of herein-referenced Crystal Structure, or the herein computer media or a herein data transmission.

The terms "binding site" or an "active site", as used herein, comprises or consists essentially of or consists of a site (such as an atom, a functional group of an amino acid residue or a plurality of such atoms and/or groups) in a binding cavity or region, which may bind to a compound such as a nucleic acid molecule, which is/are involved in binding.

The term "fitting" as used herein refers to determining by automatic, or semi-automatic means, interactions between one or more atoms of a candidate molecule and at least one atom of a structure of the invention, and calculating the extent to which such interactions are stable. Interactions include attraction and repulsion, brought about by charge, steric considerations and the like. Various computer-based methods for fitting are described further The term "root mean square (or rms) deviation" as used herein, refers to the square root of the arithmetic mean of the squares of the deviations from the mean.

The term "computer system" as used herein refers to the hardware means, software means and data storage means used to analyze atomic coordinate data. The minimum hardware means of the computer-based systems of the present invention typically comprises a central processing unit (CPU), input means, output means and data storage means. Desirably a display or monitor is provided to visualize structure data. The data storage means may be RAM or means for accessing computer readable media of the invention. Examples of such systems are computer and tablet devices running Unix, Windows or Apple operating systems.

By "computer readable media", is meant any medium or media, which can be read and accessed directly or indirectly by a computer e.g., so that the media is suitable for use in the above-mentioned computer system. Such media include, but are not limited to: magnetic storage media such as floppy discs, hard disc storage medium and magnetic tape; optical storage media such as optical discs or CD-ROM; electrical storage media such as RAM and ROM; thumb drive devices; cloud storage devices and hybrids of these categories such as magnetic/optical storage media.

The invention comprehends the use of the protected guides described herein above in the optimized functional CRISPR-Cas enzyme systems described herein.

Inactivating Nucleic Acid Editing Systems

Once intended alterations have been introduced, such as by editing intended copies of a gene in the genome of a cell, continued CRISPR-Cas expression in that cell is no longer necessary. Indeed, sustained expression would be undesirable in certain cases in case of off-target effects at unintended genomic sites, etc. Thus time-limited expression would be useful. Inducible expression offers one approach, but in addition Applicants have engineered a Self-Inactivating CRISPR-Cas system that relies on the use of a non-coding guide target sequence within the CRISPR vector itself In some embodiments, the targeting sequence in the gRNA is a CRISPR protein or argonaute gene sequence. In such instances, an additional guide RNA may be provided with a guide sequence directed to a different target sequence.

In some embodiments, the target sequence in the e gRNA and in an additional guide RNA is a CRISPR protein or argonaute gene sequence.

Thus, using these self-inactivating systems and after expression begins, the CRISPR system will lead to its own destruction, but before destruction is complete it will have time to edit the genomic copies of the target gene (which, with a normal point mutation in a diploid cell, requires at most two edits). Simply, the self-inactivating CRISPR-Cas system includes additional RNA (i.e., guide RNA) that targets the coding sequence for the CRISPR enzyme itself or that targets one or more non-coding guide target sequences complementary to unique sequences present in one or more of the following: (a) within the promoter driving expression of the non-coding RNA elements, (b) within the promoter driving expression of the Cas9 gene, (c) within 100 bp of the ATG translational start codon in the Cas9 coding sequence, (d) within the inverted terminal repeat (iTR) of a viral delivery vector, e.g., in an AAV genome.

Once all copies of a gene in the genome of a cell have been edited, continued CRISRP/Cas expression in that cell is no longer necessary. Indeed, sustained expression would be undesirable in case of off-target effects at unintended genomic sites, etc. Thus time-limited expression would be useful. Inducible expression offers one approach, but in addition Applicants have engineered a Self-Inactivating CRISPR-Cas system that relies on the use of a non-coding guide target sequence within the CRISPR vector itself. Thus, after expression begins, the CRISPR system will lead to its own destruction, but before destruction is complete it will have time to edit the genomic copies of the target gene (which, with a normal point mutation in a diploid cell, requires at most two edits). Simply, the self-inactivating CRISPR-Cas system includes additional RNA (i.e., guide RNA) that targets the coding sequence for the CRISPR enzyme itself and/or the fusion protein according to the invention as described herein or that targets one or more non-coding guide target sequences complementary to unique sequences present in one or more of the following:

(a) within the promoter driving expression of the non-coding RNA elements, (b) within the promoter driving expression of the CRISPR effector gene/fusion protein, (c) within 100 bp of the ATG translational start codon in the CRISPR effector/fusion protein coding sequence, (d) within the inverted terminal repeat (iTR) of a viral delivery vector, e.g., in the AAV genome.

Furthermore, that RNA can be delivered via a vector, e.g., a separate vector or the same vector that is encoding the CRISPR complex. When provided by a separate vector, the CRISPR RNA that targets Cas/fusion protein/gRNA expression can be administered sequentially or simultaneously. When administered sequentially, the CRISPR RNA that targets Cas/fusion protein/gRNA expression is to be delivered after the CRISPR/fusion protein/gRNA RNA that is intended for e.g. gene editing or gene engineering. This period may be a period of minutes (e.g. 5 minutes, 10 minutes, 20 minutes, 30 minutes, 45 minutes, 60 minutes). This period may be a period of hours (e.g. 2 hours, 4 hours, 6 hours, 8 hours, 12 hours, 24 hours). This period may be a period of days (e.g. 2 days, 3 days, 4 days, 7 days). This period may be a period of weeks (e.g. 2 weeks, 3 weeks, 4 weeks). This period may be a period of months (e.g. 2 months, 4 months, 8 months, 12 months). This period may be a period of years (2 years, 3 years, 4 years). In this fashion, the Cas enzyme associates with a first gRNA/chiRNA capable of hybridizing to a first target, such as a genomic locus or loci of interest and undertakes the function(s) desired of the CRISPR-Cas system (e.g., gene engineering); and subsequently the Cas enzyme may then associate with the second gRNA/chiRNA capable of hybridizing to the sequence comprising at least part of the Cas or CRISPR cassette. Where the gRNA/chiRNA targets the sequences encoding expression of the Cas protein, the enzyme becomes impeded and the system becomes self-inactivating. In the same manner, CRISPR RNA that targets Cas expression applied via, for example liposome, lipofection, particles, microvesicles as explained herein, may be administered sequentially or simultaneously. Similarly, self-inactivation may be used for inactivation of one or more guide RNA used to target one or more targets.

In some embodiments, a single gRNA is provided that is capable of hybridization to a sequence downstream of a CRISPR effector/fusion protein start codon, whereby after a period of time there is a loss of the CRISPR enzyme/fusion protein expression. In some embodiments, one or more gRNA(s) are provided that are capable of hybridization to one or more coding or non-coding regions of the polynucleotide encoding the CRISPR-Cas system, whereby after a period of time there is a inactivation of one or more, or in some cases all, of the CRISPR-Cas system. In some embodiments of the system, and not to be limited by theory, the cell may comprise a plurality of CRISPR-Cas complexes, wherein a first subset of CRISPR complexes comprise a first chiRNA capable of targeting a genomic locus or loci to be edited, and a second subset of CRISPR complexes comprise at least one second chiRNA capable of targeting the polynucleotide encoding the CRISPR-Cas system, wherein the first subset of CRISPR-Cas complexes mediate editing of the targeted genomic locus or loci and the second subset of CRISPR complexes eventually inactivate the CRISPR-Cas system, thereby inactivating further CRISPR-Cas expression in the cell.

Thus the invention provides a CRISPR-Cas system comprising one or more vectors for delivery to a eukaryotic cell, wherein the vector(s) encode(s): (i) a CRISPR enzyme; (ii) a first guide RNA capable of hybridizing to a target sequence in the cell; (iii) a second guide RNA capable of hybridizing to one or more target sequence(s) in the vector which encodes the CRISPR enzyme; (iv) at least one tracr mate sequence; and (v) at least one tracr sequence (if or where applicable), The first and second complexes can use the same tracr and tracr mate, thus differing only by the guide sequence, wherein, when expressed within the cell: the first guide RNA directs sequence-specific binding of a first CRISPR complex to the target sequence in the cell; the second guide RNA directs sequence-specific binding of a second CRISPR complex to the target sequence in the vector which encodes the CRISPR enzyme; the CRISPR complexes comprise (a) a tracr mate sequence hybridised to a tracr sequence (if applicable) and (b) a CRISPR enzyme bound to a guide RNA, such that a guide RNA can hybridize to its target sequence; and the second CRISPR complex inactivates the CRISPR-Cas system to prevent continued expression of the CRISPR enzyme by the cell.

Further characteristics of the vector(s), the encoded enzyme, the guide sequences, etc. are disclosed elsewhere herein. For instance, one or both of the guide sequence(s) can be part of a chiRNA sequence which provides the guide, tracr mate and tracr sequences (where applicable) within a single RNA, such that the system can encode (i) a CRISPR enzyme; (ii) a first chiRNA comprising a sequence capable of hybridizing to a first target sequence in the cell, a first tracr mate sequence, and a first tracr sequence; (iii) a second guide RNA capable of hybridizing to the vector which encodes the CRISPR enzyme, a second tracr mate sequence, and a second tracr sequence. Similarly, the enzyme can include one or more NLS, etc.

The various coding sequences (CRISPR enzyme, guide RNAs, tracr mate and optionally tracr) can be included on a single vector or on multiple vectors. For instance, it is possible to encode the enzyme on one vector and the various RNA sequences on another vector, or to encode the enzyme and one chiRNA on one vector, and the remaining chiRNA on another vector, or any other permutation. In general, a system using a total of one or two different vectors is preferred.

Where multiple vectors are used, it is possible to deliver them in unequal numbers, and ideally with an excess of a vector which encodes the first guide RNA relative to the second guide RNA, thereby assisting in delaying final inactivation of the CRISPR system until genome editing has had a chance to occur.

The first guide RNA can target any target sequence of interest within a genome or alternatively transcriptome, as described elsewhere herein. The second guide RNA targets a sequence within the vector which encodes the CRISPR Cas enzyme, and thereby inactivates the enzyme's expression from that vector. Thus the target sequence in the vector must be capable of inactivating expression. Suitable target sequences can be, for instance, near to or within the translational start codon for the Cas coding sequence, in a non-coding sequence in the promoter driving expression of the non-coding RNA elements, within the promoter driving expression of the Cas gene, within 100 bp of the ATG translational start codon in the Cas coding sequence, and/or within the inverted terminal repeat (iTR) of a viral delivery vector, e.g., in the AAV genome. A double stranded break near this region can induce a frame shift in the Cas coding sequence, causing a loss of protein expression. An alternative target sequence for the "self-inactivating" guide RNA would aim to edit/inactivate regulatory regions/sequences needed for the expression of the CRISPR-Cas system or for the stability of the vector. For instance, if the promoter for the Cas9 coding sequence is disrupted then transcription can be inhibited or prevented. Similarly, if a vector includes sequences for replication, maintenance or stability then it is possible to target these. For instance, in a AAV vector a useful target sequence is within the iTR. Other useful sequences to target can be promoter sequences, polyadenylation sites, etc.

Furthermore, if the guide RNAs are expressed in array format, the "self-inactivating" guide RNAs that target both promoters simultaneously will result in the excision of the intervening nucleotides from within the CRISPR-Cas expression construct, effectively leading to its complete inactivation. Similarly, excision of the intervening nucleotides will result where the guide RNAs target both ITRs, or targets two or more other CRISPR-Cas components simultaneously. Self-inactivation as explained herein is applicable, in general, with CRISPR-Cas9 systems in order to provide regulation of the CRISPR-Cas9. For example, self-inactivation as explained herein may be applied to the CRISPR repair of mutations, for example expansion disorders, as explained herein. As a result of this self-inactivation, CRISPR repair is only transiently active.

Addition of non-targeting nucleotides to the 5' end (e.g. 1-10 nucleotides, preferably 1-5 nucleotides) of the "self-inactivating" guide RNA can be used to delay its processing and/or modify its efficiency as a means of ensuring editing at the targeted genomic locus prior to CRISPR-Cas shutdown.

In one embodiment of the self-inactivating AAV-CRISPR-Cas system, plasmids that co-express one or more gRNA targeting genomic sequences of interest (e.g. 1-2, 1-5, 1-10, 1-15, 1-20, 1-30) may be established with "self-inactivating" gRNAs that target an SpCas9 sequence at or near the engineered ATG start site (e.g. within 5 nucleotides, within 15 nucleotides, within 30 nucleotides, within 50 nucleotides, within 100 nucleotides). A regulatory sequence in the U6 promoter region can also be targeted with an gRNA. The U6-driven gRNAs may be designed in an array format such that multiple gRNA sequences can be simultaneously released. When first delivered into target tissue/cells (left cell) gRNAs begin to accumulate while Ca9 levels rise in the nucleus. Cas complexes with all of the gRNAs to mediate genome editing and self-inactivation of the CRISPR-Cas plasmids.

One embodiment of a self-inactivating CRISPR-Cas system is expression of singly or in tandam array format from 1 up to 4 or more different guide sequences; e.g. up to about 20 or about 30 guides sequences. Each individual self-inactivating guide sequence may target a different target. Such may be processed from, e.g. one chimeric po13 transcript. Pol3 promoters such as U6 or H1 promoters may be used. Pol2 promoters such as those mentioned throughout herein. Inverted terminal repeat (iTR) sequences may flank the Pol3 promoter-gRNA(s)-Pol2 promoter-Cas.

One embodiment of a chimeric, tandem array transcript is that one or more guide(s) edit the one or more target(s) while one or more self-inactivating guides inactivate the CRISPR/Cas system. Thus, for example, the described CRISPR-Cas system for repairing expansion disorders may be directly combined with the self-inactivating CRISPR-Cas system described herein. Such a system may, for example, have two guides directed to the target region for repair as well as at least a third guide directed to self-inactivation of the CRISPR-Cas. Reference is made to Application Ser. No. PCT/US2014/069897, entitled "Compositions And Methods Of Use Of Crispr-Cas Systems In Nucleotide Repeat Disorders," published Dec. 12, 2014 as WO/2015/089351.

The guideRNA may be a control guide. For example it may be engineered to target a nucleic acid sequence encoding the CRISPR Enzyme itself, as described in US2015232881A1, the disclosure of which is hereby incorporated by reference. In some embodiments, a system or composition may be provided with just the guideRNA engineered to target the nucleic acid sequence encoding the CRISPR Enzyme. In addition, the system or composition may be provided with the guideRNA engineered to target the nucleic acid sequence encoding the CRISPR Enzyme, as well as nucleic acid sequence encoding the CRISPR Enzyme and, optionally a second guide RNA and, further optionally, a repair template. The second guideRNA may be the primary target of the CRISPR system or composition (such a therapeutic, diagnostic, knock out etc. as defined herein). In this way, the system or composition is self-inactivating. This is exemplified in relation to Cas9 in US2015232881A1 (also published as WO2015070083 (A1), referenced elsewhere herein).

In some embodiments, the e gRNA may include an RNA aptamer linking sequence, operably linking the escort RNA sequence to the RNA guide sequence. In some embodiments, it may include one or more photolabile bonds or non-naturally occurring residues. e gRNAs of the invention can comprise one or more RNA linking sequences which can link an RNA aptamer and an gRNA and additional elements in any order. In one non-limiting example, an exg comprises a hydrolyzable aptamer linked to the 5' end of a protecting sequence, the protecting sequence joined at its 3' end to the 5' end of an gRNA. Such an arrangement provides a protecting sequence operating to enhance on-target specificity of the gRNA. In certain embodiments, the protecting sequence functions in a cell once the aptamer located at the 5' end is cleaved.

RNA-Induced Silencing Complex (RISC)

In one embodiment, the aptamer sequence may be complementary to a target miRNA, which may or may not be present within a cell, so that only when the target miRNA is present is there binding of the escort RNA aptamer sequence to the target miRNA which results in cleavage of the gRNA by an RNA-induced silencing complex (RISC) within the cell.

In some embodiments, the guide may be a protected guide (e.g. a pgRNA) or an escorted guide (e.g. an esgRNA) as described herein. Both of these, in some embodiments, make use of RISC. A RISC is a key component of RNAi. RISC (RNA-induced silencing complex) is a multiprotein, specifically a ribonucleoprotein, complex which incorporates one strand of a double-stranded RNA (dsRNA) fragment, such as small interfering RNA (siRNA) or microRNA (miRNA), which acts as a template for RISC to recognize a complementary messenger RNA (mRNA) transcript. The mRNA is thus cleaved by one of the components of the RISC.

As such, the formation of a RISC is advantageous in some embodiments. Guide RNAs according to various embodiments of the present invention, including but not limited to protected and/or escorted guide RNAs, may be adapted to include RNA nucleotides that promote formation of a RISC, for example in combination with an siRNA or miRNA that may be provided or may, for instance, already be expressed in a cell. This may be useful, for instance, as a self-inactivating system to clear or degrade the guide.

Thus, the guide RNA may comprise a sequence complementary to a target miRNA or an siRNA, which may or may not be present within a cell. In this way, only when the miRNA or siRNA is present, for example through expression (by the cell or through human intervention), is there binding of the RNA sequence to the miRNA or siRNA which then results in cleavage of the guide RNA an RNA-induced silencing complex (RISC) within the cell. Therefore, in some embodiments, the guide RNA comprises an RNA sequence complementary to a target miRNA or siRNA, and binding of the guide RNA sequence to the target miRNA or siRNA results in cleavage of the guide RNA by an RNA-induced silencing complex (RISC) within the cell.

This is explained further below with specific reference to both protected and escorted guides.

For example, a protected guide may be described in the following embodiment: an engineered, non-naturally occurring composition comprising a Clustered Regularly Interspaced Short Palindromic Repeats (CRISPR)-CRISPR associated (Cas) (CRISPR-Cas) system having a protected guide RNA (pgRNA) polynucleotide sequence comprising (a) a protector sequence, (b) a direct repeat and (c) a guide sequence capable of hybridizing to a target sequence in a eukaryotic cell, wherein (a), (b), and (c) are arranged in a 5' to 3' orientation, wherein the protector sequence comprises two or more nucleotides that are non-complementary to the target sequence, wherein when transcribed, the guide sequence directs sequence-specific binding of a CRISPR complex to the target sequence, wherein the CRISPR complex comprises a Cpf1 protein complexed with (1) the guide sequence that is hybridized to the target sequence and wherein in the polynucleotide sequence and/or one or more of the guide RNAs are modified.

In one embodiment, this protected guide system is used for secondary structure protection for 3' extensions to the gRNA. For example, Applicants extend the gRNA such that a miRNA binding site is introduced to make the gRNA only active when the miRNA binding site is processed and cleaved by the RISC complex machinery. This would not be possible without secondary structure protection since exonuclease processing would start from the 5' end and cut back towards the gRNA. By adding a small secondary structure loop 5' to the added miRNA site, then miRNA may be protected from exonuclease chew back.

RISC Formation Through Use of Escorted Guides

Target Sequences

The target sequence can be a sequence of target polynucleotide sequence. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In the context of formation of a CRISPR complex, "target sequence" or "target polynucleotide sequence" refers to a sequence to which a guide sequence is designed to have complementarity, where hybridization between a target sequence and a guide sequence promotes the formation of a CRISPR complex. A target sequence may include RNA polynucleotides. The term "target RNA" refers to a RNA polynucleotide being or containing the target sequence. In other words, the target RNA may be a RNA polynucleotide or a part of a RNA polynucleotide to which a part of the gRNA, i.e. the guide sequence, is designed to have complementarity and to which the effector function mediated by the complex containing a CRISPR effector protein (including, but not limited to, those Cas polypeptides described herein) and a gRNA or other nucleic acid component is to be directed. In some embodiments, a target polynucleotide having a target polynucleotide sequence is located in the nucleus or cytoplasm of a cell.

In the context of formation of a CRISPR complex, such as the multi-component nucleic acid targeting system described herein, "target sequence" refers to a polynucleotide sequence to which a guide sequence is designed to have complementarity, where hybridization between a target sequence and a guide sequence promotes the formation of a CRISPR complex. The section of the guide sequence through which complementarity to the target sequence is important for cleavage activity is referred to herein as the seed sequence. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes or particles present within the cell. In some embodiments, especially for non-nuclear uses, NLSs are not preferred. In some embodiments, a CRISPR system comprises one or more nuclear exports signals (NESs). In some embodiments, a CRISPR system comprises one or more NLSs and one or more NESs. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In certain embodiments, a protospacer adjacent motif (PAM) or PAM-like motif directs recognition and/or binding of one or more of the polypeptides capable of allosterically interacting as disclosed herein to the target sequence. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence". In embodiments, one or more of the polypeptides capable of allosterically interacting as described herein may recognize a 3' PAM. In certain embodiments, one or more of the polypeptides capable of allosterically interacting may recognize a 3' PAM which is 5'H, wherein H is A, C or U.

Determination of PAM

Determination of PAM can be ensured as follows. This experiment closely parallels similar work in *E. coli* for the heterologous expression of StCas9 (Sapranauskas, R. et al. Nucleic Acids Res 39, 9275-9282 (2011)). Applicants introduce a plasmid containing both a PAM and a resistance gene into the heterologous *E. coli*, and then plate on the corresponding antibiotic. If there is DNA cleavage of the plasmid, Applicants observe no viable colonies.

In further detail, the assay is as follows for a DNA target, but can be appropriately adapted for an RNA target by one of ordinary skill in the art. Two *E. coli* strains are used in this assay. One carries a plasmid that encodes the endogenous effector protein locus from the bacterial strain. The other strain carries an empty plasmid (e.g. pACYC184, control strain). All possible 7 or 8 bp PAM sequences are presented on an antibiotic resistance plasmid (pUC19 with ampicillin resistance gene). The PAM is located next to the sequence of proto-spacer 1 (the DNA target to the first spacer in the endogenous effector protein locus). Two PAM libraries were cloned. One has a 8 random bp 5' of the proto-spacer (e.g. total of 65536 different PAM sequences=complexity). The other library has 7 random bp 3' of the proto-spacer (e.g. total complexity is 16384 different PAMs). Both libraries were cloned to have in average 500 plasmids per possible PAM. Test strain and control strain were transformed with 5'PAM and 3'PAM library in separate transformations and transformed cells were plated separately on ampicillin plates. Recognition and subsequent cutting/interference with the plasmid renders a cell vulnerable to ampicillin and prevents growth. Approximately 12 h after transformation, all colonies formed by the test and control strains where harvested and plasmid DNA was isolated. Plasmid DNA was used as template for PCR amplification and subsequent deep sequencing. Representation of all PAMs in the untransformed libraries showed the expected representation of PAMs in transformed cells. Representation of all PAMs found in control strains showed the actual representation. Representation of all PAMs in test strain showed which PAMs are not recognized by the enzyme and comparison to the control strain allows extracting the sequence of the depleted PAM.

ii. PAM Interacting Domain

In some embodiments, one or more of the Cas proteins in a CRISPR-Cas system described herein comprise at least one PAM interacting domain, including but not limited to PAM interacting domains described herein, PAM interacting domains known in the art, and domains recognized to be PAM interacting domains by comparison to consensus sequences and motifs. The PAM interacting domain can interact with, associated with, and/or bind, a PAM motif of a nucleic acid component and/or target polynucleotide.

CRISPR-Cas Complexes

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Polynucleotide Modification Using a CRISPR-Cas System or Complex

In embodiments the method of rationally designing a CRISPR-Cas system and/or CRISPR-Cas system based therapy or therapeutic can include modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a Cas enzyme complexed with protected guide RNA comprising a guide sequence hybridized to a target sequence within said target polynucleotide. In some embodiments, said cleavage comprises cleaving one or two strands at the location of the target sequence by said Cas enzyme. In some embodiments, said cleavage results in decreased transcription of a target gene. In some embodiments, the method further comprises repairing said cleaved target polynucleotide by non-homologous end joining (NHEJ)-based gene insertion mechanisms, more particularly with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the Cas enzyme, the protected guide RNA comprising the guide sequence linked to direct repeat sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one embodiment, the invention provides a method of modifying expression of a polynucleotide in a eukaryotic cell. In some embodiments, the method comprises allowing a Cas CRISPR complex to bind to the polynucleotide such that said binding results in increased or decreased expression of said polynucleotide; wherein the CRISPR complex comprises a Cas enzyme complexed with a protected guide RNA comprising a guide sequence hybridized to a target sequence within said polynucleotide. In some embodiments, the method further comprises delivering one or more vectors to said eukaryotic cells, wherein the one or more vectors drive expression of one or more of: the Cas enzyme and the protected guide RNA.

In one embodiment, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a Cas enzyme and a protected guide RNA comprising a guide sequence linked to a direct repeat sequence; and (b) allowing a CRISPR complex to bind to a target polynucleotide to effect cleavage of the target polynucleotide within said disease gene, wherein the CRISPR complex comprises the Cas enzyme complexed with the guide RNA comprising the sequence that is hybridized to the target sequence within the target polynucleotide, thereby generating a model eukaryotic cell comprising a mutated disease gene. In some embodiments, said cleavage comprises cleaving one or two strands at the location of the target sequence by said Cas enzyme. In some embodiments, said cleavage results in decreased transcription of a target gene. In some embodiments, the method further comprises repairing said cleaved target polynucleotide by non-homologous end joining (NHEJ)-based gene insertion mechanisms with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one embodiment, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

Adoptive Cell Therapy

In some embodiments, the CRISPR-based therapy or therapeutic designed or developed using a method described elsewhere herein can be a genetically modified cell that does not express a DNA-damage response signature. In some embodiments, such a cell can be used in an adoptive cell therapy. In some embodiments, a CRISPR-Cas system, including but not limited to those described herein, is used to modify cells ex vivo. In some embodiments, after modification, cells can be screened for a DNA-damage response signature. DNA-damage response signatures and methods of identifying and screening for a DNA-damage response signature in a cell or cell population is described in greater detail elsewhere herein. After cells have been identified that do not have a DNA-damage response signature, they can be isolated, cloned, and optionally expanded using various techniques including those described in greater detail below and elsewhere herein and as are generally known in the art. In some embodiments, the isolated, cloned and optionally expanded modified cell-population having a desired signature (e.g. lacking a DNA-damage response signature) is then administered as a therapy to the subject. In some embodiments, the cells modified are immune system cells. In some embodiments, the cells are not immune system cells.

As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Zacharakis et al., (2018) Nat Med. 2018 June; 24(6):724-730; Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma, metastatic breast cancer and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Embodiments of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2

(Her2/neu)); Prostate; Prostatic acid phosphatase (PAP); elongation factor 2 mutant (ELF2M); Insulin-like growth factor 1 receptor (IGF-1R); gp100; BCR-ABL (breakpoint cluster region-Abelson); tyrosinase; New York esophageal squamous cell carcinoma 1 (NY-ESO-1); K-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDG1cp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDG1cp(1-1)Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; Cyclin D 1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRLS); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDCl27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein), fAchR (Fetal acetylcholine receptor); G250 (glycoprotein 250); GAGE (G antigen); GnT-V (N-acetylglucosaminyltransferase V); HAGE (helicose antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyl-transferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triose-phosphate isomerase mutated); CD70; and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (Dl), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B Cell Maturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CIVIL), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR-T Cells Demonstrate Potent Preclinical Activity Against Both Solid and Hematological Cancer Cells).

Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172;

5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3 or scFv-CD28-OX40-CD3ζ; see U.S. Pat. Nos. 8,906,682; 8,399, 645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3 chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM 006139 (sequence version 1, 2 or 3): IEVMYPPPYLD-NEKSNGTIIHVKGKHLCPSPLFPGPSKPFWVLVVVGGV-LACYSLLVTVA FIIFWVRSKRSRLLHSDYMNMTPRRPGPTRKHYQPY-APPRDFAAYRS)) (SEQ. I.D. No. 43). Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ. I.D. No. 44) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-α molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3α chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY (SEQ ID NO: 45) and continuing all the way to the carboxy-terminus of the protein. The sequence is reproduced herein:

```
                                (SEQ ID NO: 46)
IEVMYPPPYLDNEKSNGTIIHVKGKHLCPSPLFPGPSKPFWVLVVVGGVL

ACYSLLVTVAFIIFWVRSKRSRLLHSDYMNMTPRRPGPTRKHYQPYAPPR

DFAAYRS.
```

Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signaling domains (CD28-CD3ζ; 4-1BB-CD3ζ; CD27-CD3ζ; CD28-CD27-CD3ζ, 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signaling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in WO2012058460A2 (see also, Park et al., CD70 as a target for chimeric antigen receptor T cells in head and neck squamous cell carcinoma, Oral Oncol. 2018 March; 78:145-150; and Jin et al., CD70, a novel target of CAR T-cell therapy for gliomas, Neuro Oncol. 2018 Jan. 10; 20(1):55-65). CD70 is expressed by diffuse large B-cell and follicular lymphoma and also by the malignant cells of Hodgkins lymphoma, Waldenstrom's macroglobulinemia and multiple myeloma, and by HTLV-1- and EBV-associated malignancies. (Agathanggelou et al. Am. J. Pathol. 1995; 147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its WIC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CART cells of this kind may for example be used in animal models, for example to treat tumor xenografts.

In certain embodiments, ACT includes co-transferring CD4+ Th1 cells and CD8+ CTLs to induce a synergistic antitumour response (see, e.g., Li et al., Adoptive cell therapy with CD4+ T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of $CD4^+$ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent. In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017. 00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1; 23(9):2255-2266. doi: 10.1158/1078-0432.CCR-16-1300. Epub 2016 Nov. 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MHC constituent proteins in a cell; to activate a T cell; to modulate cells such that the cells are resistant to exhaustion or dysfunction; and/or increase the differentiation and/or proliferation of functionally exhausted or dysfunctional CD8+ T-cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL 10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACT), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CART cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ, B2M and TCRα, B2M and TCRβ.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3)

knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perssodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

Desired cells (either certain cell populations to be modified or those containing a desired cell signature can be selected using positive or negative selection techniques. For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of cells (including but not limited to T cells) in an enriched cell population. Such methods are described in U.S. Pat. No. 8,637,307 and is herein incorporated by reference in its entirety. The numbers of cells (such as T cells) may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of cells (such as T cells) may be expanded using any suitable method known in the art. Exemplary methods of expanding the numbers of cells are described in International Patent Publication No. WO 2003057171, U.S. Pat. No. 8,034,334, and U.S. Patent Application Publication No. 2012/0244133, each of which is incorporated herein by reference.

In one embodiment, ex vivo cell expansion can be performed by isolation of a desired cell or population thereof and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m2/day and 2000 mg/m2/day and a dose of fludarabine between 20 mg/m2/day and 900 mg/m$^2$/day.

In certain embodiments, immediately prior to or after modification with a CRISPR-Cas system or component thereof, cells can be initially cultured at a density such that one cell per culture volume or well is present at the initial culture to obtain clonal populations of cells. It is generally known in the art that to achieve this, the initial culture desired culture density used is less than one such with a bias towards having empty culture volumes as opposed to having those with two cells to ensure those cell populations that arise will be clonal (i.e. stemming from a single cell). Where the initial culture with this density to obtain a clonal population before modification with a CRISPR-Cas system it will be appreciated that in these embodiments, it is preferred that modification takes place at a time before the cell present in the culture divides so as to maintain a modified clonal population within the culture volume. The modified clonal population of cells can then be screened for a desired cell signature (e.g. does not contain a DNA-damage response signature), optionally further isolated and divided, optionally expanded, and optionally otherwise manipulated as described elsewhere herein prior to using the cells as a therapy, such as in an adoptive cell therapy context.

After clonal expansion of cells and detection of cells within one or more clonal populations of cells having a desired cell signature (e.g. does not contain a DNA-damage response signature), those clones or cells thereof having a desired cell signature can be selected (such as chosen, isolated, or otherwise separated) and subsequently used as desired, such as for a therapy. Methods of isolating or otherwise separating clones or cells thereof from an expanded clonal population of cells are described elsewhere herein as well as generally known in the art.

CRISPR-Cas System Inhibitors

CRISPR-Cas System Inhibitors can include both Anti-CRISPR proteins (or Acrs) and small molecule inhibitors. Anti-CRISPRs (or Acrs) are the natural inhibitors for CRISPR-Cas Systems. To the extent engineered variants of Acrs are described herein, these are also included in Anti-CRISPR molecules or (Acrs) described herein. CRISPR-Cas evolved in bacteria as one strategy to resist infection by phages. As a counter to the CRISPR-Cas defense mechanism in bacteria, phages evolved the Acr proteins that can inhibit CRISPR-Cas systems to evade the bacterial CRISPR-Cas mediated immune system.

CRISPR-Cas system inhibitors can also be small molecules that can modulate (e.g. inhibit) one or more activities of one or more components of a CRISPR-Cas system. In some embodiments, they can be effective to modulate (e.g. inhibit or reduce) an activity of a Cas molecule. In some embodiments, they can be effective to modulate the formation of a CRISPR-Cas complex. In some embodiments, they can be effective to modulate stability of a guide strand. Other mechanisms of inhibition will be appreciated by those of ordinary skill in the art in view of the description herein and are within the scope of this disclosure.

As previously discussed one or more steps of the method of rationally designing or developing a CRISPR-based therapy or therapeutic or CRISPR-Cas system can be performed in the presence of a CRISPR-Cas system inhibitor, such as an Acr protein and/or a small molecule CRISPR-Cas system inhibitor as described in greater detail elsewhere herein. In some embodiments, the method can include incubating the cell, cell population with one or more CRISPR-Cas system inhibitors described herein. In some embodiments, the method can include incubating one or more components of a CRISPR-Cas system with one or more CRISPR-Cas system inhibitors described herein. In some embodiments, the CRISPR-Cas system inhibitor(s) used, the amount or concentration, the incubation duration, or any combination thereof can be varied.

The CRISPR-Cas system inhibitor(s) can be provided as a formulation, such as a pharmaceutical formulation. Details of pharmaceutical formulations are described elsewhere herein. Where applicable, the CRISPR-Cas system inhibitor(s) can be provided as a polynucleotide(s) and/or vector(s) capable of expressing the CRISPR-Cas system inhibitor(s). Polynucleotides and vectors are described elsewhere herein.

Anti-CRISPR Molecules

In some embodiments, the CRISPR-Cas system inhibitor is an Acr protein. In some embodiments, the Acr protein can any one or more of those shown in the table below. See also Zhang et al. 2019. Anim. Models Exp. Med. DOI: 10:1002, 1-7. The Acr(s) can be provided as polypeptides and/or as one or more polynucleotides and/or vectors capable of expressing the Acr(s). Acrs can inhibit CRISPR-Cas through a variety of mechanisms, and of which are appropriate for the methods described herein. In some embodiments, they can interfere with guide strand loading, interfere with or block DNA binding, interfere with complex assembly, and/or prevent DNA cleavage.

TABLE 8

Anti-CRISPRs

| Anti-CRISPR | Origin | Number of Amino Acids | CRISPR-Cas System Inhibited |
|---|---|---|---|
| AcrIC1 | Moraxella bovoculi prophage | 190 | I-C (Pae) |
| AcrID1 | Sulfolobus islandicus rudivirus 3 | 104 | I-D (Sis) |
| AcrIE1 | Pseudomonas aeruginosa phage JBD5 | 100 | I-E(Pae) |
| AcrIE2 | P. aeruginosa phage JBD88a | 84 | I-E(Pae) |
| AcrIE3 | P aeruginosa phage DMS3 | 68 | I-E(Pae) |
| AcrIE4 | P aeruginosa phage D3112 | 52 | I-E(Pae) |
| AcrIE4-F7 | Pseudomonas citronellolis prophage | 119 | I-E/I-F (Pae) |
| AcrIE5 | Pseudomonas otitidis prophage | 65 | I-E(Pae) |
| AcrIE6 | P aeruginosa prophage | 79 | I-E(Pae) |
| AcrIE7 | P aeruginosa prophage | 106 | I-E(Pae) |
| AcrIF1 | P aeruginosa phage JBD30 | 78 | I-F (Pae, Pec) |
| AcrIF2 | P aeruginosa phage D3112 | 90 | I-F (Pae, Pec) |
| AcrIF3 | P aeruginosa phage JBD5 | 139 | I-F (Pae) |
| AcrIF4 | P aeruginosa phage JBD26 | 100 | I-F (Pae) |
| AcrIF5 | P aeruginosa phage JBD5 | 79 | I-F (Pae) |
| AcrIF6 | P aeruginosa prophage | 100 | I-E (Pae),/I-F (Pae, Pec) |
| AcrIF7 | P aeruginosa prophage | 67 | I-F (Pae, Pec) |
| AcrIF8 | Pectobacterium phage ZF40 | 92 | I-F (Pae, Pec) |
| AcrIF9 | Vibrio parahaemolyticus mobile element | 68 | I-F (Pae, Pec) |
| AcrIF10 | Shewanella xiamenensis prophage | 97 | I-F (Pae, Pec) |
| AcrIF11 | P aeruginosa prophage | 132 | I-F (Pae) |
| AcrIF12 | P aeruginosa mobile element | 124 | I-F (Pae) |
| AcrIF13 | Moraxella catarrhalis prophage | 115 | I-F (Pae) |
| AcrIF14 | Moraxella phage Mcat5 | 124 | I-F (Pae) |
| AcrIIA1 | Listeria monocytogenes prophage J0161a | 149 | II-A (Lmo) |
| AcrIIA2 | L monocytogenes prophage J0161a | 123 | II-A (Lmo, Spy) |
| AcrIIA3 | L monocytogenes prophage SLCC2482 | 125 | II-A (Lmo) |
| AcrIIA4 | L monocytogenes prophage J0161b | 87 | II-A (Lmo, Spy) |
| AcrIIA5 | *Streptococcus thermophilus* phage D4276 | 140 | II-A (Sth) |
| AcrIIA6 | *S thermophilus* phage D1811 | 183 | II-A (Spy) |
| AcrIIA7 | Metagenomic libraries from human gut | 103 | II-A (Spy) |
| AcrIIA8 | Metagenomic libraries from human gut | 105 | II-A (Spy) |
| AcrIIA9 | Metagenomic libraries from human gut | 141 | II-A (Spy) |

TABLE 8-continued

Anti-CRISPRs

| Anti-CRISPR | Origin | Number of Amino Acids | CRISPR-Cas System Inhibited |
|---|---|---|---|
| AcrIIA10 | Metagenomic libraries from human gut | 109 | II-A (Spy) |
| AcrIIA11 | Metagenomic libraries from human gut/oral cavity | | II-A Forseberg et al. 2019 (eLife 2019; 8:e46540 DOI: 10.7554/ eLife.46540) |
| AcrIIC1 | Neisseria meningitidis | 85 | II-C (Nme, Cje, Geo, Hpa, Smu) |
| AcrIIC2 | Neisseria meningitidis prophage | 123 | II-C (Nme, Hpa, Smu) |
| AcrIIC2$_{Nme}$ | | | II-C (A. Thavalingam et al. Nat. comm. 2019.10(1):2806) |
| AcrIIC3 | Neisseria meningitidis prophage | 116 | II-C (Nme, Hpa, Smu) |
| AcrIIC4 | Haemophilus parainfluenzae prophage | 88 | II-C (Nme, Hpa, Smu) |
| AcrIIC5 | imonsiella muelleri prophage | 130 | II-C (Nme, Hpa, Smu) |
| AcrVA1 | M bovoculi prophage | 170 | V-A (Mb, As, Lb, Fn) |
| AcrVA2 | M bovoculi prophage | 322 | V-A (Mb) |
| AcrVA3 | M bovoculi prophage | 168 | V-A (Mb) |
| AcrVA4 | M bovoculi mobile element | 234 | V-A (Mb, Lb) |
| AcrVA5 | M bovoculi mobile element | 92 | V-A (Mb, Lb) |

Abbreviations: As, *Acidaminococcus* sp; Cje, Campylobacter jejuni; Fn, Francisella novicida; Geo, Geobacillus stearothermophilus; Hpa, Haemophilus parainfluenzae; Lb, Lachnospiraceae bacterium; Lmo, Listeria monocytogenes; Mb, Moraxella bovoculi; Nme, Neisseria meningitidis; Pae, Pseudomonas aeruginosa; Pec, Pectobacterium atrosepticum; Sis, Sulfolobus islandicus; Spy, *Streptococcus pyogenes*; Sth, *Streptococcus thermophilus*.

In some embodiments, the Acr can be any one or more described in any of the following PCT Application Pub. Nos. WO/2018/197495, WO/2017/160689, WO/2018/197520, WO/2019/034784, WO/2019/076651, WO/2019/067011, WO/2018/09399, WO/2019/089761, and/or WO/2019/094791.

Small Molecule CRISPR-Cas System Inhibitors

In some embodiments the CRISPR-Cas system inhibitor is a small molecule. In some embodiments, the CRISPR-Cas system inhibitor can modulate (e.g. inhibit) the activity of an RNA-guided endonuclease, such as a Cas molecule. By "RNA guided endonuclease" is meant a polypeptide having RNA binding activity, DNA binding activity, and/or DNA cleavage activity. RNA guided endonucleases form a complex with a guide RNA, which contains a sequence that is able to bind a target sequence on double stranded DNA. In some embodiments, the RNA guided endonuclease cleaves the double stranded target DNA. Provided herein include compounds that modulate (e.g., inhibit) RNA-guided endonuclease activity. The compounds may allow for rapid, dosable, and/or temporal control of RNA-guided endonuclease (e.g., a Cas molecule, including but not limited to a Cas9 and/or a Cas12a) activity. In some embodiments, the compounds may increase the specificity of RNA-guided endonuclease and may enable external control and manipulation of gene targeting.

In some embodiments, disclosed herein are inhibitors of Cas9, e.g., naturally occurring Cas9 in *S. pyogenes* (SpCas9) or *S. aureus* (SaCas9), or variants thereof. Cas9 recognizes foreign DNA using Protospacer Adjacent Motif (PAM) sequence and the base pairing of the target DNA by the guide RNA (gRNA). The relative ease of inducing targeted strand breaks at any genomic loci by Cas9 has enabled efficient genome editing in multiple cell types and organisms. Cas9 derivatives can also be used as transcriptional activators/repressors.

Example small molecule inhibitors include those disclosed in International Patent Publication No. WO 2019/089761, and Mali et al. Cell 117(4):1067-1070, which are incorporated herein by reference.

Rationally Designed CRISPR-Cas System Based Therapeutics and Therapies

The methods of rationally designing or developing CRISPR-Cas based therapies or therapeutics can provide CRISPR-Cas based therapies or therapeutics that do not have a DNA-damage response signature or do not induce a DNA-damage response signature.

In some embodiments, the CRISPR-Cas based therapeutic or therapy can be a modified cell. The modified cell can include one or more components of a rationally designed or developed CRISPR-Cas system, where the rationally designed or developed CRISPR-Cas system does not induce a DNA-damage response signature in a cell. The modified cell can include one or more CRISPR-Cas mediated genomic and/or transcriptomic modifications and does not include a DNA-damage response signature. In some embodiments, the modified cell can be autologous to the subject to which it is subsequently delivered. In some embodiments, the modified cell can be allogeneic to the subject to which it is subsequently delivered. Delivery can be in vivo, ex vivo, or in vitro.

In some embodiments, the modified cell can be a prokaryotic cell. The prokaryotic cells can be bacterial cells. The bacterial cell can be any suitable strain of bacterial cell.

In some embodiments, the modified cell can be a eukaryotic cell. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded.

In some embodiments, the cell is a cell obtained from a subject to be treated with a CRISPR-based therapy described herein or a cell line made therefrom. In some embodiments, the cell is a cell not obtained or derived from the subject to be treated with a CRISPR-based therapy described herein. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Pancl, PC-3, TF1, CTLL-2, C1R, Rath, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr−/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some embodiments, the CRISPR-Cas based therapeutic or therapy can be a rationally designed CRISPR-Cas system or a component thereof, where the CRISPR-Cas system or a component thereof does not induce a DNA-damage response signature when introduced into a cell. Various components of CRISPR-Cas systems, including Cas effectors and guide sequences are described elsewhere herein. The rationally designed CRISPR-Cas system or component thereof can be included in a formulation, such as a pharmaceutical formulation, and can be delivered to a. subject or cell thereof. Delivery can be in vivo, ex vivo, or in vitro.

Optimization of the CRISPR-Cas System(s) and/or Components Thereof

As previously discussed, the methods described herein can provide for developing an optimized CRISPR-Cas system or component thereof. In some embodiments, the methods of rationally designing and/or developing can provide optimized CRISPR-Cas system or component thereof that can have reduced off-target effects. In some embodiments, the optimized CRISPR-Cas system or component thereof does not induce a DNA-damage response signature in a cell that it is delivered to.

In some embodiments of the method, sets of CRISPR-Cas systems are screened for their ability to induce a DNA-damage response signature in a cell. In some embodiments, the variations within each candidate CRISPR-Cas system or component thereof are known whereby the specific variations that produce a desired result (e.g. the system or component thereof does not induce or minimally induces a DNA-damage response signature) can be used in the production of an optimized CRISPR-Cas based therapeutic. Exemplary parameters to be optimized and varied within a CRISPR-Cas system are described below. Routine methods of isolating and expanding desired clones, sequencing CRISPR-Cas systems and components thereof, in vitro synthesis of the optimized and selected CRISPR-Cas systems for production as a therapeutic are generally known in the art and can be used to translate the CRISPR-Cas systems and/or components thereof identified as capable of producing a desired outcome (e.g. the system or component thereof does not induce or minimally induces a DNA-damage response signature in the cells) into an optimized CRISPR-Cas system that can be used as a therapeutic as described in greater detail elsewhere herein.

In some embodiments of the method each CRISPR-Cas system in the set of CRISPR-Cas systems can vary in at least one parameter from at least one other CRISPR-Cas system in the set. In some embodiments, each CRISPR-Cas system in the set of CRISPR-Cas systems can vary in a) dosage; b) Cas protein; c) guide molecule design; or a combination thereof.

In some embodiments, the Cas protein can be optimized for one or more parameters. In some embodiments, the Cas protein is optimized for one or more parameters selected from the group of protein size, ability of protein to access regions of high chromatin accessibility, degree of uniform enzyme activity across genomic targets, epigenetic tolerance, mismatch/budge tolerance, effector protein specificity, effector protein stability or half-life, effector protein immunogenicity, toxicity, and combinations thereof.

The guide molecule can be any suitable guide molecule. In some embodiments, the guide molecule can be or include a tru guide, an escorted guide, or a protected guide. Guide molecules are described in greater detail elsewhere herein. The guide molecule can be varied to optimize the CRISPR-Cas system. Different guides are discussed elsewhere herein.

In some embodiments, the target sequences are further selected based on optimization of one or more parameters selected from the group of; PAM type (natural or modified), PAM nucleotide content, PAM length, target sequence length, PAM restrictiveness, target cleavage efficiency, and target sequence position within a gene, a locus or other genomic region. Target sequences are described in greater detail elsewhere herein.

In some embodiments, optimization of the CRISPR-Cas system or component thereof can be achieved by controlling the temporal/spatial expression and/or activity of the CRISPR-Cas system or component thereof.

Further CRISPR-Cas system design choices are described in greater detail below.

CRISPR Effector Choice

Size:

Currently, CRISPR single nuclease effectors demonstrating high efficiency mammalian genome editing range from 1053 amino acids (SaCas9) to 1368 amino acids (SpCas9). While smaller orthologs of Cas9 do exist and cleave DNA with high efficiency in vitro, Cas9 orthologs smaller than SaCas9 have shown diminished mammalian DNA cleavage efficiency. The large size of current single effector CRISPR nucleases is challenging for both nanoparticle protein delivery and viral vector delivery strategies. For protein delivery, payload per particle is a function of 3-D protein size, and for viral delivery of single effectors, large gene size limits flexibility for multiplexing or use of large cell-type specific promoters. Cas (e.g. Cas9 and/or Cas12) can have, in some aspects, the same or similar features for purpose of this particular discussion. Considerations relating to delivery are described detailed further herein below.

Protein Search:

The ability of the CRISPR effector to access regions of high chromatin complexity can be viewed in two ways 1) this increases the versatility of the CRISPR effector as a tool for genome editing or 2) this may be undesirable due to cellular dysregulation resulting from perturbation of the genomic structure of cells contacted with the CRISPR effector.

There have been reports that the most active Cas9 guides are ones that target low nucleosomal occupancy positions: https://elifesciences.org/content/5/e12677, and https://elifesciences.org/content/5/e13450; however, over a longer time scale, cleavage can still occur (also cleavage can occur during replication when the nucleosomal occupancy is moved).Considerations relating to choice of Cas (e.g. Cas9 and/or Cas12) and modifications thereof are described detailed further herein below.

Efficacy:

Overall efficiency: robust and uniform enzyme activity across genomic targets in regions of open chromatin is generally desirable for all single effector nucleases. On the other hand, robust and uniform enzyme activity across genomic targets with varying chromatin complexity and epigenetic marks may not be desirable for research and therapeutic applications. It has been shown that Cas9 shows robust cleavage of methylated DNA, and this increases the utility of the enzyme. On the other hand, CRISPR effector binding or cleavage at loci enriched for epigenetic marks may dysregulate cellular processes. A further embodiment to be considered is whether enzymes that do not disturb chromatin structure are desirable. If cleaving a locus in a terminally differentiated cell, it may be desirable to utilize enzymes that are not capable of penetrating silenced regions of the genome. Alternatively, when cleaving a locus in a precursor of a differentiated cell type, then it may be advantageous to be able to penetrate regions of the genome inactive at the time of editing.

Specificity:

Mismatch/Bulge tolerance: Naturally occurring Cas9 orthologs: naturally occurring CRISPR effectors show tolerance of mismatches or bulges between the RNA guide and DNA target. This tolerance is generally undesirable for therapeutic applications. For therapeutic applications, patients should be individually screened for perfect target guide RNA complementarity, and tolerance of bulges and mismatches will only increase the likelihood of off-target DNA cleavage. High specificity engineered variants have been developed, such as eSpCas9 and Cas9-HF1 for Cas9; these variants show decreased tolerance of mismatches between DNA targets and the RNA guide (relevant to mismatches in approximately the PAM distal 12-14 nucleotides of the guide RNA given 20 nt of guide RNA target complementarity).

PAM Choice:

Natural PAM vs. Modified PAM: Targets for each single effector CRISPR DNA endonuclease discovered so far require a protospacer adjacent motif (PAM) flanking the guide RNA complimentary region of the target. For the DNA endonucleases discovered so far, the PAM motifs have at least 2 nucleotides of specificity, such as 2, 3, 4, 5 or more nucleotides of specificity, such as 2-4 or 2-5 nucleotides of specificity, which curtails the fraction of possible targets in the genome that can be cleaved with a single natural enzyme. Mutation of naturally occurring DNA endonucleases has resulted in protein variants with modified PAM specificities. Cumulatively, the more such variants exist for a given protein targeting different PAMs, the greater the density of genomic targets are available for use in therapeutic design (See population efficacy).

Nucleotide Content:

Nucleotide content of PAMs can affect what fraction of the genome can be targeted with an individual protein due to differences in the abundance of a particular motif in the genome or in a specific therapeutic locus of the genome. Additionally, nucleotide content can affect PAM mutation frequencies in the genome (See population efficacy). Cas (e.g. Cas9 and/or Cas12) proteins with altered PAM specificity can address this issue (as described further herein).

Influence of PAM length/complexity on target specificity: In embodiments where the Cas (e.g. Cas9 and/or Cas12) proteins interrogate the genome by first binding to a PAM site before attempting to create a stable RNA/DNA duplex by melting the double stranded DNA. Since the complexity of the PAM limits the possible space of targets interrogated, a more complex PAM will have fewer possible sites at which off-target cleavage can occur.

crRNA Processing Capabilities of the Enzyme:

Multiplexing: For multiplexing, crRNA processing capabilities are desirable, as a transcript expressed from a single promoter can contain multiple different crRNAs. This transcript is then processed into multiple constituent crRNAs by the protein, and multiplexed editing proceeds for each target specified by the crRNA. On the other hand, the rules for RNA endonucleolytic processing of multi crRNA transcripts into crRNAs are not fully understood. Hence, for therapeutic applications, crRNA processing may be undesirable due to off-target cleavage of endogenous RNA transcripts Target Choice:

Target Length:

Although most protospacer elements observed in naturally occurring Cas9 CRISPR arrays are longer than 20 nt, protospacer complimentary regions of resulting crRNA products are often processed to 20 nt (Cas9) or do not confer specificity beyond 20 nt. Extension of the target complimentary region of the guide RNA beyond 20 nt likely is positioned outside of the footprint of the protein on the guide RNA and is often processed away by exonucleases (See protected guide RNAs for further discussion). This can also apply to Cas (e.g. Cas9 and/or Cas12) proteins.

Efficiency Screening:

Screening for CRISPR effector efficacy has been performed by studying the efficacy of knockdown of cell surface proteins using different DNA targets. These studies show some evidence that position dependent nucleotide content in CRISPR effector targets and flanking nucleotides affects the efficacy of target cleavage.

Specificity Screening:

Unbiased investigation of genome-wide CRISPR nuclease activity suggests that most off-target activity occurs at loci with at most three mismatches to the RNA guide. Current approaches for CRISPR effector target selection rank off-target candidates found in the reference human genome by both the number and position of RNA guide mismatches, with the assumption that loci containing less than 3 mismatches or containing PAM distal mismatches are more likely to be cleaved. However, in a population of individuals, this strategy is complicated by the existence of multiple haplotypes (sets of associated variants), which will contain different positions or numbers of mismatches at candidate off-target sites (See: population safety).

Guide RNA Design and Choice

Several technologies have been developed to address different embodiments of efficacy and specificity 1. Tru guide trimming 1-3 nt off from the 3' end of the target complimentary region of the gRNA often decreases activity at off-target loci containing at least one mismatch to the guide RNA. Likely, with fewer nucleotides of base-pairing between the off-target and gRNA, each mismatch has a greater thermodynamic consequence to the stability of the CRISPR effector-gRNA complex with the off-target DNA.

Percentage of successfully cleaved targets may be reduced in using tru guides: i.e., some sites that worked with a 20 nt guide may not cut efficiently with a 17 nt guide; but the ones that do work with 17 nt generally cleavage as efficiently.

Protected guide utilize an extended guide RNA and/or trans RNA/DNA elements to 1) create stable structures in the sgRNA that compete with sgRNA base-pairing at a target or off-target site or 2) (optionally) extend complimentary nucleotides between the gRNA and target. For extended RNA implementations, secondary structure results from complementarity between the 3' extension of the guide RNA and another target complimentary region of the guide RNA. For trans implementations, DNA or RNA elements bind the extended or normal length guide RNA partially obscuring the target complimentary region of the sgRNA.

Dosage Choice

The dosage of the CRISPR components should take into account the following factors 1. Target Search: CRISPR effector/guide RNA-enzyme complexes use 3-D stochastic search to locate targets. Given equal genomic accessibility, the probability of the complex finding an off-target or on-target is similar.

2. Binding (Target Dwell Time): Once located, the binding kinetics of the complex at an on-target or an off-target with few mismatches differs only slightly. Hence, target search and binding are likely not the rate-limiting steps for DNA cleavage at on-target or off-target loci. ChIP data suggests that complex dwell time does decrease accompanying increasing mismatches between the off-target locus and RNA guide, particularly in the PAM-proximal 'seed' region of the RNA guide.

3. Cutting (Thermodynamic barrier to assuming an active conformation): a) A major rate-limiting step for CRISPR effector enzymatic activity appears to be configuration of the target DNA and guide RNA-protein complex in an active conformation for DNA cleavage. Increasing mismatches at off-target loci decrease the likelihood of the complex achieving an active conformation at off-target loci. B) The difference between binding and cutting is why ChIP has very low predictive power as a tool for evaluating the off-target cleavage of Cas9. Cas (e.g. Cas9 and/or Cas12) proteins or genes can, in some embodiments, be similar. C) If the probability of finding an off-target or on-target is similar, then the difference in rate of on and off-target cleavage is likely due to the fact that the probability of cleavage at an on target sites is greater than off target sites. (See temporal control). The stochastic search can means that Cas9 (or Cas (e.g. Cas9 and/or Cas12)) can suggest that an incorrect model is to view Cas9 (or Cas (e.g. Cas9 and/or Cas12) proteins) as preferentially cleaving the on-target site first and only moving onto off-target sites after on-target cleavage is saturated; instead, all sites are interrogated at random, and the probability of progression to cutting after PAM binding is what differentiates the propensity of on vs. off-target cutting. 4. Repetition in DNA modification at an individual locus: NHEJ repair of DNA double strand breaks is generally high fidelity (Should find exact error rate). Hence, it is likely that a nuclease must cut an individual locus many times before an error in NHEJ results in an indel at the cut site. The probability of observing an indel is the compounding probability of observing a double strand break based on 1) target search probability, 2) target dwell time, and 3) overcoming the thermodynamic barrier to DNA cleavage. 5. Enzyme concentration: Even at very low concentrations, search may still encounter an off-target prior to an on-target. Thereafter, the number and location of mismatches in an off-target, and likely the nucleotide content of the target will influence the likelihood of DNA cleavage.

Thinking about on/off target cleavage in probabilistic terms, each interaction that Cas (e.g. Cas9 and/or Cas12) protein(s) has/have with the genome can be thought of as having some probability of successful cleavage. Reducing the dose will reduce the number of Cas (e.g. Cas9 and/or Cas12) molecule(s) available for interacting with the target polynucleotide (e.g. genome), and thus will limit the additive probability of repeated interactions at off-target sites.

Temporal and Spatial Control of CRISPR-Cas Systems

General Discussion

Various technologies have been developed which provide additional options for addressing efficacy, specificity and safety issues. More particularly these options can be used to allow for temporal control. Thus, in embodiments the structural and functional design of the CRISPR-Cas systems and/or components thereof can provide for temporal and/or spatial control of one or more CRISPR-Cas system mediated effects. As described herein, one or more features can be included in a CRISPR-Cas system to provide temporal and/or spatial control of one or more effects of the system. In some embodiments, temporal and/or spatial control of the CRISPR-Cas system or component thereof can by, itself or when used in combination with other specific parameters, optimize the CRISPR-Cas system or component thereof such that it does not induce a DNA-damage response signature when it is introduced into a cell. More particularly these technologies allow for temporal/spatial control (as described further herein):

1. Double nickases
2. Escorted guides
3. Split-effector protein
4. "self-inactivating" systems or "governing guides"
5. Specificity Selection of the Most Specific Guide RNA i. Guide Specificity While early reports were fairly contradictory on the ability to accurately predict guide RNAs with limited off-target activity, statistical analysis based on a large number of data has made it possible to identify rules governing off-target effects. Doench et al. (Nat Biotechnol. 2016 February; 34(2):184-91) describe the profiling of the off-target activity of thousands of sgRNAs and the development of a metric to predict off-target sites.

Accordingly, in particular embodiments, the methods of the invention involve selecting a guide RNA which, based on statistical analysis, is less likely to generate off-target effects.

ii. Guide Complementarity

It is generally envisaged that the degree of complementarity between a guide sequence and its corresponding target sequence should be as high as possible, such as more than about 50%, 60%, 75%, 80%, 85%, 90%, 95%, 97.5%, 99%, or 100%; However, in particular embodiments, a particular concern is reducing off-target interactions, e.g., reducing the guide interacting with a target sequence having low complementarity. It has been shown that certain mutations result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in particular embodiments, the guide is selected such that the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

iii. Selection of Guide/Enzyme Concentration

For minimization of toxicity and off-target effect, it can be important to control the concentration of Cas (e.g. Cas9 and/or Cas12) protein and/or guide RNA delivered. Optimal concentrations of Cas (e.g. Cas9 and/or Cas12) protein and/or guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 47) in the EMX1 gene of the human genome, deep sequencing can be used to assess the level of modification at the following two off-target loci, 1: 5'-GAGTCCTAGCAGGAGAAGAA-3' (SEQ ID NO: 48) and 2: 5'-GAGTCTAAGCAGAAGAAGAA-3' (SEQ ID NO: 49). The concentration that gives the highest level of on-target modification while minimizing the level of off-target modification should be chosen for in vivo delivery.

Selection of the Most Specific Enzyme i. Enzyme Modifications to Enhance Specificity Suitable Cas enzyme modifications which enhance specificity may selected. Example Cas enzyme modification which enhance specify are describe above under the section labeled "Modified Cas or Cas effector enzymes."

ii. Selecting Suitable PAM Recognition

In some embodiments, the Cas effector can require a protospacer adjacent motif (PAM). It will be appreciated that some Cas effectors, including some embodiments of those described elsewhere herein, do not require a PAM motif. The requirement of some CRISPR effector proteins, ensures another level of specificity in that only the target which is preceded by the relevant motif for the enzyme, will be cleaved. Thus, in particular embodiments, where available it may be of interest to select an effector protein with a stringent PAM so as to reduce off-target effects. Such an effector protein may be a Cas9 and/or Cas12 or an ortholog or a Cas effector protein having altered specificity.

On the other hand, the use of a Cas effector protein can be limited by its protospacer adjacent motif (PAM), in that it will only be able to robustly cleave target sites preceded by said motif.

Cas (e.g. Cas9 and/or Cas12) mutants can be designed that have increased target specificity as well as accommodating modifications in PAM recognition, for example by choosing mutations that alter PAM specificity and combining those mutations with nt-groove mutations that increase (or if desired, decrease) specificity for on-target sequences vs. off-target sequences. In one such embodiment, a PI domain residue is mutated to accommodate recognition of a desired PAM sequence while one or more nt-groove amino acids is mutated to alter target specificity. Kleinstiver involves SpCas9 and SaCas9 nucleases in which certain PI domain residues are mutated and recognize alternative PAM sequences (see Kleinstiver et al., Nature 523(7561):481-5 doi: 10.1038/nature14592, published online 22 Jun. 2015; Kleinstiver et al., Nature Biotechnology, doi: 10.1038/nbt.3404, published online 2 Nov. 2015), see also Hirano et al. (2016), Molecular Cell, 61(6):886-894, doi: 10.1016/j.molcel.2016.02.018; and Anders et al. (2016), Molecular Cell, 61(6):895-902, doi:10.1016/j.molcel.2016.02.020. Modification of PAM specificity has been performed by a structure-guided saturation mutagenesis screen to increase the targeting range of Cpf1 (Linyi et al. 2016, BioRxiv, http://dx.doi.org/10.1101/091611) and similar methods may be applied to Cas (e.g. Cas9 and/or Cas12) protein(s). The Cas (e.g. Cas9 and/or Cas12) methods and modifications described herein can be used to counter loss of specificity resulting from alteration of PAM recognition, enhance gain of specificity resulting from alteration of PAM recognition, counter gain of specificity resulting from alteration of PAM recognition, or enhance loss of specificity resulting from alteration of PAM recognition.

The methods and mutations can be used with any Cas (e.g. Cas9 and/or Cas12) enzyme(s) with altered PAM recognition. Non-limiting examples of PAMs included NGG, NNGRRT, NN[A/CT]RRT, NGAN, NGCG, NGAG, NGNG, NGC, and NGA.

Accordingly, these variants increase the targeting range, providing a useful addition to the CRISPR/Cas genome engineering toolbox. At the same time, the provision of Cas (e.g. Cas9 and/or Cas12) effector proteins with alternative PAM specificity allows for the selection of a particular variant with optimal specificity for a particular target sequence.

System Approaches to Reduce Off-Target Effects i. Double Nickase

Alternatively, to minimize the level of toxicity and off-target effect, a Cas (e.g. Cas9 and/or Cas12) nickase can be used with a pair of guide RNAs targeting a site of interest. Guide sequences and strategies to minimize toxicity and off-target effects can be as in WO 2014/093622 (PCT/US2013/074667); or, via mutation as described herein. The invention thus contemplates methods of using two or more nickases, in particular a dual or double nickase approach. In some embodiments and embodiments, a single type nickase may be delivered, for example a modified nickase as described herein. This results in the target DNA being bound by two nickases. In addition, it is also envisaged that different orthologs may be used, e.g., a nickase on one strand (e.g., the coding strand) of the DNA and an ortholog on the non-coding or opposite DNA strand. The ortholog can be, but is not limited to, a Cas (e.g. Cas9 and/or Cas12) nickase such as a SaCas9 nickase or a SpCas9 nickase or a StCas9. It may be advantageous to use two different orthologs that require different PAMs and may also have different guide requirements, thus allowing a greater deal of control for the user. In certain embodiments, DNA cleavage will involve at least four types of nickases, wherein each type is guided to a different sequence of target DNA, wherein each pair introduces a first nick into one DNA strand and the second introduces a nick into the second DNA strand. In such methods, at least two pairs of single stranded breaks are introduced into the target DNA wherein upon introduction of first and second pairs of single-strand breaks, target sequences between the first and second pairs of single-strand breaks are excised. In certain embodiments, one or both of the orthologs is controllable, i.e. inducible.

ii. Escorted Guides

The methods provided herein may also involve the use of escorted Cas CRISPR-Cas systems or complexes, especially such a system involving an escorted Cas CRISPR-Cas system guide. By "escorted" is meant that the Cas CRISPR-Cas system or complex or guide is delivered to a selected time or place within a cell, so that activity of the Cas CRISPR-Cas system or complex or guide is spatially or temporally controlled. For example, the activity and destination of the Cas CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time. The principle of escorted guides and embodiments thereof are described in detail in WO2016094874 incorporated by reference herein.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4). The aptamers used in this embodiment are designed to improve gRNA delivery, including delivery across the cellular membrane, to intracellular compartments, or into the nucleus. Such a structure can include, either in addition to the one or more aptamer(s) or without such one or more aptamer(s), moiety(ies) so as to render the guide deliverable, inducible or responsive to a selected effector. In particular embodiments, a gRNA is designed that responds to normal or pathological physiological conditions, including without limitation pH, hypoxia, O2 concentration, temperature, protein concentration, enzymatic concentration, lipid structure, light exposure, mechanical disruption (e.g. ultrasound waves), magnetic fields, electric fields, or electromagnetic radiation. Accordingly, in particular embodiments, the escort aptamer has binding affinity for an aptamer ligand on or in the cell, or the escort aptamer is responsive to a localized aptamer effector on or in the cell, wherein the presence of the aptamer ligand or effector on or in the cell is spatially or temporally restricted.

Once intended alterations have been introduced, such as by editing intended copies of a gene in the genome of a cell, continued CRISPR/Cas (e.g. Cas9 and/or Cas12) expression in that cell is no longer necessary. Indeed, sustained expression would be undesirable in certain cases in case of off-target effects at unintended genomic sites, etc. Thus time-limited expression is of interest.

Inducible expression offers one approach, but in addition Applicants have engineered a Self-Inactivating Cas CRISPR-Cas system that relies on the use of a non-coding guide target sequence within the CRISPR vector itself. Thus, after expression begins, the CRISPR system will lead to its own destruction, but before destruction is complete it will have time to edit the genomic copies of the target gene (which, with a normal point mutation in a diploid cell, requires at most two edits). Simply, the self-inactivating Cas CRISPR-Cas system includes additional RNA (i.e., guide RNA) that targets the coding sequence for the CRISPR enzyme itself or that targets one or more non-coding guide target sequences complementary to unique sequences present in one or more of the following: (a) within the promoter driving expression of the non-coding RNA elements, (b) within the promoter driving expression of the Cas (e.g. Cas9 and/or Cas12) gene(s), (c) within 100 bp of the ATG translational start codon in the Cas (e.g. Cas9 and/or Cas12) coding sequence(s), (d) within the inverted terminal repeat (iTR) of a viral delivery vector, e.g., in an AAV genome.

iii. Inducible Systems

Examples of inducible systems are light responsive systems. Light responsiveness of an inducible system are achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Crytochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

In particular embodiments, energy sources such as electromagnetic radiation, sound energy or thermal energy can induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 $mW/cm^2$. In a preferred embodiment, a stimulation paradigm of as low as 0.25 sec every 15 sec should result in maximal activation.

In particular embodiments, the system is chemically inducible. Exemplary designs of chemical inducible systems include: 1. ABI-PYL based system inducible by Abscisic Acid (ABA) (see, e.g., http://stke.sciencemag.org/cgi/content/ab stract/sigtrans; 4/164/r52), 2. FKBP-FRB based system inducible by rapamycin (or related chemicals based on rapamycin) (see, e.g., http://www.nature.com/nmeth/journal/v2/n6/full/nmeth763.html), 3. GID1-GAI based system inducible by Gibberellin (GA) (see, e.g., http://www.nature.com/nchembio/journal/v8/n5/full/nchembio.922.html).

Another chemical inducible system is an estrogen receptor (ER) based system inducible by 4-hydroxytamoxifen (4OHT) (see, e.g., http://www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

In particular embodiments, the chemical inducible system is based on change in sub-cellular localization. The polypeptide can include a DNA binding domain comprising at least five or more Transcription activator-like effector (TALE) monomers and at least one or more half-monomers specifically ordered to target the genomic locus of interest linked to at least one or more effector domains are further linker to a chemical or energy sensitive protein. This protein will lead to a change in the sub-cellular localization of the entire polypeptide (i.e. transportation of the entire polypeptide from cytoplasm into the nucleus of the cells) upon the binding of a chemical or energy transfer to the chemical or energy sensitive protein. This transportation of the entire polypeptide from one sub-cellular compartments or organelles, in which its activity is sequestered due to lack of substrate for the effector domain, into another one in which the substrate is present would allow the entire polypeptide to come in contact with its desired substrate (i.e. genomic DNA in the mammalian nucleus) and result in activation or repression of target gene expression.

Another inducible system is based on the design using Transient receptor potential (TRP) ion channel based system inducible by energy, heat or radio-wave (see, e.g., http://www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Caslike CRISPR-Cas complex or system, and the binding will induce the change of sub-cellular localization of the polypeptide, leading to the entire polypeptide entering the nucleus of cells. Once inside the nucleus, the guide protein and the other components of the Cas CRISPR-Cas complex will be active and modulating target gene expression in cells. This type of system could also be used to induce the cleavage of a genomic locus of interest in a cell; and, in this regard, it is noted that the Cas enzyme is a nuclease. The light could be generated with a laser or other forms of energy sources. The heat could be generated by raise of temperature results from an energy source, or from nano-particles that release heat after absorbing energy from an energy source delivered in the form of radio-wave.

Photoinducibility provides the potential for spatial precision. Taking advantage of the development of optrode technology, a stimulating fiber optic lead may be placed in a precise brain region. Stimulation region size may then be tuned by light intensity. This may be done in conjunction with the delivery of the Cas CRISPR-Cas system or complex of the invention, or, in the case of transgenic Cas (e.g. Cas9 and/or Cas12) animals, guide RNA of the invention may be delivered and the optrode technology can allow for the modulation of gene expression in precise brain regions. A culture medium for culturing host cells includes a medium commonly used for tissue culture, such as M199-earle base, Eagle MEM (E-MEM), Dulbecco MEM (DMEM), SC-UCM102, UP-SFM (GIBCO BRL), EX-CELL302 (Nichirei), EX-CELL293-S(Nichirei), TFBM-01 (Nichirei), ASF104, among others. Suitable culture media for specific cell types may be found at the American Type Culture Collection (ATCC) or the European Collection of Cell Cultures (ECACC). Culture media may be supplemented with amino acids such as L-glutamine, salts, anti-fungal or anti-bacterial agents such as Fungizone®, penicillin-streptomycin, animal serum, and the like. The cell culture medium may optionally be serum-free.

Temporal precision can also be achieved in vivo. This may be used to alter gene expression during a particular stage of development. This may be used to time a genetic cue to a particular experimental window. For example, genes implicated in learning may be overexpressed or repressed only during the learning stimulus in a precise region of the intact rodent or primate brain. Further, the invention may be used to induce gene expression changes only during particular stages of disease development. For example, an oncogene may be overexpressed only once a tumor reaches a particular size or metastatic stage. Conversely, proteins suspected in the development of Alzheimer's may be knocked down only at defined time points in the animal's life and within a particular brain region. Although these examples do not exhaustively list the potential applications of the invention, they highlight some of the areas in which the invention may be a powerful technology.

iv. Protected Guides

In one embodiment, it is of interest to further enhance the specificity of Cas (e.g. Cas9 and/or Cas12) given individual guide RNAs through thermodynamic tuning of the binding specificity of the guide RNA to target DNA. This is a general approach of introducing mismatches, elongation or truncation of the guide sequence to increase/decrease the number of complimentary bases vs. mismatched bases shared between a genomic target and its potential off-target loci, in order to give thermodynamic advantage to targeted genomic loci over genomic off-targets. Thus, it can be of interest to modify the guide sequence by secondary structure to increase the specificity of the Cas (e.g. Cas9 and/or Cas12) CRISPR-Cas system whereby the secondary structure can protect against exonuclease activity. This can be ensured by hybridizing a "protector RNA" to a guide sequence, wherein the "protector RNA" is an RNA strand complementary to the 5' end of the guide RNA (gRNA), to thereby generate a partially double-stranded gRNA. Protecting the mismatched bases with a perfectly complementary protector sequence decreases the likelihood of target DNA binding to the mismatched basepairs at the 3' end. In particular embodiments, additional sequences comprising an extended length may also be present. The principle of using protected guide RNAs is described in detail in International Patent Publication No. WO/2016/094867, which is incorporated herein by reference.

Guide RNA (gRNA) extensions matching the genomic target provide gRNA protection and enhance specificity. Extension of the gRNA with matching sequence distal to the end of the spacer seed for individual genomic targets thus provides enhanced specificity. In particular embodiments, stable forms arise from protective states, where the extension forms a closed loop with the gRNA seed due to complimentary sequences in the spacer extension and the spacer seed. Thus, the protected guide concept also includes sequences matching the genomic target sequence distal of the 20mer spacer-binding region. Thermodynamic prediction can be used to predict completely matching or partially matching guide extensions that result in protected gRNA states as described in WO/2016/094867.

An extension sequence which corresponds to the extended length (ExL) may optionally be attached directly to the guide sequence at the 3' end of the protected guide sequence. The extension sequence may be 2 to 12 nucleotides in length. Preferably ExL may be denoted as 0, 2, 4, 6, 8, 10 or 12 nucleotides in length. In a preferred embodiment the ExL is denoted as 0 or 4 nucleotides in length. In a more preferred embodiment the ExL is 4 nucleotides in length. The extension sequence may or may not be complementary to the target sequence. An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence.

v. Formation of a RISC Through Guide Engineering

In some embodiments, the guide may be a protected guide (e.g. a pgRNA) or an escorted guide (e.g. an esgRNA) as described herein. Both of these, in some embodiments, make use of RISC. A RISC is a key component of RNAi. RISC (RNA-induced silencing complex) is a multiprotein, specifically a ribonucleoprotein, complex which incorporates one strand of a double-stranded RNA (dsRNA) fragment, such as small interfering RNA (siRNA) or microRNA (miRNA), which acts as a template for RISC to recognize a complementary messenger RNA (mRNA) transcript. The mRNA is thus cleaved by one of the components of the RISC.

As such, the formation of a RISC is advantageous in some embodiments. Guide RNAs according to various embodiments of the present invention, including but not limited to protected and/or escorted guide RNAs, may be adapted to include RNA nucleotides that promote formation of a RISC, for example in combination with an siRNA or miRNA that may be provided or may, for instance, already be expressed in a cell. This may be useful, for instance, as a self-inactivating system to clear or degrade the guide.

Thus, the guide RNA may comprise a sequence complementary to a target miRNA or an siRNA, which may or may not be present within a cell. In this way, only when the miRNA or siRNA is present, for example through expression (by the cell or through human intervention), is there binding of the RNA sequence to the miRNA or siRNA which then results in cleavage of the guide RNA an RNA-induced silencing complex (RISC) within the cell. Therefore, in some embodiments, the guide RNA comprises an RNA sequence complementary to a target miRNA or siRNA, and binding of the guide RNA sequence to the target miRNA or siRNA results in cleavage of the guide RNA by an RNA-induced silencing complex (RISC) within the cell.

RISC formation through use of escorted guides is described in WO2016094874, RISC formation through use of protected guides is described in WO/2016/094867.

vi. Use of Inducible Systems

In an embodiment the invention provides a (non-naturally occurring or engineered) inducible CRISPR protein according to the invention as described herein (CRISPR-Cas system), comprising a first CRISPR protein fusion construct attached to a first half of an inducible dimer and a second CRISPR protein fusion construct attached to a second half of the inducible dimer, wherein the first Cas (e.g. Cas9 and/or Cas12) fusion construct is operably linked to one or more nuclear localization signals, wherein the second CRISPR protein fusion construct is operably linked to one or more nuclear export signals, wherein contact with an inducer energy source brings the first and second halves of the inducible dimer together, wherein bringing the first and second halves of the inducible dimer together allows the first and second CRISPR protein fusion constructs to constitute a functional CRISPR protein (optionally wherein the CRISPR-Cas system comprises a guide RNA (gRNA) comprising a guide sequence capable of hybridizing to a target sequence in a genomic locus of interest in a cell, and wherein the functional CRISPR-Cas system binds to the target sequence and, optionally, edits the genomic locus to alter gene expression). In an embodiment of the invention in the inducible CRISPR-Cas system, the inducible dimer is or comprises or consists essentially of or consists of an inducible heterodimer. In an embodiment, in inducible CRISPR-Cas system, the first half or a first portion or a first fragment of the inducible heterodimer is or comprises or consists of or consists essentially of an FKBP, optionally FKBP12. In an embodiment of the invention, in the inducible CRISPR-Cas system, the second half or a second portion or a second fragment of the inducible heterodimer is or comprises or consists of or consists essentially of FRB. In an embodiment of the invention, in the inducible CRISPR-Cas system, the arrangement of the first CRISPR fusion construct is or comprises or consists of or consists essentially of N' terminal CRISPR part-FRB-NES. In an embodiment of the invention, in the inducible CRISPR-Cas system, the arrangement of the first CRISP fusion construct is or comprises or consists of or consists essentially of NES-N' terminal CRISP part-FRB-NES. In an embodiment of the invention, in the inducible CRISPR-Cas system, the arrangement of the second CRISP fusion construct is or comprises or consists essentially of or consists of C' terminal CRISP part-FKBP-NLS. In an embodiment the invention provides in the inducible CRISPR-Cas-Cas system, the arrangement of the second CRISP fusion construct is or comprises or consists of or consists essentially of NLS-C' terminal CRISP part-FKBP-NLS. In an embodiment, in inducible CRISPR-Cas system there can be a linker that separates the CRISP part from the half or portion or fragment of the inducible dimer. In an embodiment, in the inducible CRISPR-Cas system, the inducer energy source is or comprises or consists essentially of or consists of rapamycin. In an embodiment, in inducible CRISPR-Cas system, the inducible dimer is an inducible homodimer.

In an embodiment, the invention provides a (non-naturally occurring or engineered) inducible CRISPR-Cas system, comprising: a first CRISPR fusion construct attached to a first half of an inducible heterodimer and a second CRISPR fusion construct attached to a second half of the inducible heterodimer, wherein the first CRISPR fusion construct is operably linked to one or more nuclear localization signals, wherein the second CRISPR fusion construct is operably linked to a nuclear export signal, wherein contact with an inducer energy source brings the first and second halves of the inducible heterodimer together, wherein bringing the first and second halves of the inducible heterodimer together allows the first and second CRISPR fusion constructs to constitute a functional CRISPR (optionally wherein the CRISPR-Cas system comprises a guide RNA (gRNA) comprising a guide sequence capable of hybridizing to a target sequence in a genomic locus of interest in a cell, and wherein the functional CRISPR-Cas system edits the genomic locus to alter gene expression).

Accordingly, the invention comprehends inter alia homodimers as well as heterodimers, dead-CRISPR or CRISPR protein having essentially no nuclease activity, e.g., through mutation, systems or complexes wherein there is one or more NLS and/or one or more NES; functional domain(s) linked to split Cas (e.g. Cas9 and/or Cas12); methods, including methods of treatment, and uses.

An inducer energy source may be considered to be simply an inducer or a dimerizing agent. The term 'inducer energy source' is used herein throughout for consistency. The inducer energy source (or inducer) acts to reconstitute the enzyme. In some embodiments, the inducer energy source brings the two parts of the enzyme together through the action of the two halves of the inducible dimer. The two halves of the inducible dimer therefore are brought tougher in the presence of the inducer energy source. The two halves of the dimer will not form into the dimer (dimerize) without the inducer energy source.

Thus, the two halves of the inducible dimer cooperate with the inducer energy source to dimerize the dimer. This in turn reconstitutes the CRISPR by bringing the first and second parts of the CRISPR together.

The CRISPR protein fusion constructs each comprise one part of the split CRISPR protein. These are fused, preferably via a linker such as a GlySer linker described herein, to one of the two halves of the dimer. The two halves of the dimer may be substantially the same two monomers that together that form the homodimer, or they may be different monomers that together form the heterodimer. As such, the two monomers can be thought of as one half of the full dimer.

The CRISPR protein is split in the sense that the two parts of the CRISPR protein enzyme substantially comprise a functioning CRISPR protein. That CRISPR protein may function as a genome editing enzyme (when forming a complex with the target DNA and the guide), such as a nickase or a nuclease (cleaving both strands of the DNA), or it may be a dead-CRISPR protein which is essentially a DNA-binding protein with very little or no catalytic activity, due to typically mutation(s) in its catalytic domains.

The two parts of the split CRISPR protein can be thought of as the N' terminal part and the C' terminal part of the split CRISPR protein. The fusion is typically at the split point of the CRISPR protein. In other words, the C' terminal of the N' terminal part of the split CRISPR protein is fused to one of the dimer halves, whilst the N' terminal of the C' terminal part is fused to the other dimer half.

The CRISPR protein does not have to be split in the sense that the break is newly created. The split point is typically designed in silico and cloned into the constructs. Together, the two parts of the split CRISPR protein, the N' terminal and C' terminal parts, form a full CRISPR protein, comprising preferably at least 70% or more of the wildtype amino acids (or nucleotides encoding them), preferably at least 80% or more, preferably at least 90% or more, preferably at least 95% or more, and most preferably at least 99% or more of the wildtype amino acids (or nucleotides encoding them). Some trimming may be possible, and mutants are envisaged. Nonfunctional domains may be removed entirely. What is important is that the two parts may be brought together and that the desired CRISPR protein function is restored or reconstituted.

The dimer may be a homodimer or a heterodimer.

One or more, preferably two, NLSs may be used in operable linkage to the first CRISPR protein construct. One or more, preferably two, NESs may be used in operable linkage to the first Ca9 construct. The NLSs and/or the NESs preferably flank the split Cas (e.g. Cas9 and/or Cas12)-dimer (i.e., half dimer) fusion, i.e., one NLS may be positioned at the N' terminal of the first CRISPR protein construct and one NLS may be at the C' terminal of the first CRISPR protein construct. Similarly, one NES may be positioned at the N' terminal of the second CRISPR construct and one NES may be at the C' terminal of the second CRISPR construct. Where reference is made to N' or C' terminals, it will be appreciated that these correspond to 5' ad 3' ends in the corresponding nucleotide sequence.

A preferred arrangement is that the first CRISPR protein construct is arranged 5'-NLS-(N' terminal CRISPR protein part)-linker-(first half of the dimer)-NLS-3'. A preferred arrangement is that the second CRISPR protein construct is arranged 5'-NES-(second half of the dimer)-linker-(C' terminal CRISPR protein part)-NES-3'. A suitable promoter is preferably upstream of each of these constructs. The two constructs may be delivered separately or together.

In some embodiments, one or all of the NES(s) in operable linkage to the second Cas (e.g. Cas9 and/or Cas12) construct may be swapped out for an NLS. However, this may be typically not preferred and, in other embodiments, the localization signal in operable linkage to the second Cas (e.g. Cas9 and/or Cas12) construct is one or more NES(s).

It will also be appreciated that the NES may be operably linked to the N' terminal fragment of the split CRISPR protein and that the NLS may be operably linked to the C' terminal fragment of the split CRISPR protein. However, the arrangement where the NLS is operably linked to the N' terminal fragment of the split Cas (e.g. Cas9 and/or Cas12) and that the NES is operably linked to the C' terminal fragment of the split CRISPR protein may be preferred.

The NES functions to localize the second CRISPR protein fusion construct outside of the nucleus, at least until the inducer energy source is provided (e.g., at least until an energy source is provided to the inducer to perform its function). The presence of the inducer stimulates dimerization of the two CRISPR protein fusions within the cytoplasm and makes it thermodynamically worthwhile for the dimerized, first and second, CRISPR protein fusions to localize to the nucleus. Without being bound by theory, Applicants believe that the NES sequesters the second CRISPR protein fusion to the cytoplasm (i.e., outside of the nucleus). The NLS on the first CRISPR protein fusion localizes it to the nucleus. In both cases, Applicants use the NES or NLS to shift an equilibrium (the equilibrium of nuclear transport) to a desired direction. The dimerization typically occurs outside of the nucleus (a very small fraction might happen in the nucleus) and the NLSs on the dimerized complex shift the equilibrium of nuclear transport to nuclear localization, so the dimerized and hence reconstituted CRISPR protein enters the nucleus.

Beneficially, Applicants are able to reconstitute function in the split CRISPR protein. Transient transfection is used to prove the concept and dimerization occurs in the background in the presence of the inducer energy source. No activity is seen with separate fragments of the CRISPR protein. Stable expression through lentiviral delivery is then used to develop this and show that a split CRISPR protein approach can be used.

This present split CRISPR protein approach is beneficial as it allows the CRISPR protein activity to be inducible, thus allowing for temporal control. Furthermore, different localization sequences may be used (i.e., the NES and NLS as preferred) to reduce background activity from auto-assembled complexes. Tissue specific promoters, for example one for each of the first and second CRISPR protein fusion constructs, may also be used for tissue-specific targeting, thus providing spatial control. Two different tissue specific promoters may be used to exert a finer degree of control if required. The same approach may be used in respect of stage-specific promoters or there may a mixture of stage and tissue specific promoters, where one of the first and second Cas (e.g. Cas9 and/or Cas12) fusion constructs is under the control of (i.e. operably linked to or comprises) a tissue-specific promoter, whilst the other of the first and second Cas (e.g. Cas9 and/or Cas12)fusion constructs is under the control of (i.e. operably linked to or comprises) a stage-specific promoter.

The inducible CRISPR protein CRISPR-Cas system comprises one or more nuclear localization sequences (NLSs), as described herein, for example as operably linked to the first CRISPR protein fusion construct. These nuclear localization sequences are ideally of sufficient strength to drive accumulation of said first CRISPR protein fusion construct in a detectable amount in the nucleus of a eukaryotic cell. Without wishing to be bound by theory, it is believed that a nuclear localization sequence is not necessary for CRISPR-Cas complex activity in eukaryotes, but that including such sequences enhances activity of the system, especially as to targeting nucleic acid molecules in the nucleus, and assists with the operation of the present 2-part system.

Equally, the second CRISPR protein fusion construct is operably linked to a nuclear export sequence (NES). Indeed, it may be linked to one or more nuclear export sequences. In other words, the number of export sequences used with the second CRISPR protein fusion construct is preferably 1 or 2 or 3. Typically 2 is preferred, but 1 is enough and so is preferred in some embodiments. Suitable examples of NLS and NES are known in the art. For example, a preferred nuclear export signal (NES) is human protein tyrosin kinase 2. Preferred signals will be species specific.

Where the FRB and FKBP system are used, the FKBP is preferably flanked by nuclear localization sequences (NLSs). Where the FRB and FKBP system are used, the preferred arrangement is N' terminal CRISPR protein—FRB-NES: C' terminal Cas (e.g. Cas9 and/or Cas12)-FKBP-NLS. Thus, the first CRISPR protein fusion construct would comprise the C' terminal CRISPR protein part and the second CRISPR protein fusion construct would comprise the N' terminal CRISPR protein part.

Another beneficial embodiment to that it may be turned on quickly, i.e. that is has a rapid response. It is believed, without being bound by theory, that CRISPR protein activity can be induced through dimerization of existing (already present) fusion constructs (through contact with the inducer energy source) more rapidly than through the expression (especially translation) of new fusion constructs. As such, the first and second CRISPR protein fusion constructs may be expressed in the target cell ahead of time, i.e. before CRISPR protein activity is required. CRISPR protein activity can then be temporally controlled and then quickly constituted through addition of the inducer energy source, which ideally acts more quickly (to dimerize the heterodimer and thereby provide CRISPR protein activity) than through expression (including induction of transcription) of CRISPR protein delivered by a vector, for example.

Applicants demonstrate that CRISPR protein can be split into two components, which reconstitute a functional nuclease when brought back together. Employing rapamycin sensitive dimerization domains, Applicants generate a chemically inducible CRISPR protein for temporal control of CRISPR protein-mediated genome editing and transcription modulation. Put another way, Applicants demonstrate that CRISPR protein can be rendered chemically inducible by being split into two fragments and that rapamycin-sensitive dimerization domains may be used for controlled reassembly of the CRISPR protein. Applicants show that the re-assembled CRISPR protein may be used to mediate genome editing (through nuclease/nickase activity) as well as transcription modulation (as a DNA-binding domain, the so-called “dead CRISPR protein”).

As such, the use of rapamycin-sensitive dimerization domains is preferred. Reassembly of the CRISPR protein is preferred. Reassembly can be determined by restoration of binding activity. Where the CRISPR protein is a nickase or induces a double-strand break, suitable comparison percentages compared to a wildtype are described herein.

Rapamycin treatments can last 12 days. The dose can be 200 nM. This temporal and/or molar dosage is an example of an appropriate dose for Human embryonic kidney 293FT (HEK293FT) cell lines and this may also be used in other cell lines. This figure can be extrapolated out for therapeutic use in vivo into, for example, mg/kg. However, it is also envisaged that the standard dosage for administering rapamycin to a subject is used here as well. By the “standard dosage”, it is meant the dosage under rapamycin’s normal therapeutic use or primary indication (i.e. the dose used when rapamycin is administered for use to prevent organ rejection).

It is noteworthy that the preferred arrangement of CRISPR protein-FRB/FKBP pieces are separate and inactive until rapamycin-induced dimerization of FRB and FKBP results in reassembly of a functional full-length CRISPR protein nuclease. Thus, it is preferred that first CRISPR protein fusion construct attached to a first half of an inducible heterodimer is delivered separately and/or is localized separately from the second Cas (e.g. Cas9 and/or Cas12) fusion construct attached to a first half of an inducible heterodimer.

To sequester the CRISPR protein (N)-FRB fragment in the cytoplasm, where it is less likely to dimerize with the nuclear-localized Cas (e.g. Cas9 and/or Cas12) I-FKBP fragment, it is preferable to use on CRISPR protein (N)-FRB a single nuclear export sequence (NES) from the human protein tyrosin kinase 2 (CRISPR protein (N)—FRB-NES). In the presence of rapamycin, CRISPR protein (N)—FRB-NES dimerizes with CRISPR protein I-FKBP-2×NLS to reconstitute a complete CRISPR protein, which shifts the balance of nuclear trafficking toward nuclear import and allows DNA targeting.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, and WO 2014/018423 A2 which is hereby incorporated by reference in its entirety.

vii. Use of Inducible/Split Effector Enzymes

In some embodiments or embodiments, an inducible system for providing a CRISPR protein may be used. In some embodiments, the CRISPR protein is capable, in the presence of an inducer energy source, of forming a CRISPR complex with a target sequence and polynucleotides engineered to complex with the CRISPR protein and the target sequence. In some embodiments, the inducible system comprises: a first fusion protein, or polynucleotides encoding it; and a second fusion protein, or polynucleotides encoding it. In some embodiments, the first fusion protein comprises a first portion of the CRISPR protein, a first half of an inducible dimer and one or more Nuclear Localisation Sequences (NLS); and the second fusion protein comprises a second portion of the CRISPR protein, a second half of the inducible dimer and one or more Nuclear Export Sequences (NES). In some embodiments, contact with the inducer energy source brings the first and second portions of the inducible dimer together, so as to bring the first and second portions of the CRISPR protein together, such that the CRISPR protein is thereby capable of forming the CRISPR complex. In some embodiments, the CRISPR protein or the CRISPR system is inducible. In some embodiments, the CRISPR protein may be provided as a single 'part.' In some embodiments, delivery of the CRISPR protein is in protein (including in RNP complex with the polynucleotides) or in nucleotide form (including in mRNA form). In some embodiments, polynucleotides encoding the first fusion protein and polynucleotides encoding second fusion protein are provided on same or different constructs. WO2015/089427 describes an inducible CRISPR-Cas system based on an inducible dimer, which can be a homodimer or heterodimer. The system is also described in Zetsche et al. (Nature Biotechnology 33: 139-142 (2015) DOI: doi:10.1038/nbt.3149). Basically, the CRISPR effector protein is split into two parts, each of which is fused to one half of an inducible dimer, whereby contact with an inducer energy source brings the first and second halves of the inducible dimer together, and bringing the first and second halves of the inducible dimer together allows the first and second CRISPR effector fusion constructs to constitute a functional CRISPR-Cas system, wherein the CRISPR-Cas system comprises a guide RNA (gRNA) comprising a guide sequence capable of hybridizing to a target sequence in a genomic locus of interest in a cell, and wherein the functional CRISPR-Cas system binds to the genomic locus. In particular embodiments, the functional CRISPR-Cas system edits the genomic locus to alter gene expression. In particular embodiments the first half is an FKBP and the second half is an FRB. An inducer energy source may be considered to be simply an inducer or a dimerizing agent as it acts to reconstitute the CRISPR effector protein.

Examples of inducers include light and hormones. A preferred example of first and second light-inducible dimer halves is the CIB1 and CRY2 system. The CIB1 domain is a heterodimeric binding partner of the light-sensitive Cryptochrome 2 (CRY2). In another example, the blue light-responsive Magnet dimerization system (pMag and nMag) may be fused to the two parts of a split Cas (e.g. Cas9 and/or Cas12) protein. In response to light stimulation, pMag and nMag dimerize and Cas (e.g. Cas9 and/or Cas12) reassembles. For example, such system is described in connection with Cas9 in Nihongaki et al. (Nat. Biotechnol. 33, 755-790, 2015). The inducer energy source may be heat, ultrasound, electromagnetic energy or chemical. In a preferred embodiment the inducer energy source may be an antibiotic, a small molecule, a hormone, a hormone derivative, a steroid or a steroid derivative. In a more preferred embodiment, the inducer energy source maybe abscisic acid (ABA), doxycycline (DOX), cumate, rapamycin, 4-hydroxytamoxifen (4OHT), estrogen or ecdysone. The at least one switch may be selected from the group consisting of antibiotic based inducible systems, electromagnetic energy based inducible systems, small molecule based inducible systems, nuclear receptor based inducible systems and hormone based inducible systems. In a more preferred embodiment the at least one switch may be selected from the group consisting of tetracycline (Tet)/DOX inducible systems, light inducible systems, ABA inducible systems, cumate repressor/operator systems, 4OHT/estrogen inducible systems, ecdysone-based inducible systems and FKBP12/FRAP (FKBP12-rapamycin complex) inducible systems. Such inducers are also discussed herein and in PCT/US2013/051418, incorporated herein by reference.

Also, it is described in WO2015/089427 that the half of an inducible dimer can be linked to the effector protein with a linker. Optionally the CRISPR effector protein has reduced or no nuclease activity, e.g. contains one or more inactivating mutations. Further it is described that one or more functional domains can be associated with one or both parts of the effector protein, WO2015/089427 identifies split points within SpCas9, incorporated herein by reference. This approach can be adapted for the CRISPR-Cas systems described herein.

For orthologues, it should be readily apparent what the corresponding position for a potential split site is, for example, based on a sequence alignment. One can use the crystal structure of an ortholog if a relatively high degree of homology exists between the ortholog and the intended Cas (e.g. Cas9 and/or Cas12), or one can use computational prediction.

Further it is described that the first and second fusion constructs of the CRISPR effector protein described herein (e.g. Cas (e.g. Cas9 and/or Cas12) can be delivered in the same or separate vectors. In particular embodiments, a first half of the inducible dimer is fused to one or more nuclear localization constructs while the second half is fused to one or more nuclear export signals.

The therapeutic methods which involve the use of the inducible dimer comprise the step of administering the vectors comprising the first and second fusion constructs to the subject and administering an inducer energy source to the subject. In particular embodiments, the inducer energy source is rapamycin. It is further envisaged that the methods can involve administering, a repair template, in the same or a different vector as the inducible dimer fragments. An exemplary treatment regimen with Rapamycin can last 12 days.

The use of the split Cas (e.g. Cas9 and/or Cas12) effector protein system described herein allows a further control of the CRISPR-Cas activity. More particularly the use of an inducible system allows for temporal control. In addition, the use of different localization sequences (i.e., the NES and NLS as preferred) can reduce background activity from auto-assembled complexes. Tissue specific promoters, allow for spatial control. Two different tissue specific promoters may be used to exert a finer degree of control if required.

vii. Use of Self-Inactivating Systems

Once all copies of a gene in the genome of a cell have been edited, continued CRISPR/Cas (e.g. Cas9 and/or Cas12) expression in that cell is no longer necessary. Indeed, sustained expression is undesirable to avoid off-target effects and other toxicity issues. WO 2015089351 describes self-Inactivating CRISPR systems which rely on the use of a non-coding guide target sequence within the CRISPR vector itself. Thus, after expression begins, the CRISPR system will lead to its own destruction, but before destruction is complete it will have time to edit the genomic copies of the target gene (which, with a normal point mutation in a diploid cell, requires at most two edits). Accordingly, the methods may involve the use of a self-inactivating CRISPR-Cas system which includes one additional RNA (i.e., guide RNA) that targets the coding sequence for the CRISPR enzyme itself or that targets one or more non-coding guide target sequences complementary to unique sequences present in within the promoter driving expression of the non-coding RNA elements, within the promoter driving expression of the Cas (e.g. Cas9 and/or Cas12) gene(s), within 100 bp of the ATG translational start codon in the Cas (e.g. Cas9 and/or Cas12) coding sequence, or within the inverted terminal repeat (iTR) of a viral delivery vector, e.g., in the AAV genome.

Similarly, self-inactivating systems which make use of "governing guides" are exemplified in relation to Cas9 in US2015232881A1 (also published as WO2015070083 (A1) referenced elsewhere herein and incorporated herein by reference, and may be extrapolated to Cas (e.g. Cas9 and/or Cas12). More particularly Methods and compositions that use, or include, a nucleic acid, e.g., a DNA, that encodes a Cas (e.g. Cas9 and/or Cas12) molecule or a gRNA molecule, can, in addition, use or include a "governing gRNA molecule." The governing gRNA molecule can complex with the Cas (e.g. Cas9 and/or Cas12) molecule to inactivate or silence a component of a Cas (e.g. Cas9 and/or Cas12) system. The additional gRNA molecule, referred to herein as a governing gRNA molecule, comprises a targeting domain which targets a component of the Cas (e.g. Cas9 and/or Cas12) system. In an embodiment, the governing gRNA molecule targets and silences (1) a nucleic acid that encodes a Cas (e.g. Cas9 and/or Cas12) molecule(s) (i.e., a Cas (e.g. Cas9 and/or Cas12)-targeting gRNA molecule), (2) a nucleic acid that encodes a gRNA molecule (i.e., a gRNA-targeting gRNA molecule), or (3) a nucleic acid sequence engineered into the Cas (e.g. Cas9 and/or Cas12) components that is designed with minimal homology to other nucleic acid sequences in the cell to minimize off-target cleavage (i.e., an engineered control sequence-targeting gRNA molecule).

The targeting sequence for the governing gRNA can be selected to increase regulation or control of the Cas (e.g. Cas9 and/or Cas12) system and/or to reduce or minimize off-target effects of the system. For example, a governing gRNA can minimize undesirable cleavage, e.g., "recleavage" after Cas (e.g. Cas9 and/or Cas12) mediated alteration of a target nucleic acid or off-target cutting of Cas9, by inactivating (e.g., cleaving) a nucleic acid that encodes a Cas (e.g. Cas9 and/or Cas12) molecule. In an embodiment, a governing gRNA places temporal or other limit(s) on the level of expression or activity of the Cas (e.g. Cas9 and/or Cas12) molecule/gRNA molecule complex. In an embodiment, the governing gRNA reduces off-target or other unwanted activity.

The additional guide RNA can be delivered via a vector, e.g., a separate vector or the same vector that is encoding the CRISPR complex. When provided by a separate vector, the CRISPR RNA that targets Cas (e.g. Cas9 and/or Cas12) expression can be administered sequentially or simultaneously. When administered sequentially, the CRISPR RNA that targets Cas (e.g. Cas9 and/or Cas12) expression is to be delivered after the CRISPR RNA that is intended for e.g. gene editing or gene engineering. This period may be a period of minutes (e.g. 5 minutes, 10 minutes, 20 minutes, 30 minutes, 45 minutes, 60 minutes). This period may be a period of hours (e.g. 2 hours, 4 hours, 6 hours, 8 hours, 12 hours, 24 hours). This period may be a period of days (e.g. 2 days, 3 days, 4 days, 7 days). This period may be a period of weeks (e.g. 2 weeks, 3 weeks, 4 weeks). This period may be a period of months (e.g. 2 months, 4 months, 8 months, 12 months). This period may be a period of years (2 years, 3 years, 4 years). In this fashion, the Cas enzyme associates with a first gRNA capable of hybridizing to a first target, such as a genomic locus or loci of interest and undertakes the function(s) desired of the CRISPR-Cas system (e.g., gene engineering); and subsequently the Cas (e.g. Cas9 and/or Cas12) enzyme(s) may then associate with the second gRNA capable of hybridizing to the sequence comprising at least part of the Cas (e.g. Cas9 and/or Cas12) or CRISPR cassette, when present. Where the gRNA targets the sequences encoding expression of the Cas (e.g. Cas9 and/or Cas12) protein(s), the enzyme becomes impeded and the system becomes self-inactivating. In the same manner, CRISPR RNA that targets Cas (e.g. Cas9 and/or Cas12) expression applied via, for example liposome, lipofection, nanoparticles, microvesicles as explained herein, may be administered sequentially or simultaneously. Similarly, self-inactivation may be used for inactivation of one or more guide RNA used to target one or more targets.

In some embodiments, a single gRNA is provided that is capable of hybridization to a sequence downstream of a CRISPR enzyme start codon, whereby after a period of time there is a loss of the CRISPR enzyme expression. In some embodiments, one or more gRNA(s) are provided that are capable of hybridization to one or more coding or non-coding regions of the polynucleotide encoding the CRISPR-Cas system, whereby after a period of time there is a inactivation of one or more, or in some cases all, of the CRISPR-Cas systems. In some embodiments of the system, and not to be limited by theory, the cell may comprise a plurality of CRISPR-Cas complexes, wherein a first subset of CRISPR complexes comprise a first chiRNA capable of targeting a genomic locus or loci to be edited, and a second subset of CRISPR complexes comprise at least one second chiRNA capable of targeting the polynucleotide encoding the CRISPR-Cas system, wherein the first subset of CRISPR-Cas complexes mediate editing of the targeted genomic locus or loci and the second subset of CRISPR complexes eventually inactivate the CRISPR-Cas system, thereby inactivating further CRISPR-Cas expression in the cell.

Thus the invention provides a CRISPR-Cas system comprising one or more vectors for delivery to a eukaryotic cell, wherein the vector(s) encode(s): (i) a CRISPR enzyme; (ii) a first guide RNA capable of hybridizing to a target sequence in the cell; (iii) a second guide RNA capable of hybridizing to one or more target sequence(s) in the vector which encodes the CRISPR enzyme; (iv) at least one tracr mate sequence; and (v) at least one tracr sequence. The first and second complexes can use the same tracr and tracr mate, thus differing only by the guide sequence, wherein, when expressed within the cell: the first guide RNA directs sequence-specific binding of a first CRISPR complex to the target sequence in the cell; the second guide RNA directs sequence-specific binding of a second CRISPR complex to the target sequence in the vector which encodes the CRISPR enzyme; the CRISPR complexes comprise (a) a tracr mate sequence hybridised to a tracr sequence and (b) a CRISPR enzyme bound to a guide RNA, such that a guide RNA can hybridize to its target sequence; and the second CRISPR complex inactivates the CRISPR-Cas system to prevent continued expression of the CRISPR enzyme by the cell. The CRISPR enzyme can be Cas (e.g. Cas9 and/or Cas12), particularly SpCas9, SaCas9, or StCas9.

Further characteristics of the vector(s), the encoded enzyme, the guide sequences, etc. are disclosed elsewhere herein. For instance, one or both of the guide sequence(s) can be part of a chiRNA sequence which provides the guide, tracr mate and tracr sequences within a single RNA, such that the system can encode (i) a CRISPR enzyme; (ii) a first chiRNA comprising a sequence capable of hybridizing to a first target sequence in the cell, a first tracr mate sequence, and a first tracr sequence; (iii) a second guide RNA capable of hybridizing to the vector which encodes the CRISPR enzyme, a second tracr mate sequence, and a second tracr sequence. Similarly, the enzyme can include one or more NLS, etc.

The various coding sequences (CRISPR enzyme, guide RNAs, tracr and tracr mate) can be included on a single vector or on multiple vectors. For instance, it is possible to encode the enzyme on one vector and the various RNA sequences on another vector, or to encode the enzyme and one chiRNA on one vector, and the remaining chiRNA on another vector, or any other permutation. In general, a system using a total of one or two different vectors is preferred.

Where multiple vectors are used, it is possible to deliver them in unequal numbers, and ideally with an excess of a vector which encodes the first guide RNA relative to the second guide RNA, thereby assisting in delaying final inactivation of the CRISPR system until genome editing has had a chance to occur.

Thus, the target sequence in the vector must be capable of inactivating expression of the CRISPR effector protein. Suitable target sequences can be, for instance, near to or within the translational start codon for the Cas (e.g. Cas9 and/or Cas12) coding sequence(s), in a non-coding sequence in the promoter driving expression of the non-coding RNA elements, within the promoter driving expression of the Cas (e.g. Cas9 and/or Cas12) gene(s), within 100 bp of the ATG translational start codon in the Cas (e.g. Cas9 and/or Cas12) coding sequence(s), and/or within the inverted terminal repeat (iTR) of a viral delivery vector, e.g., in the AAV genome. A double stranded break near this region can induce a frame shift in the Cas (e.g. Cas9 and/or Cas12) coding sequence(s), causing a loss of protein expression. An alternative target sequence for the "self-inactivating" guide RNA would aim to edit/inactivate regulatory regions/sequences needed for the expression of the CRISPR-Cas (e.g. Cas9 and/or Cas12) system or for the stability of the vector. For instance, if the promoter for the Cas (e.g. Cas9 and/or Cas12) coding sequence is disrupted then transcription can be inhibited or prevented. Similarly, if a vector includes sequences for replication, maintenance or stability then it is possible to target these. For instance, in a AAV vector a useful target sequence is within the iTR. Other useful sequences to target can be promoter sequences, 314annito1314ne314314 on sites, etc.

Furthermore, if the guide RNAs are expressed in array format, the "self-inactivating" guide RNAs that target both promoters simultaneously will result in the excision of the intervening nucleotides from within the CRISPR-Cas expression construct, effectively leading to its complete inactivation. Similarly, excision of the intervening nucleotides will result where the guide RNAs target both ITRs, or targets two or more other CRISPR-Cas components simultaneously. Self-inactivation as explained herein is applicable, in general, with CRISPR-Cas (e.g. Cas9 and/or Cas12) systems in order to provide regulation of the CRISPR-Cas (e.g. Cas9 and/or Cas12). For example, self-inactivation as explained herein may be applied to the CRISPR repair of mutations, for example expansion disorders, as explained herein. As a result of this self-inactivation, CRISPR repair is only transiently active.

Addition of non-targeting nucleotides to the 5' end (e.g. 1-10 nucleotides, preferably 1-5 nucleotides) of the "self-inactivating" guide RNA can be used to delay its processing and/or modify its efficiency as a means of ensuring editing at the targeted genomic locus prior to CRISPR-Cas (e.g. Cas9 and/or Cas12) shutdown.

In one embodiment of the self-inactivating AAV-CRISPR-Cas (e.g. Cas9 and/or Cas12) system, plasmids that co-express one or more sgRNA targeting genomic sequences of interest (e.g. 1-2, 1-5, 1-10, 1-15, 1-20, 1-30) may be established with "self-inactivating" sgRNAs that target an SpCas9 sequence at or near the engineered ATG start site (e.g. within 5 nucleotides, within 15 nucleotides, within 30 nucleotides, within 50 nucleotides, within 100 nucleotides). A regulatory sequence in the U6 promoter region can also be targeted with an sgRNA. The U6-driven sgRNAs may be designed in an array format such that multiple sgRNA sequences can be simultaneously released. When first delivered into target tissue/cells (left cell) sgRNAs begin to accumulate while Cas (e.g. Cas9 and/or Cas12) levels rise in the nucleus. Cas (e.g. Cas9 and/or Cas12) complexes with all of the sgRNAs to mediate genome editing and self-inactivation of the CRISPR-Cas (e.g. Cas9 and/or Cas12) plasmids.

One embodiment of a self-inactivating CRISPR-Cas (e.g. Cas9 and/or Cas12) system is expression of singly or in tandam array format from 1 up to 4 or more different guide sequences; e.g. up to about 20 or about 30 guides sequences. Each individual self-inactivating guide sequence may target a different target. Such may be processed from, e.g. one chimeric po13 transcript. Pol3 promoters such as U6 or H1 promoters may be used. Pol2 promoters such as those mentioned throughout herein. Inverted terminal repeat (iTR) sequences may flank the Pol3 promoter-sgRNA(s)-Pol2 promoter-Cas (e.g. Cas9 and/or Cas12) protein(s).

In particular embodiments one or more guide(s) edit the one or more target(s) while one or more self-inactivating guides inactivate the CRISPR/Cas (e.g. Cas9 and/or Cas12) system. Thus, for example, the described CRISPR-Cas (e.g. Cas9 and/or Cas12) system for repairing expansion disorders may be directly combined with the self-inactivating CRISPR-Cas (e.g. Cas9 and/or Cas12) system described herein. Such a system may, for example, have two guides directed to the target region for repair as well as at least a third guide directed to self-inactivation of the CRISPR-Cas (e.g. Cas9 and/or Cas12). Reference is made to Application Ser. No. PCT/US2014/069897, entitled "Compositions And Methods Of Use Of Crispr-Cas Systems In Nucleotide Repeat Disorders," published Dec. 12, 2014 as WO/2015/089351.

In particular embodiments, the gene editing systems described herein are placed under the control of a passcode kill switch, which is a mechanism which efficiently kills the host cell when the conditions of the cell are altered. This is ensured by introducing hybrid LacI-GalR family transcription factors, which require the presence of IPTG to be switched on (Chan et al. 2015 Nature Nature Chemical Biology doi:10.1038/nchembio.1979 which can be used to drive a gene encoding an enzyme critical for cell-survival. By combining different transcription factors sensitive to different chemicals, a "code" can be generated, This system can be used to spatially and temporally control the extent of CRISPR-induced genetic modifications, which can be of interest in different fields including therapeutic applications and may also be of interest to avoid the "escape" of GMOs from their intended environment.

ix. Use of "Off-Switches" and "On-Switches"

In particular embodiments, it may be possible to make use of specific inhibitors and/or agonist of Cas (e.g. Cas9 and/or Cas12). Off-switches and On-switches may be any molecules (i.e. peptides, proteins, small molecules, nucleic acids) capable of interfering with any embodiment of the Cas (e.g. Cas9 and/or Cas12) effector protein. For instance, Pawluck et al. 2016 (Cell 167, 1-10) describe mobile elements from bacteria that encode protein inhibitors of Cas9, which can be adapted and/or applied to the CRISPR-Cas (e.g. Cas9 and/or Cas12) systems described herein. Three families of anti-CRISPRs were found to inhibit *N. meningitidis* Cas9 in vivo and in vitro. The anti-CRISPRs bind directly to NmeCas9. These proteins are described to be potent "off-switches" for NmeCas9 genome editing in human cells. Methods for identifying small molecules which affect efficiency of Cas9 are described for example by Yu et al. (Cell Stem Cell 16, 142-147, 2015), which can be adapted and/or applied to the CRISPR-Cas (e.g. Cas9 and/or Cas12) systems described herein. In certain embodiments small molecules may be used for control Cas9. Maji et al. describe a small molecule-regulated protein degron domain to control Cas (e.g. Cas9 and/or Cas12) system editing. Maji et al. "Multidimensional chemical control of CRISPR-Cas9" Nature Chemical Biology (2017) 13:9-12, which can be adapted and/or applied to the CRISPR-Cas (e.g. Cas9 and/or Cas12) systems described herein. In certain example embodiments, the inhibitor may be a bacteriophage derived protein. See Rauch et al. "Inhibition of CRISPR-Cas9 with Bacteriophage Proteins" Cell (2017) 168(2):150-158, which can be adapted and/or applied to the CRISPR-Cas (e.g. Cas9 and/or Cas12) systems described herein. In certain example embodiments, the anti-CRISPR may inhibit CRISPR-Cas systems described herein by binding to guide molecules. See Shin et al. "Disabling Cas9 by an anti-CRISPR DNA mimic" bioRxiv, Apr. 22, 2017, doi:http://dx.doi.org/10.1101/129627, which can be adapted and/or applied to the CRISPR-Cas (e.g. Cas9 and/or Cas12) systems described herein.

In particular embodiments, intracellular DNA is removed by genetically encoded Dnai, which responds to a transcriptional input and degrades user-defined DNA as described in Caliando & Voigt, Nature Communications 6: 6989 (2015), which can be adapted and/or applied to the CRISPR-Cas (e.g. Cas9 and/or Cas12) systems described herein.

Efficacy

Selection of Most Active Enzyme

Enzyme Stability

The level of expression of a protein is dependent on many factors, including the quantity of mRNA, its stability and rates of ribosome initiation. The stability or degradation of mRNA is an important factor. Several strategies have been described to increase mRNA stability. One embodiment is codon-optimization. It has been found that GC-rich genes are expressed several-fold to over a 100-fold more efficiently than their GC-poor counterparts. This effect could be directly attributed to increased steady-state mRNA levels, and more particularly to efficient transcription or mRNA processing (not decreased degradation) (Kudla et al. Plos Biology http://dx.doi.org/10.1371/journal.pbio.0040180). Also, it has been found that ribosomal density has a significant effect on the transcript half-life. More particularly, it was found that an increase in stability can be achieved through the incorporation of nucleotide sequences that are capable of forming secondary structures, which often recruit ribosomes, which impede mRNA degrading enzymes. WO2011/141027 describes that slowly-read codons can be positioned in such a way as to cause high ribosome occupancy across a critical region of the 5' end of the mRNA can increase the half-life of a message by as much as 25%, and produce a similar uplift in protein production. In contrast, positioning even a single slow-read codon before this critical region can significantly destabilize the mRNA and result in an attenuation of protein expression. This understanding enables the design of mRNAs so as to suit the desired functionality. In addition, chemical modifications such as those described for guide sequences herein can be envisaged to increase mRNA stability.

Selection of Most Active Guide

Guide Stability

In certain embodiments, the methods make use of chemically modified guide RNAs. Examples of guide RNA chemical modifications include, without limitation, incorporation of 2'-O-methyl (M), 2'-O-methyl 3'phosphorothioate (MS), or 2'-O-methyl 3'thioPACE (MSP) at one or more terminal nucleotides. Such chemically modified guide RNAs can comprise increased stability and increased activity as compared to unmodified guide RNAs, though on-target vs. off-target specificity is not predictable. (See, Hendel, 2015, Nat Biotechnol. 33(9):985-9, doi: 10.1038/nbt.3290, published online 29 Jun. 2015). Chemically modified guide RNAs further include, without limitation, RNAs with phosphorothioate linkages and locked nucleic acid (LNA) nucleotides comprising a methylene bridge between the 2' and 4' carbons of the ribose ring.

Randar et al. describe methods to ensure stabilization in the tracer hybridization region (Proc Natl Acad Sci USA. 2015, 22; 112(51):E7110-7. Doi: 10.1073)

Select Best Target Site in Gene

Selection within a Target Gene

Studies to date suggest that while sgRNA activity can be quite high, there is significant variability among sgRNAs in their ability to generate the desired target cleavage. Efforts have been made to identify design criteria to maximize guide RNA efficacy. Doench et al. (Nat Biotechnol. 2014 December; 32(12): 1262-1267 and Nat Biotechnol. PubMed PMID: 26780180) describe the development of a quantitative model to optimize sgRNA activity prediction, and a tool to use this model for sgRNA design. Accordingly, in particular embodiments, the methods provided herein comprise identifying an optimal guide sequence based on a statistical comparison of active guide RNAs, such as described by Doench et al. (above). In particular embodiments, at least five gRNAs are designed per target and these are tested empirically in cells to generate at least one which has sufficiently high activity.

Identification of a Suitable Guide Sequence

Currently RNA guides are designed using the reference human genome; however, failing to take into account variation in the human population may confound the therapeutic outcome for a given RNA guide. The recently released ExAC dataset, based on 60,706 individuals, contains on average one variant per eight nucleotides in the human exome (Lek, M. et al. Analysis of protein-coding genetic variation in 60,706 humans. Nature 536, 285-291 (2016)). This highlights the potential for genetic variation to impact the efficacy of certain RNA guides across patient populations for CRISPR-based gene therapy, due to the presence of mismatches between the RNA guide and variants present in the target site of specific patients. To assess this impact, Applicants use the ExAC dataset to catalog variants present in all possible targets in the human reference exome that either (i) disrupt the target PAM sequence or (ii) introduce mismatches between the RNA guide and the genomic DNA, which can collectively be termed target variation (FIG. 1*a*). For treatment of a patient population, avoiding target variation for RNA guides administered to individual patients will maximize the consistency of outcomes for a genome editing therapeutic. The demonstration of the impact of target variation is illustrated in the examples section herein.

Ideally, personalized genomic medicine would tailor RNA-guided endonuclease therapeutics for each patient. However, it would likely be cost-prohibitive and infeasible from a regulatory standpoint to design an individual RNA guide for each patient receiving a genome editing therapy. The analysis of the impact of genetic variation on the efficacy and safety of RNA-guided endonucleases motivates the following framework to streamline the design and testing of genome editing therapeutics (FIG. 4*d*). First, use of RNA guides for platinum targets would ensure perfect targeting for 99.99% of patients. Second, these RNA guides need to be further selected to minimize the number of off-target candidates occurring on high frequency haplotypes in the patient population. Third, low frequency variation captured in large scale sequencing datasets can be used to estimate the number of guide RNA-enzyme combinations required to effectively and safely treat different sizes of patient populations. Growth of large scale sequencing datasets will improve the accuracy of these estimates. Fourth, pre-therapeutic whole genome sequencing of individual patients will be needed to select a single approved guide RNA-enzyme combination for treatment. This combination should be a perfect match to the patient's genome and be free of patient-specific off-target candidates. This framework, in combination with rapidly accumulating human sequencing data, which will further refine these selection criteria, will enable the design and validation of genome editing therapeutics minimizing both the number of guide RNA-enzyme combinations necessary for approval and the cost of delivering effective and safe gene therapies to patients.

Accordingly, in particular embodiments, the methods provided herein comprise one or more of the following steps: (1) identifying platinum targets, (2) selection of the guides to minimize the number of off-target candidates occurring on high frequency haplotypes in the patient population; (3) select guide (and/or effector protein) based low frequency variation captured in large scale sequencing datasets to estimate the number of guide RNA-enzyme combinations required to effectively and safely treat different sizes of patient populations, and (4) confirm or select guide based on pre-therapeutic whole genome sequencing of individual patient. In particular embodiments, a "platinum" target is one that does not contain variants occurring at ≥0.01% allele frequency.

Methods for Determining on/Off-Target Activity and Selecting Suitable Target Sequences/Guides In certain example embodiments, parameters such as, but not limited to, off-target candidates, PAM restrictiveness, target cleavage efficiency, or effector protein specific may be determined using sequencing-based double-strand break (DSB) detection assays. Example sequencing-based DSB detection assay sChIP-seq (Szilard et al. Nat. Struct. Mol. Biol. 18, 299-305 (2010); Iacovoni et al. EMBO J. 29, 1446-1457 (2010)), BLESS (Crosetto et al. Nat. Methods 10, 361-365 (2013); Ran et al. Nature 520, 186-191 (2015); Slaymaker et al. Science 351, 84-88 (2016)), GUIDEseq (Tsai et al. Nat. Biotech 33, 187-197 (2015)), Digenome-seq (Kim et al. Nat. Methods 12, 237-43 (2015)), IDLV-mediated DNA break capture (Wang et al. Nat. Biotechnol. 33, 179-186 (2015), HTGTS (Frock et al. Nat. Biotechnol. 33, 179-186 (2015)), End-Seq (Canela et al. Mol. Cell 63, 898-911 (2016), and DSBCapture (Lensing et al. Nat. Methods 13, 855-857 (2016). Additional methods that may be used to assess target cleavage efficiency include SITE-Seq (Cameron et al. Nature Methods, 14, 600-606 (2017), and CIRCLE-seq (Tsai et al. Nature Methods 14, 607-614 (2017)).

Methods useful for assessing Cpf1 Rnase activity include those disclosed in Zhong et al. Nature Chemical Biology Jun. 19, 2017 doi: 10.1038/NCHEMBIO.2410 and may be similarly applied to Cas (e.g. Cas9 and/or Cas12). Increased Rnase activity and the ability to excise multiple CRISPR RNAs (crRNA) from a single RNA polymerase II-driven RNA transcript can simplify modification of multiple genomic targets and can be used to increase the efficiency of Cas (e.g. Cas9 and/or Cas12)-mediated editing.

BLISS

Other suitable assays include those described in Yan et al. ("BLISS: quantitative and versatile genome-wide profiling of DNA breaks in situ" BioRxiv, Dec. 4, 2016 doi: http://dx.doi.org/10.1101/091629) describe a versatile, sensitive and quantitative method for detecting DSBs applicable to low-input specimens of both cells and tissues that is scalable for high-throughput DSB mapping in multiple samples. Breaks Labeling In Situ and Sequencing (BLISS), features efficient in situ DSB labeling in fixed cells or tissue sections immobilized onto a solid surface, linear amplification of tagged DSBs via T7-mediated in vitro transcription (IVT) for greater sensitivity, and accurate DSB quantification by incorporation of unique molecular identifiers (UMIs).

Curtain

A further method, referred to herein as "Curtain" has been developed which may also be useful in assessing certain parameters disclosed herein, the method allowing on target and off target cutting of a nuclease to be assessed in a direct and unbiased way using in vitro cutting of immobilized nucleic acid molecules. Further reference is made to U.S. Provisional 62/351,744 entitled "Unbiased Detection of Nucleic Acid Modifications" filed on Jun. 17, 2016 and U.S. Provisional No. 62/377,525 entitled "Unbiased Detection of Nucleic Acid Modifications" filed on Aug. 19, 2016.

This method may also be used to select a suitable guide RNA. The method allows the detection of a nucleic acid modification, by performing the following steps: i) contacting one or more nucleic acid molecules immobilized on a solid support (immobilized nucleic acid molecules) with an agent capable of inducing a nucleic acid modification; and ii) sequencing at least part of said one or more immobilized nucleic acid molecules that comprises the nucleic acid modification using a primer specifically binding to a primer binding site. This method further allows the selection of a guide RNA from a plurality of guide RNAs specific for a selected target sequence. In particular embodiments, the method comprises contacting a plurality of nucleic acid molecules immobilized on a solid support (immobilized nucleic acid molecules) with a plurality of RNA-guided nuclease complexes capable of inducing a nucleic acid break, said plurality of RNA-guided nuclease complexes comprising a plurality of different guide RNA's, thereby inducing one or more nucleic acid breaks; attaching an adapter comprising a primer binding site to said one or more immobilized nucleic acid molecules comprising a nucleic acid break; sequencing at least part of said one or more immobilized nucleic acid molecules comprising a nucleic acid break using a primer specifically binding to said primer binding site; and selecting a guide RNA based on location and/or amount of said one or more breaks.

In particular embodiments, the method comprises determining one or more locations in said one or more immobilized nucleic acid molecules comprising a break other than a location comprising said selected target sequence (off-target breaks) and selecting a guide RNA based on said one or more locations. In particular embodiments, step v comprises determining a number of sites in said one or more immobilized nucleic acid molecules comprising off-target breaks and selecting a guide RNA based on said number of sites. In a further embodiment, step iv comprises both determining the location of off-targets breaks and the number of locations of off-target breaks.

Safety

Select Protein with Shortest Half-Life

Inherent Half-Life of the Effector Protein

The extended presence of an effector protein after having performed its function at the target site is a potential safety concern, both for off-target effects and direct toxicity of the effector protein. It has been reported that upon direct delivery to the cell by LNP, CRISPR effector proteins degrade rapidly within the cell (Kim et al. Genome Res. 2014 June; 24(6): 1012-1019). Where the effector protein is to be expressed from a plasmid, strategies to actively reduce the half-life of the protein may be of interest.

Use of Destabilized Domains

In certain embodiments, the methods provided herein involve the use of a Cas (e.g. Cas9 and/or Cas12) effector protein which is associated with or fused to a destabilization domain (DD). The technology relating to the use of destabilizing domains is described in detail in WO2016/106244, which is incorporated by reference herein.

Destabilizing domains (DD) are domains which can confer instability to a wide range of proteins; see, e.g., Miyazaki, J Am Chem Soc. Mar. 7, 2012; 134(9): 3942-3945, and Chung H Nature Chemical Biology Vol. 11 Sep. 2015 pgs 713-720, incorporated herein by reference. DD can be associated with, e.g., fused to, advantageously with a linker, to a CRISPR enzyme, whereby the DD can be stabilized in the presence of a ligand and when there is the absence thereof the DD can become destabilized, whereby the CRISPR enzyme is entirely destabilized, or the DD can be stabilized in the absence of a ligand and when the ligand is present the DD can become destabilized; the DD allows the Cas (e.g. Cas9 and/or Cas12) effector to be regulated or controlled, thereby providing means for regulation or control of the system. For instance, when a protein of interest is expressed as a fusion with the DD tag, it is destabilized and rapidly degraded in the cell, e.g., by proteasomes. Thus, absence of stabilizing ligand leads to a DD-associated Cas (e.g. Cas9 and/or Cas12) being degraded. Peak activity of the Cas (e.g. Cas9 and/or Cas12) effector is relevant to reduce off-target effects and for the general safety of the system. Advantages of the DD system include that it can be dosable, orthogonal (e.g., a ligand only affects its cognate DD so two or more systems can operate independently), transportable (e.g., may work in different cell types or cell lines) and allows for temporal control.

Suitable DD—stabilizing ligand pairs are known in the art and also described in WO2016/106244. The size of Destabilization Domain varies but is typically 323 annito.-323annito. 100-300 amino acids in size. Suitable examples include ER50 and/or DHFR50. A corresponding stabilizing ligand for ER50 is, for example, 4HT or CMP8. In some embodiments, one or two DDs may be fused to the N-terminal end of the CRISPR enzyme with one or two DDs fused to the C-terminal of the CRISPR enzyme. While the DD can be provided directly at N and/or C terminal(s) of the Cas (e.g. Cas9 and/or Cas12) effector protein, they can also be fused via a linker, such as a GlySer linker, or an NLS and/or NES. A commercially available DD system is the CloneTech, ProteoTuner™ system; the stabilizing ligand is Shield1. In some embodiments, the stabilizing ligand is a 'small molecule', preferably it is cell-permeable and has a high affinity for its corresponding DD.

In some embodiments, the CRISPR enzyme is fused to Destabilization Domain (DD). In other words, the DD may be associated with the CRISPR enzyme by fusion with said CRISPR enzyme. The AAV can then, by way of nucleic acid molecule(s) deliver the stabilizing ligand (or such can be otherwise delivered) In some embodiments, the enzyme may be considered to be a modified CRISPR enzyme, wherein the CRISPR enzyme is fused to at least one destabilization domain (DD) and VP2.

Select Least Immunogenic RNP

When administering an agent to a mammal, there is always the risk of an immune response to the agent and/or its delivery vehicle. Circumventing the immune response is a major challenge for most delivery vehicles. Viral vectors, which express immunogenic epitopes within the organism typically induce an immune response. Nanoparticle and lipid-based vectors to some extent address this problem. Yin et al. demonstrate a therapeutic approach combining viral delivery of the guide RNA with lipid nanoparticle-mediated delivery of the CRISPR effector protein (Nature Biotechnology 34:328-33(2016)). Ziris et al. describes cationin-lipid mediated delivery of Cas9:guideRNA nuclease complexes to cells, which can be applied to the Cas CRISPR systems described herein. The CRISPR-Cas (e.g. Cas9 and/or Cas12) effector proteins, which can also of bacterial origin, also inherently carry the risk of eliciting an immune response. This may be addressed by humanizing the Cas (e.g. Cas9 and/or Cas12)effector protein.

Introduce Modifications in Guide RNA to Minimize Immunogenicity

Chemical modifications of RNAs have been used to avoid reactions of the innate immune system. Judge et al. (2006) demonstrated that immune stimulation by synthetic siRNA can be completely abrogated by selective incorporation of 2'-O-methyl (2'Ome) uridine or guanosine nucleosides into one strand of the siRNA duplex (Mol. Ther., 13 (2006), pp. 494-505). Cekaite et al. (J. Mol. Biol., 365 (2007), pp. 90-108) observed that replacement of only uridine bases of siRNA with either 2'-fluoro or 2'-O-methyl modified counterparts abrogated upregulation of genes involved in the regulation of the immune response. Similarly, Hendel et al. tested sgRNAs with both backbone and sugar modifications that confer nuclease stability and can reduce immunostimulatory effects (Hendel et al., Nat. Biotechnol., 33 (2015), pp. 985-989).

Accordingly, in particular embodiments, the methods comprise modifying the guide RNA so as to minimize immunogenicity using one or more of these methods.

Identify Optimal Dosage to Minimize Toxicity and Maximize Specificity

It is generally accepted that the dosage of CRISPR components will be relevant to toxicity and specificity of the system (Pattanayak et al. Nat Biotechnol. 2013 September; 31(9): 839-843). Hsu et al. (Nat Biotechnol. 2013 September; 31(9): 827-832) demonstrated that the dosage of SpCas9 and sgRNA can be titrated to address these issues and can be applied and/or adapted for the CRISPR-Cas systems described herein. In certain example embodiments, toxicity is minimized by saturating complex with guide by either pre-forming complex, putting guide under control of a strong promoter, or via timing of delivery to ensure saturating conditions available during expression of the effector protein.

Identifying Appropriate Delivery Method

To increase safety, the delivery method and/or vehicle can be optimized. Delivery methods, including but not limited to, polynucleotides, vectors, virus particles, particles etc. are described in greater detail herein. Further, advantages of various delivery compositions, formulations and techniques, with respect to e.g. safety are also discussed elsewhere herein. In some embodiments, multiple delivery techniques can be mixed and utilized to achieve the appropriate effect. Further, administration route can be altered to increase safety. Various administration routes are described elsewhere herein. Delivery timing and regimen can also be modified to increase safety of the CRISPR-Cas systems described herein. Various exemplary and non-limiting delivery regimens are described elsewhere herein. One of ordinary skill in the art will appreciate appropriate delivery compositions and approaches for specific embodiments of the CRISPR-Cas system and methods of using the CRISPR-Cas system in view of this disclosure.

Formulations

In embodiments, the rationally designed CRISPR-Cas therapy, therapeutic or a component thereof can be included in a formulation, such as a pharmaceutical formulation, that can be administered to a subject. In some embodiments, a CRISPR-Cas system or component there of that has not been previously identified as having or not having a DNA-damage response signature (i.e. has not yet been rationally designed or developed using one of the methods described herein) can be used to introduce a modification into a cell as previously described. These CRISPR-Cas system molecules can be delivered as a formulation. It will be appreciated that any other suitable molecule described elsewhere herein (polynucleotide, vector, protein, etc.) can be contained in a formulation, such as a pharmaceutical formulation, that can be delivered to a subject or a cell thereof.

In some embodiments, the amount of the one or more of the polypeptides, polynucleotides, CRISPR-Cas complexes, vectors, cells, virus particles, nanoparticles, other delivery particles, and combinations thereof described herein contained in the pharmaceutical formulation can range from about 1 pg/kg to about 10 mg/kg based upon the bodyweight of the subject in need thereof or average bodyweight of the specific patient population to which the pharmaceutical formulation can be administered. The amount of the one or more of the polypeptides, polynucleotides, vectors, cells, and combinations thereof described herein in the pharmaceutical formulation can range from about 1 pg to about 10 g, from about 10 nL to about 10 ml. In embodiments where the pharmaceutical formulation contains one or more cells, the amount can range from about 1 cell to 1×102, 1×103, 1×104, 1×105, 1×106, 1×107, 1×108, 1×109, 1×1010 or more cells. In embodiments where the pharmaceutical formulation contains one or more cells, the amount can range from about 1 cell to 1×102, 1×103, 1×104, 1×105, 1×106, 1×107, 1×108, 1×109, 1×1010 or more cells per nL, μL, mL, or L.

Also provided is a pharmaceutical composition comprising the CRISPR enzyme which is part of or tethered to a VP2 domain of Adeno-Associated Virus (AAV) capsid; or the non-naturally occurring modified AAV; or a polynucleotide encoding them.

In embodiments, the nucleic acid component (e.g. gRNA, modified gRNA, sgRNA, modified sgRNA, the inactivated AAV-CRISPR enzyme (with or without functional domains), and the binding protein with one or more functional domains, may each individually be comprised in a composition or pharmaceutical formulation as described herein and administered to a host individually or collectively. Alternatively, these components may be provided in a single composition for administration to a host, e.g., the AAV-CRISPR enzyme can deliver the RNA or guide or sgRNA or modified sgRNA and/or other components of the CRISPR system. Administration to a host may be performed via viral vectors, advantageously using the AAV-CRISPR enzyme as the delivery vehicle, although other vehicles can be used to deliver components other than the enzyme of the CRISPR system, and such viral vectors can be, for example, lentiviral vector, adenoviral vector, AAV vector. Several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes as described elsewhere herein).

Pharmaceutically Acceptable Carriers and Auxiliary Ingredients and Agents

In embodiments, the pharmaceutical formulation containing an amount of one or more of the polypeptides, polynucleotides, CRISPR-Cas complexes, vectors, cells, virus particles, nanoparticles, other delivery particles, and combinations thereof described herein can further include a pharmaceutically acceptable carrier. Suitable pharmaceutically acceptable carriers include, but are not limited to, water, salt solutions, alcohols, gum 326annit, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to an amount of one or more of the polypeptides, polynucleotides, CRISPR-Cas complexes, vectors, cells, virus particles, nanoparticles, other delivery particles, and combinations thereof described herein, the pharmaceutical formulation can also include an effective amount of an auxiliary active agent, including but not limited to, polynucleotides, amino acids, peptides, polypeptides, antibodies, aptamers, ribozymes, hormones, immunomodulators, antipyretics, anxiolytics, antipsychotics, analgesics, antispasmodics, anti-inflammatories, anti-histamines, anti-infectives, chemotherapeutics, and combinations thereof.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eicosanoids (e.g. arachidonic acid, lipoxins, and prostaglandins), and steroid hormones (e.g. estradiol, testosterone, tetrahydro 327 annitol 327 ne 327 Cortisol). Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-a, IFN-β, IFN-ε, IFN-K, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium 327 annitol 327 n, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepressants, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, 328 annitol 328 ne, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzapine, paliperidone, perospirone, quetiapine, remoxipride, risperidone, sertindole, trimipramine, ziprasidone, zotepine, alstonie, 328annito1328n, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, nonsteroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene. Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, H1-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, 328annito1328, mirtazapine, olopatadine, orphenadrine, phenindamine, pheniramine, phenyltoloxamine, promethazine, pyrilamine, quetiapine, rupatadine, tripelennamine, and triprolidine), H2-receptor antagonists (e.g. cimetidine, famotidine, lafutidine, nizatidine, rafitidine, and roxatidine), tritoqualine, catechin, cromoglicate, nedocromil, and p2-adrenergic agonists.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, thiabendazole, oxamniquine), antifungals (e.g. azole antifungals (e.g. itraconazole, fluconazole, 329annito1329ne329, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antiviral s (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, 330 annitol 330 ne 330, azithromycin, clarithromycin, dirithromycin, and troleandomycin), linezolid, sulfamethoxazole/trimethoprim, rifaximin, chloramphenicol, 330 annitol 330 n, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, 330 annitol 330 ne 330, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, 330annito1330n, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, Cytoxan, cyclophosphamide, decitabine, dexamethasone, docetaxel, hydroxyurea, 330 annitol 330 ne, leuprolide, epirubicin, oxaliplatin, asparaginase, estramustine, cetuximab, vismodegib, asparginase *Erwinia chrysanthemi*, amifostine, etoposide, flutamide, toremifene, fulvestrant, letrozole, degarelix, pralatrexate, methotrexate, floxuridine, 330 annitol 330 ne 330, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, predni sone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, 331 annito trioxide, lapatinib, valrubicin, panitumumab, vinblastine, bortezomib, tretinoin, 331annitol331ne, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

In embodiments where there is an auxiliary active agent contained in the pharmaceutical formulation in addition to the one or more of the polypeptides, polynucleotides, CRISPR-Cas complexes, vectors, cells, virus particles, nanoparticles, other delivery particles, and combinations thereof described herein, amount, such as an effective amount, of the auxiliary active agent will vary depending on the auxiliary active agent. In some embodiments, the amount of the auxiliary active agent ranges from 0.001 micrograms to about 1 milligram. In other embodiments, the amount of the auxiliary active agent ranges from about 0.01 IU to about 1000 IU. In further embodiments, the amount of the auxiliary active agent ranges from 0.001 mL to about 1 mL. In yet other embodiments, the amount of the auxiliary active agent ranges from about 1% w/w to about 50% w/w of the total pharmaceutical formulation. In additional embodiments, the amount of the auxiliary active agent ranges from about 1% v/v to about 50% v/v of the total pharmaceutical formulation. In still other embodiments, the amount of the auxiliary active agent ranges from about 1% w/v to about 50% w/v of the total pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravitreal, intracerebral, gingival, subgingival, intracerebroventricular, and intradermal. Such formulations may be prepared by any method known in the art.

Dosage forms adapted for oral administration can be discrete dosage units such as capsules, pellets or tablets, powders or granules, solutions, or suspensions in aqueous or nonaqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of the targeted effector fusion protein and/or complex thereof or composition containing the one or more of the polypeptides, polynucleotides, vectors, cells, and combinations thereof described herein. The oral dosage form can be administered to a subject in need thereof.

Where appropriate, the dosage forms described herein can be microencapsulated.

The dosage form can also be prepared to prolong or sustain the release of any ingredient. In some embodiments, the one or more of the polypeptides, polynucleotides, vectors, cells, and combinations thereof described herein can be the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", $20^{th}$ ed., Lippincott Williams & Wilkins, Baltimore, MD, 2000, and "Pharmaceutical dosage forms and drug delivery systems", $6^{th}$ Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water-soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the one or more of the polypeptides, polynucleotides, vectors, cells, and combinations thereof described herein can be formulated with a paraffinic or water-miscible ointment base. In some embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the one or more of the polypeptides, polynucleotides, vectors, cells, and combinations thereof described herein is contained in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient (e.g. the one or more of the polypeptides, polynucleotides, vectors, cells, and combinations thereof described herein and/or auxiliary active agent), which may be generated by various types of metered dose pressurized aerosols, nebulizers, or insufflators.

In some embodiments, the dosage forms can be aerosol formulations suitable for administration by inhalation. In some of these embodiments, the aerosol formulation can contain a solution or fine suspension of the one or more of the polypeptides, polynucleotides, vectors, cells, and combinations thereof described herein and a pharmaceutically acceptable aqueous or nonaqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of one or more of the polypeptides, polynucleotides, vectors, cells, and combinations thereof described herein. In further embodiments, the aerosol formulation can also contain co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulation. In addition to the one or more of the polypeptides, polynucleotides, vectors, cells, and combinations thereof described herein, an auxiliary active ingredient, and/or pharmaceutically acceptable salt thereof, such a dosage form can contain a powder base such as lactose, glucose, trehalose, 334annitol, and/or starch. In some of these embodiments, the one or more of the polypeptides, polynucleotides, vectors, cells, and combinations thereof described herein is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol dosage forms can be arranged so that each metered dose of aerosol contains a predetermined amount of an active ingredient, such as the one or more of the one or more of the polypeptides, polynucleotides, vectors, cells, and combinations thereof described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraperitoneal, subcutaneous, intramuscular, intradermal, intraosseous, epidural, intracardiac, intraarticular, intracavernous, gingival, subginigival, intrathecal, intravireal, intracerebral, and intracerebroventricular) can include aqueous and/or nonaqueous sterile injection solutions, which can contain anti-oxidants, buffers, bacteriostats, solutes that render the composition isotonic with the blood of the subject, and aqueous and nonaqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or nonaqueous sterile solutions that can optionally be adapted for injection, and which can optionally contain anti-oxidants, buffers, bacteriostats, solutes that render the composition isotonic with the eye or fluid contained therein or around the eye of the subject, and aqueous and nonaqueous sterile suspensions, which can include suspending agents and thickening agents.

For some embodiments, the dosage form contains a predetermined amount of the one or more of the polypeptides, polynucleotides, vectors, cells, and combinations thereof described herein per unit dose. In some embodiments, the predetermined amount of the Such unit doses may therefore be administered once or more than once a day. Such pharmaceutical formulations may be prepared by any of the methods well known in the art.

Kits

Also described herein are kits that that contain one or more of the one or more of the polypeptides, polynucleotides, vectors, cells, or other components described herein and combinations thereof and pharmaceutical formulations described herein. In some embodiments, the kit can contain one or more CRISPR-Cas based therapies or therapeutics that are developed and/or designed using embodiments of the methods of rationally designing and/or developing a CRISPR=Cas based therapy or therapeutic or CRISPR-Cas system or component thereof described elsewhere herein. In some embodiments, the kit can contain one or more rationally designed CRISPR-Cas systems or components thereof, where the CRISPR-Cas system(s) or component(s) thereof do not induce a DNA-damage response signature when introduced into a cell. In some embodiments, the kit can contain one or more CRISPR-Cas modified cells, where the cells do not express a DNA-damage response signature.

In other embodiments, the kit can contain one or more reagents, polynucleotides, vectors, CRISPR-Cas systems, and the like necessary to perform one or more embodiments of a method or rationally designing and/or developing a CRISPR-Cas based therapy or therapeutic described elsewhere herein.

In embodiments, one or more of the polypeptides, polynucleotides, vectors, cells, and combinations thereof described herein can be presented as a combination kit. As used herein, the terms "combination kit" or "kit of parts" refers to the compounds, or formulations and additional components that are used to package, screen, test, sell, market, deliver, and/or administer the combination of elements or a single element, such as the active ingredient, contained therein. Such additional components include but are not limited to, packaging, syringes, blister packages, bottles, and the like. The combination kit can contain one or more of the components (e.g. one or more of the one or more of the polypeptides, polynucleotides, vectors, cells, and combinations thereof) or formulation thereof can be provided in a single formulation (e.g. a liquid, lyophilized powder, etc.), or in separate formulations. The separate components or formulations can be contained in a single package or in separate packages within the kit. The kit can also include instructions in a tangible medium of expression that can contain information and/or directions regarding the content of the components and/or formulations contained therein, safety information regarding the content of the components(s) and/or formulation(s) contained therein, information regarding the amounts, dosages, indications for use, screening methods, component design recommendations and/or information, recommended treatment regimen(s) for the components(s) and/or formulations contained therein. As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory drive or CD-ROM or on a server that can be accessed by a user via, e.g. a web interface.

In one embodiment, the invention provides a kit comprising one or more of the components described herein. In some embodiments, the kit comprises a vector system and instructions for using the kit. In some embodiments, the vector system comprises (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) said AAV-CRISPR enzyme optionally comprising a nuclear localization sequence. In some embodiments, the kit comprises components (a) and (b) located on or in the same or different vectors of the system, e.g., (a) can be contained in (b). In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas (e.g. Cas9 and/or Cas12) enzyme. In some embodiments, the Cas (e.g. Cas9 and/or Cas12) enzyme is derived from *S. pneumoniae, S. pyogenes, S. thermophilus, F. novicida* or *S. aureus* Cas9 (e.g., modified to have or be associated with at least one AAV), and may include further alteration or mutation of the Cas9, and can be a chimeric Cas9. In some embodiments, the coding for the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length.

Methods of CRISPR-Cas System Delivery

Any of the polynucleotides, vectors, polypeptides, CRISPR-Cas Systems or components thereof, rationally designed CRISPR-based therapeutic or therapy can be delivered to a subject, which can include a cell or cell population. Various delivery compositions and techniques are now discussed. Herein, where a CRISPR-Cas system is discussed, this would include both rationally designed (i.e. those developed and/or designed through a method that screens based on the DNA-damage based signature described herein) and non-rationally designed (i.e. those not developed or designed through a method that screens based on the DNA-damage based signature described herein) CRISPR-Cas systems and components thereof. Through this disclosure and the knowledge in the art, CRISPR-Cas systems, or components thereof or nucleic acid molecules thereof (including, for instance HDR template) or nucleic acid molecules encoding or providing components thereof may be delivered by a delivery system herein described both generally and in detail.

The present disclosure also provides delivery systems for introducing components of the systems and compositions herein to cells, tissues, organs, or organisms. A delivery system may comprise one or more delivery vehicles and/or cargos. Exemplary delivery systems and methods include those described in paragraphs [00117] to [00278] of Feng Zhang et al., (WO2016106236A1), and pages 1241-1251 and Table 1 of Lino C A et al., Delivering CRISPR: a review of the challenges and approaches, DRUG DELIVERY, 2018, VOL. 25, NO. 1, 1234-1257, which are incorporated by reference herein in their entireties.

In some embodiments, the delivery systems may be used to introduce the components of the systems and compositions to plant cells. For example, the components may be delivered to plant using electroporation, microinjection, aerosol beam injection of plant cell protoplasts, biolistic methods, DNA particle bombardment, and/or *Agrobacterium*-mediated transformation. Examples of methods and delivery systems for plants include those described in Fu et al., Transgenic Res. 2000 February; 9(1):11-9; Klein R M, et al., Biotechnology. 1992; 24:384-6; Casas A M et al., Proc Natl Acad Sci USA. 1993 Dec. 1; 90(23): 11212-11216; and U.S. Pat. No. 5,563,055, Davey M R et al., Plant Mol Biol. 1989 September; 13(3):273-85, which are incorporated by reference herein in their entireties.

Cargos

The delivery systems may comprise one or more cargos. The cargos may comprise one or more components of the CRISPR-Cas systems and compositions herein. A cargo may comprise one or more of the following: i) a vector or vector system (viral or non-viral) encoding one or more Cas proteins; ii) a vector or vector system (viral or non-viral) encoding one or more guide RNAs described herein, iii) mRNA of one or more Cas proteins; iv) one or more guide RNAs; v) one or more Cas proteins; vi) one or more polynucleotides encoding one or more Cas proteins; vii) one or more polynucleotides encoding one or more guide RNAs, or viii) any combination thereof. In some examples, a cargo may comprise a plasmid encoding one or more Cas protein and one or more (e.g., a plurality of) guide RNAs. In some embodiments, a cargo may comprise mRNA encoding one or more Cas proteins and one or more guide RNA.

In some embodiments, a cargo may comprise one or more Cas proteins described herein and one or more guide RNAs, e.g., in the form of ribonucleoprotein complexes (RNP). The ribonucleoprotein complexes may be delivered by methods and systems herein. In some cases, the ribonucleoprotein may be delivered by way of a polypeptide-based shuttle agent. In one example, the ribonucleoprotein may be delivered using synthetic peptides comprising an endosome leakage domain (ELD) operably linked to a cell penetrating domain (CPD), to a histidine-rich domain and a CPD, e.g., as describe in WO2016161516. RNP may also be used for delivering the compositions and systems to plant cells, e.g., as described in Wu J W, et al., Nat Biotechnol. 2015 November; 33(11):1162-4.

In some embodiments, the cargo(s) can be any of the polynucleotide(s), e.g. CRISPR-Cas System polynucleotides described herein.

Physical Delivery

In some embodiments, the cargos may be introduced to cells by physical delivery methods. Examples of physical methods include microinjection, electroporation, and hydrodynamic delivery. Both nucleic acid and proteins may be delivered using such methods. For example, Cas protein may be prepared in vitro, isolated, (refolded, purified if needed), and introduced to cells.

Microinjection

Microinjection of the cargo directly to cells can achieve high efficiency, e.g., above 90% or about 100%. In some embodiments, microinjection may be performed using a microscope and a needle (e.g., with 0.5-5.0 μm in diameter) to pierce a cell membrane and deliver the cargo directly to a target site within the cell. Microinjection may be used for in vitro and ex vivo delivery.

Plasmids comprising coding sequences for Cas proteins and/or guide RNAs, mRNAs, and/or guide RNAs, may be microinjected. In some cases, microinjection may be used i) to deliver DNA directly to a cell nucleus, and/or ii) to deliver mRNA (e.g., in vitro transcribed) to a cell nucleus or cytoplasm. In certain examples, microinjection may be used to delivery sgRNA directly to the nucleus and Cas-encoding mRNA to the cytoplasm, e.g., facilitating translation and shuttling of Cas to the nucleus.

Microinjection may be used to generate genetically modified animals. For example, gene editing cargos may be injected into zygotes to allow for efficient germline modification. Such approach can yield normal embryos and full-term mouse pups harboring the desired modification(s). Microinjection can also be used to provide transiently up- or down-regulate a specific gene within the genome of a cell, e.g., using CRISPRa and CRISPRi.

Electroporation

In some embodiments, the cargos and/or delivery vehicles may be delivered by electroporation. Electroporation may use pulsed high-voltage electrical currents to transiently open nanometer-sized pores within the cellular membrane of cells suspended in buffer, allowing for components with hydrodynamic diameters of tens of nanometers to flow into the cell. In some cases, electroporation may be used on various cell types and efficiently transfer cargo into cells. Electroporation may be used for in vitro and ex vivo delivery.

Electroporation may also be used to deliver the cargo to into the nuclei of mammalian cells by applying specific voltage and reagents, e.g., by nucleofection. Such approaches include those described in Wu Y, et al. (2015). Cell Res 25:67-79; Ye L, et al. (2014). Proc Natl Acad Sci USA 111:9591-6; Choi P S, Meyerson M. (2014). Nat Commun 5:3728; Wang J, Quake S R. (2014). Proc Natl Acad Sci 111:13157-62. Electroporation may also be used to deliver the cargo in vivo, e.g., with methods described in Zuckermann M, et al. (2015). Nat Commun 6:7391.

Hydrodynamic Delivery

Hydrodynamic delivery may also be used for delivering the cargos, e.g., for in vivo delivery. In some examples, hydrodynamic delivery may be performed by rapidly pushing a large volume (8-10% body weight) solution containing the gene editing cargo into the bloodstream of a subject (e.g., an animal or human), e.g., for mice, via the tail vein. As blood is incompressible, the large bolus of liquid may result in an increase in hydrodynamic pressure that temporarily enhances permeability into endothelial and parenchymal cells, allowing for cargo not normally capable of crossing a cellular membrane to pass into cells. This approach may be used for delivering naked DNA plasmids and proteins. The delivered cargos may be enriched in liver, kidney, lung, muscle, and/or heart.

Transfection

The cargos, e.g., nucleic acids and/or polypeptides, may be introduced to cells by transfection methods for introducing nucleic acids into cells. Examples of transfection methods include calcium phosphate-mediated transfection, cationic transfection, liposome transfection, dendrimer transfection, heat shock transfection, magnetofection, lipofection, impalefection, optical transfection, proprietary agent-enhanced uptake of nucleic acid.

Transduction

The cargos, e.g. nucleic acids and/or polypeptides, can be introduced to cells by transduction by a viral or pseudoviral particle. Methods of packaging the cargos in viral particles can be accomplished using any suitable viral vector or vector systems. Such viral vector and vector systems are described in greater detail elsewhere herein. As used in this context herein "transduction" refers to the process by which foreign nucleic acids and/or proteins are introduced to a cell (prokaryote or eukaryote) by a viral or pseudo viral particle. After packaging in a viral particle or pseudo viral particle, the viral particles can be exposed to cells (e.g. in vitro, ex vivo, or in vivo) where the viral or pseudoviral particle infects the cell and delivers the cargo to the cell via transduction. Viral and pseudoviral particles can be optionally concentrated prior to exposure to target cells. In some embodiments, the virus titer of a composition containing viral and/or pseudoviral particles can be obtained and a specific titer be used to transduce cells.

Biolistics

The cargos, e.g. nucleic acids and/or polypeptides, can be introduced to cells using a biolistic method or technique. The term of art "biolistic", as used herein refers to the delivery of nucleic acids to cells by high-speed particle bombardment. In some embodiments, the cargo(s) can be attached, associated with, or otherwise coupled to particles, which than can be delivered to the cell via a gene-gun (see e.g., Liang et al. 2018. Nat. Protocol. 13:413-430; Svitashev et al. 2016. Nat. Comm. 7:13274; Ortega-Escalante et al., 2019. Plant. J. 97:661-672). In some embodiments, the particles can be gold, tungsten, palladium, rhodium, platinum, or iridium particles.

Implantable Devices

In some embodiments, the delivery system can include an implantable device that incorporates or is coated with a CRISPR-Cas system or component thereof described herein. Various implantable devices are described in the art, and include any device, graft, or other composition that can be implanted into a subject.

Delivery Vehicles

The delivery systems may comprise one or more delivery vehicles. The delivery vehicles may deliver the cargo into cells, tissues, organs, or organisms (e.g., animals or plants). The cargos may be packaged, carried, or otherwise associated with the delivery vehicles. The delivery vehicles may be selected based on the types of cargo to be delivered, and/or the delivery is in vitro and/or in vivo. Examples of delivery vehicles include vectors, viruses (e.g. virus particles), non-viral vehicles, and other delivery reagents described herein.

The delivery vehicles in accordance with the present invention may a greatest dimension (e.g. diameter) of less than 100 microns (μm). In some embodiments, the delivery vehicles have a greatest dimension of less than 10 μm. In some embodiments, the delivery vehicles may have a greatest dimension of less than 2000 nanometers (nm). In some embodiments, the delivery vehicles may have a greatest dimension of less than 1000 nanometers (nm). In some embodiments, the delivery vehicles may have a greatest dimension (e.g., diameter) of less than 900 nm, less than 800 nm, less than 700 nm, less than 600 nm, less than 500 nm, less than 400 nm, less than 300 nm, less than 200 nm, less than 150 nm, or less than 100 nm, less than 50 nm. In some embodiments, the delivery vehicles may have a greatest dimension ranging between 25 nm and 200 nm.

In some embodiments, the delivery vehicles may be or comprise particles. For example, the delivery vehicle may be or comprise nanoparticles (e.g., particles with a greatest dimension (e.g., diameter) no greater than 1000 nm. The particles may be provided in different forms, e.g., as solid particles (e.g., metal such as silver, gold, iron, titanium), non-metal, lipid-based solids, polymers), suspensions of particles, or combinations thereof. Metal, dielectric, and semiconductor particles may be prepared, as well as hybrid structures (e.g., core-shell particles).

Nanoparticles may also be used to deliver the compositions and systems to plant cells, e.g., as described in WO 2008042156, US 20130185823, and WO2015089419. In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm. It will be appreciated that reference made herein to particles or nanoparticles can be interchangeable, where appropriate. Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention. Semi-solid and soft nanoparticles have been manufactured, and are within the scope of the present invention. Nanoparticles with one half hydrophilic and the other half hydrophobic are termed Janus particles and are particularly effective for stabilizing emulsions. They can self-assemble at water/oil interfaces and act as solid surfactants.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarization interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, describing particles, methods of making and using them and measurements thereof.

Vectors and Vector Systems

Also provided herein are vectors that can contain one or more of the CRISPR-Cas system polynucleotides described herein. In certain embodiments, the vector can contain one or more polynucleotides encoding one or more elements of a CRISPR-Cas system described herein. The vectors can be useful in producing bacterial, fungal, yeast, plant cells, animal cells, and transgenic animals that can express one or more components of the CRISPR-Cas system described herein. Within the scope of this disclosure are vectors containing one or more of the polynucleotide sequences described herein. One or more of the polynucleotides that are part of the CRISPR-Cas system described herein can be included in a vector or vector system. The vectors and/or vector systems can be used, for example, to express one or more of the polynucleotides in a cell, such as a producer cell, to produce CRISPR-Cas system containing virus particles described elsewhere herein. Other uses for the vectors and vector systems described herein are also within the scope of this disclosure. In general, and throughout this specification, the term "vector" refers to a tool that allows or facilitates the transfer of an entity from one environment to another. In some contexts which will be appreciated by those of ordinary skill in the art, "vector" can be a term of art to refer to a nucleic acid molecule capable of transporting another nucleic acid to which it has been linked. A vector can be a replicon, such as a plasmid, phage, or cosmid, into which another DNA segment may be inserted so as to bring about the replication of the inserted segment. Generally, a vector is capable of replication when associated with the proper control elements.

Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can be composed of a nucleic acid (e.g. a polynucleotide) of the invention in a form suitable for expression of the nucleic acid in a host cell, which means that the recombinant expression vectors include one or more regulatory elements, which can be selected on the basis of the host cells to be used for expression, that is operatively-linked to the nucleic acid sequence to be expressed. Within a recombinant expression vector, "operably linked" and "operatively-linked" are used interchangeably herein and further defined elsewhere herein. In the context of a vector, the term "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Advantageous vectors include lentiviruses and adeno-associated viruses, and types of such vectors can also be selected for targeting particular types of cells. These and other embodiments of the vectors and vector systems are described elsewhere herein.

In some embodiments, the vector can be a bicistronic vector. In some embodiments, a bicistronic vector can be used for one or more elements of the CRISPR-Cas system described herein. In some embodiments, expression of elements of the CRISPR-Cas system described herein can be driven by the CBh promoter or other ubiquitous promoter. Where the element of the CRISPR-Cas system is an RNA, its expression can be driven by a Pol III promoter, such as a U6 promoter. In some embodiments, the two are combined.

In some embodiments, a vector capable of delivering an effector protein and optionally at least one CRISPR guide RNA to a cell can be composed of or contain a minimal promoter operably linked to a polynucleotide sequence encoding the effector protein and a second minimal promoter operably linked to a polynucleotide sequence encoding at least one guide RNA, wherein the length of the vector sequence comprising the minimal promoters and polynucleotide sequences is less than 4.4 Kb. In an embodiment, the vector can be a viral vector. In certain embodiments, the viral vector is an is an adeno-associated virus (AAV) or an adenovirus vector. In another embodiment, the effector protein is a Cas protein. In a further embodiment, the CRISPR enzyme is Cas9 and/or Cas12 protein.

In some embodiments, the vector capable of delivering a lentiviral vector for an effector protein and at least one CRISPR guide RNA to a cell can be composed of or contain a promoter operably linked to a polynucleotide sequence encoding Cas and a second promoter operably linked to a polynucleotide sequence encoding at least one guide RNA, wherein the polynucleotide sequences are in reverse orientation.

In one embodiment, the invention provides a vector system comprising one or more vectors. In some embodiments, the system comprises: (a) a first regulatory element operably linked to a direct repeat sequence and one or more insertion sites for inserting one or more guide sequences up- or downstream (whichever applicable) of the direct repeat sequence, wherein when expressed, the one or more guide sequence(s) direct(s) sequence-specific binding of the CRISPR complex to the one or more target sequence(s) in a eukaryotic cell, wherein the CRISPR complex comprises a Cas enzyme complexed with the one or more guide sequence(s) that is hybridized to the one or more target sequence(s); and (b) a second regulatory element operably linked to an enzyme-coding sequence encoding said Cas enzyme, preferably comprising at least one nuclear localization sequence and/or at least one NES; wherein components (a) and (b) are located on the same or different vectors of the system. Where applicable, a tracr sequence may also be provided. In some embodiments, component (a) further comprises two or more guide sequences operably linked to the first regulatory element, wherein when expressed, each of the two or more guide sequences direct sequence specific binding of a Cas CRISPR complex to a different target sequence in a eukaryotic cell. In some embodiments, the CRISPR complex comprises one or more nuclear localization sequences and/or one or more NES of sufficient strength to drive accumulation of said Cas CRISPR complex in a detectable amount in or out of the nucleus of a eukaryotic cell. In some embodiments, the first regulatory element is a polymerase III promoter. In some embodiments, the second regulatory element is a polymerase II promoter. In some embodiments, each of the guide sequences is at least 16, 17, 18, 19, 20, 25 nucleotides, or between 16-30, or between 16-25, or between 16-20 nucleotides in length.

These and others are further detailed and described elsewhere herein.

Cell-Based Vector Amplification and Expression

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). The vectors can be viral-based or non-viral based. In some embodiments, a prokaryote is used to amplify copies of a vector and express one or more nucleic acids, such as to provide a source of one or more proteins for delivery to a host cell or host organism.

Vectors can be designed for expression of one or more elements of the CRISPR-Cas system described herein (e.g. nucleic acid transcripts, proteins, enzymes, and combinations thereof) in a suitable host cell. In some embodiments, the suitable host cell is a prokaryotic cell. Suitable host cells include, but are not limited to, bacterial cells, yeast cells, insect cells, and mammalian cells. In some embodiments, the suitable host cell is a eukaryotic cell.

In some embodiments, the suitable host cell is a suitable bacterial cell. Suitable bacterial cells include, but are not limited to bacterial cells from the bacteria of the species *Escherichia coli*. Many suitable strains of *E. coli* are known in the art for expression of vectors. These include, but are not limited to Pirl, Stb12, Stb13, Stb14, TOP10, XL1 Blue, and XL10 Gold. In some embodiments, the host cell is a suitable insect cell. Suitable insect cells include those from *Spodoptera frugiperda*. Suitable strains of *S. frugiperda* cells include, but are not limited to, Sf9 and Sf21. In some embodiments, the host cell is a suitable yeast cell. In some embodiments, the yeast cell can be from *Saccharomyces cerevisiae*. In some embodiments, the host cell is a suitable mammalian cell. Many types of mammalian cells have been developed to express vectors. Suitable mammalian cells include, but are not limited to, HEK293, Chinese Hamster Ovary Cells (CHOs), mouse myeloma cells, HeLa, U205, A549, HT1080, CAD, P19, NIH 3T3, L929, N2a, MCF-7, Y79, SO-Rb50, HepG G2, DIKX-X11, J558L, Baby hamster kidney cells (BHK), and chicken embryo fibroblasts (CEFs). Suitable host cells are discussed further in Goeddel, GENE EXPRESSION TECHNOLOGY: METHODS IN ENZYMOLOGY 185, Academic Press, San Diego, Calif. (1990).

In some embodiments, the vector can be a yeast expression vector. Examples of vectors for expression in yeast *Saccharomyces cerevisiae* include pYepSecl (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in in Yeast Protocols, 2nd edition, Xiao, W., ed. (Humana Press, New York, 2007) and Buckholz, R. G. and Gleeson, M. A. (1991) Biotechnology (NY) 9(11): 1067-72. Yeast vectors can contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2μ plasmids, yeast integrative plasmids, yeast replicative plasmids, shuttle vectors, and episomal plasmids.

In some embodiments, the vector is a baculovirus vector or expression vector and can be suitable for expression of polynucleotides and/or proteins in insect cells. In some embodiments, the suitable host cell is an insect cell. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39). rAAV (recombinant Adeno-associated viral) vectors are preferably produced in insect cells, e.g., *Spodoptera frugiperda* Sf9 insect cells, grown in serum-free suspension culture. Serum-free insect cells can be purchased from commercial vendors, e.g., Sigma Aldrich (EX-CELL 405).

In some embodiments, the vector is a mammalian expression vector. In some embodiments, the mammalian expression vector is capable of expressing one or more polynucleotides and/or polypeptides in a mammalian cell. Examples of mammalian expression vectors include, but are not limited to, pCDM8 (Seed, 1987. Nature 329: 840) and pMT2PC (Kaufman, et al., 1987. EMBO J. 6: 187-195). The mammalian expression vector can include one or more suitable regulatory elements capable of controlling expression of the one or more polynucleotides and/or proteins in the mammalian cell. For example, commonly used promoters are derived from polyoma, adenovirus 2, cytomegalovirus, simian virus 40, and others disclosed herein and known in the art. More detail on suitable regulatory elements are described elsewhere herein.

For other suitable expression vectors and vector systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740;

Queen and Baltimore, 1983. *Cell* 33: 741-748), Neuron-Specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments can utilize viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element can be operably linked to one or more elements of a CRISPR-Cas system so as to drive expression of the one or more elements of the CRISPR-Cas system described herein.

In some embodiments, the vector can be a fusion vector or fusion expression vector. In some embodiments, fusion vectors add a number of amino acids to a protein encoded therein, such as to the amino terminus, carboxy terminus, or both of a recombinant protein. Such fusion vectors can serve one or more purposes, such as: (i) to increase expression of recombinant protein; (ii) to increase the solubility of the recombinant protein; and (iii) to aid in the purification of the recombinant protein by acting as a ligand in affinity purification. In some embodiments, expression of polynucleotides (such as non-coding polynucleotides) and proteins in prokaryotes can be carried out in *Escherichia coli* with vectors containing constitutive or inducible promoters directing the expression of either fusion or non-fusion polynucleotides and/or proteins. In some embodiments, the fusion expression vector can include a proteolytic cleavage site, which can be introduced at the junction of the fusion vector backbone or other fusion moiety and the recombinant polynucleotide or protein to enable separation of the recombinant polynucleotide or protein from the fusion vector backbone or other fusion moiety subsequent to purification of the fusion polynucleotide or protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, one or more vectors driving expression of one or more elements of a CRISPR-Cas system described herein are introduced into a host cell such that expression of the elements of the engineered delivery system described herein direct formation a CRISPR-Cas complex at one or more target sites. For example, a CRISPR-Cas effector protein describe herein and a nucleic acid component (e.g., a guide polynucleotide) can each be operably linked to separate regulatory elements on separate vectors. RNA(s) of different elements of CRISPR-Cas system described herein can be delivered to an animal, plant, microorganism or cell thereof to produce an animal (e.g., a mammal, reptile, avian, etc.), plant, microorganism or cell thereof that constitutively, inducibly, or conditionally expresses different elements of the CRIPSR-Cas system described herein that incorporates one or more elements of the CRISPR-Cas system described herein or contains one or more cells that incorporates and/or expresses one or more elements of the CRISPR-Cas system described herein.

In some embodiments, two or more of the elements expressed from the same or different regulatory element(s), can be combined in a single vector, with one or more additional vectors providing any components of the system not included in the first vector. CRISPR-Cas system polynucleotides that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding one or more CRISPR-Cas system proteins, embedded within one or more intron sequences (e.g., each in a different intron, two or more in at least one intron, or all in a single intron). In some embodiments, the CRISPR-Cas system polynucleotides can be operably linked to and expressed from the same promoter.

Cell-Free Vector and Polynucleotide Expression

In some embodiments, the polynucleotide encoding one or more features of the CRISPR-Cas system can be expressed from a vector or suitable polynucleotide in a cell-free in vitro system. In other words, the polynucleotide can be transcribed and optionally translated in vitro. In vitro transcription/translation systems and appropriate vectors are generally known in the art and commercially available. Generally, in vitro transcription and in vitro translation systems replicate the processes of RNA and protein synthesis, respectively, outside of the cellular environment. Vectors and suitable polynucleotides for in vitro transcription can include T7, SP6, T3, promoter regulatory sequences that can be recognized and acted upon by an appropriate polymerase to transcribe the polynucleotide or vector.

In vitro translation can be stand-alone (e.g. translation of a purified polyribonucleotide) or linked/coupled to transcription. In some embodiments, the cell-free (or in vitro) translation system can include extracts from rabbit reticulocytes, wheat germ, and/or *E. coli*. The extracts can include various macromolecular components that are needed for translation of exogenous RNA (e.g. 70S or 80S ribosomes, tRNAs, aminoacyl-tRNA, synthetases, initiation, elongation factors, termination factors, etc.). Other components can be included or added during the translation reaction, including but not limited to, amino acids, energy sources (ATP, GTP), energy regenerating systems (creatine phosphate and creatine phosphokinase (eukaryotic systems)) (phosphoenol pyruvate and pyruvate kinase for bacterial systems), and other co-factors (Mg2+, K+, etc.). As previously mentioned, in vitro translation can be based on RNA or DNA starting material. Some translation systems can utilize an RNA template as starting material (e.g. reticulocyte lysates and wheat germ extracts). Some translation systems can utilize a DNA template as a starting material (e.g. *E coli*-based systems). In these systems transcription and translation are coupled and DNA is first transcribed into RNA, which is subsequently translated. Suitable standard and coupled cell-free translation systems are generally known in the art and are commercially available.

Vector Features

The vectors can include additional features that can confer one or more functionalities to the vector, the polynucleotide to be delivered, a virus particle produced there from, or polypeptide expressed thereof. Such features include, but are not limited to, regulatory elements, selectable markers, molecular identifiers (e.g. molecular barcodes), stabilizing elements, and the like. It will be appreciated by those skilled in the art that the design of the expression vector and additional features included can depend on such factors as the choice of the host cell to be transformed, the level of expression desired, etc.

Regulatory Elements

In certain embodiments, the polynucleotides and/or vectors thereof described herein (such as the CRISPR-Cas system polynucleotides of the present invention) can include one or more regulatory elements that can be operatively linked to the polynucleotide. The term “regulatory element” is intended to include promoters, enhancers, internal ribosomal entry sites (IRES), other expression control elements (e.g., transcription termination signals, such as polyadenylation signals and poly-U sequences) and cellular localization signals (e.g. nuclear localization signals). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter can direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the β-actin promoter, the phosphoglycerol kinase (PGK) promoter, and the EFla promoter. Also encompassed by the term “regulatory element” are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981).

In some embodiments, the regulatory sequence can be a regulatory sequence described in U.S. Pat. No. 7,776,321, U.S. Pat. Pub. No. 2011/0027239, and International Patent Publication No. WO 2011/028929, the contents of which are incorporated by reference herein in their entirety. In some embodiments, the vector can contain a minimal promoter. In some embodiments, the minimal promoter is the Mecp2 promoter, tRNA promoter, or U6. In a further embodiment, the minimal promoter is tissue specific. In some embodiments, the length of the vector polynucleotide the minimal promoters and polynucleotide sequences is less than 4.4 Kb.

To express a polynucleotide, the vector can include one or more transcriptional and/or translational initiation regulatory sequences, e.g. promoters, that direct the transcription of the gene and/or translation of the encoded protein in a cell. In some embodiments a constitutive promoter may be employed. Suitable constitutive promoters for mammalian cells are generally known in the art and include, but are not limited to SV40, CAG, CMV, EF-1α, β-actin, RSV, and PGK. Suitable constitutive promoters for bacterial cells, yeast cells, and fungal cells are generally known in the art, such as a T-7 promoter for bacterial expression and an alcohol dehydrogenase promoter for expression in yeast.

In some embodiments, the regulatory element can be a regulated promoter. “Regulated promoter” refers to promoters that direct gene expression not constitutively, but in a temporally- and/or spatially-regulated manner, and includes tissue-specific, tissue-preferred and inducible promoters. Regulated promoters include conditional promoters and inducible promoters. In some embodiments, conditional promoters can be employed to direct expression of a polynucleotide in a specific cell type, under certain environmental conditions, and/or during a specific state of development. Suitable tissue specific promoters can include, but are not limited to, liver specific promoters (e.g. APOA2, SERPIN A1 (hAAT), CYP3A4, and MIR122), pancreatic cell promoters (e.g. INS, IRS2, Pdx1, Alx3, Ppy), cardiac specific promoters (e.g. Myh6 (alpha MHC), MYL2 (MLC-2v), TNI3 (cTnl), NPPA (ANF), Slc8a1 (Ncx1)), central nervous system cell promoters (SYN1, GFAP, INA, NES, MOBP, MBP, TH, FOXA2 (HNF3 beta)), skin cell specific promoters (e.g. FLG, K14, TGM3), immune cell specific promoters, (e.g. ITGAM, CD43 promoter, CD14 promoter, CD45 promoter, CD68 promoter), urogenital cell specific promoters (e.g. Pbsn, Upk2, Sbp, Fer114), endothelial cell specific promoters (e.g. ENG), pluripotent and embryonic germ layer cell specific promoters (e.g. Oct4, NANOG, Synthetic Oct4, T brachyury, NES, SOX17, FOXA2, MIR122), and muscle cell specific promoter (e.g. Desmin). Other tissue and/or cell specific promoters are generally known in the art and are within the scope of this disclosure.

Inducible/conditional promoters can be positively inducible/conditional promoters (e.g. a promoter that activates transcription of the polynucleotide upon appropriate interaction with an activated activator, or an inducer (compound, environmental condition, or other stimulus) or a negative/conditional inducible promoter (e.g. a promoter that is repressed (e.g. bound by a repressor) until the repressor condition of the promotor is removed (e.g. inducer binds a repressor bound to the promoter stimulating release of the promoter by the repressor or removal of a chemical repressor from the promoter environment). The inducer can be a compound, environmental condition, or other stimulus. Thus, inducible/conditional promoters can be responsive to any suitable stimuli such as chemical, biological, or other molecular agents, temperature, light, and/or pH. Suitable inducible/conditional promoters include, but are not limited to, Tet-On, Tet-Off, Lac promoter, pBad, AlcA, LexA, Hsp70 promoter, Hsp90 promoter, pDawn, XVE/OlexA, GVG, and pOp/LhGR.

Where expression in a plant cell is desired, the components of the CRISPR-Cas system described herein are typically placed under control of a plant promoter, i.e. a promoter operable in plant cells. The use of different types of promoters is envisaged.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. Different promoters may direct the expression of a gene in different tissues or cell types, or at different stages of development, or in response to different environmental conditions. In particular embodiments, one or more of the CRISPR-Cas system components are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed. Examples of particular promoters for use in the CRISPR-Cas system are found in Kawamata et al., (1997) Plant Cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

Examples of promoters that are inducible and that can allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc.), or light inducible systems (Phytochrome, LOV domains, or cryptochrome)., such as a Light Inducible Transcriptional Effector (LITE) that direct changes in transcriptional activity in a sequence-specific manner. The components of a light inducible system may include one or more elements of the CRISPR-Cas system described herein, a light-responsive cytochrome heterodimer (e.g. from *Arabidopsis thaliana*), and a transcriptional activation/repression domain. In some embodiments, the vector can include one or more of the inducible DNA binding proteins provided in International Patent Publication No. WO 2014/018423 and US Patent Publication Nos., 2015/0291966, 2017/0166903, 2019/0203212, which describe e.g. embodiments of inducible DNA binding proteins and methods of use and can be adapted for use with the present invention.

In some embodiments, transient or inducible expression can be achieved by including, for example, chemical-regulated promotors, i.e. whereby the application of an exogenous chemical induces gene expression. Modulation of gene expression can also be obtained by including a chemical-repressible promoter, where application of the chemical represses gene expression. Chemical-inducible promoters include, but are not limited to, the maize 1n2-2 promoter, activated by benzene sulfonamide herbicide safeners (De Veylder et al., (1997) Plant Cell Physiol 38:568-77), the maize GST promoter (GST-11-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227:229-37; U.S. Pat. Nos. 5,814,618 and 5,789,156) can also be used herein.

In some embodiments, the polynucleotide, vector or system thereof can include one or more elements capable of translocating and/or expressing a CRISPR-Cas polynucleotide to/in a specific cell component or organelle. Such organelles can include, but are not limited to, nucleus, ribosome, endoplasmic reticulum, Golgi apparatus, chloroplast, mitochondria, vacuole, lysosome, cytoskeleton, plasma membrane, cell wall, peroxisome, centrioles, etc. Such regulatory elements can include, but are not limited to, nuclear localization signals (examples of which are described in greater detail elsewhere herein), any such as those that are annotated in the LocSigDB database (see e.g. http://genome.unmc.edu/LocSigDB/and Negi et al., 2015. Database. 2015: bav003; doi: 10.1093/database/bav003), nuclear export signals (e.g. LXXXLXXLXL and others described elsewhere herein), endoplasmic reticulum localization/retention signals (e.g. KDEL, KDXX, KKXX, KXX, and others described elsewhere herein; and see e.g. Liu et al. 2007 Mol. Biol. Cell. 18(3):1073-1082 and Gorleku et al., 2011. J. Biol. Chem. 286:39573-39584), mitochondria (see e.g. Cell Reports. 22:2818-2826, particularly at FIG. 2; Doyle et al. 2013. PLoS ONE 8, e67938; Funes et al. 2002. J. Biol. Chem. 277:6051-6058; Matouschek et al. 1997. PNAS USA 85:2091-2095; Oca-Cossio et al., 2003. 165:707-720; Waltner et al., 1996. J. Biol. Chem. 271:21226-21230; Wilcox et al., 2005. PNAS USA 102:15435-15440; Galanis et al., 1991. FEBS Lett 282:425-430, peroxisome (e.g. (S/A/C)-(K/R/H)-(L/A), SLK, (R/K)-(L/V/I)-XXXXX-(H/Q)-(L/A/F). Suitable protein targeting motifs can also be designed or identified using any suitable database or prediction tool, including but not limited to Minimotif Miner (http:minimotifminer.org, http://mitominer.mrc-mbu.cam.ac.uk/release-4.0/embodiment.do?name=Protein %20MTS), LocDB (see above), PTSs predictor ( ) TargetP-2.0 (http://www.cbs.dtu.dk/services/TargetP/), ChloroP (http://www.cbs.dtu.dk/services/ChloroP/); NetNES (http://www.cbs.dtu.dk/services/NetNES/), Predotar (https://urgi.versailles.inra.fr/predotar/), and SignalP (http://www.cbs.dtu.dk/services/SignalP/).

Selectable Markers and Tags

One or more of the CRISPR-Cas system polynucleotides can be operably linked, fused to, or otherwise modified to include a polynucleotide that encodes or is a selectable marker or tag, which can be a polynucleotide or polypeptide. In some embodiments, the polypeptide encoding a polypeptide selectable marker can be incorporated in the CRISPR-Cas system polynucleotide such that the selectable marker polypeptide, when translated, is inserted between two amino acids between the N- and C-terminus of the CRISPR-Cas system polypeptide or at the N- and/or C-terminus of the CRISPR-Cas system polypeptide. In some embodiments, the selectable marker or tag is a polynucleotide barcode or unique molecular identifier (UMI).

It will be appreciated that the polynucleotide encoding such selectable markers or tags can be incorporated into a polynucleotide encoding one or more components of the CRISPR-Cas system described herein in an appropriate manner to allow expression of the selectable marker or tag. Such techniques and methods are described elsewhere herein and will be instantly appreciated by one of ordinary skill in the art in view of this disclosure. Many such selectable markers and tags are generally known in the art and are intended to be within the scope of this disclosure.

Suitable selectable markers and tags include, but are not limited to, affinity tags, such as chitin binding protein (CBP), maltose binding protein (MBP), glutathione-S-transferase (GST), poly(His) tag; solubilization tags such as thioredoxin (TRX) and poly(NANP), MBP, and GST; chromatography tags such as those consisting of polyanionic amino acids, such as FLAG-tag; epitope tags such as V5-tag, Myc-tag, HA-tag and NE-tag; protein tags that can allow specific enzymatic modification (such as biotinylation by biotin ligase) or chemical modification (such as reaction with FlAsH-EDT2 for fluorescence imaging), DNA and/or RNA segments that contain restriction enzyme or other enzyme cleavage sites; DNA segments that encode products that provide resistance against otherwise toxic compounds including antibiotics, such as, spectinomycin, ampicillin, kanamycin, tetracycline, Basta, neomycin phosphotransferase II (NEO), hygromycin phosphotransferase (HPT)) and the like; DNA and/or RNA segments that encode products that are otherwise lacking in the recipient cell (e.g., tRNA genes, auxotrophic markers); DNA and/or RNA segments that encode products which can be readily identified (e.g., phenotypic markers such as β-galactosidase, GUS; fluorescent proteins such as green fluorescent protein (GFP), cyan (CFP), yellow (YFP), red (RFP), luciferase, and cell surface proteins); polynucleotides that can generate one or more new primer sites for PCR (e.g., the juxtaposition of two DNA sequences not previously juxtaposed), DNA sequences not acted upon or acted upon by a restriction endonuclease or other DNA modifying enzyme, chemical, etc.; epitope tags (e.g. GFP, FLAG- and His-tags), and, DNA sequences that make a molecular barcode or unique molecular identifier (UMI), DNA sequences required for a specific modification (e.g., methylation) that allows its identification. Other suitable markers will be appreciated by those of skill in the art.

Selectable markers and tags can be operably linked to one or more components of the CRISPR-Cas system described herein via suitable linker, such as a glycine or glycine serine linkers as short as GS or GG up to $(GGGGG)_3$ (SEQ ID NO: 50) or $(GGGGS)_3$(SEQ ID NO: 9). Other suitable linkers are described elsewhere herein.

The vector or vector system can include one or more polynucleotides encoding one or more targeting moieties. In some embodiments, the targeting moiety encoding polynucleotides can be included in the vector or vector system, such as a viral vector system, such that they are expressed within and/or on the virus particle(s) produced such that the virus particles can be targeted to specific cells, tissues, organs, etc. In some embodiments, the targeting moiety encoding polynucleotides can be included in the vector or vector system such that the CRISPR-Cas system polynucleotide(s) and/or products expressed therefrom include the targeting moiety and can be targeted to specific cells, tissues, organs, etc. In some embodiments, such as non-viral carriers, the targeting moiety can be attached to the carrier (e.g. polymer, lipid, inorganic molecule etc.) and can be capable of targeting the carrier and any attached or associated CRISPR-Cas system polynucleotide(s) to specific cells, tissues, organs, etc.

Codon Optimization of Vector Polynucleotides

As described elsewhere herein, the polynucleotide encoding one or more embodiments of the CRISPR-Cas system described herein can be codon optimized. In some embodiments, one or more polynucleotides contained in a vector ("vector polynucleotides") described herein that are in addition to an optionally codon optimized polynucleotide encoding embodiments of the CRISPR-Cas system described herein can be codon optimized. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, P A), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at http://www.yeastgenome.org/community/codon_usage.shtml, or *Codon selection in yeast*, Bennetzen and Hall, J Biol Chem. 1982 Mar. 25; 257(6):3026-31. As to codon usage in plants including algae, reference is made to *Codon usage in higher plants, green algae, and cyanobacteria*, Campbell and Gowri, Plant Physiol. 1990 January; 92(1): 1-11.; as well as *Codon usage in plant genes*, Murray et al, Nucleic Acids Res. 1989 Jan. 25; 17(2):477-98; or *Selection on the codon bias of chloroplast and cyanelle genes in different plant and algal lineages*, Morton B R, J Mol Evol. 1998 April; 46(4):449-59.

The vector polynucleotide can be codon optimized for expression in a specific cell-type, tissue type, organ type, and/or subject type. In some embodiments, a codon optimized sequence is a sequence optimized for expression in a eukaryote, e.g., humans (i.e. being optimized for expression in a human or human cell), or for another eukaryote, such as another animal (e.g. a mammal or avian) as is described elsewhere herein. Such codon optimized sequences are within the ambit of the ordinary skilled artisan in view of the description herein. In some embodiments, the polynucleotide is codon optimized for a specific cell type. Such cell types can include, but are not limited to, epithelial cells (including skin cells, cells lining the gastrointestinal tract, cells lining other hollow organs), nerve cells (nerves, brain cells, spinal column cells, nerve support cells (e.g. astrocytes, glial cells, Schwann cells etc.), muscle cells (e.g. cardiac muscle, smooth muscle cells, and skeletal muscle cells), connective tissue cells (fat and other soft tissue padding cells, bone cells, tendon cells, cartilage cells), blood cells, stem cells and other progenitor cells, immune system cells, germ cells, and combinations thereof. Such codon optimized sequences are within the ambit of the ordinary skilled artisan in view of the description herein. In some embodiments, the polynucleotide is codon optimized for a specific tissue type. Such tissue types can include, but are not limited to, muscle tissue, connective tissue, connective tissue, nervous tissue, and epithelial tissue. Such codon optimized sequences are within the ambit of the ordinary skilled artisan in view of the description herein. In some embodiments, the polynucleotide is codon optimized for a specific organ. Such organs include, but are not limited to, muscles, skin, intestines, liver, spleen, brain, lungs, stomach, heart, kidneys, gallbladder, pancreas, bladder, thyroid, bone, blood vessels, blood, and combinations thereof. Such codon optimized sequences are within the ambit of the ordinary skilled artisan in view of the description herein.

In some embodiments, a vector polynucleotide is codon optimized for expression in particular cells, such as prokaryotic or eukaryotic cells. The eukaryotic cells may be those of or derived from a particular organism, such as a plant or a mammal, including but not limited to human, or non-human eukaryote or animal or mammal as discussed herein, e.g., mouse, rat, rabbit, dog, livestock, or non-human mammal or primate.

Vector Construction

The vectors described herein can be constructed using any suitable process or technique. In some embodiments, one or more suitable recombination and/or cloning methods or techniques can be used to the vector(s) described herein. Suitable recombination and/or cloning techniques and/or methods can include, but not limited to, those described in U.S. Patent Publication No. US 2004/0171156 A1. Other suitable methods and techniques are described elsewhere herein.

Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Any of the techniques and/or methods can be used and/or adapted for constructing an AAV or other vector described herein. nAAV vectors are discussed elsewhere herein.

In some embodiments, a vector comprises one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. When multiple different guide polynucleotides are used, a single expression construct may be used to target nucleic acid-targeting activity to multiple different, corresponding target sequences within a cell. For example, a single vector may comprise about or more than about 1, 2, 3, 4, 5, 6, 7, 8, 9, 10, 15, 20, or more guide s polynucleotides. In some embodiments, about or more than about 1, 2, 3, 4, 5, 6, 7, 8, 9, 10, or more such guide-polynucleotide-containing vectors may be provided, and optionally delivered to a cell.

Delivery vehicles, vectors, particles, nanoparticles, formulations and components thereof for expression of one or more elements of a CRISPR-Cas system described herein are as used in the foregoing documents, such as International Patent Publication No. WO 2014/093622 (PCT/US2013/074667) and are discussed in greater detail herein.

Viral Vectors

In some embodiments, the vector is a viral vector. The term of art "viral vector" and as used herein in this context refers to polynucleotide based vectors that contain one or more elements from or based upon one or more elements of a virus that can be capable of expressing and packaging a polynucleotide, such as a CRISPR-Cas system polynucleotide of the present invention, into a virus particle and producing said virus particle when used alone or with one or more other viral vectors (such as in a viral vector system). Viral vectors and systems thereof can be used for producing viral particles for delivery of and/or expression of one or more components of the CRISPR-Cas system described herein. The viral vector can be part of a viral vector system involving multiple vectors. In some embodiments, systems incorporating multiple viral vectors can increase the safety of these systems. Suitable viral vectors can include retroviral-based vectors, lentiviral-based vectors, adenoviral-based vectors, adeno associated vectors, helper-dependent adenoviral (HdAd) vectors, hybrid adenoviral vectors, herpes simplex virus-based vectors, poxvirus-based vectors, and Epstein-Barr virus-based vectors. Other embodiments of viral vectors and viral particles produce therefrom are described elsewhere herein. In some embodiments, the viral vectors are configured to produce replication incompetent viral particles for improved safety of these systems.

In certain embodiments, the virus structural component, which can be encoded by one or more polynucleotides in a viral vector or vector system, comprises one or more capsid proteins including an entire capsid. In certain embodiments, such as wherein a viral capsid comprises multiple copies of different proteins, the delivery system can provide one or more of the same protein or a mixture of such proteins. For example, AAV comprises 3 capsid proteins, VP1, VP2, and VP3, thus delivery systems of the invention can comprise one or more of VP1, and/or one or more of VP2, and/or one or more of VP3. Accordingly, the present invention is applicable to a virus within the family Adenoviridae, such as Atadenovirus, e.g., Ovine atadenovirus D, Aviadenovirus, e.g., Fowl aviadenovirus A, Ichtadenovirus, e.g., Sturgeon ichtadenovirus A, Mastadenovirus (which includes adenoviruses such as all human adenoviruses), e.g., Human mastadenovirus C, and Siadenovirus, e.g., Frog siadenovirus A. Thus, a virus of within the family Adenoviridae is contemplated as within the invention with discussion herein as to adenovirus applicable to other family members. Target-specific AAV capsid variants can be used or selected. Non-limiting examples include capsid variants selected to bind to chronic myelogenous leukemia cells, human CD34 PBPC cells, breast cancer cells, cells of lung, heart, dermal fibroblasts, melanoma cells, stem cell, glioblastoma cells, coronary artery endothelial cells and keratinocytes. See, e.g., Buning et al, 2015, Current Opinion in Pharmacology 24, 94-104. From teachings herein and knowledge in the art as to modifications of adenovirus (see, e.g., U.S. Pat. Nos. 9,410,129, 7,344,872, 7,256,036, 6,911,199, 6,740,525; Matthews, "Capsid-Incorporation of Antigens into Adenovirus Capsid Proteins for a Vaccine Approach," Mol Pharm, 8(1): 3-11 (2011)), as well as regarding modifications of AAV, the skilled person can readily obtain a modified adenovirus that has a large payload protein or a CRISPR-protein, despite that heretofore it was not expected that such a large protein could be provided on an adenovirus. And as to the viruses related to adenovirus mentioned herein, as well as to the viruses related to AAV mentioned elsewhere herein, the teachings herein as to modifying adenovirus and AAV, respectively, can be applied to those viruses without undue experimentation from this disclosure and the knowledge in the art.

In some embodiments, the viral vector is configured such that when the cargo is packaged the cargo(s) (e.g. one or more components of the CRISPR-Cas system, including but not limited to a Cas effector, is external to the capsid or virus particle. In the sense that it is not inside the capsid (enveloped or encompassed with the capsid), but is externally exposed so that it can contact the target genomic DNA. In some embodiments, the viral vector is configured such that all the carog(s) are contained within the capsid after packaging.

Split Viral Vector Systems

When the CRISPR-Cas system viral vector or vector system (be it a retroviral (e.g. AAV) or lentiviral vector) is designed so as to position the cargo(s) (e.g., one or more CRISPR-Cas system components) at the internal surface of the capsid once formed, the cargo(s) will fill most or all of internal volume of the capsid. In other embodiments, the CRISPR protein may be modified or divided so as to occupy a less of the capsid internal volume. Accordingly, in certain embodiments, the CRISPR-Cas system or component thereof (e.g. a Cas effector protein) can be divided in two portions, one portion comprises in one viral particle or capsid and the second portion comprised in a second viral particle or capsid. In certain embodiments, by splitting the CRISPR-Cas system or component thereof in two portions, space is made available to link one or more heterologous domains to one or both CRISPR-Cas system component (e.g., Cas protein) portions. Such systems can be referred to as "split vector systems" or in the context of the present disclosure a "split CRISPR-Cas system" a "split CRISPR protein", a "split Cas protein" and the like. This split protein approach is also described elsewhere herein. When the concept is applied to a vector system, it thus describes putting pieces of the split proteins on different vectors thus reducing the payload of any one vector. This approach can facilitate delivery of systems where the total system size is close to or exceeds the packaging capacity of the vector. This is independent of any regulation of the CRISPR-Cas system that can be achieved with a split system or split protein design.

Split CRISPR proteins that can be incorporated into the AAV or other vectors described herein are set forth elsewhere herein and in documents incorporated herein by reference in further detail herein. In certain embodiments, each part of a split CRISPR proteins are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In general, according to the invention, CRISPR proteins may preferably split between domains, leaving domains intact. Preferred, non-limiting examples of such CRISPR proteins include, without limitation, Cas protein, and orthologues. Preferred, non-limiting examples of split points include, with reference to SpCas9: a split position between 202A/203S; a split position between 255F/256D; a split position between 310E/3111; a split position between 534R/535K; a split position between 572E/573C; a split position between 713S/714G; a split position between 1003L/104E; a split position between 1054G/1055E; a split position between 1114N/1115S; a split position between 1152K/1153S; a split position between 1245K/1246G; or a split between 1098 and 1099. Corresponding positions in other Cas proteins can be appreciated in view of these positions made with reference to SpCas9.

In some embodiments, any AAV serotype is preferred. In some embodiments, the VP2 domain associated with the CRISPR enzyme is an AAV serotype 2 VP2 domain. In some embodiments, the VP2 domain associated with the CRISPR enzyme is an AAV serotype 8 VP2 domain. The serotype can be a mixed serotype as is known in the art.

Retroviral and Lentiviral Vectors

Retroviral vectors can be composed of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Suitable retroviral vectors for the CRISPR-Cas systems can include those based upon murine leukemia virus (MuLV), gibbon ape leukemia virus (GaLV), Simian immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). Selection of a retroviral gene transfer system may therefore depend on the target tissue.

The tropism of a retrovirus can be altered by incorporating foreign envelope proteins, expanding the potential target population of target cells. Lentiviral vectors are retroviral vectors that are able to transduce or infect non-dividing cells and are described in greater detail elsewhere herein. A retrovirus can also be engineered to allow for conditional expression of the inserted transgene, such that only certain cell types are infected by the lentivirus.

Lentiviruses are complex retroviruses that have the ability to infect and express their genes in both mitotic and post-mitotic cells. Advantages of using a lentiviral approach can include the ability to transduce or infect non-dividing cells and their ability to typically produce high viral titers, which can increase efficiency or efficacy of production and delivery. Suitable lentiviral vectors include, but are not limited to, human immunodeficiency virus (HIV)-based lentiviral vectors, feline immunodeficiency virus (FIV)-based lentiviral vectors, simian immunodeficiency virus (SIV)-based lentiviral vectors, Moloney Murine Leukaemia Virus (Mo-MLV), Visna.maedi virus (VMV)-based lentiviral vector, carpine arthritis-encephalitis virus (CAEV)-based lentiviral vector, bovine immune deficiency virus (BIV)-based lentiviral vector, and Equine infectious anemia (EIAV)-based lentiviral vector. In some embodiments, an HIV-based lentiviral vector system can be used. In some embodiments, a FIV-based lentiviral vector system can be used.

In some embodiments, the lentiviral vector is an EIAV-based lentiviral vector or vector system. EIAV vectors have been used to mediate expression, packaging, and/or delivery in other contexts, such as for ocular gene therapy (see, e.g., Balagaan, J Gene Med 2006; 8: 275-285). In another embodiment, RetinoStat®, (see, e.g., Binley et al., HUMAN GENE THERAPY 23:980-991 (September 2012)), which describes RetinoStat®, an equine infectious anemia virus-based lentiviral gene therapy vector that expresses angiostatic proteins endostatin and angiostatin that is delivered via a subretinal injection for the treatment of the wet form of age-related macular degeneration. Any of these vectors described in these publications can be modified for the elements of the CRISPR-Cas system described herein.

In some embodiments, the lentiviral vector or vector system thereof can be a first-generation lentiviral vector or vector system thereof. First-generation lentiviral vectors can contain a large portion of the lentivirus genome, including the gag and pol genes, other additional viral proteins (e.g. VSV-G) and other accessory genes (e.g. vif, vprm vpu, nef, and combinations thereof), regulatory genes (e.g. tat and/or rev) as well as the gene of interest between the LTRs. First generation lentiviral vectors can result in the production of virus particles that can be capable of replication in vivo, which may not be appropriate for some instances or applications.

In some embodiments, the lentiviral vector or vector system thereof can be a second-generation lentiviral vector or vector system thereof. Second-generation lentiviral vectors do not contain one or more accessory virulence factors and do not contain all components necessary for virus particle production on the same lentiviral vector. This can result in the production of a replication-incompetent virus particle and thus increase the safety of these systems over first-generation lentiviral vectors. In some embodiments, the second-generation vector lacks one or more accessory virulence factors (e.g. vif, vprm, vpu, nef, and combinations thereof). Unlike the first-generation lentiviral vectors, no single second generation lentiviral vector includes all features necessary to express and package a polynucleotide into a virus particle. In some embodiments, the envelope and packaging components are split between two different vectors with the gag, pol, rev, and tat genes being contained on one vector and the envelope protein (e.g. VSV-G) are contained on a second vector. The gene of interest, its promoter, and LTRs can be included on a third vector that can be used in conjunction with the other two vectors (packaging and envelope vectors) to generate a replication-incompetent virus particle.

In some embodiments, the lentiviral vector or vector system thereof can be a third-generation lentiviral vector or vector system thereof. Third-generation lentiviral vectors and vector systems thereof have increased safety over first- and second-generation lentiviral vectors and systems thereof because, for example, the various components of the viral genome are split between two or more different vectors but used together in vitro to make virus particles, they can lack the tat gene (when a constitutively active promoter is included up-stream of the LTRs), and they can include one or more deletions in the 3'LTR to create self-inactivating (SIN) vectors having disrupted promoter/enhancer activity of the LTR. In some embodiments, a third-generation lentiviral vector system can include (i) a vector plasmid that contains the polynucleotide of interest and upstream promoter that are flanked by the 5' and 3' LTRs, which can optionally include one or more deletions present in one or both of the LTRs to render the vector self-inactivating; (ii) a "packaging vector(s)" that can contain one or more genes involved in packaging a polynucleotide into a virus particle that is produced by the system (e.g. gag, pol, and rev) and upstream regulatory sequences (e.g. promoter(s)) to drive expression of the features present on the packaging vector, and (iii) an "envelope vector" that contains one or more envelope protein genes and upstream promoters. In certain embodiments, the third-generation lentiviral vector system can include at least two packaging vectors, with the gag-pol being present on a different vector than the rev gene.

In some embodiments, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) can be used/and or adapted to the CRISPR-Cas system of the present invention.

In some embodiments, the pseudotype and infectivity or tropisim of a lentivirus particle can be tuned by altering the type of envelope protein(s) included in the lentiviral vector or system thereof. As used herein, an "envelope protein" or "outer protein" means a protein exposed at the surface of a viral particle that is not a capsid protein. For example, envelope or outer proteins typically comprise proteins embedded in the envelope of the virus. In some embodiments, a lentiviral vector or vector system thereof can include a VSV-G envelope protein. VSV-G mediates viral attachment to an LDL receptor (LDLR) or an LDLR family member present on a host cell, which triggers endocytosis of the viral particle by the host cell. Because LDLR is expressed by a wide variety of cells, viral particles expressing the VSV-G envelope protein can infect or transduce a wide variety of cell types. Other suitable envelope proteins can be incorporated based on the host cell that a user desires to be infected by a virus particle produced from a lentiviral vector or system thereof described herein and can include, but are not limited to, feline endogenous virus envelope protein (RD114) (see e.g. Hanawa et al. Molec. Ther. 2002 5(3) 242-251), modified Sindbis virus envelope proteins (see e.g. Morizono et al. 2010. J. Virol. 84(14) 6923-6934; Morizono et al. 2001. J. Virol. 75:8016-8020; Morizono et al. 2009. J. Gene Med. 11:549-558; Morizono et al. 2006 Virology 355:71-81; Morizono et al J. Gene Med. 11:655-663, Morizono et al. 2005 Nat. Med. 11:346-352), baboon retroviral envelope protein (see e.g. Girard-Gagnepain et al. 2014. Blood. 124: 1221-1231); Tupaia paramyxovirus glycoproteins (see e.g. Enkirch T. et al., 2013. Gene Ther. 20:16-23); measles virus glycoproteins (see e.g. Funke et al. 2008. Molec. Ther. 16(8): 1427-1436), rabies virus envelope proteins, MLV envelope proteins, Ebola envelope proteins, baculovirus envelope proteins, filovirus envelope proteins, hepatitis E1 and E2 envelope proteins, gp41 and gp120 of HIV, hemagglutinin, neuraminidase, M2 proteins of influenza virus, and combinations thereof.

In some embodiments, the tropism of the resulting lentiviral particle can be tuned by incorporating cell targeting peptides into a lentiviral vector such that the cell targeting peptides are expressed on the surface of the resulting lentiviral particle. In some embodiments, a lentiviral vector can contain an envelope protein that is fused to a cell targeting protein (see e.g. Buchholz et al. 2015. Trends Biotechnol. 33:777-790; Bender et al. 2016. PLoS Pathog. 12(e1005461); and Friedrich et al. 2013. Mol. Ther. 2013. 21: 849-859.

In some embodiments, a split-intein-mediated approach to target lentiviral particles to a specific cell type can be used (see e.g. Chamoun-Emaneulli et al. 2015. Biotechnol. Bioeng. 112:2611-2617, Ramirez et al. 2013. Protein. Eng. Des. Sel. 26:215-233. In these embodiments, a lentiviral vector can contain one half of a splicing-deficient variant of the naturally split intein from *Nostoc punctiforme* fused to a cell targeting peptide and the same or different lentiviral vector can contain the other half of the split intein fused to an envelope protein, such as a binding-deficient, fusion-competent virus envelope protein. This can result in production of a virus particle from the lentiviral vector or vector system that includes a split intein that can function as a molecular Velcro linker to link the cell-binding protein to the pseudotyped lentivirus particle. This approach can be advantageous for use where surface-incompatibilities can restrict the use of, e.g., cell targeting peptides.

In some embodiments, a covalent-bond-forming protein-peptide pair can be incorporated into one or more of the lentiviral vectors described herein to conjugate a cell targeting peptide to the virus particle (see e.g. Kasaraneni et al. 2018. Sci. Reports (8) No. 10990). In some embodiments, a lentiviral vector can include an N-terminal PDZ domain of InaD protein (PDZ1) and its pentapeptide ligand (TEFCA) from NorpA, which can conjugate the cell targeting peptide to the virus particle via a covalent bond (e.g. a disulfide bond). In some embodiments, the PDZ1 protein can be fused to an envelope protein, which can optionally be binding deficient and/or fusion competent virus envelope protein and included in a lentiviral vector. In some embodiments, the TEFCA can be fused to a cell targeting peptide and the TEFCA-CPT fusion construct can be incorporated into the same or a different lentiviral vector as the PDZ1-envenlope protein construct. During virus production, specific interaction between the PDZ1 and TEFCA facilitates producing virus particles covalently functionalized with the cell targeting peptide and thus capable of targeting a specific cell-type based upon a specific interaction between the cell targeting peptide and cells expressing its binding partner. This approach can be advantageous for use where surface-incompatibilities can restrict the use of, e.g., cell targeting peptides.

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015. Any of these systems or a variant thereof can be used to deliver an CRISPR-Cas system polynucleotide described herein to a cell.

In some embodiments, a lentiviral vector system can include one or more transfer plasmids. Transfer plasmids can be generated from various other vector backbones and can include one or more features that can work with other retroviral and/or lentiviral vectors in the system that can, for example, improve safety of the vector and/or vector system, increase virial titers, and/or increase or otherwise enhance expression of the desired insert to be expressed and/or packaged into the viral particle. Suitable features that can be included in a transfer plasmid can include, but are not limited to, 5'LTR, 3'LTR, SIN/LTR, origin of replication (Ori), selectable marker genes (e.g. antibiotic resistance genes), Psi (Ψ) RRE (rev response element), cPPT (central polypurine tract), promoters, WPRE (woodchuck hepatitis post-transcriptional regulatory element), SV40 polyadenylation signal, pUC origin, SV40 origin, F1 origin, and combinations thereof.

In another embodiment, Cocal vesiculovirus envelope pseudotyped retroviral or lentiviral vector particles are contemplated (see, e.g., US Patent Publication No. 20120164118 assigned to the Fred Hutchinson Cancer Research Center). Cocal virus is in the Vesiculovirus genus, and is a causative agent of vesicular stomatitis in mammals. Cocal virus was originally isolated from mites in Trinidad (Jonkers et al., Am. J. Vet. Res. 25:236-242 (1964)), and infections have been identified in Trinidad, Brazil, and Argentina from insects, cattle, and horses. Many of the vesiculoviruses that infect mammals have been isolated from naturally infected arthropods, suggesting that they are vector-borne. Antibodies to vesiculoviruses are common among people living in rural areas where the viruses are endemic and laboratory-acquired; infections in humans usually result in influenza-like symptoms. The Cocal virus envelope glycoprotein shares 71.5% identity at the amino acid level with VSV-G Indiana, and phylogenetic comparison of the envelope gene of vesiculoviruses shows that Cocal virus is serologically distinct from, but most closely related to, VSV-G Indiana strains among the vesiculoviruses. Jonkers et al., Am. J. Vet. Res. 25:236-242 (1964) and Travassos da Rosa et al., Am. J. Tropical Med. & Hygiene 33:999-1006 (1984). The Cocal vesiculovirus envelope pseudotyped retroviral vector particles may include for example, lentiviral, alpharetroviral, betaretroviral, gammaretroviral, deltaretroviral, and epsilonretroviral vector particles that may comprise retroviral Gag, Pol, and/or one or more accessory protein(s) and a Cocal vesiculovirus envelope protein. In certain embodiments of these embodiments, the Gag, Pol, and accessory proteins are lentiviral and/or gammaretroviral. In some embodiments, a retroviral vector can contain encoding polypeptides for one or more Cocal vesiculovirus envelope proteins such that the resulting viral or pseudoviral particles are Cocal vesiculovirus envelope pseudotyped.

Adenoviral Vectors, Helper-Dependent Adenoviral Vectors, and Hybrid Adenoviral Vectors In some embodiments, the vector can be an adenoviral vector. In some embodiments, the adenoviral vector can include elements such that the virus particle produced using the vector or system thereof can be serotype 2 or serotype 5. In some embodiments, the polynucleotide to be delivered via the adenoviral particle can be up to about 8 kb. Thus, in some embodiments, an adenoviral vector can include a DNA polynucleotide to be delivered that can range in size from about 0.001 kb to about 8 kb. Adenoviral vectors have been used successfully in several contexts (see e.g. Teramato et al. 2000. Lancet. 355:1911-1912; Lai et al. 2002. DNA Cell. Biol. 21:895-913; Flotte et al., 1996. Hum. Gene. Ther. 7:1145-1159; and Kay et al. 2000. Nat. Genet. 24:257-261.

In some embodiments the vector can be a helper-dependent adenoviral vector or system thereof. These are also referred to in the art as "gutless" or "gutted" vectors and are a modified generation of adenoviral vectors (see e.g. Thrasher et al. 2006. Nature. 443:E5-7). In certain embodiments of the helper-dependent adenoviral vector system one vector (the helper) can contain all the viral genes required for replication but contains a conditional gene defect in the packaging domain. The second vector of the system can contain only the ends of the viral genome, one or more CRISPR-Cas polynucleotides, and the native packaging recognition signal, which can allow selective packaged release from the cells (see e.g. Cideciyan et al. 2009. N Engl J Med. 361:725-727). Helper-dependent adenoviral vector systems have been successful for gene delivery in several contexts (see e.g. Simonelli et al. 2010. J Am Soc Gene Ther. 18:643-650; Cideciyan et al. 2009. N Engl J Med. 361:725-727; Crane et al. 2012. Gene Ther. 19(4):443-452; Alba et al. 2005. Gene Ther. 12:18-S27; Croyle et al. 2005. Gene Ther. 12:579-587; Amalfitano et al. 1998. J. Virol. 72:926-933; and Morral et al. 1999. PNAS. 96:12816-12821). The techniques and vectors described in these publications can be adapted for inclusion and delivery of the CRISPR-Cas system polynucleotides described herein. In some embodiments, the polynucleotide to be delivered via the viral particle produced from a helper-dependent adenoviral vector or system thereof can be up to about 37 kb. Thus, in some embodiments, a adenoviral vector can include a DNA polynucleotide to be delivered that can range in size from about 0.001 kb to about 37 kb (see e.g. Rosewell et al. 2011. J. Genet. Syndr. Gene Ther. Suppl. 5:001).

In some embodiments, the vector is a hybrid-adenoviral vector or system thereof. Hybrid adenoviral vectors are composed of the high transduction efficiency of a gene-deleted adenoviral vector and the long-term genome-integrating potential of adeno-associated, retroviruses, lentivirus, and transposon based-gene transfer. In some embodiments, such hybrid vector systems can result in stable transduction and limited integration site. See e.g. Balague et al. 2000. Blood. 95:820-828; Morral et al. 1998. Hum. Gene Ther. 9:2709-2716; Kubo and Mitani. 2003. J. Virol. 77(5): 2964-2971; Zhang et al. 2013. PloS One. 8(10) e76771; and Cooney et al. 2015. Mol. Ther. 23(4):667-674), whose techniques and vectors described therein can be modified and adapted for use in the CRISPR-Cas system of the present invention. In some embodiments, a hybrid-adenoviral vector can include one or more features of a retrovirus and/or an adeno-associated virus. In some embodiments the hybrid-adenoviral vector can include one or more features of a spuma retrovirus or foamy virus (FV). See e.g. Ehrhardt et al. 2007. Mol. Ther. 15:146-156 and Liu et al. 2007. Mol. Ther. 15:1834-1841, whose techniques and vectors described therein can be modified and adapted for use in the CRISPR-Cas system of the present invention. Advantages of using one or more features from the FVs in the hybrid-adenoviral vector or system thereof can include the ability of the viral particles produced therefrom to infect a broad range of cells, a large packaging capacity as compared to other retroviruses, and the ability to persist in quiescent (non-dividing) cells. See also e.g. Ehrhardt et al. 2007. Mol. Ther. 156:146-156 and Shuji et al. 2011. Mol. Ther. 19:76-82, whose techniques and vectors described therein can be modified and adapted for use in the CRISPR-Cas system of the present invention.

Adeno Associated Viral (AAV) Vectors

In an embodiment, the vector can be an adeno-associated virus (AAV) vector. See, e.g., West et al., Virology 160:38-47 (1987); U.S. Pat. No. 4,797,368; WO 93/24641; Kotin, Human Gene Therapy 5:793-801 (1994); and Muzyczka, J. Clin. Invest. 94:1351 (1994). Although similar to adenoviral vectors in some of their features, AAVs have some deficiency in their replication and/or pathogenicity and thus can be safer that adenoviral vectors. In some embodiments the AAV can integrate into a specific site on chromosome 19 of a human cell with no observable side effects. In some embodiments, the capacity of the AAV vector, system thereof, and/or AAV particles can be up to about 4.7 kb. In some embodiments, utilizing homologs of the Cas effector protein that are shorter can be utilized, such for example those in Table 9.

TABLE 9

Exemplary shorter Cas effector homologs.

| Species | Cas9 Size (nt) |
|---|---|
| *Corynebacter diphtheriae* | 3252 |
| *Eubacterium ventriosum* | 3321 |
| *Streptococcus pasteurianus* | 3390 |
| *Lactobacillus farciminis* | 3378 |
| *Sphaerochaeta globus* | 3537 |
| *Azospirillum* B510 | 3504 |
| *Gluconacetobacter diazotrophicus* | 3150 |
| *Neisseria cinerea* | 3246 |
| *Roseburia intestinalis* | 3420 |
| *Parvibaculum lavamentivorans* | 3111 |
| *Staphylococcus aureus* | 3159 |
| *Nitratifractor salsuginis* DSM 16511 | 3396 |
| *Campylobacter lari* CF89-12 | 3009 |
| *Campylobacter jejuni* | 2952 |
| *Streptococcus thermophilus* LMD-9 | 3396 |

The AAV vector or system thereof can include one or more regulatory molecules. In some embodiments the regulatory molecules can be promoters, enhancers, repressors and the like, which are described in greater detail elsewhere herein. In some embodiments, the AAV vector or system thereof can include one or more polynucleotides that can encode one or more regulatory proteins. In some embodiments, the one or more regulatory proteins can be selected from Rep78, Rep68, Rep52, Rep40, variants thereof, and combinations thereof.

The AAV vector or system thereof can include one or more polynucleotides that can encode one or more capsid proteins. The capsid proteins can be selected from VP1, VP2, VP3, and combinations thereof. The capsid proteins can be capable of assembling into a protein shell of the AAV virus particle. In some embodiments, the AAV capsid can contain 60 capsid proteins. In some embodiments, the ratio of VP1:VP2:VP3 in a capsid can be about 1:1:10.

In some embodiments, the AAV vector or system thereof can include one or more adenovirus helper factors or polynucleotides that can encode one or more adenovirus helper factors. Such adenovirus helper factors can include, but are not limited, E1A, E1B, E2A, E4ORF6, and VA RNAs. In some embodiments, a producing host cell line expresses one or more of the adenovirus helper factors.

The AAV vector or system thereof can be configured to produce AAV particles having a specific serotype. In some embodiments, the serotype can be AAV-1, AAV-2, AAV-3, AAV-4, AAV-5, AAV-6, AAV-8, AAV-9 or any combinations thereof. In some embodiments, the AAV can be AAV1, AAV-2, AAV-5 or any combination thereof. One can select the AAV of the AAV with regard to the cells to be targeted; e.g., one can select AAV serotypes 1, 2, 5 or a hybrid capsid AAV-1, AAV-2, AAV-5 or any combination thereof for targeting brain and/or neuronal cells; and one can select AAV-4 for targeting cardiac tissue; and one can select AAV8 for delivery to the liver. Thus, in some embodiments, an AAV vector or system thereof capable of producing AAV particles capable of targeting the brain and/or neuronal cells can be configured to generate AAV particles having serotypes 1, 2, 5 or a hybrid capsid AAV-1, AAV-2, AAV-5 or any combination thereof. In some embodiments, an AAV vector or system thereof capable of producing AAV particles capable of targeting cardiac tissue can be configured to generate an AAV particle having an AAV-4 serotype. In some embodiments, an AAV vector or system thereof capable of producing AAV particles capable of targeting the liver can be configured to generate an AAV having an AAV-8 serotype. In some embodiments, the AAV vector is a hybrid AAV vector or system thereof. Hybrid AAVs are AAVs that include genomes with elements from one serotype that are packaged into a capsid derived from at least one different serotype. For example, if it is the rAAV2/5 that is to be produced, and if the production method is based on the helper-free, transient transfection method discussed above, the 1st plasmid and the 3rd plasmid (the adeno helper plasmid) will be the same as discussed for rAAV2 production. However, the second plasmid, the pRepCap will be different. In this plasmid, called pRep2/Cap5, the Rep gene is still derived from AAV2, while the Cap gene is derived from AAVS. The production scheme is the same as the above-mentioned approach for AAV2 production. The resulting rAAV is called rAAV2/5, in which the genome is based on recombinant AAV2, while the capsid is based on AAVS. It is assumed the cell or tissue-tropism displayed by this AAV2/5 hybrid virus should be the same as that of AAVS.

A tabulation of certain AAV serotypes as to these cells can be found in Grimm, D. et al, J. Virol. 82: 5887-5911 (2008), which is recapitulated in Table 10 below.

TABLE 10

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

In some embodiments, the AAV vector or system thereof is configured as a "gutless" vector, similar to that described in connection with a retroviral vector. In some embodiments, the "gutless" AAV vector or system thereof can have the cis-acting viral DNA elements involved in genome amplification and packaging in linkage with the heterologous sequences of interest (e.g. the CRISPR-Cas system polynucleotide(s)).

In some embodiments, the AAV vectors are produced in in insect cells, e.g., *Spodoptera frugiperda* Sf9 insect cells, grown in serum-free suspension culture. Serum-free insect cells can be purchased from commercial vendors, e.g., Sigma Aldrich (EX-CELL 405).

In some embodiments, an AAV vector or vector system can contain or consists essentially of one or more polynucleotides encoding one or more components of a CRISPR system. In some embodiments, the AAV vector or vector system can contain a plurality of cassettes comprising or consisting a first cassette comprising or consisting essentially of a promoter, a nucleic acid molecule encoding a CRISPR-associated (Cas) protein (putative nuclease or helicase proteins), e.g., a Cas protein and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., a Cas and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator . . . Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. In some embodiments, the promoter is a tissue specific promoter or another tissue specific regulatory element. Suitable tissue specific regulatory elements, including promoters, are described in greater detail elsewhere herein.

In another embodiment, the invention provides a non-naturally occurring or engineered CRISPR protein associated with Adeno Associated Virus (AAV), e.g., an AAV comprising a CRISPR protein as a fusion, with or without a linker, to or with an AAV capsid protein such as VP1, VP2, and/or VP3; and, for shorthand purposes, such a non-naturally occurring or engineered CRISPR protein is herein termed a "AAV-CRISPR protein" More in particular, modifying the knowledge in the art, e.g., Rybniker et al., "Incorporation of Antigens into Viral Capsids Augments Immunogenicity of Adeno-Associated Virus Vector-Based Vaccines," J Virol. December 2012; 86(24): 13800-13804, Lux K, et al. 2005. Green fluorescent protein-tagged adeno-associated virus particles allow the study of cytosolic and nuclear trafficking. J. Virol. 79:11776-11787, Munch R C, et al. 2012. "Displaying high-affinity ligands on adeno-associated viral vectors enables tumor cell-specific and safe gene transfer." Mol. Ther. [Epub ahead of print.] doi:10.1038/mt.2012.186 and Warrington K H, Jr, et al. 2004. Adeno-associated virus type 2 VP2 capsid protein is nonessential and can tolerate large peptide insertions at its N terminus. J. Virol. 78:6595-6609, each incorporated herein by reference, one can obtain a modified AAV capsid of the invention. It will be understood by those skilled in the art that the modifications described herein if inserted into the AAV cap gene may result in modifications in the VP1, VP2 and/or VP3 capsid subunits. Alternatively, the capsid subunits can be expressed independently to achieve modification in only one or two of the capsid subunits (VP1, VP2, VP3, VP1+VP2, VP1+VP3, or VP2+VP3). One can modify the cap gene to have expressed at a desired location a non-capsid protein advantageously a large payload protein, such as a CRISPR-protein. Likewise, these can be fusions, with the protein, e.g., large payload protein such as a CRISPR-protein fused in a manner analogous to prior art fusions. See, e.g., US Patent Publication 20090215879; Nance et al., "Perspective on Adeno-Associated Virus Capsid Modification for Duchenne Muscular Dystrophy Gene Therapy," Hum Gene Ther. 26(12):786-800 (2015) and documents cited therein, incorporated herein by reference. The skilled person, from this disclosure and the knowledge in the art can make and use modified AAV or AAV capsid as in the herein invention, and through this disclosure one knows now that large payload proteins can be fused to the AAV capsid. Applicants provide AAV capsid-CRISPR protein (e.g., Cas, (e.g. Cas9 or Cas12), dCas (e.g. dCas12) fusions and those AAV-capsid CRISPR protein (e.g., Cas, Cas9 (e.g. Cas9 or Cas12) fusions can be a recombinant AAV that contains nucleic acid molecule(s) encoding or providing CRISPR-Cas or CRISPR system or complex RNA guide(s), whereby the CRISPR protein (e.g., Cas, Cas9 (e.g. Cas9 or Cas12) fusion delivers a CRISPR-Cas or CRISPR system complex (e.g., the CRISPR protein or Cas (e.g. Cas9 and/or Cas12) is provided by the fusion, e.g., VP1, VP2, or VP3 fusion, and the guide RNA is provided by the coding of the recombinant virus, whereby in vivo, in a cell, the CRISPR-Cas or CRISPR system is assembled from the nucleic acid molecule(s) of the recombinant providing the guide RNA and the outer surface of the virus providing the CRISPR-Enzyme (e.g., Cas (e.g. Cas9 or Cas12). Such as complex may herein be termed an “AAV-CRISPR system” or an “AAV—CRISPR-Cas” or “AAV-CRISPR complex” or AAV—CRISPR-Cas complex.” Accordingly, the instant invention is also applicable to a virus in the genus Dependoparvovirus or in the family Parvoviridae, for instance, AAV, or a virus of Amdoparvovirus, e.g., Carnivore amdoparvovirus 1, a virus of Aveparvovirus, e.g., Galliform aveparvovirus 1, a virus of Bocaparvovirus, e.g., Ungulate bocaparvovirus 1, a virus of Copiparvovirus, e.g., Ungulate copiparvovirus 1, a virus of Dependoparvovirus, e.g., Adeno-associated dependoparvovirus A, a virus of Erythroparvovirus, e.g., Primate erythroparvovirus 1, a virus of Protoparvovirus, e.g., Rodent protoparvovirus 1, a virus of Tetraparvovirus, e.g., Primate tetraparvovirus 1. Thus, a virus of within the family Parvoviridae or the genus Dependoparvovirus or any of the other foregoing genera within Parvoviridae is contemplated as within the invention with discussion herein as to AAV applicable to such other viruses.

In some embodiments, the CRISPR enzyme is external to the capsid or virus particle. In the sense that it is not inside the capsid (enveloped or encompassed with the capsid), but is externally exposed so that it can contact the target genomic DNA). In some embodiments, the CRISPR enzyme is associated with the AAV VP2 domain by way of a fusion protein. In some embodiments, the association may be considered to be a modification of the VP2 domain. Where reference is made herein to a modified VP2 domain, then this will be understood to include any association discussed herein of the VP2 domain and the CRISPR enzyme. In some embodiments, the AAV VP2 domain may be associated (or tethered) to the CRISPR enzyme via a connector protein, for example using a system such as the streptavidin-biotin system. In an embodiment, the present invention provides a polynucleotide encoding the present CRISPR enzyme and associated AAV VP2 domain. In one embodiment, the invention provides a non-naturally occurring modified AAV having a VP2-CRISPR enzyme capsid protein, wherein the CRISPR enzyme is part of or tethered to the VP2 domain. In some preferred embodiments, the CRISPR enzyme is fused to the VP2 domain so that, in another embodiment, the invention provides a non-naturally occurring modified AAV having a VP2-CRISPR enzyme fusion capsid protein. Thus, reference herein to a VP2-CRISPR enzyme capsid protein may also include a VP2-CRISPR enzyme fusion capsid protein. In some embodiments, the VP2-CRISPR enzyme capsid protein further comprises a linker, whereby the VP2-CRISPR enzyme is distanced from the remainder of the AAV. In some embodiments, the VP2-CRISPR enzyme capsid protein further comprises at least one protein complex, e.g., CRISPR complex, such as a CRISPR-Cas complex guide RNA that targets a particular DNA, TALE, etc. A CRISPR complex, such as CRISPR-Cas system comprising the VP2-CRISPR enzyme capsid protein and at least one CRISPR complex, such as a CRISPR-Cas complex guide RNA that targets a particular DNA, is also provided in one embodiment.

In one embodiment, the invention provides a non-naturally occurring or engineered composition comprising a CRISPR enzyme which is part of or tethered to an AAV capsid domain, i.e., VP1, VP2, or VP3 domain of Adeno-Associated Virus (AAV) capsid. In some embodiments, part of or tethered to an AAV capsid domain includes associated with associated with a AAV capsid domain. In some embodiments, the CRISPR enzyme may be fused to the AAV capsid domain. In some embodiments, the fusion may be to the N-terminal end of the AAV capsid domain. As such, in some embodiments, the C-terminal end of the CRISPR enzyme is fused to the N-terminal end of the AAV capsid domain. In some embodiments, an NLS and/or a linker (such as a GlySer linker) may be positioned between the C-terminal end of the CRISPR enzyme and the N-terminal end of the AAV capsid domain. In some embodiments, the fusion may be to the C-terminal end of the AAV capsid domain. In some embodiments, this is not preferred due to the fact that the VP1, VP2 and VP3 domains of AAV are alternative splices of the same RNA and so a C-terminal fusion may affect all three domains. In some embodiments, the AAV capsid domain is truncated. In some embodiments, some or all of the AAV capsid domain is removed. In some embodiments, some of the AAV capsid domain is removed and replaced with a linker (such as a GlySer linker), typically leaving the N-terminal and C-terminal ends of the AAV capsid domain intact, such as the first 2, 5 or 10 amino acids. In this way, the internal (non-terminal) portion of the VP3 domain may be replaced with a linker. It is particularly preferred that the linker is fused to the CRISPR protein. A branched linker may be used, with the CRISPR protein fused to the end of one of the branches. This allows for some degree of spatial separation between the capsid and the CRISPR protein. In this way, the CRISPR protein is part of (or fused to) the AAV capsid domain.

In other embodiments, the CRISPR enzyme may be fused in frame within, i.e. internal to, the AAV capsid domain. Thus, in some embodiments, the AAV capsid domain again preferably retains its N-terminal and C-terminal ends. In this case, a linker is preferred, in some embodiments, either at one or both ends of the CRISPR enzyme. In this way, the CRISPR enzyme is again part of (or fused to) the AAV capsid domain. In certain embodiments, the positioning of the CRISPR enzyme is such that the CRISPR enzyme is at the external surface of the viral capsid once formed. In one embodiment, the invention provides a non-naturally occurring or engineered composition comprising a CRISPR enzyme associated with a AAV capsid domain of Adeno-Associated Virus (AAV) capsid. Here, associated may mean in some embodiments fused, or in some embodiments bound to, or in some embodiments tethered to. The CRISPR protein may, in some embodiments, be tethered to the VP1, VP2, or VP3 domain. This may be via a connector protein or tethering system such as the biotin-streptavidin system. In one example, a biotinylation sequence (15 amino acids) could therefore be fused to the CRISPR protein. When a fusion of the AAV capsid domain, especially the N-terminus of the AAV AAV capsid domain, with streptavidin is also provided, the two will therefore associate with very high affinity. Thus, in some embodiments, provided is a composition or system comprising a CRISPR protein-biotin fusion and a streptavidin-AAV capsid domain arrangement, such as a fusion. The CRISPR protein-biotin and streptavidin-AAV capsid domain forms a single complex when the two parts are brought together. NLSs may also be incorporated between the CRISPR protein and the biotin; and/or between the streptavidin and the AAV capsid domain.

As such, provided is a fusion of a CRISPR enzyme with a connector protein specific for a high affinity ligand for that connector, whereas the AAV VP2 domain is bound to said high affinity ligand. For example, streptavidin may be the connector fused to the CRISPR enzyme, while biotin may be bound to the AAV VP2 domain. Upon co-localization, the streptavidin will bind to the biotin, thus connecting the CRISPR enzyme to the AAV VP2 domain. The reverse arrangement is also possible. In some embodiments, a biotinylation sequence (15 amino acids) could therefore be fused to the AAV VP2 domain, especially the N-terminus of the AAV VP2 domain. A fusion of the CRISPR enzyme with streptavidin is also preferred, in some embodiments. In some embodiments, the biotinylated AAV capsids with streptavidin-CRISPR enzyme are assembled in vitro. This way the AAV capsids should assemble in a straightforward manner and the CRISPR enzyme-streptavidin fusion can be added after assembly of the capsid. In other embodiments a biotinylation sequence (15 amino acids) could therefore be fused to the CRISPR enzyme, together with a fusion of the AAV VP2 domain, especially the N-terminus of the AAV VP2 domain, with streptavidin. For simplicity, a fusion of the CRISPR enzyme and the AAV VP2 domain is preferred in some embodiments. In some embodiments, the fusion may be to the N-terminal end of the CRISPR enzyme. In other words, in some embodiments, the AAV and CRISPR enzyme are associated via fusion. In some embodiments, the AAV and CRISPR enzyme are associated via fusion including a linker. Suitable linkers are discussed herein, but include Gly Ser linkers. Fusion to the N-term of AAV VP2 domain is preferred, in some embodiments. In some embodiments, the CRISPR enzyme comprises at least one Nuclear Localization Signal (NLS). In a further embodiment, the present invention provides compositions comprising the CRISPR enzyme and associated AAV VP2 domain or the polynucleotides or vectors described herein. Such compositions and formulations are discussed elsewhere herein.

An alternative tether may be to fuse or otherwise associate the AAV capsid domain to an adaptor protein which binds to or recognizes to a corresponding RNA sequence or motif. In some embodiments, the adaptor is or comprises a binding protein which recognizes and binds (or is bound by) an RNA sequence specific for said binding protein. In some embodiments, a preferred example is the MS2 (see Konermann et al. December 2014, cited infra, incorporated herein by reference) binding protein which recognizes and binds (or is bound by) an RNA sequence specific for the MS2 protein.

With the AAV capsid domain associated with the adaptor protein, the CRISPR protein may, in some embodiments, be tethered to the adaptor protein of the AAV capsid domain. The CRISPR protein may, in some embodiments, be tethered to the adaptor protein of the AAV capsid domain via the CRISPR enzyme being in a complex with a modified guide, see Konermann et al. The modified guide is, in some embodiments, a sgRNA. In some embodiments, the modified guide comprises a distinct RNA sequence; see, e.g., International Patent Application No. PCT/US14/70175, incorporated herein by reference.

In some embodiments, distinct RNA sequence is an aptamer. Thus, corresponding aptamer-adaptor protein systems are preferred. One or more functional domains may also be associated with the adaptor protein. An example of a preferred arrangement would be: [AAV AAV capsid domain-adaptor protein]-[modified guide-CRISPR protein]

In certain embodiments, the positioning of the CRISPR protein is such that the CRISPR protein is at the internal surface of the viral capsid once formed. In one embodiment, the invention provides a non-naturally occurring or engineered composition comprising a CRISPR protein associated with an internal surface of an AAV capsid domain. Here again, associated may mean in some embodiments fused, or in some embodiments bound to, or in some embodiments tethered to. The CRISPR protein may, in some embodiments, be tethered to the VP1, VP2, or VP3 domain such that it locates to the internal surface of the viral capsid once formed. This may be via a connector protein or tethering system such as the biotin-streptavidin system as described above and/or elsewhere herein.

In one embodiment, the invention provides an engineered, non-naturally occurring CRISPR-Cas system comprising a AAV-Cas protein and a guide RNA that targets a DNA molecule encoding a gene product in a cell, whereby the guide RNA targets the DNA molecule encoding the gene product and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. In a preferred embodiment the Cas protein is a Cas protein. In some embodiments, the polynucleotide encoding the Cas protein is codon optimized for expression in a eukaryotic cell. In some embodiments, the eukaryotic cell is a mammalian cell and in a more preferred embodiment the mammalian cell is a human cell. In a further embodiment, the expression of the gene product is decreased.

In another embodiment, the invention provides an engineered, non-naturally occurring vector system comprising one or more vectors comprising a first regulatory element operably linked to a CRISPR-Cas system guide RNA that targets a DNA molecule encoding a gene product and a AAV-Cas protein. The components may be located on same or different vectors of the system, or may be the same vector whereby the AAV-Cas protein also delivers the RNA of the CRISPR system. The guide RNA targets the DNA molecule encoding the gene product in a cell and the AAV-Cas protein may cleaves the DNA molecule encoding the gene product (it may cleave one or both strands or have substantially no nuclease activity), whereby expression of the gene product is altered; and, wherein the AAV-Cas protein and the guide RNA do not naturally occur together. The invention comprehends the guide RNA comprising a guide sequence fused to a tracr sequence. In an embodiment of the invention the AAV-Cas protein is a type II AAV—CRISPR-Cas protein and in a preferred embodiment the AAV-Cas protein is an AAV-Cas protein. The invention further comprehends the coding for the AAV-Cas protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In one embodiment, the invention provides a vector system comprising one or more vectors. In some embodiments, the system comprises: (a) a first regulatory element operably linked to a tracr mate sequence and one or more insertion sites for inserting one or more guide sequences upstream of the tracr mate sequence, wherein when expressed, the guide sequence directs sequence-specific binding of a AAV-CRISPR complex to a target sequence in a eukaryotic cell, wherein the CRISPR complex comprises a AAV-CRISPR enzyme complexed with (1) the guide sequence that is hybridized to the target sequence, and (2) the tracr mate sequence that is hybridized to the tracr sequence; and (b) said AAV-CRISPR enzyme comprising at least one nuclear localization sequence and/or at least one NES; wherein components (a) and (b) are located on or in the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of an AAV-CRISPR complex to a different target sequence in a eukaryotic cell. In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publicly and commercially available alignment algorithms and programs such as, but not limited to, ClustalW, Smith-Waterman in matlab, Bowtie, Geneious, Biopython and SeqMan. In some embodiments, the AAV-CRISPR complex comprises one or more nuclear localization sequences of sufficient strength to drive accumulation of said CRISPR complex in a detectable amount in the nucleus of a eukaryotic cell. Without wishing to be bound by theory, it is believed that a nuclear localization sequence is not necessary for AAV-CRISPR complex activity in eukaryotes, but that including such sequences enhances activity of the system, especially as to targeting nucleic acid molecules in the nucleus and/or having molecules exit the nucleus. In some embodiments, the AAV-CRISPR enzyme is an AAV-Cas enzyme. In some embodiments, the AAV-Cas enzyme is derived from *S. pneumoniae, S. pyogenes, S. thermophiles, F. novicida* or *S. aureus* Cas9 (e.g., a Cas protein of one of these organisms modified to have or be associated with at least one AAV) and may include further mutations or alterations or be a chimeric Cas9. The enzyme may be an AAV-Cas9 homolog or ortholog. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length.

In general, in some embodiments, the AAV further comprises a repair template. It will be appreciated that comprises here may mean encompassed within the viral capsid or that the virus encodes the comprised protein. In some embodiments, one or more, preferably two or more guide RNAs, may be comprised/encompassed within the AAV vector. Two may be preferred, in some embodiments, as it allows for multiplexing or dual nickase approaches. Particularly for multiplexing, two or more guides may be used. In fact, in some embodiments, three or more, four or more, five or more, or even six or more guide RNAs may be comprised/encompassed within the AAV. More space has been freed up within the AAV by virtue of the fact that the AAV no longer needs to comprise/encompass the CRISPR enzyme. In each of these instances, a repair template may also be provided comprised/encompassed within the AAV. In some embodiments, the repair template corresponds to or includes the DNA target.

Herpes Simplex Viral Vectors

In some embodiments, the vector can be a Herpes Simplex Viral (HSV)-based vector or system thereof. HSV systems can include the disabled infections single copy (DISC) viruses, which are composed of a glycoprotein H defective mutant HSV genome. When the defective HSV is propagated in complementing cells, virus particles can be generated that are capable of infecting subsequent cells permanently replicating their own genome but are not capable of producing more infectious particles. See e.g. 2009. Trobridge. Exp. Opin. Biol. Ther. 9:1427-1436, whose techniques and vectors described therein can be modified and adapted for use in the CRISPR-Cas system of the present invention. In some embodiments where an HSV vector or system thereof is utilized, the host cell can be a complementing cell. In some embodiments, HSV vector or system thereof can be capable of producing virus particles capable of delivering a polynucleotide cargo of up to 150 kb. Thus, in some embodiment the CRISPR-Cas system polynucleotide(s) included in the HSV-based viral vector or system thereof can sum from about 0.001 to about 150 kb. HSV-based vectors and systems thereof have been successfully used in several contexts including various models of neurologic disorders. See e.g. Cockrell et al. 2007. Mol. Biotechnol. 36:184-204; Kafri T. 2004. Mol. Biol. 246:367-390; Balaggan and Ali. 2012. Gene Ther. 19:145-153; Wong et al. 2006. Hum. Gen. Ther. 2002. 17:1-9; Azzouz et al. J. Neruosci. 22L10302-10312; and Betchen and Kaplitt. 2003. Curr. Opin. Neurol. 16:487-493, whose techniques and vectors described therein can be modified and adapted for use in the CRISPR-Cas system of the present invention.

Poxvirus Vectors

In some embodiments, the vector can be a poxvirus vector or system thereof. In some embodiments, the poxvirus vector can result in cytoplasmic expression of one or more CRISPR-Cas system polynucleotides of the present invention. In some embodiments the capacity of a poxvirus vector or system thereof can be about 25 kb or more. In some embodiments, a poxvirus vector or system thereof can include one or more CRISPR-Cas system polynucleotides described herein.

Viral Vectors for Delivery to Plants

The systems and compositions may be delivered to plant cells using viral vehicles. In particular embodiments, the compositions and systems may be introduced in the plant cells using a plant viral vector (e.g., as described in Scholthof et al. 1996, Annu Rev Phytopathol. 1996; 34:299-323). Such viral vector may be a vector from a DNA virus, e.g., geminivirus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., *Faba* bean necrotic yellow virus). The viral vector may be a vector from an RNA virus, e.g., tobravirus (e.g., tobacco rattle virus, tobacco mosaic virus), potexvirus (e.g., potato virus X), or hordeivirus (e.g., barley stripe mosaic virus). The replicating genomes of plant viruses may be non-integrative vectors.

Virus Particle Production from Viral Vectors
Retroviral Production

In some embodiments, one or more viral vectors and/or system thereof can be delivered to a suitable cell line for production of virus particles containing the polynucleotide or other payload to be delivered to a host cell. Suitable host cells for virus production from viral vectors and systems thereof described herein are known in the art and are commercially available. For example, suitable host cells include HEK 293 cells and its variants (HEK 293T and HEK 293TN cells). In some embodiments, the suitable host cell for virus production from viral vectors and systems thereof described herein can stably express one or more genes involved in packaging (e.g. pol, gag, and/or VSV-G) and/or other supporting genes.

In some embodiments, after delivery of one or more viral vectors to the suitable host cells for or virus production from viral vectors and systems thereof, the cells are incubated for an appropriate length of time to allow for viral gene expression from the vectors, packaging of the polynucleotide to be delivered (e.g. an CRISPR-Cas system polynucleotide), and virus particle assembly, and secretion of mature virus particles into the culture media. Various other methods and techniques are generally known to those of ordinary skill in the art.

Mature virus particles can be collected from the culture media by a suitable method. In some embodiments, this can involve centrifugation to concentrate the virus. The titer of the composition containing the collected virus particles can be obtained using a suitable method. Such methods can include transducing a suitable cell line (e.g. NIH 3T3 cells) and determining transduction efficiency, infectivity in that cell line by a suitable method. Suitable methods include PCR-based methods, flow cytometry, and antibiotic selection-based methods. Various other methods and techniques are generally known to those of ordinary skill in the art. The concentration of virus particle can be adjusted as needed. In some embodiments, the resulting composition containing virus particles can contain $1 \times 10^1$-$1 \times 10^{20}$ particles/mL.

Lentiviruses may be prepared from any lentiviral vector or vector system described herein. In one example embodiment, after cloning pCasES10 (which contains a lentiviral transfer plasmid backbone), HEK293FT at low passage (p=5) can be seeded in a T-75 flask to 50% confluence the day before transfection in DMEM with 10% fetal bovine serum and without antibiotics. After 20 hours, the media can be changed to OptiMEM (serum-free) media and transfection of the lentiviral vectors can done 4 hours later. Cells can be transfected with 10 µg of lentiviral transfer plasmid (pCasES10) and the appropriate packaging plasmids (e.g., 5 µg of pMD2.G (VSV-g pseudotype), and 7.5 ug of psPAX2 (gag/pol/rev/tat)). Transfection can be carried out in 4 mL OptiMEM with a cationic lipid delivery agent (50 uL Lipofectamine 2000 and 100u1 Plus reagent). After 6 hours, the media can be changed to antibiotic-free DMEM with 10% fetal bovine serum. These methods can use serum during cell culture, but serum-free methods are preferred.

Following transfection and allowing the producing cells (also referred to as packaging cells) to package and produce virus particles with packaged cargo, the lentiviral particles can be purified. In an exemplary embodiment, virus-containing supernatants can be harvested after 48 hours. Collected virus-containing supernatants can first be cleared of debris and filtered through a 0.45 um low protein binding (PVDF) filter. They can then be spun in an ultracentrifuge for 2 hours at 24,000 rpm. The resulting virus-containing pellets can be resuspended in 50u1 of DMEM overnight at 4 degrees C. They can be then aliquoted and used immediately or immediately frozen at −80 degrees C. for storage.

AAV Particle Production

There are two main strategies for producing AAV particles from AAV vectors and systems thereof, such as those described herein, which depend on how the adenovirus helper factors are provided (helper v. helper free). In some embodiments, a method of producing AAV particles from AAV vectors and systems thereof can include adenovirus infection into cell lines that stably harbor AAV replication and capsid encoding polynucleotides along with AAV vector containing the polynucleotide to be packaged and delivered by the resulting AAV particle (e.g. the CRISPR-Cas system polynucleotide(s)). In some embodiments, a method of producing AAV particles from AAV vectors and systems thereof can be a "helper free" method, which includes co-transfection of an appropriate producing cell line with three vectors (e.g. plasmid vectors): (1) an AAV vector that contains a polynucleotide of interest (e.g. the CRISPR-Cas system polynucleotide(s)) between 2 ITRs; (2) a vector that carries the AAV Rep-Cap encoding polynucleotides; and (helper polynucleotides. One of skill in the art will appreciate various methods and variations thereof that are both helper and -helper free and as well as the different advantages of each system.

Non-Viral Vectors

In some embodiments, the vector is a non-viral vector or vector system. The term of art "Non-viral vector" and as used herein in this context refers to molecules and/or compositions that are vectors but that are not based on one or more component of a virus or virus genome (excluding any nucleotide to be delivered and/or expressed by the non-viral vector) that can be capable of incorporating CRISPR-Cas polynucleotide(s) and delivering said CRISPR-Cas polynucleotide(s) to a cell and/or expressing the polynucleotide in the cell. It will be appreciated that this does not exclude vectors containing a polynucleotide designed to target a virus-based polynucleotide that is to be delivered. For example, if a gRNA to be delivered is directed against a virus component and it is inserted or otherwise coupled to an otherwise non-viral vector or carrier, this would not make said vector a "viral vector". Non-viral vectors can include, without limitation, naked polynucleotides and polynucleotide (non-viral) based vector and vector systems.

Naked Polynucleotides

In some embodiments one or more CRISPR-Cas system polynucleotides described elsewhere herein can be included in a naked polynucleotide. The term of art "naked polynucleotide" as used herein refers to polynucleotides that are not associated with another molecule (e.g. proteins, lipids, and/or other molecules) that can often help protect it from environmental factors and/or degradation. As used herein, associated with includes, but is not limited to, linked to, adhered to, adsorbed to, enclosed in, enclosed in or within, mixed with, and the like. Naked polynucleotides that include one or more of the CRISPR-Cas system polynucleotides described herein can be delivered directly to a host cell and optionally expressed therein. The naked polynucleotides can have any suitable two- and three-dimensional configurations. By way of non-limiting examples, naked polynucleotides can be single-stranded molecules, double stranded molecules, circular molecules (e.g. plasmids and artificial chromosomes), molecules that contain portions that are single stranded and portions that are double stranded (e.g. ribozymes), and the like. In some embodiments, the naked polynucleotide contains only the CRISPR-Cas system polynucleotide(s) of the present invention. In some embodiments, the naked polynucleotide can contain other nucleic acids and/or polynucleotides in addition to the CRISPR-Cas system polynucleotide(s) of the present invention. The naked polynucleotides can include one or more elements of a transposon system. Transposons and system thereof are described in greater detail elsewhere herein.

Non-Viral Polynucleotide Vectors

In some embodiments, one or more of the CRISPR-Cas system polynucleotides can be included in a non-viral polynucleotide vector. Suitable non-viral polynucleotide vectors include, but are not limited to, transposon vectors and vector systems, plasmids, bacterial artificial chromosomes, yeast artificial chromosomes, AR(antibiotic resistance)-free plasmids and miniplasmids, circular covalently closed vectors (e.g. minicircles, minivectors, miniknots,), linear covalently closed vectors ("dumbbell shaped"), MIDGE (minimalistic immunologically defined gene expression) vectors, MiLV (micro-linear vector) vectors, Ministrings, mini-intronic plasmids, PSK systems (post-segregationally killing systems), ORT (operator repressor titration) plasmids, and the like. See e.g. Hardee et al. 2017. Genes. 8(2):65.

In some embodiments, the non-viral polynucleotide vector can have a conditional origin of replication. In some embodiments, the non-viral polynucleotide vector can be an ORT plasmid. In some embodiments, the non-viral polynucleotide vector can have a minimalistic immunologically defined gene expression. In some embodiments, the non-viral polynucleotide vector can have one or more post-segregationally killing system genes. In some embodiments, the non-viral polynucleotide vector is AR-free. In some embodiments, the non-viral polynucleotide vector is a minivector. In some embodiments, the non-viral polynucleotide vector includes a nuclear localization signal. In some embodiments, the non-viral polynucleotide vector can include one or more CpG motifs. In some embodiments, the non-viral polynucleotide vectors can include one or more scaffold/matrix attachment regions (S/MARs). See e.g. Mirkovitch et al. 1984. Cell. 39:223-232, Wong et al. 2015. Adv. Genet. 89:113-152, whose techniques and vectors can be adapted for use in the present invention. S/MARs are AT-rich sequences that play a role in the spatial organization of chromosomes through DNA loop base attachment to the nuclear matrix. S/MARs are often found close to regulatory elements such as promoters, enhancers, and origins of DNA replication. Inclusion of one or S/MARs can facilitate a once-per-cell-cycle replication to maintain the non-viral polynucleotide vector as an episome in daughter cells. In certain embodiments, the S/MAR sequence is located downstream of an actively transcribed polynucleotide (e.g. one or more CRISPR-Cas system polynucleotides of the present invention) included in the non-viral polynucleotide vector. In some embodiments, the S/MAR can be a S/MAR from the beta-interferon gene cluster. See e.g. Verghese et al. 2014. Nucleic Acid Res. 42:e53; Xu et al. 2016. Sci. China Life Sci. 59:1024-1033; Jin et al. 2016. 8:702-711; Koirala et al. 2014. Adv. Exp. Med. Biol. 801:703-709; and Nehlsen et al. 2006. Gene Ther. Mol. Biol. 10:233-244, whose techniques and vectors can be adapted for use in the present invention.

In some embodiments, the non-viral vector is a transposon vector or system thereof. As used herein, "transposon" (also referred to as transposable element) refers to a polynucleotide sequence that is capable of moving form location in a genome to another. There are several classes of transposons. Transposons include retrotransposons and DNA transposons. Retrotransposons require the transcription of the polynucleotide that is moved (or transposed) in order to transpose the polynucleotide to a new genome or polynucleotide. DNA transposons are those that do not require reverse transcription of the polynucleotide that is moved (or transposed) in order to transpose the polynucleotide to a new genome or polynucleotide. In some embodiments, the non-viral polynucleotide vector can be a retrotransposon vector. In some embodiments, the retrotransposon vector includes long terminal repeats. In some embodiments, the retrotransposon vector does not include long terminal repeats. In some embodiments, the non-viral polynucleotide vector can be a DNA transposon vector. DNA transposon vectors can include a polynucleotide sequence encoding a transposase. In some embodiments, the transposon vector is configured as a non-autonomous transposon vector, meaning that the transposition does not occur spontaneously on its own. In some of these embodiments, the transposon vector lacks one or more polynucleotide sequences encoding proteins required for transposition. In some embodiments, the non-autonomous transposon vectors lack one or more Ac elements.

In some embodiments a non-viral polynucleotide transposon vector system can include a first polynucleotide vector that contains the CRISPR-Cas system polynucleotide(s) of the present invention flanked on the 5' and 3' ends by transposon terminal inverted repeats (TIRs) and a second polynucleotide vector that includes a polynucleotide capable of encoding a transposase coupled to a promoter to drive expression of the transposase. When both are expressed in the same cell the transposase can be expressed from the second vector and can transpose the material between the TIRs on the first vector (e.g. the CRISPR-Cas system polynucleotide(s) of the present invention) and integrate it into one or more positions in the host cell's genome. In some embodiments the transposon vector or system thereof can be configured as a gene trap. In some embodiments, the TIRs can be configured to flank a strong splice acceptor site followed by a reporter and/or other gene (e.g. one or more of the CRISPR-Cas system polynucleotide(s) of the present invention) and a strong poly A tail. When transposition occurs while using this vector or system thereof, the transposon can insert into an intron of a gene and the inserted reporter or other gene can provoke a mis-splicing process and as a result it in activates the trapped gene.

Any suitable transposon system can be used. Suitable transposon and systems thereof can include, Sleeping Beauty transposon system (Tc1/mariner superfamily) (see e.g. Ivies et al. 1997. Cell. 91(4): 501-510), piggyBac (piggyBac superfamily) (see e.g. Li et al. 2013 110(25): E2279-E2287 and Yusa et al. 2011. PNAS. 108(4): 1531-1536), To12 (superfamily hAT), Frog Prince (Tc1/mariner superfamily) (see e.g. Miskey et al. 2003 Nucleic Acid Res. 31(23):6873-6881) and variants thereof.

Non-Vector Delivery Vehicles

The delivery vehicles may comprise non-viral vehicles. In general, methods and vehicles capable of delivering nucleic acids and/or proteins may be used for delivering the systems compositions herein. Examples of non-viral vehicles include lipid nanoparticles, cell-penetrating peptides (CPPs), DNA nanoclews, metal nanoparticles, streptolysin 0, multifunctional envelope-type nanodevices (MENDs), lipid-coated mesoporous silica particles, and other inorganic nanoparticles.

Lipid Particles

The delivery vehicles may comprise lipid particles, e.g., lipid nanoparticles (LNPs) and liposomes. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, International Patent Publication Nos. WO 91/17424 and WO 91/16024. The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Lipid Nanoparticles (LNPs)

LNPs may encapsulate nucleic acids within cationic lipid particles (e.g., liposomes), and may be delivered to cells with relative ease. In some examples, lipid nanoparticles do not contain any viral components, which helps minimize safety and immunogenicity concerns. Lipid particles may be used for in vitro, ex vivo, and in vivo deliveries. Lipid particles may be used for various scales of cell populations.

In some examples. LNPs may be used for delivering DNA molecules (e.g., those comprising coding sequences of Cas and/or gRNA) and/or RNA molecules (e.g., mRNA of Cas, gRNAs). In certain cases, LNPs may be use for delivering RNP complexes of Cas/gRNA.

Components in LNPs may comprise cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), R-3-[(ro-methoxy-poly(ethylene glycol) 2000) carbamoyl]-1,2-dimyristyloxlpropyl-3-amine (PEG-C-DOMG, and any combination thereof. Preparation of LNPs and encapsulation may be adapted from Rosin et al, Molecular Therapy, vol. 19, no. 12, pages 1286-2200, December 2011).

In some embodiments, an LNP delivery vehicle can be used to deliver a virus particle containing a CRISPR-Cas system and/or component(s) thereof. In some embodiments, the virus particle(s) can be adsorbed to the lipid particle, such as through electrostatic interactions, and/or can be attached to the liposomes via a linker.

In some embodiments, the LNP contains a nucleic acid, wherein the charge ratio of nucleic acid backbone phosphates to cationic lipid nitrogen atoms is about 1: 1.5-7 or about 1:4.

In some embodiments, the LNP also includes a shielding compound, which is removable from the lipid composition under in vivo conditions. In some embodiments, the shielding compound is a biologically inert compound. In some embodiments, the shielding compound does not carry any charge on its surface or on the molecule as such. In some embodiments, the shielding compounds are polyethylenglycoles (PEGs), hydroxyethylglucose (HEG) based polymers, polyhydroxyethyl starch (polyHES) and polypropylene. In some embodiments, the PEG, HEG, polyHES, and a polypropylene weight between about 500 to 10,000 Da or between about 2000 to 5000 Da. In some embodiments, the shielding compound is PEG2000 or PEG5000.

In some embodiments, the LNP can include one or more helper lipids. In some embodiments, the helper lipid can be a phosphor lipid or a steroid. In some embodiments, the helper lipid is between about 20 mol % to 80 mol % of the total lipid content of the composition. In some embodiments, the helper lipid component is between about 35 mol % to 65 mol % of the total lipid content of the LNP. In some embodiments, the LNP includes lipids at 50 mol % and the helper lipid at 50 mol % of the total lipid content of the LNP.

Other non-limiting, exemplary LNP delivery vehicles are described in U.S. Patent Publication Nos. US 20160174546, US 20140301951, US 20150105538, US 20150250725, Wang et al., J. Control Release, 2017 Jan. 31. pii: 50168-3659(17)30038-X. doi: 10.1016/j.jconrel.2017.01.037. [Epub ahead of print]; Altinoglu et al., Biomater Sci., 4(12):1773-80, Nov. 15, 2016; Wang et al., PNAS, 113(11): 2868-73 Mar. 15, 2016; Wang et al., PloS One, 10(11): e0141860. doi: 10.1371/journal.pone.0141860. eCollection 2015, Nov. 3, 2015; Takeda et al., Neural Regen Res. 10(5):689-90, May 2015; Wang et al., Adv. Healthc Mater., 3(9):1398-403, September 2014; and Wang et al., Agnew Chem Int Ed Engl., 53(11):2893-8, Mar. 10, 2014; James E. Dahlman and Carmen Barnes et al. Nature Nanotechnology (2014) published online 11 May 2014, doi:10.1038/nnano.2014.84; Coelho et al., N Engl J Med 2013; 369:819-29; Aleku et al., Cancer Res., 68(23): 9788-98 (Dec. 1, 2008), Strumberg et al., Int. J. Clin. Pharmacol. Ther., 50(1): 76-8 (January 2012), Schultheis et al., J. Clin. Oncol., 32(36): 4141-48 (Dec. 20, 2014), and Fehring et al., Mol. Ther., 22(4): 811-20 (Apr. 22, 2014); Novobrantseva, Molecular Therapy—Nucleic Acids (2012) 1, e4; doi: 10.1038/mtna.2011.3; WO2012135025; US 20140348900; US 20140328759; US 20140308304; WO 2005/105152; WO 2006/069782; WO 2007/121947; US 2015/082080; US 20120251618; 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316;

Liposomes

In some embodiments, a lipid particle may be liposome. Liposomes are spherical vesicle structures composed of a uni- or multilamellar lipid bilayer surrounding internal aqueous compartments and a relatively impermeable outer lipophilic phospholipid bilayer. In some embodiments, liposomes are biocompatible, nontoxic, can deliver both hydrophilic and lipophilic drug molecules, protect their cargo from degradation by plasma enzymes, and transport their load across biological membranes and the blood brain barrier (BBB).

Liposomes can be made from several different types of lipids, e.g., phospholipids. A liposome may comprise natural phospholipids and lipids such as 1,2-distearoryl-sn-glycero-3-phosphatidyl choline (DSPC), sphingomyelin, egg phosphatidylcholines, monosialoganglioside, or any combination thereof.

Several other additives may be added to liposomes in order to modify their structure and properties. For instance, liposomes may further comprise cholesterol, sphingomyelin, and/or 1,2-dioleoyl-sn-glycero-3-phosphoethanolamine (DOPE), e.g., to increase stability and/or to prevent the leakage of the liposomal inner cargo.

In some embodiments, a liposome delivery vehicle can be used to deliver a virus particle containing a CRISPR-Cas system and/or component(s) thereof. In some embodiments, the virus particle(s) can be adsorbed to the liposome, such as through electrostatic interactions, and/or can be attached to the liposomes via a linker.

In some embodiments, the liposome can be a Trojan Horse liposome (also known in the art as Molecular Trojan Horses), see e.g. http://cshprotocols.cshlp.org/content/2010/

4/pdb.prot5407.long, the teachings of which can be applied and/or adapted to generated and/or deliver the CRISPR-Cas systems described herein.

Other non-limiting, exemplary liposomes can be those as set forth in Wang et al., ACS Synthetic Biology, 1, 403-07 (2012); Wang et al., PNAS, 113(11) 2868-2873 (2016); Spuch and Navarro, Journal of Drug Delivery, vol. 2011, Article ID 469679, 12 pages, 2011. doi:10.1155/2011/469679; WO 2008/042973; U.S. Pat. No. 8,071,082; WO 2014/186366; 20160257951; US20160129120; US 20160244761; 20120251618; WO2013/093648; Lipofectin (a combination of DOTMA and DOPE), Lipofectase, LIPOFECTAMINE® (e.g., LIPOFECTAMINE® 2000, LIPOFECTAMINE® 3000, LIPOFECTAMINE® RNAiMAX, LIPOFECTAMINE® LTX), SAINT-RED (Synvolux Therapeutics, Groningen Netherlands), DOPE, Cytofectin (Gilead Sciences, Foster City, Calif.), and Eufectins (JBL, San Luis Obispo, Calif.).

Stable Nucleic-Acid-Lipid Particles (SNALPs)

In some embodiments, the lipid particles may be stable nucleic acid lipid particles (SNALPs). SNALPs may comprise an ionizable lipid (DLinDMA) (e.g., cationic at low pH), a neutral helper lipid, cholesterol, a diffusible polyethylene glycol (PEG)-lipid, or any combination thereof. In some examples, SNALPs may comprise synthetic cholesterol, dipalmitoylphosphatidylcholine, 3-N-[(w-methoxy polyethylene glycol)2000)carbamoyl]-1,2-dimyrestyloxy-propylamine, and cationic 1,2-dilinoleyloxy-3-N,Ndimethylaminopropane. In some examples, SNALPs may comprise synthetic cholesterol, 1,2-distearoyl-sn-glycero-3-phosphocholine, PEG-cDMA, and 1,2-dilinoleyloxy-3-(N;N-dimethyl)aminopropane (DLinDMAo).

Other non-limiting, exemplary SNALPs that can be used to deliver the CRISPR-Cas systems described herein can be any such SNALPs as described in Morrissey et al., Nature Biotechnology, Vol. 23, No. 8, August 2005, Zimmerman et al., Nature Letters, Vol. 441, 4 May 2006; Geisbert et al., Lancet 2010; 375: 1896-905; Judge, J. Clin. Invest. 119: 661-673 (2009); and Semple et al., Nature Niotechnology, Volume 28 Number 2 Feb. 2010, pp. 172-177.

Other Lipids

The lipid particles may also comprise one or more other types of lipids, e.g., cationic lipids, such as amino lipid 2,2-dilinoleyl-4-dimethylaminoethyl[1,3]-dioxolane (DLin-KC2-DMA), DLin-KC2-DMA4, C12-200 and colipids disteroylphosphatidyl choline, cholesterol, and PEG-DMG.

In some embodiments, the delivery vehicle can be or include a lipidoid, such as any of those set forth in, for example, US 20110293703.

In some embodiments, the delivery vehicle can be or include an amino lipid, such as any of those set forth in, for example, Jayaraman, Angew. Chem. Int. Ed. 2012, 51, 8529-8533.

In some embodiments, the delivery vehicle can be or include a lipid envelope, such as any of those set forth in, for example, Korman et al., 2011. Nat. Biotech. 29:154-157.

Lipoplexes/Polyplexes

In some embodiments, the delivery vehicles comprise lipoplexes and/or polyplexes. Lipoplexes may bind to negatively charged cell membrane and induce endocytosis into the cells. Examples of lipoplexes may be complexes comprising lipid(s) and non-lipid components. Examples of lipoplexes and polyplexes include FuGENE-6 reagent, a non-liposomal solution containing lipids and other components, zwitterionic amino lipids (ZALs), Ca2k (e.g., forming DNA/$Ca^{2+}$ microcomplexes), polyethenimine (PEI) (e.g., branched PEI), and poly(L-lysine) (PLL).

Sugar-Based Particles

In some embodiments, the delivery vehicle can be a sugar-based particle. In some embodiments, the sugar-based particles can be or include GalNAc, such as any of those described in WO2014118272; US 20020150626; Nair, J K et al., 2014, Journal of the American Chemical Society 136 (49), 16958-16961; Ostergaard et al., Bioconjugate Chem., 2015, 26 (8), pp 1451-1455;

Cell Penetrating Peptides

In some embodiments, the delivery vehicles comprise cell penetrating peptides (CPPs). CPPs are short peptides that facilitate cellular uptake of various molecular cargo (e.g., from nanosized particles to small chemical molecules and large fragments of DNA).

CPPs may be of different sizes, amino acid sequences, and charges. In some examples, CPPs can translocate the plasma membrane and facilitate the delivery of various molecular cargoes to the cytoplasm or an organelle. CPPs may be introduced into cells via different mechanisms, e.g., direct penetration in the membrane, endocytosis-mediated entry, and translocation through the formation of a transitory structure.

CPPs may have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. Another type of CPPs is the trans-activating transcriptional activator (Tat) from Human Immunodeficiency Virus 1 (HIV-1). Examples of CPPs include to Penetratin, Tat (48-60), Transportan, and (R-AhX-R4) (Ahx refers to aminohexanoyl), Kaposi fibroblast growth factor (FGF) signal peptide sequence, integrin β3 signal peptide sequence, polyarginine peptide Args sequence, Guanine rich-molecular transporters, and sweet arrow peptide. Examples of CPPs and related applications also include those described in U.S. Pat. No. 8,372,951.

CPPs can be used for in vitro and ex vivo work quite readily, and extensive optimization for each cargo and cell type is usually required. In some examples, CPPs may be covalently attached to the Cas protein directly, which is then complexed with the gRNA and delivered to cells. In some examples, separate delivery of CPP-Cas and CPP-gRNA to multiple cells may be performed. CPP may also be used to delivery RNPs.

CPPs may be used to deliver the compositions and systems to plants. In some examples, CPPs may be used to deliver the components to plant protoplasts, which are then regenerated to plant cells and further to plants.

DNA Nanoclews

In some embodiments, the delivery vehicles comprise DNA nanoclews. A DNA nanoclew refers to a sphere-like structure of DNA (e.g., with a shape of a ball of yarn). The nanoclew may be synthesized by rolling circle amplification with palindromic sequences that aide in the self-assembly of the structure. The sphere may then be loaded with a payload. An example of DNA nanoclew is described in Sun W et al, J Am Chem Soc. 2014 Oct. 22; 136(42):14722-5; and Sun W et al, Angew Chem Int Ed Engl. 2015 Oct. 5; 54(41):12029-33. DNA nanoclew may have a palindromic sequences to be partially complementary to the gRNA within the Cas:gRNA ribonucleoprotein complex. A DNA nanoclew may be coated, e.g., coated with PEI to induce endosomal escape.

Metal Nanoparticles

In some embodiments, the delivery vehicles comprise gold nanoparticles (also referred to AuNPs or colloidal gold). Gold nanoparticles may form complex with cargos, e.g., Cas:gRNA RNP. Gold nanoparticles may be coated, e.g., coated in a silicate and an endosomal disruptive polymer, PAsp(DET). Examples of gold nanoparticles include AuraSense Therapeutics' Spherical Nucleic Acid (SNA™) constructs, and those described in Mout R, et al. (2017). ACS Nano 11:2452-8; Lee K, et al. (2017). Nat Biomed Eng 1:889-901. Other metal nanoparticles can also be complexed with cargo(s). Such metal particles include, tungsten, palladium, rhodium, platinum, and iridium particles. Other non-limiting, exemplary metal nanoparticles are described in US 20100129793.

iTOP

In some embodiments, the delivery vehicles comprise iTOP. iTOP refers to a combination of small molecules drives the highly efficient intracellular delivery of native proteins, independent of any transduction peptide. iTOP may be used for induced transduction by osmocytosis and propanebetaine, using NaCl-mediated hyperosmolality together with a transduction compound (propanebetaine) to trigger macropinocytotic uptake into cells of extracellular macromolecules. Examples of iTOP methods and reagents include those described in D'Astolfo D S, Pagliero R J, Pras A, et al. (2015). Cell 161:674-690.

Polymer-Based Particles

In some embodiments, the delivery vehicles may comprise polymer-based particles (e.g., nanoparticles). In some embodiments, the polymer-based particles may mimic a viral mechanism of membrane fusion. The polymer-based particles may be a synthetic copy of Influenza virus machinery and form transfection complexes with various types of nucleic acids ((siRNA, miRNA, plasmid DNA or shRNA, mRNA) that cells take up via the endocytosis pathway, a process that involves the formation of an acidic compartment. The low pH in late endosomes acts as a chemical switch that renders the particle surface hydrophobic and facilitates membrane crossing. Once in the cytosol, the particle releases its payload for cellular action. This Active Endosome Escape technology is safe and maximizes transfection efficiency as it is using a natural uptake pathway. In some embodiments, the polymer-based particles may comprise alkylated and carboxyalkylated branched polyethylenimine. In some examples, the polymer-based particles are VIROMER, e.g., VIROMER RNAi, VIROMER RED, VIROMER mRNA, VIROMER CRISPR. Example methods of delivering the systems and compositions herein include those described in Bawage S S et al., Synthetic mRNA expressed Cas13a mitigates RNA virus infections, www.biorxiv.org/content/10.1101/370460v1.full doi: doi.org/10.1101/370460, Viromer® RED, a powerful tool for transfection of keratinocytes. doi: 10.13140/RG.2.2.16993.61281, Viromer® Transfection—Factbook 2018: technology, product overview, users' data., doi: 10.13140/RG.2.2.23912.16642. Other exemplary and non-limiting polymeric particles are described in US 20170079916, US 20160367686, US 20110212179, US 20130302401, 6,007,845, 5,855,913, 5,985,309, 5,543,158, WO2012135025, US 20130252281, US 20130245107, US 20130244279; US 20050019923, 20080267903;

Streptolysin O (SLO)

The delivery vehicles may be streptolysin 0 (SLO). SLO is a toxin produced by Group A streptococci that works by creating pores in mammalian cell membranes. SLO may act in a reversible manner, which allows for the delivery of proteins (e.g., up to 100 kDa) to the cytosol of cells without compromising overall viability. Examples of SLO include those described in Sierig G, et al. (2003). Infect Immun 71:446-55; Walev I, et al. (2001). Proc Natl Acad Sci USA 98:3185-90; Teng K W, et al. (2017). Elife 6:e25460.

Multifunctional Envelope-Type Nanodevice (MEND)

The delivery vehicles may comprise multifunctional envelope-type nanodevice (MENDs). MENDs may comprise condensed plasmid DNA, a PLL core, and a lipid film shell. A MEND may further comprise cell-penetrating peptide (e.g., stearyl octaarginine). The cell penetrating peptide may be in the lipid shell. The lipid envelope may be modified with one or more functional components, e.g., one or more of: polyethylene glycol (e.g., to increase vascular circulation time), ligands for targeting of specific tissues/cells, additional cell-penetrating peptides (e.g., for greater cellular delivery), lipids to enhance endosomal escape, and nuclear delivery tags. In some examples, the MEND may be a tetra-lamellar MEND (T-MEND), which may target the cellular nucleus and mitochondria. In certain examples, a MEND may be a PEG-peptide-DOPE-conjugated MEND (PPD-MEND), which may target bladder cancer cells. Examples of MENDs include those described in Kogure K, et al. (2004). J Control Release 98:317-23; Nakamura T, et al. (2012). Acc Chem Res 45:1113-21.

Lipid-Coated Mesoporous Silica Particles

The delivery vehicles may comprise lipid-coated mesoporous silica particles. Lipid-coated mesoporous silica particles may comprise a mesoporous silica nanoparticle core and a lipid membrane shell. The silica core may have a large internal surface area, leading to high cargo loading capacities. In some embodiments, pore sizes, pore chemistry, and overall particle sizes may be modified for loading different types of cargos. The lipid coating of the particle may also be modified to maximize cargo loading, increase circulation times, and provide precise targeting and cargo release. Examples of lipid-coated mesoporous silica particles include those described in Du X, et al. (2014). Biomaterials 35:5580-90; Durfee P N, et al. (2016). ACS Nano 10:8325-45.

Inorganic Nanoparticles

The delivery vehicles may comprise inorganic nanoparticles. Examples of inorganic nanoparticles include carbon nanotubes (CNTs) (e.g., as described in Bates K and Kostarelos K. (2013). Adv Drug Deliv Rev 65:2023-33.), bare mesoporous silica nanoparticles (MSNPs) (e.g., as described in Luo G F, et al. (2014). Sci Rep 4:6064), and dense silica nanoparticles (SiNPs) (as described in Luo D and Saltzman W M. (2000). Nat Biotechnol 18:893-5).

Exosomes

The delivery vehicles may comprise exosomes. Exosomes include membrane bound extracellular vesicles, which can be used to contain and delivery various types of biomolecules, such as proteins, carbohydrates, lipids, and nucleic acids, and complexes thereof (e.g., RNPs). Examples of exosomes include those described in Schroeder A, et al., J Intern Med. 2010 January; 267(1):9-21; El-Andaloussi S, et al., Nat Protoc. 2012 December; 7(12):2112-26; Uno Y, et al., Hum Gene Ther. 2011 June; 22(6):711-9; Zou W, et al., Hum Gene Ther. 2011 April; 22(4):465-75.

In some examples, the exosome may form a complex (e.g., by binding directly or indirectly) to one or more components of the cargo. In certain examples, a molecule of an exosome may be fused with first adapter protein and a component of the cargo may be fused with a second adapter protein. The first and the second adapter protein may specifically bind each other, thus associating the cargo with the exosome. Examples of such exosomes include those described in Ye Y, et al., Biomater Sci. 2020 Apr. 28. doi: 10.1039/d0bm00427h.

Other non-limiting, exemplary exosomes include any of those set forth in Alvarez-Erviti et al. 2011, Nat Biotechnol 29: 341; [1401] El-Andaloussi et al. (Nature Protocols 7:2112-2126(2012); and Wahlgren et al. (Nucleic Acids Research, 2012, Vol. 40, No. 17 e130).

Spherical Nucleic Acids (SNAs)

In some embodiments, the delivery vehicle can be a SNA. SNAs are three dimensional nanostructures that can be composed of densely functionalized and highly oriented nucleic acids that can be covalently attached to the surface of spherical nanoparticle cores. The core of the spherical nucleic acid can impart the conjugate with specific chemical and physical properties, and it can act as a scaffold for assembling and orienting the oligonucleotides into a dense spherical arrangement that gives rise to many of their functional properties, distinguishing them from all other forms of matter. In some embodiments, the core is a cross-linked polymer. Non-limiting, exemplary SNAs can be any of those set forth in Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., and Small, 10:186-192.

Self-Assembling Nanoparticles

In some embodiments, the delivery vehicle is a self-assembling nanoparticle. The self-assembling nanoparticles can contain one or more polymers. The self-assembling nanoparticles can be PEGylated. Self-assembling nanoparticles are known in the art. Non-limiting, exemplary self-assembling nanoparticles can any as set forth in Schiffelers et al., Nucleic Acids Research, 2004, Vol. 32, No. 19, Bartlett et al. (PNAS, Sep. 25, 2007, vol. 104, no. 39; Davis et al., Nature, Vol 464, 15 Apr. 2010.

Supercharged Proteins

In some embodiments, the delivery vehicle can be a supercharged protein. As used herein "Supercharged proteins" are a class of engineered or naturally occurring proteins with unusually high positive or negative net theoretical charge. Non-limiting, exemplary supercharged proteins can be any of those set forth in Lawrence et al., 2007, Journal of the American Chemical Society 129, 10110-10112.

Targeted Delivery

In some embodiments, the delivery vehicle can allow for targeted delivery to a specific cell, tissue, organ, or system. In such embodiments, the delivery vehicle can include one or more targeting moieties that can direct targeted delivery of the cargo(s). In an embodiment, the delivery vehicle comprises a targeting moiety, such as active targeting of a lipid entity of the invention, e.g., lipid particle or nanoparticle or liposome or lipid bilayer of the invention comprising a targeting moiety for active targeting.

With regard to targeting moieties, mention is made of Deshpande et al, "Current trends in the use of liposomes for tumor targeting," Nanomedicine (Lond). 8(9), doi:10.2217/nnm.13.118 (2013), and the documents it cites, all of which are incorporated herein by reference and the teachings of which can be applied and/or adapted for targeted delivery of one or more CRISPR-Cas molecules described herein. Mention is also made of International Patent Publication No. WO 2016/027264, and the documents it cites, all of which are incorporated herein by reference, the teachings of which can be applied and/or adapted for targeted delivery of one or more CRISPR-Cas molecules described herein. And mention is made of Lorenzer et al, "Going beyond the liver: Progress and challenges of targeted delivery of siRNA therapeutics," Journal of Controlled Release, 203: 1-15 (2015), and the documents it cites, all of which are incorporated herein by reference, the teachings of which can be applied and/or adapted for targeted delivery of one or more CRISPR-Cas molecules described herein.

An actively targeting lipid particle or nanoparticle or liposome or lipid bilayer delivery system (generally as to embodiments of the invention, "lipid entity of the invention" delivery systems) are prepared by conjugating targeting moieties, including small molecule ligands, peptides and monoclonal antibodies, on the lipid or liposomal surface; for example, certain receptors, such as folate and transferrin (Tf) receptors (TfR), are overexpressed on many cancer cells and have been used to make liposomes tumor cell specific. Liposomes that accumulate in the tumor microenvironment can be subsequently endocytosed into the cells by interacting with specific cell surface receptors. To efficiently target liposomes to cells, such as cancer cells, it is useful that the targeting moiety have an affinity for a cell surface receptor and to link the targeting moiety in sufficient quantities to have optimum affinity for the cell surface receptors; and determining these embodiments are within the ambit of the skilled artisan. In the field of active targeting, there are a number of cell-, e.g., tumor-, specific targeting ligands.

Also, as to active targeting, with regard to targeting cell surface receptors such as cancer cell surface receptors, targeting ligands on liposomes can provide attachment of liposomes to cells, e.g., vascular cells, via a noninternalizing epitope; and, this can increase the extracellular concentration of that which is being delivered, thereby increasing the amount delivered to the target cells. A strategy to target cell surface receptors, such as cell surface receptors on cancer cells, such as overexpressed cell surface receptors on cancer cells, is to use receptor-specific ligands or antibodies. Many cancer cell types display upregulation of tumor-specific receptors. For example, TfRs and folate receptors (FRs) are greatly overexpressed by many tumor cell types in response to their increased metabolic demand. Folic acid can be used as a targeting ligand for specialized delivery owing to its ease of conjugation to nanocarriers, its high affinity for FRs and the relatively low frequency of FRs, in normal tissues as compared with their overexpression in activated macrophages and cancer cells, e.g., certain ovarian, breast, lung, colon, kidney and brain tumors. Overexpression of FR on macrophages is an indication of inflammatory diseases, such as psoriasis, Crohn's disease, rheumatoid arthritis and atherosclerosis; accordingly, folate-mediated targeting of the invention can also be used for studying, addressing or treating inflammatory disorders, as well as cancers. Folate-linked lipid particles or nanoparticles or liposomes or lipid bylayers of the invention ("lipid entity of the invention") deliver their cargo intracellularly through receptor-mediated endocytosis. Intracellular trafficking can be directed to acidic compartments that facilitate cargo release, and, most importantly, release of the cargo can be altered or delayed until it reaches the cytoplasm or vicinity of target organelles. Delivery of cargo using a lipid entity of the invention having a targeting moiety, such as a folate-linked lipid entity of the invention, can be superior to nontargeted lipid entity of the invention. The attachment of folate directly to the lipid head groups may not be favorable for intracellular delivery of folate-conjugated lipid entity of the invention, since they may not bind as efficiently to cells as folate attached to the lipid entity of the invention surface by a spacer, which may can enter cancer cells more efficiently. A lipid entity of the invention coupled to folate can be used for the delivery of complexes of lipid, e.g., liposome, e.g., anionic liposome and virus or capsid or envelope or virus outer protein, such as those herein discussed such as adenovirous or AAV. Tf is a monomeric serum glycoprotein of approximately 80 KDa involved in the transport of iron throughout the body. Tf binds to the TfR and translocates into cells via receptor-mediated endocytosis. The expression of TfR is can be higher in certain cells, such as tumor cells (as compared with normal cells and is associated with the increased iron demand in rapidly proliferating cancer cells. Accordingly, the invention comprehends a TfR-targeted lipid entity of the invention, e.g., as to liver cells, liver cancer, breast cells such as breast cancer cells, colon such as colon cancer cells, ovarian cells such as ovarian cancer cells, head, neck and lung cells, such as head, neck and non-small-cell lung cancer cells, cells of the mouth such as oral tumor cells.

Also, as to active targeting, a lipid entity of the invention can be multifunctional, i.e., employ more than one targeting moiety such as CPP, along with Tf; a bifunctional system; e.g., a combination of Tf and poly-L-arginine which can provide transport across the endothelium of the blood-brain barrier. EGFR, is a tyrosine kinase receptor belonging to the ErbB family of receptors that mediates cell growth, differentiation and repair in cells, especially non-cancerous cells, but EGF is overexpressed in certain cells such as many solid tumors, including colorectal, non-small-cell lung cancer, squamous cell carcinoma of the ovary, kidney, head, pancreas, neck and prostate, and especially breast cancer. The invention comprehends EGFR-targeted monoclonal antibody(ies) linked to a lipid entity of the invention. HER-2 is often overexpressed in patients with breast cancer, and is also associated with lung, bladder, prostate, brain and stomach cancers. HER-2, encoded by the ERBB2 gene. The invention comprehends a HER-2-targeting lipid entity of the invention, e.g., an anti-HER-2-antibody(or binding fragment thereof)-lipid entity of the invention, a HER-2-targeting-PEGylated lipid entity of the invention (e.g., having an anti-HER-2-antibody or binding fragment thereof), a HER-2-targeting-maleimide-PEG polymer-lipid entity of the invention (e.g., having an anti-HER-2-antibody or binding fragment thereof). Upon cellular association, the receptor-antibody complex can be internalized by formation of an endosome for delivery to the cytoplasm.

With respect to receptor-mediated targeting, the skilled artisan takes into consideration ligand/target affinity and the quantity of receptors on the cell surface, and that PEGylation can act as a barrier against interaction with receptors. The use of antibody-lipid entity of the invention targeting can be advantageous. Multivalent presentation of targeting moieties can also increase the uptake and signaling properties of antibody fragments. In practice of the invention, the skilled person takes into account ligand density (e.g., high ligand densities on a lipid entity of the invention may be advantageous for increased binding to target cells). Preventing early by macrophages can be addressed with a sterically stabilized lipid entity of the invention and linking ligands to the terminus of molecules such as PEG, which is anchored in the lipid entity of the invention (e.g., lipid particle or nanoparticle or liposome or lipid bilayer). The microenvironment of a cell mass such as a tumor microenvironment can be targeted; for instance, it may be advantageous to target cell mass vasculature, such as the tumor vasculature microenvironment. Thus, the invention comprehends targeting VEGF. VEGF and its receptors are well-known proangiogenic molecules and are well-characterized targets for antiangiogenic therapy. Many small-molecule inhibitors of receptor tyrosine kinases, such as VEGFRs or basic FGFRs, have been developed as anticancer agents and the invention comprehends coupling any one or more of these peptides to a lipid entity of the invention, e.g., phage IVO peptide(s) (e.g., via or with a PEG terminus), tumor-homing peptide APRPG such as APRPG-PEG-modified. VCAM, the vascular endothelium plays a key role in the pathogenesis of inflammation, thrombosis and atherosclerosis. CAMs are involved in inflammatory disorders, including cancer, and are a logical target, E- and P-selectins, VCAM-1 and ICAMs. Can be used to target a lipid entity of the invention., e.g., with PEGylation.

Matrix metalloproteases (MMPs) belong to the family of zinc-dependent endopeptidases. They are involved in tissue remodeling, tumor invasiveness, resistance to apoptosis and metastasis. There are four MMP inhibitors called TIMP1-4, which determine the balance between tumor growth inhibition and metastasis; a protein involved in the angiogenesis of tumor vessels is MT1-MMP, expressed on newly formed vessels and tumor tissues. The proteolytic activity of MT1-MMP cleaves proteins, such as fibronectin, elastin, collagen and laminin, at the plasma membrane and activates soluble MMPs, such as MMP-2, which degrades the matrix. An antibody or fragment thereof such as a Fab' fragment can be used in the practice of the invention such as for an antihuman MT1-MMP monoclonal antibody linked to a lipid entity of the invention, e.g., via a spacer such as a PEG spacer. αβ-integrins or integrins are a group of transmembrane glycoprotein receptors that mediate attachment between a cell and its surrounding tissues or extracellular matrix.

Integrins contain two distinct chains (heterodimers) called α- and β-subunits. The tumor tissue-specific expression of integrin receptors can be been utilized for targeted delivery in the invention, e.g., whereby the targeting moiety can be an RGD peptide such as a cyclic RGD.

Aptamers are ssDNA or RNA oligonucleotides that impart high affinity and specific recognition of the target molecules by electrostatic interactions, hydrogen bonding and hydro phobic interactions as opposed to the Watson-Crick base pairing, which is typical for the bonding interactions of oligonucleotides. Aptamers as a targeting moiety can have advantages over antibodies: aptamers can demonstrate higher target antigen recognition as compared with antibodies; aptamers can be more stable and smaller in size as compared with antibodies; aptamers can be easily synthesized and chemically modified for molecular conjugation; and aptamers can be changed in sequence for improved selectivity and can be developed to recognize poorly immunogenic targets. Such moieties as a sgc8 aptamer can be used as a targeting moiety (e.g., via covalent linking to the lipid entity of the invention, e.g., via a spacer, such as a PEG spacer).

Also, as to active targeting, the invention also comprehends intracellular delivery. Since liposomes follow the endocytic pathway, they are entrapped in the endosomes (pH 6.5-6) and subsequently fuse with lysosomes (pH<5), where they undergo degradation that results in a lower therapeutic potential. The low endosomal pH can be taken advantage of to escape degradation. Fusogenic lipids or peptides, which destabilize the endosomal membrane after the conformational transition/activation at a lowered pH. Amines are protonated at an acidic pH and cause endosomal swelling and rupture by a buffer effect Unsaturated dioleoylphosphatidylethanolamine (DOPE) readily adopts an inverted hexagonal shape at a low pH, which causes fusion of liposomes to the endosomal membrane. This process destabilizes a lipid entity containing DOPE and releases the cargo into the cytoplasm; fusogenic lipid GALA, cholesteryl-GALA and PEG-GALA may show a highly efficient endosomal release; a pore-forming protein listeriolysin O may provide an endosomal escape mechanism; and, histidine-rich peptides have the ability to fuse with the endosomal membrane, resulting in pore formation, and can buffer the proton pump causing membrane lysis.

(e.g., elevated), pH (e.g., decreased), respond to externally applied stimuli such as a magnetic field, light, energy, heat or ultrasound and/or promote intracellular delivery of the cargo. All of these are considered actively targeting moieties.

It should be understood that as to each possible targeting or active targeting moiety herein-discussed, there is an embodiment of the invention wherein the delivery system comprises such a targeting or active targeting moiety. Likewise, Table 11 provides exemplary targeting moieties that can be used in the practice of the invention an as to each an embodiment of the invention provides a delivery system that comprises such a targeting moiety.

TABLE 11

Exemplary Targeting Moieties

| Targeting Moiety | Target Molecule | Target Cell or Tissue |
|---|---|---|
| folate | folate receptor | cancer cells |
| transferrin | transferrin receptor | cancer cells |
| Antibody CC52 | rat CC531 | rat colon adenocarcinoma CC531 |
| anti- HER2 antibody | HER2 | HER2 -overexpressing tumors |
| anti-GD2 | GD2 | neuroblastoma, melanoma |
| anti-EGFR | EGFR | tumor cells overexpressing EGFR |
| pH-dependent fusogenic peptide diINF-7 | | ovarian carcinoma |
| anti-VEGFR | VEGF Receptor | tumor vasculature |
| anti-CD19 | CD19 (B cell marker) | leukemia, lymphoma |
| cell-penetrating peptide | | blood-brain barrier |
| cyclic arginine-glycine-aspartic acid-tyrosine-cysteine peptide (c(RGDyC)-LP) | avβ3 | glioblastoma cells, human umbilical vein endothelial cells, tumor angiogenesis |
| ASSHN peptide | | endothelial progenitor cells; anti-cancer |
| PR b peptide | $\alpha_5\beta_1$ integrin | cancer cells |
| AG86 peptide | $\alpha_6\beta_4$ integrin | cancer cells |
| KCCYSL (P6.1 peptide) | HER-2 receptor | cancer cells |
| affinity peptide LN (YEVGHRC) | Aminopeptidase N (APN/CD13) | APN-positive tumor |
| synthetic somatostatin analogue | Somatostatin receptor 2 (SSTR2) | breast cancer |
| anti-CD20 monoclonal antibody | B-lymphocytes | B cell lymphoma |

The invention comprehends a lipid entity of the invention modified with CPP(s), for intracellular delivery that may proceed via energy dependent macropinocytosis followed by endosomal escape. The invention further comprehends organelle-specific targeting. A lipid entity of the invention surface-functionalized with the triphenylphosphonium (TPP) moiety or a lipid entity of the invention with a lipophilic cation, rhodamine 123 can be effective in delivery of cargo to mitochondria. DOPE/sphingomyelin/stearyl-octa-arginine can delivers cargos to the mitochondrial interior via membrane fusion. A lipid entity of the invention surface modified with a lysosomotropic ligand, octadecyl rhodamine B can deliver cargo to lysosomes. Ceramides are useful in inducing lysosomal membrane permeabilization; the invention comprehends intracellular delivery of a lipid entity of the invention having a ceramide. The invention further comprehends a lipid entity of the invention targeting the nucleus, e.g., via a DNA-intercalating moiety. The invention also comprehends multifunctional liposomes for targeting, i.e., attaching more than one functional group to the surface of the lipid entity of the invention, for instance to enhances accumulation in a desired site and/or promotes organelle-specific delivery and/or target a particular type of cell and/or respond to the local stimuli such as temperature Thus, in an embodiment of the delivery system, the targeting moiety comprises a receptor ligand, such as, for example, hyaluronic acid for CD44 receptor, galactose for hepatocytes, or antibody or fragment thereof such as a binding antibody fragment against a desired surface receptor, and as to each of a targeting moiety comprising a receptor ligand, or an antibody or fragment thereof such as a binding fragment thereof, such as against a desired surface receptor, there is an embodiment of the invention wherein the delivery system comprises a targeting moiety comprising a receptor ligand, or an antibody or fragment thereof such as a binding fragment thereof, such as against a desired surface receptor, or hyaluronic acid for CD44 receptor, galactose for hepatocytes (see, e.g., Surace et al, "Lipoplexes targeting the CD44 hyaluronic acid receptor for efficient transfection of breast cancer cells," J. Mol Pharm 6(4):1062-73; doi: 10.1021/mp800215d (2009); Sonoke et al, "Galactose-modified cationic liposomes as a liver-targeting delivery system for small interfering RNA," Biol Pharm Bull. 34(8): 1338-42 (2011); Torchilin, "Antibody-modified liposomes for cancer chemotherapy," Expert Opin. Drug Deliv. 5 (9), 1003-1025 (2008); Manjappa et al, "Antibody derivatization and conjugation strategies: application in preparation of stealth immunoliposome to target chemotherapeutics to tumor," J. Control. Release 150 (1), 2-22 (2011); Sofou S "Antibody-targeted liposomes in cancer therapy and imaging," Expert Opin. Drug Deliv. 5 (2): 189-204 (2008); Gao J et al, "Antibody-targeted immunoliposomes for cancer treatment," Mini. Rev. Med. Chem. 13(14): 2026-2035 (2013); Molavi et al, "Anti-CD30 antibody conjugated liposomal doxorubicin with significantly improved therapeutic efficacy against anaplastic large cell lymphoma," Biomaterials 34(34):8718-25 (2013), each of which and the documents cited therein are hereby incorporated herein by reference), the teachings of which can be applied and/or adapted for targeted delivery of one or more CRISPR-Cas molecules described herein.

Other exemplary targeting moieties are described elsewhere herein, such as epitope tags and the like.

Responsive Delivery

In some embodiments, the delivery vehicle can allow for responsive delivery of the cargo(s). Responsive delivery, as used in this context herein, refers to delivery of cargo(s) by the delivery vehicle in response to an external stimuli. Examples of suitable stimuli include, without limitation, an energy (light, heat, cold, and the like), a chemical stimuli (e.g. chemical composition, etc.), and a biologic or physiologic stimuli (e.g. environmental pH, osmolarity, salinity, biologic molecule, etc.). In some embodiments, the targeting moiety can be responsive to an external stimuli and facilitate responsive delivery. In other embodiments, responsiveness is determined by a non-targeting moiety component of the delivery vehicle.

The delivery vehicle can be stimuli-sensitive, e.g., sensitive to an externally applied stimuli, such as magnetic fields, ultrasound or light; and pH-triggering can also be used, e.g., a labile linkage can be used between a hydrophilic moiety such as PEG and a hydrophobic moiety such as a lipid entity of the invention, which is cleaved only upon exposure to the relatively acidic conditions characteristic of the a particular environment or microenvironment such as an endocytic vacuole or the acidotic tumor mass. pH-sensitive copolymers can also be incorporated in embodiments of the invention can provide shielding; diortho esters, vinyl esters, cysteine-cleavable lipopolymers, double esters and hydrazones are a few examples of pH-sensitive bonds that are quite stable at pH 7.5, but are hydrolyzed relatively rapidly at pH 6 and below, e.g., a terminally alkylated copolymer of N-isopropylacrylamide and methacrylic acid that copolymer facilitates destabilization of a lipid entity of the invention and release in compartments with decreased pH value; or, the invention comprehends ionic polymers for generation of a pH-responsive lipid entity of the invention (e.g., poly (methacrylic acid), poly(diethylaminoethyl methacrylate), poly(acrylamide) and poly(acrylic acid)).

Temperature-triggered delivery is also within the ambit of the invention. Many pathological areas, such as inflamed tissues and tumors, show a distinctive hyperthermia compared with normal tissues. Utilizing this hyperthermia is an attractive strategy in cancer therapy since hyperthermia is associated with increased tumor permeability and enhanced uptake. This technique involves local heating of the site to increase microvascular pore size and blood flow, which, in turn, can result in an increased extravasation of embodiments of the invention. Temperature-sensitive lipid entity of the invention can be prepared from thermosensitive lipids or polymers with a low critical solution temperature. Above the low critical solution temperature (e.g., at site such as tumor site or inflamed tissue site), the polymer precipitates, disrupting the liposomes to release. Lipids with a specific gel-to-liquid phase transition temperature are used to prepare these lipid entities of the invention; and a lipid for a thermosensitive embodiment can be dipalmitoylphosphatidylcholine. Thermosensitive polymers can also facilitate destabilization followed by release, and a useful thermosensitive polymer is poly (N-isopropylacrylamide). Another temperature triggered system can employ lysolipid temperature-sensitive liposomes.

The invention also comprehends redox-triggered delivery. The difference in redox potential between normal and inflamed or tumor tissues, and between the intra- and extra-cellular environments has been exploited for delivery, e.g., GSH is a reducing agent abundant in cells, especially in the cytosol, mitochondria and nucleus. The GSH concentrations in blood and extracellular matrix are just one out of 100 to one out of 1000 of the intracellular concentration, respectively. This high redox potential difference caused by GSH, cysteine and other reducing agents can break the reducible bonds, destabilize a lipid entity of the invention and result in release of payload. The disulfide bond can be used as the cleavable/reversible linker in a lipid entity of the invention, because it causes sensitivity to redox owing to the disulfideto-thiol reduction reaction; a lipid entity of the invention can be made reduction sensitive by using two (e.g., two forms of a disulfide-conjugated multifunctional lipid as cleavage of the disulfide bond (e.g., via tris(2-carboxyethyl) phosphine, dithiothreitol, L-cysteine or GSH), can cause removal of the hydrophilic head group of the conjugate and alter the membrane organization leading to release of payload. Calcein release from reduction-sensitive lipid entity of the invention containing a disulfide conjugate can be more useful than a reduction-insensitive embodiment.

Enzymes can also be used as a trigger to release payload. Enzymes, including MMPs (e.g. MMP2), phospholipase A2, alkaline phosphatase, transglutaminase or phosphatidylinositol-specific phospholipase C, have been found to be overexpressed in certain tissues, e.g., tumor tissues. In the presence of these enzymes, specially engineered enzyme-sensitive lipid entity of the invention can be disrupted and release the payload. an MMP2-cleavable octapeptide (Gly-Pro-Leu-Gly-Ile-Ala-Gly-Gln) can be incorporated into a linker, and can have antibody targeting, e.g., antibody 2C5.

The invention also comprehends light- or energy-triggered delivery, e.g., the lipid entity of the invention can be light-sensitive, such that light or energy can facilitate structural and conformational changes, which lead to direct interaction of the lipid entity of the invention with the target cells via membrane fusion, photo-isomerism, photofragmentation or photopolymerization; such a moiety therefor can be benzoporphyrin photosensitizer. Ultrasound can be a form of energy to trigger delivery; a lipid entity of the invention with a small quantity of particular gas, including air or perfluorated hydrocarbon can be triggered to release with ultrasound, e.g., low-frequency ultrasound (LFUS). Magnetic delivery: A lipid entity of the invention can be magnetized by incorporation of magnetites, such as Fe3O4 or γ-Fe2O3, e.g., those that are less than 10 nm in size. Targeted delivery can be then by exposure to a magnetic field.

Delivery Dosages and Administration Techniques

The CRISPR-Cas system, components thereof, polynucleotides, vectors, viral particles, and pharmaceutical formulations thereof can be delivered to a cell and/or subject by any suitable administration route. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses.

One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc. Specific dosages etc. are described below and elsewhere herein.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In embodiments, the delivery is via an adenovirus, which may be at a single booster dose containing at least $1\times10^5$ particles (also referred to as particle units, pu) of adenoviral vector. In an embodiment herein, the dose preferably is at least about $1\times10^6$ particles (for example, about $1\times10^6$-$10^{12}$ particles), more preferably at least about $1\times10^7$ particles, more preferably at least about $1\times10^8$ particles (e.g., about $1\times10^8\times10^{11}$ particles or about $1\times10^8\times10^{12}$ particles), and most preferably at least about $1\times10^{10}$ particles (e.g., about $1\times10^9$-$10^{10}$ particles or about $1\times10^9$-$10^{12}$ particles), or even at least about $1\times10^{10}$ particles (e.g., about $1\times10^{10}\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about 1×106 particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In embodiments, the delivery is via an AAV. A therapeutically effective dosage for in vivo delivery of the AAV to a human is believed to be in the range of from about 20 to about 50 ml of saline solution containing from about $1\times10^{10}$ functional AAV/ml solution. The dosage may be adjusted to balance the therapeutic benefit against any side effects. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about 1×1013 genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

Zou et al. ((HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 μl of a recombinant lentivirus having a titer of $1\times10^9$ transducing units (TU)/ml by an intrathecal catheter. A similar dosage of CRISPR Cas expressed in a lentiviral vector may be contemplated for humans in the present invention, for example, about 10-50 ml of CRISPR Cas in a lentivirus having a titer of $1\times10^9$ transducing units (TU)/ml may be contemplated. A similar dosage of CRISPR Cas expressed in a lentiviral vector targeted to the brain may be contemplated for humans in the present invention, for example, about 10-50 ml of CRISPR Cas targeted to the brain in a lentivirus having a titer of $1\times10^9$ transducing units (TU)/ml may be contemplated. These types of dosages can be adapted or extrapolated to use of a retroviral or lentiviral vector in the present invention.

Doses of about 5 mg/kg are contemplated, with single or multiple doses, depending on the target tissue. In embodiments, these dosages can be applied to delivery of particles/nanoparticles that include one or more of the CRISPR-Cas system molecules described herein that are based on self-assembling bioadhesive polymers by an appropriate route.

An epoxide-modified lipid-polymer, which is described in greater detail elsewhere herein, may be utilized to deliver the CRISPR-Cas system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

Doses of LNPs described elsewhere herein of about 0.01 to about 1 mg per kg of body weight administered intravenously are contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. LNPs adapted for liver delivery are described elsewhere herein. A dosage of LNPs for liver delivery of about four doses of about 6 mg/kg of the LNP containing one or more CRISPR-Cas system molecules described herein every two weeks is contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

As discussed elsewhere herein, the CRISPR-Cas system components can be delivered with one or more additional active agents. In some embodiments, medications or additional active agents to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

A dosage of 1 μg/ml of LNP or CRISPR-Cas RNA in or associated with the LNP may be contemplated, especially for a formulation containing DLinKC2-DMA.

A dosage of about 100 to 1000 mg of CRISPR Cas encapsulated in about 100 to 1000 mg of RVG exosomes may be contemplated for the present invention.

In some embodiments, daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated SNALP) administered by intravenous injection to at doses of about 1 or 2.5 mg/kg are also contemplated (see, e.g., Zimmerman et al., Nature Letters, Vol. 441, 4 May 2006, the teachings of which can be applied and/or adapted to generated and/or deliver the CRISPR-Cas system nanoparticle(s) described herein).

Formulations that include SNALPs containing the CRISPR-Cas system molecule(s) described herein used for administration in some embodiments (e.g. in vivo administration) may comprise a final lipid/RNA mass ratio of about 9:1.

In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

In embodiments where delivery of the CRISPR-Cas system or components thereof is via plasmid compositions, the dosage can be a sufficient amount of plasmid to elicit a response (e.g. an effective dosage or effective amount). For instance, suitable quantities of plasmid DNA in plasmid compositions can be from about 0.1 to about 2 mg, or from about 1 μg to about 10 μg per 70 kg individual. Plasmids of the invention will generally comprise (i) a promoter; (ii) a sequence encoding a CRISPR enzyme, operably linked to said promoter; (iii) a selectable marker; (iv) an origin of replication; and (v) a transcription terminator downstream of and operably linked to (ii).

In terms of local delivery to the brain, this can be achieved in various ways. For instance, material can be delivered intrastriatally e.g. by injection. Injection can be performed stereotactically via a craniotomy.

CRISPR enzyme mRNA and guide RNA might also be delivered separately. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA.

In embodiments, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA.

As described elsewhere herein, particles/nanoparticles that include one or more of the CRISPR-Cas system molecules described herein can be based on self-assembling bioadhesive polymers are contemplated. These particles can be applied oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199), the teachings of which can be applied and/or adapted to generate and/or deliver one or more CRISPR-Cas system molecules described herein.

Methods of Treatment Using a Rationally Designed CRISPR-Cas System Based Theraputic The rationally designed CRISPR-Cas therapeutics and/or therapies can be used to treat or prevent one or more diseases or symptoms thereof in a subject in need thereof. As discussed elsewhere herein, the rationally designed CRISPR-Cas based therapeutic can be a cell, such as a genetically modified cell, that does not express a DNA-damage response signature. In some embodiments, the rationally designed CRISPR-Cas based therapeutic can be a CRISPR-Cas system or component thereof that does not induce a DNA-damage response signature when introduced into a cell.

In some embodiments, such as those where the rationally designed CRISPR-Cas based therapeutic is a cell, the cell can be introduced into a subject, such as the subject where the initial cell was isolated, to treat or prevent one or more diseases or symptoms thereof in the subject. Additional embodiments of adoptive therapies using the rationally designed CRISPR-Cas based therapeutics are described elsewhereherein.

In some embodiments, the rationally designed CRISPR-Cas system(s) or component(s) thereof described herein can be administer to a subject or cell thereof to treat or prevent one or more disease or symptoms thereof in a subject. In some of these embodiments, prevention or treatment is provided when the genome and/or transcriptome is modified by the rationally designed CRISPR-Cas system described herein. Stated differently, the rationally designed CRISPR-Cas system or component thereof can be used, inter alia, to modify a polynucleotide sequence, in various cell screening methods and applications, and/or as or in the development of a therapeutic. In general, one or more of the rationally designed CRISPR-Cas systems or components thereof described herein can be introduced to a cell directly (e.g. as proteins) or expressed from one or more polynucleotides encoding one or more components of rationally designed CRISPR-Cas system described herein. Once present inside a cell, the CRISPR-Cas or components thereof can act to result in modification of a polynucleotide and/or other enzymatic or biological event. Other effects of activity of the rationally designed CRISPR-Cas systems or components thereof descried herein are described elsewhere herein.

The nucleic acid-targeting systems, the vector systems, the vectors and the compositions described herein may be used in various nucleic acids-targeting applications, altering or modifying synthesis of a gene product, such as a protein, nucleic acids cleavage, nucleic acids editing, nucleic acids splicing; trafficking of target nucleic acids, tracing of target nucleic acids, isolation of target nucleic acids, visualization of target nucleic acids, etc.

EXAMPLES

Example 1—Differences in Cas9-Expressing Cells Compared to Wild-Type

Figure 6A:
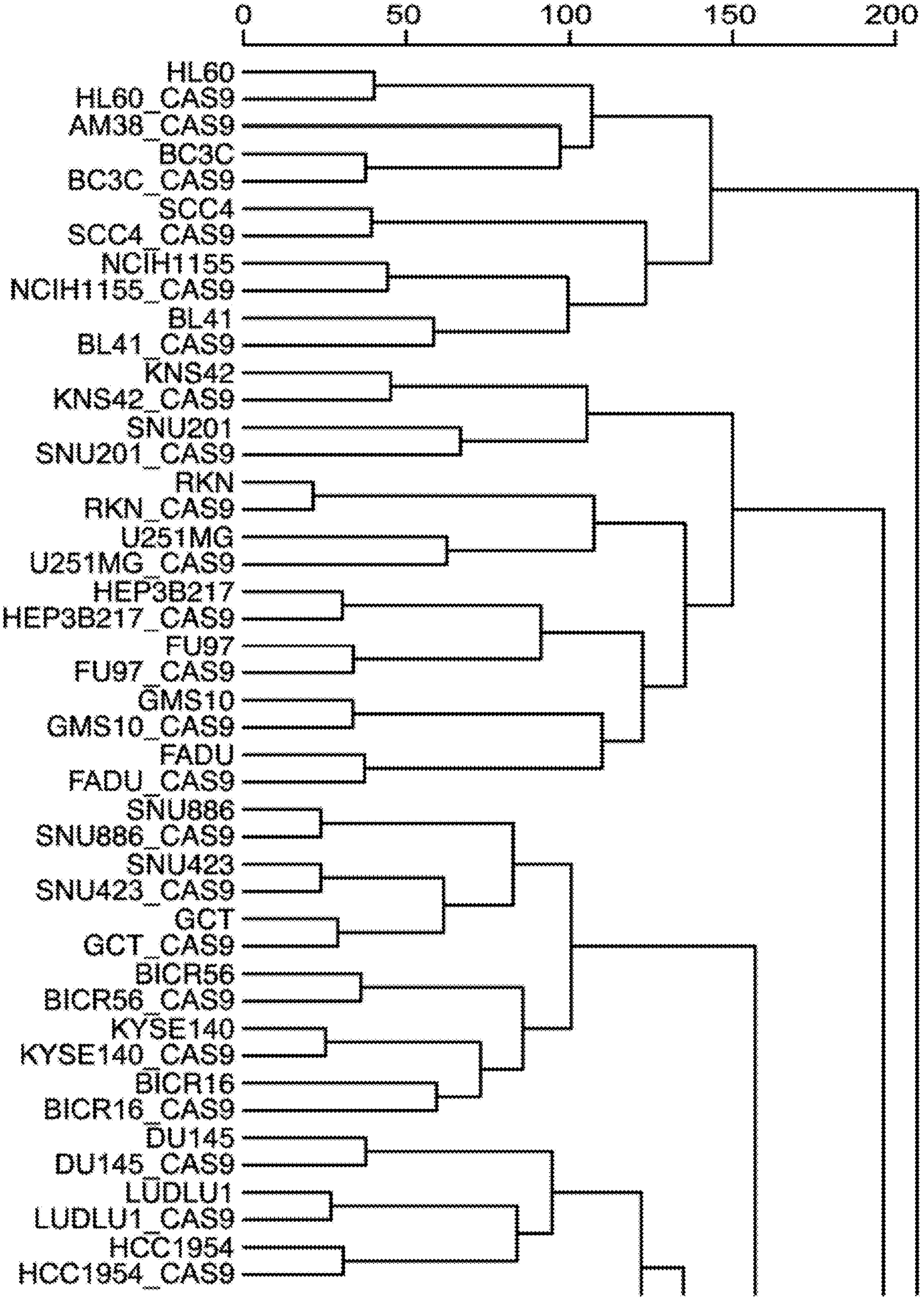
FIGS. 6A-6G—Cas9 introduction activates the p53 pathway.
Figure 6A:
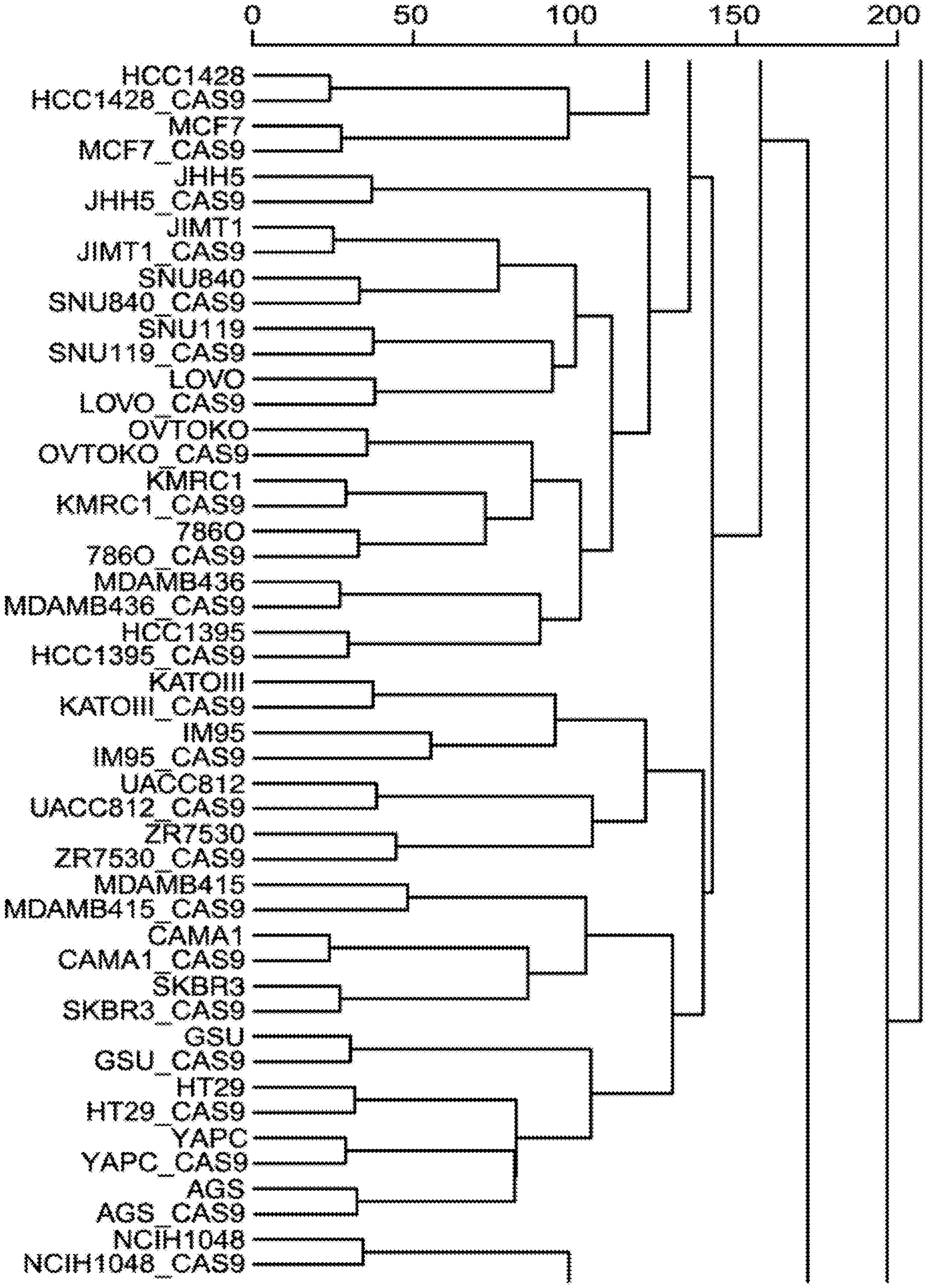
Figure 6A:
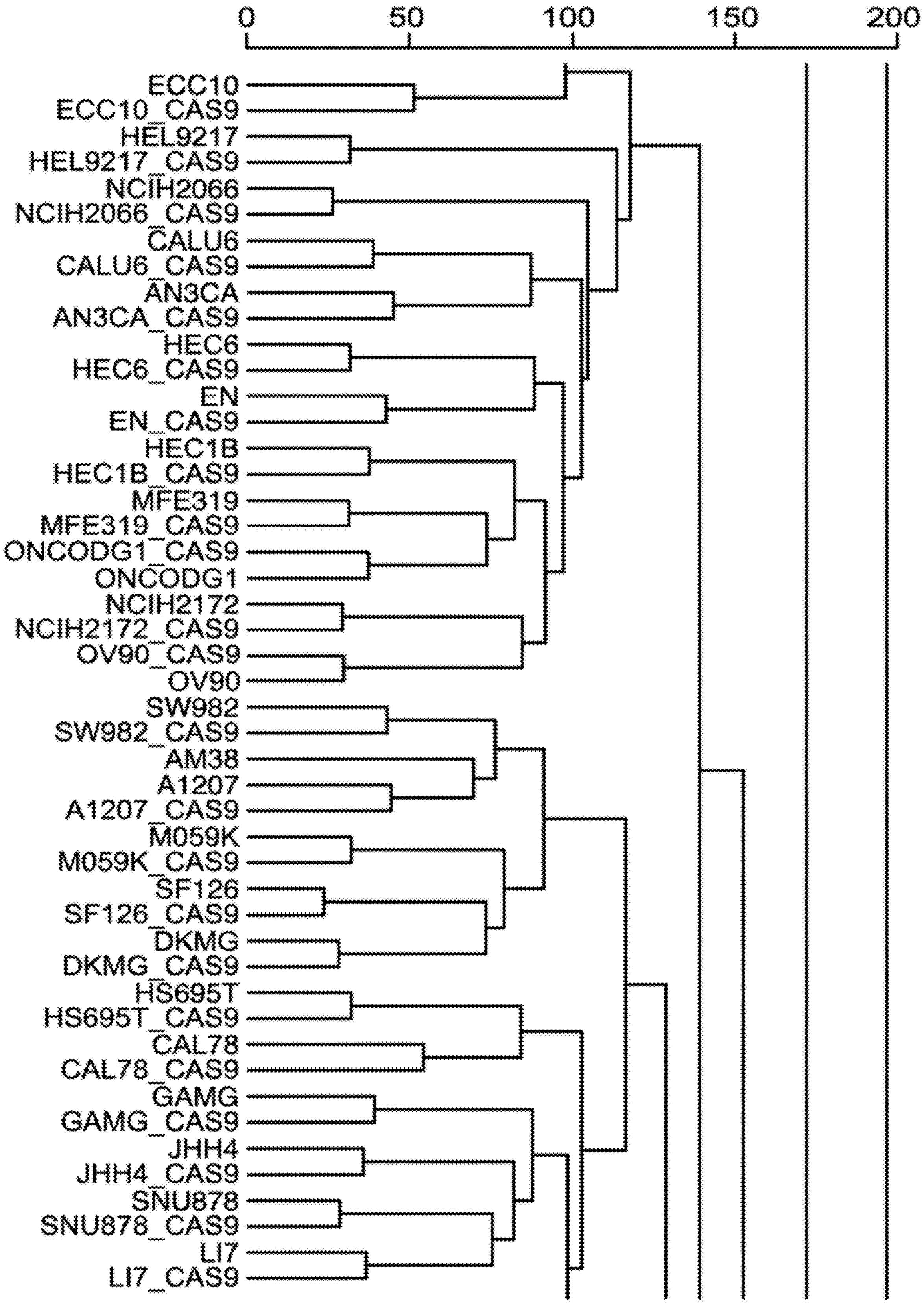
Figure 6A:
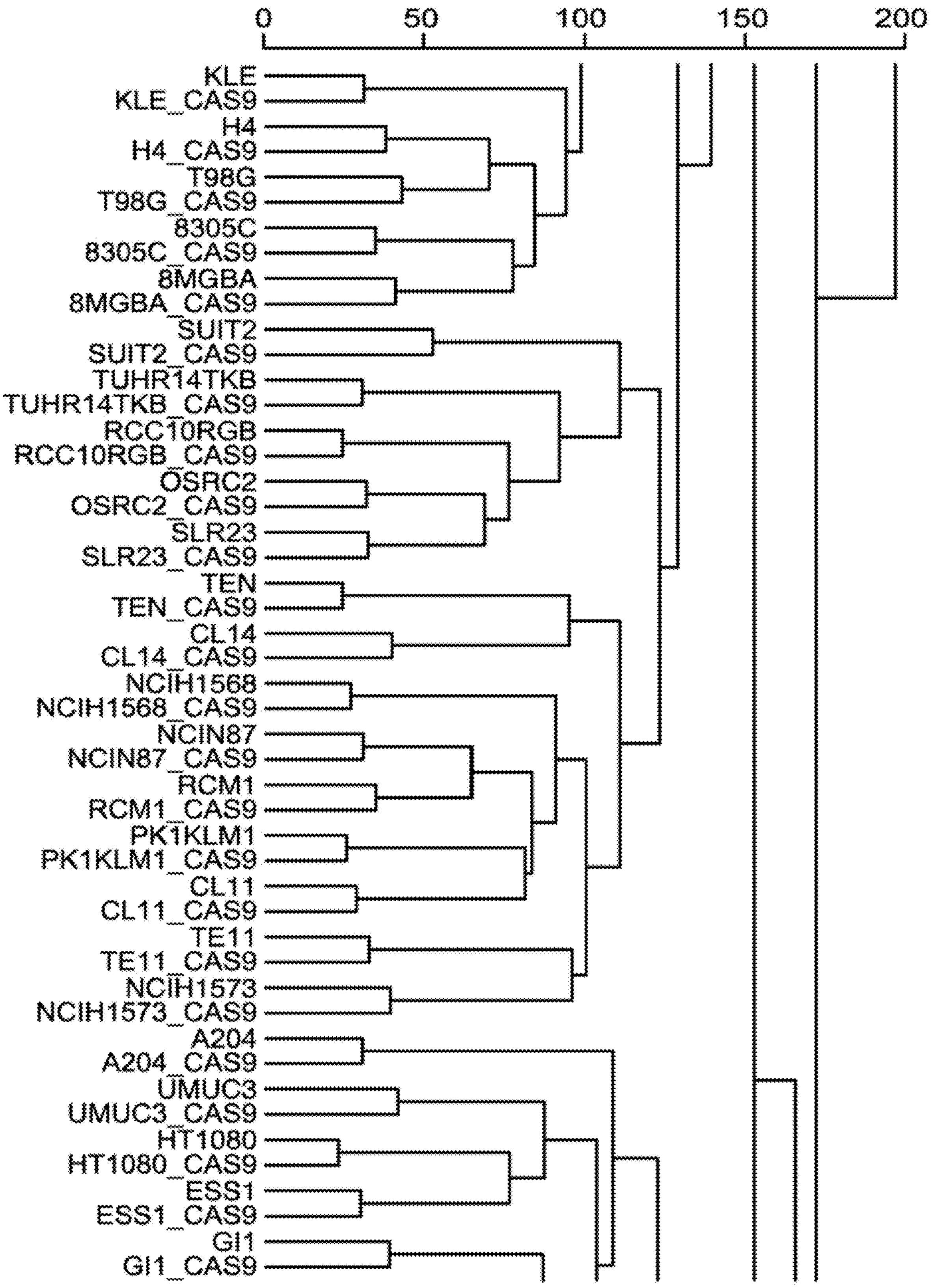
Figure 6A:
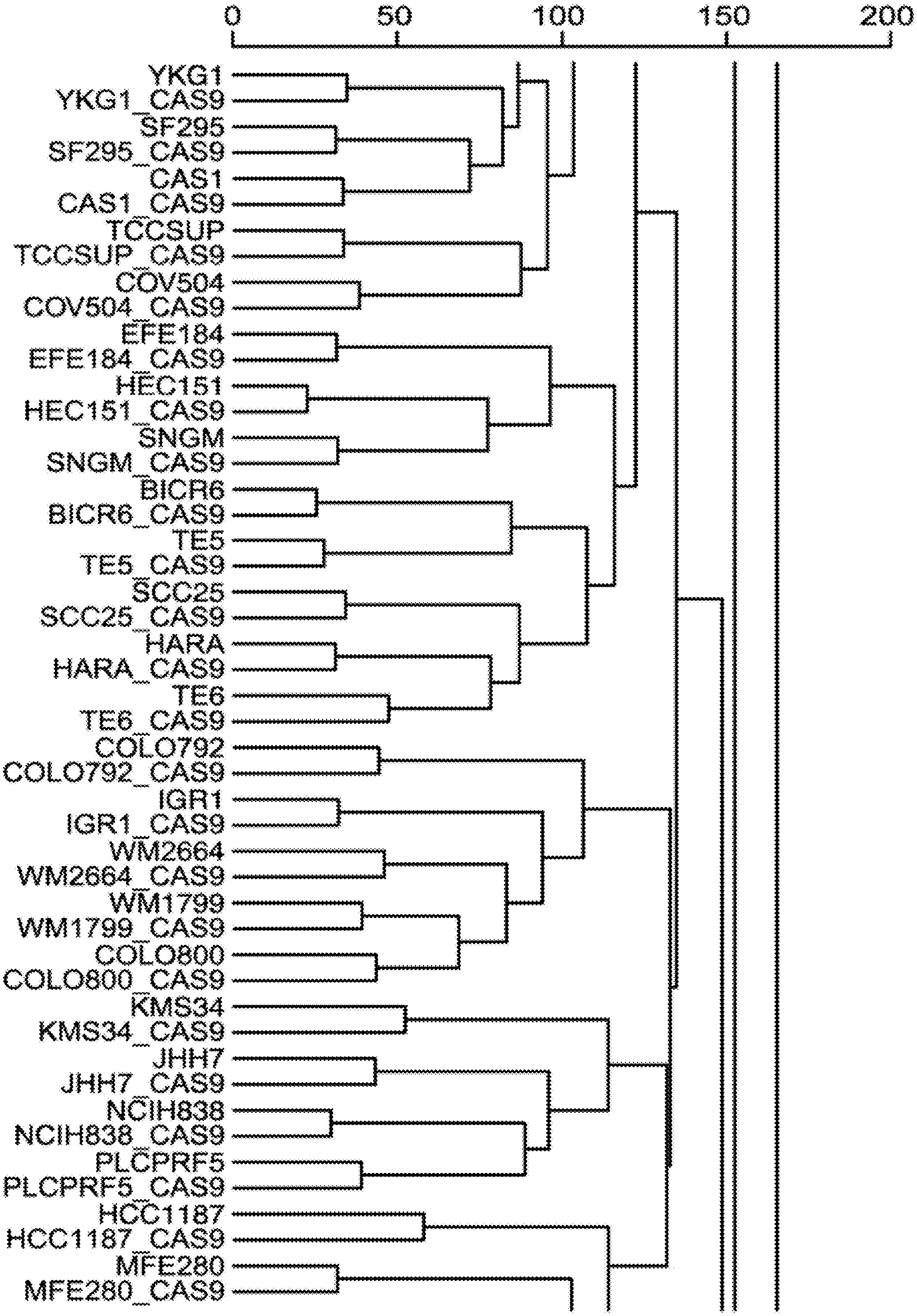
Figure 6A:
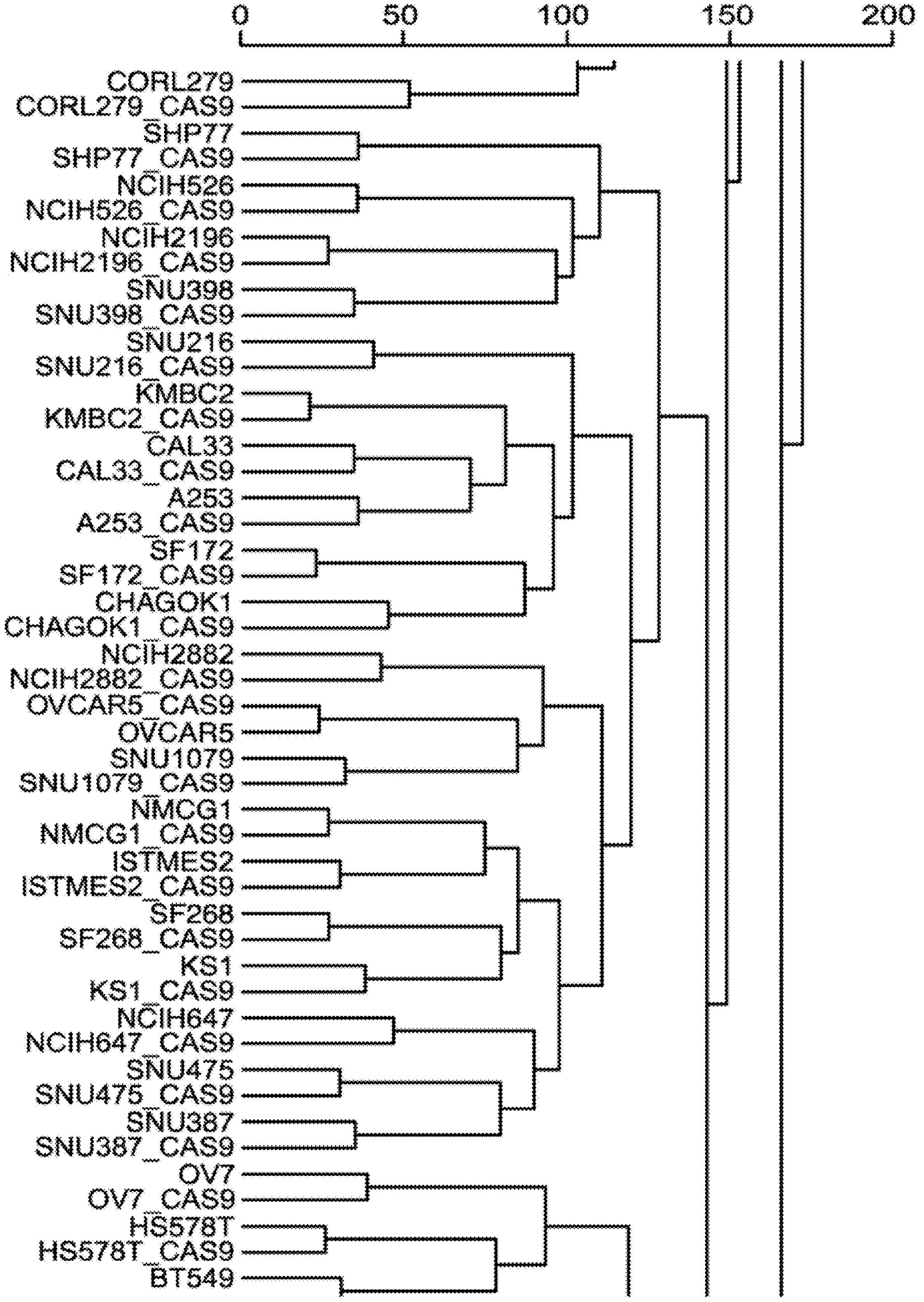
Figure 6A:
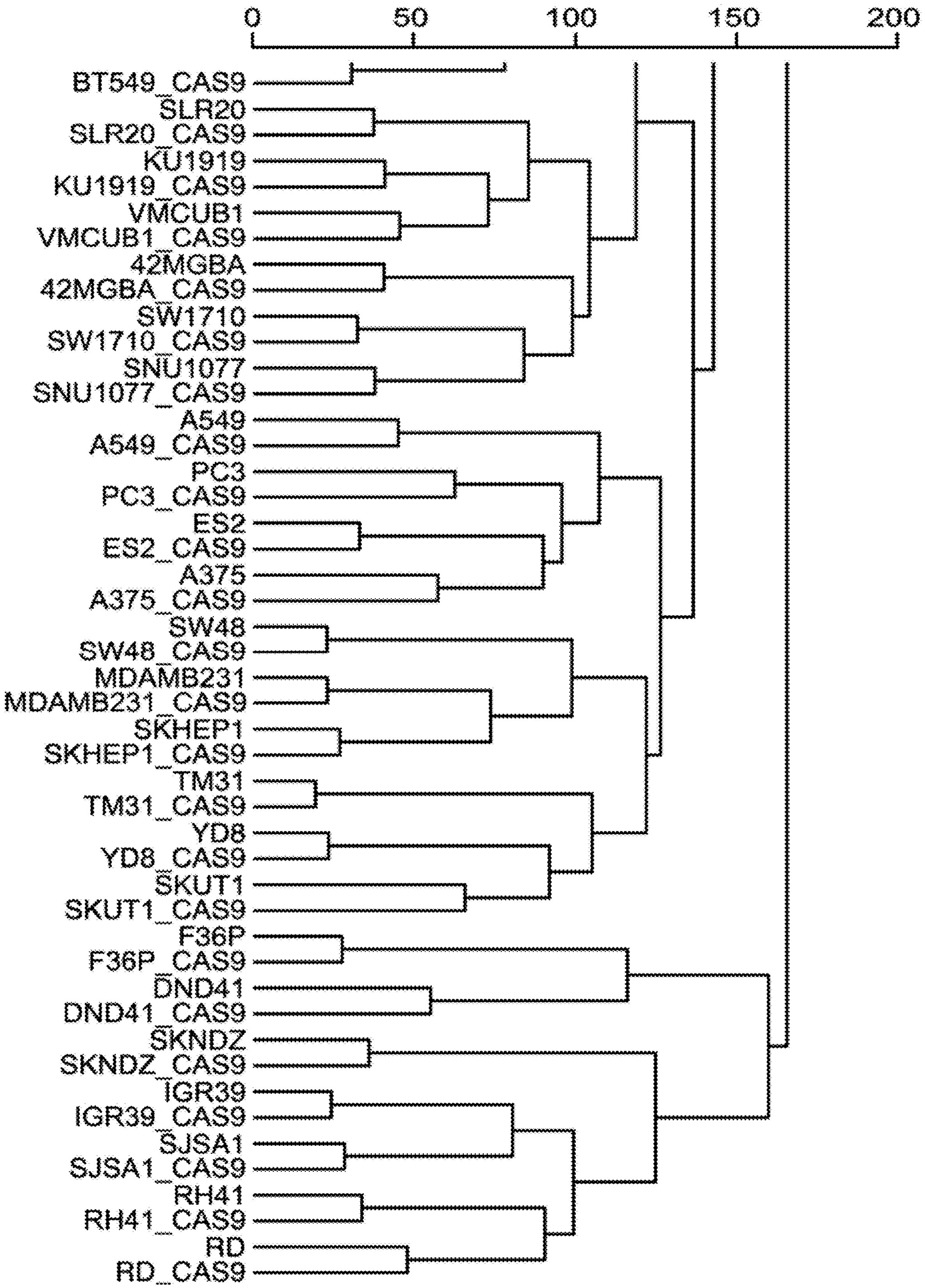
Figure 6B:
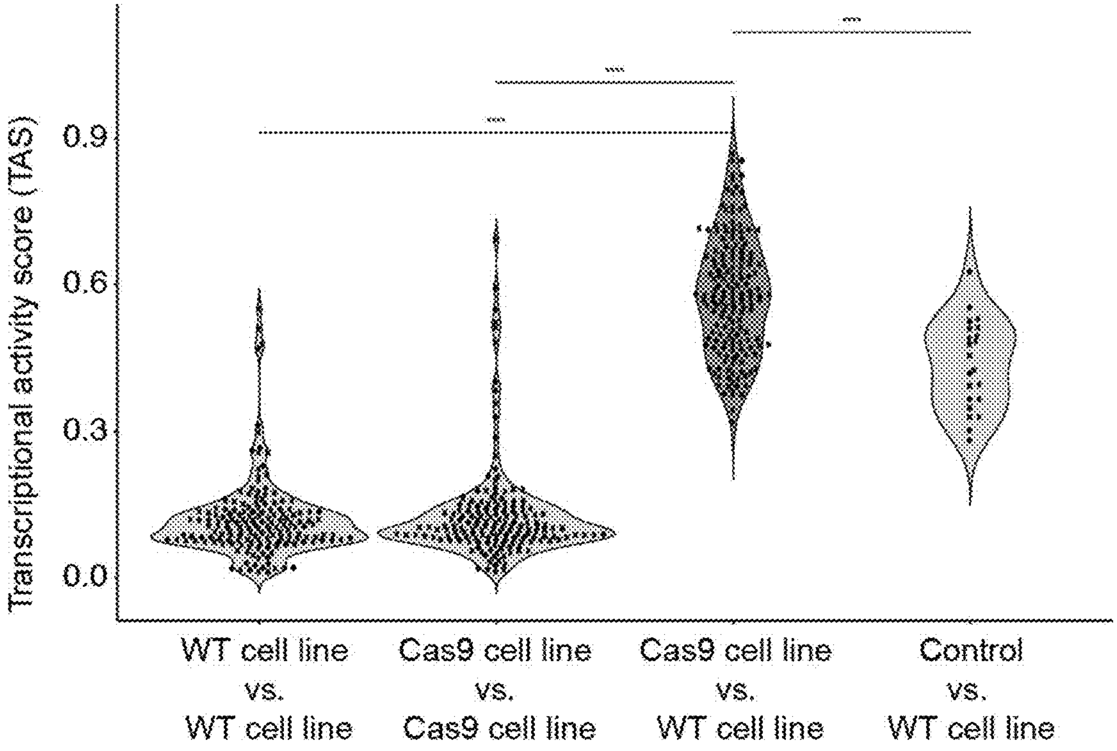

To test whether Cas9-expressing cell lines (hereinafter: Cas9 lines) differ in any systematic way from their parental lines (hereinafter: WT lines) genome-wide expression profiling of 165 pairs of WT/Cas9 lines was performed using the L1000 assay[6] (See Supplementary Data 1 of Enache, O. M., Rendo, V., Abdusamad, M. et al. Cas9 activates the p53 pathway and selects for p53-inactivating mutations. Nat Genet 52, 662-668 (2020). https://doi.org/10.1038/s41588-020-0623-4, which is incorporated by reference herein as if expressed in its entirety and also Appendix A to U.S. Provisional Ser. No. 62/909,131). Each line was profiled in 16 technical replicates, and global expression profiles were then compared between WT and Cas9 lines to characterize a Cas9 transcriptional signature (See methods in Example 8). As expected, the expression patterns of all Cas9 lines were similar to those of their parental WT lines, and all of the pairs (165/165) clustered together in an unsupervised hierarchical clustering (FIG. 6A). However, significant transcriptional differences were observed when comparing Cas9 and WT lines. The pair-wise transcriptional difference between the groups significantly exceeded the transcriptional variation observed when comparing replicates within each group (FIG. 6B). A median of 87 genes (range: 2 to 1,650) were differentially expressed by at least two-fold between pairs ($p<0.05$; $q<0.05$; FIG. 1A, Table 12). CRISPR-Cas9 editing is often performed in two steps: first, a stable Cas9-expressing cell line is generated; then, single guide RNA (sgRNA) is introduced. Both of these steps involve several events that could potentially lead to genomic evolution, including the transduction, passaging and antibiotic selection of cells. As the Cas9-expressing cell line is often used as a control to its gene-knockout counterpart, genetic or transcriptional alterations that accumulated in the Cas9 expressing cell line prior to sgRNA introduction would likely go unnoticed. Of note, in the top 10% of the most transctiptionally-different cell line pairs (17 of 165), a median of 735 genes were differentially expressed by at least two-fold out of a median of 6,134 expressed genes per cell line (considering only the 10, 147 genes included in the transcriptional analysis). Therefore, about 12% of the transcriptome was altered by at least two-fold following Cas9 introduction in these cell lines (see e.g., FIG. 1A and Table 12).

Figure 1B:
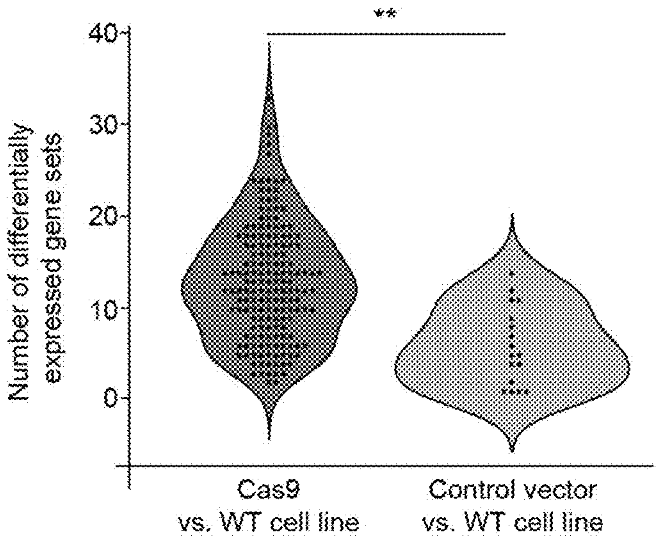
Figure 1C:
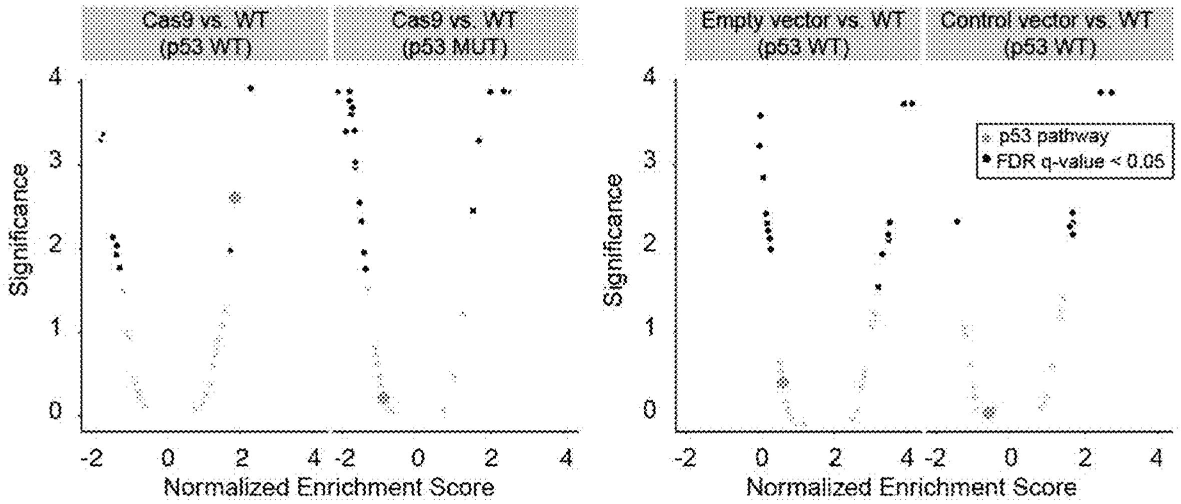
Figure 6C:
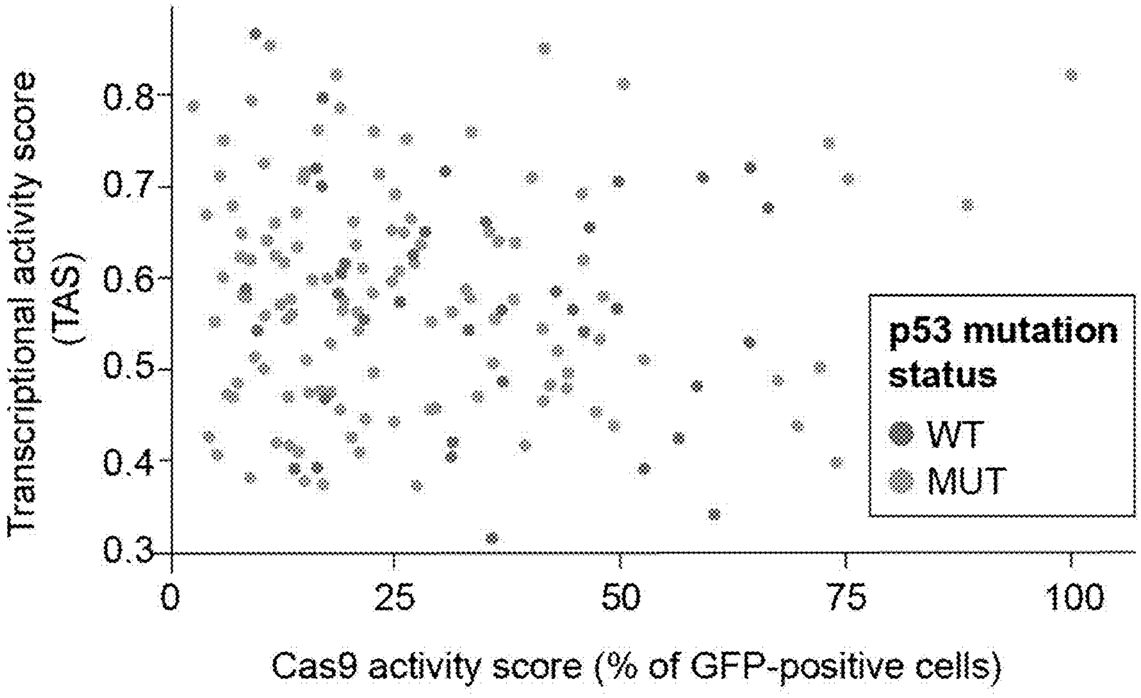

Gene set enrichment analysis (GSEA)[7,8] revealed that differentially expressed genes often converged on MSigDB Hallmark gene sets (FIG. 1B). Importantly, the transcriptional effect of Cas9 was stronger than that observed in a similar analysis of lines expressing empty or reporter vectors ($p=0.001$; FIG. 1B and FIG. 6B) and was not merely a reflection of Cas9 infectability (FIG. 6C).

TABLE 12

| Type of Profiling | p53 Status | # of unique cell lines | % cell lines w/>100 genes deregulated (>2X) | % cell lines w/p53 pathway activation | % cell lines/emergence or expansion of p53 ($\Delta AF > 0.05$) |
|---|---|---|---|---|---|
| Gene | WT (wild-type) | 43 | 44.2% | 32.6% | NA |
| Expression | Mutant | 122 | 43.4% | 9.1% | |
| WB + | WT | 5 | NA | 80% | NA |
| RT-qPCR | Mutant | 4 | | 0% | |
| Targeted DNA | WT | 14 | NA | NA | 10% |
| sequencing | Mutant | 26 | | | |

Figure 6D:
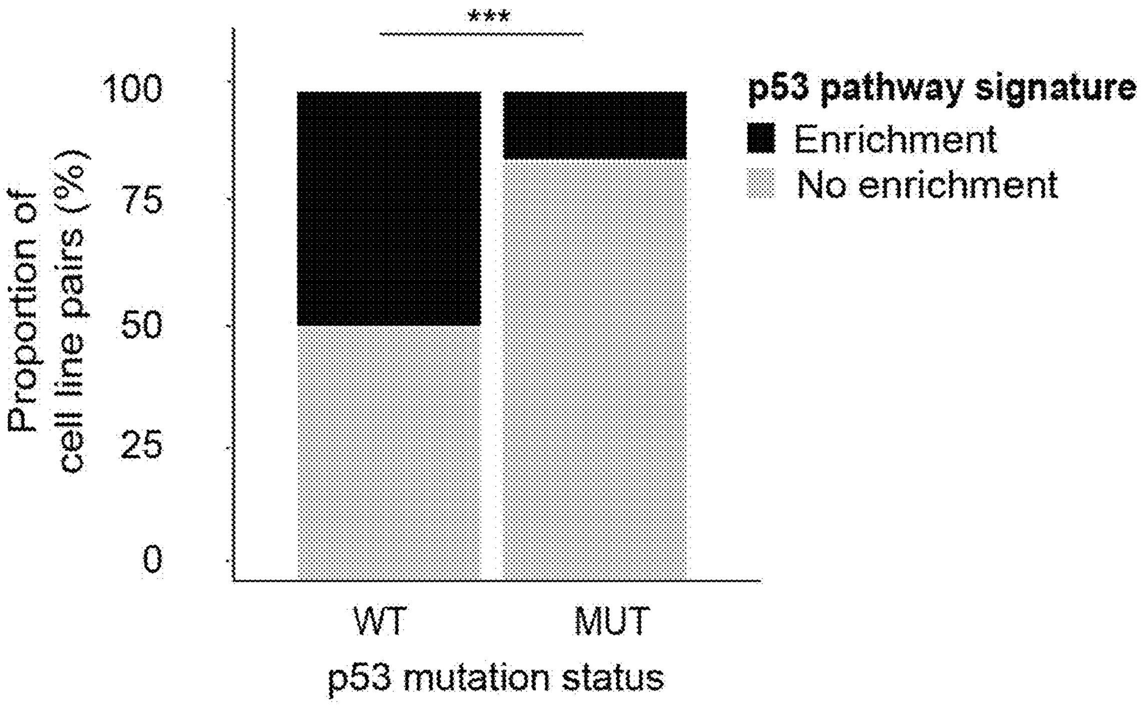
Figure 6E:
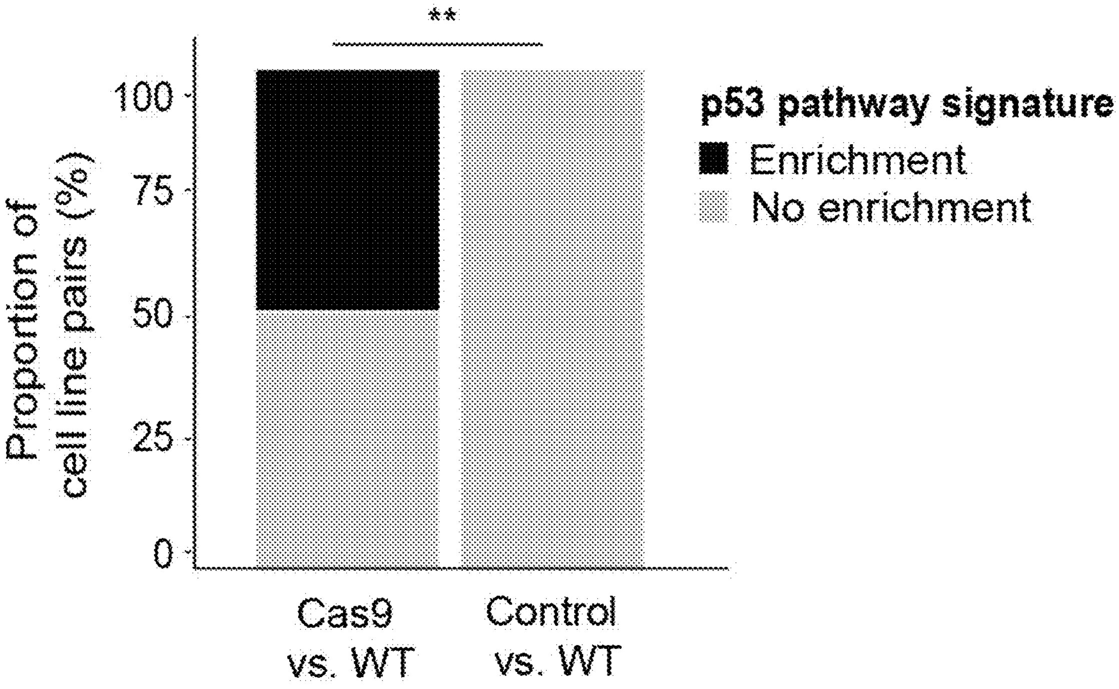
Figure 6F:
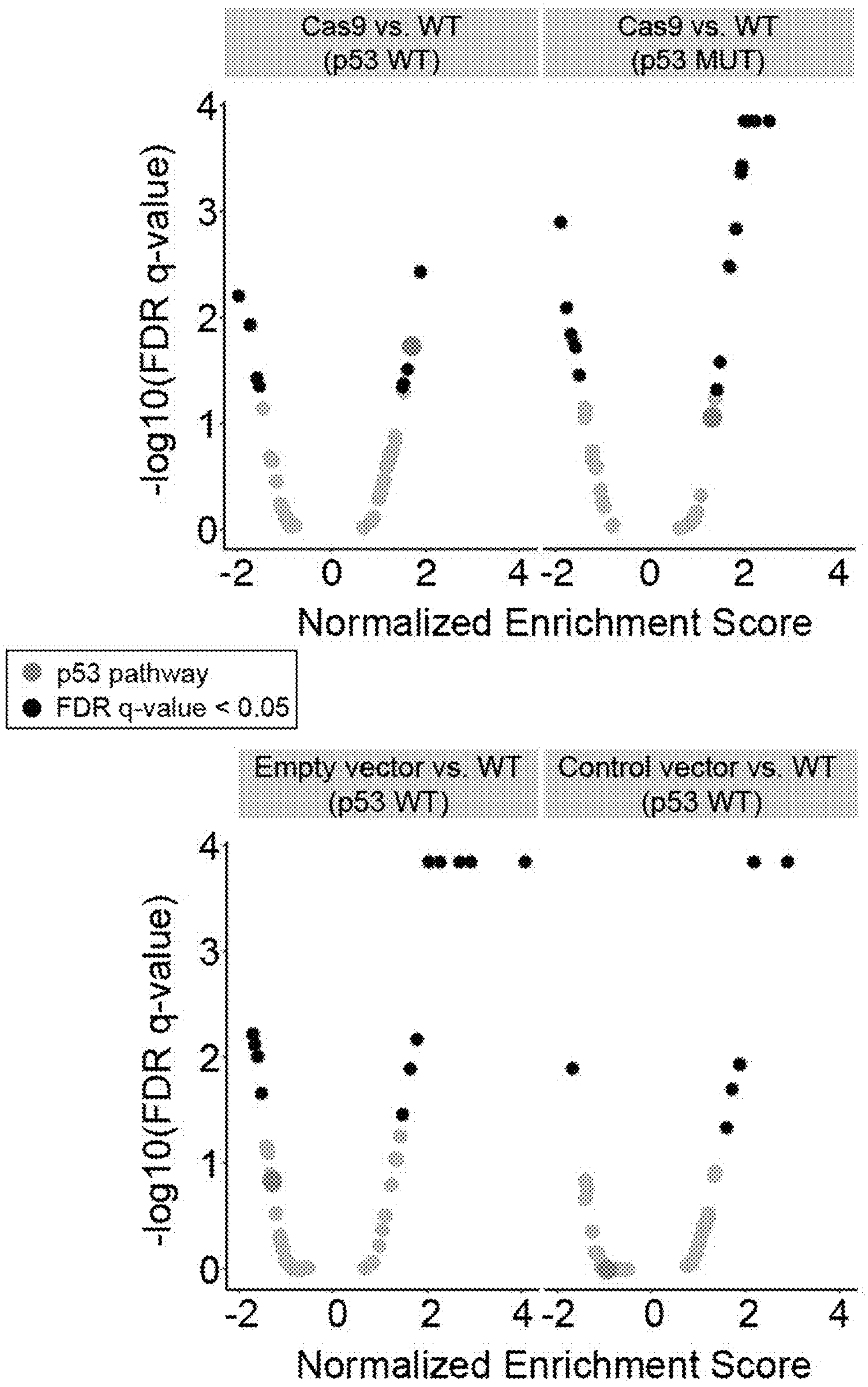
Figure 6G:
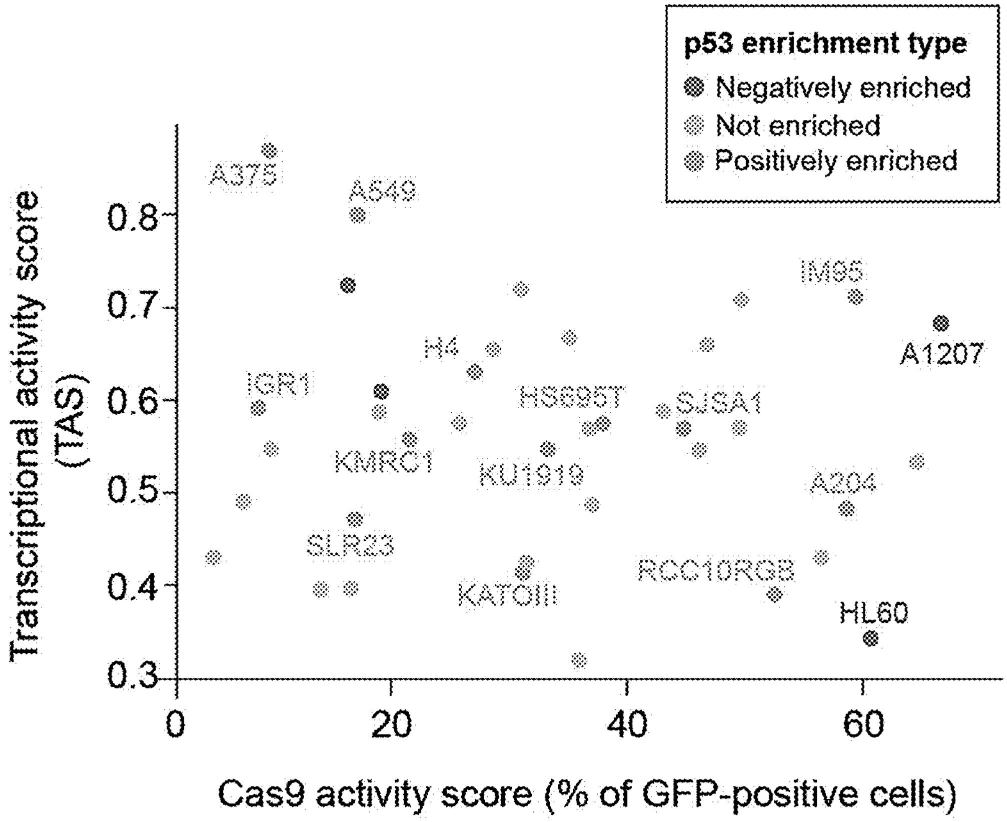

Example 2—Activation and/or Suppression of Cellular Pathways in Cas9 Expressing Cells Next, it was examined whether any specific cellular pathways were consistently activated or suppressed in Cas9 compared to WT lines. GSEA revealed a significant activation ($p<0.05$; $q<0.05$) of the p53 pathway in 25 (15.2%) of the pairs. Importantly, this activation was drastically enriched in TP53-WT lines compared to lines harboring an inactivating TP53 mutation (33% of the TP53-WT pairs vs. 9% of the TP53-mutant pairs, $p=0.0008$; FIG. 6D). When individual pairwise comparisons of Cas9 vs. WT lines were aggregated to generate a universal signature of Cas9 activation across lines (See methods in Example 8), activation of the p53 pathway was one of the two most significantly activated pathways in the Cas9 lines (together with NF-kB signaling). This was significantly enriched in TP53-WT lines and was not observed in lines expressing empty or reporter vectors (FIG. 1C, FIGS. 6E-6G, and Tables 13-16). The observed p53 pathway upregulation was not associated with Cas9 activity or with the strength of the global effect of Cas9 expression on the transcriptome (FIG. 6G), indicating that its detection is not merely a byproduct of a stronger overall transcriptional response.

TABLE 13

| p53WT Cas9 v. Parental | | | | | |
|---|---|---|---|---|---|
| Signature Name | Size | ES | NES | NOM p-val | FDR_qval |
| HALLMARK_TNFA_SIGNALING_VIA_NFKB | 192 | 0.45470044 | 2.1939049 | 0 | 0 |
| HALLMARK_P53_PATHWAY | 191 | 0.36109486 | 1.7563992 | 0 | 0.007588383 |
| HALLMARK_APOPTOSIS | 148 | 0.35048905 | 1.6233149 | 0.00189036 | 0.025717301 |
| HALLMARK_INTERFERON_GAMMA_RESPONSE | 170 | −0.3083673 | −1.4913926 | 0.00412371 | 0.03816425 |
| HALLMARK_E2F_TARGETS | 183 | −0.3238316 | −1.5665112 | 0 | 0.02270621 |
| HALLMARK_FATTY_ACID_METABOLISM | 131 | −0.3420386 | −1.5813001 | 0.00208333 | 0.022780957 |
| HALLMARK_MITOTIC_SPINDLE | 176 | −0.32779 | −1.5831753 | 0 | 0.028292863 |
| HALLMARK_ADIPOGENESIS | 168 | −0.3472919 | −1.6764458 | 0 | 0.018936243 |
| HALLMARK_MYC_TARGETS_V1 | 194 | −0.3984568 | −1.9517298 | 0 | 0.001759491 |
| HALLMARK_INTERFERON_ALPHA_RESPONSE | 81 | −0.4714323 | −2.0172863 | 0 | 0.002016667 |
| HALLMARK_TNFA_SIGNALING_VIA_NFKB | 192 | 0.4011172 | 1.8915232 | 0 | 0.00379164 |
| HALLMARK_P53_PATHWAY | 191 | 0.35638142 | 1.7061555 | 0.0015873 | 0.01901647 |
| HALLMARK_APOPTOSIS | 148 | 0.35089958 | 1.6185219 | 0 | 0.03155001 |
| HALLMARK_INFLAMMATORY_RESPONSE | 170 | 0.32662812 | 1.5376334 | 0.00327332 | 0.04291142 |
| HALLMARK_MYC_TARGETS_V2 | 55 | 0.38862917 | 1.5112739 | 0.01525424 | 0.04645116 |
| HALLMARK_OXIDATIVE_PHOSPHORYLATION | 194 | −0.3012778 | −1.531322 | 0 | 0.04523123 |
| HALLMARK_FATTY_ACID_METABOLISM | 131 | −0.3327412 | −1.5820347 | 0.00540541 | 0.03803603 |
| HALLMARK_MYC_TARGETS_V1 | 194 | −0.3387692 | −1.7217597 | 0 | 0.01202457 |
| HALLMARK_INTERFERON_ALPHA_RESPONSE | 81 | −0.4410329 | −1.9683917 | 0 | 0.00638191 |
| HALLMARK_TNFA_SIGNALING_VIA_NFKB | 192 | 0.4011172 | 1.8915232 | 0 | 0.00379164 |
| HALLMARK_P53_PATHWAY | 191 | 0.35638142 | 1.7061555 | 0.0015873 | 0.01901647 |

| Signature Name | Signature_type |
|---|---|
| HALLMARK_TNFA_SIGNALING_VIA_NFKB | p53_WT_aggregate_Cas9_vs_Parental |
| HALLMARK_P53_PATHWAY | p53_WT_aggregate_Cas9_vs_Parental |
| HALLMARK_APOPTOSIS | p53_WT_aggregate_Cas9_vs_Parental |
| HALLMARK_INTERFERON_GAMMA_RESPONSE | p53_WT_aggregate_Cas9_vs_Parental |
| HALLMARK_E2F_TARGETS | p53_WT_aggregate_Cas9_vs_Parental |
| HALLMARK_FATTY_ACID_METABOLISM | p53_WT_aggregate_Cas9_vs_Parental |
| HALLMARK_MITOTIC_SPINDLE | p53_WT_aggregate_Cas9_vs_Parental |
| HALLMARK_ADIPOGENESIS | p53_WT_aggregate_Cas9_vs_Parental |
| HALLMARK_MYC_TARGETS_V1 | p53_WT_aggregate_Cas9_vs_Parental |
| HALLMARK_INTERFERON_ALPHA_RESPONSE | p53_WT_aggregate_Cas9_vs_Parental |
| HALLMARK_TNFA_SIGNALING_VIA_NFKB | p53_WT_meta_cas9_vs_parental |
| HALLMARK_P53_PATHWAY | p53_WT_meta_cas9_vs_parental |
| HALLMARK_APOPTOSIS | p53_WT_meta_cas9_vs_parental |
| HALLMARK_INFLAMMATORY_RESPONSE | p53_WT_meta_cas9_vs_parental |
| HALLMARK_MYC_TARGETS_V2 | p53_WT_meta_cas9_vs_parental |
| HALLMARK_OXIDATIVE_PHOSPHORYLATION | p53_WT_meta_cas9_vs_parental |
| HALLMARK_FATTY_ACID_METABOLISM | p53_WT_meta_cas9_vs_parental |
| HALLMARK_MYC_TARGETS_V1 | p53_WT_meta_cas9_vs_parental |
| HALLMARK_INTERFERON_ALPHA_RESPONSE | p53_WT_meta_cas9_vs_parental |
| HALLMARK_TNFA_SIGNALING_VIA_NFKB | p53_WT_meta_cas9_vs_parental |
| HALLMARK_P53_PATHWAY | p53_WT_meta_cas9_vs_parental |

TABLE 14

| p53mut Cas9 v. Parental | | | | | |
|---|---|---|---|---|---|
| Signature Name | Size | ES | NES | NOM p-val | FDR_qval |
| HALLMARK_E2F_TARGETS | 183 | 0.5550177 | 2.6395845 | 0 | 0 |
| HALLMARK_MYC_TARGETS_V1 | 194 | 0.5575601 | 2.626304 | 0 | 0 |
| HALLMARK_G2M_CHECKPOINT | 195 | 0.5407961 | 2.594342 | 0 | 0 |
| HALLMARK_MYC_TARGETS_V2 | 55 | 0.6715449 | 2.5552053 | 0 | 0 |
| HALLMARK_UNFOLDED_PROTEIN_RESPONSE | 107 | 0.5477837 | 2.4258528 | 0 | 0 |
| HALLMARK_DNA_REPAIR | 128 | 0.45505545 | 2.0449944 | 0 | 0 |
| HALLMARK_MTORC1_SIGNALING | 195 | 0.3684585 | 1.7560692 | 0 | 0.00181988 |
| HALLMARK_OXIDATIVE_PHOSPHORYLATION | 194 | 0.3636112 | 1.7358756 | 0 | 0.00190254 |
| HALLMARK_SPERMATOGENESIS | 77 | 0.37748834 | 1.5650069 | 0.00336134 | 0.00959095 |
| HALLMARK_INFLAMMATORY_RESPONSE | 170 | −0.2893959 | −1.451835 | 0.00549451 | 0.03650026 |
| HALLMARK_HEDGEHOG_SIGNALING | 30 | −0.4191447 | −1.4966764 | 0.03432494 | 0.02516555 |
| HALLMARK_BILE_ACID_METABOLISM | 85 | −0.3497032 | −1.5749267 | 0 | 0.01227755 |
| HALLMARK_INTERFERON_GAMMA_RESPONSE | 170 | −0.31475 | −1.5905329 | 0.00287356 | 0.01218031 |
| HALLMARK_COMPLEMENT | 164 | −0.3261111 | −1.6344079 | 0 | 0.00793542 |
| HALLMARK_NOTCH_SIGNALING | 26 | −0.4991429 | −1.7362854 | 0.00229358 | 0.00314998 |
| HALLMARK_GLYCOLYSIS | 175 | −0.3482411 | −1.7428205 | 0 | 0.00349997 |
| HALLMARK_COAGULATION | 96 | −0.383397 | −1.7716936 | 0 | 0.00150393 |
| HALLMARK_ANGIOGENESIS | 32 | −0.5109052 | −1.8327966 | 0 | 8.85E−04 |
| HALLMARK_KRAS_SIGNALING_DN | 105 | −0.395604 | −1.8609637 | 0 | 0.00103277 |
| HALLMARK_EPITHELIAL_MESENCHYMAL_TRANSITION | 188 | −0.3723047 | −1.9067988 | 0 | 6.17E−04 |
| HALLMARK_ALLOGRAFT_REJECTION | 172 | −0.3794377 | −1.9104357 | 0 | 7.71E−04 |

TABLE 14-continued

| p53mut Cas9 v. Parental | | | | | |
|---|---|---|---|---|---|
| HALLMARK_MYOGENESIS | 165 | −0.3886325 | −1.9296448 | 0 | 0.00102826 |
| HALLMARK_APICAL_JUNCTION | 169 | −0.4023739 | −1.9962245 | 0 | 0.00154239 |
| HALLMARK_HYPOXIA | 179 | −0.4421759 | −2.2291427 | 0 | 0 |
| HALLMARK_MYC_TARGETS_V1 | 194 | 0.55907196 | 2.545917 | 0 | 0 |
| HALLMARK_UNFOLDED_PROTEIN_RESPONSE | 107 | 0.53204685 | 2.2489417 | 0 | 0 |
| HALLMARK_MYC_TARGETS_V2 | 55 | 0.5642699 | 2.1159031 | 0 | 0 |
| HALLMARK_G2M_CHECKPOINT | 195 | 0.45417103 | 2.0940845 | 0 | 0 |
| HALLMARK_DNA_REPAIR | 128 | 0.47058904 | 2.0241897 | 0 | 1.44E−04 |
| HALLMARK_OXIDATIVE_PHOSPHORYLATION | 194 | 0.43168533 | 1.9697614 | 0 | 3.81E−04 |
| HALLMARK_PROTEIN_SECRETION | 94 | 0.47237247 | 1.947323 | 0 | 4.41E−04 |
| HALLMARK_E2F_TARGETS | 183 | 0.40342113 | 1.8408355 | 0 | 0.00149061 |
| HALLMARK_MTORC1_SIGNALING | 195 | 0.37375557 | 1.7231494 | 0 | 0.00346937 |
| HALLMARK_TNFA_SIGNALING_VIA_NFKB | 192 | 0.3675395 | 1.697546 | 0 | 0.00335589 |
| HALLMARK_PI3K_AKT_MTOR_SIGNALING | 95 | 0.36371583 | 1.5039989 | 0.00987306 | 0.02693045 |
| HALLMARK_TGF_BETA_SIGNALING | 50 | 0.3783123 | 1.4351299 | 0.04517134 | 0.04903993 |
| HALLMARK_HYPOXIA | 179 | −0.2913958 | −1.4922879 | 0 | 0.035727 |
| HALLMARK_GLYCOLYSIS | 175 | −0.3067291 | −1.5715631 | 0 | 0.0195093 |
| HALLMARK_APICAL_SURFACE | 29 | −0.4495046 | −1.6105906 | 0.01546392 | 0.01751023 |
| HALLMARK_KRAS_SIGNALING_DN | 105 | −0.3547268 | −1.6696823 | 0 | 0.0147291 |
| HALLMARK_MYOGENESIS | 165 | −0.3439297 | −1.7583498 | 0 | 0.0082793 |
| HALLMARK_CHOLESTEROL_HOMEOSTASIS | 59 | −0.44074 | −1.887215 | 0 | 0.00129412 |

| Signature Name | Signature_type |
|---|---|
| HALLMARK_E2F_TARGETS | p53_MUT_aggregate_Cas9_vs_Parental |
| HALLMARK_MYC_TARGETS_V1 | p53_MUT_aggregate_Cas9_vs_Parental |
| HALLMARK_G2M_CHECKPOINT | p53_MUT_aggregate_Cas9_vs_Parental |
| HALLMARK_MYC_TARGETS_V2 | p53_MUT_aggregate_Cas9_vs_Parental |
| HALLMARK_UNFOLDED_PROTEIN_RESPONSE | p53_MUT_aggregate_Cas9_vs_Parental |
| HALLMARK_DNA_REPAIR | p53_MUT_aggregate_Cas9_vs_Parental |
| HALLMARK_MTORC1_SIGNALING | p53_MUT_aggregate_Cas9_vs_Parental |
| HALLMARK_OXIDATIVE_PHOSPHORYLATION | p53_MUT_aggregate_Cas9_vs_Parental |
| HALLMARK_SPERMATOGENESIS | p53_MUT_aggregate_Cas9_vs_Parental |
| HALLMARK_INFLAMMATORY_RESPONSE | p53_MUT_aggregate_Cas9_vs_Parental |
| HALLMARK_HEDGEHOG_SIGNALING | p53_MUT_aggregate_Cas9_vs_Parental |
| HALLMARK_BILE_ACID_METABOLISM | p53_MUT_aggregate_Cas9_vs_Parental |
| HALLMARK_INTERFERON_GAMMA_RESPONSE | p53_MUT_aggregate_Cas9_vs_Parental |
| HALLMARK_COMPLEMENT | p53_MUT_aggregate_Cas9_vs_Parental |
| HALLMARK_NOTCH_SIGNALING | p53_MUT_aggregate_Cas9_vs_Parental |
| HALLMARK_GLYCOLYSIS | p53_MUT_aggregate_Cas9_vs_Parental |
| HALLMARK_COAGULATION | p53_MUT_aggregate_Cas9_vs_Parental |
| HALLMARK_ANGIOGENESIS | p53_MUT_aggregate_Cas9_vs_Parental |
| HALLMARK_KRAS_SIGNALING_DN | p53_MUT_aggregate_Cas9_vs_Parental |
| HALLMARK_EPITHELIAL_MESENCHYMAL_TRANSITION | p53_MUT_aggregate_Cas9_vs_Parental |
| HALLMARK_ALLOGRAFT_REJECTION | p53_MUT_aggregate_Cas9_vs_Parental |
| HALLMARK_MYOGENESIS | p53_MUT_aggregate_Cas9_vs_Parental |
| HALLMARK_APICAL_JUNCTION | p53_MUT_aggregate_Cas9_vs_Parental |
| HALLMARK_HYPOXIA | p53_MUT_aggregate_Cas9_vs_Parental |
| HALLMARK_MYC_TARGETS_V1 | p53_MUT_meta_cas9_vs_parental |
| HALLMARK_UNFOLDED_PROTEIN_RESPONSE | p53_MUT_meta_cas9_vs_parental |
| HALLMARK_MYC_TARGETS_V2 | p53_MUT_meta_cas9_vs_parental |
| HALLMARK_G2M_CHECKPOINT | p53_MUT_meta_cas9_vs_parental |
| HALLMARK_DNA_REPAIR | p53_MUT_meta_cas9_vs_parental |
| HALLMARK_OXIDATIVE_PHOSPHORYLATION | p53_MUT_meta_cas9_vs_parental |
| HALLMARK_PROTEIN_SECRETION | p53_MUT_meta_cas9_vs_parental |
| HALLMARK_E2F_TARGETS | p53_MUT_meta_cas9_vs_parental |
| HALLMARK_MTORC1_SIGNALING | p53_MUT_meta_cas9_vs_parental |
| HALLMARK_TNFA_SIGNALING_VIA_NFKB | p53_MUT_meta_cas9_vs_parental |
| HALLMARK_PI3K_AKT_MTOR_SIGNALING | p53_MUT_meta_cas9_vs_parental |
| HALLMARK_TGF_BETA_SIGNALING | p53_MUT_meta_cas9_vs_parental |
| HALLMARK_HYPOXIA | p53_MUT_meta_cas9_vs_parental |
| HALLMARK_GLYCOLYSIS | p53_MUT_meta_cas9_vs_parental |
| HALLMARK_APICAL_SURFACE | p53_MUT_meta_cas9_vs_parental |
| HALLMARK_KRAS_SIGNALING_DN | p53_MUT_meta_cas9_vs_parental |
| HALLMARK_MYOGENESIS | p53_MUT_meta_cas9_vs_parental |
| HALLMARK_CHOLESTEROL_HOMEOSTASIS | p53_MUT_meta_cas9_vs_parental |

TABLE 15

| p53WT empty vector v. parental | | | | | |
|---|---|---|---|---|---|
| Signature name | Size | ES | NES | NOM p-val | FDR_qval |
| HALLMARK_E2F_TARGETS | 183 | 0.6525211 | 4.0678716 | 0 | 0 |
| HALLMARK_MYC_TARGETS_V1 | 194 | 0.6472384 | 4.0669246 | 0 | 0 |

TABLE 15-continued

| p53WT empty vector v. parental | | | | | |
|---|---|---|---|---|---|
| HALLMARK_G2M_CHECKPOINT | 195 | 0.5685229 | 3.273654 | 0 | 0 |
| HALLMARK_MTORC1_SIGNALING | 195 | 0.41445196 | 2.5154781 | 0 | 0 |
| HALLMARK_MYC_TARGETS_V2 | 55 | 0.4906395 | 2.4695451 | 0 | 0 |
| HALLMARK_MITOTIC_SPINDLE | 176 | 0.34478587 | 2.2369454 | 0 | 0 |
| HALLMARK_DNA_REPAIR | 128 | 0.30733964 | 1.8412334 | 0 | 0.009501188 |
| HALLMARK_UNFOLDED_PROTEIN_RESPONSE | 107 | 0.33678356 | 1.809335 | 0 | 0.014251782 |
| HALLMARK_CHOLESTEROL_HOMEOSTASIS | 59 | 0.35262248 | 1.7997544 | 0 | 0.012668251 |
| HALLMARK_PI3K_AKT_MTOR_SIGNALING | 95 | 0.26882893 | 1.6203853 | 0 | 0.019809976 |
| HALLMARK_REACTIVE_OXIGEN_SPECIES_PATHWAY | 43 | 0.33177683 | 1.5186088 | 0.00952381 | 0.042064346 |
| HALLMARK_PANCREAS_BETA_CELLS | 27 | −0.4871108 | −1.49999 | 0.028070176 | 0.017760886 |
| HALLMARK_TNFA_SIGNALING_VIA_NFKB | 192 | −0.3858866 | −1.5387725 | 0 | 0.013672495 |
| HALLMARK_HEDGEHOG_SIGNALING | 30 | −0.485339 | −1.5440404 | 0.012514221 | 0.0144661 |
| HALLMARK_IL6_JAK_STAT3_SIGNALING | 75 | −0.4329089 | −1.5783926 | 0.002114165 | 0.011472867 |
| HALLMARK_KRAS_SIGNALING_UP | 174 | −0.4051738 | −1.6041077 | 0 | 0.00976468 |
| HALLMARK_INTERFERON_GAMMA_RESPONSE | 170 | −0.4137799 | −1.6332697 | 0 | 0.007790408 |
| HALLMARK_KRAS_SIGNALING_DN | 105 | −0.4487752 | −1.7158874 | 0.001030928 | 0.003366055 |
| HALLMARK_INTERFERON_ALPHA_RESPONSE | 81 | −0.4820397 | −1.7915936 | 0 | 8.08E−04 |
| HALLMARK_INFLAMMATORY_RESPONSE | 170 | −0.4577662 | −1.8251553 | 0 | 0.00161583 |
| HALLMARK_E2F_TARGETS | 185 | 0.6765837 | 4.0831795 | 0 | 0 |
| HALLMARK_G2M_CHECKPOINT | 196 | 0.5458789 | 2.9248586 | 0 | 0 |
| HALLMARK_MTORC1_SIGNALING | 197 | 0.468578 | 2.6882317 | 0 | 0 |
| HALLMARK_MYC_TARGETS_V2 | 55 | 0.46745232 | 2.26935 | 0 | 0 |
| HALLMARK_CHOLESTEROL_HOMEOSTASIS | 60 | 0.40998343 | 2.0666344 | 0 | 0 |
| HALLMARK_MITOTIC_SPINDLE | 177 | 0.33918 | 2.0326 | 0 | 0 |
| HALLMARK_UNFOLDED_PROTEIN_RESPONSE | 110 | 0.32251096 | 1.7795836 | 0 | 0.006766918 |
| HALLMARK_DNA_REPAIR | 133 | 0.29778996 | 1.6400503 | 0 | 0.012828946 |
| HALLMARK_OXIDATIVE_PHOSPHORYLATION | 195 | 0.21181697 | 1.4783561 | 0 | 0.034605265 |
| HALLMARK_KRAS_SIGNALING_UP | 179 | −0.4029828 | −1.5264843 | 0.001002004 | 0.02182828 |
| HALLMARK_IL6_JAK_STAT3_SIGNALING | 75 | −0.4569614 | −1.6044878 | 0.00104712 | 0.009849568 |
| HALLMARK_INFLAMMATORY_RESPONSE | 171 | −0.4484536 | −1.6624985 | 0 | 0.007629674 |
| HALLMARK_KRAS_SIGNALING_DN | 107 | −0.4682871 | −1.7049506 | 0 | 0.006051905 |

| Signature name | signature_type |
|---|---|
| HALLMARK_E2F_TARGETS | p53_WT_aggregate_EMPTY_VECTOR_VS_Parental |
| HALLMARK_MYC_TARGETS_V1 | p53_WT_aggregate_EMPTY_VECTOR_VS_Parental |
| HALLMARK_G2M_CHECKPOINT | p53_WT_aggregate_EMPTY_VECTOR_VS_Parental |
| HALLMARK_MTORC1_SIGNALING | p53_WT_aggregate_EMPTY_VECTOR_VS_Parental |
| HALLMARK_MYC_TARGETS_V2 | p53_WT_aggregate_EMPTY_VECTOR_VS_Parental |
| HALLMARK_MITOTIC_SPINDLE | p53_WT_aggregate_EMPTY_VECTOR_VS_Parental |
| HALLMARK_DNA_REPAIR | p53_WT_aggregate_EMPTY_VECTOR_VS_Parental |
| HALLMARK_UNFOLDED_PROTEIN_RESPONSE | p53_WT_aggregate_EMPTY_VECTOR_VS_Parental |
| HALLMARK_CHOLESTEROL_HOMEOSTASIS | p53_WT_aggregate_EMPTY_VECTOR_VS_Parental |
| HALLMARK_PI3K_AKT_MTOR_SIGNALING | p53_WT_aggregate_EMPTY_VECTOR_VS_Parental |
| HALLMARK_REACTIVE_OXIGEN_SPECIES_PATHWAY | p53_WT_aggregate_EMPTY_VECTOR_VS_Parental |
| HALLMARK_PANCREAS_BETA_CELLS | p53_WT_aggregate_EMPTY_VECTOR_VS_Parental |
| HALLMARK_TNFA_SIGNALING_VIA_NFKB | p53_WT_aggregate_EMPTY_VECTOR_VS_Parental |
| HALLMARK_HEDGEHOG_SIGNALING | p53_WT_aggregate_EMPTY_VECTOR_VS_Parental |
| HALLMARK_IL6_JAK_STAT3_SIGNALING | p53_WT_aggregate_EMPTY_VECTOR_VS_Parental |
| HALLMARK_KRAS_SIGNALING_UP | p53_WT_aggregate_EMPTY_VECTOR_VS_Parental |
| HALLMARK_INTERFERON_GAMMA_RESPONSE | p53_WT_aggregate_EMPTY_VECTOR_VS_Parental |
| HALLMARK_KRAS_SIGNALING_DN | p53_WT_aggregate_EMPTY_VECTOR_VS_Parental |
| HALLMARK_INTERFERON_ALPHA_RESPONSE | p53_WT_aggregate_EMPTY_VECTOR_VS_Parental |
| HALLMARK_INFLAMMATORY_RESPONSE | p53_WT_aggregate_EMPTY_VECTOR_VS_Parental |
| HALLMARK_E2F_TARGETS | p53_WT_meta_empty_vector_vs_parental |
| HALLMARK_G2M_CHECKPOINT | p53_WT_meta_empty_vector_vs_parental |
| HALLMARK_MTORC1_SIGNALING | p53_WT_meta_empty_vector_vs_parental |
| HALLMARK_MYC_TARGETS_V2 | p53_WT_meta_empty_vector_vs_parental |
| HALLMARK_CHOLESTEROL_HOMEOSTASIS | p53_WT_meta_empty_vector_vs_parental |
| HALLMARK_MITOTIC_SPINDLE | p53_WT_meta_empty_vector_vs_parental |
| HALLMARK_UNFOLDED_PROTEIN_RESPONSE | p53_WT_meta_empty_vector_vs_parental |
| HALLMARK_DNA_REPAIR | p53_WT_meta_empty_vector_vs_parental |
| HALLMARK_OXIDATIVE_PHOSPHORYLATION | p53_WT_meta_empty_vector_vs_parental |
| HALLMARK_KRAS_SIGNALING_UP | p53_WT_meta_empty_vector_vs_parental |
| HALLMARK_IL6_JAK_STAT3_SIGNALING | p53_WT_meta_empty_vector_vs_parental |
| HALLMARK_INFLAMMATORY_RESPONSE | p53_WT_meta_empty_vector_vs_parental |
| HALLMARK_KRAS_SIGNALING_DN | p53_WT_meta_empty_vector_vs_parental |

TABLE 16

| p53WT reporter v. parental | | | | | |
|---|---|---|---|---|---|
| Signature name | Size | ES | NES | NOM p-val | FDR_qval |
| HALLMARK_E2F_TARGETS | 183 | 0.46516845 | 2.7787433 | 0 | 0 |
| HALLMARK_G2M_CHECKPOINT | 195 | 0.34390748 | 2.4616764 | 0 | 0 |
| HALLMARK_PROTEIN_SECRETION | 94 | 0.29004312 | 1.685494 | 0 | 0.01646707 |
| HALLMARK_DNA_REPAIR | 128 | 0.25392953 | 1.683337 | 0 | 0.0123503 |
| HALLMARK_MTORC1_SIGNALING | 195 | 0.25299588 | 1.6734779 | 0 | 0.00988024 |
| HALLMARK_PI3K_AKT_MTOR_SIGNALING | 95 | 0.26599732 | 1.5981929 | 0 | 0.01362275 |
| HALLMARK_KRAS_SIGNALING_DN | 105 | −0.4316061 | −1.5689245 | 0 | 0.01226742 |
| HALLMARK_E2F_TARGETS | 185 | 0.475731 | 2.8951576 | 0 | 0 |
| HALLMARK_G2M_CHECKPOINT | 196 | 0.34552246 | 2.1840568 | 0 | 0 |
| HALLMARK_MTORC1_SIGNALING | 197 | 0.31198257 | 1.8833632 | 0 | 0.01163127 |
| HALLMARK_PROTEIN_SECRETION | 94 | 0.31877753 | 1.7189786 | 0 | 0.01993932 |
| HALLMARK_OXIDATIVE_PHOSPHORYLATION | 195 | 0.2420729 | 1.5999786 | 0 | 0.04605982 |
| HALLMARK_KRAS_SIGNALING_DN | 107 | −0.4518344 | −1.6716644 | 0 | 0.01272217 |

| Signature name | signature_type |
|---|---|
| HALLMARK_E2F_TARGETS | p53_WT_aggregate_CTL_VECTOR_VS_Parental |
| HALLMARK_G2M_CHECKPOINT | p53_WT_aggregate_CTL_VECTOR_VS_Parental |
| HALLMARK_PROTEIN_SECRETION | p53_WT_aggregate_CTL_VECTOR_VS_Parental |
| HALLMARK_DNA_REPAIR | p53_WT_aggregate_CTL_VECTOR_VS_Parental |
| HALLMARK_MTORC1_SIGNALING | p53_WT_aggregate_CTL_VECTOR_VS_Parental |
| HALLMARK_PI3K_AKT_MTOR_SIGNALING | p53_WT_aggregate_CTL_VECTOR_VS_Parental |
| HALLMARK_KRAS_SIGNALING_DN | p53_WT_aggregate_CTL_VECTOR_VS_Parental |
| HALLMARK_E2F_TARGETS | p53_WT_meta_ctl_vector_vs_parental |
| HALLMARK_G2M_CHECKPOINT | p53_WT_meta_ctl_vector_vs_parental |
| HALLMARK_MTORC1_SIGNALING | p53_WT_meta_ctl_vector_vs_parental |
| HALLMARK_PROTEIN_SECRETION | p53_WT_meta_ctl_vector_vs_parental |
| HALLMARK_OXIDATIVE_PHOSPHORYLATION | p53_WT_meta_ctl_vector_vs_parental |
| HALLMARK_KRAS_SIGNALING_DN | p53_WT_meta_ctl_vector_vs_parental |

Figure 1D:
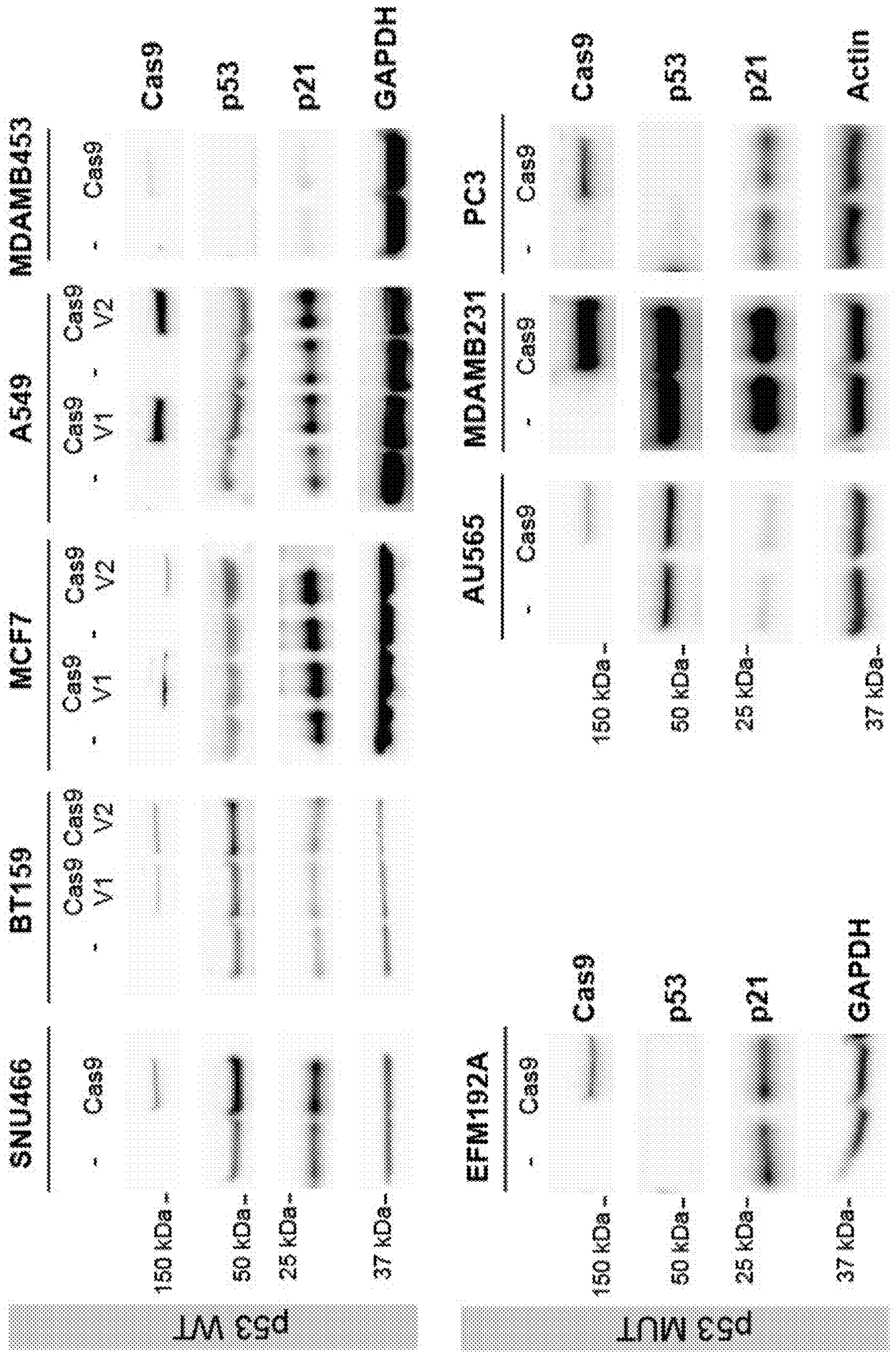
Figure 1E:
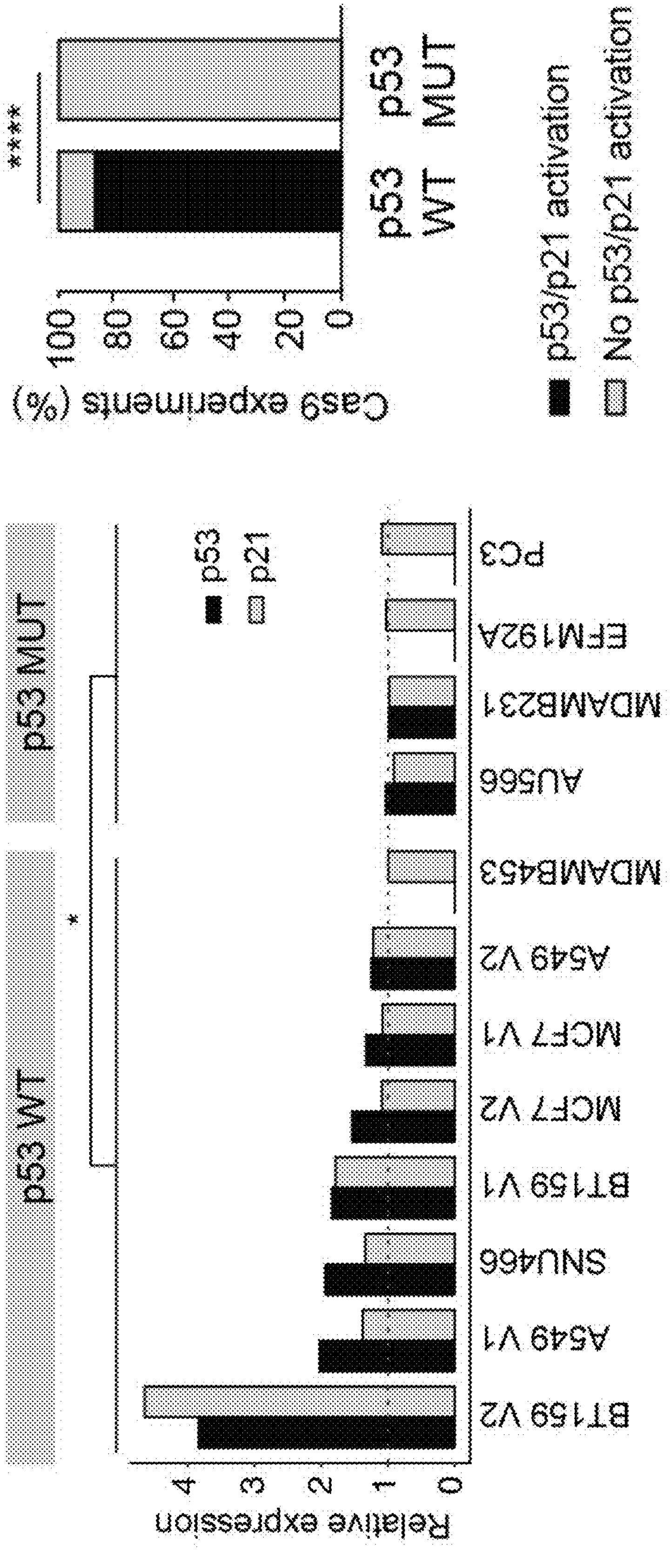
Figure 1F:
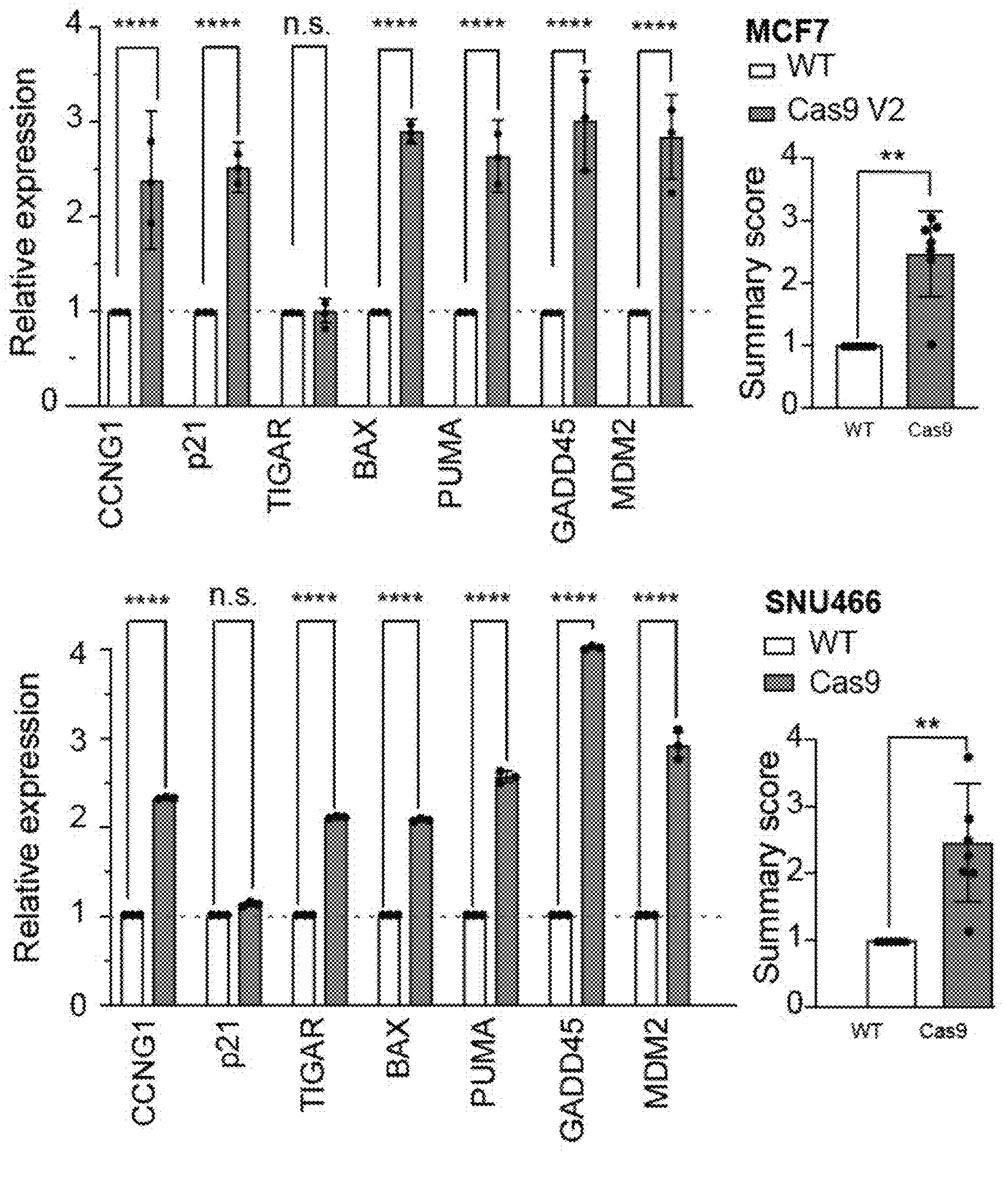
Figure 7A:
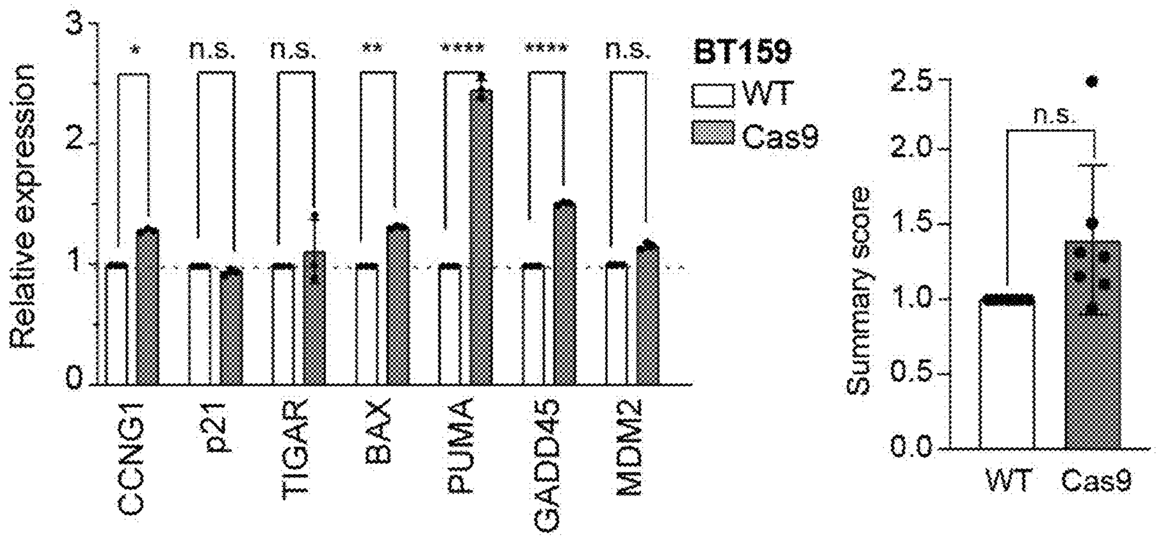
FIG. 7A-7E—Confirmation of p53 activation following Cas9 introduction.
Figure 7B:
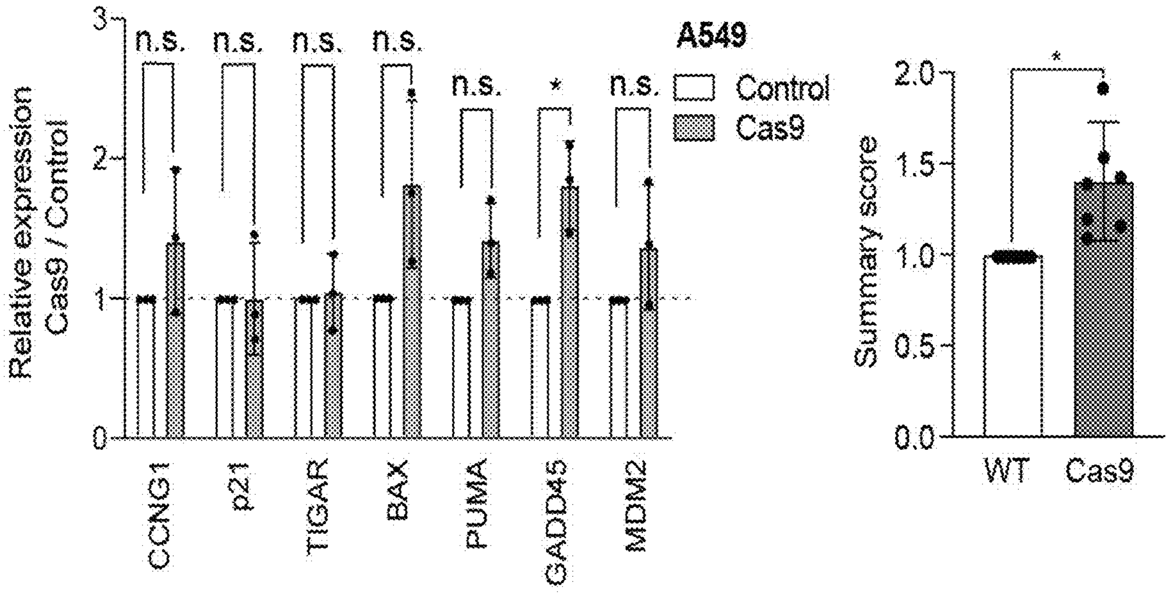

Immunoblotting confirmed p53 pathway activation upon Cas9 introduction into TP53-WT cells. Modestly elevated levels of p53 and/or p21 protein expression were observed in 7 out of 8 independent Cas9 introduction experiments across 5 TP53-WT lines (p=0.027 and p=0.024 for p53 and p21, respectively; FIGS. 1D-1E), but was not detected in 4 independent Cas9 introduction experiments across 4 TP53-mutant lines (p=0.01 for the comparison between groups; FIGS. 1D-1E). RT-qPCR analysis confirmed that Cas9 lines—but not lines expressing GFP, luciferase or a DNA barcode—exhibited elevated mRNA levels of multiple p53 transcriptional targets (FIG. 1F, FIGS. 7A and 7B, and Table 12).

Figure 1G:
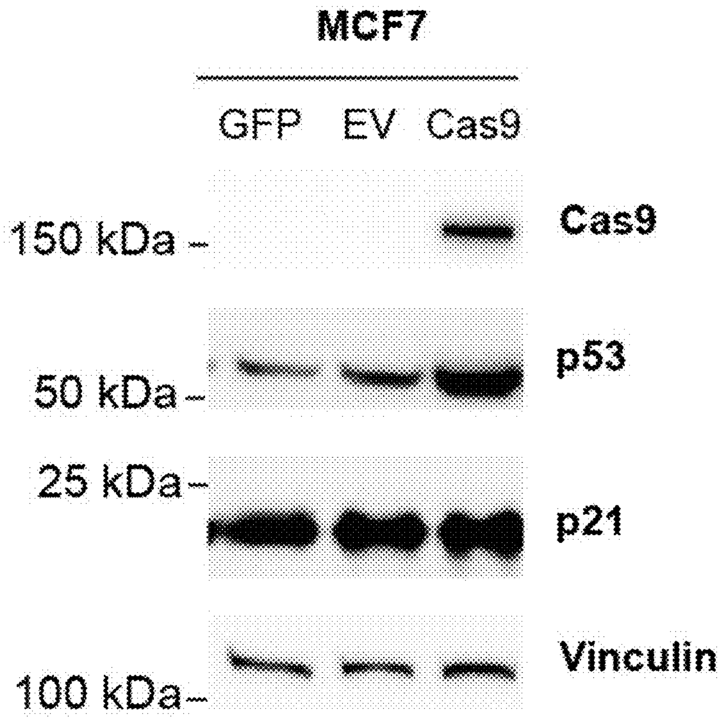
(FIG. 1G) Protein levels of Cas9, p53, p21 and a housekeeping protein in MCF7 cells transfected with GFP, Cas9 or a backbone-matched empty vector (EV). Representative results of 3 independent experiments are shown.
Figure 1H:
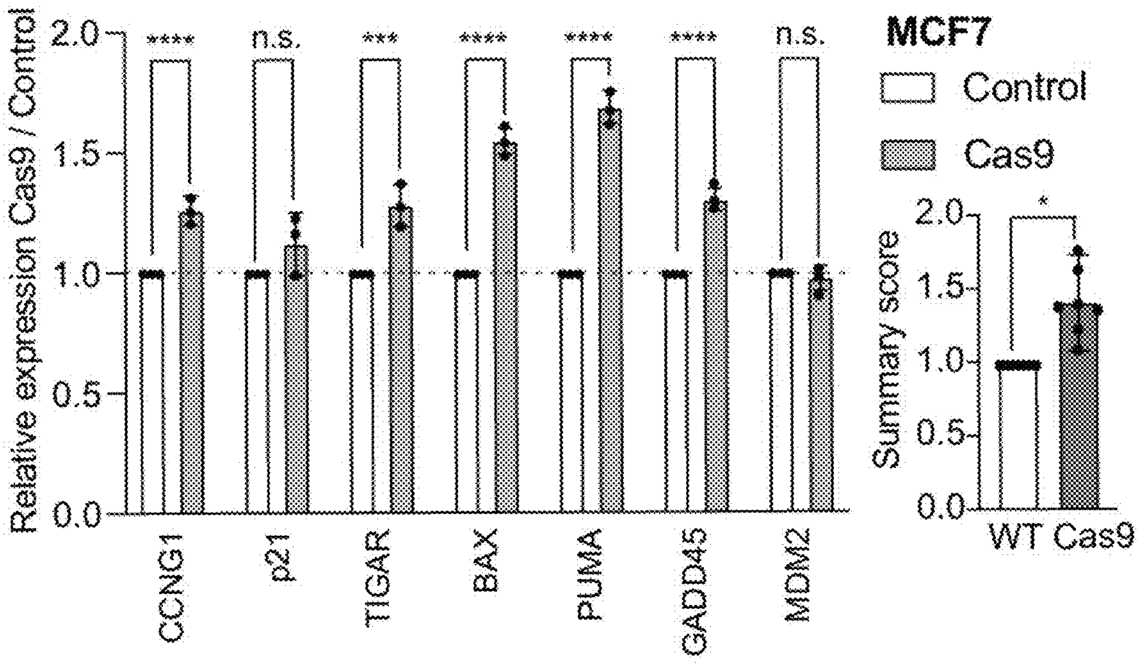
(FIG. 1H) Left: confirmation of p53 activation in MCF7 cells transfected with Cas9 by RT-qPCR analysis of 7 p53 transcriptional targets. Shown is the relative activation in cells transfected with Cas9 compared to cells transfected with control vectors. *, $p=0.0002$, **, $p<0.0001$, one-tailed t-test. Right: the average activation of p53 transcriptional targets. *, $p<0.05$, two-sided one-sample t-test. For all bar plots: data values, the means of the 7 targets; error bars, S.D.
Figure 7C:
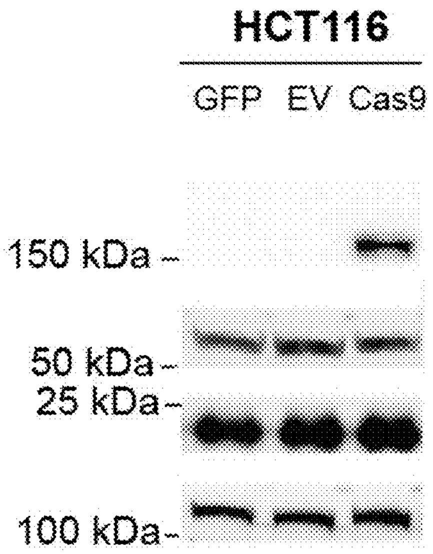
Figure 7D:
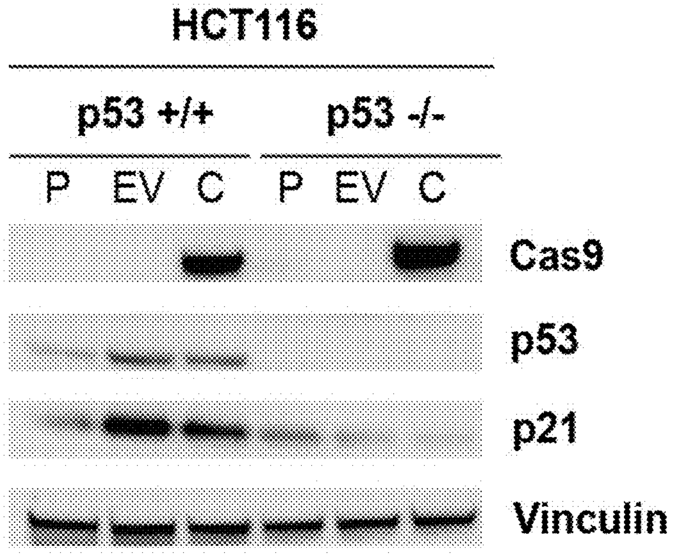
Figure 7E:
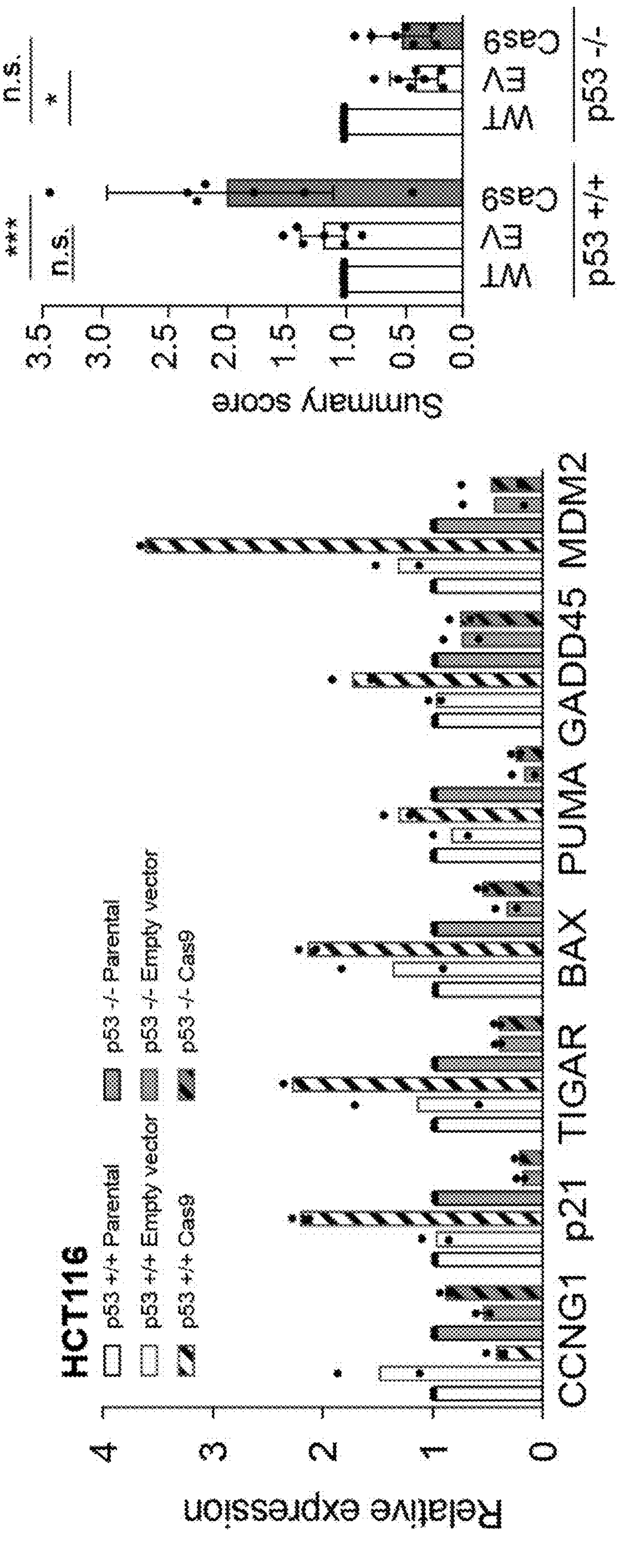

To further rule out the possibility that the observed p53 activation is merely a consequence of viral transduction, or that it would occur following the overexpression of any gene, the following experiments were performed. The TP53-WT lines MCF7 and HCT116 were transfected with either Cas9, GFP or a backbone-matched empty vector. In MCF7 cells, p53 activation was significantly stronger in the Cas9-expressing cells (FIGS. 1G-1H). In HCT116 cells, a significant difference in p53 pathway activity between the different transfections was note observed (FIG. 7C). However, when isogenic TP53-WT and TP53-null HCT116 lines[9] were transduced with viruses carrying either Cas9 or a backbone-matched empty vector, p53 activation was significantly stronger upon Cas9 transduction (and was specific to the TP53-WT cells; FIGS. 7D-7E). Together, these findings demonstrate that Cas9-induced p53 activation cannot be explained by technical noise, by the effect of viral transduction, or by a general selection bottleneck.

Example 3—Activation of p53 Pathway Post Cas9 Introduction

The well-established role of p53 in response to DNA damage makes its activation in the context of Cas9 expression particularly interesting[10-13] It was recently reported that p53 inhibits CRISPR-Cas9 genome editing[10-13], but the p53-mediated DNA damage response was detected in the presence of DNA-cutting sgRNAs. Here, it was observed that p53 activation could be induced by the expression of Cas9 alone. Moreover, the inhibitory effect of p53 was suggested to be linked to the increased sensitivity of non-transformed cells to double strand breaks[10,11], whereas here p53 activation was observed in cancer cells.

Figure 8A:
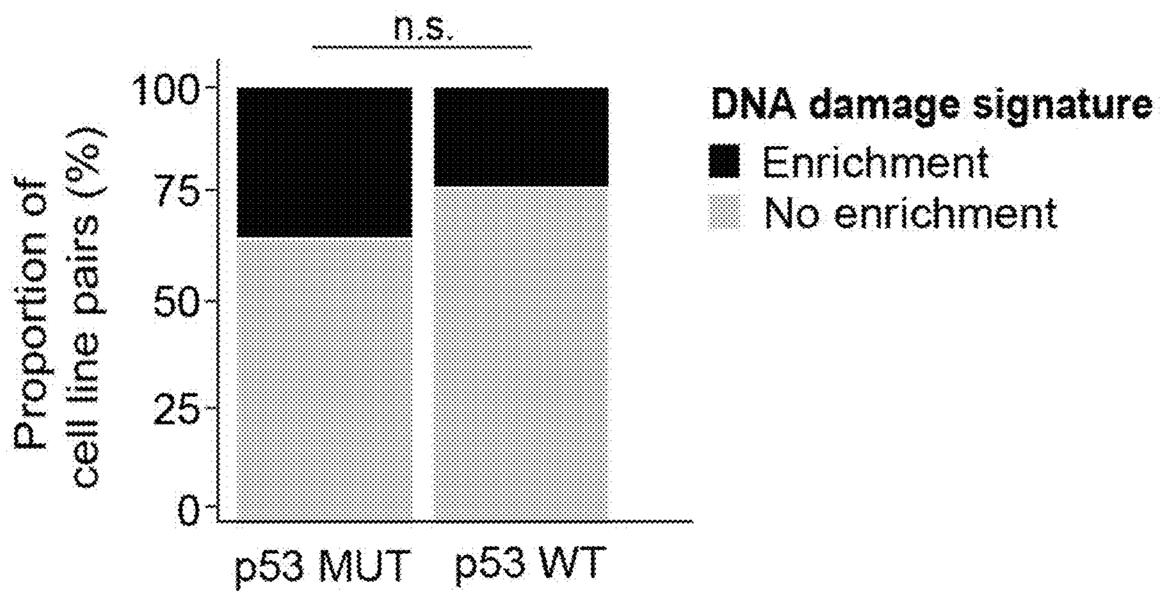
FIGS. 8A-8C—Cas9 introduction activates the DNA damage response.
Figure 8B:
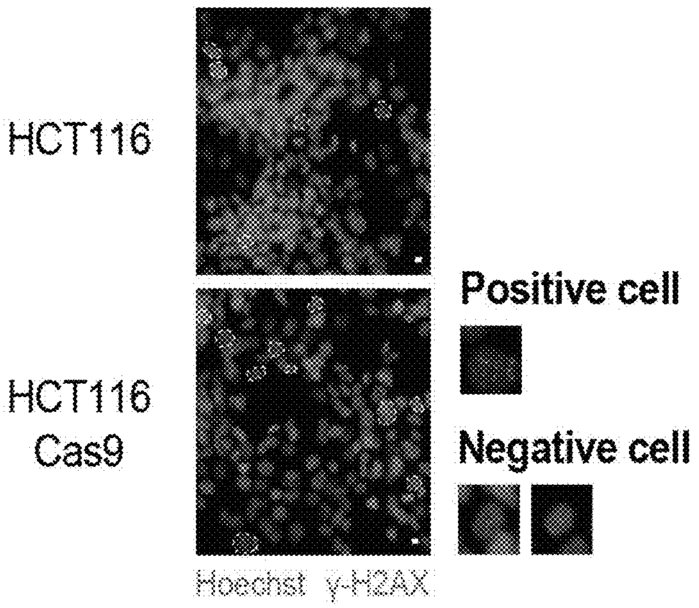
Figure 8C:
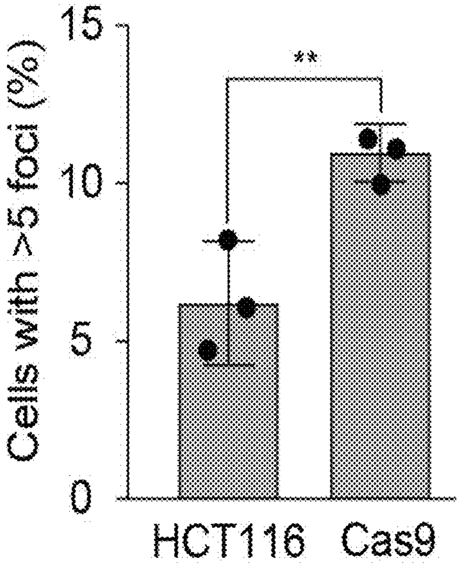

Interestingly, NF-kB signaling was the other top pathway significantly activated specifically following Cas9 introduction (Tables 13-16). p53 and NF-kB are the major regulators of the transcriptional response to DNA damage[14,15], alluding to a potential involvement of DNA damage in the observed p53 response. Indeed, a DNA repair transcriptional signature[7] was positively enriched following Cas9 introduction in 32 (19.4%) of the line pairs, in both TP53-WT and TP53-mutant lines (p=0.07; FIG. 8A). Immunofluorescence of three pairs confirmed that expression of Cas9 increased the number of DNA double-strand breaks, as measured by yH2AX foci (p<0.0001; FIGS. 2A-2B and FIGS. 8B-8C).

Figure 2A:
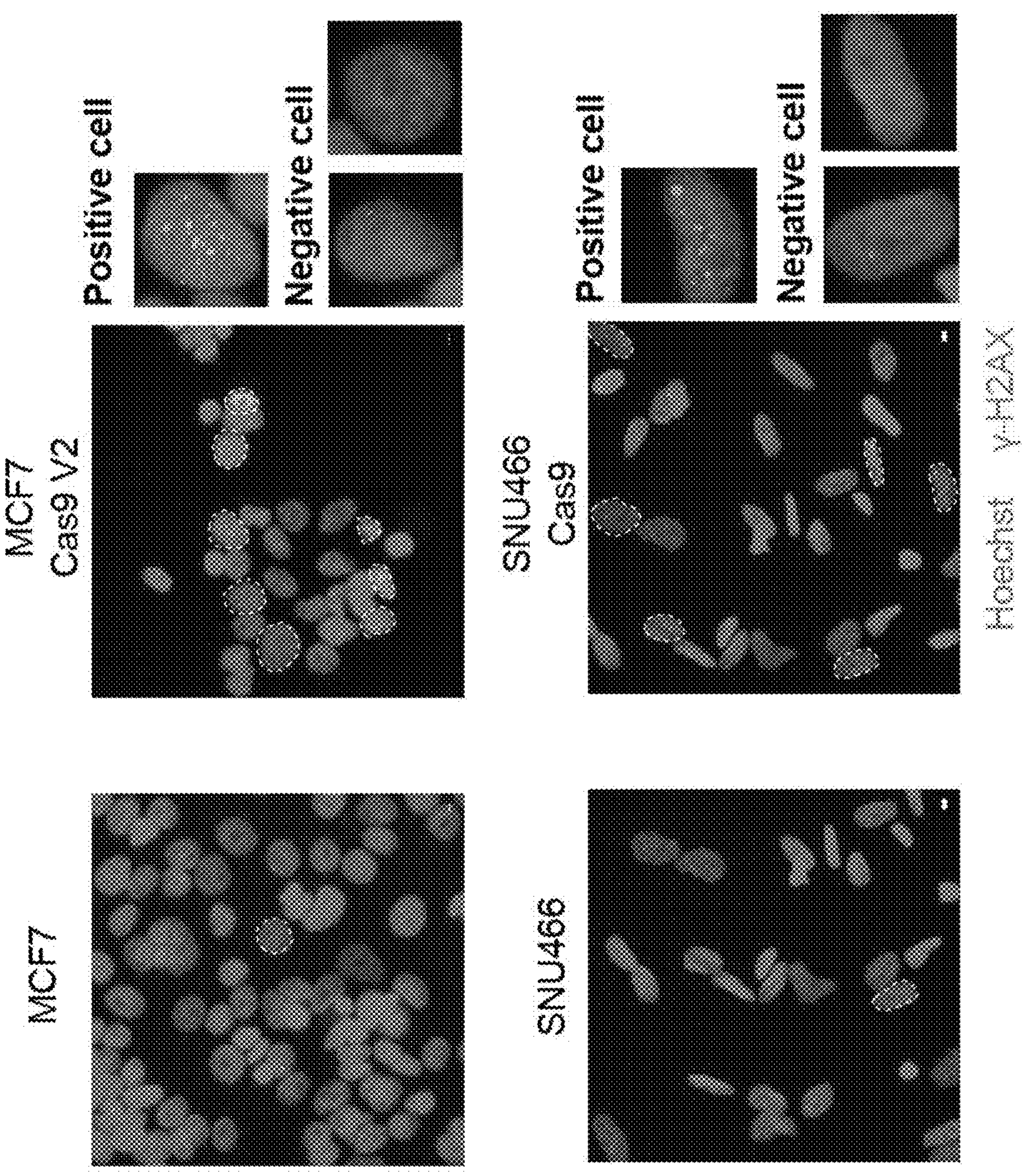
FIGS. 2A-2B—Cas9 introduction is associated with elevated DNA damage.
Figure 2B:
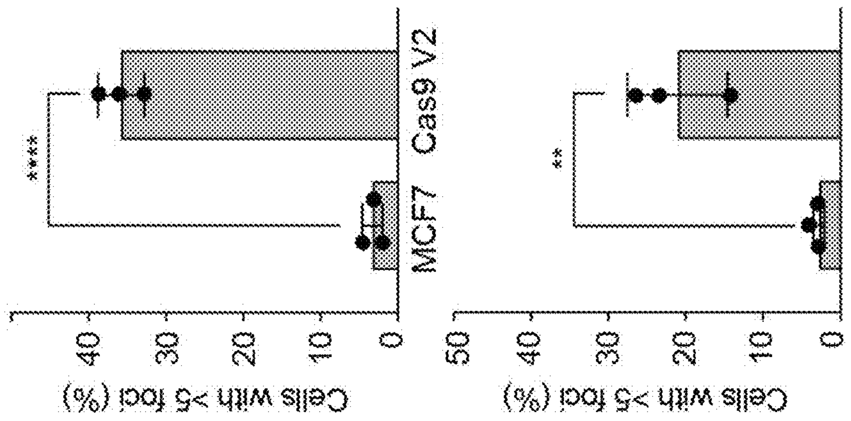
Figure 3A:
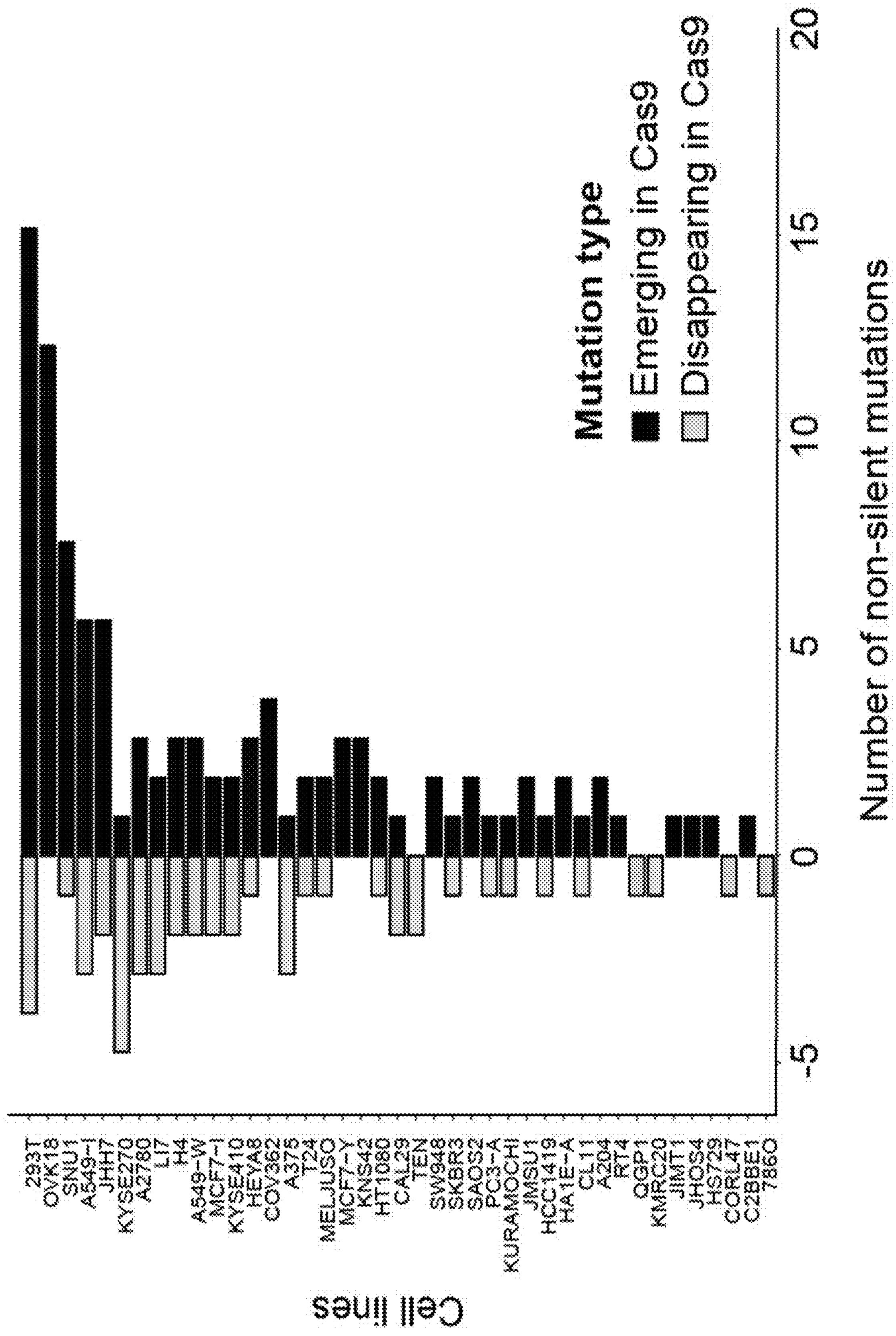
FIGS. 3A-3E—Cas9 introduction selects for inactivating TP53 mutations.
Figure 9A:
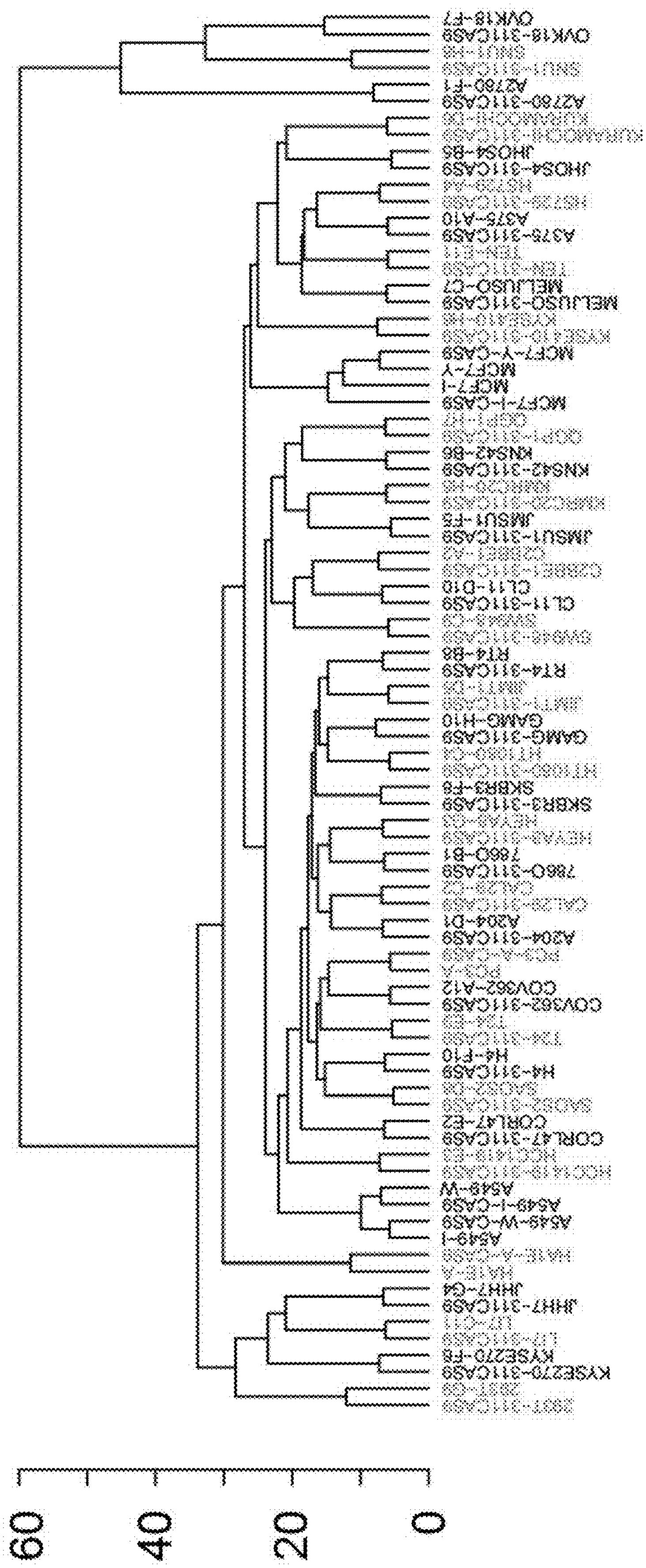
FIGS. 9A-9G—Cas9 introduction selects for inactivating TP53 mutations.
Figure 9B:
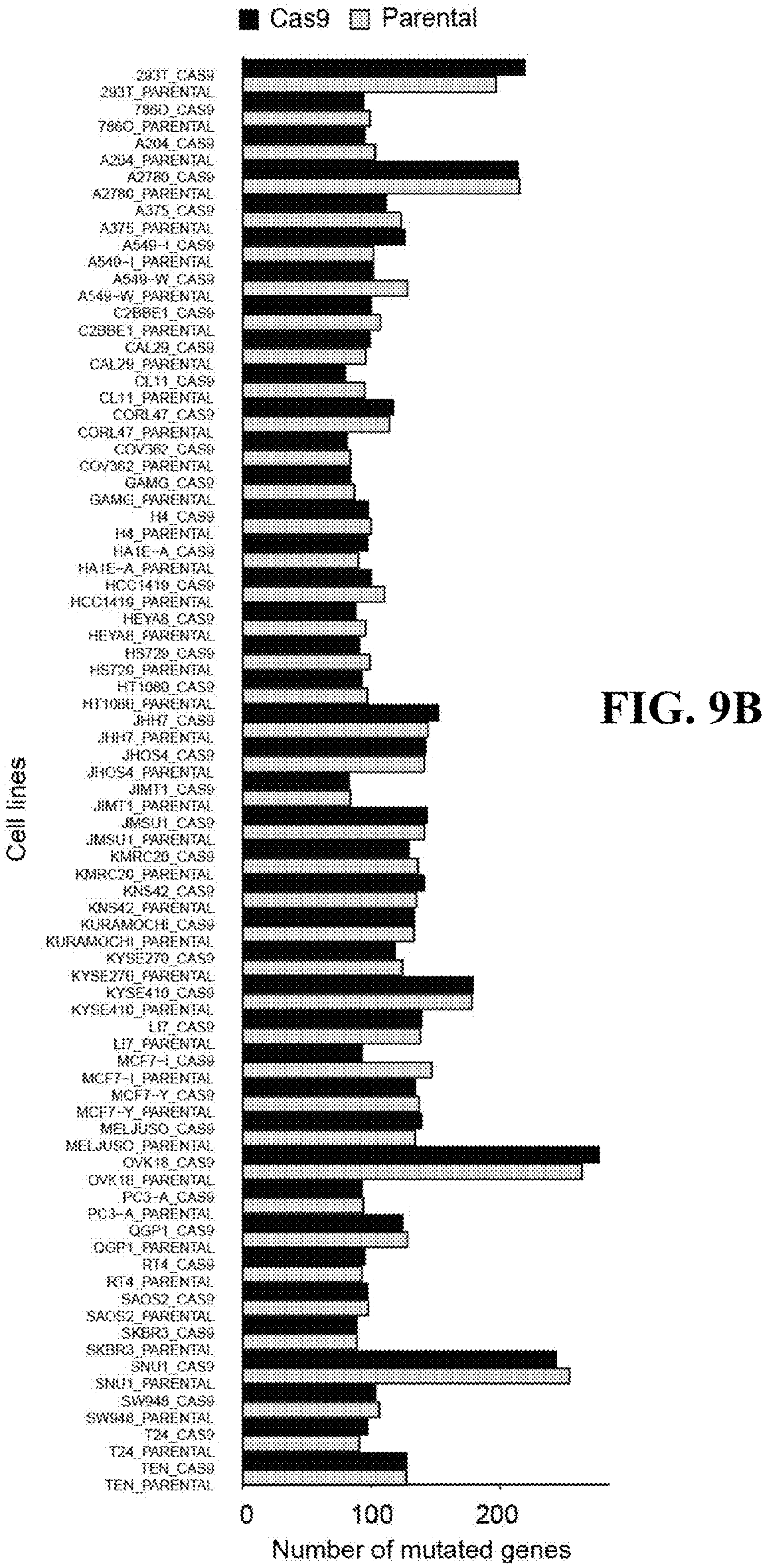
Figure 9C:
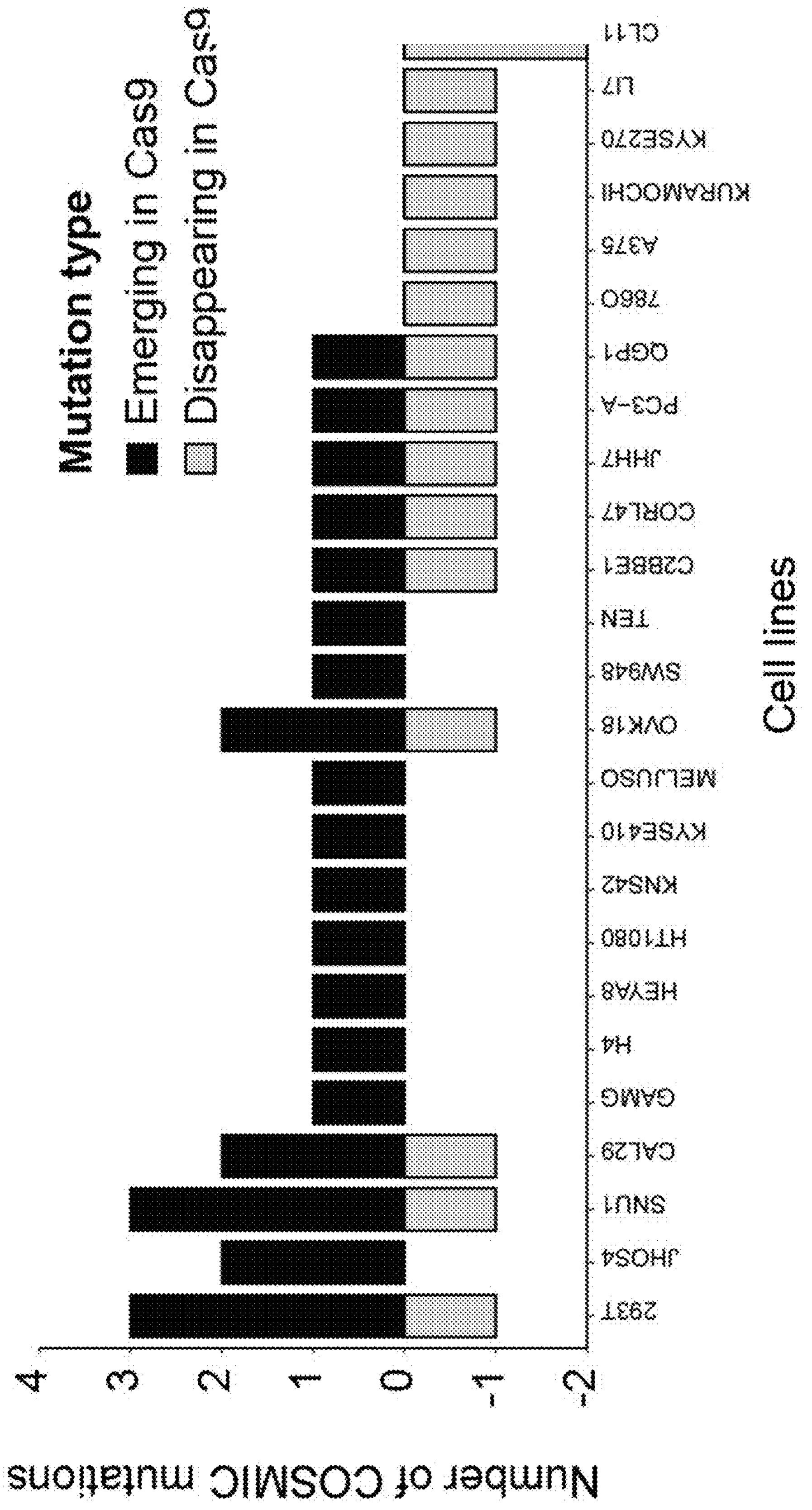

Activation of the p53 pathway following Cas9 introduction suggests that p53 activity is a barrier that cells need to overcome in order to stably express Cas9. Cas9 introduction might therefore select for p53 inactivating mutations. To test this hypothesis, point mutations of 447 cancer genes in 42 pairs of WT/Cas9 lines were characterized using deep (283×) targeted exon sequencing[16] (See methods in Example 8 and Supplementary Data 3 of Enache, O. M., Rendo, V., Abdusamad, M. et al. Cas9 activates the p53 pathway and selects for p53-inactivating mutations. Nat Genet 52, 662-668 (2020). https://doi.org/10.1038/s41588-020-0623-4, which is incorporated by reference herein as if expressed in its entirety). The mutational landscapes of all Cas9 lines were all highly similar to those of their parental counterparts, as expected (FIGS. 9A-9B). When considering only non-synonymous single nucleotide variants (SNVs) and indels affecting the coding sequence, an average of 2.6 mutations were detected in Cas9 lines but not in their parental WT lines, and an average of 1.3 mutations were detected in WT lines but not in their derivative Cas9 lines (FIG. 3A). This means that Cas9 lines tend to acquire new mutations more often than they tend to lose them (p=0.003). On average, ~4.5 non-silent mutations in bona fide cancer genes separated Cas9 lines from their parental WT lines (FIG. 2A and FIG. 9C). It is noted that these differences may have nothing to do with Cas9 per se, but may result from cell line diversification due to culture bottlenecks[2]. The analysis was repeated using only the subset of mutations listed as recurrent somatic mutations in the COSMIC database[30], and found that they followed the same trend, with an average of 0.62 mutations appearing, and 0.38 mutations disappearing, in the Cas9 vs. the WT lines (p=0.038; FIG. 9C).

Figure 3B:
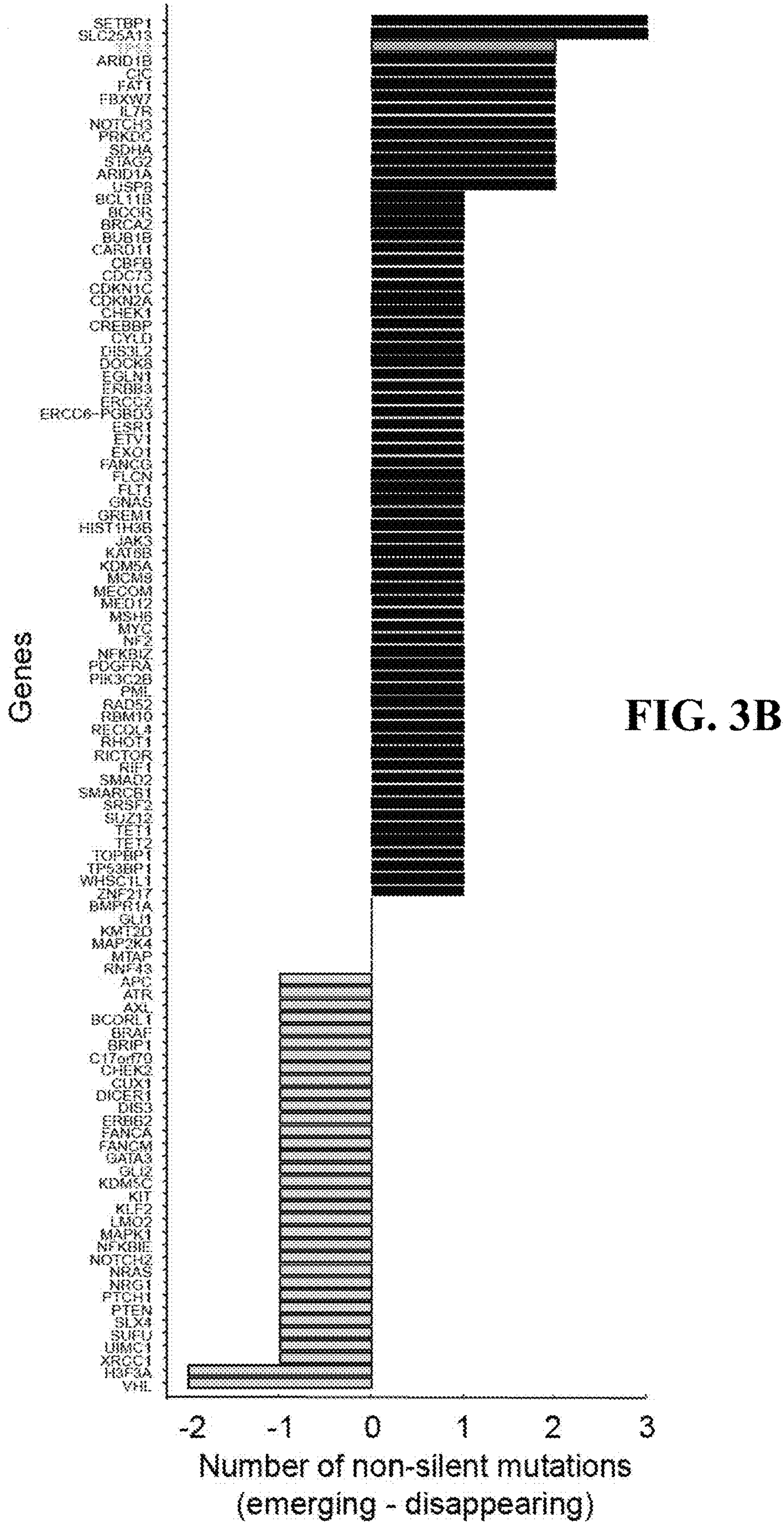
Figure 3C:
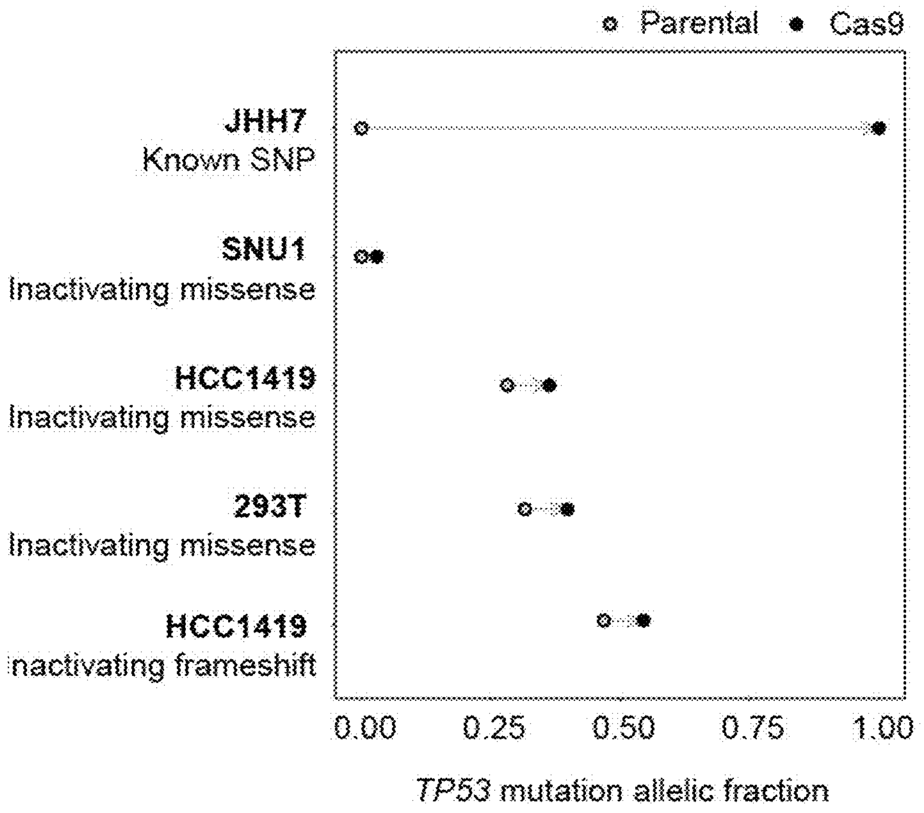
Figure 9D:
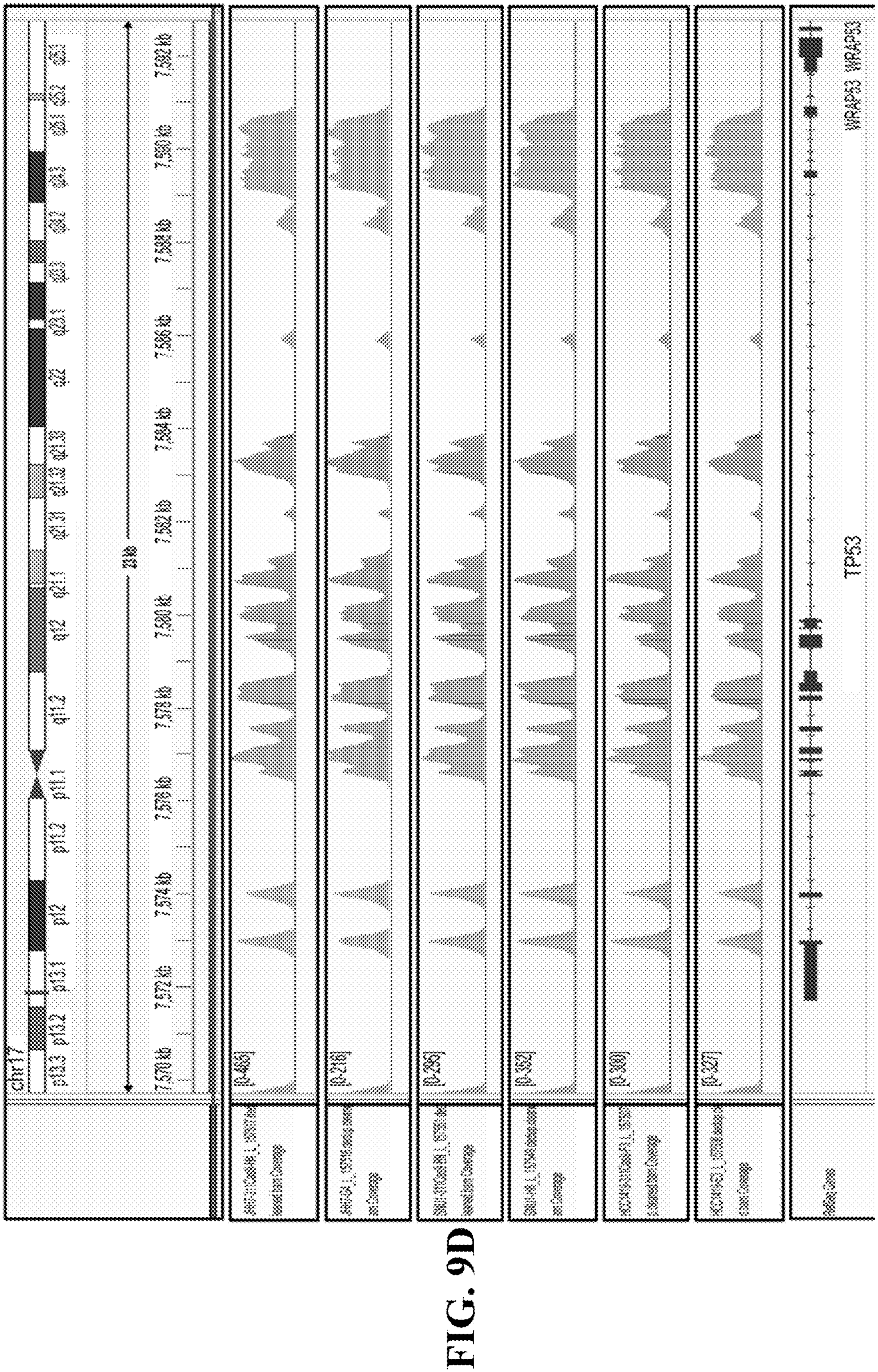

TP53 was among the top 4% of genes in its tendency to acquire new mutations upon Cas9 introduction (FIG. 3B). Non-silent TP53 mutations emerged in the Cas9 line of 2 out of the 42 examined pairs, SNU1 and JHH7, and significantly expanded in two additional lines, 293T and HCC1419 (which had two such mutations, both of which expanded; p=0.008 and p=0.047; FIG. 3C and Table 12). For JHH7, the mutation was not detected in the parental WT line but became clonally homozygous (AF=1) in the Cas9 line (FIG. 3C and FIG. 9D). It was confirmed by visual inspection that the appearance of these mutations was not an artifact of low sequencing coverage or misalignment issues (FIG. 9D), and found that in SNU1, the mutation pre-existed in the WT line and expanded beyond the calling threshold (2%) in the Cas9 line, whereas in JHH7 no evidence for the mutation was found in the WT line.

Figure 3D:
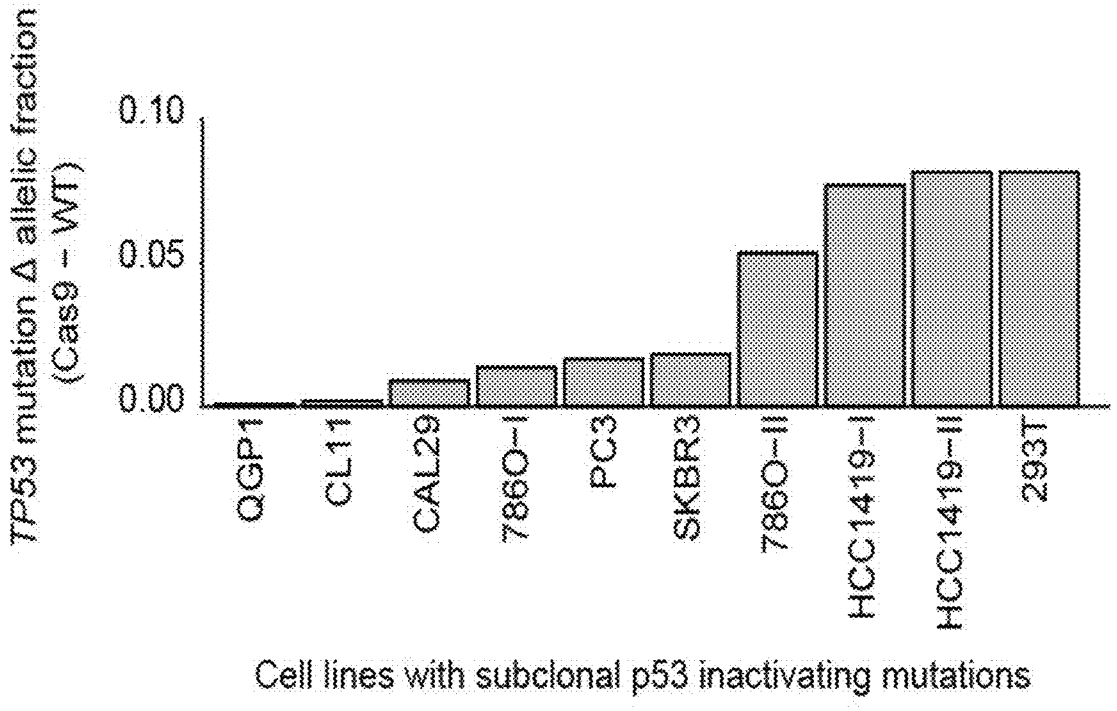
Figure 9E:
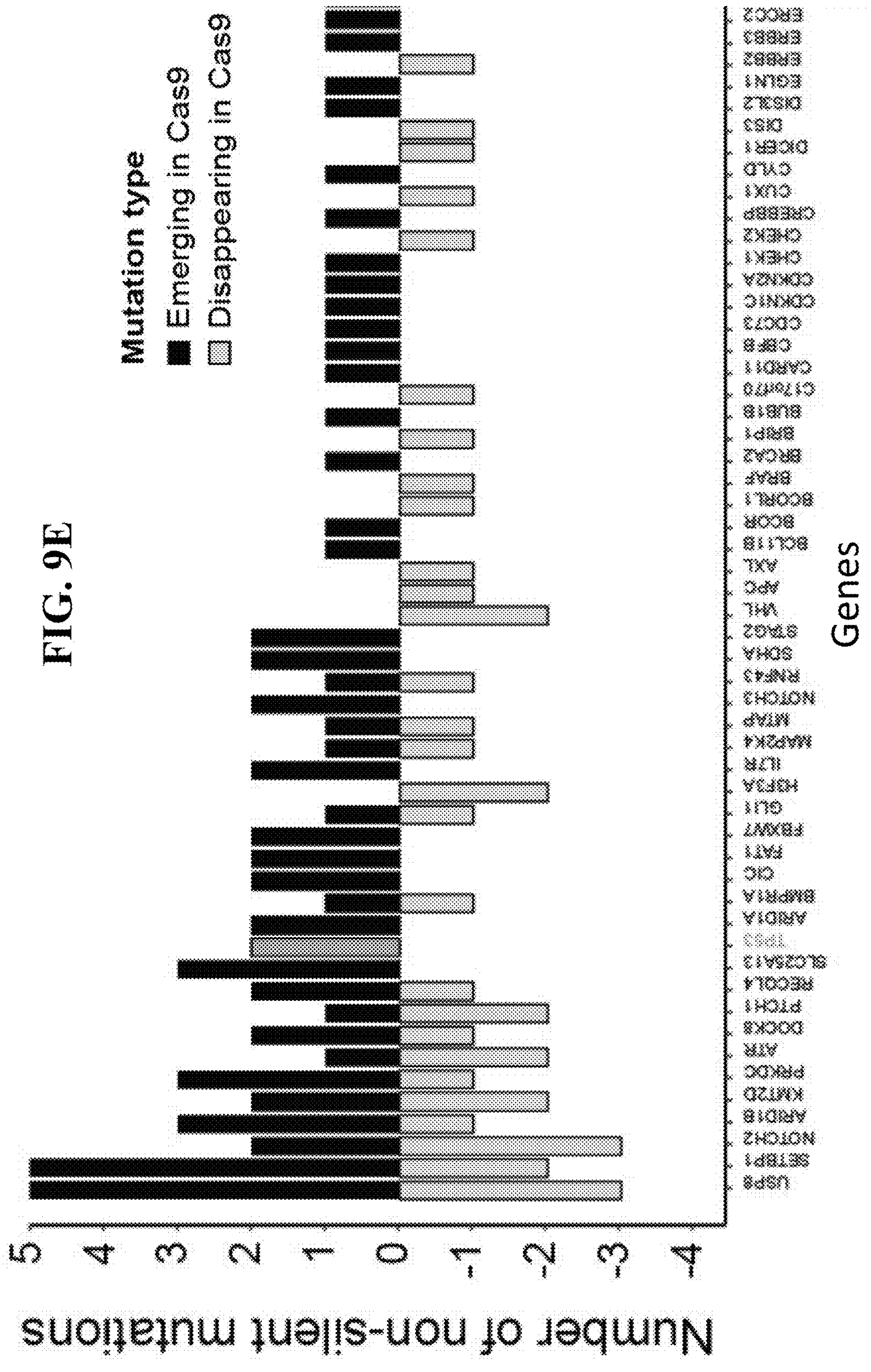
Figure 9E:
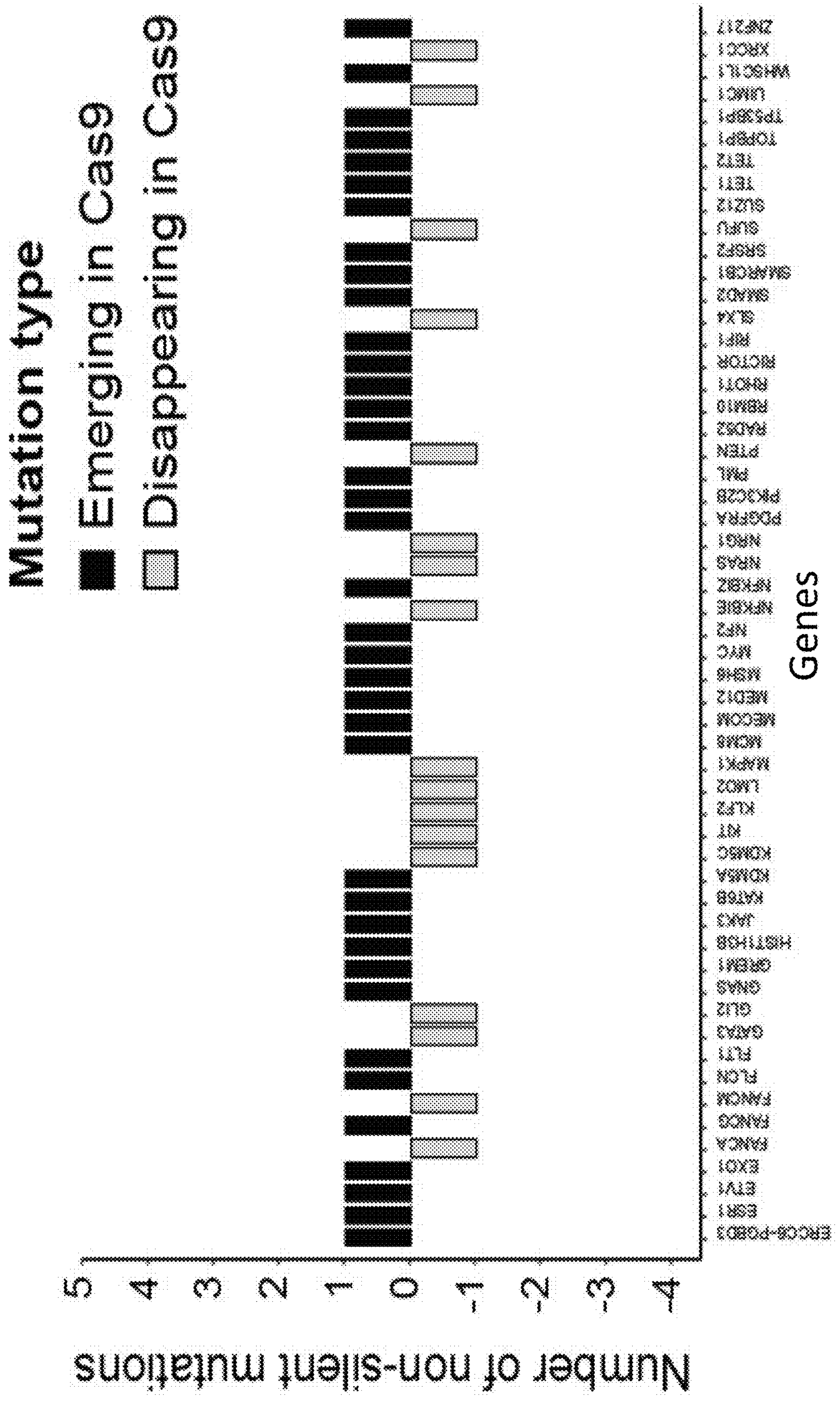
Figure 9F:
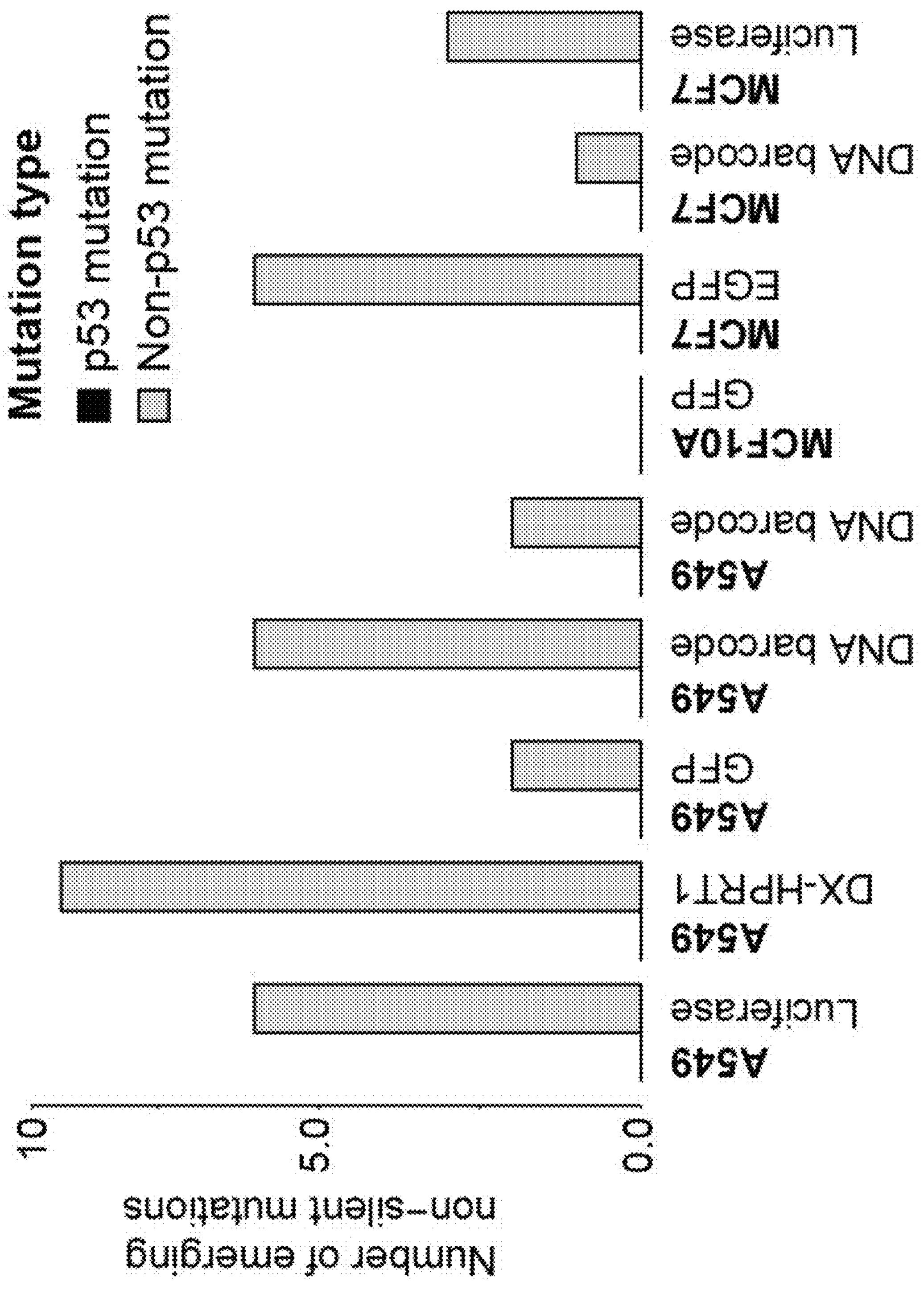

In three of these four lines (SNU1, HCC1419 and 293T), the mutations that emerged or expanded in the Cas9 line were bona fide inactivating mutations[17]. Importantly, changes in the opposite direction—i.e., detection of a non-silent TP53 mutation only in the WT line and not in its Cas9 derivative—were never observed (FIG. 9E). Moreover, a total of 10 pre-existing subclonal inactivating TP53 mutations in 8 lines were identified and a mild but significant (p=0.005) tendency towards expansion of these mutations in the Cas9 lines was observed (FIG. 3D). Notably, no non-silent TP53 mutation emerging or expanding following lentiviral transduction of a reporter or a DNA barcode was detected, in 9 independent experiments across 3 TP53-WT lines (FIG. 9F), further supporting the Cas9-specificity of the phenomenon.

Figure 3E:
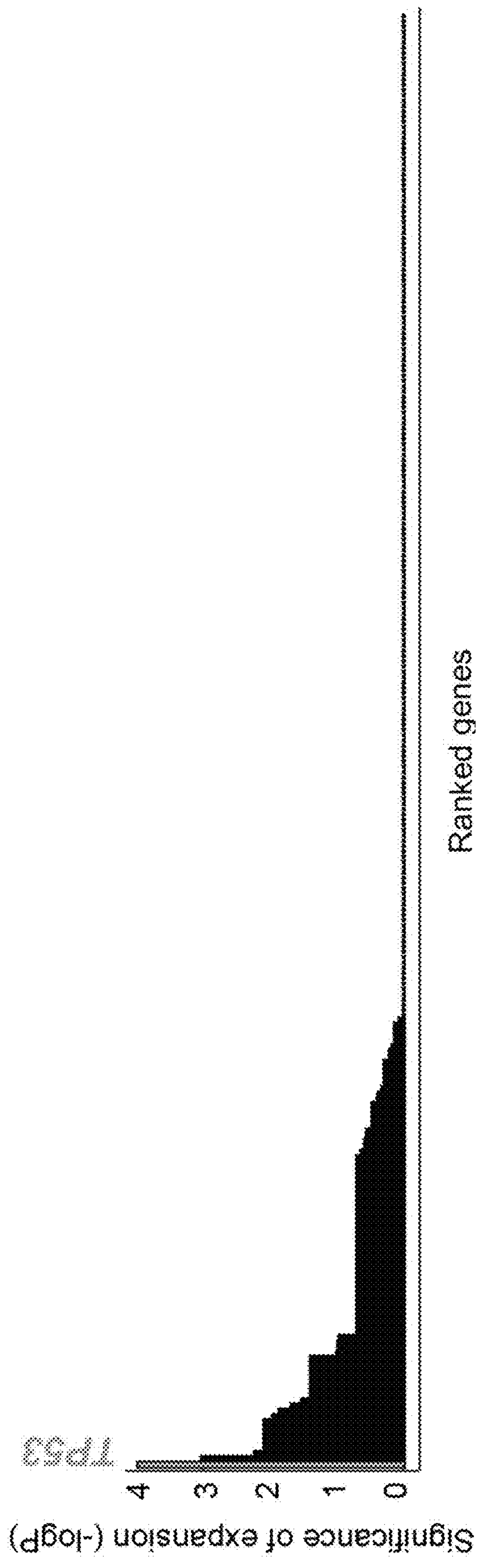
Figure 9G:
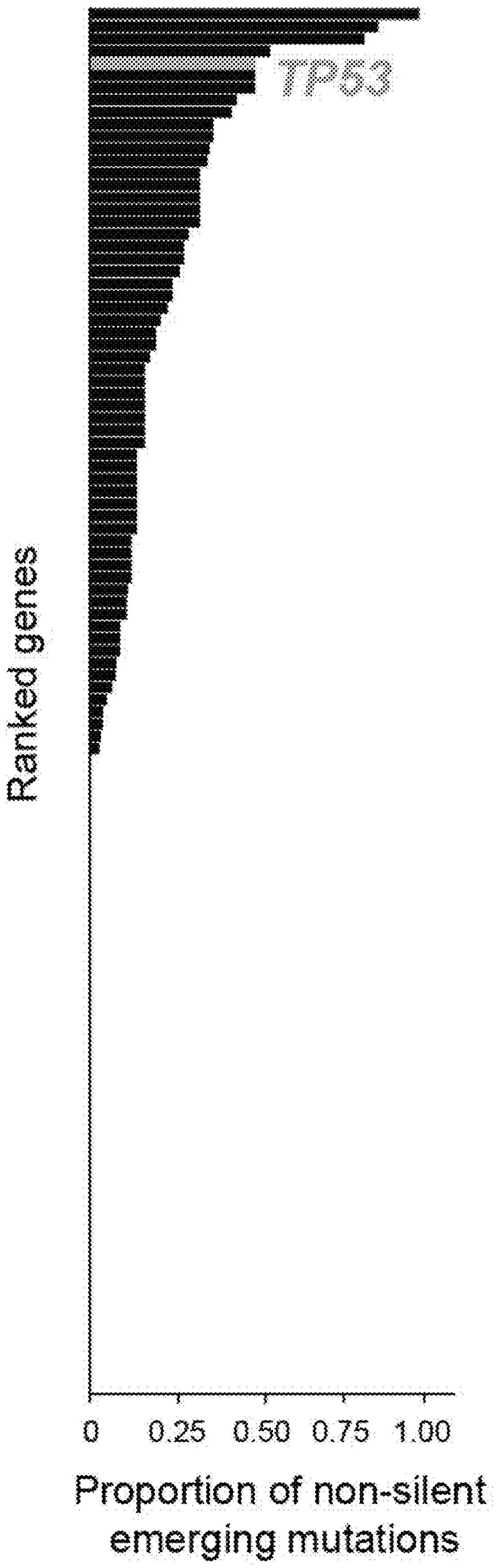

To address whether the significant tendency of TP53-inactivating mutations to expand following Cas9 introduction is unique to this gene, or common to all/other tumor suppressor genes, the allelic fractions of all subclonal non-silent mutations across all 447 genes included in the sequencing panel was analyzed. The tendency of mutated subclones to expand (increased allelic fraction) was greater for TP53 than for any other gene (FIG. 3E and Tables 17-18). Next, the relative abundance of emerging silent vs. non-silent mutations in TP53 and all other genes was compared to ask whether TP53 is significantly enriched for functional non-silent mutations in comparison to other tumor suppressor genes. The ratio of silent to non-silent emerging mutations in TP53 ranked #5 (that is, top ~1%) of all genes (FIG. 9G and Tables 17-18). The possibility that functional mutations in additional genes that are rarely mutated (and therefore not sufficiently represented in this dataset) could also be similarly selected for on Cas9 introduction cannot be ruled out. However, the results here indicate that acquisition of p53-inactivating mutations is the most common selection event in Cas9-expressing cultures.

TABLE 17

| Subclonal Expansion | | | | | |
|---|---|---|---|---|---|
| Gene Symbol | Wilcox_pval | Gene Symbol2 | Wilcox_pval3 | Gene Symbol4 | Wilcox_pval5 |
| TP53 | 0.019 | BCL6 | 1 | MRE11A | 1 |
| KMT2D | 0.049 | BCOR | 1 | MSH2 | 1 |
| FAT1 | 0.108 | BCORL1 | 1 | MSH6 | 1 |
| CIC | 0.125 | BMPR1A | 1 | MTOR | 1 |
| FANCD2 | 0.125 | BRCA1 | 1 | MYBL1 | 1 |
| NRG1 | 0.125 | BRD3 | 1 | MYD88 | 1 |
| POLE | 0.125 | BRD4 | 1 | NEIL2 | 1 |
| PRSS1 | 0.125 | CARD11 | 1 | NF2 | 1 |
| WHSC1L1 | 0.125 | CASP8 | 1 | NFE2L2 | 1 |
| NOTCH2 | 0.141 | CBFA2T3 | 1 | NFKBIA | 1 |
| COL7A1 | 0.156 | CBLB | 1 | NFKBIZ | 1 |
| APC | 0.188 | CD274 | 1 | NOTCH3 | 1 |
| BRCA2 | 0.219 | CDH4 | 1 | NPM1 | 1 |
| BRAF | 0.25 | CDKN1C | 1 | NR0B1 | 1 |
| BRIP1 | 0.25 | CEBPA | 1 | NSD1 | 1 |
| DNMT3A | 0.25 | CHEK1 | 1 | NUTM1 | 1 |
| FANCE | 0.25 | CHEK2 | 1 | PALB2 | 1 |
| FGFR3 | 0.25 | CIITA | 1 | PAXIP1 | 1 |
| ITK | 0.25 | CRTC1 | 1 | PBRM1 | 1 |
| SETD2 | 0.25 | CSF3R | 1 | PDGFRA | 1 |
| TSC2 | 0.25 | CTCF | 1 | PDGFRB | 1 |
| FLT1 | 0.371 | CTNNB1 | 1 | PHOX2B | 1 |
| MECOM | 0.375 | CYLD | 1 | PIK3CA | 1 |
| RPTOR | 0.375 | DAXX | 1 | PMS1 | 1 |
| KRAS | 0.383 | DCLRE1C | 1 | PNKP | 1 |
| ALK | 0.5 | DDB1 | 1 | POLH | 1 |
| BABAM1 | 0.5 | DDB2 | 1 | POT1 | 1 |
| C17orf70 | 0.5 | DDR2 | 1 | PPARG | 1 |
| CREBBP | 0.5 | DOCK8 | 1 | PPM1D | 1 |
| CTNNA1 | 0.5 | EGFR | 1 | PRF1 | 1 |
| DIS3 | 0.5 | EGLN1 | 1 | PRKAR1A | 1 |

TABLE 17-continued

| Subclonal Expansion | | | | | |
|---|---|---|---|---|---|
| Gene Symbol | Wilcox_pval | Gene Symbol2 | Wilcox_pval3 | Gene Symbol4 | Wilcox_pval5 |
| ERBB3 | 0.5 | EP300 | 1 | PTEN | 1 |
| ERCC5 | 0.5 | EPCAM | 1 | PTK2B | 1 |
| EXO1 | 0.5 | ERBB2 | 1 | PTPN11 | 1 |
| FANCM | 0.5 | ERBB4 | 1 | PTPN14 | 1 |
| FGFR1 | 0.5 | ERCC1 | 1 | RAC1 | 1 |
| FGFR4 | 0.5 | ERCC2 | 1 | RAD51C | 1 |
| GEN1 | 0.5 | ERCC6-PGBD3 | 1 | RAD52 | 1 |
| GNA11 | 0.5 | ERG | 1 | RAD54B | 1 |
| HFE | 0.5 | ESR1 | 1 | RASA1 | 1 |
| JAK1 | 0.5 | ETV1 | 1 | RB1 | 1 |
| JAK2 | 0.5 | ETV5 | 1 | RBBP8 | 1 |
| MBD4 | 0.5 | ETV6 | 1 | RECQL4 | 1 |
| MDM2 | 0.5 | EWSR1 | 1 | REL | 1 |
| MEF2B | 0.5 | EXT2 | 1 | RET | 1 |
| MYC | 0.5 | EZH2 | 1 | RHBDF2 | 1 |
| MYCL | 0.5 | FANCA | 1 | RHOA | 1 |
| NEIL1 | 0.5 | FANCB | 1 | RHOT1 | 1 |
| NF1 | 0.5 | FANCC | 1 | RIF1 | 1 |
| NRAS | 0.5 | FANCI | 1 | RINT1 | 1 |
| NTRK3 | 0.5 | FANCL | 1 | RNF43 | 1 |
| RICTOR | 0.5 | FGFR2 | 1 | RNF8 | 1 |
| ROS1 | 0.5 | FH | 1 | RSPO2 | 1 |
| RSPO3 | 0.5 | FLCN | 1 | RUNX1 | 1 |
| SETBP1 | 0.5 | FLT4 | 1 | RUNX1T1 | 1 |
| SH2B3 | 0.5 | FUS | 1 | SDHA | 1 |
| SMC3 | 0.5 | GATA2 | 1 | SF3B1 | 1 |
| SOX2 | 0.5 | GLI1 | 1 | SH2D1A | 1 |
| STAT3 | 0.5 | H3F3A | 1 | SLC34A2 | 1 |
| USP8 | 0.529 | HELQ | 1 | SMAD4 | 1 |
| GNAS | 0.563 | HIST1H3B | 1 | SMARCB1 | 1 |
| MGA | 0.563 | HIST1H3C | 1 | SMO | 1 |
| ATM | 0.577 | HNF1A | 1 | SOCS1 | 1 |
| SMARCA4 | 0.578 | HOXB13 | 1 | SOS1 | 1 |
| ARID1B | 0.625 | HRAS | 1 | SPOP | 1 |
| BLM | 0.625 | ID4 | 1 | STAT6 | 1 |
| PML | 0.625 | IDH1 | 1 | STK11 | 1 |
| POLQ | 0.625 | JAZF1 | 1 | SUFU | 1 |
| RAD50 | 0.625 | KAT6A | 1 | SUZ12 | 1 |
| PRKDC | 0.674 | KAT6B | 1 | TAL1 | 1 |
| FLT3 | 0.688 | KCNQ1 | 1 | TAX1BP1 | 1 |
| ARID1A | 0.726 | KDM5A | 1 | TAZ | 1 |
| ARID2 | 0.75 | KDM5C | 1 | TCF7L2 | 1 |
| NOTCH1 | 0.75 | KDM6A | 1 | TDG | 1 |
| PTCH1 | 0.75 | KDR | 1 | TET1 | 1 |
| SLX4 | 0.75 | KEAP1 | 1 | TET2 | 1 |
| TERT | 0.75 | KIF1B | 1 | TMEM127 | 1 |
| ATR | 0.812 | KIT | 1 | TMPRSS2 | 1 |
| NBN | 0.813 | KMT2A | 1 | TNFAIP3 | 1 |
| ERCC6 | 0.844 | LIG4 | 1 | TOPBP1 | 1 |
| IL7R | 0.875 | LMO2 | 1 | TRIM37 | 1 |
| MLH3 | 0.875 | MAF | 1 | U2AF1 | 1 |
| PIK3C2B | 0.875 | MAP2K2 | 1 | USP28 | 1 |
| POLD1 | 0.875 | MAP3K1 | 1 | WHSC1 | 1 |
| ASXL1 | 0.938 | MAX | 1 | WRN | 1 |
| ABCB11 | 1 | MCL1 | 1 | WT1 | 1 |
| ABL1 | 1 | MCM8 | 1 | WWTR1 | 1 |
| ATRX | 1 | MDM4 | 1 | XPC | 1 |
| BAP1 | 1 | MED12 | 1 | XRCC4 | 1 |
| BARD1 | 1 | MEN1 | 1 | ZNF217 | 1 |
| BCL11B | 1 | MITF | 1 | ZNRF3 | 1 |
| BCL2L1 | 1 | MLH1 | 1 | KLF4 | NaN |

TABLE 18

| Nonsilent Proportion | | |
|---|---|---|
| Gene Symbol | Proportion of nonsilent mutations | # of emerging mutations |
| SETBP1 | 1 | 11 |
| KMT2D | 0.875 | 8 |
| CIC | 0.833333333 | 6 |
| FAT1 | 0.545454545 | 11 |

TABLE 18-continued

| Nonsilent Proportion | | |
|---|---|---|
| Gene Symbol | Proportion of nonsilent mutations | # of emerging mutations |
| TP53 | 0.5 | 10 |
| ARID1B | 0.5 | 10 |
| NOTCH2 | 0.5 | 10 |
| COL7A1 | 0.444444444 | 9 |

TABLE 18-continued

| Nonsilent Proportion | | |
|---|---|---|
| Gene Symbol | Proportion of nonsilent mutations | # of emerging mutations |
| ERCC6 | 0.428571429 | 14 |
| APC | 0.375 | 8 |
| TSC2 | 0.375 | 8 |
| ATR | 0.363636364 | 11 |
| PRKDC | 0.357142857 | 14 |
| FLT1 | 0.333333333 | 6 |
| PAX5 | 0.333333333 | 6 |
| POLD1 | 0.333333333 | 6 |
| SLX4 | 0.333333333 | 6 |
| WRN | 0.333333333 | 6 |
| MECOM | 0.3 | 10 |
| ATM | 0.285714286 | 14 |
| NOTCH3 | 0.285714286 | 7 |
| BRCA2 | 0.272727273 | 11 |
| EGLN1 | 0.25 | 8 |
| KRAS | 0.25 | 8 |
| TP53BP1 | 0.235294118 | 17 |
| PIK3CA | 0.214285714 | 14 |
| PDGFRA | 0.2 | 10 |
| RICTOR | 0.2 | 10 |
| BRIP1 | 0.181818182 | 11 |
| DNMT3A | 0.166666667 | 6 |
| IGF1R | 0.166666667 | 6 |
| KIF1B | 0.166666667 | 6 |
| RBBP8 | 0.166666667 | 6 |
| RET | 0.166666667 | 6 |
| RHOT1 | 0.166666667 | 6 |
| SMC3 | 0.166666667 | 6 |
| ABCB11 | 0.142857143 | 7 |
| BCL6 | 0.142857143 | 14 |
| BRD3 | 0.142857143 | 7 |
| CASP8 | 0.142857143 | 7 |
| DOCK8 | 0.142857143 | 21 |
| JAK3 | 0.142857143 | 7 |
| MRE11A | 0.142857143 | 7 |
| FGFR2 | 0.125 | 8 |
| MSH6 | 0.125 | 8 |
| MTOR | 0.125 | 8 |
| TMPRSS2 | 0.125 | 16 |
| ROS1 | 0.115384615 | 26 |
| CDC73 | 0.111111111 | 9 |
| FANCI | 0.111111111 | 9 |
| KMT2A | 0.090909091 | 22 |
| PDGFRB | 0.090909091 | 11 |
| RIF1 | 0.090909091 | 22 |
| NTRK3 | 0.08 | 25 |
| KDM5A | 0.076923077 | 13 |
| CBFB | 0.066666667 | 15 |
| PPARG | 0.05 | 20 |
| EWSR1 | 0.04 | 25 |
| NRG1 | 0.038461538 | 130 |
| FGFR1 | 0.032258065 | 31 |
| ESR1 | 0.027777778 | 72 |
| ABL1 | 0 | 23 |
| ARHGEF12 | 0 | 14 |
| BRAF | 0 | 21 |
| CIITA | 0 | 11 |
| CRTC1 | 0 | 34 |
| CTCF | 0 | 7 |
| CUX1 | 0 | 10 |
| CYLD | 0 | 7 |
| DICER1 | 0 | 9 |
| EGFR | 0 | 6 |
| EP300 | 0 | 9 |
| ERG | 0 | 26 |
| ETV4 | 0 | 15 |
| ETV5 | 0 | 25 |
| ETV6 | 0 | 34 |
| EXT1 | 0 | 9 |
| FANCD2 | 0 | 7 |
| FIP1L1 | 0 | 33 |
| FLT4 | 0 | 6 |
| FOXO1 | 0 | 72 |
| GEN1 | 0 | 7 |
| JAK2 | 0 | 24 |
| KDR | 0 | 6 |
| MET | 0 | 7 |
| MGA | 0 | 7 |
| MLH1 | 0 | 6 |
| MYB | 0 | 20 |
| MYBL1 | 0 | 18 |
| NCOA2 | 0 | 16 |
| NFE2L2 | 0 | 6 |
| NPM1 | 0 | 16 |
| NT5C2 | 0 | 7 |
| NTRK2 | 0 | 6 |
| PARK2 | 0 | 6 |
| PBRM1 | 0 | 21 |
| PIK3R1 | 0 | 6 |
| QKI | 0 | 27 |
| RAF1 | 0 | 19 |
| RASA1 | 0 | 16 |
| RB1 | 0 | 8 |
| RSPO3 | 0 | 8 |
| RUNX1 | 0 | 55 |
| SMARCE1 | 0 | 6 |
| SS18 | 0 | 16 |
| TCF3 | 0 | 8 |
| TERT | 0 | 9 |
| TRIM37 | 0 | 12 |
| TSC1 | 0 | 6 |
| TSHR | 0 | 6 |
| WT1 | 0 | 10 |
| WWTR1 | 0 | 61 |
| YWHAE | 0 | 6 |

Figure 4A:
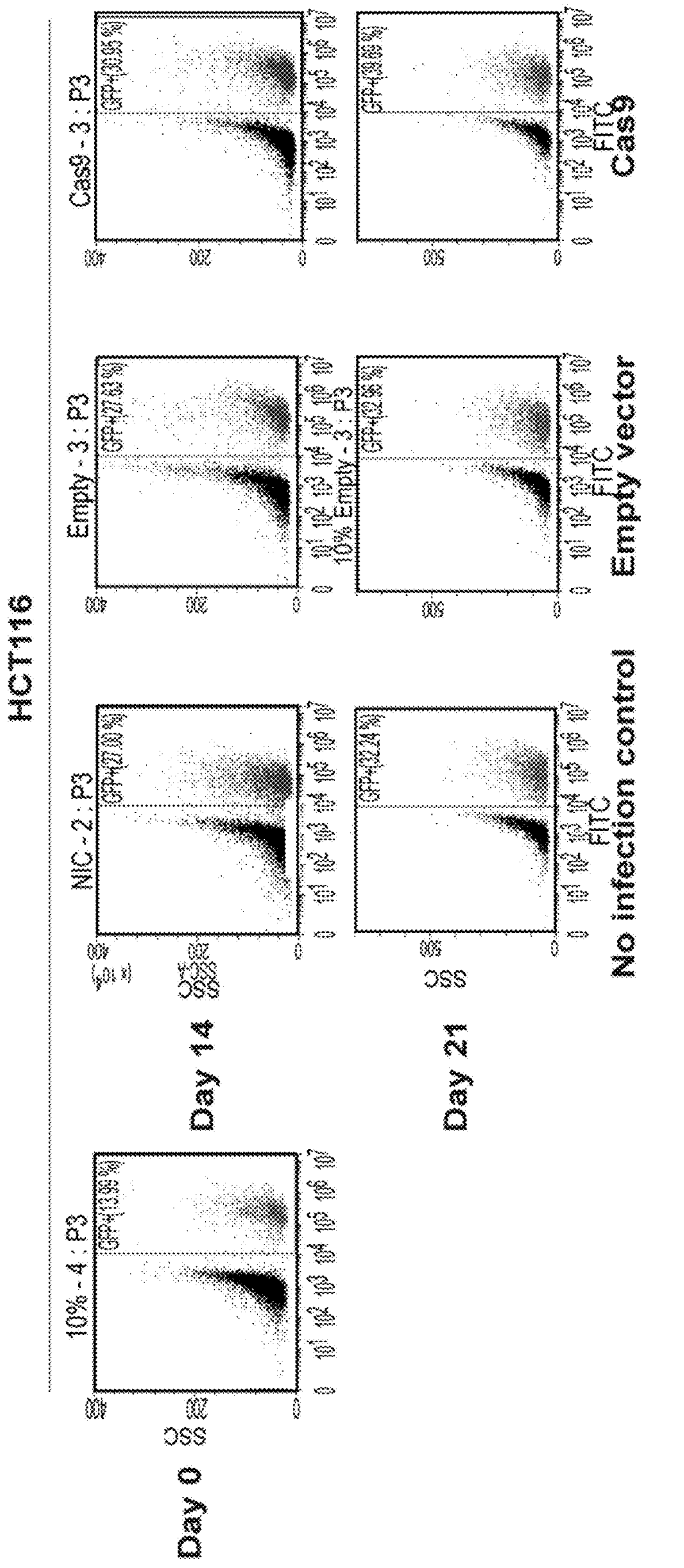
FIGS. 4A-4C—Expansion of inactivating TP53 mutations is accelerated by Cas9 in a cell competition assay.
Figure 4B:
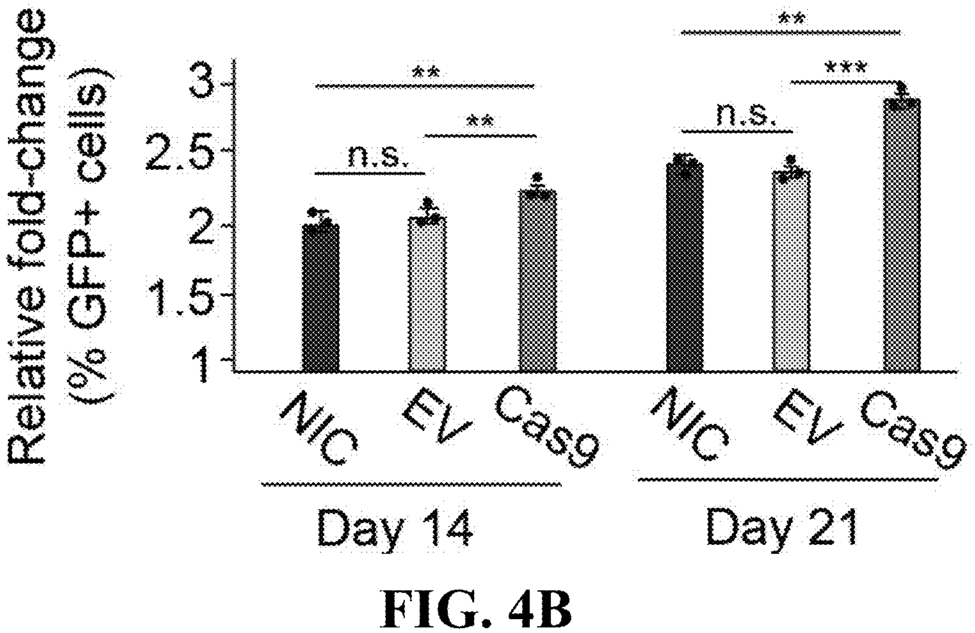
Figure 4C:
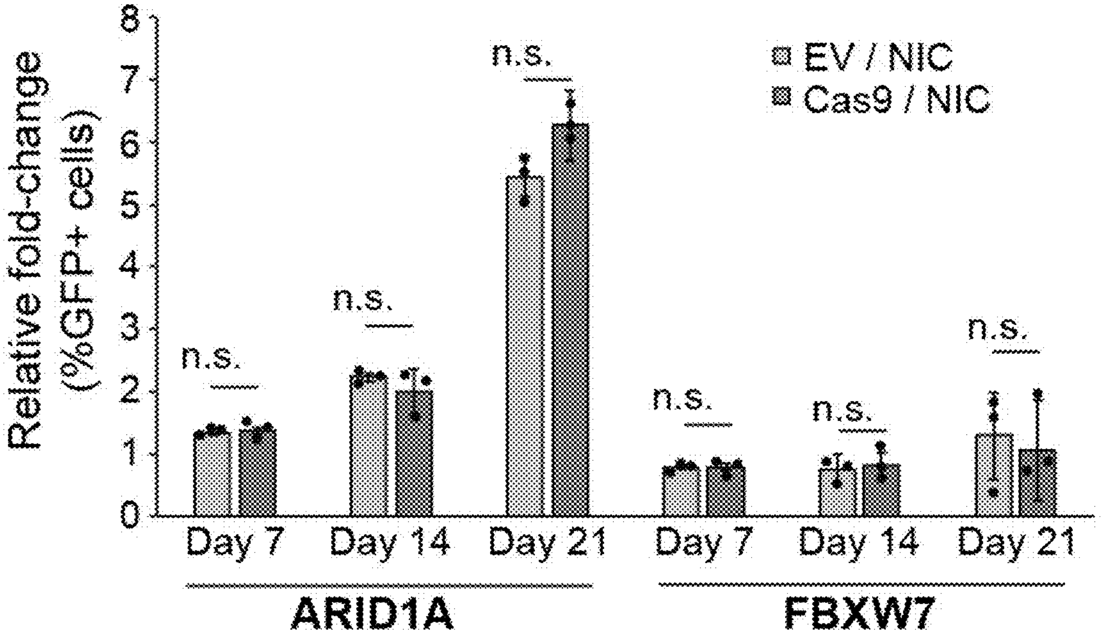

Next, a cell competition assay with the isogenic HCT116 lines was performed: EGFP-labeled TP53-null cells were transduced with viruses carrying either Cas9 or a backbone-matched empty vector, mixed with their isogenic TP53-WT cells (1:8 ratio), and their proportion in the population was monitored over time by flow cytometry. As expected, the proportion of TP53-null cells gradually increased with time. Importantly, this expansion was faster when cells were infected with Cas9 compared to the empty vector and no-infection controls (p=0.0013 and p=6.3e-5, respectively; FIGS. 4A-4B), indicating that Cas9 increases the adaptive value of p53 inactivation. The cell competition experiment was repeated with two additional tumor suppressor genes, ARID1A and FBXW7. These were selected these because mutations in these genes were also observed as emerging in Cas9 cell lines (FIG. 2B), and because knockout HCT116 cells could be obtained from the same source as the TP53 knockout cells (online Methods). In contrast to the Cas9-induced expansion of the TP53-null cells, ARID1A-null and FBXW7-null cells did not expand more quickly following Cas9 introduction compared to the empty vector controls (FIG. 4C). These data demonstrate that Cas9 expression selects specifically for p53 inactivating mutations, rather than for mutations in all tumor suppressor genes.

Example 4—Comparison of Cas9 Activity in Wild Type and Mutant Cell Lines

Figure 5A:
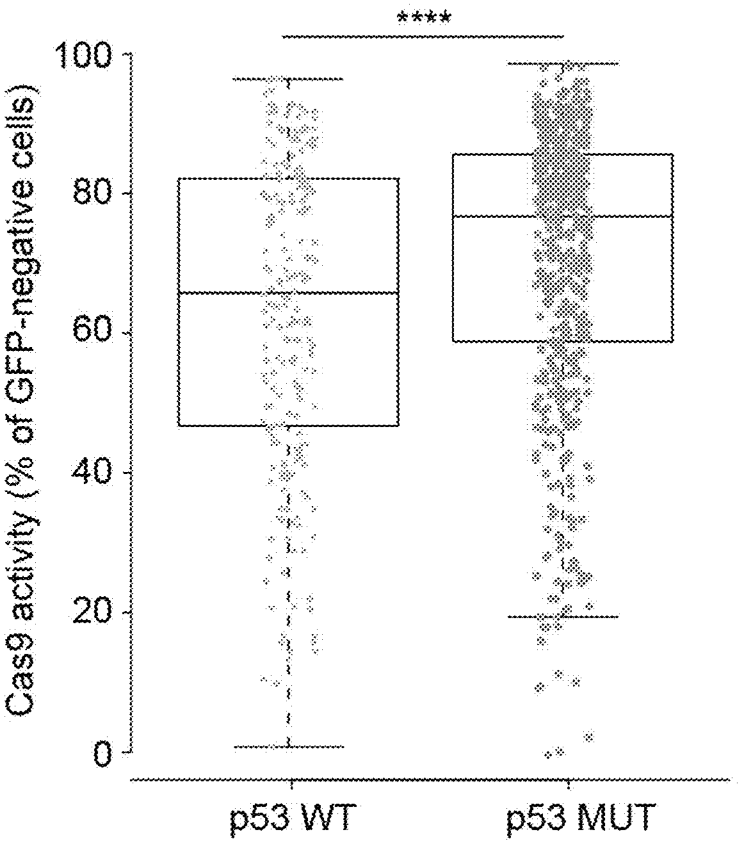
FIGS. 5A-5E—Cas9-induced p53 activation can functionally affect genetic and chemical perturbation assays.

Based on all previous findings (see e.g. Examples 1-3), it was predicted that Cas9 activity in TP53-WT lines would be lower, on average, than that in TP53-mutant lines. Therefore, Cas9 activity was compared between 226 TP53-WT and 493 TP53-mutant lines, using a quantitative functional assay of Cas9 activity[18]. Indeed, Cas9 activity was significantly lower in TP53-WT lines (p=3.1e-5; FIG. 5A and Supplementary Data 5 of Enache, O. M., Rendo, V., Abdusamad, M. et al. Cas9 activates the p53 pathway and selects for p53-inactivating mutations. Nat Genet 52, 662-668 (2020). https://doi.org/10.1038/s41588-020-0623-4, which is incorporated by reference herein as if expressed in its entirety and also Appendix C to U.S. Provisional Ser. No. 62/909,131), confirming that p53 activity jeopardizes the efficient expression of Cas9.

Example 5—Effect of Cas9-Induced p53 Mutations on Prior CRISPR-Cas9 Screens

Figure 5B:
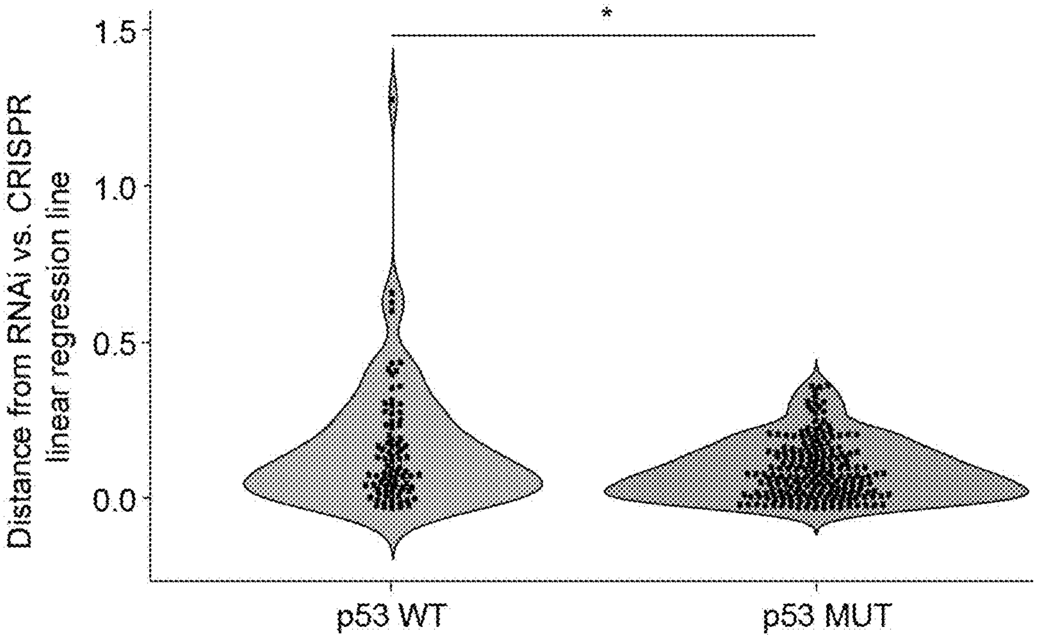
Figure 5C:
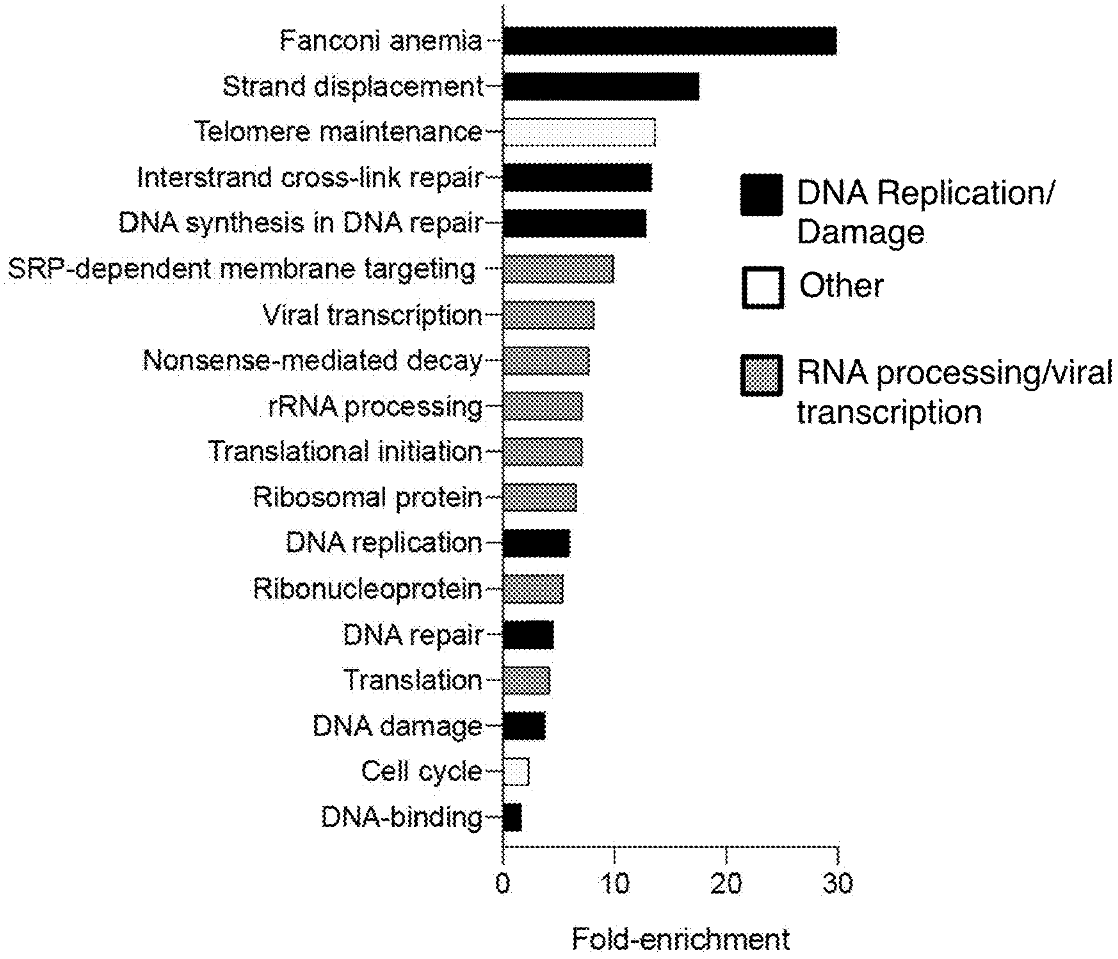
Figure 5D:
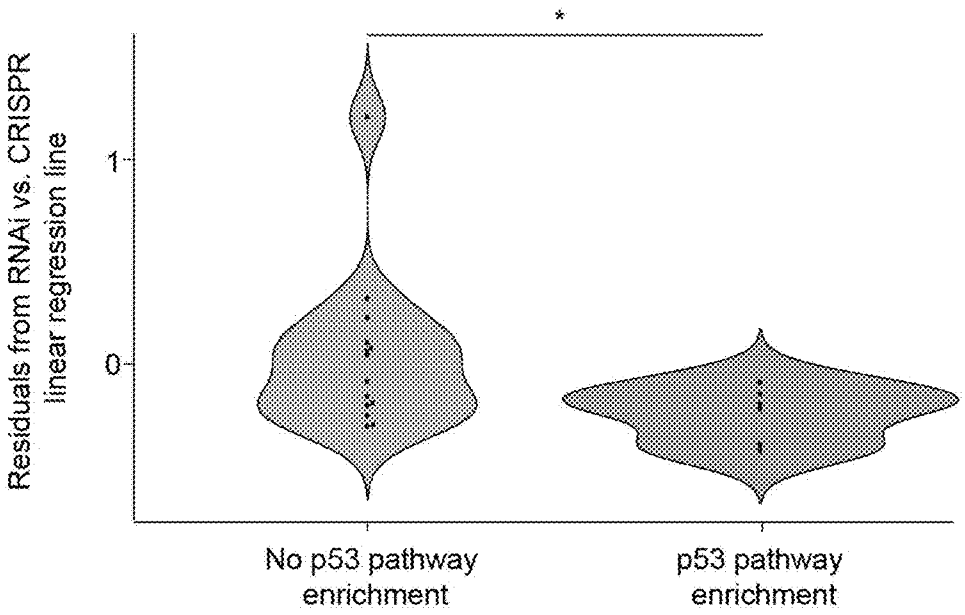
Figure 5E:
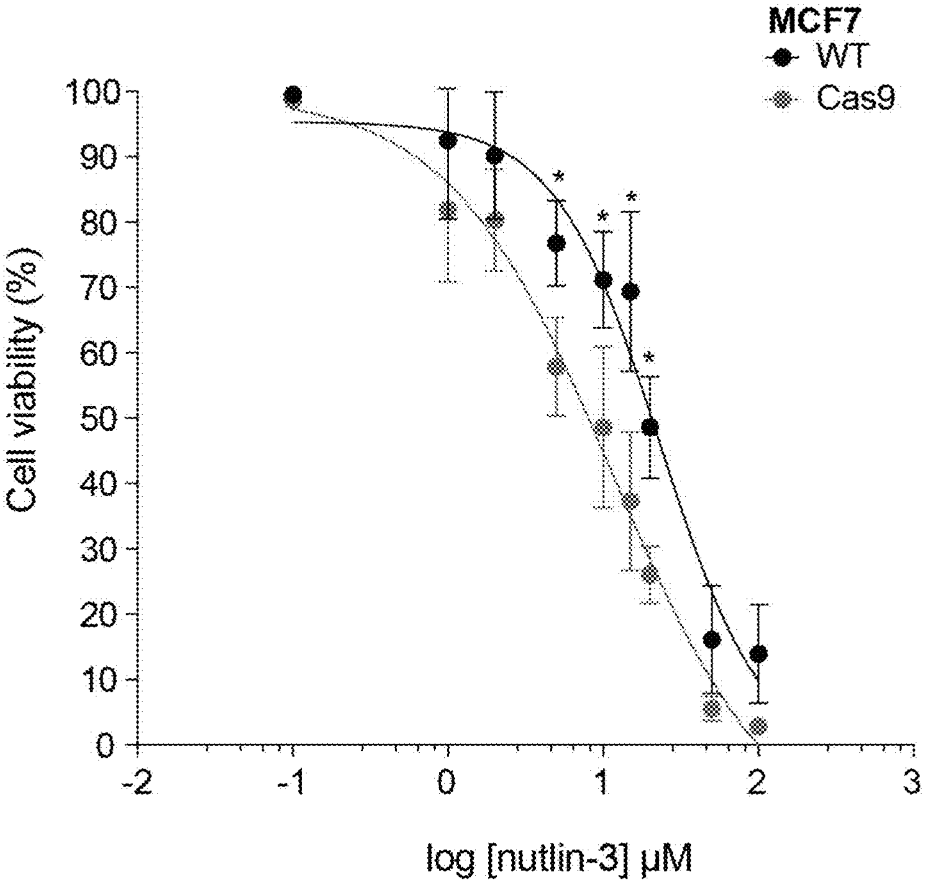

To address whether the phenomenon described in these Examples (e.g. Examples 1-4) has affected previous CRISPR-Cas9 screens, the Broad Institute's CRISPR-Cas9 and RNAi genetic perturbation screens were compared(see methods in Example 8). The concordance in genetic dependencies between the CRISPR-Cas9 and the RNAi datasets was significantly lower in TP53-WT lines (p=0.022; FIG. 5B). Next, a functional annotation enrichment analysis was performed on the list of genes that were more essential in the TP53-WT cells in the CRISPR-Cas9 screens, but not in the RNAi screens. This list was significantly enriched for genes related to two major functional categories: 1) DNA replication and DNA damage repair, and 2) RNA processing and viral transcription (FIG. 5C and Table 19). This suggests that Cas9-induced DNA damage in TP53-WT cells increased the dependency on functional DNA repair machinery, consistent with a similar recent analysis[19]. Finally, the dependency on TP53 itself between TP53-WT lines in which p53 pathway activation was identified and TP53-WT lines in which such activation was not observed was compared. The proliferation effect of TP53 CRISPR-Cas9 knockout (relative to TP53 RNAi knockdown) was significantly stronger in lines with Cas9-induced p53 pathway activation (p=0.02; FIG. 5D). Together, these findings demonstrate that the phenomenon described in this paper has indeed affected previous CRISPR-Cas9 screens.

TABLE 19

| Functional Annotation | | | | | |
|---|---|---|---|---|---|
| Category | Term | P Value | Genes | Fold Enrichment | Benjamini |
| Functional categories related to DNA replication and DNA damage | | | | | |
| UP_KEYWORDS | Fanconi anaemia | 2.86E−04 | FANCF, FANCG, FANCA, FANCB | 29.99807692 | 0.011771685 |
| GOTERM_BP_DIRECT | GO:0000732~strand displacement | 0.001410173 | EXO1, WRN, BRCA1, BARD1 | 17.66551181 | 0.109411338 |
| GOTERM_BP_DIRECT | GO:0036297~interstrand cross-link repair | 4.87E−04 | DCLRE1B, FANCF, FANCG, FANCA, FANCB | 13.46456693 | 0.050094288 |
| GOTERM_BP_DIRECT | GO:0000731~DNA synthesis involved in DNA repair | 0.003459365 | EXO1, WRN, BRCA1, BARD1 | 12.98934692 | 0.192173992 |
| GOTERM_BP_DIRECT | GO:0006260~DNA replication | 3.31E−04 | EXO1, POLE2, STRA8, WRN, BRCA1, NFIA, DSCC1, BARD1 | 6.091555797 | 0.039992282 |
| UP_KEYWORDS | DNA repair | 2.86E−04 | EXO1, DCLRE1B, ERCC6L2, FANCF, WRN, FANCG, FANCA, BRCA1, FANCB, BARD1 | 4.668961389 | 0.014673072 |
| UP_KEYWORDS | DNA damage | 0.00104888 | EXO1, DCLRE1B, ERCC6L2, FANCF, WRN, FANCG, FANCA, BRCA1, FANCB, BARD1 | 3.895854146 | 0.030556565 |
| UP_KEYWORDS | DNA-binding | 0.005519155 | ERCC6L2, TAF1D, MITF, | 1.750729517 | 0.11952361 |

TABLE 19-continued

Functional Annotation

| Category | Term | P Value | Genes | Fold Enrichment | Benjamini |
|---|---|---|---|---|---|
| | | | ZNF639, PDCD2, MLF1, POLE4, ZNF324, ACD, POLE2, TERF1, EXO1, SPTY2D1, ADNP, PPP1R10, HNF4G, ZNF668, WRN, NCL, BRCA1, HNRNPU, ZNF417, ZNF214, EEF1D, NFIA, DSCC1 | | |
| Functional categories related to the RNA processing and viral transcription | | | | | |
| GOTERM_BP_DIRECT | GO:0006614~SRP-dependent cotranslational protein targeting to membrane | 1.39E−05 | RPL23, RPL31, RPL9, RPL34, RPL36, RPL27, RPS11, RPL39 | 10.03722262 | 0.005121341 |
| GOTERM_BP_DIRECT | GO:0019083~viral transcription | 4.67E−05 | RPL23, RPL31, RPL9, RPL34, RPL36, RPL27, RPS11, RPL39 | 8.33278859 | 0.011432891 |
| GOTERM_BP_DIRECT | GO:0000184~nuclear-transcribed mRNA catabolic process, nonsense-mediated decay | 6.64E−05 | RPL23, RPL31, RPL9, RPL34, RPL36, RPL27, RPS11, RPL39 | 7.886389201 | 0.0121882 |
| GOTERM_BP_DIRECT | GO:0006364~rRNA processing | 7.65E−07 | WDR75, NAF1, RPL23, RPL31, RPL9, RPL34, RPL36, RPL27, HEATR1, RPS11, RPL39, TEX10 | 7.239963857 | 5.66E−04 |
| GOTERM_BP_DIRECT | GO:0006413~translational initiation | 1.14E−04 | RPL23, RPL31, RPL9, RPL34, RPL36, RPL27, RPS11, RPL39 | 7.239963857 | 0.016704053 |
| UP_KEYWORDS | Ribosomal protein | 5.48E−05 | RPL23, RPL31, RPL9, RPL34, RPL36, RPL27, | 6.749567308 | 0.003776499 |

TABLE 19-continued

| Category | Term | P Value | Genes | Fold Enrichment | Benjamini |
|---|---|---|---|---|---|
| Functional Annotation | | | | | |
| | | | RPS11, RPL39, RPL36AL | | |
| UP_KEYWORDS | Ribonucleoprotein | 1.05E−05 | NAF1, RPL23, RPL31, RPL9, RPL34, RPL36, RPL27, HEATR1, RPS11, RPL39, HNRNPU, RPL36AL | 5.538106509 | 0.001084324 |
| GOTERM_BP_DIRECT | GO:0006412~translation | 0.001077835 | RPL23, RPL31, RPL9, RPL34, RPL36. RPL27, RPS11, RPL39, RPL36AL | 4.33923598 | 0.094817482 |
| Other functional categories | | | | | |
| GOTERM_BP_DIRECT | GO:0000723~telomere maintenance | 0.002905052 | DCLRE1B, ACD, WRN, TERF1 | 13.8011811 | 0.193455138 |
| UP_KEYWORDS | Cell cycle | 0.009234807 | PARD6B, TP53BP2, KNTC1, PSME3, MAPRE1, ZWILCH, CCNG1, BRCA1, MLF1, URGCP, DSCC1, TERF1 | 2.461380671 | 0.160198465 |

Example 6—Functional Implication of Cas9-Induced p53 Activation

To further test the functional implications of Cas9-induced p53 activation, compared the response of parental and Cas9-expressing MCF7 cells to the MDM2-inhibitor nutlin-3 was compared. A modest, but significant, increase was observed in drug sensitivity in the Cas9-expressing cells (FIG. 5E), consistent with the rest of the findings discussed herein. Without being bound by theory, these findings conclude that Cas9-induced p53 activation can affect both genetic and chemical perturbation assays.

Example 7—Brief Summary of Examples 1-6

In summary, it was observed that Cas9 expression frequently elicits activation of the p53 pathway when introduced into human cell lines, leading to the emergence or expansion of inactivating TP53 mutations ($\Delta AF>0.05$) in ~10% of cases (Table 12). These observations suggest at least that Cas9-induced DNA damage may underlie p53 activation. While it cannot be ruled out that some of the observed p53 activation should be attributed to the viral transduction itself[20,1], and that the presence of a sgRNA could exacerbate p53 activation further", these findings at least demonstrate Cas9-specific p53 activation. Albeit relatively mild, this p53 activation is persistent, and is sufficient to select for p53-inactivating mutations.

Figure 10:
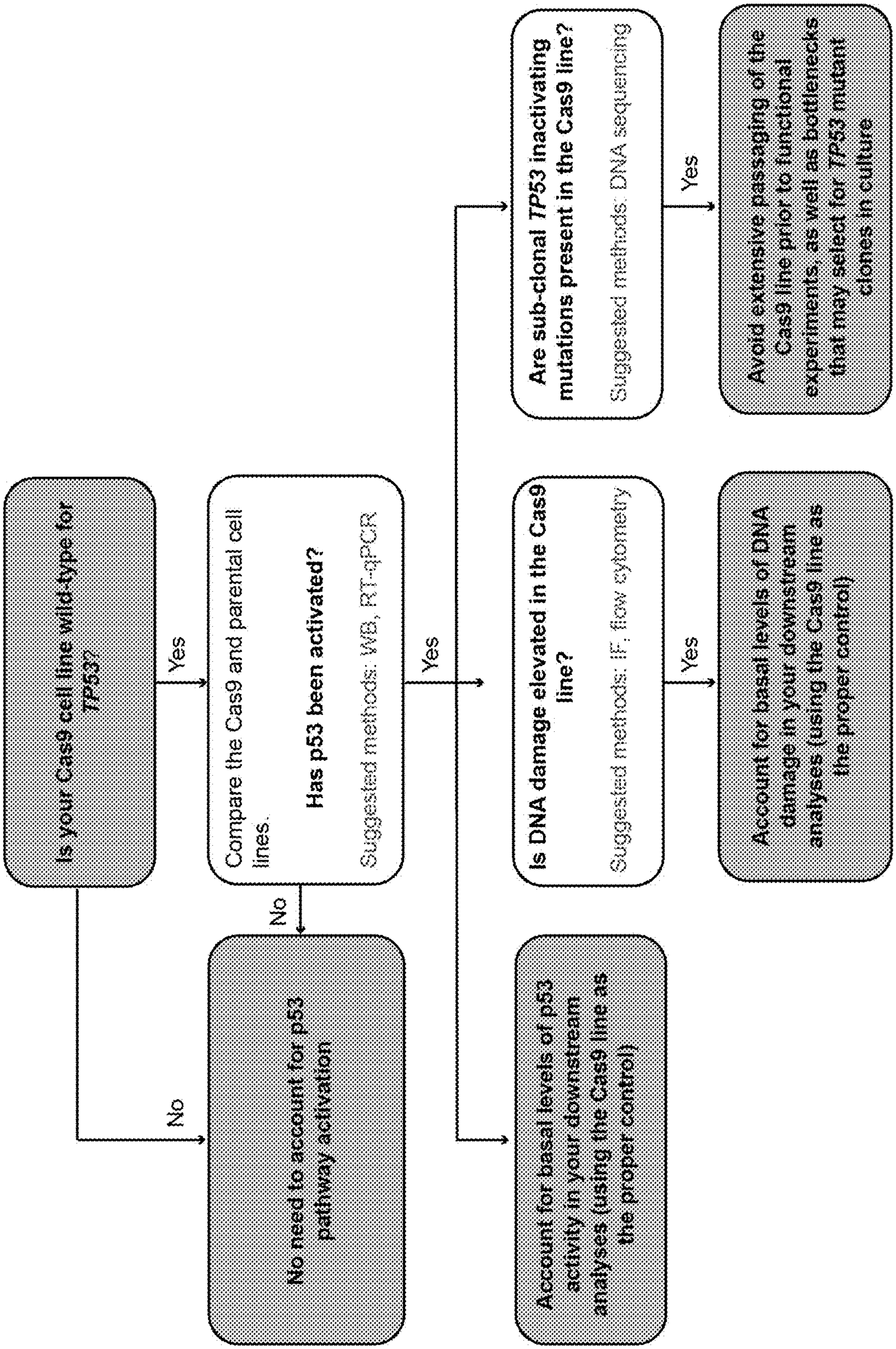
FIG. 10—Workflow for Cas9-related investigation. When conducting systematic CRISPR-Cas9 screens or focused studies in TP53-WT cancer cell lines, it is recommended that the basal activation level of the p53 pathway in the Cas9-expressing line is determined. If there is p53 activation, it is recommended to assess Cas9-ongoing DNA damage accumulation as well. Finally, as continuous Cas9 expression poses a selection pressure that over time may be reflected in the emergence or expansion of TP53 inactivating mutations, it is recommended to avoid extensive passaging and culture bottlenecks that may accelerate this process.

It is therefore important to confirm p53 status following the introduction of Cas9 into TP53-WT cells, as it may have important implications for the interpretation of genetic and chemical CRISPR-Cas9 screens, as well as for additional applications of the CRISPR-Cas9 technology (FIG. 10). A recent study suggested that CRISPR-induced p53 activation could be overcome by transient p53 silencing[12]. Without being bound by theory, these findings demonstrated herein suggest that cells may overcome such p53 activation in another way—by selecting for TP53 inactivating mutations—which could have long-term irreversible consequences.

Example 8—Methods for Examples 1-7

Cell Culture.

Culture media used for all experiments is available in Supplementary Data 7 of Enache, O. M., Rendo, V., Abdusamad, M. et al. Cas9 activates the p53 pathway and selects for p53-inactivating mutations. Nat Genet 52, 662-668 (2020). https://doi.org/10.1038/s41588-020-0623-4, which is incorporated by reference herein as if expressed in its entirety and also Appendix D to U.S. Provisional Ser. No. 62/909,131. All cell lines were maintained at 37° C. in 5% CO2. Cas9-expressing versions of all cell lines were generated by lentiviral transduction followed by selection with 4-10 μg/mL blasticidin (Gibco).

Cas9 Transduction and Transfection.

Human cancer cell lines were transduced with a lentiviral vector expressing the S. *Pyogenes* Cas9 nuclease under blasticidin selection (pXPR-311Cas9), and Cas9 expression was confirmed with a GFP reporter assay, as previously reported[2,22,23]. For validation experiments, human cancer cell lines were transduced with a lentiviral vector expressing the S. *Pyogenes* Cas9 nuclease under blasticidin selection (pLX311-Cas9) or with an empty vector control (pLX311-empty), and Cas9 expression was confirmed by western blotting. For transfection experiments, cells were transfected with 1 μg of an expression vector expressing GFP (pLX307-eGFP), Cas9 (pLX311-Cas9), or an empty vector control (pLX311-empty) using TransIT®-LT1 Transfection Reagent (Minis), as per manufacturer's protocol. After 72 hr, cell lysates were collected and subjected to immunoblot analysis.

L1000 Data Processing.

For each cell line, 16 wells of WT samples and Cas9-expressing samples were processed using the L1000 data processing pipeline, which has been described in depth elsewhere[6]. Briefly, cells were transferred to 384-well plates and kept in media without additives prior to lysis. 384-well oligo dT-coated Turbocapture plates were used to capture mRNA; after removing lysate and adding a reverse-transcription mix containing MLLV, the plate was washed and a mixture of both upstream and downstream probes (each containing a gene-specific sequence and a universal primer site) for each of the 978 ("Landmark") genes measured was added. The probes were first annealed to cDNA over a six-hour period, and then ligated together to form a PCR template. After ligation, Hot Start Taq and universal primers were added to the plate, and the upstream primer was biotinylated to allow for later staining with streptavidin-phycoerythrin. Next, the PCR amplicon was hybridized to Luminex microbeads using the complementary and probe-specific barcode on each bead; after overnight hybridization, the beads were washed and stained with streptavidin-phycoerythrin. Luminex FlexMap 3D scanners then used to measure each bead independently, reporting bead color, identity, and fluorescence intensity of the stain; the last of these was converted into median fluorescence intensity values for each of the 978 measured genes using a deconvolution algorithm (resulting in GEX level data). These GEX data were then normalized relative to a set of invariant genes, and then quantile normalized to produce QNORM level data. An inference model was applied to the QNORM data to infer gene expression changes for a total of 10,174 genes, which corresponds to the "BING" (Best INferred Genes) space of genes reported above.

L1000 Data Quality Control.

All samples from the 165 unique cell lines profiled passed internal technical L1000 assay quality control measures described elsewhere[6]. Additionally, all samples included passed an internal fingerprinting algorithm that verifies the identity of cell lines on L1000 plates by comparing quantile-normalized gene expression data in each well with respect to a ranked reference library of over 1000 cell lines; samples are defined as passing if their Spearman correlation to their respective reference profile is higher than equivalent correlation values to all other reference cell line profiles.

Generation of Transcriptional Data Dendrograms.

Within each cell line (considering Cas9 and WT cells separately), the median expression value was calculated for each of the 978 directly measured genes. A dendrogram was then constructed from the aggregate of each of these signatures using Euclidean distance and complete linkage hierarchical clustering.

Generation of Cas9 Transcriptional Signatures.

For individual Cas9 vs. WT transcriptional signatures within a cell line, a signal to noise ratio was calculated for each of the 10,174 genes of QNORM-level data using the following formula: $(\mu^*GeneA\_Cas9-\mu^*GeneA\_WT)/(\sigma^*GeneA_{cas9}+\sigma^*GeneA\_WT)$. When the number of samples within a class (Cas9 or WT) was below 10, the within-class standard deviation value was adjusted to $\sigma=\max(\sigma, \max(0.025^*\mu, 0.025))$ to avoid zero values in the denominator. Fold change values were calculated as $\mu^*GeneA\_Cas9-\mu^*GeneA\_WT$. Meta Cas9 vs. WT transcriptional signatures within each class of p53 mutation statuses considered (TP53 WT or TP53 MUT, based on the functional mutation classification reported in Giacomelli et al.[17]) were composed by taking the median value of the signal to noise ratio for each of the 10,174 genes across cell lines in the p53 mutation class. Aggregate Cas9 vs. WT transcriptional signatures were composed across all cell lines sharing a p53 mutation status by calculating a signal to noise ratio as above for each of the 10,174 genes using all samples available for all cell lines in that class.

Generation of Control Transcriptional Signatures.

To control for the possible transcriptional consequences of viral introduction, significant enrichment of pairwise Cas9 vs. WT L1000 signatures was compared to enrichment values of LacZ vs. WT, GFP vs. WT, and empty lentiviral vector vs. WT pairwise signatures. These signatures were composed from previously existing QNORM-level data by identifying untreated (hereafter: WT), LacZ or GFP (hereafter: control vector), and empty vector cell line samples previously used as negative controls in the L1000 NIH LINCS Phase I and II datasets (GSE92742 and GSE70138 on Gene Expression Omnibus respectively). In total, five separate cell lines (A375, HAlE, MCF7, PC3, and VCAP) had sufficient samples of good technical quality per class to compose pairwise transcriptional signatures; as these samples generally came from distinct experimental batches and clustered by project codes, batch effects were removed using the COMBAT algorithm[24]. 15 pairwise signatures (5 empty vectors vs. WT and 10 control vectors vs. WT) were ultimately generated in each of the available cell lines with sufficient data, as described above.

Gene Set Enrichment Analysis.

Gene Set Enrichment Analysis (GSEA)[8] was performed using the best inferred 10,147 genes by the L1000 inference model[6]. Samples were divided into the pairwise, meta, and aggregate sets of two classes described above ("Generation of Cas9 transcriptional signatures" and "Generation of control transcriptional signatures") to generate several transcriptional signatures. For each signature, a ranked gene list and signal-to-noise values were used as input for the GSEA preranked module of GSEA, using the Java application (version 3.0). The analysis was run using the curated "Hallmark" signature collection from the Molecular Signature Database (MSigDB)[7]. Signatures were considered to have p53 activation if the HALLMARK P53 PATHWAY gene set was significantly positively enriched (FDR q-value<0.05), and signatures were considered to have a DNA damage response if the HALLMARK DNA REPAIR gene set was significantly positively enriched (FDR q-value<0.05).

Deep Targeted Sequencing.

Prior to library preparation, DNA was fragmented (Covaris sonication) to 250 bp and further purified using Agentcourt AMPure XP beads. Size-selected DNA was ligated to sequencing adaptors with sample-specific barcodes during automated library preparation (SPRlworks, Beckman-Coulter). Libraries were pooled and sequenced on an Illumina Miseq to estimate library concentration based on the number of index reads per sample. Library construction was considered to be successful if the yield was ≥250 ng, and all samples yielded sufficient library. Normalized libraries were pooled in batches, and hybrid capture was performed using the Agilent Sureselect Hybrid Capture kit with the POPv3_824272 bait set[16]. The list of 447 genes included in POPv3_824272 is provided as Supplementary Data 3 of Enache, O. M., Rendo, V., Abdusamad, M. et al. Cas9 activates the p53 pathway and selects for p53-inactivating mutations. Nat Genet 52, 662-668 (2020). https://doi.org/10.1038/s41588-020-0623-4, which is incorporated by reference herein as if expressed in its entirety. Captures were then pooled and sequenced on one HiSeq3000 lane. Pooled sample reads were de-convoluted and sorted using the Picard tools (http://broadinstitute.github.io/picard). The reads were aligned to the reference sequence b37 edition from the Human Genome Reference Consortium using "bwa aln" (http://bio-bwa.sourceforge.net/bwa.shtml), with the following parameters: "-q 5-l 32-k 2-o 1", and duplicate reads were identified and removed using the Picard tools[25]. The alignments were further refined using the GATK tool for localized realignment around indel sites (https://software-.broadinstitute.org/gatk/documentation/tooldocs/current/org broadinstitute gatk tools walkers indels IndelRealigner.php). Recalibration of the quality scores was also performed using GATK tools (http://gatkforums.broadinstitute.org/discussion/44/base-quality-score-recalibration-bqsr)[26,27]. Metrics for the representation of each sample in the pool were generated on the unaligned reads after sorting on the barcode (http://broadinstitute.github.io/picard/picard-metric-definitions.html). All samples achieved the target threshold of >30× coverage for >80% of the targeted bases. The average mean exon target coverage was 283.17× (range: 92.42×-494.11×). MCF7 and A549 WT/Cas9 pairs were previously characterized, and analyzed together with all other cell lines. MCF7, A549 and MCF10A cell lines expressing reporter vectors and DNA barcodes were previously characterized[1] and used for the analysis presented in FIG. 4B.

Targeted Sequencing Data Analysis.

Mutation analysis for single nucleotide variants (point mutations, or SNVs) was performed using MuTect v1.1.4[28]. Indel calling was performed using the SomaticlndelDetector tool in GATK ((http://www.broadinstitute.org/cancer/cga/indelocator). Consecutive variants in the same codon were re-annotated to maximize the effect on the codon and marked as "Phased" variants. MuTect was run in paired mode, pairing all samples to a normal sample, CEPH1408. Mutations were called if detected in >2% of the reads (AF>0.02). All SNVs, indels, and phased variants were annotated with Variant Effect Predictor (VEP)[29]. Variants that affect protein coding regions underwent further filtering/classification based on frequency in the gnomAD, ESP, and COSMIC (version 80) databases. If the frequency of the variant was more than 1% in all gnomAD and ESP populations and if the variant was not present at least twice in the COSMIC database, the variant was considered to be germline (given that no matched normal samples were available). If the frequency of the variant was more than 10% in any of the gnomAD and ESP populations, it was considered to be germline (regardless of its frequency in COSMIC). Non-silent mutations were considered to be those with the following BestEffect Variant Classification: missense, initiator codon, nonsense, frameshift, inframe insertion or inframe deletion. Mutations that appeared more than once in COSMIC were regarded as COSMIC mutations. The complete list of variants (SNVs, indels, and phased) are provided as Supplementary Data 3 of Enache, O. M., Rendo, V., Abdusamad, M. et al. Cas9 activates the p53 pathway and selects for p53-inactivating mutations. Nat Genet 52, 662-668 (2020). https://doi.org/10.1038/s41588-020-0623-4, which is incorporated by reference herein as if expressed in its entirety. TP53 mutations were manually inspected by visualizing the sequencing BAM files in Integrative Genomics Viewer (https://software.broadinstitute.org/software/igv), and the frameshift mutation at location 17:7,579,460 in HCC1419 was updated based on this inspection. To examine the potential expansion of pre-existing inactivating mutations, only somatic missense, nonsense and frameshift mutations present at 0.02<AF<0.48 or 0.52<AF<0.98 in the parental WT lines were considered. To rank the genes based on the fraction of non-silent mutations out of all emerging mutations, mutations were first filtered to only those whose change in allelic fraction was at least 0.05 and genes were filtered to only those that exhibited at least 5 such mutations. Then, the proportion of non-silent mutations out of all occurring mutations was calculated for each gene.

Generation of Sequencing Data Dendrograms.

A dendrogram was constructed using complete linkage hierarchical clustering for all cell lines profiled with targeted sequencing, where Euclidean distance was calculated between vectors composed of a count value of all mutations in a given gene (if present) or zero values (for non-mutated genes in the sequencing panel) within each cell line (considering Cas9 and WT samples separately).

Pairwise Detection of Mutation Emergence and Disappearance.

Mutations were determined to be acquired in Cas9 (present in Cas9 but not the WT sample of a cell line) or removed in Cas9 (present in the WT but not Cas9 sample of a cell line) at three levels of mutation-calling stringency: all mutations, non-silent mutations (variants classified as frameshifts, inframe deletions, inframe insertions, initiator codons, missense, nonsense, splice acceptors or splice donors), and mutations in the Catalogue of Somatic Mutations in Cancer[30] (COSMIC; variants with COSMIC count >2), and a gnomAD[31] population frequency percentage below 1% in both African American and European populations. Within a given cell line, a given mutation in a gene was considered 'emerging' in Cas9 if its specific cDNA change was present in the Cas9 sample but not in the WT sample, and was considered 'disappearing' in Cas9 if its specific cDNA change was present in the WT sample but not in the Cas9 sample.

Dependency Map Data Analysis.

The Data Explorer tool from the DepMap portal (depmap.org/portal) was used to download CERES-corrected CRISPR (Public 19Q3) and RNAi dependency scores (DEMETER2, Broad) corresponding to TP53 dependency scores in 326 cell lines with both CRISPR and RNAi annotations[32-34]. These data were fitted with a linear regression line, and then differences in residuals for TP53-WT vs. TP53-MUT cell lines were compared using a one-sided Wilcoxon rank test. Dependency data was also subsetted to only include TP53 WT cell lines overlapping with available transcriptional data (n=20 cell lines), and the same analysis of linear regression residuals was performed again, this time comparing cell lines whose transcriptional signature was positively enriched for the Hallmark p53 gene set vs. cell lines without such enrichment, using a one-sided Wilcoxon rank test. To analyze the genes with significantly different dependency scores between TP53-WT and TP53-mutant cell lines, CERES-corrected CRISPR (Public 2019Q3) and RNAi (DEMETER2, Broad) dependency data were obtained from the DepMap portal and subsetted to overlapping cell lines and genes (n=326 and n=15,468, respectively). For each gene, a one-sided Wilcoxon rank test was performed comparing dependency scores in the TP53-WT and TP53-mutant lines in which scores were available for CRISPR and RNAi perturbations separately, and p-values were corrected using the Benjamini-Hochberg (FDR) adjustment. Genes that were significantly (adjusted p-value <0.1) more essential in TP53-WT than in TP53-mutant cell lines in the CRISPR but not (adjusted p-value >0.1) in RNAi were determined. This gene list was subjected to a functional annotation enrichment analysis using the DAVID functional annotation tool[35], with the list of genes included in the CRISPR and RNAi screens serving as a background list.

Immunoblotting.

Cells were lysed with RIPA lysis buffer (25 mM Tris-HCl at pH 7.6, 150 mM NaCl, 1% NP-40 and 0.1% SDS) and centrifuged at 15,000×g at 4° C. for 15 min. Protein concentration was determined by the BCA assay (Novex®, Life Technologies). Thirty μg of each sample and a PageRuler™ Prestained protein ladder (Thermo Scientific) were loaded on a NuPAGE® 4-12% Bis-Tris gradient gel with 1×NuPAGE® MOPS running buffer (Novex®, Life Technologies) and separated at 150 V for 1 h. Next, a dry transfer was done at 20 V for 6 min using PVDF mini stacks in an iBlot 2 instrument (Thermo Fisher Scientific). The membrane was blocked in 5% dry milk in TBS-T for 30 min and immunoblotted overnight at 4° C. with primary antibodies against Cas9 (#14697, CST), p53 (#9282, CST), p21 (#2947, CST), b-actin (sc-47778, Santa Cruz Biotechnology), GAPDH (#5174, CST) and vinculin (V9131, Sigma-Aldrich) diluted 1:1000 in PBS containing 5% milk. The membrane was washed in TBS-T and further incubated for 1 hour with goat anti-rabbit and goat anti-mouse secondary antibodies (sc-2027 and sc-2025, Santa Cruz Biotechnology) diluted 1:10000 in TBS-T containing 5% milk. Signal detection was performed with the SuperSignal West Femto and Pico kits (Thermo Scientific) in the ImageQuant LAS 4000 imager (GE Healthcare Life Sciences).

Real-Time Quantitative PCR Analysis.

Total RNA was extracted from cell lysates using the RNeasy Mini Kit (Qiagen). First-strand cDNA synthesis was performed with 2 mg of RNA following the M-MLV Reverse Transcriptase protocol (Thermo Fisher Scientific). Briefly, samples were mixed with 250 ng random primers, 10 mM dNTPs and heated at 65° C. for 5 min. Next, 5× First-Strand Buffer (Invitrogen), 0.1 M DTT, RNaseOUT Recombinant Ribonuclease Inhibitor (40 units/mL) and M-MLV Reverse Transcriptase (200 units/mL) were added to each tube. The synthesis reaction was continued by incubation at 25° C. for 10 min, followed by 37° C. for 50 min and 70° C. for 15 min. To measure gene expression, 500 ng of cDNA were amplified in 20 mL reactions including 1× Maxima SYBR Green/ROX qPCR Master Mix (Thermo Fisher Scientific) and 0.3 mM of forward and reverse primers. Primers used for the amplification of p53 transcriptional targets have been previously reported[36], using β-Actin as an internal reference gene. Data were analyzed by the AACt method in the StepOne™ Software v2.1 (Thermo Fisher Scientific).

Immunofluorescence Analysis.

Cells were seeded in 3-well slides (Electron Microscopy Science) the day before the experiment. After washing with DBPS containing $Ca^{2+}$(DBPS/Ca2+), cells were fixed with 4% paraformaldehyde at room temperature for 20 min. Following washes with DBPS/$Ca^{2+}$, cells were permeabilized with 0.5% Triton-X-100 in PBS at room temperature for 10 min. Next, blocking buffer (5% BSA in TBS) was added, and slides were incubated at room temperature for 1 h. For the detection of DNA damage, a primary rabbit antibody against γ-H2AX (#9718, Cell Signaling Technology) was used at a 1/400 dilution. The slides were incubated at room temperature for 2 h and washed in DPBS/$Ca^{2+}$. Next, secondary rabbit AF 488 antibody (A-21206, Thermo Fisher Scientific) and Hoechst (H3570, Thermo Fisher Scientific) for nuclei counterstaining were added at a dilution of 1/500 and 1/10000 respectively. After incubation at room temperature for 1 h, samples were washed with DPBS/$Ca^{2+}$ and mounted using ProLong Diamond Antifade Mountant solution (P36970, Thermo Fisher Scientific). Slides were stored in the dark and visualized in a Revolve microscope (Echo Laboratories). Cells were scored as positive for DNA damage if >5 foci per cell were detected for phospho-histone H2AX.

Cell Competition Assay.

Figure 11:
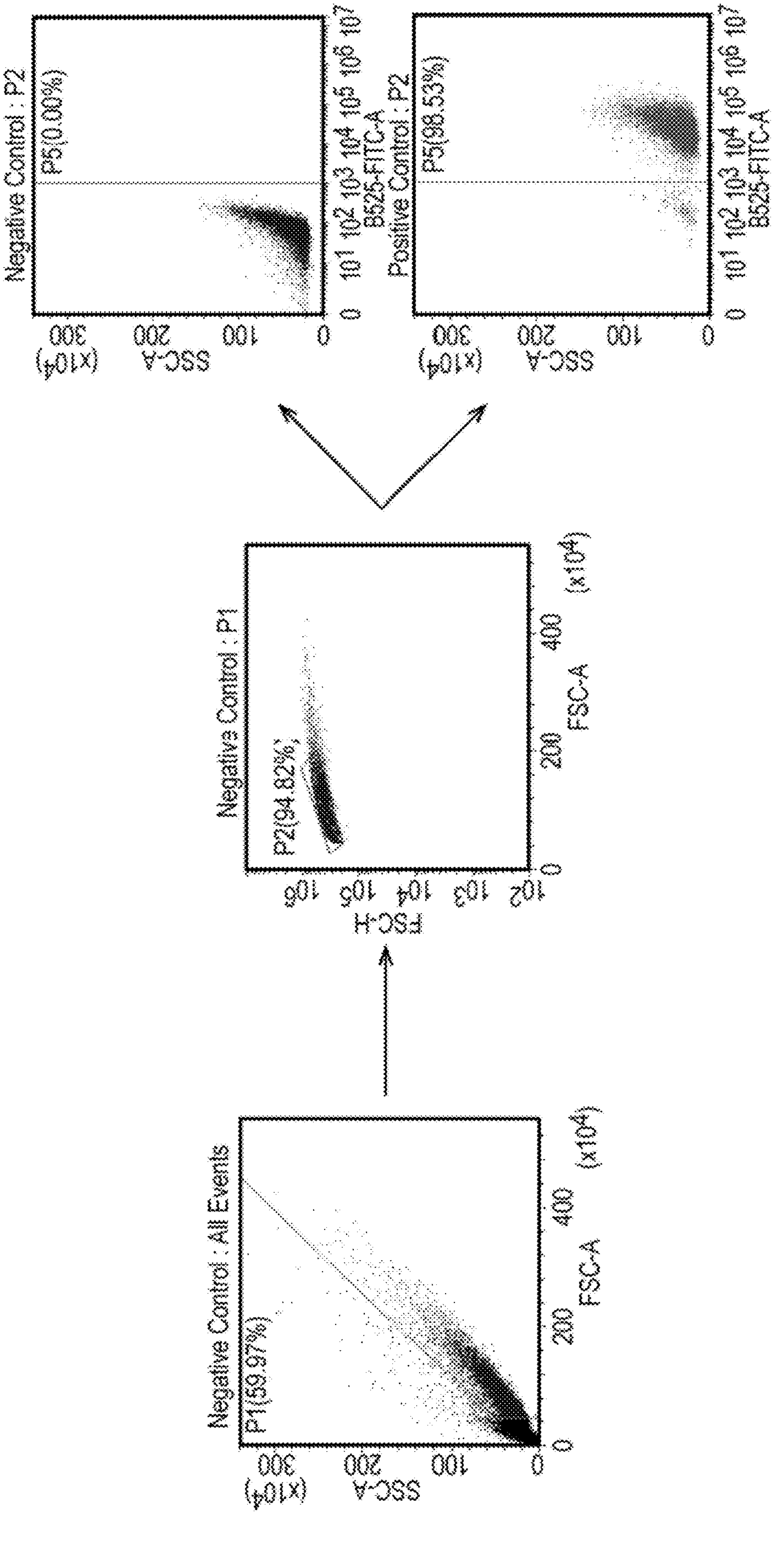
FIG. 11—Example of the gating strategy used in the cell competition experiments shown in the Working Examples herein.

Isogenic TP53-WT and TP53-null HCT116 cell lines were purchased from Horizon. Knockout of TP53 in these cell lines was achieved through homologous recombination of targeting vectors[9]. The status of p53 was confirmed by western blotting. TP53-null cells were transduced with a lentiviral vector expressing the EGFP under puromycin selection (pLX317-eGFP), and GFP expression was confirmed by flow cytometry. GFP-expressing TP53-null cells were mixed with TP53-WT cells in a 1:8 ratio and transduced 24 hr later with either Cas9 (pLX311-Cas9) or a backbone-matched control vector (pLX311-empty) under blasticidin selection. Cas9 expression was confirmed by western blotting. The ratio of green (TP53-null) to non-green (TP53-WT) cells was quantified throughout time using a CytoFLEX Flow Cytometer (Beckman Coulter). Both data acquisition and data analysis were performed on the CytoFLEX machine. A figure exemplifying the gating strategy is provided as FIG. 11.

Drug Response Assay.

MCF7 cells were seeded at a density of 9,000 cells per well in a 96-well plate. The next day, media was washed and fresh media containing nutlin-3 (Sigma-Aldrich) was added to the corresponding wells in a concentration range of 0 μM-100 μM. After 72 h of incubation, levels of ATP were measured as a surrogate marker for cell viability using the CellTiter-Glo assay (Promega). Luminescence measurements were acquired in a SpectraMax reader (ATC) using an integration time of 500 ms.

Statistical Analyses.

The significance of the differences in transcriptional activity scores was determined by a two-tailed t-test. The significance of the difference in the number of enriched MSigDB Hallmark signatures between the introduction of Cas9 and that of control/empty vectors was determined by a one-sided Kolmogorov-Smirnov test. The significance of enrichment values was determined using a false discovery rate measure[8]. The significance of the differences in the transcriptional enrichment of the p53 and the DNA repair MSigDB Hallmark signatures between TP53-WT and TP53-mutant cell lines, and between Cas9 and empty/reporter vectors, were determined by a two-tailed Fisher's exact test. The significance of the difference in p53 and p21 protein expression levels between TP53-WT and TP53-mutant cell lines, and that of the differences in the concordance between CRISPR and RNAi screens in TP53-WT and TP53-mutant cell lines, were determined by a one-tailed Wilcoxon rank test. The significance of the difference between the fraction of line showing activation following Cas9 introduction was determined by a one-tailed Fisher's exact test. The significance of the differences in mRNA levels of p53 targets between WT and Cas9 lines, and that of the difference in Cas9 activity between TP53-WT and TP53-mutant cell lines, were determined by a one-tailed t-test. The significance of the difference in the overall activation of p53 transcriptional targets was determined by a two-tailed one-sample t-test. The significance of the tendency of non-silent mutations to emerge was determined by a two-tailed one-sample Wilcoxon rank test. The significance of the differences between the number of mutations emerging in the Cas9 lines and the number of mutations disappearing in the Cas9 lines, that of the differences in the allelic fraction of pre-existing subclonal inactivating TP53 mutations, and that of the difference between the number of γH2AX foci, were determined by a one-tailed paired t-test. The significance of the expansion of TP53 mutations in HCC1419 was determined by a binomial test, based on the allelic fraction of each mutation in the WT line. The cell line Cas9 activity levels (Supplementary Data 5 of Enache, O. M., Rendo, V., Abdusamad, M. et al. Cas9 activates the p53 pathway and selects for p53-inactivating mutations. Nat Genet 52, 662-668 (2020). https://doi.org/10.1038/s41588-020-0623-4, which is incorporated by reference herein as if expressed in its entirety and also Appendix C to U.S. Provisional Ser. No. 62/909,131) were correlated with the cell line transcriptional activity scores (TAS, as defined in[6]) using a two-sided test for association using Spearman's rho. The significance of the differences in nutlin-3 sensitivity were determined using a two-way ANOVA test.

Code Availability.

The code used to generate and/or analyze the data are publicly available.

Software Packages.

L1000 data were analyzed using the 'cmapR' package (v1.0.1)[37]; sequencing data were analyzed using the software described above; all other data were processed and graphed using the 'tidyverse' suite of R packages (v1.2.1; https://peerj.com/preprints/3180/) and 'ggpubr' (v0.2; https://rpkgs.datanovia.com/ggpubr/index.html). Dendrograms and statistical tests were performed using the 'stats' package (v3.5.2)[38], and analyses involving R were performed using R v3.5.0[39]. GSEA analysis was run using Java 1.8 and version 3.0 of the GSEA Java application.

REFERENCES IN EXAMPLES

1. Ben-David, U., Beroukhim, R. & Golub, T. R. Genomic evolution of cancer models: perils and opportunities. *Nat Rev Cancer* 19, 97-109 (2019).
2. Ben-David, U. et al. Genetic and transcriptional evolution alters cancer cell line drug response. *Nature* 560, 325-330 (2018).
3. Cong, L. et al. Multiplex genome engineering using CRISPR/Cas systems. *Science* 339, 819-23 (2013).
4. Jinek, M. et al. RNA-programmed genome editing in human cells. Elife 2, e00471 (2013).
5. Mali, P. et al. RNA-guided human genome engineering via Cas9. *Science* 339, 823-6 (2013).
6. Subramanian, A. et al. A Next Generation Connectivity Map: L1000 Platform and the First 1,000,000 Profiles. *Cell* 171, 1437-1452 e17 (2017).
7. Liberzon, A. et al. The Molecular Signatures Database (MSigDB) hallmark gene set collection. *Cell Syst* 1, 417-425 (2015).
8. Subramanian, A. et al. Gene set enrichment analysis: a knowledge-based approach for interpreting genome-wide expression profiles. *Proc Natl Acad Sci USA* 102, 15545-50 (2005).
9. Bunz, F. et al. Requirement for p53 and p21 to sustain G2 arrest after DNA damage. *Science* 282, 1497-501 (1998).
10. Haapaniemi, E., Botla, S., Persson, J., Schmierer, B. & Taipale, J. CRISPR-Cas9 genome editing induces a p53-mediated DNA damage response. *Nat Med* 24, 927-930 (2018).
11. Ihry, R. J. et al. p53 inhibits CRISPR-Cas9 engineering in human pluripotent stem cells. *Nat Med* 24, 939-946 (2018).
12. Schiroli, G. et al. Precise Gene Editing Preserves Hematopoietic Stem Cell Function following Transient p53-Mediated DNA Damage Response. *Cell Stem Cell* 24, 551-565 e8 (2019).
13. Wu, Y. et al. Highly efficient therapeutic gene editing of human hematopoietic stem cells. *Nat Med* 25, 776-783 (2019).
14. Elkon, R. et al. Dissection of a DNA-damage-induced transcriptional network using a combination of microarrays, RNA interference and computational promoter analysis. *Genome Biol* 6, R43 (2005).
15. Wang, W., Mani, A. M. & Wu, Z. H. DNA damage-induced nuclear factor-kappa B activation and its roles in cancer progression. *J Cancer Metastasis Treat* 3, 45-59 (2017).
16. Sholl, L. M. et al. Institutional implementation of clinical tumor profiling on an unselected cancer population. *JCI Insight* 1, e87062 (2016).
17. Giacomelli, A. O. et al. Mutational processes shape the landscape of TP53 mutations in human cancer. *Nat Genet* 50, 1381-1387 (2018).
18. Doench, J. G. et al. Rational design of highly active sgRNAs for CRISPR-Cas9-mediated gene inactivation. *Nat Biotechnol* 32, 1262-7 (2014).
19. Sinha, S. et al. Integrated computational and experimental identification of p53, KRAS and VHL mutant selection associated with CRISPR-Cas9 editing. *bioRxiv,* 407767 (2019).
20. Piras, F. et al. Lentiviral vectors escape innate sensing but trigger p53 in human hematopoietic stem and progenitor cells. *EMBO Mol Med* 9, 1198-1211 (2017).
21. Zacharias, J., Romanova, L. G., Menk, J. & Philpott, N. J. p53 inhibits adeno-associated viral vector integration. *Hum Gene Ther* 22, 1445-51 (2011).
22. Ben-David, U. et al. The landscape of chromosomal aberrations in breast cancer mouse models reveals driver-specific routes to tumorigenesis. *Nat Commun* 7, 12160 (2016).
23. Meyers, R. M. et al. Computational correction of copy number effect improves specificity of CRISPR-Cas9 essentiality screens in cancer cells. *Nat Genet* 49, 1779-1784 (2017).
24. Johnson, W. E., Li, C. & Rabinovic, A. Adjusting batch effects in microarray expression data using empirical Bayes methods. Biostatistics 8, 118-27 (2007).
25. Li, H. & Durbin, R. Fast and accurate short read alignment with Burrows-Wheeler transform. *Bioinformatics* 25, 1754-60 (2009).

26. DePristo, M. A. et al. A framework for variation discovery and genotyping using next-generation DNA sequencing data. *Nat Genet* 43, 491-8 (2011).
27. McKenna, A. et al. The Genome Analysis Toolkit: a MapReduce framework for analyzing next-generation DNA sequencing data. *Genome Res* 20, 1297-303 (2010).
28. Cibulskis, K. et al. Sensitive detection of somatic point mutations in impure and heterogeneous cancer samples. *Nat Biotechnol* 31, 213-9 (2013).
29. McLaren, W. et al. Deriving the consequences of genomic variants with the Ensembl API and SNP Effect Predictor. *Bioinformatics* 26, 2069-70 (2010).
30. Bamford, S. et al. The COSMIC (Catalogue of Somatic Mutations in Cancer) database and website. *Br J Cancer* 91, 355-8 (2004).
31. Karczewski, K. J. et al. Variation across 141,456 human exomes and genomes reveals the spectrum of loss-of-function intolerance across human protein-coding genes. 531210 (2019).
32. Dempster, J. M. et al. Extracting Biological Insights from the Project Achilles Genome-Scale CRISPR Screens in Cancer Cell Lines. 720243 (2019).
33. McFarland, J. M. et al. Improved estimation of cancer dependencies from large-scale RNAi screens using model-based normalization and data integration. *Nat Commun* 9, 4610 (2018).
34. Tsherniak, A. et al. Defining a Cancer Dependency Map. *Cell* 170, 564-576 e16 (2017).
35. Huang, D. W. et al. The DAVID Gene Functional Classification Tool: a novel biological module-centric algorithm to functionally analyze large gene lists. *Genome Biol* 8, R183 (2007).
36. Kung, C. P., Khaku, S., Jennis, M., Zhou, Y. & Murphy, M. E. Identification of TRIML2, a novel p53 target, that enhances p53 SUMOylation and regulates the transactivation of proapoptotic genes. *Mol Cancer Res* 13, 250-62 (2015).
37. Enache, O. M. et al. The GCTx format and cmap{Py, R, M, J} packages: resources for optimized storage and integrated traversal of annotated dense matrices. *Bioinformatics* 35, 1427-1429 (2019).
38. Team, R. D. C. R: A language and environment for statistical computing. (R Foundation for Statistical Computing, Vienna, Austria, 2010).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method for developing or designing a CRISPR-Cas based therapy or therapeutic comprising:

modifying one or more target sequence in an initial cell or initial cell population by expressing a Cas-protein and optionally a CRISPR-Cas system in the initial cell or initial cell population, thereby generating a modified cell or modified cell population;

clonally expanding the modified cell or modified cell population to obtain an expanded cell population;

detecting, in cells from the expanded cell population, expression of a Cas-induced DNA damage response protein signature; and selecting clones from the expanded cell population that do not express the Cas-induced DNA-damage response signature and that do not have a p53 inactivating mutation.

2. The method of claim 1, wherein the Cas-induced DNA-damage response signature indicates Cas-induced activation of a p53 pathway.

3. The method of claim 1, wherein the selected clones are administered to a subject in need thereof.

4. The method of claim 3, wherein the initial cell or initial cell population is isolated from the subject in need thereof.

5. The method of claim 1, wherein the CRISPR-Cas system comprises a guide molecule and wherein the guide molecule is or comprises a truncated guide, an escorted guide, or a protected guide.

6. The method of claim 1, wherein the modifying the one or more target genes is done in the presence of one or more anti-CRISPR molecules or CRISPR inhibitors.

7. A method of developing or designing a CRISPR-Cas based therapeutic comprising:

expressing a set of CRISPR-Cas systems or components thereof in a test cell population and modifying one or more target sequence in the test cell population;

screening, in the test cell population for each CRISPR-Cas system or components thereof, for expression of a DNA-damage response signature and the presence of p53 inactivating mutations; and selecting one or more CRISPR-Cas systems or components thereof that do not result in: (i) expression of a Cas-induced DNA-damage response signature and (ii) a p53 inactivating mutation.

8. The method of claim 7, wherein the test cell population expresses only Cas.

9. The method of claim 7, wherein the DNA-damage response signature indicates Cas-induced activation of a p53 pathway.

10. The method of claim 7, wherein each CRISPR-Cas system in the set of CRISPR-Cas systems varies in:

(a) dosage;

(b) Cas protein;

(c) guide molecule design; or (d) a combination thereof.

11. The method of claim 7, wherein the set of CRISPR-Cas systems or components thereof comprises one or more guide molecules and wherein one or more of the guide molecules is/are or comprises a truncated guide, an escorted guide, or a protected guide.

12. The method of claim 7, wherein the set of CRISPR-Cas systems or components thereof comprises one or more Cas proteins, one or more guide molecules, or both and wherein the one or more Cas proteins, the one or more guide molecules, or both are constitutively expressed.

13. The method of claim 7, wherein the set of CRISPR-Cas systems or components thereof comprises one or more Cas proteins, one or more guide molecules, or both and wherein the one or more Cas proteins, the one or more guide molecules, or both are inducibly expressed.

14. The method of claim 7, wherein a Cas protein and one or more guide molecules are delivered to the test cell population on the same or different vectors or delivery particles.

15. The method of claim 7, wherein a Cas protein and a guide molecule are delivered to the test cell population as a ribonucleoprotein complex (RNP).

16. The method of claim 7, wherein the test cell population is modified to express a Cas protein or guide molecule prior to screening.

17. The method of claim 7, wherein the set of CRISPR-Cas systems or components thereof are delivered to the test cell populations by liposomes, lipid particles, nanoparticles, biolistics, viral-based expression, or viral based delivery systems.

18. The method of claim 7, wherein screening the set of CRISPR-Cas systems or components thereof is done in the presence of one or more anti-CRISPR molecules or CRISPR inhibitors.

19. The method of claim 7, wherein the test cell population is obtained from a subject to be treated with the CRISPR-Cas therapeutic.

20. A method of treating a subject in need thereof with a CRISPR-Cas therapeutic comprising: performing a method of developing or designing a CRISPR-Cas based therapeutic as in claim 7, wherein the test cell population is obtained from the subject; and administering the CRISPR-Cas therapeutic to the subject in need thereof.

21. The method of claim 20, wherein the CRISPR-Cas therapeutic is expressed in one or more cells ex vivo and modifies the one or more cells to obtain one or more modified cells, wherein the one or more cells are optionally obtained from the subject in need thereof.

22. The method of claim 21, wherein the one or more modified cells are administered to the subject in need thereof.

* * * * *